United States Patent
Huynh et al.

(10) Patent No.: US 12,313,634 B2
(45) Date of Patent: May 27, 2025

(54) METHODS FOR PREDICTION AND EARLY DETECTION OF DIABETES

(71) Applicants: Zora Biosciences Oy, Espoo (FI); BAKER HEART AND DIABETES INSTITUTE, Melbourne (AU)

(72) Inventors: Kevin Huynh, Footscray (AU); Dianna Magliano, St Kilda West (AU); Jonathan Shaw, North Caulfield (AU); Mika Hilvo, Helsinki (FI); Reijo Laaksonen, Lempäälä (FI); Peter Meikle, Lower Plenty (AU)

(73) Assignees: ZORA BIOSCIENCES OY, Espoo (FI); BAKER HEART AND DIABETES INSTITUTE, Melbourne (AU)

( * ) Notice: Subject to any disclaimer, the term of this patent is extended or adjusted under 35 U.S.C. 154(b) by 1234 days.

(21) Appl. No.: 16/762,612

(22) PCT Filed: Nov. 20, 2018

(86) PCT No.: PCT/EP2018/081959
§ 371 (c)(1),
(2) Date: May 8, 2020

(87) PCT Pub. No.: WO2019/097089
PCT Pub. Date: May 23, 2019

(65) Prior Publication Data
US 2020/0348316 A1    Nov. 5, 2020

Related U.S. Application Data

(60) Provisional application No. 62/588,779, filed on Nov. 20, 2017.

(51) Int. Cl.
| | | |
|---|---|---|
| *G01N 33/68* | (2006.01) | |
| *G01N 33/92* | (2006.01) | |
| *G16H 10/60* | (2018.01) | |
| *G16H 20/10* | (2018.01) | |
| *G16H 50/20* | (2018.01) | |
| *G16H 50/30* | (2018.01) | |

(52) U.S. Cl.
CPC ......... *G01N 33/6893* (2013.01); *G01N 33/92* (2013.01); *G16H 10/60* (2018.01); *G16H 20/10* (2018.01); *G16H 50/20* (2018.01); *G16H 50/30* (2018.01); *G01N 2405/00* (2013.01); *G01N 2800/042* (2013.01); *G01N 2800/085* (2013.01)

(58) Field of Classification Search
CPC .............. G01N 33/6893; G01N 33/92; G01N 2400/00; G01N 2800/042; G01N 2800/085; G16H 10/60; G16H 50/30; G16H 50/20; G16H 20/10
See application file for complete search history.

(56) References Cited

U.S. PATENT DOCUMENTS

| | | | | |
|---|---|---|---|---|
| 2015/0011424 A1* | 1/2015 | Oresic | .................. | G01N 33/492 |
| | | | | 250/282 |
| 2015/0362513 A1* | 12/2015 | Laaksonen | ............. | G01N 33/92 |
| | | | | 506/12 |
| 2018/0267018 A1* | 9/2018 | Kamp | ................. | G01N 33/6893 |

FOREIGN PATENT DOCUMENTS

| | | |
|---|---|---|
| WO | 2007/128884 A1 | 11/2007 |
| WO | 2011/059721 A1 | 5/2011 |
| WO | 2012000770 A1 | 1/2012 |
| WO | 2013113992 A1 | 8/2013 |
| WO | 2014/118634 A1 | 8/2014 |
| WO | 2016081534 A1 | 5/2016 |
| WO | 2017/070114 A2 | 4/2017 |

OTHER PUBLICATIONS

Gorden D.L. et al., "Biomarkers of NAFLD Progression: A Lipidomics Approach To An Epidemic", J. Lipid Res., vol. 56, No. 3, Jan. 17, 2015 (Jan. 17, 2015), pp. 722-736.
European Search Report mailed Jul. 20, 2023 for corresponding European U.S. Appl. No. 18807298, 12 pages.
International Search Report and Written Opinion dated Apr. 4, 2019 from International Application No. PCT/EP2018/081959 (Authorized officer, Murielle Giry), 18 pages.
Wigger et al., "Plasma Dihydroceramides Are Diabetes Susceptibility Biomarker Candidates in Mice and Humans", Cell Reports, Feb. 2017, vol. 18, No. 9, pp. 2269-2279.
Tarasov et al., "Molecular Lipids Identify Cardiovascular Risk and Are Efficiently Lowered by Simvastatin and PCSK9 Deficiency", J. Clin. Endocrinol. Metabol., Jan. 2014, vol. 99, No. 1, pp. E45-E52.
Tikhonenko et al., "N-3 Polyunsaturated Fatty Acids Prevent Diabetic Retinopathy by Inhibition of Retinal Vascular Damage and Enhanced Endothelial Progenitor Cell Reparative Function", Plos One, Jan. 2013, vol. 8, No. 1, 10 pages.
Havulinna et al., "Circulating Ceramides Predict Cardiovascular Outcomes in the Population-Based FINRISK 2002 Cohort", Arterioscler. Thromb. Vasc. Biol., Dec. 2016, vol. 36, No. 12, pp. 2424-2430.
Hilvo et al., "Ceramide stearic to palmitic acid ratio predicts incident diabetes", Diabetologia, Mar. 2018, vol. 61, No. 6, pp. 1424-1434.

* cited by examiner

*Primary Examiner* — Kathryn Elizabeth Limbaugh
(74) *Attorney, Agent, or Firm* — MH2 Technology Law Group, LLP

(57) ABSTRACT

An in vitro method for assessing whether a subject is at risk to develop or is suffering from fatty liver disease comprising: (a) assaying a sample from said subject to determine a concentration of at least one fatty liver biomarker from Group E; (b) assaying a sample from said subject to determine a concentration of at least one fatty liver biomarker from Group F; and (c) determining that the subject is suffering from or is at an increased risk of developing fatty liver disease, if said sample contains an increased combination biomarker value of the at least one fatty liver biomarker from Group E and the at least one fatty liver biomarker from Group F, when compared to a control.

17 Claims, No Drawings

METHODS FOR PREDICTION AND EARLY DETECTION OF DIABETES

CROSS-REFERENCE TO RELATED APPLICATIONS

This application is a U.S. National Stage application of PCT/EP2018/081959 filed 20 Nov. 2018, which claims priority to U.S. Provisional Application No. 62/588,779 filed 20 Nov. 2017, the entire disclosures of which are herein incorporated by reference.

FIELD OF THE INVENTION

The present disclosure is related to the field of diagnostic and prognostic biomarkers for diabetes. In particular, it provides a novel in vitro method for assessing whether a subject is at risk to develop or is suffering from type 2 diabetes and/or its complications. In addition, the present biomarkers can be used in methods to evaluate the effectiveness of a diabetes treatment and the progression of the disease.

In addition to diabetes biomarkers, the present disclosure presents novel diagnostic and prognostic biomarkers for fatty liver disease.

BACKGROUND

Type 2 diabetes (Diabetes mellitus type 2, DM2) is a serious progressive metabolic disorder in which the body becomes resistant to insulin and gradually loses the capacity to produce sufficient amounts of insulin. Globally, an estimated 422 million adults were living with diabetes in 2014, and the global age-standardized prevalence has doubled since 1980 being now 8.5% in the adult population (World Health Organization: Global Report on Diabetes, 2016). DM2 can lead to severe complications, including kidney, retinal or neural damage, and accelerated cardiovascular disease resulting in myocardial infarctions or strokes.

According to World Health Organization guidelines, Type 2 diabetes is diagnosed if a) fasting plasma glucose level is higher than 7 mmol/l, or b) 2-hour plasma glucose level is higher than 11.1 mmol/l during a glucose tolerance test or c) hemoglobin A1c level is 6.5% or higher (World Health Organization: Global Report on Diabetes, 2016). Pre-diabetes is an intermediate state of hyperglycemia with glycemic parameters above normal but below the DM2 threshold; however, the exact diagnostic criteria of pre-diabetes are not uniform across various international professional organizations. Notably, lifestyle interventions affecting diet, weight management and physical activity may significantly reduce the risk of conversion from a prediabetic state to DM2. Thus, identifying those subjects at greatest risk for DM2 and promoting lifestyle changes in such individuals may help to prevent DM2 and its complications.

The above glycemic parameters are used in clinical practice for diagnosing type 2 diabetes, however, they are not used for predicting the appearance of the disease. Therefore, prognostic markers are needed for detecting individuals at increased risk of developing DM2 and prediabetic individuals at risk of progressing to DM2. According to the International Diabetes Federation (IDF Diabetes Atlas, Seventh Edition, 2015), globally, 50% of adults suffering from diabetes are estimated to be undiagnosed. As diabetes can lead to severe complications and premature mortality, identification of those individuals at high-risk of developing type 2 diabetes would allow for earlier lifestyle interventions, and if needed, medication, thus providing a longer and healthier life for these high-risk individuals.

Existing diabetes risk panels are based on different combinations of several risk factors and measures, for example age, sex, ethnicity, family history of diabetes, history of gestational diabetes, blood pressure, body mass index, waist circumference, smoking status, vegetable, fruit and berry consumption and physical activity. The existing panels provide general information of known risk factors, but more precise risk assessments are still needed to identify those individuals who are at high-risk of developing type 2 diabetes.

Despite some attempts to find predictive biomarkers for diabetes, however, most previous disclosures have failed to provide simple and reliable diabetes biomarkers from blood samples that could be conveniently used in clinical practice. See, for example, WO 2017/070114 A2 which describes a panel of biomarkers consisting of, e.g., bile acids, amino acids and free fatty acids. WO 2011/059721 A1 describes a multimarker panel of glucose combined with several protein and lipid biomarkers. Genetic biomarkers for diabetes have been searched as well, see, for example, WO 2014/118634 and WO 2007/128884 A1.

Generally, some of the existing biomarker panels are too large for clinical use and there is no teaching regarding how the panels may be reduced in size.

Accordingly, there is utility for additional, focused biomarker panels, which may be used to continue to improve the ability to assess, for example, a patient's risk of developing diabetes, their prognosis and/or the expected effectiveness of a proposed treatment.

Fatty liver disease (FLD) is a condition in which excess fat builds up in the liver. Fatty liver disease is becoming increasingly common health problem around the world. It is estimated that 80 to 100 million people in the United States alone are suffering from non-alcoholic fatty liver disease (NAFLD) which is the other main type of fatty liver disease. The other is alcoholic fatty liver disease.

NAFLD comprises a range of conditions which are not related to heavy alcohol use. Early stages of NAFLD can be symptomless so many people are suffering from NAFLD undiagnosed. If not detected and managed, NAFLD can progress to serious liver damage, so identifying people suffering from NAFLD is crucial. NAFLD can progress from a harmless fatty liver stage (steatosis) to non-alcoholic steatohepatitis (NASH), a more serious form of NAFLD, and eventually to fibrosis, cirrhosis, liver failure and liver cancer.

There is a need for a simple and reliable test for predicting and diagnosing fatty liver disease, especially NAFLD which can not be detected in its early stages with the current methods.

SUMMARY

The present disclosure identifies novel lipid biomarker combinations for predicting type 2 diabetes by quantifying defined combinations of molecular species concentrations. The present novel biomarker combinations also include newly identified lipid species, e.g., phospholipids esterified with methylhexadecanoic acid, which were found to be associated with type 2 diabetes risk.

The present inventors have surprisingly found novel lipid biomarkers and biomarker combinations for type 2 diabetes. Specifically, it has been found that each marker combination displays a characteristic increase or decrease in combination biomarker values as described herein in samples obtained from subjects having diabetes, and are useful for the methods and uses in accordance with the present disclosure. The present biomarkers are sensitive and specific and they can be used in diagnostic and prognostic assays.

The risk determination based on the novel lipid biomarkers disclosed herein allow for better assessment of future type 2 diabetes risk by identifying individuals at risk of developing type 2 diabetes while their blood glucose levels may be normal, or below diagnostic thresholds, i.e., at the range where current tests fail to measure increased risk. This allows earlier intervention and prevention or delay of the onset of diabetes and/or its complications. The present disclosure therefore represents a significant advantage and great improvement over the prior methods currently used to predict type 2 diabetes.

Further, the present markers find use in determining effectiveness of treatment in patients having diabetes. In addition, the predictive or prognostic information from the lipid biomarkers can be combined with traditional clinical markers of diabetes, such as fasting glucose or hemoglobin A1c.

The four distinct classes of diabetes biomarkers, Group A, Group B, Group C and Group D were found to provide improved prognostic and diagnostic power when combined. Group A and Group B, and Group C and Group D diabetes biomarkers are shown in Table 1 and Table 2, respectively, below.

TABLE 1

Group A and B diabetes biomarkers. Abbreviations are described in the detailed description of the present disclosure.

| Group A | Group B |
|---|---|
| Cer(d16:1/18:0) | Cer(d18:2/26:0) |
| Cer(d16:1/20:0) | Cer(d19:1/26:0) |
| Cer(d16:1/22:0) | LPC(17:0) [sn2] |
| Cer(d17:1/20:0) | LPC(MHDA) [sn1] |
| Cer(d18:1/16:0) | LPC(MHDA) [sn2] |
| Cer(d18:1/18:0) | LPC(17:0) [sn1] |
| Cer(d18:1/20:0) | LPC(18:2) [sn1] |
| Cer(d18:1/21:0) | LPC(18:2) [sn2] |
| Cer(d18:1/22:0) | LPC(19:0) [sn2] |
| Cer(d19:1/18:0) | LPC(19:0) [sn1] |
| Cer(d20:1/22:0) | LPC(20:0) [sn2] |
| Cer(d20:1/23:0) | LPC(20:1) [sn1] |
| Cer(d20:1/24:0) | LPC(20:1) [sn2] |
| Cer(d20:1/24:1) | LPC(20:2) [sn1] |
| LPC(14:0) [sn1] | LPC(22:0) [sn1] |
| LPC(14:0) [sn2] | LPC(22:1) [sn1] |
| LPE(18:0) [sn1] | LPC(22:1) [sn2] |
| LPE(18:0) [sn2] | LPC(24:0) [sn1] |
| LPI(18:0) [sn2] | LPC(24:0) [sn2] |
| LPI(20:4) [sn1] | LPC(26:0) [sn1] |
| LPI(20:4) [sn2] | LPC(26:0) [sn2] |
| PC(36:0) | LPC(P-16:0) |
| SM(d18:0/22:0) | LPC(P-17:0) |
| TG(O-50:1) | LPC(P-18:0) |
| TG(O-52:0) | LPC(P-18:1) |
| TG(O-52:2) | LPC(P-20:0) |
| | LPE(P-20:0) |
| | PC(MHDA_18:1) |
| | PC(MHDA_18:2) |
| | PC(MHDA_22:6) |
| | PC(17:0 22:6) |
| | PI(37:6) |
| | SM(d16:1/19:0) |
| | SM(d17:1/14:0) |
| | SM(d17:1/16:0) |
| | SM(d17:1/24:1) |
| | SM(d18:2/17:0) |
| | SM(d18:2/18:1) |

TABLE 1-continued

Group A and B diabetes biomarkers. Abbreviations are described in the detailed description of the present disclosure.

| Group A | Group B |
|---|---|
| | SM(d18:2/23:0) |
| | SM(d18:2/24:0) |

In addition to the novel combinations of Group A and Group B diabetes biomarkers, the inventors of the present disclosure have found combinations of Group C and Group D diabetes biomarkers that unexpectedly associate strongly with type 2 diabetes.

TABLE 2

Group C and D diabetes biomarkers. Abbreviations are described in the detailed description of the present disclosure.

| Group C | Group D |
|---|---|
| Cer(d16:1/18:0) | Cer(d18:1/16:0) |
| Cer(d18:1/18:0) | |
| Cer(d18:1/20:0) | |
| Cer(d18:1/22:0) | |

According to a first aspect of the disclosure there is provided an in vitro method for assessing whether a subject is at risk to develop or is suffering from type 2 diabetes comprising:
(a) assaying a sample from said subject to determine a concentration of at least one diabetes biomarker from Group A;
(b) assaying a sample from said subject to determine a concentration of at least one diabetes biomarker from Group B; and
(c) determining that the subject is suffering from or is at an increased risk of developing type 2 diabetes, if said sample contains an increased combination biomarker value of the at least one diabetes biomarker from Group A and the at least one diabetes biomarker from Group B, when compared to a control.

In some embodiments, the subject is capable of being treated with a therapy as described herein. For example, the therapy may comprise any therapeutic treatment typically given to a subject at risk of developing diabetes or a subject having diabetes, such as, but not limited to, lifestyle interventions and/or counselling to effect a change in diet, weight management and/or physical activity, controlling the progression of diabetes and/or its complications (e.g. by blood glucose and/or blood pressure monitoring, lipid monitoring and control, eye, kidney and feet examination), diabetes medication (e.g. insulin, metformin, GLP-1 analogues, DPP-4 inhibitors, SGLT2 inhibitors, sulfonylureas, meglitinides, thiazolidinediones and alpha-glucosidase inhibitors), blood pressure and lipid modifying medications as described in the detailed description of the present disclosure, or any combination thereof.

In some embodiments, the method for assessing whether a subject is at risk to develop or is suffering from type 2 diabetes further comprises after the determining step (c), (d) diagnosing the subject as suffering from or having an increased risk of developing type 2 diabetes from the results in step (c), and (e) administering a treatment to the subject diagnosed in step (d).

In one aspect, the present disclosure is directed to a method of treating or preventing type 2 diabetes in a subject identified as being at risk to develop or suffering from type 2 diabetes, the method comprising: administering to the subject a treatment as described herein, wherein prior to administering the treatment, the subject has been identified as being at risk to develop or suffering from type 2 diabetes by the method described herein. Assaying Group A and Group B biomarkers and/or Group C and Group D biomarkers in a biological sample and/or the determination of combination biomarker values from Group A and Group B biomarker levels and/or Group C and Group D biomarker levels are unconventional indicators for type 2 diabetes and/or the risk thereof. Moreover, the present biomarkers and methods generally allow for the sensitive indication of type 2 diabetes and/or the risk of developing type 2 diabetes. Thus, the present methods ensure that subjects having and/or at risk for type 2 diabetes can be properly identified and receive treatment as opposed to the large numbers of individuals who have and/or are at risk of developing this disease, but remain unidentified and untreated, and consequently are unnecessarily subjected to the possibility of severe complications and/or premature mortality as is commonplace in this field. Furthermore, the generally high level of specificity of the instant methods allows for the proper indication of type 2 diabetes and/or the risk thereof, thus allowing subjects to avoid unnecessary treatment as is also commonplace in this field.

According to another aspect of the disclosure there is provided an in vitro method for assessing whether a subject is at risk to develop or is suffering from type 2 diabetes comprising:
 (a) assaying a sample from said subject to determine a concentration of at least one diabetes biomarker from Group C;
 (b) assaying a sample from said subject to determine a concentration of a diabetes biomarker from Group D; and
 (c) determining that the subject is suffering from or is at an increased risk of developing type 2 diabetes, if said sample contains an increased combination biomarker value of the at least one diabetes biomarker from Group C and the diabetes biomarker from Group D, when compared to a control.

In some embodiments, the subject is capable of being treated with a therapy as described herein. For example, the therapy may comprise any therapeutic treatment typically given to a subject at risk of developing diabetes or a subject having diabetes, such as, but not limited to, lifestyle interventions and/or counselling to effect a change in diet, weight management and/or physical activity, controlling the progression of diabetes and/or its complications (e.g. by blood glucose and/or blood pressure monitoring, lipid monitoring and control, eye, kidney and feet examination), diabetes medication (e.g. insulin, metformin, GLP-1 analogues, DPP-4 inhibitors, SGLT2 inhibitors, sulfonylureas, meglitinides, thiazolidinediones and alpha-glucosidase inhibitors), blood pressure and lipid modifying medications as described in the detailed description of the present disclosure, or any combination thereof.

In some embodiments, the method for assessing whether a subject is at risk to develop or is suffering from type 2 diabetes further comprises after the determining step (c), (d) diagnosing the subject as suffering from or having an increased risk of developing type 2 diabetes from the results in step (c), and (e) administering a treatment to the subject diagnosed in step (d).

In one aspect, the present disclosure is directed to a method of treating or preventing type 2 diabetes in a subject identified as being at risk to develop or suffering from type 2 diabetes, the method comprising: administering to the subject a treatment as described herein, wherein prior to administering the treatment, the subject has been identified as being at risk to develop or suffering from type 2 diabetes by the method described herein.

Assaying Group A and Group B biomarkers and/or Group C and Group D biomarkers in a biological sample and/or the determination of combination biomarker values from Group A and Group B biomarker levels and/or Group C and Group D biomarker levels are unconventional indicators for type 2 diabetes and/or the risk thereof. Moreover, the present biomarkers and methods generally allow for the sensitive indication of type 2 diabetes and/or the risk of developing type 2 diabetes. Thus, the present methods ensure that subjects having and/or at risk for type 2 diabetes can be properly identified and receive treatment as opposed to the large numbers of individuals who have and/or are at risk of developing this disease, but remain unidentified and untreated, and consequently are unnecessarily subjected to the possibility of severe complications and/or premature mortality as is commonplace in this field. Furthermore, the generally high level of specificity of the instant methods allows for the proper indication of type 2 diabetes and/or the risk thereof, thus allowing subjects to avoid unnecessary treatment as is also commonplace in this field.

According to another aspect of the disclosure there is provided an in vitro method for assessing whether a subject undergoing statin treatment is at risk to develop or is suffering from type 2 diabetes comprising:
 (a) assaying a sample from said subject to determine a concentration of at least one diabetes biomarker from Group A;
 (b) assaying a sample from said subject to determine a concentration of at least one diabetes biomarker from Group B; and
 (c) determining that the subject is suffering from or is at an increased risk of developing type 2 diabetes, if said sample contains an increased combination biomarker value of the at least one diabetes biomarker from Group A and the at least one diabetes biomarker from Group B, when compared to a control.

In some embodiments, the method for assessing whether a subject undergoing statin treatment is at risk to develop or is suffering from type 2 diabetes further comprises after the determining step (c), (d) diagnosing the subject as suffering from or having an increased risk of developing type 2 diabetes from the results in step (c), and (e) administering a treatment to the subject diagnosed in step (d).

In some embodiments, the subject undergoing statin treatment is suffering from cardiovascular disease (CVD).

In some embodiments, the subject undergoing statin treatment has been or is being additionally treated with another lipid modifying drug(s) as described herein.

In some embodiments, the subject is capable of being treated with a therapy as described herein. For example, the therapy may comprise any therapeutic treatment typically given to a subject at risk of developing diabetes or a subject having diabetes, such as, but not limited to, lifestyle interventions and/or counselling to effect a change in diet, weight management and/or physical activity, controlling the progression of diabetes and/or its complications (e.g. by blood glucose and/or blood pressure monitoring, lipid monitoring and control, eye, kidney and feet examination), diabetes medication (e.g. insulin, metformin, GLP-1 analogues, DPP-4 inhibitors, SGLT2 inhibitors, sulfonylureas, meglitinides, thiazolidinediones and alpha-glucosidase inhibitors), blood pressure and lipid modifying medications as described in the detailed description of the present disclosure, or any combination thereof.

In one aspect, the present disclosure is directed to a method of treating or preventing type 2 diabetes in a subject undergoing statin treatment and identified as being at risk to develop or suffering from type 2 diabetes, the method comprising: administering to the subject a treatment as described herein, wherein prior to administering the treatment, the subject has been identified as being at risk to develop or suffering from type 2 diabetes by the method described herein.

According to another aspect of the disclosure there is provided an in vitro method for assessing whether a subject undergoing statin treatment is at risk to develop or is suffering from type 2 diabetes comprising:
(a) assaying a sample from said subject to determine a concentration of at least one diabetes biomarker from Group C;
(b) assaying a sample from said subject to determine a concentration of a diabetes biomarker from Group D; and
(c) determining that the subject is suffering from or is at an increased risk of developing type 2 diabetes, if said sample contains an increased combination of biomarker value of the at least one diabetes biomarker from Group C and the diabetes biomarker from Group D, when compared to a control.

In some embodiments, the method for assessing whether a subject undergoing statin treatment is at risk to develop or is suffering from type 2 diabetes further comprises after the determining step (c), (d) diagnosing the subject as suffering from or having an increased risk of developing type 2 diabetes from the results in step (c), and (e) administering a treatment to the subject diagnosed in step (d).

In some embodiments, the subject undergoing statin treatment is suffering from cardiovascular disease (CVD).

In some embodiments, the subject undergoing statin treatment has been or is being additionally treated with another lipid modifying drug(s) as described herein.

In some embodiments, the subject is capable of being treated with a therapy as described herein. For example, the therapy may comprise any therapeutic treatment typically given to a subject at risk of developing diabetes or a subject having diabetes, such as, but not limited to, lifestyle interventions and/or counselling to effect a change in diet, weight management and/or physical activity, controlling the progression of diabetes and/or its complications (e.g. by blood glucose and/or blood pressure monitoring, lipid monitoring and control, eye, kidney and feet examination), diabetes medication (e.g. insulin, metformin, GLP-1 analogues, DPP-4 inhibitors, SGLT2 inhibitors, sulfonylureas, meglitinides, thiazolidinediones and alpha-glucosidase inhibitors), blood pressure and lipid modifying medications as described in the detailed description of the present disclosure, or any combination thereof.

In one aspect, the present disclosure is directed to a method of treating or preventing type 2 diabetes in a subject undergoing statin treatment and identified as being at risk to develop or suffering from type 2 diabetes, the method comprising: administering to the subject a treatment as described herein, wherein prior to administering the treatment, the subject has been identified as being at risk to develop or suffering from type 2 diabetes by the method described herein.

Assaying Group A and Group B biomarkers and/or Group C and Group D biomarkers in a biological sample and/or the determination of combination biomarker values from Group A and Group B biomarker levels and/or Group C and Group D biomarker levels are unconventional indicators for type 2 diabetes and/or the risk thereof. Moreover, the present biomarkers and methods generally allow for the sensitive indication of type 2 diabetes and/or the risk of developing type 2 diabetes. Thus, the present methods ensure that subjects having and/or at risk for type 2 diabetes can be properly identified and receive treatment as opposed to the large numbers of individuals who have and/or are at risk of developing this disease, but remain unidentified and untreated, and consequently are unnecessarily subjected to the possibility of severe complications and/or premature mortality as is commonplace in this field. Furthermore, the generally high level of specificity of the instant methods allows for the proper indication of type 2 diabetes and/or the risk thereof, thus allowing subjects to avoid unnecessary treatment as is also commonplace in this field.

According to yet another aspect of the invention there is provided an in vitro method of evaluating the effectiveness of a diabetes therapy in a subject comprising:
(a) assaying a sample from said subject to determine a concentration of at least one diabetes biomarker from Group A;
(b) assaying a sample from said subject to determine a concentration of at least one diabetes biomarker from Group B; and
(c) determining that the therapy is effective, if said sample contains a decreased combination biomarker value of the at least one diabetes biomarker from Group A and the at least one diabetes biomarker from Group B, when compared to a control.

In the method, the effectiveness of the therapy is monitored by analysing the combination biomarker value as described herein of the diabetes biomarkers described herein. The combination biomarker value of the selected biomarkers reflects the progress of diabetes and the combination biomarker value approaches that of the control when the subject responds to a therapy, such as the therapies described herein. Accordingly, a therapy may be tailored based on the response of a subject such that only a therapy which shows a positive response, e.g., the combination biomarker value of the biomarker concentrations approaching that of a control, and is thus found effective, is continued, and a therapy which shows minimal or no response, and is thus found ineffective, is discontinued.

In some embodiments, the subject is capable of being treated with a therapy as described herein, which is escalated. For example, the therapy to be escalated may comprise any therapeutic treatment typically given to a subject at risk of developing diabetes or a subject having diabetes, such as, but not limited to, lifestyle interventions and/or counselling to affect a change in diet, weight management and/or physical activity, controlling the progression of diabetes and/or its complications (e.g. by blood glucose and/or blood pressure monitoring, lipid monitoring and control, eye, kidney and feet examination), diabetes medication (e.g. insulin, metformin, GLP-1 analogues, DPP-4 inhibitors, SGLT2 inhibitors, sulfonylureas, meglitinides, thiazolidinediones and alpha-glucosidase inhibitors), blood pressure and lipid modifying medications as described in the detailed description of the present disclosure, or any combination thereof.

In some embodiments, the method for evaluating the effectiveness of a diabetes therapy in a subject further comprises, (d) determining that the therapy is not effective in the subject from the results in step (c), and (e) escalating the therapy of the subject.

In one aspect, the present disclosure is directed to a method of treating diabetes in a subject identified as being ineffectively treated, the method comprising: administering to the subject a further treatment as described herein, wherein prior to administering the treatment, the subject has been identified as being ineffectively treated for diabetes by the methods described herein.

In some embodiments, the therapy may comprise any therapeutic treatment typically given to a subject at risk of developing diabetes or a subject having diabetes, such as, but not limited to, lifestyle interventions and/or counselling affecting diet, weight management and physical activity, control of progression of diabetes and/or its complications (e.g. blood glucose monitoring, blood pressure and lipid control and eye, kidney and feet examination), diabetes medication (e.g. insulin, metformin, GLP-1 analogues, DPP-4 inhibitors, SGLT2 inhibitors, sulfonylureas, meglitinides, thiazolidinediones and alpha-glucosidase inhibitors), blood pressure and lipid modifying medications as described in the detailed description of the present disclosure, or any combination thereof.

In some embodiments of the aforementioned methods, the method of treating diabetes further comprises identifying the subject as in need of the treatment or prevention, for example, by requesting a test or receiving the test results, for example, from a commercial laboratory, which provides the results of an assay useful for determining the combination biomarker value of the at least one diabetes biomarker from Group A and the at least one diabetes biomarker from Group B and administering to the subject a treatment, for example, a therapeutically effective dose of a drug, if the subject has an increased combination biomarker value of the at least one diabetes biomarker from Group A and the at least one diabetes biomarker from Group B, as compared to the control.

According to yet another aspect of the invention there is provided an in vitro method of evaluating the effectiveness of a diabetes therapy in a subject comprising:
(a) assaying a sample from said subject to determine a concentration of at least one diabetes biomarker from Group C;
(b) assaying a sample from said subject to determine a concentration of a diabetes biomarker from Group D; and
(c) determining that the therapy is effective, if said sample contains a decreased combination biomarker value of the at least one diabetes biomarker from Group C and the diabetes biomarker from Group D, when compared to a control.

In the method, the effectiveness of the therapy is monitored by analysing the combination biomarker value of the diabetes biomarkers described herein. The combination biomarker value of the selected biomarkers reflects the progress of diabetes and the combination biomarker value approaches that of the control when the subject responds to a therapy, such as the therapies described herein. Accordingly, a therapy may be tailored based on the response of a subject such that only a therapy which shows a positive response, e.g., the combination biomarker value approaching that of a control, and is thus found effective, is continued, and a therapy which shows minimal or no response, and is thus found ineffective, is discontinued.

In some embodiments, the subject is capable of being treated with a therapy as described herein, which is escalated. For example, the therapy to be escalated may comprise any therapeutic treatment typically given to a subject at risk of developing diabetes or a subject having diabetes, such as, but not limited to, lifestyle interventions and/or counselling to affect a change in diet, weight management and/or physical activity, controlling the progression of diabetes and/or its complications (e.g. by blood glucose and/or blood pressure monitoring, lipid monitoring and control, eye, kidney and feet examination), diabetes medication (e.g. insulin, metformin, GLP-1 analogues, DPP-4 inhibitors, SGLT2 inhibitors, sulfonylureas, meglitinides, thiazolidinediones and alpha-glucosidase inhibitors), blood pressure and lipid modifying medications as described in the detailed description of the present disclosure, or any combination thereof.

In some embodiments, the method for evaluating the effectiveness of a diabetes therapy in a subject further comprises, (d) determining that the therapy is not effective in the subject from the results in step (c), and (e) escalating the therapy of the subject.

In one aspect, the present disclosure is directed to a method of treating diabetes in a subject identified as being ineffectively treated, the method comprising: administering to the subject a further treatment as described herein, wherein prior to administering the treatment, the subject has been identified as being ineffectively treated for diabetes by the methods described herein.

In some embodiments, the therapy may comprise any therapeutic treatment typically given to a subject at risk of developing diabetes or a subject having diabetes, such as, but not limited to, lifestyle interventions and/or counselling affecting diet, weight management and physical activity, control of progression of diabetes and/or its complications (e.g. blood glucose monitoring, blood pressure and lipid control and eye, kidney and feet examination), diabetes medication (e.g. insulin, metformin, GLP-1 analogues, DPP-4 inhibitors, SGLT2 inhibitors, sulfonylureas, meglitinides, thiazolidinediones and alpha-glucosidase inhibitors), blood pressure and lipid modifying medications as described in the detailed description of the present disclosure, or any combination thereof.

In some embodiments of the aforementioned methods, the method of treating diabetes further comprises identifying the subject as in need of the treatment or prevention, for example, by requesting a test or receiving the test results, for example, from a commercial laboratory, which provides the results of an assay useful for determining the combination biomarker value of the at least one diabetes biomarker from Group C and the diabetes biomarker from Group D and administering to the subject a treatment, for example, a therapeutically effective dose of a drug, if the subject has an increased combination biomarker value of the at least one diabetes biomarker from Group C and the diabetes biomarker from Group D, as compared to the control.

According to another aspect of the disclosure there is provided an in vitro method for assessing whether a subject is at risk to develop type 2 diabetes, wherein the risk to develop type 2 diabetes is determined according to the following formula:

$$r = \text{intercept} + a\text{—Cer}(d18:1/18:0)/\text{Cer}(d18:1/16:0) + b \times \text{BMI} + c \times \text{glucose} + d \times \text{HbA1c} + e \times \text{age} + f \times \text{LDL-cholesterol} + g \times \text{HDL-cholesterol} + h \times \text{triglycerides} + i \times \text{systolic blood pressure} + j \times \text{insulin} + k \times \text{CRP} + l \times \text{gender},$$

wherein a, b, c, d, e, f, g, h, i, j, k and l are real numbers and logistic transformation (risk=(exp(r)/1+exp(r))*100) is optionally performed for the formula.

In some embodiments of the above-mentioned methods, the risk to develop type 2 diabetes is determined according to the following formula:

$$r=\text{intercept}+a\times\text{Cer}(d18:1/18:0)/\text{Cer}(d18:1/16:0)+b\times\text{BMI}+e\times\text{age},$$

wherein a, b and e are real numbers and logistic transformation (risk=(exp(r)/1+exp(r))*100) is optionally performed for the formula.

In some embodiments of the above-mentioned methods, the risk to develop type 2 diabetes is determined according to the following formula:

$$r=(\exp(r)/1+\exp(r))*100, \text{ wherein}$$

$$r=\text{intercept}+b\times\text{BMI}+a\times\text{Cer}(d18:1/18:0)/\text{Cer}(d18:1/16:0)+e\times\text{age, wherein}$$

for men intercept is a value from −14 to −10, b is a value from 0.14 to 0.22, a is a value from 4.0 to 4.6 and e is a value from 0.035 to 0.045; and for women intercept is a value from −13 to −8, b is a value from 0.10 to 0.18, a is a value from 3.5 to 4.5 and e is a value from 0.030 to 0.040.

In some embodiments of the above-mentioned methods, the risk to develop type 2 diabetes is determined according to the following formula:

$$r=(\exp(r)/1+\exp(r))*100, \text{ wherein}$$

for men $r=-11.66+0.18\times\text{BMI}+4.30\times\text{Cer}(d18:1/18:0)/\text{Cer}(d18:1/16:0)+0.040\times\text{age}$; and for women $r=-10.43+0.13\times\text{BMI}+4.01\times\text{Cer}(d18:1/18:0)/\text{Cer}(d18:1/16:0)+0.036\times\text{age}$.

In some embodiments of the above-mentioned methods, the risk to develop type 2 diabetes is determined according to the following formula:

$$r=\text{intercept}+a\times\text{Cer}(d18:1/18:0)/\text{Cer}(d18:1/16:0)+b\times\text{BMI}+c\times\text{glucose},$$

wherein a, b and c are real numbers and logistic transformation (risk=(exp(r)/1+exp(r))*100) is optionally performed for the formula.

In some embodiments of the above-mentioned methods, the risk to develop type 2 diabetes is determined according to the following formula:

$$r=(\exp(r)/1+\exp(r))*100, \text{ wherein}$$

$$r=\text{intercept}+a\times\text{Cer}(d18:1/18:0)/\text{Cer}(d18:1/16:0)+b\times\text{BMI}+c\times\text{glucose, wherein}$$

page for men intercept is a value from −22 to −15, a is a value from 3.00 to 6.00, b is a value from 0.10 to 0.20, and c is a value from 1.00 to 2.00; and for women intercept is a value from −22 to −15, a is a value from 2.00 to 5.00, b is a value from 0.03 to 0.11, and c is a value from 1.50 to 2.50.

Further, in some embodiments of the above-mentioned methods, the risk to develop type 2 diabetes is determined according to the following formula:

$$\text{risk}=(\exp(r)/1+\exp(r))*100, \text{ wherein}$$

for men $r=-18.64+4.55\times\text{Cer}(d18:1/18:0)/\text{Cer}(d18:1/16:0)+0.15\times\text{BMI}+1.60\times\text{glucose}$; and for women $r=-18.63+3.35\times\text{Cer}(d18:1/18:0)/\text{Cer}(d18:1/16:0)+0.07\times\text{BMI}+2.11\times\text{glucose}$.

In some embodiments of the above-mentioned methods, the risk to develop type 2 diabetes is determined according to the following formula:

$$r=a\times\text{Cer}(d18:1/18:0)/\text{Cer}(d18:1/16:0)+b\times\text{BMI},$$

wherein a and b are real numbers and logistic transformation (risk=(exp(r)/1+exp(r))*100) is optionally performed for the formula.

In some embodiments of the above-mentioned methods, the risk to develop type 2 diabetes is determined according to the following formula:

$$r=a\times\text{Cer}(d18:1/18:0)/\text{Cer}(d18:1/16:0)+c\times\text{glucose},$$

wherein a and c are real numbers and logistic transformation (risk=(exp(r)/1+exp(r))*100) is optionally performed for the formula.

Further, in some embodiments of the above-mentioned methods, the risk to develop type 2 diabetes is determined according to the following formula:

$$r=a\times\text{Cer}(d18:1/18:0)/\text{Cer}(d18:1/16:0)+d\times\text{HbA1c},$$

wherein a and d are real numbers and logistic transformation (risk=(exp(r)/1+exp(r))*100) is optionally performed for the formula.

According to another aspect of the disclosure there is provided a method of detecting in a sample obtained from a subject the concentration of at least one diabetes biomarker from Group A and at least one diabetes biomarker from Group B comprising:
  (a) assaying the sample from said subject to determine the concentration of the at least one diabetes biomarker from Group A;
  (b) assaying the sample from said subject to determine the concentration of the at least one diabetes biomarker from Group B; and optionally
  (c) comparing a combination biomarker value of the at least one diabetes biomarker from Group A and the at least one diabetes biomarker from Group B to a control.

In some embodiments, the subject used in the foregoing detecting method is a subject undergoing statin treatment.

In some embodiments, the subject is capable of being treated with a therapy as described herein. For example, the therapy may comprise any therapeutic treatment typically given to a subject at risk of developing diabetes or a subject having diabetes, such as, but not limited to, lifestyle interventions and/or counselling to effect a change in diet, weight management and/or physical activity, controlling the progression of diabetes and/or its complications (e.g. by blood glucose and/or blood pressure monitoring, lipid monitoring and control, eye, kidney and feet examination), diabetes medication (e.g. insulin, metformin, GLP-1 analogues, DPP-4 inhibitors, SGLT2 inhibitors, sulfonylureas, meglitinides, thiazolidinediones and alpha-glucosidase inhibitors), blood pressure and lipid modifying medications as described in the detailed description of the present disclosure, or any combination thereof.

According to another aspect of the disclosure there is provided a method of detecting in a sample obtained from a subject the concentration of at least one diabetes biomarker from Group C and a diabetes biomarker from Group D comprising:
  (a) assaying the sample from said subject to determine the concentration of the at least one diabetes biomarker from Group C;
  (b) assaying the sample from said subject to determine the concentration of the diabetes biomarker from Group D; and optionally
  (c) comparing a combination biomarker value of the at least one diabetes biomarker from Group C and the diabetes biomarker from Group D to a control.

In some embodiments, the subject used in the foregoing detecting method is a subject undergoing statin treatment.

In some embodiments, the subject is capable of being treated with a therapy as described herein. For example, the therapy may comprise any therapeutic treatment typically given to a subject at risk of developing diabetes or a subject having diabetes, such as, but not limited to, lifestyle interventions and/or counselling to effect a change in diet, weight management and/or physical activity, controlling the progression of diabetes and/or its complications (e.g. by blood glucose and/or blood pressure monitoring, lipid monitoring and control, eye, kidney and feet examination), diabetes medication (e.g. insulin, metformin, GLP-1 analogues, DPP-4 inhibitors, SGLT2 inhibitors, sulfonylureas, meglitinides, thiazolidinediones and alpha-glucosidase inhibitors), blood pressure and lipid modifying medications as described in the detailed description of the present disclosure, or any combination thereof.

According to another aspect of the disclosure, there is provided an in vitro method of assessing the progression of diabetes in a subject comprising:
(a) assaying a sample from said subject to determine a concentration of at least one diabetes biomarker from Group A;
(b) assaying a sample from said subject to determine a concentration of at least one diabetes biomarker from Group B; and
(c) determining that diabetes has progressed, if said sample contains an increased combination biomarker value of the at least one diabetes biomarker from Group A and the at least one diabetes biomarker from Group B, when compared to a control.

According to another aspect of the disclosure, there is provided an in vitro method of assessing the progression of diabetes in a subject comprising:
(a) assaying a sample from said subject to determine a concentration of at least one diabetes biomarker from Group C;
(b) assaying a sample from said subject to determine a concentration of a diabetes biomarker from Group D; and
(c) determining that diabetes has progressed, if said sample contains an increased combination biomarker value of the at least one diabetes biomarker from Group C and the diabetes biomarker from Group D, when compared to a control.

In some embodiments, the subject is capable of being treated with a therapy as described herein. For example, the therapy may comprise any therapeutic treatment typically given to a subject at risk of developing diabetes or a subject having diabetes, such as, but not limited to, lifestyle interventions and/or counselling to effect a change in diet, weight management and/or physical activity, controlling the progression of diabetes and/or its complications (e.g. by blood glucose and/or blood pressure monitoring, lipid monitoring and control, eye, kidney and feet examination), diabetes medication (e.g. insulin, metformin, GLP-1 analogues, DPP-4 inhibitors, SGLT2 inhibitors, sulfonylureas, meglitinides, thiazolidinediones and alpha-glucosidase inhibitors), blood pressure and lipid modifying medications as described in the detailed description of the present disclosure, or any combination thereof.

In some embodiments, the method for assessing the progression of diabetes in a subject further comprises after the determining step (c), (d) administering a treatment to the subject.

In some embodiments of the above-mentioned methods, progression of the subject's condition from a healthy condition to a pre-diabetic phase or type 2 diabetes is assessed. In other embodiments, progression from a pre-diabetic phase to type 2 diabetes is assessed. In other embodiments, the severity of type 2 diabetes is assessed.

In some embodiments, the above-mentioned methods are used in assessing a subject's glucose tolerance status, e.g., if a subject's condition is developed from normal glucose tolerance (NGT) to impaired glucose tolerance (IGT) or from IGT to type 2 diabetes.

In some embodiments, the progress of diabetes is monitored to assess if supplementary treatment, e.g., lifestyle interventions or medication, is needed in order to prevent or delay the progression of diabetes and onset of the complications.

In some embodiments, the progress of diabetes is monitored to assess if an administered treatment has affected to, e.g. delayed, the progress of the disease.

Type 2 diabetes is a progressive disease, and medication is often needed to control the disease. In some embodiments, the above-mentioned methods are used to adjust diabetes treatment, e.g., assessing if a subject needs a medication, assessing if an administered medication needs adjustment or if a subject's medication needs to be supplemented with another medication, such as insulin.

In some embodiments, the progression of diabetes over time in a subject is monitored by comparing the combination biomarker value of the at least one diabetes biomarker from Group A and the at least one diabetes biomarker from Group B to a previously determined combination biomarker value in a sample obtained from the same subject. In some embodiments, the progression of diabetes in a subject over time is monitored by comparing the combination biomarker value of the at least one diabetes biomarker from Group C and the diabetes biomarker from Group D to a previously determined combination biomarker value in a sample obtained from the same subject.

According to another aspect of the disclosure there is provided an in vitro method for assessing whether a subject is at risk to develop or is suffering from diabetes complication(s) comprising:
(a) assaying a sample from said subject to determine a concentration of at least one diabetes biomarker from Group A;
(b) assaying a sample from said subject to determine a concentration of at least one diabetes biomarker from Group B; and
(c) determining that the subject is suffering from or is at an increased risk of developing diabetes complication(s), if said sample contains an increased combination biomarker value of the at least one diabetes biomarker from Group A and the at least one diabetes biomarker from Group B, when compared to a control.

According to another aspect of the disclosure there is provided an in vitro method for assessing whether a subject is at risk to develop or is suffering from diabetes complication(s) comprising:
(a) assaying a sample from said subject to determine a concentration of at least one diabetes biomarker from Group C;
(b) assaying a sample from said subject to determine a concentration of a diabetes biomarker from Group D; and
(c) determining that the subject is suffering from or is at an increased risk of developing diabetes complication(s), if said sample contains an increased combination biomarker value of the at least one diabetes biomarker from Group C and the diabetes biomarker from Group D, when compared to a control.

In some embodiments, the subject is capable of being treated with a therapy as described herein. For example, the therapy may comprise any therapeutic treatment typically given to a subject at risk of developing diabetes or a subject having diabetes, such as, but not limited to, lifestyle interventions and/or counselling to effect a change in diet, weight management and/or physical activity, controlling the progression of diabetes and/or its complications (e.g. by blood glucose and/or blood pressure monitoring, lipid monitoring and control, eye, kidney and feet examination), diabetes medication (e.g. insulin, metformin, GLP-1 analogues, DPP-4 inhibitors, SGLT2 inhibitors, sulfonylureas, meglitinides, thiazolidinediones and alpha-glucosidase inhibitors), blood pressure and lipid modifying medications as described in the detailed description of the present disclosure, or any combination thereof.

In some embodiments, the method for assessing whether a subject is at risk to develop or is suffering from diabetes complication(s) further comprises after the determining step (c), (d) diagnosing the subject as suffering from or having an increased risk of developing diabetes complication(s) from the results in step (c), and (e) administering a treatment to the subject diagnosed in step (d).

In one aspect, the present disclosure is directed to a method of treating or preventing type 2 diabetes and/or its complication(s) in a subject identified as being at risk to develop or suffering from diabetes complication(s), the method comprising: administering to the subject a treatment as described herein, wherein prior to administering the treatment, the subject has been identified as being at risk to develop or suffering from diabetes complication(s) by the method described herein.

Type 2 diabetes can lead to severe complications, therefore it is beneficial to detect individuals that are at high risk of developing, or are suffering from, diabetes complications, and provide preventive measures and/or treatment. The major complications caused by high blood glucose in T2D include, e.g., cardiovascular disease and its complications, kidney disease, neural damage, eye and foot damage and oral health problems. In addition, high blood glucose levels can cause, e.g., pregnancy complications.

According to another aspect of the disclosure, there is provided a method of collecting data for assessing whether a subject is at risk to develop or is suffering from type 2 diabetes comprising:
(a) assaying a sample from said subject to determine a concentration of at least one diabetes biomarker from Group A;
(b) assaying a sample from said subject to determine a concentration of at least one diabetes biomarker from Group B; and
(c) determining that the subject is suffering from or is at an increased risk of developing type 2 diabetes, if said sample contains an increased combination of the concentrations of the at least one diabetes biomarker from Group A and the at least one diabetes biomarker from Group B, when compared to a control.

According to another aspect of the disclosure, there is provided a method of collecting data for assessing whether a subject is at risk to develop or is suffering from type 2 diabetes comprising:
(a) assaying a sample from said subject to determine a concentration of at least one diabetes biomarker from Group C;
(b) assaying a sample from said subject to determine a concentration of a diabetes biomarker from Group D; and
(c) determining that the subject is suffering from or is at an increased risk of developing type 2 diabetes, if said sample contains an increased combination biomarker value of the at least one diabetes biomarker from Group C and the diabetes biomarker from Group D, when compared to a control.

According to another aspect of the disclosure there is provided a method of collecting data for assessing whether a subject undergoing statin treatment is at risk to develop or is suffering from type 2 diabetes comprising:
(a) assaying a sample from said subject to determine a concentration of at least one diabetes biomarker from Group A;
(b) assaying a sample from said subject to determine a concentration of at least one diabetes biomarker from Group B; and
(c) determining that the subject is suffering from or is at an increased risk of developing type 2 diabetes, if said sample contains an increased combination biomarker value of the at least one diabetes biomarker from Group A and the at least one diabetes biomarker from Group B, when compared to a control.

According to another aspect of the disclosure there is provided a method of collecting data for assessing whether a subject undergoing statin treatment is at risk to develop or is suffering from type 2 diabetes comprising:
(a) assaying a sample from said subject to determine a concentration of at least one diabetes biomarker from Group C;
(b) assaying a sample from said subject to determine a concentration of a diabetes biomarker from Group D; and
(c) determining that the subject is suffering from or is at an increased risk of developing type 2 diabetes, if said sample contains an increased combination biomarker value of the at least one diabetes biomarker from Group C and the diabetes biomarker from Group D, when compared to a control.

According to yet another aspect of the disclosure there is provided a method of collecting data for evaluating the effectiveness of a diabetes therapy in a subject comprising:
(a) assaying a sample from said subject to determine a concentration of at least one diabetes biomarker from Group A;
(b) assaying a sample from said subject to determine a concentration of at least one diabetes biomarker from Group B; and
(c) determining that the therapy is effective, if said sample contains a decreased combination biomarker value of the at least one diabetes biomarker from Group A and the at least one diabetes biomarker from Group B, when compared to a control.

According to yet another aspect of the disclosure there is provided a method of collecting data for evaluating the effectiveness of a diabetes therapy in a subject comprising:
(a) assaying a sample from said subject to determine a concentration of at least one diabetes biomarker from Group C;
(b) assaying a sample from said subject to determine a concentration of a diabetes biomarker from Group D; and
(c) determining that the therapy is effective, if said sample contains a decreased combination biomarker value of the at least one diabetes biomarker from Group C and the diabetes biomarker from Group D, when compared to a control.

According to another aspect of the disclosure, there is provided a method of collecting data for assessing the progression of diabetes in a subject comprising:

(a) assaying a sample from said subject to determine a concentration of at least one diabetes biomarker from Group A;

(b) assaying a sample from said subject to determine a concentration of at least one diabetes biomarker from Group B; and (c) determining that diabetes has progressed, if said sample contains an increased combination biomarker value of the at least one diabetes biomarker from Group A and the at least one diabetes biomarker from Group B, when compared to a control.

According to another aspect of the disclosure, there is provided a method of collecting data for assessing the progression of diabetes in a subject comprising:

(a) assaying a sample from said subject to determine a concentration of at least one diabetes biomarker from Group C;

(b) assaying a sample from said subject to determine a concentration of a diabetes biomarker from Group D; and (c) determining that diabetes has progressed, if said sample contains an increased combination biomarker value of the at least one diabetes biomarker from Group C and the diabetes biomarker from Group D, when compared to a control.

According to another aspect of the disclosure there is provided a method of collecting data for assessing whether a subject is at risk to develop or is suffering from diabetes complication(s) comprising:

(a) assaying a sample from said subject to determine a concentration of at least one diabetes biomarker from Group A;

(b) assaying a sample from said subject to determine a concentration of at least one diabetes biomarker from Group B; and (c) determining that the subject is suffering from or is at an increased risk of developing diabetes complication (s), if said sample contains an increased combination biomarker value of the at least one diabetes biomarker from Group A and the at least one diabetes biomarker from Group B, when compared to a control.

According to yet another aspect of the disclosure there is provided a method of collecting data for assessing whether a subject is at risk to develop or is suffering from diabetes complication(s) comprising:

(a) assaying a sample from said subject to determine a concentration of at least one diabetes biomarker from Group C;

(b) assaying a sample from said subject to determine a concentration of a diabetes biomarker from Group D; and (c) determining that the subject is suffering from or is at an increased risk of developing diabetes complication (s), if said sample contains an increased combination biomarker value of the at least one diabetes biomarker from Group C and the diabetes biomarker from Group D, when compared to a control.

According to yet another aspect of the disclosure there is provided a method of collecting data for assessing whether a subject is at risk to develop type 2 diabetes, wherein the risk to develop type 2 diabetes is determined according to the following formula:

$$r = \text{intercept} + a \times \text{Cer}(d18:1/18:0)/\text{Cer}(d18:1/16:0) + b \times \text{BMI} + c \times \text{glucose} + d \times \text{HbA1c} + e \times \text{age} + f \times \text{LDL-cholesterol} + g \times \text{HDL-cholesterol} + h \times \text{triglycerides} + i \times \text{systolic blood pressure} + j \times \text{insulin} + k \times \text{CRP} + l \times \text{gender},$$

wherein a, b, c, d, e, f, g, h, i, j, k and l are real numbers and logistic transformation (risk=(exp(r)/1+exp(r))*100) is optionally performed for the formula.

Yet another aspect of the present disclosure is a composition or kit for diagnosing, predicting or detecting type 2 diabetes or for performing any of the methods or uses disclosed herein. In some embodiments, the composition or kit comprises at least one diabetes biomarker from Group A and at least one diabetes biomarker from Group B. In other embodiments, the composition or kit comprises at least one isotope (e.g. deuterium)-labelled diabetes biomarker from Group A and at least one isotope (e.g. deuterium)-labelled diabetes biomarker from Group B.

In some embodiments, the at least one Group B biomarker is(are) selected from LPC(MHDA) [sn1], LPC(MHDA) [sn2], PC(MHDA_18:1), PC(MHDA_18:2), PC(MHDA_18:2) or PC(MHDA_22:6). In some embodiments, the at least one isotope (e.g. deuterium)-labelled diabetes biomarker from Group B is selected from LPC (MHDA) [sn1], LPC(MHDA) [sn2], PC(MHDA_18:1), PC(MHDA_18:2), PC(MHDA_18:2) or PC(MHDA_22:6).

In some embodiments, the composition or kit comprises at least one diabetes biomarker from Group C and a diabetes biomarker from Group D. In other embodiments, the composition or kit comprises at least one isotope (e.g. deuterium)-labelled diabetes biomarker from Group C and an isotope (e.g. deuterium)-labelled diabetes biomarker from Group D.

In some embodiments, the composition or kit comprises at least 1, at least 2, at least 3, at least 4, at least 5, at least 6, at least 7, at least 8, at least 9 or at least 10 diabetes biomarkers from Group A and at least 1, at least 2, at least 3, at least 4, at least 5, at least 6, at least 7, at least 8, at least 9 or at least 10 diabetes biomarkers from Group B.

Yet another aspect of the present disclosure is a composition or kit for diagnosing, predicting or detecting type 2 diabetes or for performing any of the methods or uses disclosed herein, wherein the composition or kit comprises at least one diabetes biomarker from from Group B selected from LPC(MHDA) [sn1], LPC(MHDA) [sn2], PC(MHDA_18:1), PC(MHDA_18:2), PC(MHDA_18:2). In other embodiments, the composition or kit comprises at least one isotope (e.g. deuterium)-labelled diabetes biomarker from Group B selected from LPC(MHDA) [sn1], LPC (MHDA) [sn2], PC(MHDA_18:1), PC(MHDA_18:2), PC(MHDA_18:2).

In some embodiments, the composition or kit comprises at least 1, at least 2, at least 3 or at least 4 diabetes biomarkers from Group C and a diabetes biomarker from Group D. In yet other embodiments, the composition or kit comprises at least 1, at least 2, at least 3, at least 4, at least 5, at least 6, at least 7, at least 8, at least 9 or at least 10 isotope (e.g. deuterium)-labelled diabetes biomarkers from Group A and at least 1, at least 2, at least 3, at least 4, at least 5, at least 6, at least 7, at least 8, at least 9 or at least 10 isotope (e.g. deuterium)-labelled diabetes biomarkers from Group B.

In yet other embodiments, the composition or kit comprises at least 1, at least 2, at least 3 or at least 4 isotope (e.g. deuterium)-labelled diabetes biomarkers from Group C and an isotope (e.g. deuterium)-labelled diabetes biomarker from Group B. The composition or kit may further include standard(s), control(s), reagent(s), solution(s), solvent(s), container(s), instruction(s) to use it for the methods or uses disclosed herein or other element(s) for performing the methods or uses disclosed herein.

In some embodiments, the composition or kit includes element(s) for collecting a blood sample, for example, a dried blood spot on a filter.

The composition or kit may be a test kit for used in a laboratory or a home use test kit (over-the-counter test). The composition or kit may be used in assays performed with various chemical and high-resolution analytical techniques, as appropriate. Suitable analytical techniques according to the present methods and uses include, but are not limited to, mass spectrometry (MS) and nuclear magnetic resonance (NMR). Any high-resolution technique capable of resolving individual biomarkers can be used to collect the information on the biomarker in question, such as the concentration of biomarker profile from the biological sample. Typically, the information is collected using mass spectrometry. The MS analysis can be coupled to another high performance separation method, such as gas chromatography (GC), two-dimensional gas chromatography (GC×GC), liquid chromatography (LC), high performance liquid chromatography (HPLC) or ultra-high performance liquid chromatography (UHPLC).

According to another aspect of the disclosure there is provided a use of one or more reagent(s) in the manufacture of a kit, composition, preparation or medicament for assessing whether a subject is at risk to develop or is suffering from type 2 diabetes comprising:
(a) a reagent for assaying a sample from said subject to determine a concentration of at least one diabetes biomarker from Group A;
(b) a reagent for assaying a sample from said subject to determine a concentration of at least one diabetes biomarker from Group B; and
(c) determining that the subject is suffering from or is at an increased risk of developing type 2 diabetes, if said sample contains an increased combination biomarker value of the at least one diabetes biomarker from Group A and the at least one diabetes biomarker from Group B, when compared to a control.

According to another aspect of the disclosure there is provided a use of one or more reagent(s) in the manufacture of a kit, composition, preparation or medicament for assessing whether a subject is at risk to develop or is suffering from type 2 diabetes comprising:
(a) a reagent for assaying a sample from said subject to determine a concentration of at least one diabetes biomarker from Group C;
(b) a reagent for assaying a sample from said subject to determine a concentration of a diabetes biomarker from Group D; and
(c) determining that the subject is suffering from or is at an increased risk of developing type 2 diabetes, if said sample contains an increased combination biomarker value of the at least one diabetes biomarker from Group C and the diabetes biomarker from Group D, when compared to a control.

According to another aspect of the disclosure there is provided a use of one or more reagent(s) in the manufacture of a kit, composition, preparation or medicament for assessing whether a subject undergoing statin treatment is at risk to develop or is suffering from type 2 diabetes comprising:
(a) a reagent for assaying a sample from said subject to determine a concentration of at least one diabetes biomarker from Group A;
(b) a reagent for assaying a sample from said subject to determine a concentration of at least one diabetes biomarker from Group B; and
(c) determining that the subject is suffering from or is at an increased risk of developing type 2 diabetes, if said sample contains an increased combination biomarker value of the at least one diabetes biomarker from Group A and the at least one diabetes biomarker from Group B, when compared to a control.

According to another aspect of the disclosure there is provided a use of one or more reagent(s) in the manufacture of a kit, composition, preparation or medicament for assessing whether a subject undergoing statin treatment is at risk to develop or is suffering from type 2 diabetes comprising:
(a) a reagent for assaying a sample from said subject to determine a concentration of at least one diabetes biomarker from Group C;
(b) a reagent for assaying a sample from said subject to determine a concentration of a diabetes biomarker from Group D; and
(c) determining that the subject is suffering from or is at an increased risk of developing type 2 diabetes, if said sample contains an increased combination biomarker value of the at least one diabetes biomarker from Group C and the diabetes biomarker from Group D, when compared to a control.

According to yet another aspect of the disclosure there is provided a use of one or more reagent(s) in the manufacture of a kit, composition, preparation or medicament for evaluating the effectiveness of a diabetes therapy in a subject comprising:
(a) a reagent for assaying a sample from said subject to determine a concentration of at least one diabetes biomarker from Group A;
(b) a reagent for assaying a sample from said subject to determine a concentration of at least one diabetes biomarker from Group B; and
(c) determining that the therapy is effective, if said sample contains a decreased combination biomarker value of the at least one diabetes biomarker from Group A and the at least one diabetes biomarker from Group B, when compared to a control.

According to yet another aspect of the disclosure there is provided a use of one or more reagent(s) in the manufacture of a kit, composition, preparation or medicament for evaluating the effectiveness of a diabetes therapy in a subject comprising:
(a) a reagent for assaying a sample from said subject to determine a concentration of at least one diabetes biomarker from Group C;
(b) a reagent for assaying a sample from said subject to determine a concentration of a diabetes biomarker from Group D; and
(c) determining that the therapy is effective, if said sample contains a decreased combination biomarker value of the at least one diabetes biomarker from Group C and the diabetes biomarker from Group D, when compared to a control.

According to yet another aspect of the disclosure, there is provided a use of one or more reagent(s) in the manufacture of a kit, composition, preparation or medicament for assessing the progression of diabetes in a subject comprising:
(a) a reagent for assaying a sample from said subject to determine a concentration of at least one diabetes biomarker from Group A;

(b) a reagent for assaying a sample from said subject to determine a concentration of at least one diabetes biomarker from Group B; and (c) determining that diabetes has progressed, if said sample contains an increased combination biomarker value of the at least one diabetes biomarker from Group A and the at least one diabetes biomarker from Group B, when compared to a control.

According to another aspect of the disclosure, there is provided a use of one or more reagent(s) in the manufacture of a kit, composition, preparation or medicament for assessing the progression of diabetes in a subject comprising:

(a) a reagent for assaying a sample from said subject to determine a concentration of at least one diabetes biomarker from Group C;

(b) a reagent for assaying a sample from said subject to determine a concentration of a diabetes biomarker from Group D; and (c) determining that diabetes has progressed, if said sample contains an increased combination biomarker value of the at least one diabetes biomarker from Group C and the diabetes biomarker from Group D, when compared to a control.

According to another aspect of the disclosure there is provided a use of one or more reagent(s) in the manufacture of a kit, composition, preparation or medicament for assessing whether a subject is at risk to develop or is suffering from diabetes complication(s) comprising:

(a) a reagent for assaying a sample from said subject to determine a concentration of at least one diabetes biomarker from Group A;

(b) a reagent for assaying a sample from said subject to determine a concentration of at least one diabetes biomarker from Group B; and (c) determining that the subject is suffering from or is at an increased risk of developing diabetes complication(s), if said sample contains an increased combination biomarker value of the at least one diabetes biomarker from Group A and the at least one diabetes biomarker from Group B, when compared to a control.

According to yet another aspect of the disclosure there is provided a use of one or more reagent(s) in the manufacture of a kit, composition, preparation or medicament for assessing whether a subject is at risk to develop or is suffering from diabetes complication(s) comprising:

(a) a reagent for assaying a sample from said subject to determine a concentration of at least one diabetes biomarker from Group C;

(b) a reagent for assaying a sample from said subject to determine a concentration of a diabetes biomarker from Group D; and (c) determining that the subject is suffering from or is at an increased risk of developing diabetes complication(s), if said sample contains an increased combination biomarker value of the at least one diabetes biomarker from Group C and the diabetes biomarker from Group D, when compared to a control.

According to yet another aspect of the disclosure there is provided a use of one or more reagent(s) in the manufacture of a kit, composition, preparation or medicament for assessing whether a subject is at risk to develop type 2 diabetes, wherein the risk to develop type 2 diabetes is determined according to the following formula:

$$r = \text{intercept} + a \times \text{Cer}(d18:1/18:0)/\text{Cer}(d18:1/16:0) + b \times \text{BMI} + c \times \text{glucose} + d \times \text{HbA1c} + e \times \text{age} + f \times \text{LDL-cholesterol} + g \times \text{HDL-cholesterol} + h \times \text{triglycerides} + i \times \text{systolic blood pressure} + j \times \text{insulin} + k \times \text{CRP} + l \times \text{gender},$$

wherein a, b, c, d, e, f, g, h, i, j, k and l are real numbers and logistic transformation (risk=(exp(r)/1+exp(r))*100) is optionally performed for the formula.

In addition to diabetes biomarkers, the present disclosure identifies novel lipid biomarker combinations for predicting and diagnosing fatty liver disease by quantifying defined combinations of molecular species concentrations. The present novel fatty liver biomarker combinations also include newly identified lipid species, e.g., phospholipids esterified with methylhexadecanoic acid, which were found to be associated with type 2 diabetes risk and fatty liver disease as well.

The present inventors have surprisingly found novel lipid biomarkers and biomarker combinations which are associated with both type 2 diabetes and fatty liver disease. Specifically, it has been found that each marker combination displays a characteristic increase or decrease in combination biomarker values as described herein in samples obtained from subjects having diabetes and/or fatty liver disease. The present biomarkers are sensitive and specific and they can be used in diagnostic and prognostic assays.

The risk determination based on the novel lipid biomarkers disclosed herein allow for better assessment of future fatty liver disease risk by identifying individuals at risk of developing fatty liver disease while their traditional risk factors may be normal, or below diagnostic thresholds, i.e., at the range where current tests fail to measure increased risk. This allows earlier intervention and prevention or delay of the onset and progression of fatty liver disease and/or its complications. The present disclosure therefore represents a significant advantage and great improvement over the prior methods currently used to predict or diagnose fatty liver disease. Further, the present markers find use in determining effectiveness of treatment in patients having fatty liver disease.

The present inventors have surprisingly found that the novel diabetes biomarkers from Group A, Group B, Group C and Group D, presented in Tables 1 and 2, also show strong association with fatty liver disease. Both diseases can advantageously be predicted and diagnosed by one assay which detects concentrations of both the diabetes and fatty liver biomarkers of the present disclosure. More advantageously, both diabetes and fatty liver disease are predicted and diagnosed using the same biomarker combination.

In addition to Group A, Group B, Group C and Group D biomarkers, two other groups of novel fatty liver biomarkers, Group E and Group F, are presented. Group E and Group F fatty liver biomarkers were found to provide improved prognostic and diagnostic power when combined. Group E and Group F fatty liver biomarkers are shown in Table 2a below.

TABLE 2a

Group E and F fatty liver biomarkers. Abbreviations are described in the detailed description of the present disclosure.

| Group E | Group F |
| --- | --- |
| DAG(18:0/18:1) | LPC(MHDA) [sn1] |
| DAG(16:0/18:1) | LPC(MHDA) [sn2] |
| DAG(14:0/18:1) | AcylCarnitine(13:0) |
| DAG(14:0/18:2) | AcylCarnitine(18:2) |
| DAG(16:0/16:1) | CE(15:0) |
| DAG(16:0/18:2) | CE(17:0) |

TABLE 2a-continued

Group E and F fatty liver biomarkers. Abbreviations are described in the detailed description of the present disclosure.

| Group E | Group F |
|---|---|
| DAG(16:0/20:4) | CE(18:1) |
| DAG(16:0/22:6) | CE(22:4) |
| DAG(16:1/16:1) | CE(24:5) |
| DAG(16:1/18:1) | Gb3(d18:1/16:0) |
| DAG(18:0/18:2) | Gb3(d18:1/22:0) |
| DAG(18:0/20:4) | Gb3(d18:1/23:0) |
| DAG(18:1/18:1) | Gb3(d18:1/24:0) |
| DAG(18:1/18:2) | Gb3(d18:1/24:1) |
| DAG(18:1/18:3) | Glc/GalCer(d16:1/23:0) |
| DAG(18:1/20:3) | Glc/GalCer(d16:1/24:1) |
| DAG(18:1/20:4) | Glc/GalCer(d18:1/20:0) |
| DAG(18:2/18:2) | Glc/GalCer(d18:1/23:0) |
| DAG(18:2/20:4) | Glc/GalCer(d18:1/24:1) |
| AcylCarnitine(12:0) | Glc/GalCer(d18:1/26:1) |
| AcylCarnitine(14:0) | Glc/GalCer(d18:2/20:0) |
| AcylCarnitine(14:1) | Glc/GalCer(d18:2/22:0) |
| AcylCarnitine(16:0) | Glc/GalCer(d18:2/23:0) |
| AcylCarnitine(16:1) | Glc/GalCer(d18:2/24:0) |
| AcylCarnitine(18:0) | Glc/GalCer(d18:2/24:1) |
| AcylCarnitine(18:1) | LPC(15:0) [sn1] |
| CE(14:0) | LPC(15:0) [sn2] |
| CE(14:1) | LPC(17:0) [sn1] |
| CE(16:0) | LPC(17:0) [sn2] |
| CE(16:1) | LPC(17:1) [sn1] |
| CE(16:2) | LPC(17:1) [sn2] |
| CE(17:1) | LPC(18:0) [sn1] |
| CE(18:0) | LPC(18:0) [sn2] |
| CE(18:2) | LPC(18:1) [sn1] |
| CE(18:3) | LPC(18:1) [sn2] |
| CE(20:2) | LPC(18:2) [sn1] |
| CE(20:3) | LPC(18:2) [sn2] |
| CE(20:4) | LPC(19:0) [sn1] |
| CE(20:5) | LPC(19:0) [sn2] |
| CE(22:3) | LPC(20:0) [sn1] |
| CE(22:5) | LPC(20:0) [sn2] |
| CE(22:6) | LPC(20:1) [sn1] |
| CE(24:6) | LPC(20:1) [sn2] |
| Cer(d16:1/16:0) | LPC(20:2) [sn1] |
| Cer(d16:1/18:0) | LPC(20:2) [sn2] |
| Cer(d16:1/20:0) | LPC(20:4) [sn1] |
| Cer(d16:1/22:0) | LPC(20:5) [sn1] |
| Cer(d16:1/23:0) | LPC(22:0) [sn1] |
| Cer(d16:1/24:0) | LPC(22:0) [sn2] |
| Cer(d16:1/24:1) | LPC(22:1) [sn1] |
| Cer(d18:1/14:0) | LPC(22:1) [sn2] |
| Cer(d18:1/16:0) | LPC(22:5) [sn1] |
| Cer(d18:1/18:0) | LPC(22:5) [sn2] |
| Cer(d18:1/20:0) | LPC(22:6) [sn1] |
| Cer(d18:1/22:0) | LPC(22:6) [sn2] |
| Cer(d18:1/23:0) | LPC(24:0) [sn1] |
| Cer(d18:1/24:0) | LPC(24:0) [sn2] |
| Cer(d18:1/24:1) | LPC(O-16:0) |
| Cer(d18:1/26:0) | LPC(O-18:0) |
| Cer(d18:1/26:1) | LPC(O-18:1) |
| Cer(d18:2/16:0) | LPC(O-20:0) |
| Cer(d18:2/18:0) | LPC(O-20:1) |
| Cer(d18:2/20:0) | LPC(O-22:0) |
| Cer(d18:2/22:0) | LPC(O-22:1) |
| Cer(d18:2/23:0) | LPC(O-24:0) |
| Cer(d18:2/24:0) | LPC(O-24:1) |
| Cer(d18:2/24:1) | LPC(O-24:2) |
| Cer(d18:2/26:1) | LPC(P-16:0) |
| Cer(d20:1/22:0) | LPC(P-18:0) |
| Cer(d20:1/23:0) | LPC(P-18:1) |
| Cer(d20:1/24:0) | LPE(16:0) [sn1] |
| Cer(d20:1/24:1) | LPE(16:0) [sn2] |
| Gb3(d18:1/18:0) | LPE(18:1) [sn1] |
| Glc/GalCer(d16:1/16:0) | LPE(18:1) [sn2] |
| Glc/GalCer(d16:1/18:0) | LPE(18:2) [sn1] |
| Glc/GalCer(d16:1/20:0) | LPE(18:2) [sn2] |
| Glc/GalCer(d16:1/22:0) | LPE(20:1) [sn1] |
| Glc/GalCer(d16:1/24:0) | LPE(22:6) [sn1] |
| Glc/GalCer(d18:1/16:0) | LPE(P-18:0) |
| Glc/GalCer(d18:1/18:0) | LPE(P-18:1) |
| Glc/GalCer(d18:1/22:0) | LPE(P-20:0) |
| Glc/GalCer(d18:1/24:0) | LacCer(d16:1/22:0) |
| Glc/GalCer(d18:1/26:0) | LacCer(d18:1/16:0) |
| Glc/GalCer(d18:2/16:0) | LacCer(d18:1/20:0) |
| LPC(14:0) [sn1] | LacCer(d18:1/22:0) |
| LPC(14:0) [sn2] | LacCer(d18:1/24:0) |
| LPC(16:0) [sn1] | LacCer(d18:1/24:1) |
| LPC(16:0) [sn2] | LacCer(d18:2/16:0) |
| LPC(20:3) [sn1] | LacCer(d18:2/22:0) |
| LPC(20:3) [sn2] | LacCer(d18:2/22:0) |
| LPC(20:4) [sn2] | LacCer(d18:2/24:1) |
| LPC(20:5) [sn2] | PC(31:0) |
| LPC(22:4) [sn2] | PC(33:2) |
| LPC(22:4) [sn2] | PC(33:3) |
| LPE(18:0) [sn1] | PC(34:3) |
| LPE(20:3) [sn1] | PC(35:2) |
| LPE(20:3) [sn2] | PC(35:3) |
| LPE(20:4) [sn1] | PC(36:7) |
| LPE(20:4) [sn2] | PC(37:1) |
| LPE(22:6) [sn2] | PC(37:2) |
| LPE(P-16:0) | PC(37:6) |
| LacCer(d16:1/16:0) | PC(38:7) |
| LacCer(d16:1/24:1) | PC(39:4) |
| LacCer(d18:1/18:0) | PC(17:0_22:6) |
| LacCer(d18:1/23:0) | PC(O-32:0) |
| PC(28:0) | PC(O-32:1) |
| PC(30:0) | PC(O-34:0) |
| PC(30:2) | PC(O-34:1) |
| PC(31:1) | PC(O-34:2) |
| PC(32:0) | PC(O-36:2) |
| PC(32:1) | PC(O-36:3) |
| PC(32:2) | PC(O-38:0) |
| PC(32:3) | PC(O-38:2) |
| PC(33:1) | PC(O-38:4) |
| PC(34:0) | PC(O-40:3) |
| PC(34:1) | PC(O-40:4) |
| PC(34:2) | PC(O-40:6) |
| PC(34:4) | PC(P-36:2) |
| PC(34:5) | PC(P-32:0) |
| PC(35:0) | PC(P-32:1) |
| PC(35:1) | PC(P-34:1) |
| PC(35:4) | PC(P-36:1) |
| PC(35:5) | PC(P-36:5) |
| PC(36:0) | PC(P-38:4) |
| PC(36:1) | PC(P-38:6) |
| PC(36:2) | PC(P-40:2) |
| PC(36:3) | PC(P-40:4) |
| PC(36:4) | PC(P-40:5) |
| PC(36:5) | PC(P-40:6) |
| PC(36:6) | PE(30:1) |
| PC(37:3) | PE(40:8) |
| PC(37:4) | PE(42:7) |
| PC(38:0) | PE(O-34:1) |
| PC(38:1) | PE(O-34:2) |
| PC(38:2) | PE(O-36:1) |
| PC(38:3) | PE(O-36:4) |
| PE(38:4) | PE(O-36:5) |
| PC(38:4) | PE(O-38:4) |
| PC(38:5) | PE(O-38:6) |
| PC(38:6) | PE(P-34:1) |
| PC(39:0) | PE(P-34:2) |
| PC(39:2) | PE(P-36:1) |
| PC(40:1) | PE(P-36:2) |
| PC(40:2) | PE(P-40:6) |
| PC(40:3) | PI(38:1) |
| PC(40:4) | SM(31:0) |
| PC(40:5) | SM(d17:1/14:0) |
| PC(40:6) | SM(33:0) |
| PC(O-36:1) | SM(34:1) |
| PC(O-36:5) | SM(37:1) |
| PC(O-38:1) | SM(37:2) |
| PC(O-38:3) | SM(39:2) |
| PC(O-38:4) | SM(41:2) |
| PC(O-38:6) | SM(44:3) |
| PC(O-40:1) | |
| PC(O-40:2) | |

TABLE 2a-continued

Group E and F fatty liver biomarkers. Abbreviations are described in the detailed description of the present disclosure.

| Group E | Group F |
|---|---|
| PC(O-40:5) | |
| PC(P-36:3) | |
| PC(P-38:5) | |
| PC(P-40:3) | |
| PE(32:1) | |
| PE(34:1) | |
| PE(34:2) | |
| PE(34:3) | |
| PE(36:1) | |
| PE(36:2) | |
| PE(36:4) | |
| PE(36:5) | |
| PE(38:1) | |
| PE(38:2) | |
| PE(38:3) | |
| PE(38:4) | |
| PE(38:5) | |
| PE(38:6) | |
| PE(40:4) | |
| PE(40:5) | |
| PE(40:6) | |
| PE(40:7) | |
| PE(O-38:5) | |
| PE(P-36:4) | |
| PE(P-38:4) | |
| PE(P-38:6) | |
| PG(34:1) | |
| PG(36:1) | |
| PI(32:0) | |
| PI(32:1) | |
| PI(34:0) | |
| PI(34:1) | |
| PI(34:2) | |
| PI(36:1) | |
| PI(36:4) | |
| PI(38:2) | |
| PI(38:3) | |
| PI(38:4) | |
| PI(40:4) | |
| PI(40:5) | |
| SM(30:2) | |
| SM(31:2) | |
| SM(32:0) | |
| SM(32:1) | |
| SM(32:2) | |
| SM(33:2) | |
| SM(34:0) | |
| SM(34:2) | |
| SM(36:0) | |
| SM(36:1) | |
| SM(36:2) | |
| SM(38:0) | |
| SM(38:1) | |
| SM(38:2) | |
| SM(38:3) | |
| SM(39:1) | |
| SM(d18:0/22:0) | |
| SM(40:1) | |
| SM(40:2) | |
| SM(41:0) | |
| SM(41:1) | |
| SM(42:1) | |
| SM(42:3) | |
| SM(44:1) | |
| SM(44:2) | |
| TG(14:0/16:0/18:1) | |
| TG(14:0/16:0/18:2) | |
| TG(14:0/16:1/18:1) | |
| TG(14:0/16:1/18:2) | |
| TG(14:0/17:0/18:1) | |
| TG(14:0/18:0/18:1) | |
| TG(14:0/18:2/18:2) | |
| TG(14:1/16:0/18:1) | |
| TG(14:1/16:1/18:0) | |
| TG(14:1/18:0/18:2) | |
| TG(14:1/18:1/18:1) | |
| TG(15:0/16:0/18:1) | |
| TG(15:0/18:1/18:1) | |
| TG(16:0/16:0/16:0) | |
| TG(16:0/16:0/18:0) | |
| TG(16:0/16:0/18:1) | |
| TG(16:0/16:0/18:2) | |
| TG(16:0/16:1/17:0) | |
| TG(16:0/16:1/18:1) | |
| TG(16:0/17:0/18:1) | |
| TG(16:0/17:0/18:2) | |
| TG(16:0/18:0/18:1) | |
| TG(16:0/18:1/18:1) | |
| TG(16:0/18:1/18:2) | |
| TG(16:0/18:2/18:2) | |
| TG(16:1/16:1/16:1) | |
| TG(16:1/16:1/18:0) | |
| TG(16:1/16:1/18:1) | |
| TG(16:1/17:0/18:1) | |
| TG(16:1/18:1/18:1) | |
| TG(16:1/18:1/18:2) | |
| TG(17:0/18:1/18:1) | |
| TG(18:0/18:0/18:1) | |
| TG(18:0/18:1/18:1) | |
| TG(18:0/18:2/18:2) | |
| TG(18:1/18:1/18:1) | |
| TG(18:1/18:1/18:2) | |
| TG(18:1/18:1/20:4) | |
| TG(18:1/18:1/22:6) | |
| TG(18:1/18:2/18:2) | |
| TG(18:2/18:2/18:2) | |
| TG(18:2/18:2/20:4) | |

According to another aspect of the disclosure there is provided an in vitro method for assessing whether a subject is at risk to develop or is suffering from fatty liver disease comprising:

(a) assaying a sample from said subject to determine a concentration of at least one fatty liver biomarker from Group E;

(b) assaying a sample from said subject to determine a concentration of at least one fatty liver biomarker from Group F; and (c) determining that the subject is suffering from or is at an increased risk of developing fatty liver disease, if said sample contains an increased combination biomarker value of the at least one fatty liver biomarker from Group E and the at least one fatty liver biomarker from Group F, when compared to a control.

In some embodiments, the subject is capable of being treated with a therapy as described herein. For example, the therapy may comprise any therapeutic treatment typically given to a subject at risk of developing fatty liver disease or a subject having fatty liver disease, such as, but not limited to, lifestyle interventions and/or counselling to effect a change in diet, weight management and/or physical activity, controlling the progression of fatty liver disease and/or its complications, a medication, or any combination thereof.

In some embodiments, the method for assessing whether a subject is at risk to develop or is suffering from fatty liver disease further comprises after the determining step (c), (d) diagnosing the subject as suffering from or having an increased risk of developing fatty liver disease from the results in step (c), and (e) administering a treatment to the subject diagnosed in step (d).

In one aspect, the present disclosure is directed to a method of treating or preventing fatty liver disease in a subject identified as being at risk to develop or suffering from fatty liver disease, the method comprising: administering to the subject a treatment as described herein, wherein prior to administering the treatment, the subject has been identified as being at risk to develop or suffering from fatty liver disease by the method described herein.

Assaying Group E and Group F biomarkers in a biological sample and/or the determination of combination biomarker values from Group E and Group F biomarker levels are unconventional indicators for fatty liver disease and/or the risk thereof. Moreover, the present biomarkers and methods generally allow for the sensitive indication of fatty liver disease and/or the risk of developing fatty liver disease. Thus, the present methods ensure that subjects having and/or at risk for fatty liver disease can be properly identified and receive treatment as opposed to the large numbers of individuals who have and/or are at risk of developing this disease, but remain unidentified and untreated, and consequently are unnecessarily subjected to the possibility of severe complications and/or premature mortality as is commonplace in this field.

According to another aspect of the invention there is provided an in vitro method of evaluating the effectiveness of a fatty liver disease therapy in a subject comprising:
(a) assaying a sample from said subject to determine a concentration of at least one fatty liver biomarker from Group E;
(b) assaying a sample from said subject to determine a concentration of at least one fatty liver biomarker from Group F; and
(c) determining that the therapy is effective, if said sample contains a decreased combination biomarker value of the at least one fatty liver biomarker from Group E and the at least one fatty liver biomarker from Group F, when compared to a control.

In the method, the effectiveness of the therapy is monitored by analysing the combination biomarker value as described herein of the fatty liver biomarkers described herein. The combination biomarker value of the selected biomarkers reflects the progress of fatty liver disease and the combination biomarker value approaches that of the control when the subject responds to a therapy, such as the therapies described herein. Accordingly, a therapy may be tailored based on the response of a subject such that only a therapy which shows a positive response, e.g., the combination biomarker value of the biomarker concentrations approaching that of a control, and is thus found effective, is continued, and a therapy which shows minimal or no response, and is thus found ineffective, is discontinued.

In some embodiments, the subject is capable of being treated with a therapy as described herein. For example, the therapy may comprise any therapeutic treatment typically given to a subject at risk of developing fatty liver disease or a subject having fatty liver disease, such as, but not limited to, lifestyle interventions and/or counselling to effect a change in diet, weight management and/or physical activity, controlling the progression of fatty liver disease and/or its complications, a medication, or any combination thereof.

In some embodiments, the method for evaluating the effectiveness of a fatty liver disease therapy in a subject further comprises, (d) determining that the therapy is not effective in the subject from the results in step (c), and (e) escalating the therapy of the subject.

In one aspect, the present disclosure is directed to a method of treating fatty liver disease in a subject identified as being ineffectively treated, the method comprising: administering to the subject a further treatment as described herein, wherein prior to administering the treatment, the subject has been identified as being ineffectively treated for fatty liver disease by the methods described herein.

In some embodiments, the therapy may comprise any therapeutic treatment typically given to a subject at risk of developing fatty liver disease or a subject having fatty liver disease, such as, but not limited to, lifestyle interventions and/or counselling affecting diet, weight management and physical activity, control of progression of fatty liver disease and/or its complications, a medication, or any combination thereof.

In some embodiments of the aforementioned methods, the method of treating fatty liver disease further comprises identifying the subject as in need of the treatment or prevention, for example, by requesting a test or receiving the test results, for example, from a commercial laboratory, which provides the results of an assay useful for determining the combination biomarker value of the at least one fatty liver biomarker from Group E and the at least one fatty liver biomarker from Group F and administering to the subject a treatment, for example, a therapeutically effective dose of a drug, if the subject has an increased combination biomarker value of the at least one fatty liver biomarker from Group E and the at least one fatty liver biomarker from Group F, as compared to the control.

According to another aspect of the disclosure there is provided a method of detecting in a sample obtained from a subject the concentration of at least one fatty liver biomarker from Group E and at least one fatty liver biomarker from Group F comprising:
(a) assaying the sample from said subject to determine the concentration of the at least one fatty liver biomarker from Group E;
(b) assaying the sample from said subject to determine the concentration of the at least one fatty liver biomarker from Group F; and optionally
(c) comparing a combination biomarker value of the at least one fatty liver biomarker from Group E and the at least one fatty liver biomarker from Group F to a control.

In some embodiments, the subject is capable of being treated with a therapy as described herein. For example, the therapy may comprise any therapeutic treatment typically given to a subject at risk of developing fatty liver disease or a subject having fatty liver disease, such as, but not limited to, lifestyle interventions and/or counselling to effect a change in diet, weight management and/or physical activity, controlling the progression of fatty liver disease and/or its complications, a medication, or any combination thereof.

According to another aspect of the disclosure, there is provided an in vitro method of assessing the progression of fatty liver disease in a subject comprising:
(a) assaying a sample from said subject to determine a concentration of at least one fatty liver biomarker from Group E;
(b) assaying a sample from said subject to determine a concentration of at least one fatty liver biomarker from Group F; and
(c) determining that fatty liver disease has progressed, if said sample contains an increased combination biomarker value of the at least one fatty liver biomarker from Group E and the at least one fatty liver biomarker from Group F, when compared to a control.

In some embodiments, the subject is capable of being treated with a therapy as described herein. For example, the therapy may comprise any therapeutic treatment typically given to a subject at risk of developing fatty liver disease or a subject having fatty liver disease, such as, but not limited to, lifestyle interventions and/or counselling to effect a change in diet, weight management and/or physical activity, controlling the progression of fatty liver disease and/or its complications, a medication, or any combination thereof.

In some embodiments, the method for assessing the progression of fatty liver disease in a subject further comprises after the determining step (c), (d) administering a treatment to the subject.

Fatty liver disease, such as NAFLD, can lead to severe complications, such as fibrosis, cirrhosis, liver failure and liver cancer, therefore it is beneficial to detect individuals that are at high risk of developing, or are suffering from, fatty liver disease, and provide preventive measures and/or treatment.

In some embodiments of the above-mentioned methods, progression of the subject's condition from a healthy condition to a fatty liver phase, to NASH and/or to fibrosis, cirrhosis, liver failure and/or liver cancer is assessed. In other embodiments, progression from a fatty liver stage or NASH to fibrosis, cirrhosis, liver failure and/or liver cancer is assessed. In other embodiments, the severity of fatty liver disease is assessed.

In some embodiments, progression of the subject's condition from a healthy condition to NAFLD is assessed. In some embodiments, progression from NAFLD to NASH is assessed. In some embodiments, progression from NAFLD to severe fatty liver stages is assessed. In some embodiments, progression from NAFLD to fibrosis, cirrhosis, liver failure and/or liver cancer is assessed.

In some embodiments, the progress of fatty liver disease is monitored to assess if supplementary treatment, e.g., lifestyle interventions or medication, is needed in order to prevent or delay the progression of fatty liver disease and onset of the complications.

In some embodiments, the progress of fatty liver disease is monitored to assess if an administered treatment has affected to, e.g. delayed, the progress of the disease.

Fatty liver disease is a progressive disease, and medication is often needed to control the disease. In some embodiments, the above-mentioned methods are used to adjust fatty liver disease treatment, e.g., assessing if a subject needs a medication, assessing if an administered medication needs adjustment or if a subject's medication needs to be supplemented with another medication.

In some embodiments, the progression of fatty liver disease over time in a subject is monitored by comparing the combination biomarker value of the at least one fatty liver biomarker from Group E and the at least one fatty liver biomarker from Group F to a previously determined combination biomarker value in a sample obtained from the same subject.

In addition to Group E and Group F biomarkers, fatty liver disease can also be predicted and diagnosed using Group A and Group B biomarkers presented in the present disclosure for predicting and diagnosing diabetes.

According to another aspect of the disclosure there is provided an in vitro method for assessing whether a subject is at risk to develop or is suffering from fatty liver disease comprising:
(a) assaying a sample from said subject to determine a concentration of at least one fatty liver biomarker from Group A;
(b) assaying a sample from said subject to determine a concentration of at least one fatty liver biomarker from Group B; and
(c) determining that the subject is suffering from or is at an increased risk of developing fatty liver disease, if said sample contains an increased combination biomarker value of the at least one fatty liver biomarker from Group A and the at least one fatty liver biomarker from Group B, when compared to a control.

In some embodiments, the method for assessing whether a subject is at risk to develop or is suffering from fatty liver disease further comprises after the determining step (c), (d) diagnosing the subject as suffering from or having an increased risk of developing fatty liver disease from the results in step (c), and (e) administering a treatment to the subject diagnosed in step (d).

In one aspect, the present disclosure is directed to a method of treating or preventing fatty liver disease in a subject identified as being at risk to develop or suffering from fatty liver disease, the method comprising: administering to the subject a treatment as described herein, wherein prior to administering the treatment, the subject has been identified as being at risk to develop or suffering from fatty liver disease by the method described herein.

Assaying Group A and Group B biomarkers in a biological sample and/or the determination of combination biomarker values from Group A and Group B biomarker levels are unconventional indicators for both diabetes and fatty liver disease and/or the risk thereof. Moreover, the present biomarkers and methods generally allow for the sensitive indication of diabetes and fatty liver disease and/or the risk of developing the diseases. Thus, the present methods ensure that subjects having and/or at risk for diabetes and/or fatty liver disease can be properly identified and receive treatment as opposed to the large numbers of individuals who have and/or are at risk of developing these diseases, but remain unidentified and untreated, and consequently are unnecessarily subjected to the possibility of severe complications and/or premature mortality as is commonplace in this field.

In addition to Group A, Group B, Group E and Group F biomarkers, fatty liver disease can also be predicted and diagnosed using Group C and Group D biomarkers presented in the present disclosure for predicting and diagnosing diabetes.

According to another aspect of the disclosure there is provided an in vitro method for assessing whether a subject is at risk to develop or is suffering from fatty liver disease comprising:
(a) assaying a sample from said subject to determine a concentration of at least one fatty liver biomarker from Group C;
(b) assaying a sample from said subject to determine a concentration of at least one fatty liver biomarker from Group D; and
(c) determining that the subject is suffering from or is at an increased risk of developing fatty liver disease, if said sample contains an increased combination biomarker value of the at least one fatty liver biomarker from Group C and the at least one fatty liver biomarker from Group D, when compared to a control.

In some embodiments, the method for assessing whether a subject is at risk to develop or is suffering from fatty liver disease further comprises after the determining step (c), (d) diagnosing the subject as suffering from or having an increased risk of developing fatty liver disease from the results in step (c), and (e) administering a treatment to the subject diagnosed in step (d).

In one aspect, the present disclosure is directed to a method of treating or preventing fatty liver disease in a subject identified as being at risk to develop or suffering from fatty liver disease, the method comprising: administering to the subject a treatment as described herein, wherein prior to administering the treatment, the subject has been identified as being at risk to develop or suffering from fatty liver disease by the method described herein.

Assaying Group C and Group D biomarkers in a biological sample and/or the determination of combination biomarker values from Group C and Group D biomarker levels are unconventional indicators for both diabetes and fatty liver disease and/or the risk thereof. Moreover, the present biomarkers and methods generally allow for the sensitive indication of diabetes and fatty liver disease and/or the risk of developing the diseases. Thus, the present methods ensure that subjects having and/or at risk for diabetes and/or fatty liver disease can be properly identified and receive treatment as opposed to the large numbers of individuals who have and/or are at risk of developing these diseases, but remain unidentified and untreated, and consequently are unnecessarily subjected to the possibility of severe complications and/or premature mortality as is commonplace in this field.

According to another aspect of the invention there is provided an in vitro method of evaluating the effectiveness of a fatty liver disease therapy in a subject comprising:
- (a) assaying a sample from said subject to determine a concentration of at least one fatty liver biomarker from Group A;
- (b) assaying a sample from said subject to determine a concentration of at least one fatty liver biomarker from Group B; and
- (c) determining that the therapy is effective, if said sample contains a decreased combination biomarker value of the at least one fatty liver biomarker from Group A and the at least one fatty liver biomarker from Group B, when compared to a control.

According to another aspect of the invention there is provided an in vitro method of evaluating the effectiveness of a fatty liver disease therapy in a subject comprising:
- (d) assaying a sample from said subject to determine a concentration of at least one fatty liver biomarker from Group C;
- (e) assaying a sample from said subject to determine a concentration of at least one fatty liver biomarker from Group D; and
- (f) determining that the therapy is effective, if said sample contains a decreased combination biomarker value of the at least one fatty liver biomarker from Group C and the at least one fatty liver biomarker from Group D, when compared to a control.

According to another aspect of the disclosure there is provided a method of detecting in a sample obtained from a subject the concentration of at least one fatty liver biomarker from Group A and at least one fatty liver biomarker from Group B comprising:
- (a) assaying the sample from said subject to determine the concentration of the at least one fatty liver biomarker from Group A;
- (b) assaying the sample from said subject to determine the concentration of the at least one fatty liver biomarker from Group B; and optionally
- (c) comparing a combination biomarker value of the at least one fatty liver biomarker from Group A and the at least one fatty liver biomarker from Group B to a control.

According to another aspect of the disclosure there is provided a method of detecting in a sample obtained from a subject the concentration of at least one fatty liver biomarker from Group C and at least one fatty liver biomarker from Group D comprising:
- (a) assaying the sample from said subject to determine the concentration of the at least one fatty liver biomarker from Group C;
- (b) assaying the sample from said subject to determine the concentration of the at least one fatty liver biomarker from Group D; and optionally
- (c) comparing a combination biomarker value of the at least one fatty liver biomarker from Group C and the at least one fatty liver biomarker from Group D to a control.

According to another aspect of the disclosure, there is provided an in vitro method of assessing the progression of fatty liver disease in a subject comprising:
- (a) assaying a sample from said subject to determine a concentration of at least one fatty liver biomarker from Group A;
- (b) assaying a sample from said subject to determine a concentration of at least one fatty liver biomarker from Group B; and
- (c) determining that fatty liver disease has progressed, if said sample contains an increased combination biomarker value of the at least one fatty liver biomarker from Group A and the at least one fatty liver biomarker from Group B, when compared to a control.

According to another aspect of the disclosure, there is provided an in vitro method of assessing the progression of fatty liver disease in a subject comprising:
- (a) assaying a sample from said subject to determine a concentration of at least one fatty liver biomarker from Group C;
- (b) assaying a sample from said subject to determine a concentration of at least one fatty liver biomarker from Group D; and
- (c) determining that fatty liver disease has progressed, if said sample contains an increased combination biomarker value of the at least one fatty liver biomarker from Group C and the at least one fatty liver biomarker from Group D, when compared to a control.

According to another aspect of the disclosure, there is provided a method of collecting data for assessing whether a subject is at risk to develop or is suffering from fatty liver disease comprising:
- (a) assaying a sample from said subject to determine a concentration of at least one fatty liver biomarker from Group E;
- (b) assaying a sample from said subject to determine a concentration of at least one fatty liver biomarker from Group F; and
- (c) determining that the subject is suffering from or is at an increased risk of developing fatty liver disease, if said sample contains an increased combination of the concentrations of the at least one fatty liver biomarker from Group E and the at least one fatty liver biomarker from Group F, when compared to a control.

According to yet another aspect of the disclosure there is provided a method of collecting data for evaluating the effectiveness of a fatty liver disease therapy in a subject comprising:
- (a) assaying a sample from said subject to determine a concentration of at least one fatty liver biomarker from Group E;
- (b) assaying a sample from said subject to determine a concentration of at least one fatty liver biomarker from Group F; and (c) determining that the therapy is effective, if said sample contains a decreased combination biomarker value of the at least one fatty liver biomarker from Group E and the at least one fatty liver biomarker from Group F, when compared to a control.

According to another aspect of the disclosure, there is provided a method of collecting data for assessing the progression of fatty liver disease in a subject comprising:
(a) assaying a sample from said subject to determine a concentration of at least one fatty liver biomarker from Group E;
(b) assaying a sample from said subject to determine a concentration of at least one fatty liver biomarker from Group F; and
(c) determining that fatty liver disease has progressed, if said sample contains an increased combination biomarker value of the at least one fatty liver biomarker from Group E and the at least one fatty liver biomarker from Group F, when compared to a control.

Yet another aspect of the present disclosure is a composition or kit for diagnosing, predicting or detecting fatty liver disease or for performing any of the methods or uses disclosed herein. In some embodiments, the composition or kit comprises at least one fatty liver biomarker from Group E and at least one fatty liver biomarker from Group F. In other embodiments, the composition or kit comprises at least one isotope (e.g. deuterium)-labelled fatty liver biomarker from Group E and at least one isotope (e.g. deuterium)-labelled fatty liver biomarker from Group F. In some embodiments, the at least one isotope-labelled fatty liver biomarker is $^{13}$C-labelled or $^{15}$N-labelled.

In some embodiments, the at least one Group F biomarker is selected from LPC(MHDA) [sn1] and LPC(MHDA) [sn2]. In some embodiments, the at least one isotope (e.g. deuterium)-labelled biomarker from Group F is selected from LPC(MHDA) [sn1] and LPC(MHDA) [sn2].

In some embodiments, the composition or kit comprises at least one, at least 2, at least 3, at least 4, at least 5, at least 6, at least 7, at least 8, at least 9, at least 10 or more fatty liver biomarkers from Group E and at least one, at least 2, at least 3, at least 4, at least 5, at least 6, at least 7, at least 8, at least 9, at least 10 or more fatty liver biomarkers from Group F.

In yet other embodiments, the composition or kit comprises at least one, at least 2, at least 3, at least 4, at least 5, at least 6, at least 7, at least 8, at least 9, or at least 10 or more isotope (e.g. deuterium)-labelled fatty liver biomarkers from Group E and/or at least one, at least 2, at least 3, at least 4, at least 5, at least 6, at least 7, at least 8, at least 9, at least 10 or more isotope (e.g. deuterium)-labelled fatty liver biomarkers from Group F.

The composition or kit may further include standard(s), control(s), reagent(s), solution(s), solvent(s), container(s), instruction(s) to use it for the methods or uses disclosed herein or other element(s) for performing the methods or uses disclosed herein.

In some embodiments, the composition or kit includes element(s) for collecting a blood sample, for example, a dried blood spot on a filter.

The composition or kit may be a test kit for used in a laboratory or a home use test kit (over-the-counter test). The composition or kit may be used in assays performed with various chemical and high-resolution analytical techniques, as appropriate. Suitable analytical techniques according to the present methods and uses include, but are not limited to, mass spectrometry (MS) and nuclear magnetic resonance (NMR). Any high-resolution technique capable of resolving individual biomarkers can be used to collect the information on the biomarker in question, such as the concentration of biomarker profile from the biological sample. Typically, the information is collected using mass spectrometry. The MS analysis can be coupled to another high performance separation method, such as gas chromatography (GC), two-dimensional gas chromatography (GC×GC), liquid chromatography (LC), high performance liquid chromatography (HPLC) or ultra-high performance liquid chromatography (UHPLC).

According to another aspect of the disclosure there is provided a use of one or more reagent(s) in the manufacture of a kit, composition, preparation or reagent for assessing whether a subject is at risk to develop or is suffering from fatty liver disease comprising:
(a) a reagent for assaying a sample from said subject to determine a concentration of at least one fatty liver biomarker from Group E;
(b) a reagent for assaying a sample from said subject to determine a concentration of at least one fatty liver biomarker from Group F; and
(c) determining that the subject is suffering from or is at an increased risk of developing fatty liver disease, if said sample contains an increased combination biomarker value of the at least one fatty liver biomarker from Group E and the at least one fatty liver biomarker from Group F, when compared to a control.

According to yet another aspect of the disclosure there is provided a use of one or more reagent(s) in the manufacture of a kit, composition, preparation or reagent for evaluating the effectiveness of a fatty liver disease therapy in a subject comprising:
(a) a reagent for assaying a sample from said subject to determine a concentration of at least one fatty liver biomarker from Group E;
(b) a reagent for assaying a sample from said subject to determine a concentration of at least one fatty liver biomarker from Group F; and
(c) determining that the therapy is effective, if said sample contains a decreased combination biomarker value of the at least one fatty liver biomarker from Group E and the at least one fatty liver biomarker from Group F, when compared to a control.

According to yet another aspect of the disclosure, there is provided a use of one or more reagent(s) in the manufacture of a kit, composition, preparation or reagent for assessing the progression of fatty liver disease in a subject comprising:
(a) a reagent for assaying a sample from said subject to determine a concentration of at least one fatty liver biomarker from Group E;
(b) a reagent for assaying a sample from said subject to determine a concentration of at least one fatty liver biomarker from Group F; and
(c) determining that fatty liver disease has progressed, if said sample contains an increased combination biomarker value of the at least one fatty liver biomarker from Group E and the at least one fatty liver biomarker from Group F, when compared to a control.

According to yet another aspect of the disclosure, there is provided a use of one or more reagent(s) in the manufacture of a kit, composition, preparation or reagent for detecting in a sample from a subject a concentration of at least one fatty liver biomarker from Group E and a concentration of at least one fatty liver biomarker from Group F comprising:
(a) a reagent for assaying a sample from said subject to determine a concentration of at least one fatty liver biomarker from Group E;

(b) a reagent for assaying a sample from said subject to determine a concentration of at least one fatty liver biomarker from Group F; and optionally (c) comparing a combination biomarker value of the at least one fatty liver biomarker from Group E and the at least one fatty liver biomarker from Group F to a control.

In some embodiments of the methods and uses of the present disclosure, the at least one fatty liver biomarker from Group E is at least one, at least 2, at least 3, at least 4, at least 5, at least 6, at least 7, at least 8, at least 9, at least 10 or more fatty liver biomarkers from Group E and/or the at least one fatty liver biomarker from Group F is at least one, at least 2, at least 3, at least 4, at least 5, at least 6, at least 7, at least 8, at least 9, at least 10 or more fatty liver biomarkers from Group F.

In some embodiments of the methods and uses of the present disclosure, the methods and uses further comprise a step of spiking the sample with at least one isotope-labelled fatty liver biomarker from Group E and/or at least one isotope-labelled fatty liver biomarker from Group F prior to determining the concentration of the at least one fatty liver biomarker from Group E and the concentration of the at least one fatty liver biomarker from Group F. The at least one isotope-labelled fatty liver biomarker from Group E and/or the at least one isotope-labelled fatty liver biomarker from Group F may be, but is not limited to, deuterium-labelled, $^{13}C$-labelled or $^{15}N$-labelled fatty liver biomarker from Group E and/or Group F.

In some embodiments of all aspects of the present disclosure, the combination of the concentrations of the at least one fatty liver biomarker from Group E and the at least one fatty liver biomarker from Group F is (are) selected from Table 7.

In some embodiments of the methods and uses of the present disclosure, the at least one fatty liver biomarker from Group F is LPC(MHDA) [sn1] and/or LPC(MHDA) [sn2].

In some embodiments of the methods and uses of the present disclosure, determining that the subject is suffering from or is at an increased risk of developing diabetes and/or fatty liver disease is determined by one assay. In some embodiments, the same biomarkers are used for diabetes and fatty liver prediction and diagnosis. In some embodiments, the diabetes and fatty liver biomarkers are selected from Table 6 or Table 7.

The determination of the biomarkers is typically performed using an assay. The assay can be performed with various chemical and high-resolution analytical techniques, as appropriate. Suitable analytical techniques according to the present methods and uses include, but are not limited to, mass spectrometry (MS) and nuclear magnetic resonance (NMR). Any high-resolution technique capable of resolving individual small molecule biomarkers can be used to collect the information on the biomarker in question, such as the concentration of biomarker profile from the biological sample, such as blood, blood serum, blood plasma, tissue, urine or saliva. Typically, the information is collected using mass spectrometry. The MS analysis can be coupled to another high performance separation method, such as gas chromatography (GC), two-dimensional gas chromatography (GC×GC), liquid chromatography (LC), high performance liquid chromatography (HPLC) or ultra-high performance liquid chromatography (UHPLC).

The sample from the subject and the control sample may be a blood sample, a blood serum sample, a blood plasma sample, a saliva sample or an urine sample. Blood serum and plasma samples are typically used. The sample can be prepared with techniques well known in the art.

In some embodiments, the sample is a non-sedimented sample. In other embodiments, the plasma sample is substantially free of residual cells. In yet other embodiments, the blood sample is treated with clot activators and serum is separated by centrifugation, optionally followed by freezing and thawing, prior to analysis.

In some embodiments, before the mass spectrometric analysis, the biomarkers of the sample are extracted with a solvent or a solvent mixture from the sample. Suitable solvents include organic solvents such as methanol, chloroform/methanol or other similar solvents.

In other embodiments, the biomarkers are derivatized before the mass spectrometric analysis. In some embodiments, the derivatization comprises extraction with an organic solvent, evaporation of the solvent under reduced pressure, and derivatization.

In other embodiments, the sample is filtered before determining the biomarkers by using a filter which removes cells. In other embodiments, a filter having a cut-off value of 30 kDa is used to remove cells. In yet other embodiments, a filter is used which removes proteins. In other embodiments, the sample is reconstituted after the filtering.

In other embodiments, the sample or the reconstituted sample is diluted prior to determining the biomarkers. In other embodiments, the sample is diluted at least 1:2 before determining the biomarkers.

In other embodiments, a preservative or an internal mass standard is added to the sample.

In yet other embodiments of the methods and uses of the present disclosure, the methods and uses further comprise a step of spiking the sample with at least one isotope-labelled diabetes biomarker from Group A and/or at least one isotope-labelled diabetes biomarker from Group B prior to determining the concentration of the at least one diabetes biomarker from Group A and the concentration of the at least one diabetes biomarker from Group B. The at least one isotope-labelled diabetes biomarker from Group A and/or the at least one isotope-labelled diabetes biomarker from Group B may be, but is not limited to, deuterium-labelled diabetes biomarker from Group A and/or Group B.

In yet other embodiments of the methods and uses of the present disclosure, the methods and uses further comprise a step of spiking the sample with at least one isotope-labelled diabetes biomarker from Group C and/or an isotope-labelled diabetes biomarker from Group D prior to determining the concentration of the at least one diabetes biomarker from Group C and the concentration of the diabetes biomarker from Group D. The at least one isotope-labelled diabetes biomarker from Group C and/or the isotope-labelled diabetes biomarker from Group D may be, but is not limited to, deuterium-labelled diabetes biomarker from Group C and/or Group D.

In some embodiments of the aforementioned methods and uses of the present disclosure, the subject has a blood glucose level in the normal range. For example, in some embodiments, the blood glucose level of the subject includes a haemoglobin A1c level of about 5.7% or less, such as about 5.5% or less, such as about 5.0% or less. In some embodiments, the subject has a fasting blood sugar on awakening of about 100 mg/dL or less. In some embodiments, the subject has a before-meal glucose level of about 70 mg/dL to about about 99 mg/dL. In some embodiments, the subject has a glucose level of about 140 mg/dL or less about two hours after a meal. Typically, the subject has a fasting venous plasma glucose concentration of less than 6.1 mmol/L (110 mg/dL).

The diabetes biomarkers of the present disclosure allow for easy, reliable and early prediction of type 2 diabetes. This will facilitate e.g. earlier intervention, less symptom development and suffering and decreased morbidity. The present biomarkers also allow easy monitoring of the progress of diabetes as the analysis can be performed on, for example, serum or plasma samples without the need of uncomfortable and time-consuming oral glucose tolerance test.

In some embodiments of all aspects of the present disclosure, the above-mentioned methods are used as screening methods.

As described elsewhere in the present disclosure, the control may be a concentration determined from a single healthy individual. The control may also be a sample that represents a combination of samples from a generalized population of healthy individuals. Alternatively, the control may be a control value or a set of data concerning the biomarker in a sample previously determined, calculated or extrapolated, or may have yet to be determined, calculated or extrapolated, or may also be taken from the literature.

In some embodiments, the above methods and uses comprise determining the combination biomarker value of at least 1, at least 2, at least 3, at least 4, at least 5, at least 6, at least 7, at least 8, at least 9, at least 10 or more diabetes biomarkers from Group A and at least 1, at least 2, at least 3, at least 4, at least 5, at least 6, at least 7, at least 8, at least 9, at least 10 or more diabetes biomarkers from Group B.

In some embodiments, the above methods and uses comprise determining the combination biomarker value of at least 1, at least 2, at least 3 or at least 4 diabetes biomarkers from Group C and a diabetes biomarkers from Group D. In some embodiments of all aspects of the present disclosure, the combination of the concentrations of the at least one diabetes biomarker from Group A and the at least one diabetes biomarker from Group B, or the combination of the concentrations of the at least one diabetes biomarker from Group C and the diabetes biomarker from Group D are selected from Table 3.

In some embodiments, the biomarker concentration is determined by using mass spectrometry, nuclear magnetic resonance spectroscopy, fluorescence spectroscopy or dual polarization interferometry, an immunoassay, enzymatic assay, colorimetric assay, fluorometric assay, a rapid test, a breath test and/or with a binding moiety capable of specifically binding the biomarker.

In another aspect, there is provided a use of a pharmaceutical for treating diabetes or one or more of its complications in a subject in need thereof, the use comprising using an effective pharmaceutical for diabetes, wherein the effectiveness of the treatment with the pharmaceutical is evaluated using the aforementioned method for evaluating the effectiveness of a diabetes therapy.

Typically, the pharmaceutical is administered at a dose which causes the concentration of the at least one diabetes biomarker in the sample to change from the initial level towards the concentration in the control, and wherein the concentration of the at least one diabetes biomarker is determined according to the aforementioned methods or uses.

According to yet another aspect of the disclosure there is provided an in vitro method for assessing whether a subject is at risk to develop type 2 diabetes, wherein the risk to develop type 2 diabetes is determined according to the following formula:

$$r = a \times Cer(d18:1/18:0)/Cer(d18:1/16:0) + b \times BMI,$$

wherein a and b are real numbers and transformation to logistic (risk=(exp(r)/1+exp(r))*100) or time-to-event model is optionally performed for the formula.

According to yet another aspect of the disclosure there is provided an in vitro method for assessing whether a subject is at risk to develop type 2 diabetes, wherein the risk to develop type 2 diabetes is determined according to the following formula:

$$r = intercept + a \times Cer(d18:1/18:0)/Cer(d18:1/16:0) + b \times BMI + e \times age,$$

wherein a, b and e are real numbers and transformation to logistic (risk=(exp(r)/1+exp(r))*100) or time-to-event model is optionally performed for the formula.

According to yet another aspect of the disclosure there is provided an in vitro method for assessing whether a subject is at risk to develop type 2 diabetes, wherein the risk to develop type 2 diabetes is determined according to the following formula:

$$r = a \times Cer(d18:1/18:0)/Cer(d18:1/16:0),$$

wherein a is a real number and transformation to logistic (risk=(exp(r)/1+exp(r))*100) or time-to-event model is optionally performed for the formula.

DETAILED DESCRIPTION OF THE INVENTION

Reference will now be made in detail to various exemplary embodiments, examples of which are discussed in the detailed description that follows. It is to be understood that the following detailed description is provided to give the reader a fuller understanding of certain embodiments, features, and details of aspects of the invention, and should not be interpreted as limiting the scope of the invention.

Abbreviations

Unless indicated otherwise, the abbreviations used in this description have the following meanings: ACE—angiotensin-converting enzyme, ARB—angiotensin II receptor blocker, AUC—area under the curve, AusDiab—Australian Diabetes, Obesity and Lifestyle study, BMI—body mass index, Cer—ceramide, CETP—cholesteryl ester transfer protein, CI—confidence interval, CRP—C-reactive protein, CVD—cardiovascular disease, DM2—diabetes mellitus type 2, DPP-4—dipeptidyl peptidase-4, EI—electron ionization, FA—fatty acid, GC—gas chromatography, GC×GC—two dimensional gas chromatography, GLP-1—glucagon-like peptide 1, HbA1C—glycated haemoglobin, haemoglobin A1C, HDL—high density lipoprotein, HMG-CoA—3-hydroxy-3-methylglutaryl-coenzyme A, HPLC—high performance liquid chromatography, HR—hazard ratio, IDF—the International Diabetes Federation, IGT—impaired glucose tolerance, IS—internal standard, LC—liquid chromatography, LDL—low density lipoprotein, LPC—lysophosphatidylcholine, LPC(P-)—lysoalkenylphosphatidylcholine, LPE—lysophosphatidylethanolamine, LPE(P-)—lysoalkenylphosphatidylethanolamine, LPI—lysophosphatidylinositol, MHDA—15-methylhexadecanoic acid and/or 14-methylhexadecanoic acid, MRM—multiple reaction monitoring, MS—mass spectrometry, NGT—normal glucose tolerance, NMR—nuclear magnetic resonance, OR odds ratio, PC—phosphatidylcholine, PCSK9—proprotein convertase subtilisin/kexin type 9, PI—phosphatidylinositol, QC—quality control sample, ROC— receiver operating characteristic, SB—sphingoid base, SE—sensitivity, SIM—selected ion monitoring, SGLT2—sodium-glucose transporter, SM—sphingomyelin, sMRM—scheduled multiple reaction monitoring, SP—specificity, T2D—type 2 diabetes, TG—triacylglyserol, TG(O-)—alkyltriacylglyserol, TOF—time-of-flight, TQC—technical quality control sample, UHPLC—ultra-high performance liquid chromatography, WHO—World Health Organization.

In addition, the following abbreviations are used in the present disclosure: CE—cholesterylester, DAG—diacylglycerol, FA—fatty acid or formic acid, FL—fatty liver, FLD—fatty liver disease, Gb3—globotriasoylceramide, Glc/GalCer—glucosyl/galactosylceramide, LacCer—lactosylceramide, LPC(O-)—lysoalkylphosphatidylcholine, NAFL—non-alcoholic fatty liver, NAFLD—non-alcoholic fatty liver disease, NASH—non-alcoholic steatohepatitis, PC (O-)—alkyl-linked phosphatidylcholine, PC (P-)—alkenyl-linked phosphatidylcholine, PE—phosphatidylethanolamine, PE (O-)—alkyl-linked phosphatidylethanolamine, PE (P-)—alkenyl-linked phosphatidylethanolamine, PG—phosphatidylglycerol.

Definitions

In order that the present disclosure may be more readily understood, certain terms are first defined. Additional definitions are set forth throughout the present description.

As used herein, "diabetes" or "diabetes mellitus" is a chronic condition in which the body is not able to produce enough insulin or is not able to use insulin properly. This leads to elevated blood glucose levels. There are three main types of diabetes: type 1 diabetes, type 2 diabetes and gestational diabetes. "Diabetes" and "type 2 diabetes" are used interchangeably in this disclosure.

The terms "type 2 diabetes", "type 2 diabetes mellitus", "diabetes mellitus type 2", "T2D" or "DM2" are used interchangeably herein to refer to the most common type of diabetes. Type 2 diabetes is a condition in which the body becomes resistant to insulin and gradually loses the capacity to produce sufficient amounts of insulin.

As used herein, "diabetes complications" refers to, but is not limited to, e.g., cardiovascular disease and its complications, kidney disease, neural damage, eye and foot damage, oral health problems and pregnancy complications.

As used herein, "cardiovascular disease" or "CVD" is a general term of art used to classify numerous conditions that affect the heart, heart valves, blood, and vasculature of the body, including coronary artery disease.

The terms "subject," "host," "patient," and "individual" are used interchangeably herein to refer to any mammalian subject for whom prognosis, diagnosis or therapy is desired, particularly humans. The subject may have previously suffered or is suffering from diabetes, pre-diabetes and/or diabetes complication(s), may be suspected of suffering from diabetes and/or its complication(s) or the subject may be a healthy individual with no previous signs or symptoms of diabetes.

The subject may be or may have been under a treatment, such as, but not limited to, diabetes, blood pressure or lipid modifying medication, or may not have had any previous treatment or medication.

The subject may have previously suffered or is suffering from cardiovascular disease and/or its complication(s) and may have been or may be undergoing statin treatment.

As used herein, "statins" is a class of lipid-lowering medications (HMG-CoA reductase inhibitors). Statin is selected from the group consisting of atorvastatin, cerivastatin, fluvastatin, fluvastatin XL, lovastatin, pitavastatin, pravastatin, rosuvastatin and simvastatin or a combination thereof.

As used in this disclosure, a "diabetes biomarker" relates to the biomarkers of Group A, Group B, Group C and Group D listed in Tables 1 and 2.

As used in this disclosure, a "diabetes biomarker from Group A" and a "diabetes biomarker from Group B" relate to the biomarkers listed in Table 1.

As used in this disclosure, a "diabetes biomarker from Group C" and a "diabetes biomarker from Group D" relate to the biomarkers listed in Table 2.

The term "combination biomarker" as used herein refers to a combination of at least one diabetes biomarker from Group A and at least one diabetes biomarker from Group B or a combination of at least one diabetes biomarker from Group C and the diabetes biomarker from Group D.

The term "biomarker value" as used herein refers to a value determined by quantifying the amount of, abundance of, level of, concentration of, quantity of, or activity of, a biomarker within a sample as defined herein.

The term "combination biomarker value" as used herein refers to a value determined by quantifying the amount of, abundance of, level of, concentration of, quantity of, or activity of a combination of biomarker values within a sample as defined herein. The "combination biomarker value" can be based on a measured combination of biomarker values or on a combination of biomarker values derived from the measured combination. The "combination biomarker value" may be e.g., a ratio of biomarker values, a sum of biomarker values, a difference between biomarker values, a multiplied product of biomarker values, a remainder, a score, a calculation, a formula, an equation, an algorithm or any combination thereof. In some embodiments the "combination biomarker value" may be calculated from the concentrations of at least one diabetes biomarker from Group A and at least one diabetes biomarker from Group B or from the concentrations of at least one diabetes biomarker from Group C and the diabetes biomarker from Group D. In some embodiments the "combination biomarker value" is a concentration ratio of at least one diabetes biomarker from Group A and at least one diabetes biomarker from Group B or a concentration ratio of at least one diabetes biomarker from Group C and the diabetes biomarker from Group D.

As used herein, a "sample" is a biological sample obtained from a subject or a group or population of subjects. The sample may be a blood sample, a serum sample, a plasma sample, a saliva sample, an urine sample or a fraction thereof. Blood serum and plasma samples are typical. The sample can be prepared with techniques well known in the art. In certain embodiments, the blood sample is a blood spot dried on a filter. Alternatively, both the sample from the subject and the control sample may also be tissue samples.

As used herein, a "control" may be a control sample. A control may also be a concentration determined from a sample from a single healthy individual. The control may also be a sample that represents a combination of samples from a generalized population of healthy individuals. Alternatively, the control may be a control value or a set of data concerning the biomarker in a sample previously determined, calculated or extrapolated, or may have yet to be determined, calculated or extrapolated, or may also be taken from the literature.

A control as used herein, i.e., a control value or a control sample, is typically representative of a group of subjects or a population of subjects. In this context, "representative" means that the biomarker concentration(s) reflected by said control value to which a comparison is made in the context of the present disclosure correspond(s) to the average concentration value(s) of said biomarker concentration(s) in corresponding individual samples from the subjects of said group or population. Likewise, in the case of a control sample "representative" means that the biomarker concentration(s) in said control sample to which a comparison is made in the context of the present disclosure correspond(s) to the average concentration(s) of said biomarker concentration(s) in corresponding individual samples from the subjects of said group or population. Typically, the concentrations of all biomarker concentrations in said control sample correspond to the average concentrations of said biomarker concentrations in corresponding individual samples from the subjects of said group or population. An individual with such values can be considered a "healthy individual" for the purposes of the present disclosure.

A control sample can be particularly suitably compared to the subject's sample if it has been obtained from the same type of biological tissue or source in the same, or essentially the same, manner. For example, if the subject's sample is a serum sample or a plasma sample, a corresponding control sample will likewise be a serum sample or a plasma sample, respectively.

In some embodiments of the methods described herein, a control may be a control value, e.g., a combination biomarker value of the at least one diabetes biomarker from Group A and the at least one diabetes biomarker from Group B or a combination biomarker value of the at least one diabetes biomarker from Group C and the diabetes biomarker from Group D. The control value may be obtained from a previously taken sample from the same subject.

It will be appreciated that a useful control value for the purposes of the present disclosure is typically one that has been, or is, obtained using any one of the suitable control samples described herein.

As used herein, the nomenclature of ceramides (Cer) and sphingomyelins (SM) is presented as a first pair of numbers corresponding to the sphingoid base (SB) and a second pair of numbers corresponding to the fatty acid (FA) chain of the molecule. In SB and FA nomenclature, the first number of each pair refers to the number of carbon atoms in the SB or FA chain, and the second number refers to the number of carbon-carbon double bonds of the SB or FA chain.

The nomenclature of LPCs, LPEs and LPIs is presented with a number corresponding to the FA chain of the molecule. In FA nomenclature, the first number refers to the number of carbon atoms in the FA chain, and the second number refers to the number of carbon-carbon double bonds of the FA chain.

The nomenclature of TGs is presented with a number corresponding to the total number of carbon atoms and total number of carbon-carbon double bonds in the FA chains of the molecule.

The nomenclature of PCs and PIs is presented with a number corresponding to the total number of carbon atoms and total number of carbon-carbon double bonds in the molecule. Some PC molecules are presented with a MHDA (methylhexadecanoic acid) chain and a FA chain. In FA nomenclature, the first number refers to the number of carbon atoms in the FA chain, and the second number refers to the number of carbon-carbon double bonds of the FA chain.

The nomenclature sn1 and sn2 indicate the sn1 and sn2 positions of the glycerol backbone, respectively, to which the fatty acid moiety is attached.

A "treatment" and "therapy" are used interchangeably in the present disclosure and may comprise any therapeutic treatment typically given to a subject at risk of developing diabetes or a subject having diabetes, such as, but not limited to, lifestyle interventions and/or counselling affecting diet, weight management and physical activity, control of progression of diabetes and/or its complications (e.g. blood glucose monitoring, blood pressure and lipid control and eye, kidney and feet examination), diabetes medication (e.g. insulin, metformin, GLP-1 analogues, DPP-4 inhibitors, SGLT2 inhibitors, sulfonylureas, meglitinides, thiazolidinediones and alpha-glucosidase inhibitors), blood pressure medication (e.g. diuretics, beta-blockers, angiotensin-converting enzyme (ACE) inhibitors, angiotensin II receptor blockers (ARBs), calcium channel blockers, alpha-blockers, alpha-beta-blockers, central agonists, alpha-2 receptor agonists, peripheral adrenergic inhibitors, vasodilators, aldosterone receptor antagonists and direct renin inhibitors), lipid modifying medications (e.g. statins, other HMG-CoA reductase inhibitors, niacin (nicotinic acid), cholesterol absorption inhibitors, cholesteryl ester transfer protein (CETP) inhibitors, bile acid sequestrants, fibrates, phytosterols and PCSK9 inhibitors), or any combination thereof.

The term "effectiveness of a treatment" and "effectiveness of a therapy" are taken to mean the ability of a treatment and therapy to achieve the therapeutic purpose for which it is administered.

A "pharmaceutical", "drug", "medicament", "medicine" and "medication" are used interchangeably in the present disclosure and may comprise any pharmaceutical typically given to a subject having diabetes, such as, but not limited to, insulin, metformin, GLP-1 analogues, DPP-4 inhibitors, SGLT2 inhibitors, sulfonylureas, meglitinides, thiazolidinediones, alpha-glucosidase inhibitors, blood pressure medications, such as, but not limited to, diuretics, beta-blockers, angiotensin-converting enzyme (ACE) inhibitors, angiotensin II receptor blockers (ARBs), calcium channel blockers, alpha-blockers, alpha-beta-blockers, central agonists, alpha-2 receptor agonists, peripheral adrenergic inhibitors, vasodilators, aldosterone receptor antagonists and direct renin inhibitors and lipid modifying medications, such as, but not limited to, statins, other HMG-CoA reductase inhibitors, niacin (nicotinic acid), cholesterol absorption inhibitors, cholesteryl ester transfer protein (CETP) inhibitors, bile acid sequestrants, fibrates, phytosterols and PCSK9 inhibitors, or any combination thereof.

As used herein, a "composition" and "kit" are used for predicting, diagnosing and detecting diabetes and comprise means and elements for assaying the diabetes biomarkers described in the present disclosure.

As used herein, a "preparation" is used in the assays determining the biomarkers described in the present disclosure for predicting, diagnosing and detecting diabetes.

For the purposes of the present disclosure, the terms "obtaining data", "collecting data", "obtaining information" and "collecting information" may be used interchangeably.

The terms "the disclosure, description or invention", "in accordance with the disclosure, description or invention", "according to the disclosure, description or invention", "the present disclosure, description or invention" as used herein, are intended to refer to all aspects and embodiments of the disclosure described and/or claimed herein.

As used herein, the term "comprising" is to be construed as encompassing both "including" and "consisting of".

As used herein, "determining" in reference to a biomarker as disclosed herein refers to quantitatively or relatively determining an amount of a biomarker in a sample. For quantitative determination, either the absolute or precise amount of the biomarker in a sample is determined. The relative amount or level of a biomarker in a sample, may alternatively be determined, e.g., the biomarker amount in the sample is determined to be enlarged or diminished with respect to a control as described herein.

As used herein, "assaying" or "detecting" refers to a measurement of a quantity of the diabetes biomarkers of this disclosure in a biological sample using e.g., mass spectrometry.

As used herein, the phrase "normal glucose levels" refers to the range where current tests fail to measure increased risk. For example, in some embodiments, the blood glucose level of the subject of the present disclosure includes a haemoglobin A1c level of about 5.7% or less, such as about 5.5% or less, such as about 5.0% or less. In some embodiments, the present subject has a fasting blood sugar on awakening of about 100 mg/dL or less. In some embodiments, the present subject has a before-meal glucose level of about 70 mg/dL to about about 99 mg/dL. In some embodiments, the present subject has a glucose level of about 140 mg/dL or less about two hours after a meal. Typically, the present subject has a fasting venous plasma glucose concentration of of less than 6.1 mmol/L (110 mg/dL).

As used herein, "fatty liver disease" or "FLD" is a condition in which excess fat builds up in the liver. The two main types of fatty liver disease are alcoholic fatty liver disease and non-alcoholic fatty liver disease (NAFLD).

As used herein, "alcoholic fatty liver disease" is a fatty liver disease related to heavy alcohol use.

As used herein, "non-alcoholic fatty liver disease" or "NAFLD" is a range of fatty liver conditions which are not related to heavy alcohol use. Early stages of NAFLD can be symptomless but if not detected and managed, NAFLD can progress to serious liver damage. NAFLD can progress from a harmless fatty liver stage (steatosis) to non-alcoholic steatohepatitis (NASH), a more serious form of NAFLD, and eventually to fibrosis, cirrhosis, liver failure and liver cancer. As used herein, "non-alcoholic steatohepatitis" or "NASH" is a severe fatty liver condition, in which the liver is often inflamed.

As used in this disclosure, a "fatty liver biomarker" relates to the biomarkers of Group A, Group B, Group C, Group D, Group E and Group F listed in Tables 1, 2 and 2a, respectively.

As used in this disclosure, a "fatty liver biomarker from Group A" and a "fatty liver biomarker from Group B" relate to the biomarkers listed in Table 1.

As used in this disclosure, a "fatty liver biomarker from Group C" and a "fatty liver biomarker from Group D" relate to the biomarkers listed in Table 2.

As used in this disclosure, a "fatty liver biomarker from Group E" and a "fatty liver biomarker from Group F" relate to the biomarkers listed in Table 2a.

The term "combination biomarker" as used herein refers also to a combination of at least one fatty liver biomarker from Group A and at least one fatty liver biomarker from Group B.

The term "combination biomarker" as used herein refers also to a combination of at least one fatty liver biomarker from Group C and at least one fatty liver biomarker from Group D.

The term "combination biomarker" as used herein refers also to a combination of at least one fatty liver biomarker from Group E and at least one fatty liver biomarker from Group F.

The term "combination biomarker value" as used herein refers to a value determined by quantifying the amount of, abundance of, level of, concentration of, quantity of, or activity of a combination of biomarker values within a sample as defined herein. The "combination biomarker value" can be based on a measured combination of biomarker values or on a combination of biomarker values derived from the measured combination. The "combination biomarker value" may be e.g., a ratio of biomarker values, a sum of biomarker values, a difference between biomarker values, a multiplied product of biomarker values, a remainder, a score, a calculation, a formula, an equation, an algorithm or any combination thereof. In some embodiments the "combination biomarker value" may be calculated from the concentrations of at least one fatty liver biomarker from Group E and at least one fatty liver biomarker from Group F. In some embodiments the "combination biomarker value" is a concentration ratio of at least one fatty liver biomarker from Group E and at least one fatty liver biomarker from Group F.

In some embodiments the "combination biomarker value" may be calculated from the concentrations of at least one fatty liver biomarker from Group A and at least one fatty liver biomarker from Group B. In some embodiments the "combination biomarker value" is a concentration ratio of at least one fatty liver biomarker from Group A and at least one fatty liver biomarker from Group B.

In some embodiments the "combination biomarker value" may be calculated from the concentrations of at least one fatty liver biomarker from Group C and at least one fatty liver biomarker from Group D. In some embodiments the "combination biomarker value" is a concentration ratio of at least one fatty liver biomarker from Group C and at least one fatty liver biomarker from Group D.

In some embodiments of the methods and uses described herein, a control may also be a control value, e.g., a combination biomarker value of the at least one fatty liver biomarker from Group E and the at least one fatty liver biomarker from Group F. The control value may be obtained from a previously taken sample from the same subject.

In some embodiments of the methods and uses described herein, a control may also be a control value, e.g., a combination biomarker value of the at least one fatty liver biomarker from Group A and the at least one fatty liver biomarker from Group B. The control value may be obtained from a previously taken sample from the same subject.

In some embodiments of the methods and uses described herein, a control may also be a control value, e.g., a combination biomarker value of the at least one fatty liver biomarker from Group C and the at least one fatty liver biomarker from Group D. The control value may be obtained from a previously taken sample from the same subject.

As used herein, the sphingomyelins (SM) are presented either as brutto species, e.g. SM(30:2) where the first number refers to the total number of carbon atoms and the second number refers to the total number of carbon-carbon double bonds of the molecule, or as molecular species, e.g. SM(d18:0/22:0), where the first pair of numbers corresponds to the sphingoid base (SB) and the second pair of numbers corresponds to the fatty acid (FA) chain of the molecule. In SB and FA nomenclature, the first number of each pair refers to the number of carbon atoms in the SB or FA chain, and the second number refers to the number of carbon-carbon double bonds of the SB or FA chain.

A "treatment" and "therapy" are used interchangeably in the present disclosure and may also comprise any therapeutic treatment typically given to a subject at risk of developing fatty liver disease or a subject having fatty liver disease, such as, but not limited to, lifestyle interventions and/or counselling affecting diet, weight management and physical activity, control of progression of fatty liver disease and/or its complications, a medication, or any combination thereof.

A "pharmaceutical", "drug", "medicament", "medicine" and "medication" are used interchangeably in the present disclosure and may also comprise any pharmaceutical typically given to a subject having fatty liver disease.

As used herein, a "composition" and "kit" are used also for predicting, diagnosing and detecting fatty liver disease and comprise means and elements for assaying the fatty liver biomarkers described in the present disclosure.

As used herein, a "preparation" is also used in the assays determining the biomarkers described in the present disclosure for predicting, diagnosing and detecting fatty liver disease.

As used herein, a "reagent" is used in the assays determining the biomarkers described in the present disclosure for predicting, diagnosing and detecting diabetes and/or fatty liver disease.

As used herein, a "reagent" may be any standard(s), control(s), substance(s), compound(s), solution(s), solvent (s), agent(s), ingredient(s), preparation(s), or any combination thereof used for the methods and uses of the present disclosure. A reagent may also be a combination or mixture of any standard(s), control(s), substance(s), compound(s), solution(s), solvent(s), agent(s), ingredient(s) and preparation(s) used in the methods and uses of the present disclosure.

In some embodiments, one or more of any components of a reagent is isotope-labelled. In some embodiments, the isotope of the isotope-labelled component is deuterium. In some embodiments, the isotope of the isotope-labelled component is $^{13}C$ or $^{15}N$.

In some embodiments, a reagent is used for assaying in a sample a concentration of at least one Group A, Group B, Group C, Group D, Group E and/or Group F biomarker of the present disclosure.

In some embodiments, a reagent is used in a preparation of a reagent, kit or composition for performing the methods and uses of the present disclosure.

As used herein, "assaying" or "detecting" refers also to a measurement of a quantity of the fatty liver biomarkers of this disclosure in a biological sample using e.g., mass spectrometry.

EXAMPLES

The following examples are provided to illustrate various aspects of the present disclosure. They are not intended to limit the disclosure, which is defined by the accompanying claims.

Example 1. Materials and Methods

Description of Study Cohorts and Samples
AusDiab
A subcohort from the Australian Diabetes, Obesity and Lifestyle (AusDiab) study was utilized. AusDiab is a prospective study examining the prevalence and risk factors of T2D and CVD in the Australian population. The AusDiab subcohort is a case control cohort (age and gender matched, n=426 controls, 220 cases). Cases are those individuals who develop type 2 diabetes in the 5-year follow-up period, controls are those individuals who do not develop type 2 diabetes in the five-year follow-up period.

FINRISK 2002
The FINRISK survey has been performed every 5 years since 1972 mainly to monitor trends in cardiovascular risk factors in the Finnish population. The FINRISK 2002 study is a stratified random sample of the population aged 25-74 years from specific geographical areas of Finland. The survey included participants from North Karelia and Northern Savo in eastern Finland, Turku and Loimaa regions in southwestern Finland, the cities of Helsinki and Vantaa in the capital region, the provinces of Northern Ostrobothnia and Kainuu in northwestern Finland and the province of Lapland in northern Finland. The sampling was stratified by sex, region and 10-year age groups so that each stratum had 250 participants. In North Karelia, Lapland and the cities of Helsinki and Vantaa, the strata of 65-74 year old men and women were also sampled, each with 250 participants. The original population sample was thus 13,500 (minus 64 who had died or moved away between sampling and the survey); the overall participation rate was 65.5%, including a questionnaire and a health examination where blood samples were drawn. The study protocol was approved by the Coordinating Ethics Committee of the Helsinki University Hospital District and all participants gave a written informed consent.

Participants (N=8,045), of whom 442 had prevalent DM2 and 455 developed incident DM2 during follow-up, were advised to fast for ≥4 hrs and avoid heavy meals earlier during the day. Serum was separated and stored in −70° C. Some analytes, e.g. conventional lipids, were measured immediately. The participants were followed through 31 Dec. 2014, i.e. 13 years. Only participants who had moved permanently abroad (<1%) prior to disease event or Dec. 31, 2014 were lost to follow-up. Prevalent diseases were defined as those prior to or at the baseline examination date, incident events as those thereafter. Cases of incident diabetes during the follow-up were identified by record linkage of the FINRISK data with the country-wide electronic health registers on the basis of the personal ID-code, unique to every permanent resident of Finland. These included Causes-of-Death Register, Hospital Discharge Register and the Drug Reimbursement Registers. Pregnant women were excluded from all analyses.

Young Finns Study
The Cardiovascular Risk in Young Finns Study is a Finnish longitudinal general population study on the evolution of cardiovascular risk factors from childhood to adulthood. The study was initiated in 1980, when children and adolescents aged 3-18 years were randomly selected from five university hospital areas in Finland. Here, we used samples obtained in 2007, when 2,200 participants aged 30-45 years attended the 27-year follow-up.

Analytical Methods
AusDiab
Liquid Chromatography Mass Spectrometry
The extraction process was as follows: 10 μL of plasma was mixed with 100 μL of butanol:methanol (1:1) with 10 mM ammonium formate which contained a mixture of internal standards. Samples were vortexed thoroughly and set in a sonicator bath for 1 hour, maintained at room temperature. Samples were then centrifuged (14,000×g, 10 min, 20° C.) before the supernatant was transferred into sample vials with glass inserts for analysis.

Mass spectrometry analysis of extracted samples was carried out on an Agilent 6490 QQQ mass spectrometer with an Agilent 1290 series HPLC system and a ZORBAX eclipse plus C18 column (2.1×100 mm 1.8 µm, rapid resolution high definition column, Agilent) with the thermostat set at 60° C. Mass spectrometry analysis was performed in positive ion mode with dynamic scheduled multiple reaction monitoring (MRM). The solvent system consisted of solvent a) 50% $H_2O$/30% acetonitrile/20% isopropanol (v/v/v) with 10 mM ammonium formate and solvent b) 1% $H_2O$/9% acetonitrile/90% isopropanol (v/v/v) with 10 mM ammonium formate. A nonlinear gradient with a 15 minute cycle time and a 1 µL sample injection was utilized. The following mass spectrometer conditions were used; gas temperature, 150° C., gas flow rate 17 L/min, nebulizer 20 psi, Sheath gas temperature 200° C. and sheath gas flow 10 L/min.

Quality control samples (QC) consisted of a pooled plasma sample and were incorporated into the analysis at 1 QC per 10 plasma samples. Technical quality control samples (TQC) consisted of QC extracts which were pooled and split into individual vials to provide a measure of technical variation from the mass spectrometer only. These were included at a ratio of 1 TQC per 20 plasma samples. TQCs were monitored for changes in peak area, width and retention time to determine the performance of the LC-MS/MS analysis and was subsequently used to align for chromatographic drift.

FINRISK 2002
Liquid Chromatography Mass Spectrometry

Ceramide quantification from serum samples was performed using a validated high-throughput mass spectrometry approach. 10 µL of serum or plasma was spiked with deuterated internal standards, D7-Cer(d18:1/16:0), D7-Cer (d18:1/18:0), D7-Cer(d18:1/24:0) and D7-Cer(d18:1/24:1), and extracted in isopropanol:ethyl acetate (8:2, v/v) using a Hamilton MICROLAB® STAR robot. The levels of Cer (d18:1/16:0), Cer(d18:1/18:0), Cer(d18:1/24:0) and Cer (d18:1/24:1) were quantified on a QTRAP™ 6500 (SCIEX, Concord, Canada) mass spectrometer equipped with an Eksigent 100-XL UHPLC system. The individual ceramides were quantified in MRM mode. Quantification was assessed through calibration line samples comprising of known amounts of synthetic Cer(d18:1/16:0), Cer(d18:1/18:0), Cer (d18:1/24:0) and Cer(d18:1/24:1) and corresponding deuterated standards. The peak area ratios of each ceramide to its corresponding deuterated form were calculated and plotted against the added ceramide concentration and fitted by linear regression analysis. Final ceramide concentrations were presented in µM.

Young Finns Study
Liquid Chromatography Mass Spectrometry

10 µl of sample was used for the extraction of the lipids using a modified Folch extraction. The analysis was performed on a hybrid triple quadrupole/linear ion trap mass spectrometer (QTRAP 5500, AB Sciex, Concords, Canada) equipped with ultra-high-performance liquid chromatography (UHPLC) (Nexera-X2, Shimadzu, Kyoto, Japan). Chromatographic separation was performed on Acquity BEH C18, 2.1×50 mm id. 1.7 µm column (Waters, Massachusetts, USA). Mobile phases consisted of (A) 10 mM ammonium acetate in LC-MS grade water with 0.1% formic acid, and (B) 10 mM ammonium acetate in acetonitrile:2-propanol (3:4, V/V) with 0.1% formic acid (FA). The following LC gradient was used: 0.3 min at 45% B, linear increase of B from 45% to 95% in 10 min, 95% to 100% B in 0.1 min, 2.5 min at 100% B, 100% to 45% B in 0.1 min and 1.5 min equilibration at 45% prior to the next injection. Flow rate was 600 µl/min and column temperature 60° C. For the MS analysis, a targeted approach in the positive ion mode was used. The data were collected using a scheduled multiple reaction monitoring (sMRM™) algorithm. The lipidomic data were processed using Analyst and MultiQuant 3.0 software (AB Sciex), and the area or height ratios of the analyte and its corresponding IS peak were normalized with the IS amount and the sample volume.

Statistical Analyses
AusDiab

Logistic regression models were constructed to obtain the odds ratios (ORs), 95% confidence interval for ORs and p-values for lipid ratios or individual lipids. The significance of the lipid ratios vs. individual lipids was estimated based on the p-values.

FINRISK 2002

Cross-validated logistic regression models were constructed based on FINRISK to predict the 10-year risk of incident diabetes: ⅔ of incident diabetes cases and those who remained event-free during the 10 year period were taken as a training set, and ⅓ as a validation set, drawn randomly 1000 times for men and women separately, and the mean cross-validated regression coefficients were obtained. Mean AUC values were determined form the validation set. In FINRISK, all those subjects who had died before 10 and had not developed incident diabetes, were excluded from the analyses.

Young Finns Study

Logistic regression models were constructed to obtain the odds ratios (ORs), 95% confidence interval for ORs and p-values for lipid ratios or individual lipids. The significance of the lipid ratios vs. individual lipids was estimated based on the p-values.

Example 2. Results

AusDiab

Table 3 shows statistically significant Odds Ratios (p<0.05) based on combination biomarker values of at least one diabetes biomarker from Group A and at least one diabetes biomarker from Group B, and Odds Ratios based on combination biomarker values of at least one diabetes biomarker from Group C and the diabetes biomarker from Group D in subjects who developed diabetes during the follow-up as compared to a control group.

TABLE 3

Odds Ratios based on combination biomarker values of Group A and Group B, and Group C and Group D diabetes biomarkers in subjects who developed diabetes during the follow-up as compared to a control group in AusDiab study cohort according to some embodiments of all aspects of the present disclosure. Abbreviations are described in the detailed description of the present disclosure.

| Lipids | OR | CI_LOW | CI_HIGH | p_value |
|---|---|---|---|---|
| Cer(d16:1/18:0)/Cer(d18:1/16:0) | 1.52 | 1.28 | 1.79 | 1.2E−06 |
| Cer(d16:1/18:0)/Cer(d18:2/26:0) | 1.73 | 1.46 | 2.06 | 4.1E−10 |
| Cer(d16:1/18:0)/Cer(d19:1/26:0) | 1.65 | 1.39 | 1.97 | 1.6E−08 |

TABLE 3-continued

Odds Ratios based on combination biomarker values of Group A and Group B, and Group C and Group D diabetes biomarkers in subjects who developed diabetes during the follow-up as compared to a control group in AusDiab study cohort according to some embodiments of all aspects of the present disclosure. Abbreviations are described in the detailed description of the present disclosure.

| Lipids | OR | CI_LOW | CI_HIGH | p_value |
|---|---|---|---|---|
| Cer(d16:1/18:0)/LPC(17:0) [sn2] | 1.64 | 1.38 | 1.95 | 1.7E−08 |
| Cer(d16:1/18:0)/LPC(MHDA) [sn1] | 1.67 | 1.40 | 1.99 | 7.1E−09 |
| Cer(d16:1/18:0)/LPC(MHDA) [sn2] | 1.68 | 1.41 | 2.00 | 4.3E−09 |
| Cer(d16:1/18:0)/LPC(17:0) [sn1] | 1.56 | 1.31 | 1.85 | 3.1E−07 |
| Cer(d16:1/18:0)/LPC(18:2) [sn2] | 1.51 | 1.28 | 1.79 | 1.4E−06 |
| Cer(d16:1/18:0)/LPC(20:2) [sn1] | 1.49 | 1.26 | 1.76 | 2.8E−06 |
| Cer(d16:1/18:0)/LPC(22:1) [sn1] | 1.49 | 1.26 | 1.76 | 3.2E−06 |
| Cer(d16:1/18:0)/LPC(24:0) [sn1] | 1.52 | 1.28 | 1.79 | 1.0E−06 |
| Cer(d16:1/18:0)/LPC(24:0) [sn2] | 1.57 | 1.33 | 1.86 | 1.6E−07 |
| Cer(d16:1/18:0)/LPC(26:0) [sn1] | 1.66 | 1.40 | 1.97 | 7.3E−09 |
| Cer(d16:1/18:0)/LPC(26:0) [sn2] | 1.64 | 1.39 | 1.94 | 1.1E−08 |
| Cer(d16:1/18:0)/LPC(P-17:0) | 1.54 | 1.30 | 1.82 | 5.4E−07 |
| Cer(d16:1/18:0)/LPC(P-18:0) | 1.51 | 1.27 | 1.78 | 1.8E−06 |
| Cer(d16:1/18:0)/LPC(P-20:0) | 1.67 | 1.39 | 2.00 | 2.8E−08 |
| Cer(d16:1/18:0)/LPE(P-20:0) | 1.54 | 1.30 | 1.83 | 6.9E−07 |
| Cer(d16:1/18:0)/PC(MHDA_18:1) | 1.64 | 1.38 | 1.94 | 1.5E−08 |
| Cer(d16:1/18:0)/PC(MHDA_18:2) | 1.72 | 1.45 | 2.05 | 8.5E−10 |
| Cer(d16:1/18:0)/PC(MHDA_22:6) | 1.90 | 1.58 | 2.28 | 6.3E−12 |
| Cer(d16:1/18:0)/PC(17:0_22:6) | 1.72 | 1.44 | 2.07 | 5.0E−09 |
| Cer(d16:1/18:0)/PI(37:6) | 1.62 | 1.36 | 1.94 | 1.1E−07 |
| Cer(d16:1/18:0)/SM(d16:1/19:0) | 1.79 | 1.50 | 2.13 | 1.2E−10 |
| Cer(d16:1/18:0)/SM(d17:1/14:0) | 1.88 | 1.58 | 2.25 | 2.8E−12 |
| Cer(d16:1/18:0)/SM(d17:1/16:0) | 1.82 | 1.53 | 2.17 | 2.3E−11 |
| Cer(d16:1/18:0)/SM(d17:1/24:1) | 1.84 | 1.54 | 2.20 | 1.8E−11 |
| Cer(d16:1/18:0)/SM(d18:2/17:0) | 1.84 | 1.54 | 2.20 | 1.3E−11 |
| Cer(d16:1/18:0)/SM(d18:2/18:1) | 1.73 | 1.45 | 2.06 | 1.2E−09 |
| Cer(d16:1/18:0)/SM(d18:2/23:0) | 1.85 | 1.54 | 2.21 | 2.2E−11 |
| Cer(d16:1/18:0)/SM(d18:2/24:0) | 1.67 | 1.40 | 1.98 | 5.9E−09 |
| Cer(d16:1/20:0)/Cer(d18:2/26:0) | 1.72 | 1.44 | 2.04 | 1.6E−09 |
| Cer(d16:1/20:0)/Cer(d19:1/26:0) | 1.60 | 1.34 | 1.91 | 1.7E−07 |
| Cer(d16:1/20:0)/LPC(17:0) [sn2] | 1.64 | 1.39 | 1.95 | 1.0E−08 |
| Cer(d16:1/20:0)/LPC(MHDA) [sn1] | 1.67 | 1.41 | 1.98 | 4.4E−09 |
| Cer(d16:1/20:0)/LPC(MHDA) [sn2] | 1.68 | 1.41 | 1.99 | 3.2E−09 |
| Cer(d16:1/20:0)/LPC(17:0) [sn1] | 1.54 | 1.30 | 1.82 | 3.9E−07 |
| Cer(d16:1/20:0)/LPC(18:2) [sn1] | 1.51 | 1.27 | 1.78 | 2.0E−06 |
| Cer(d16:1/20:0)/LPC(18:2) [sn2] | 1.53 | 1.29 | 1.81 | 1.0E−06 |
| Cer(d16:1/20:0)/LPC(19:0) [sn2] | 1.52 | 1.28 | 1.80 | 1.8E−06 |
| Cer(d16:1/20:0)/LPC(19:0) [sn1] | 1.50 | 1.27 | 1.78 | 2.7E−06 |
| Cer(d16:1/20:0)/LPC(20:1) [sn1] | 1.48 | 1.25 | 1.75 | 4.9E−06 |
| Cer(d16:1/20:0)/LPC(20:2) [sn1] | 1.49 | 1.26 | 1.76 | 2.3E−06 |
| Cer(d16:1/20:0)/LPC(22:0) [sn1] | 1.48 | 1.25 | 1.75 | 4.1E−06 |
| Cer(d16:1/20:0)/LPC(22:1) [sn1] | 1.49 | 1.26 | 1.76 | 3.4E−06 |
| Cer(d16:1/20:0)/LPC(24:0) [sn1] | 1.50 | 1.27 | 1.77 | 2.0E−06 |
| Cer(d16:1/20:0)/LPC(24:0) [sn2] | 1.55 | 1.31 | 1.83 | 4.6E−07 |
| Cer(d16:1/20:0)/LPC(26:0) [sn1] | 1.64 | 1.38 | 1.96 | 2.3E−08 |
| Cer(d16:1/20:0)/LPC(26:0) [sn2] | 1.59 | 1.34 | 1.89 | 7.9E−08 |
| Cer(d16:1/20:0)/LPC(P-17:0) | 1.52 | 1.28 | 1.80 | 1.3E−06 |
| Cer(d16:1/20:0)/LPC(P-18:0) | 1.48 | 1.25 | 1.75 | 6.1E−06 |
| Cer(d16:1/20:0)/LPC(P-20:0) | 1.69 | 1.40 | 2.04 | 3.6E−08 |
| Cer(d16:1/20:0)/LPE(P-20:0) | 1.54 | 1.29 | 1.83 | 1.2E−06 |
| Cer(d16:1/20:0)/PC(MHDA_18:1) | 1.58 | 1.34 | 1.87 | 8.0E−08 |
| Cer(d16:1/20:0)/PC(MHDA_18:2) | 1.73 | 1.46 | 2.06 | 4.7E−10 |
| Cer(d16:1/20:0)/PC(MHDA_22:6) | 1.85 | 1.55 | 2.21 | 1.5E−11 |
| Cer(d16:1/20:0)/PC(17:0_22:6) | 1.66 | 1.39 | 1.98 | 1.8E−08 |
| Cer(d16:1/20:0)/PI(37:6) | 1.66 | 1.38 | 1.98 | 3.8E−08 |
| Cer(d16:1/20:0)/SM(d16:1/19:0) | 1.72 | 1.44 | 2.05 | 1.5E−09 |
| Cer(d16:1/20:0)/SM(d17:1/14:0) | 1.90 | 1.59 | 2.28 | 2.7E−12 |
| Cer(d16:1/20:0)/SM(d17:1/16:0) | 1.79 | 1.50 | 2.13 | 8.2E−11 |
| Cer(d 16:1/20:0)/SM(d17:1/24:1) | 1.81 | 1.52 | 2.17 | 5.6E−11 |
| Cer(d16:1/20:0)/SM(d18:2/17:0) | 1.78 | 1.49 | 2.14 | 2.6E−10 |
| Cer(d16:1/20:0)/SM(d18:2/18:1) | 1.66 | 1.39 | 1.98 | 1.5E−08 |
| Cer(d16:1/20:0)/SM(d18:2/23:0) | 1.81 | 1.51 | 2.16 | 1.6E−10 |
| Cer(d16:1/20:0)/SM(d18:2/24:0) | 1.62 | 1.36 | 1.92 | 3.8E−08 |
| Cer(d16:1/22:0)/Cer(d18:2/26:0) | 1.65 | 1.39 | 1.97 | 1.9E−08 |
| Cer(d16:1/22:0)/Cer(d19:1/26:0) | 1.53 | 1.28 | 1.82 | 2.7E−06 |
| Cer(d16:1/22:0)/LPC(17:0) [sn2] | 1.65 | 1.39 | 1.96 | 7.0E−09 |
| Cer(d16:1/22:0)/LPC(MHDA) [sn1] | 1.68 | 1.42 | 2.00 | 2.4E−09 |
| Cer(d16:1/22:0)/LPC(MHDA) [sn2] | 1.69 | 1.42 | 2.00 | 1.8E−09 |
| Cer(d16:1/22:0)/LPC(17:0) [sn1] | 1.54 | 1.31 | 1.83 | 3.6E−07 |
| Cer(d16:1/22:0)/LPC(18:2) [sn1] | 1.58 | 1.33 | 1.89 | 3.2E−07 |
| Cer(d16:1/22:0)/LPC(18:2) [sn2] | 1.58 | 1.32 | 1.89 | 4.1E−07 |
| Cer(d16:1/22:0)/LPC(19:0) [sn2] | 1.53 | 1.29 | 1.81 | 8.1E−07 |

TABLE 3-continued

Odds Ratios based on combination biomarker values of Group A and Group B, and Group C and Group D diabetes biomarkers in subjects who developed diabetes during the follow-up as compared to a control group in AusDiab study cohort according to some embodiments of all aspects of the present disclosure. Abbreviations are described in the detailed description of the present disclosure.

| Lipids | OR | CI_LOW | CI_HIGH | p_value |
|---|---|---|---|---|
| Cer(d16:1/22:0)/LPC(19:0) [sn1] | 1.53 | 1.29 | 1.81 | 8.1E−07 |
| Cer(d16:1/22:0)/LPC(20:0) [sn2] | 1.46 | 1.24 | 1.73 | 8.0E−06 |
| Cer(d16:1/22:0)/LPC(20:1) [sn1] | 1.48 | 1.25 | 1.75 | 6.0E−06 |
| Cer(d16:1/22:0)/LPC(20:1) [sn2] | 1.45 | 1.23 | 1.71 | 1.3E−05 |
| Cer(d16:1/22:0)/LPC(20:2) [sn1] | 1.51 | 1.28 | 1.78 | 1.4E−06 |
| Cer(d16:1/22:0)/LPC(22:0) [sn1] | 1.49 | 1.26 | 1.76 | 3.6E−06 |
| Cer(d16:1/22:0)/LPC(22:1) [sn1] | 1.49 | 1.25 | 1.77 | 6.9E−06 |
| Cer(d16:1/22:0)/LPC(22:1) [sn2] | 1.50 | 1.25 | 1.81 | 1.1E−05 |
| Cer(d16:1/22:0)/LPC(24:0) [sn1] | 1.49 | 1.26 | 1.76 | 3.8E−06 |
| Cer(d16:1/22:0)/LPC(24:0) [sn2] | 1.53 | 1.29 | 1.82 | 8.0E−07 |
| Cer(d16:1/22:0)/LPC(26:0) [sn1] | 1.59 | 1.33 | 1.89 | 2.0E−07 |
| Cer(d16:1/22:0)/LPC(26:0) [sn2] | 1.57 | 1.32 | 1.86 | 3.0E−07 |
| Cer(d16:1/22:0)/LPC(P-16:0) | 1.47 | 1.24 | 1.74 | 1.2E−05 |
| Cer(d16:1/22:0)/LPC(P-17:0) | 1.52 | 1.28 | 1.80 | 1.7E−06 |
| Cer(d16:1/22:0)/LPC(P-18:0) | 1.49 | 1.25 | 1.78 | 1.0E−05 |
| Cer(d16:1/22:0)/LPC(P-18:1) | 1.41 | 1.19 | 1.67 | 8.9E−05 |
| Cer(d16:1/22:0)/LPC(P-20:0) | 1.72 | 1.42 | 2.10 | 4.3E−08 |
| Cer(d16:1/22:0)/LPE(P-20:0) | 1.54 | 1.29 | 1.83 | 1.5E−06 |
| Cer(d16:1/22:0)/PC(MHDA_18:1) | 1.54 | 1.31 | 1.82 | 3.3E−07 |
| Cer(d16:1/22:0)/PC(MHDA_18:2) | 1.75 | 1.46 | 2.08 | 5.8E−10 |
| Cer(d16:1/22:0)/PC(MHDA_22:6) | 1.75 | 1.47 | 2.08 | 2.9E−10 |
| Cer(d16:1/22:0)/PC(17:0_22:6) | 1.57 | 1.32 | 1.86 | 1.8E−07 |
| Cer(d16:1/22:0)/PI(37:6) | 1.68 | 1.39 | 2.02 | 4.6E−08 |
| Cer(d16:1/22:0)/SM(d16:1/19:0) | 1.63 | 1.37 | 1.94 | 4.2E−08 |
| Cer(d16:1/22:0)/SM(d17:1/14:0) | 1.83 | 1.53 | 2.17 | 1.7E−11 |
| Cer(d16:1/22:0)/SM(d17:1/16:0) | 1.71 | 1.43 | 2.03 | 2.0E−09 |
| Cer(d16:1/22:0)/SM(d17:1/24:1) | 1.66 | 1.39 | 1.97 | 1.2E−08 |
| Cer(d16:1/22:0)/SM(d18:2/17:0) | 1.66 | 1.40 | 1.98 | 1.3E−08 |
| Cer(d16:1/22:0)/SM(d18:2/18:1) | 1.56 | 1.32 | 1.86 | 3.9E−07 |
| Cer(d16:1/22:0)/SM(d18:2/23:0) | 1.73 | 1.45 | 2.06 | 1.4E−09 |
| Cer(d16:1/22:0)/SM(d18:2/24:0) | 1.57 | 1.33 | 1.87 | 2.0E−07 |
| Cer(d17:1/20:0)/Cer(d18:2/26:0) | 1.41 | 1.20 | 1.66 | 4.5E−05 |
| Cer(d17:1/20:0)/Cer(d19:1/26:0) | 1.40 | 1.19 | 1.65 | 5.8E−05 |
| Cer(d17:1/20:0)/LPC(17:0) [sn2] | 1.48 | 1.26 | 1.75 | 3.0E−06 |
| Cer(d17:1/20:0)/LPC(MHDA) [sn1] | 1.51 | 1.28 | 1.79 | 9.1E−07 |
| Cer(d17:1/20:0)/LPC(MHDA) [sn2] | 1.52 | 1.29 | 1.79 | 7.8E−07 |
| Cer(d17:1/20:0)/LPC(17:0) [sn1] | 1.39 | 1.18 | 1.64 | 7.4E−05 |
| Cer(d17:1/20:0)/LPC(18:2) [sn1] | 1.41 | 1.20 | 1.66 | 3.7E−05 |
| Cer(d17:1/20:0)/LPC(18:2) [sn2] | 1.39 | 1.18 | 1.63 | 8.6E−05 |
| Cer(d17:1/20:0)/LPC(19:0) [sn2] | 1.36 | 1.16 | 1.60 | 1.9E−04 |
| Cer(d17:1/20:0)/LPC(19:0) [sn1] | 1.37 | 1.16 | 1.61 | 1.6E−04 |
| Cer(d17:1/20:0)/LPC(20:0) [sn2] | 1.32 | 1.12 | 1.55 | 7.2E−04 |
| Cer(d17:1/20:0)/LPC(20:1) [sn1] | 1.36 | 1.16 | 1.60 | 2.1E−04 |
| Cer(d17:1/20:0)/LPC(20:1) [sn2] | 1.33 | 1.13 | 1.56 | 5.3E−04 |
| Cer(d17:1/20:0)/LPC(20:2) [sn1] | 1.34 | 1.14 | 1.57 | 4.6E−04 |
| Cer(d17:1/20:0)/LPC(22:0) [sn1] | 1.32 | 1.13 | 1.56 | 6.7E−04 |
| Cer(d17:1/20:0)/LPC(22:1) [sn1] | 1.36 | 1.16 | 1.60 | 1.9E−04 |
| Cer(d17:1/20:0)/LPC(22:1) [sn2] | 1.37 | 1.16 | 1.62 | 1.8E−04 |
| Cer(d17:1/20:0)/LPC(24:0) [sn1] | 1.30 | 1.11 | 1.53 | 1.3E−03 |
| Cer(d17:1/20:0)/LPC(24:0) [sn2] | 1.34 | 1.14 | 1.58 | 3.5E−04 |
| Cer(d17:1/20:0)/LPC(26:0) [sn2] | 1.42 | 1.21 | 1.67 | 2.6E−05 |
| Cer(d17:1/20:0)/LPC(P-16:0) | 1.34 | 1.14 | 1.58 | 3.7E−04 |
| Cer(d17:1/20:0)/LPC(P-17:0) | 1.40 | 1.19 | 1.65 | 4.8E−05 |
| Cer(d17:1/20:0)/LPC(P-18:0) | 1.38 | 1.17 | 1.63 | 1.1E−04 |
| Cer(d17:1/20:0)/LPC(P-18:1) | 1.30 | 1.11 | 1.53 | 1.3E−03 |
| Cer(d17:1/20:0)/LPE(P-20:0) | 1.37 | 1.16 | 1.61 | 2.0E−04 |
| Cer(d17:1/20:0)/PC(MHDA_18:1) | 1.38 | 1.17 | 1.62 | 1.3E−04 |
| Cer(d17:1/20:0)/PC(MHDA_18:2) | 1.52 | 1.29 | 1.80 | 8.7E−07 |
| Cer(d17:1/20:0)/PC(MHDA_22:6) | 1.62 | 1.37 | 1.92 | 1.8E−08 |
| Cer(d17:1/20:0)/PC(17:0_22:6) | 1.46 | 1.24 | 1.73 | 7.8E−06 |
| Cer(d17:1/20:0)/PI(37:6) | 1.49 | 1.26 | 1.76 | 4.2E−06 |
| Cer(d17:1/20:0)/SM(d16:1/19:0) | 1.46 | 1.24 | 1.73 | 8.0E−06 |
| Cer(d17:1/20:0)/SM(d17:1/14:0) | 1.49 | 1.25 | 1.78 | 6.8E−06 |
| Cer(d17:1/20:0)/SM(d17:1/16:0) | 1.46 | 1.23 | 1.73 | 1.4E−05 |
| Cer(d17:1/20:0)/SM(d17:1/24:1) | 1.49 | 1.26 | 1.76 | 3.9E−06 |
| Cer(d17:1/20:0)/SM(d18:2/17:0) | 1.49 | 1.25 | 1.77 | 6.1E−06 |
| Cer(d17:1/20:0)/SM(d18:2/18:1) | 1.40 | 1.19 | 1.65 | 6.9E−05 |
| Cer(d17:1/20:0)/SM(d18:2/23:0) | 1.48 | 1.25 | 1.76 | 5.3E−06 |
| Cer(d17:1/20:0)/SM(d18:2/24:0) | 1.37 | 1.16 | 1.61 | 1.6E−04 |
| Cer(d18:1/16:0)/Cer(d18:2/26:0) | 1.44 | 1.22 | 1.71 | 2.0E−05 |
| Cer(d18:1/16:0)/Cer(d19:1/26:0) | 1.31 | 1.11 | 1.55 | 1.1E−03 |
| Cer(d18:1/16:0)/LPC(17:0) [sn2] | 1.37 | 1.16 | 1.61 | 1.5E−04 |

TABLE 3-continued

Odds Ratios based on combination biomarker values of Group A and Group B, and Group C and Group D diabetes biomarkers in subjects who developed diabetes during the follow-up as compared to a control group in AusDiab study cohort according to some embodiments of all aspects of the present disclosure. Abbreviations are described in the detailed description of the present disclosure.

| Lipids | OR | CI_LOW | CI_HIGH | p_value |
|---|---|---|---|---|
| Cer(d18:1/16:0)/LPC(MHDA) [sn1] | 1.39 | 1.18 | 1.64 | 6.9E−05 |
| Cer(d18:1/16:0)/LPC(MHDA) [sn2] | 1.40 | 1.19 | 1.65 | 5.4E−05 |
| Cer(d18:1/16:0)/LPC(17:0) [sn1] | 1.31 | 1.11 | 1.54 | 1.2E−03 |
| Cer(d18:1/16:0)/LPC(20:0) [sn2] | 1.23 | 1.04 | 1.45 | 1.4E−02 |
| Cer(d18:1/16:0)/LPC(20:1) [sn1] | 1.30 | 1.10 | 1.53 | 1.6E−03 |
| Cer(d18:1/16:0)/LPC(22:0) [sn1] | 1.26 | 1.07 | 1.49 | 4.8E−03 |
| Cer(d18:1/16:0)/LPC(22:1) [sn1] | 1.31 | 1.11 | 1.54 | 1.2E−03 |
| Cer(d18:1/16:0)/LPC(22:1) [sn2] | 1.31 | 1.11 | 1.54 | 1.4E−03 |
| Cer(d18:1/16:0)/LPC(24:0) [sn1] | 1.30 | 1.10 | 1.53 | 1.5E−03 |
| Cer(d18:1/16:0)/LPC(24:0) [sn2] | 1.33 | 1.13 | 1.57 | 5.1E−04 |
| Cer(d18:1/16:0)/LPC(26:0) [sn2] | 1.45 | 1.23 | 1.71 | 1.2E−05 |
| Cer(d18:1/16:0)/LPC(P-16:0) | 1.29 | 1.10 | 1.52 | 1.8E−03 |
| Cer(d18:1/16:0)/LPC(P-17:0) | 1.32 | 1.13 | 1.56 | 6.4E−04 |
| Cer(d18:1/16:0)/LPC(P-18:0) | 1.32 | 1.12 | 1.55 | 7.9E−04 |
| Cer(d18:1/16:0)/LPC(P-18:1) | 1.27 | 1.08 | 1.49 | 3.5E−03 |
| Cer(d18:1/16:0)/LPE(P-200) | 1.34 | 1.14 | 1.58 | 5.3E−04 |
| Cer(d18:1/16:0)/PC(MHDA_18:1) | 1.30 | 1.11 | 1.53 | 1.5E−03 |
| Cer(d18:1/16:0)/PC(MHDA_18:2) | 1.45 | 1.23 | 1.71 | 1.0E−05 |
| Cer(d18:1/16:0)/PC(MHDA_22:6) | 1.57 | 1.32 | 1.86 | 2.2E−07 |
| Cer(d18:1/16:0)/PC(17:0_22:6) | 1.42 | 1.20 | 1.67 | 4.7E−05 |
| Cer(d18:1/16:0)/PI(37:6) | 1.48 | 1.24 | 1.75 | 9.1E−06 |
| Cer(d18:1/16:0)/SM(d16:1/19:0) | 1.42 | 1.20 | 1.67 | 4.4E−05 |
| Cer(d18:1/16:0)/SM(d17:1/14:0) | 1.41 | 1.19 | 1.68 | 9.0E−05 |
| Cer(d18:1/16:0)/SM(d17:1/16:0) | 1.45 | 1.22 | 1.72 | 2.5E−05 |
| Cer(d18:1/16:0)/SM(d17:1/24:1) | 1.50 | 1.26 | 1.78 | 4.2E−06 |
| Cer(d18:1/16:0)/SM(d18:2/17:0) | 1.45 | 1.22 | 1.72 | 2.5E−05 |
| Cer(d18:1/16:0)/SM(d18:2/18:1) | 1.40 | 1.18 | 1.65 | 7.4E−05 |
| Cer(d18:1/16:0)/SM(d18:2/23:0) | 1.54 | 1.29 | 1.84 | 2.1E−06 |
| Cer(d18:1/16:0)/SM(d18:2/24:0) | 1.45 | 1.22 | 1.72 | 1.7E−05 |
| Cer(d18:1/18:0)/Cer(d18:1/16:0) | 1.56 | 1.32 | 1.85 | 2.5E−07 |
| Cer(d18:1/18:0)/Cer(d18:2/26:0) | 1.69 | 1.42 | 2.01 | 2.1E−09 |
| Cer(d18:1/18:0)/Cer(d19:1/26:0) | 1.56 | 1.31 | 1.86 | 5.1E−07 |
| Cer(d18:1/18:0)/LPC(17:0) [sn2] | 1.59 | 1.34 | 1.89 | 1.2E−07 |
| Cer(d18:1/18:0)/LPC(MHDA) [sn1] | 1.61 | 1.35 | 1.91 | 6.5E−08 |
| Cer(d18:1/18:0)/LPC(MHDA) [sn2] | 1.62 | 1.36 | 1.93 | 4.7E−08 |
| Cer(d18:1/18:0)/LPC(17:0) [sn1] | 1.54 | 1.30 | 1.83 | 8.0E−07 |
| Cer(d18:1/18:0)/LPC(24:0) [sn2] | 1.52 | 1.29 | 1.80 | 8.4E−07 |
| Cer(d18:1/18:0)/LPC(26:0) [sn1] | 1.62 | 1.37 | 1.92 | 2.8E−08 |
| Cer(d18:1/18:0)/LPC(26:0) [sn2] | 1.60 | 1.34 | 1.90 | 1.1E−07 |
| Cer(d18:1/18:0)/LPC(P-17:0) | 1.52 | 1.28 | 1.80 | 1.6E−06 |
| Cer(d18:1/18:0)/LPC(P-18:0) | 1.51 | 1.27 | 1.78 | 2.0E−06 |
| Cer(d18:1/18:0)/LPC(P-20:0) | 1.70 | 1.42 | 2.02 | 3.0E−09 |
| Cer(d18:1/18:0)/LPE(P-20:0) | 1.55 | 1.30 | 1.84 | 7.2E−07 |
| Cer(d18:1/18:0)/PC(MHDA_18:1) | 1.57 | 1.32 | 1.86 | 3.6E−07 |
| Cer(d18:1/18:0)/PC(MHDA_18:2) | 1.66 | 1.38 | 1.98 | 4.3E−08 |
| Cer(d18:1/18:0)/PC(MHDA_22:6) | 1.83 | 1.52 | 2.19 | 6.4E−11 |
| Cer(d18:1/18:0)/PC(17:0_22:6) | 1.72 | 1.43 | 2.06 | 4.7E−09 |
| Cer(d18:1/18:0)/PI(37:6) | 1.65 | 1.37 | 2.00 | 2.1E−07 |
| Cer(d18:1/18:0)/SM(d16:1/19:0) | 1.74 | 1.46 | 2.07 | 8.0E−10 |
| Cer(d18:1/18:0)/SM(d17:1/14:0) | 1.62 | 1.36 | 1.93 | 6.8E−08 |
| Cer(d18:1/18:0)/SM(d17:1/16:0) | 1.69 | 1.42 | 2.01 | 2.8E−09 |
| Cer(d18:1/18:0)/SM(d17:1/24:1) | 1.79 | 1.50 | 2.13 | 1.1E−10 |
| Cer(d18:1/18:0)/SM(d18:2/17:0) | 1.84 | 1.54 | 2.20 | 2.6E−11 |
| Cer(d18:1/18:0)/SM(d18:2/18:1) | 1.75 | 1.47 | 2.09 | 7.1E−10 |
| Cer(d18:1/18:0)/SM(d18:2/23:0) | 1.78 | 1.49 | 2.12 | 1.7E−10 |
| Cer(d18:1/18:0)/SM(d18:2/24:0) | 1.65 | 1.39 | 1.96 | 7.4E−09 |
| Cer(d18:1/20:0)/Cer(d18:1/16:0) | 1.52 | 1.28 | 1.80 | 1.3E−06 |
| Cer(d18:1/20:0)/Cer(d18:2/26:0) | 1.68 | 1.41 | 2.00 | 4.5E−09 |
| Cer(d18:1/20:0)/Cer(d19:1/26:0) | 1.53 | 1.29 | 1.82 | 1.4E−06 |
| Cer(d18:1/20:0)/LPC(17:0) [sn2] | 1.59 | 1.34 | 1.88 | 9.7E−08 |
| Cer(d18:1/20:0)/LPC(MHDA) [sn1] | 1.59 | 1.34 | 1.88 | 9.2E−08 |
| Cer(d18:1/20:0)/LPC(MHDA) [sn2] | 1.60 | 1.34 | 1.90 | 9.8E−08 |
| Cer(d18:1/20:0)/LPC(17:0) [sn1] | 1.54 | 1.30 | 1.82 | 5.3E−07 |
| Cer(d18:1/20:0)/LPC(18:2) [sn1] | 1.51 | 1.28 | 1.79 | 1.8E−06 |
| Cer(d18:1/20:0)/LPC(18:2) [sn2] | 1.53 | 1.29 | 1.81 | 8.4E−07 |
| Cer(d18:1/20:0)/LPC(20:1) [sn1] | 1.50 | 1.26 | 1.77 | 3.0E−06 |
| Cer(d18:1/20:0)/LPC(20:2) [sn1] | 1.49 | 1.26 | 1.76 | 2.6E−06 |
| Cer(d18:1/20:0)/LPC(22:0) [sn1] | 1.49 | 1.26 | 1.77 | 3.7E−06 |
| Cer(d18:1/20:0)/LPC(22:1) [sn1] | 1.51 | 1.27 | 1.78 | 1.8E−06 |
| Cer(d18:1/20:0)/LPC(22:1) [sn2] | 1.52 | 1.28 | 1.80 | 1.7E−06 |
| Cer(d18:1/20:0)/LPC(24:0) [sn1] | 1.51 | 1.28 | 1.79 | 1.6E−06 |
| Cer(d18:1/20:0)/LPC(24:0) [sn2] | 1.55 | 1.31 | 1.84 | 4.0E−07 |

TABLE 3-continued

Odds Ratios based on combination biomarker values of Group A and Group B, and Group C and Group D diabetes biomarkers in subjects who developed diabetes during the follow-up as compared to a control group in AusDiab study cohort according to some embodiments of all aspects of the present disclosure. Abbreviations are described in the detailed description of the present disclosure.

| Lipids | OR | CI_LOW | CI_HIGH | p_value |
| --- | --- | --- | --- | --- |
| Cer(d18:1/20:0)/LPC(26:0) [sn1] | 1.64 | 1.38 | 1.94 | 1.8E−08 |
| Cer(d18:1/20:0)/LPC(26:0) [sn2] | 1.64 | 1.37 | 1.95 | 2.7E−08 |
| Cer(d18:1/20:0)/LPC(P-16:0) | 1.47 | 1.24 | 1.75 | 7.0E−06 |
| Cer(d18:1/20:0)/LPC(P-17:0) | 1.48 | 1.25 | 1.75 | 5.3E−06 |
| Cer(d18:1/20:0)/LPC(P-18:0) | 1.50 | 1.26 | 1.77 | 3.8E−06 |
| Cer(d18:1/20:0)/LPC(P-20:0) | 1.72 | 1.44 | 2.05 | 1.4E−09 |
| Cer(d18:1/20:0)/LPE(P-20:0) | 1.55 | 1.30 | 1.85 | 9.2E−07 |
| Cer(d18:1/20:0)/PC(MHDA_18:1) | 1.53 | 1.29 | 1.81 | 8.7E−07 |
| Cer(d18:1/20:0)/PC(MHDA_18:2) | 1.69 | 1.42 | 2.01 | 5.7E−09 |
| Cer(d18:1/20:0)/PC(MHDA_22:6) | 1.80 | 1.51 | 2.14 | 7.7E−11 |
| Cer(d18:1/20:0)/PC(17:0_22:6) | 1.67 | 1.40 | 2.00 | 1.4E−08 |
| Cer(d18:1/20:0)/PI(37:6) | 1.65 | 1.36 | 2.00 | 3.4E−07 |
| Cer(d18:1/20:0)/SM(d16:1/19:0) | 1.66 | 1.40 | 1.98 | 8.9E−09 |
| Cer(d18:1/20:0)/SM(d17:1/14:0) | 1.63 | 1.37 | 1.94 | 2.8E−08 |
| Cer(d18:1/20:0)/SM(d17:1/16:0) | 1.69 | 1.42 | 2.00 | 3.0E−09 |
| Cer(d18:1/20:0)/SM(d17:1/24:1) | 1.78 | 1.49 | 2.12 | 1.3E−10 |
| Cer(d18:1/20:0)/SM(d18:2/17:0) | 1.79 | 1.50 | 2.15 | 1.4E−10 |
| Cer(d18:1/20:0)/SM(d18:2/18:1) | 1.72 | 1.43 | 2.05 | 3.6E−09 |
| Cer(d18:1/20:0)/SM(d18:2/23:0) | 1.80 | 1.50 | 2.15 | 1.4E−10 |
| Cer(d18:1/20:0)/SM(d18:2/24:0) | 1.67 | 1.41 | 1.98 | 5.4E−09 |
| Cer(d18:1/21:0)/Cer(d18:2/26:0) | 1.55 | 1.31 | 1.84 | 5.3E−07 |
| Cer(d18:1/21:0)/Cer(d19:1/26:0) | 1.39 | 1.18 | 1.64 | 1.1E−04 |
| Cer(d18:1/21:0)/LPC(17:0) [sn2] | 1.47 | 1.24 | 1.73 | 5.2E−06 |
| Cer(d18:1/21:0)/LPC(MHDA) [sn1] | 1.49 | 1.26 | 1.76 | 2.6E−06 |
| Cer(d18:1/21:0)/LPC(MHDA) [sn2] | 1.49 | 1.26 | 1.76 | 2.5E−06 |
| Cer(d18:1/21:0)/LPC(17:0) [sn1] | 1.39 | 1.18 | 1.64 | 6.4E−05 |
| Cer(d18:1/21:0)/LPC(18:2) [sn2] | 1.39 | 1.18 | 1.64 | 6.7E−05 |
| Cer(d18:1/21:0)/LPC(19:0) [sn2] | 1.38 | 1.17 | 1.63 | 1.2E−04 |
| Cer(d18:1/21:0)/LPC(19:0) [sn1] | 1.37 | 1.16 | 1.62 | 1.7E−04 |
| Cer(d18:1/21:0)/LPC(20:0) [sn2] | 1.32 | 1.13 | 1.55 | 6.9E−04 |
| Cer(d18:1/21:0)/LPC(20:1) [sn1] | 1.37 | 1.16 | 1.61 | 1.6E−04 |
| Cer(d18:1/21:0)/LPC(20:1) [sn2] | 1.36 | 1.15 | 1.60 | 2.2E−04 |
| Cer(d18:1/21:0)/LPC(20:2) [sn1] | 1.37 | 1.17 | 1.61 | 1.4E−04 |
| Cer(d18:1/21:0)/LPC(22:0) [sn1] | 1.34 | 1.13 | 1.57 | 4.9E−04 |
| Cer(d18:1/21:0)/LPC(22:1) [sn1] | 1.37 | 1.16 | 1.61 | 1.4E−04 |
| Cer(d18:1/21:0)/LPC(22:1) [sn2] | 1.39 | 1.18 | 1.63 | 1.0E−04 |
| Cer(d18:1/21:0)/LPC(24:0) [sn1] | 1.36 | 1.16 | 1.60 | 2.0E−04 |
| Cer(d18:1/21:0)/LPC(24:0) [sn2] | 1.39 | 1.18 | 1.64 | 9.1E−05 |
| Cer(d18:1/21:0)/LPC(26:0) [sn2] | 1.47 | 1.24 | 1.75 | 1.3E−05 |
| Cer(d18:1/21:0)/LPC(P-16:0) | 1.33 | 1.13 | 1.57 | 5.5E−04 |
| Cer(d18:1/21:0)/LPC(P-17:0) | 1.38 | 1.17 | 1.62 | 1.2E−04 |
| Cer(d18:1/21:0)/LPC(P-18:0) | 1.34 | 1.14 | 1.58 | 4.5E−04 |
| Cer(d18:1/21:0)/LPC(P-18:1) | 1.31 | 1.11 | 1.54 | 1.1E−03 |
| Cer(d18:1/21:0)/LPE(P-20:0) | 1.37 | 1.17 | 1.62 | 1.5E−04 |
| Cer(d18:1/21:0)/PC(MHDA_18:1) | 1.43 | 1.22 | 1.69 | 1.7E−05 |
| Cer(d18:1/21:0)/PC(MHDA_18:2) | 1.59 | 1.34 | 1.89 | 1.2E−07 |
| Cer(d18:1/21:0)/PC(MHDA_22:6) | 1.70 | 1.43 | 2.02 | 2.2E−09 |
| Cer(d18:1/21:0)/PC(17:0_22:6) | 1.56 | 1.31 | 1.84 | 3.1E−07 |
| Cer(d18:1/21:0)/PI(37:6) | 1.56 | 1.30 | 1.87 | 1.7E−06 |
| Cer(d18:1/21:0)/SM(d16:1/19:0) | 1.51 | 1.27 | 1.79 | 2.4E−06 |
| Cer(d18:1/21:0)/SM(d17:1/14:0) | 1.55 | 1.31 | 1.84 | 3.2E−07 |
| Cer(d18:1/21:0)/SM(d17:1/16:0) | 1.52 | 1.28 | 1.81 | 2.0E−06 |
| Cer(d18:1/21:0)/SM(d17:1/24:1) | 1.61 | 1.35 | 1.91 | 1.2E−07 |
| Cer(d18:1/21:0)/SM(d18:2/17:0) | 1.65 | 1.38 | 1.97 | 4.4E−08 |
| Cer(d18:1/21:0)/SM(d18:2/18:1) | 1.57 | 1.32 | 1.87 | 2.3E−07 |
| Cer(d18:1/21:0)/SM(d18:2/23:0) | 1.65 | 1.38 | 1.97 | 2.7E−08 |
| Cer(d18:1/21:0)/SM(d18:2/24:0) | 1.46 | 1.23 | 1.73 | 1.4E−05 |
| Cer(d18:1/22:0)/Cer(d18:1/16:0) | 1.46 | 1.24 | 1.73 | 9.0E−06 |
| Cer(d18:1/22:0)/Cer(d18:2/26:0) | 1.72 | 1.44 | 2.04 | 8.9E−10 |
| Cer(d18:1/22:0)/Cer(d19:1/26:0) | 1.51 | 1.27 | 1.78 | 2.4E−06 |
| Cer(d18:1/22:0)/LPC(17:0) [sn2] | 1.66 | 1.40 | 1.97 | 6.8E−09 |
| Cer(d18:1/22:0)/LPC(MHDA) [sn1] | 1.66 | 1.40 | 1.96 | 6.8E−09 |
| Cer(d18:1/22:0)/LPC(MHDA) [sn2] | 1.67 | 1.40 | 1.98 | 5.6E−09 |
| Cer(d18:1/22:0)/LPC(17:0) [sn1] | 1.60 | 1.35 | 1.89 | 7.7E−08 |
| Cer(d18:1/22:0)/LPC(18:2) [sn1] | 1.63 | 1.37 | 1.95 | 3.4E−08 |
| Cer(d18:1/22:0)/LPC(18:2) [sn2] | 1.66 | 1.40 | 1.98 | 1.2E−08 |
| Cer(d18:1/22:0)/LPC(19:0) [sn2] | 1.56 | 1.30 | 1.86 | 1.2E−06 |
| Cer(d18:1/22:0)/LPC(19:0) [sn1] | 1.55 | 1.29 | 1.85 | 1.5E−06 |
| Cer(d18:1/22:0)/LPC(20:0) [sn2] | 1.52 | 1.28 | 1.80 | 1.7E−06 |
| Cer(d18:1/22:0)/LPC(20:1) [sn1] | 1.52 | 1.29 | 1.80 | 1.0E−06 |
| Cer(d18:1/22:0)/LPC(20:1) [sn2] | 1.49 | 1.26 | 1.77 | 3.1E−06 |
| Cer(d18:1/22:0)/LPC(20:2) [sn1] | 1.57 | 1.33 | 1.86 | 1.1E−07 |

TABLE 3-continued

Odds Ratios based on combination biomarker values of Group A and Group B, and Group C and Group D diabetes biomarkers in subjects who developed diabetes during the follow-up as compared to a control group in AusDiab study cohort according to some embodiments of all aspects of the present disclosure. Abbreviations are described in the detailed description of the present disclosure.

| Lipids | OR | CI_LOW | CI_HIGH | p_value |
|---|---|---|---|---|
| Cer(d18:1/22:0)/LPC(22:0) [sn1] | 1.56 | 1.31 | 1.85 | 3.7E−07 |
| Cer(d18:1/22:0)/LPC(22:1) [sn1] | 1.52 | 1.28 | 1.80 | 1.1E−06 |
| Cer(d18:1/22:0)/LPC(22:1) [sn2] | 1.55 | 1.30 | 1.84 | 8.1E−07 |
| Cer(d18:1/22:0)/LPC(24:0) [sn1] | 1.58 | 1.33 | 1.87 | 1.6E−07 |
| Cer(d18:1/22:0)/LPC(24:0) [sn2] | 1.63 | 1.38 | 1.94 | 2.1E−08 |
| Cer(d18:1/22:0)/LPC(26:0) [sn1] | 1.68 | 1.41 | 1.99 | 4.0E−09 |
| Cer(d18:1/22:0)/LPC(26:0) [sn2] | 1.67 | 1.40 | 2.00 | 1.3E−08 |
| Cer(d18:1/22:0)/LPC(P-16:0) | 1.53 | 1.29 | 1.82 | 9.4E−07 |
| Cer(d18:1/22:0)/LPC(P-17:0) | 1.53 | 1.29 | 1.82 | 7.6E−07 |
| Cer(d18:1/22:0)/LPC(P-18:0) | 1.56 | 1.32 | 1.86 | 4.1E−07 |
| Cerfd 18:1/22:0)/LPC(P-18:1) | 1.47 | 1.24 | 1.74 | 9.6E−06 |
| Cer(d18:1/22:0)/LPC(P-20:0) | 1.81 | 1.51 | 2.18 | 2.3E−10 |
| Cer(d18:1/22:0)/LPE(P-20:0) | 1.65 | 1.38 | 1.97 | 3.8E−08 |
| Cer(d18:1/22:0)/PC(MHDA_18:1) | 1.56 | 1.32 | 1.85 | 1.6E−07 |
| Cer(d18:1/22:0)/PC(MHDA_18:2) | 1.75 | 1.47 | 2.09 | 3.7E−10 |
| Cer(d18:1/22:0)/PC(MHDA_22:6) | 1.76 | 1.48 | 2.11 | 3.1E−10 |
| Cer(d18:1/22:0)/PC(17:0_22:6) | 1.62 | 1.36 | 1.93 | 9.6E−08 |
| Cer(d18:1/22:0)/PI(37:6) | 1.66 | 1.37 | 2.00 | 1.7E−07 |
| Cer(d18:1/22:0)/SM(d16:1/19:0) | 1.67 | 1.41 | 1.99 | 3.7E−09 |
| Cer(d18:1/22:0)/SM(d17:1/14:0) | 1.69 | 1.42 | 2.00 | 1.9E−09 |
| Cer(d18:1/22:0)/SM(d17:1/16:0) | 1.73 | 1.46 | 2.06 | 4.2E−10 |
| Cer(d18:1/22:0)/SM(d17:1/24:1) | 1.69 | 1.42 | 2.00 | 2.4E−09 |
| Cer(d18:1/22:0)/SM(d18:2/17:0) | 1.75 | 1.46 | 2.08 | 5.2E−10 |
| Cer(d18:1/22:0)/SM(d18:2/18:1) | 1.66 | 1.39 | 1.97 | 1.2E−08 |
| Cer(d18:1/22:0)/SM(d18:2/23:0) | 1.88 | 1.57 | 2.26 | 1.1E−11 |
| Cer(d18:1/22:0)/SM(d18:2/24:0) | 1.76 | 1.47 | 2.11 | 5.9E−10 |
| Cer(d19:1/18:0)/Cer(d18:2/26:0) | 1.38 | 1.17 | 1.63 | 1.5E−04 |
| Cer(d19:1/18:0)/Cer(d19:1/26:0) | 1.47 | 1.25 | 1.74 | 5.1E−06 |
| Cer(d19:1/18:0)/LPC(17:0) [sn2] | 1.37 | 1.16 | 1.62 | 2.4E−04 |
| Cer(d19:1/18:0)/LPC(MHDA) [sn1] | 1.41 | 1.19 | 1.67 | 7.2E−05 |
| Cer(d19:1/18:0)/LPC(MHDA) [sn2] | 1.41 | 1.20 | 1.67 | 5.1E−05 |
| Cer(d19:1/18:0)/LPC(17:0) [sn1] | 1.29 | 1.09 | 1.53 | 2.5E−03 |
| Cer(d19:1/18:0)/LPC(20:0) [sn2] | 1.24 | 1.05 | 1.45 | 1.2E−02 |
| Cer(d19:1/18:0)/LPC(22:0) [sn1] | 1.26 | 1.07 | 1.48 | 4.9E−03 |
| Cer(d19:1/18:0)/LPC(22:1) [sn1] | 1.27 | 1.08 | 1.49 | 3.9E−03 |
| Cer(d19:1/18:0)/LPC(22:1) [sn2] | 1.29 | 1.10 | 1.52 | 1.9E−03 |
| Cer(d19:1/18:0)/LPC(24:0) [sn1] | 1.26 | 1.07 | 1.48 | 4.7E−03 |
| Cer(d19:1/18:0)/LPC(24:0) [sn2] | 1.29 | 1.10 | 1.52 | 1.7E−03 |
| Cer(d19:1/18:0)/LPC(P-16:0) | 1.27 | 1.08 | 1.49 | 3.4E−03 |
| Cer(d19:1/18:0)/LPC(P-17:0) | 1.35 | 1.14 | 1.58 | 3.7E−04 |
| Cer(d19:1/18:0)/LPC(P-18:0) | 1.31 | 1.11 | 1.54 | 1.2E−03 |
| Cer(d19:1/18:0)/LPE(P-20:0) | 1.30 | 1.10 | 1.54 | 1.8E−03 |
| Cer(d19:1/18:0)/PC(MHDA_18:1) | 1.34 | 1.14 | 1.58 | 4.6E−04 |
| Cer(d19:1/18:0)/PC(17:0_22:6) | 1.37 | 1.16 | 1.61 | 1.8E−04 |
| Cer(d19:1/18:0)/PI(37:6) | 1.40 | 1.19 | 1.66 | 8.1E−05 |
| Cer(d19:1/18:0)/SM(d16:1/19:0) | 1.46 | 1.24 | 1.72 | 7.4E−06 |
| Cer(d19:1/18:0)/SM(d17:1/14:0) | 1.37 | 1.16 | 1.61 | 1.8E−04 |
| Cer(d19:1/18:0)/SM(d17:1/16:0) | 1.34 | 1.14 | 1.58 | 3.6E−04 |
| Cer(d19:1/18:0)/SM(d18:2/17:0) | 1.39 | 1.18 | 1.63 | 7.5E−05 |
| Cer(d19:1/18:0)/SM(d18:2/18:1) | 1.33 | 1.13 | 1.57 | 5.1E−04 |
| Cer(d20:1/22:0)/Cer(d18:2/26:0) | 1.78 | 1.49 | 2.13 | 2.1E−10 |
| Cer(d20:1/22:0)/Cer(d19:1/26:0) | 1.87 | 1.55 | 2.26 | 1.0E−10 |
| Cer(d20:1/22:0)/LPC(17:0) [sn2] | 1.79 | 1.49 | 2.14 | 2.3E−10 |
| Cer(d20:1/22:0)/LPC(MHDA) [sn1] | 1.81 | 1.51 | 2.18 | 2.8E−10 |
| Cer(d20:1/22:0)/LPC(MHDA) [sn2] | 1.82 | 1.51 | 2.19 | 1.7E−10 |
| Cer(d20:1/22:0)/LPC(17:0) [sn1] | 1.69 | 1.42 | 2.02 | 6.6E−09 |
| Cer(d20:1/22:0)/LPC(18:2) [sn1] | 1.73 | 1.45 | 2.07 | 2.2E−09 |
| Cer(d20:1/22:0)/LPC(18:2) [sn2] | 1.77 | 1.48 | 2.12 | 3.5E−10 |
| Cer(d20:1/22:0)/LPC(19:0) [sn2] | 1.65 | 1.38 | 1.98 | 6.6E−08 |
| Cer(d20:1/22:0)/LPC(19:0) [sn1] | 1.61 | 1.34 | 1.93 | 2.7E−07 |
| Cer(d20:1/22:0)/LPC(20:0) [sn2] | 1.58 | 1.33 | 1.89 | 2.0E−07 |
| Cer(d20:1/22:0)/LPC(20:1) [sn1] | 1.59 | 1.34 | 1.88 | 8.9E−08 |
| Cer(d20:1/22:0)/LPC(20:1) [sn2] | 1.55 | 1.31 | 1.84 | 2.6E−07 |
| Cer(d20:1/22:0)/LPC(20:2) [sn1] | 1.60 | 1.35 | 1.89 | 6.8E−08 |
| Cer(d20:1/22:0)/LPC(22:0) [sn1] | 1.64 | 1.38 | 1.94 | 2.1E−08 |
| Cer(d20:1/22:0)/LPC(22:1) [sn1] | 1.59 | 1.34 | 1.88 | 9.5E−08 |
| Cer(d20:1/22:0)/LPC(22:1) [sn2] | 1.59 | 1.34 | 1.89 | 1.1E−07 |
| Cer(d20:1/22:0)/LPC(24:0) [sn1] | 1.63 | 1.38 | 1.93 | 1.8E−08 |
| Cer(d20:1/22:0)/LPC(24:0) [sn2] | 1.70 | 1.43 | 2.02 | 2.8E−09 |
| Cer(d20:1/22:0)/LPC(26:0) [sn1] | 1.74 | 1.46 | 2.07 | 4.0E−10 |
| Cer(d20:1/22:0)/LPC(26:0) [sn2] | 1.75 | 1.46 | 2.10 | 1.8E−09 |
| Cer(d20:1/22:0)/LPC(P-16:0) | 1.65 | 1.39 | 1.96 | 1.3E−08 |

TABLE 3-continued

Odds Ratios based on combination biomarker values of Group A and Group B, and Group C and Group D diabetes biomarkers in subjects who developed diabetes during the follow-up as compared to a control group in AusDiab study cohort according to some embodiments of all aspects of the present disclosure. Abbreviations are described in the detailed description of the present disclosure.

| Lipids | OR | CI_LOW | CI_HIGH | p_value |
|---|---|---|---|---|
| Cer(d20:1/22:0)/LPC(P-17:0) | 1.68 | 1.41 | 2.00 | 6.3E−09 |
| Cer(d20:1/22:0)/LPC(P-18:0) | 1.70 | 1.43 | 2.02 | 1.8E−09 |
| Cer(d20:1/22:0)/LPC(P-18:1) | 1.59 | 1.34 | 1.88 | 1.1E−07 |
| Cer(d20:1/22:0)/LPC(P-20:0) | 1.90 | 1.59 | 2.27 | 1.9E−12 |
| Cer(d20:1/22:0)/LPE(P-200) | 1.77 | 1.46 | 2.14 | 6.1E−09 |
| Cer(d20:1/22:0)/PC(MHDA_18:1) | 1.66 | 1.39 | 1.98 | 2.3E−08 |
| Cer(d20:1/22:0)/PC(MHDA_18:2) | 1.89 | 1.57 | 2.27 | 1.7E−11 |
| Cer(d20:1/22:0)/PC(MHDA_22:6) | 1.94 | 1.61 | 2.34 | 3.8E−12 |
| Cer(d20:1/22:0)/PC(17:0_22:6) | 1.74 | 1.46 | 2.08 | 1.2E−09 |
| Cer(d20:1/22:0)/PI(37:6) | 1.76 | 1.46 | 2.12 | 2.6E−09 |
| Cer(d20:1/22:0)/SM(d16:1/19:0) | 1.93 | 1.60 | 2.32 | 3.0E−12 |
| Cer(d20:1/22:0)/SM(d17:1/14:0) | 1.75 | 1.47 | 2.08 | 4.1E−10 |
| Cer(d20:1/22:0)/SM(d17:1/16:0) | 1.79 | 1.51 | 2.13 | 5.5E−11 |
| Cer(d20:1/22:0)/SM(d17:1/24:1) | 1.76 | 1.48 | 2.10 | 2.7E−10 |
| Cer(d20:1/22:0)/SM(d18:2/17:0) | 1.81 | 1.52 | 2.17 | 3.6E−11 |
| Cer(d20:1/22:0)/SM(d18:2/18:1) | 1.71 | 1.44 | 2.04 | 1.8E−09 |
| Cer(d20:1/22:0)/SM(d18:2/23:0) | 1.83 | 1.53 | 2.19 | 4.1E−11 |
| Cer(d20:1/22:0)/SM(d18:2/24:0) | 1.75 | 1.47 | 2.08 | 5.0E−10 |
| Cer(d20:1/23:0)/Cer(d18:2/26:0) | 1.52 | 1.29 | 1.79 | 7.5E−07 |
| Cer(d20:1/23:0)/Cer(d19:1/26:0) | 1.59 | 1.34 | 1.89 | 9.9E−08 |
| Cer(d20:1/23:0)/LPC(17:0) [sn2] | 1.52 | 1.29 | 1.79 | 8.2E−07 |
| Cer(d20:1/23:0)/LPC(MHDA) [sn1] | 1.54 | 1.30 | 1.82 | 5.1E−07 |
| Cer(d20:1/23:0)/LPC(MHDA) [sn2] | 1.55 | 1.31 | 1.83 | 3.3E−07 |
| Cer(d20:1/23:0)/LPC(17:0) [sn1] | 1.44 | 1.22 | 1.69 | 1.4E−05 |
| Cer(d20:1/23:0)/LPC(18:2) [sn1] | 1.49 | 1.26 | 1.75 | 2.9E−06 |
| Cer(d20:1/23:0)/LPC(18:2) [sn2] | 1.50 | 1.27 | 1.77 | 1.6E−06 |
| Cer(d20:1/23:0)/LPC(19:0) [sn2] | 1.42 | 1.20 | 1.67 | 3.0E−05 |
| Cer(d20:1/23:0)/LPC(19:0) [sn1] | 1.40 | 1.18 | 1.64 | 6.6E−05 |
| Cer(d20:1/23:0)/LPC(20:0) [sn2] | 1.36 | 1.16 | 1.60 | 1.8E−04 |
| Cer(d20:1/23:0)/LPC(20:1) [sn1] | 1.38 | 1.17 | 1.62 | 9.5E−05 |
| Cer(d20:1/23:0)/LPC(20:1) [sn2] | 1.36 | 1.16 | 1.60 | 1.9E−04 |
| Cer(d20:1/23:0)/LPC(20:2) [sn1] | 1.37 | 1.16 | 1.61 | 1.7E−04 |
| Cer(d20:1/23:0)/LPC(22:0) [sn1] | 1.40 | 1.19 | 1.64 | 5.6E−05 |
| Cer(d20:1/23:0)/LPC(22:1) [sn1] | 1.38 | 1.18 | 1.63 | 8.9E−05 |
| Cer(d20:1/23:0)/LPC(22:1) [sn2] | 1.40 | 1.19 | 1.65 | 6.4E−05 |
| Cer(d20:1/23:0)/LPC(24:0) [sn1] | 1.39 | 1.18 | 1.63 | 7.8E−05 |
| Cer(d20:1/23:0)/LPC(24:0) [sn2] | 1.44 | 1.22 | 1.70 | 1.4E−05 |
| Cer(d20:1/23:0)/LPC(26:0) [sn1] | 1.51 | 1.28 | 1.78 | 9.6E−07 |
| Cer(d20:1/23:0)/LPC(26:0) [sn2] | 1.52 | 1.29 | 1.80 | 1.2E−06 |
| Cer(d20:1/23:0)/LPC(P-16:0) | 1.40 | 1.19 | 1.65 | 5.2E−05 |
| Cer(d20:1/23:0)/LPC(P-17:0) | 1.45 | 1.23 | 1.71 | 8.8E−06 |
| Cer(d20:1/23:0)/LPC(P-18:0) | 1.44 | 1.22 | 1.70 | 1.3E−05 |
| Cer(d20:1/23:0)/LPC(P-18:1) | 1.36 | 1.16 | 1.60 | 1.8E−04 |
| Cer(d20:1/23:0)/LPC(P-20:0) | 1.61 | 1.36 | 1.90 | 3.3E−08 |
| Cer(d20:1/23:0)/LPE(P-20:0) | 1.45 | 1.22 | 1.72 | 1.9E−05 |
| Cer(d20:1/23:0)/PC(MHDA_18:1) | 1.45 | 1.22 | 1.71 | 1.7E−05 |
| Cer(d20:1/23:0)/PC(MHDA_18:2) | 1.61 | 1.36 | 1.90 | 3.8E−08 |
| Cer(d20:1/23:0)/PC(MHDA_22:6) | 1.70 | 1.43 | 2.02 | 1.5E−09 |
| Cer(d20:1/23:0)/PC(17:0_22:6) | 1.51 | 1.28 | 1.79 | 1.4E−06 |
| Cer(d20:1/23:0)/PI(37:6) | 1.56 | 1.31 | 1.85 | 3.8E−07 |
| Cer(d20:1/23:0)/SM(d16:1/19:0) | 1.64 | 1.39 | 1.95 | 7.5E−09 |
| Cer(d20:1/23:0)/SM(d17:1/14:0) | 1.53 | 1.30 | 1.81 | 4.5E−07 |
| Cer(d20:1/23:0)/SM(d17:1/16:0) | 1.55 | 1.31 | 1.83 | 2.6E−07 |
| Cer(d20:1/23:0)/SM(d17:1/24:1) | 1.53 | 1.30 | 1.81 | 4.6E−07 |
| Cer(d20:1/23:0)/SM(d18:2/17:0) | 1.55 | 1.31 | 1.83 | 2.5E−07 |
| Cer(d20:1/23:0)/SM(d18:2/18:1) | 1.47 | 1.24 | 1.73 | 5.2E−06 |
| Cer(d20:1/23:0)/SM(d18:2/23:0) | 1.58 | 1.34 | 1.87 | 8.5E−08 |
| Cer(d20:1/23:0)/SM(d18:2/24:0) | 1.47 | 1.25 | 1.73 | 4.7E−06 |
| Cer(d20:1/24:0)/Cer(d18:2/26:0) | 1.57 | 1.33 | 1.86 | 1.6E−07 |
| Cer(d20:1/24:0)/Cer(d19:1/26:0) | 1.64 | 1.38 | 1.94 | 2.4E−08 |
| Cer(d20:1/24:0)/LPC(17:0) [sn2] | 1.58 | 1.32 | 1.89 | 3.9E−07 |
| Cer(d20:1/24:0)/LPC(MHDA) [sn1] | 1.60 | 1.34 | 1.92 | 3.9E−07 |
| Cer(d20:1/24:0)/LPC(MHDA) [sn2] | 1.60 | 1.33 | 1.91 | 3.3E−07 |
| Cer(d20:1/24:0)/LPC(17:0) [sn1] | 1.51 | 1.27 | 1.79 | 3.6E−06 |
| Cer(d20:1/24:0)/LPC(18:2) [sn1] | 1.59 | 1.34 | 1.89 | 1.4E−07 |
| Cer(d20:1/24:0)/LPC(18:2) [sn2] | 1.61 | 1.36 | 1.91 | 5.3E−08 |
| Cer(d20:1/24:0)/LPC(19:0) [sn2] | 1.48 | 1.24 | 1.76 | 1.0E−05 |
| Cer(d20:1/24:0)/LPC(19:0) [sn1] | 1.46 | 1.23 | 1.73 | 1.7E−05 |
| Cer(d20:1/24:0)/LPC(20:0) [sn2] | 1.46 | 1.24 | 1.73 | 8.7E−06 |
| Cer(d20:1/24:0)/LPC(20:1) [sn1] | 1.46 | 1.24 | 1.72 | 5.9E−06 |
| Cer(d20:1/24:0)/LPC(20:1) [sn2] | 1.43 | 1.22 | 1.69 | 1.6E−05 |
| Cer(d20:1/24:0)/LPC(20:2) [sn1] | 1.45 | 1.23 | 1.72 | 8.1E−06 |

TABLE 3-continued

Odds Ratios based on combination biomarker values of Group A and Group B, and Group C and Group D diabetes biomarkers in subjects who developed diabetes during the follow-up as compared to a control group in AusDiab study cohort according to some embodiments of all aspects of the present disclosure. Abbreviations are described in the detailed description of the present disclosure.

| Lipids | OR | CI_LOW | CI_HIGH | p_value |
|---|---|---|---|---|
| Cer(d20:1/24:0)/LPC(22:0) [sn1] | 1.52 | 1.28 | 1.79 | 9.6E−07 |
| Cer(d20:1/24:0)/LPC(22:1) [sn1] | 1.46 | 1.24 | 1.72 | 6.5E−06 |
| Cer(d20:1/24:0)/LPC(22:1) [sn2] | 1.47 | 1.24 | 1.73 | 6.1E−06 |
| Cer(d20:1/24:0)/LPC(24:0) [sn1] | 1.51 | 1.28 | 1.78 | 1.2E−06 |
| Cer(d20:1/24:0)/LPC(24:0) [sn2] | 1.57 | 1.32 | 1.85 | 2.0E−07 |
| Cer(d20:1/24:0)/LPC(26:0) [sn1] | 1.61 | 1.36 | 1.90 | 3.4E−08 |
| Cer(d20:1/24:0)/LPC(26:0) [sn2] | 1.61 | 1.36 | 1.91 | 5.2E−08 |
| Cer(d20:1/24:0)/LPC(P-16:0) | 1.48 | 1.26 | 1.75 | 3.5E−06 |
| Cer(d20:1/24:0)/LPC(P-17:0) | 1.51 | 1.27 | 1.79 | 3.4E−06 |
| Cer(d20:1/24:0)/LPC(P-18:0) | 1.54 | 1.30 | 1.82 | 6.2E−07 |
| Cer(d20:1/24:0)/LPC(P-18:1) | 1.43 | 1.22 | 1.69 | 1.8E−05 |
| Cer(d20:1/24:0)/LPC(P-20:0) | 1.77 | 1.49 | 2.10 | 1.2E−10 |
| Cer(d20:1/24:0)/LPE(P-20:0) | 1.54 | 1.29 | 1.84 | 1.8E−06 |
| Cer(d20:1/24:0)/PC(MHDA_18:1) | 1.47 | 1.23 | 1.75 | 1.8E−05 |
| Cer(d20:1/24:0)/PC(MHDA_18:2) | 1.65 | 1.38 | 1.97 | 5.8E−08 |
| Cer(d20:1/24:0)/PC(MHDA_22:6) | 1.68 | 1.41 | 1.99 | 4.5E−09 |
| Cer(d20:1/24:0)/PC(17:0_22:6) | 1.52 | 1.28 | 1.79 | 1.0E−06 |
| Cer(d20:1/24:0)/PI(37:6) | 1.58 | 1.32 | 1.88 | 3.0E−07 |
| Cer(d20:1/24:0)/SM(d16:1/19:0) | 1.65 | 1.38 | 1.97 | 2.4E−08 |
| Cer(d20:1/24:0)/SM(d17:1/14:0) | 1.53 | 1.29 | 1.81 | 9.2E−07 |
| Cer(d20:1/24:0)/SM(d17:1/16:0) | 1.56 | 1.32 | 1.84 | 2.6E−07 |
| Cer(d20:1/24:0)/SM(d17:1/24:1) | 1.55 | 1.30 | 1.83 | 6.0E−07 |
| Cer(d20:1/24:0)/SM(d18:2/17:0) | 1.55 | 1.31 | 1.83 | 3.8E−07 |
| Cer(d20:1/24:0)/SM(d18:2/18:1) | 1.48 | 1.25 | 1.74 | 3.6E−06 |
| Cer(d20:1/24:0)/SM(d18:2/23:0) | 1.61 | 1.36 | 1.91 | 4.0E−08 |
| Cer(d20:1/24:0)/SM(d18:2/24:0) | 1.58 | 1.34 | 1.87 | 9.6E−08 |
| Cer(d20:1/24:1)/Cer(d18:2/26:0) | 1.46 | 1.24 | 1.73 | 8.5E−06 |
| Cer(d20:1/24:1)/Cer(d19:1/26:0) | 1.52 | 1.28 | 1.80 | 1.3E−06 |
| Cer(d20:1/24:1)/LPC(17:0) [sn2] | 1.42 | 1.20 | 1.67 | 3.6E−05 |
| Cer(d20:1/24:1)/LPC(MHDA) [sn1] | 1.44 | 1.22 | 1.70 | 1.9E−05 |
| Cer(d20:1/24:1)/LPC(MHDA) [sn2] | 1.44 | 1.22 | 1.69 | 1.9E−05 |
| Cer(d20:1/24:1)/LPC(17:0) [sn1] | 1.35 | 1.15 | 1.59 | 3.3E−04 |
| Cer(d20:1/24:1)/LPC(18:2) [sn2] | 1.40 | 1.18 | 1.66 | 9.6E−05 |
| Cer(d20:1/24:1)/LPC(19:0) [sn2] | 1.34 | 1.13 | 1.59 | 9.0E−04 |
| Cer(d20:1/24:1)/LPC(19:0) [sn1] | 1.32 | 1.11 | 1.57 | 1.4E−03 |
| Cer(d20:1/24:1)/LPC(20:0) [sn2] | 1.31 | 1.10 | 1.54 | 1.8E−03 |
| Cer(d20:1/24:1)/LPC(20:1) [sn1] | 1.35 | 1.14 | 1.59 | 4.3E−04 |
| Cer(d20:1/24:1)/LPC(20:1) [sn2] | 1.33 | 1.13 | 1.57 | 6.6E−04 |
| Cer(d20:1/24:1)/LPC(20:2) [sn1] | 1.32 | 1.12 | 1.55 | 9.8E−04 |
| Cer(d20:1/24:1)/LPC(22:0) [sn1] | 1.35 | 1.14 | 1.59 | 4.2E−04 |
| Cer(d20:1/24:1)/LPC(22:1) [sn1] | 1.38 | 1.17 | 1.63 | 1.4E−04 |
| Cer(d20:1/24:1)/LPC(22:1) [sn2] | 1.39 | 1.18 | 1.64 | 1.2E−04 |
| Cer(d20:1/24:1)/LPC(24:0) [sn1] | 1.36 | 1.15 | 1.60 | 2.3E−04 |
| Cer(d20:1/24:1)/LPC(24:0) [sn2] | 1.40 | 1.19 | 1.65 | 6.0E−05 |
| Cer(d20:1/24:1)/LPC(26:0) [sn1] | 1.47 | 1.25 | 1.74 | 3.8E−06 |
| Cer(d20:1/24:1)/LPC(26:0) [sn2] | 1.46 | 1.23 | 1.72 | 8.6E−06 |
| Cer(d20:1/24:1)/LPC(P-16:0) | 1.33 | 1.13 | 1.57 | 5.9E−04 |
| Cer(d20:1/24:1)/LPC(P-17:0) | 1.37 | 1.16 | 1.61 | 1.8E−04 |
| Cer(d20:1/24:1)/LPC(P-18:0) | 1.36 | 1.15 | 1.60 | 3.0E−04 |
| Cer(d20:1/24:1)/LPC(P-18:1) | 1.30 | 1.11 | 1.53 | 1.3E−03 |
| Cer(d20:1/24:1)/LPC(P-20:0) | 1.54 | 1.30 | 1.82 | 5.1E−07 |
| Cer(d20:1/24:1)/LPE(P-20:0) | 1.38 | 1.16 | 1.63 | 2.3E−04 |
| Cer(d20:1/24:1)/PC(MHDA_18:1) | 1.40 | 1.18 | 1.65 | 7.0E−05 |
| Cer(d20:1/24:1)/PC(MHDA_18:2) | 1.49 | 1.26 | 1.76 | 3.6E−06 |
| Cer(d20:1/24:1)/PC(MHDA_22:6) | 1.62 | 1.36 | 1.92 | 5.6E−08 |
| Cer(d20:1/24:1)/PC(17:0_22:6) | 1.46 | 1.23 | 1.73 | 1.3E−05 |
| Cer(d20:1/24:1)/PI(37:6) | 1.51 | 1.27 | 1.79 | 3.1E−06 |
| Cer(d20:1/24:1)/SM(d16:1/19:0) | 1.51 | 1.27 | 1.78 | 2.0E−06 |
| Cer(d20:1/24:1)/SM(d17:1/14:0) | 1.43 | 1.21 | 1.68 | 1.9E−05 |
| Cer(d20:1/24:1)/SM(d17:1/16:0) | 1.42 | 1.20 | 1.67 | 3.4E−05 |
| Cer(d20:1/24:1)/SM(d17:1/24:1) | 1.49 | 1.26 | 1.76 | 2.5E−06 |
| Cer(d20:1/24:1)/SM(d18:2/17:0) | 1.44 | 1.22 | 1.70 | 1.4E−05 |
| Cer(d20:1/24:1)/SM(d18:2/18:1) | 1.40 | 1.19 | 1.65 | 4.7E−05 |
| Cer(d20:1/24:1)/SM(d18:2/23:0) | 1.45 | 1.22 | 1.71 | 1.4E−05 |
| Cer(d20:1/24:1)/SM(d18:2/24:0) | 1.39 | 1.18 | 1.64 | 8.2E−05 |
| LPC(14:0) [sn1]/Cer(d18:2/26:0) | 1.33 | 1.13 | 1.57 | 6.3E−04 |
| LPC(14:0) [sn1]/Cer(d19:1/26:0) | 1.27 | 1.08 | 1.50 | 4.4E−03 |
| LPC(14:0) [sn1]/LPC(17:0) [sn2] | 1.54 | 1.30 | 1.83 | 5.4E−07 |
| LPC(14:0) [sn1]/LPC(MHDA) [sn1] | 1.58 | 1.33 | 1.87 | 2.6E−07 |
| LPC(14:0) [sn1]/LPC(MHDA) [sn2] | 1.59 | 1.34 | 1.89 | 1.3E−07 |
| LPC(14:0) [sn1]/LPC(17:0) [sn1] | 1.43 | 1.21 | 1.69 | 2.2E−05 |
| LPC(14:0) [sn1]/LPC(18:2) [sn1] | 1.51 | 1.28 | 1.79 | 1.3E−06 |

TABLE 3-continued

Odds Ratios based on combination biomarker values of Group A and Group B, and Group C and Group D diabetes biomarkers in subjects who developed diabetes during the follow-up as compared to a control group in AusDiab study cohort according to some embodiments of all aspects of the present disclosure. Abbreviations are described in the detailed description of the present disclosure.

| Lipids | OR | CI_LOW | CI_HIGH | p_value |
|---|---|---|---|---|
| LPC(14:0) [sn1]/LPC(18:2) [sn2] | 1.49 | 1.26 | 1.76 | 2.4E−06 |
| LPC(14:0) [sn1]/LPC(19:0) [sn2] | 1.50 | 1.27 | 1.77 | 1.9E−06 |
| LPC(14:0) [sn1]/LPC(19:0) [sn1] | 1.45 | 1.23 | 1.71 | 8.8E−06 |
| LPC(14:0) [sn1]/LPC(20:0) [sn2] | 1.42 | 1.20 | 1.67 | 4.1E−05 |
| LPC(14:0) [sn1]/LPC(20:1) [sn1] | 1.50 | 1.27 | 1.77 | 2.1E−06 |
| LPC(14:0) [sn1]/LPC(20:1) [sn2] | 1.46 | 1.24 | 1.73 | 8.2E−06 |
| LPC(14:0) [sn1]/LPC(20:2) [sn1] | 1.57 | 1.32 | 1.86 | 1.9E−07 |
| LPC(14:0) [sn1]/LPC(22:0) [sn1] | 1.36 | 1.16 | 1.61 | 2.4E−04 |
| LPC(14:0) [sn1]/LPC(22:1) [sn1] | 1.41 | 1.19 | 1.66 | 5.3E−05 |
| LPC(14:0) [sn1]/LPC(22:1) [sn2] | 1.43 | 1.21 | 1.70 | 2.6E−05 |
| LPC(14:0) [sn1]/LPC(24:0) [sn1] | 1.39 | 1.18 | 1.64 | 6.8E−05 |
| LPC(14:0) [sn1]/LPC(24:0) [sn2] | 1.40 | 1.19 | 1.66 | 5.3E−05 |
| LPC(14:0) [sn1]/LPC(26:0) [sn1] | 1.54 | 1.30 | 1.82 | 5.3E−07 |
| LPC(14:0) [sn1]/LPC(26:0) [sn2] | 1.50 | 1.27 | 1.78 | 2.4E−06 |
| LPC(14:0) [sn1]/LPC(P-16:0) | 1.44 | 1.22 | 1.69 | 1.7E−05 |
| LPC(14:0) [sn1]/LPC(P-17:0) | 1.43 | 1.22 | 1.69 | 1.8E−05 |
| LPC(14:0) [sn1]/LPC(P-18:0) | 1.38 | 1.17 | 1.63 | 1.3E−04 |
| LPC(14:0) [sn1]/LPC(P-18:1) | 1.40 | 1.19 | 1.65 | 4.8E−05 |
| LPC(14:0) [sn1]/LPC(P-20:0) | 1.52 | 1.29 | 1.80 | 8.4E−07 |
| LPC(14:0) [sn1]/LPE(P-20:0) | 1.42 | 1.20 | 1.68 | 3.4E−05 |
| LPC(14:0) [sn1]/PC(MHDA_18:1) | 1.42 | 1.20 | 1.68 | 5.3E−05 |
| LPC(14:0) [sn1]/PC(MHDA_18:2) | 1.46 | 1.22 | 1.75 | 3.4E−05 |
| LPC(14:0) [sn1]/PC(MHDA_22:6) | 1.54 | 1.29 | 1.83 | 1.5E−06 |
| LPC(14:0) [sn1]/PC(17:0_22:6) | 1.37 | 1.16 | 1.62 | 1.7E−04 |
| LPC(14:0) [sn1]/PI(37:6) | 1.55 | 1.31 | 1.85 | 7.1E−07 |
| LPC(14:0) [sn1]/SM(d16:1/19:0) | 1.40 | 1.17 | 1.68 | 2.3E−04 |
| LPC(14:0) [sn1]/SM(d17:1/14:0) | 1.52 | 1.27 | 1.83 | 8.4E−06 |
| LPC(14:0) [sn1]/SM(d17:1/16:0) | 1.40 | 1.17 | 1.66 | 1.7E−04 |
| LPC(14:0) [sn1]/SM(d17:1/24:1) | 1.42 | 1.20 | 1.69 | 4.5E−05 |
| LPC(14:0) [sn1]/SM(d18:2/17:0) | 1.36 | 1.14 | 1.62 | 5.2E−04 |
| LPC(14:0) [sn1]/SM(d18:2/18:1) | 1.34 | 1.14 | 1.58 | 5.6E−04 |
| LPC(14:0) [sn1]/SM(d18:2/24:0) | 1.39 | 1.18 | 1.64 | 9.6E−05 |
| LPC(14:0) [sn2]/Cer(d18:2/26:0) | 1.32 | 1.12 | 1.55 | 1.0E−03 |
| LPC(14:0) [sn2]/Cer(d19:1/26:0) | 1.26 | 1.07 | 1.49 | 6.2E−03 |
| LPC(14:0) [sn2]/LPC(17:0) [sn2] | 1.52 | 1.29 | 1.80 | 1.2E−06 |
| LPC(14:0) [sn2]/LPC(MHDA) [sn1] | 1.56 | 1.31 | 1.85 | 5.0E−07 |
| LPC(14:0) [sn2]/LPC(MHDA) [sn2] | 1.58 | 1.33 | 1.87 | 2.3E−07 |
| LPC(14:0) [sn2]/LPC(17:0) [sn1] | 1.41 | 1.20 | 1.67 | 4.0E−05 |
| LPC(14:0) [sn2]/LPC(18:2) [sn1] | 1.49 | 1.26 | 1.76 | 3.3E−06 |
| LPC(14:0) [sn2]/LPC(18:2) [sn2] | 1.47 | 1.25 | 1.74 | 5.2E−06 |
| LPC(14:0) [sn2]/LPC(19:0) [sn2] | 1.47 | 1.25 | 1.74 | 4.3E−06 |
| LPC(14:0) [sn2]/LPC(19:0) [sn1] | 1.43 | 1.22 | 1.69 | 1.9E−05 |
| LPC(14:0) [sn2]/LPC(20:0) [sn2] | 1.40 | 1.18 | 1.65 | 7.4E−05 |
| LPC(14:0) [sn2]/LPC(20:1) [sn1] | 1.47 | 1.25 | 1.74 | 4.8E−06 |
| LPC(14:0) [sn2]/LPC(20:1) [sn2] | 1.45 | 1.23 | 1.71 | 1.3E−05 |
| LPC(14:0) [sn2]/LPC(20:2) [sn1] | 1.53 | 1.30 | 1.82 | 6.8E−07 |
| LPC(14:0) [sn2]/LPC(22:0) [sn1] | 1.34 | 1.14 | 1.59 | 5.0E−04 |
| LPC(14:0) [sn2]/LPC(22:1) [sn1] | 1.39 | 1.17 | 1.63 | 1.1E−04 |
| LPC(14:0) [sn2]/LPC(22:1) [sn2] | 1.42 | 1.20 | 1.68 | 4.0E−05 |
| LPC(14:0) [sn2]/LPC(24:0) [sn1] | 1.37 | 1.16 | 1.61 | 1.7E−04 |
| LPC(14:0) [sn2]/LPC(24:0) [sn2] | 1.38 | 1.17 | 1.63 | 1.2E−04 |
| LPC(14:0) [sn2]/LPC(26:0) [sn1] | 1.51 | 1.27 | 1.78 | 1.7E−06 |
| LPC(14:0) [sn2]/LPC(26:0) [sn2] | 1.48 | 1.25 | 1.75 | 7.0E−06 |
| LPC(14:0) [sn2]/LPC(P-16:0) | 1.41 | 1.19 | 1.66 | 4.5E−05 |
| LPC(14:0) [sn2]/LPC(P-17:0) | 1.41 | 1.19 | 1.66 | 4.3E−05 |
| LPC(14:0) [sn2]/LPC(P-18:0) | 1.36 | 1.15 | 1.60 | 2.8E−04 |
| LPC(14:0) [sn2]/LPC(P-18:1) | 1.39 | 1.18 | 1.63 | 9.1E−05 |
| LPC(14:0) [sn2]/LPE(P-20:0) | 1.40 | 1.19 | 1.65 | 6.4E−05 |
| LPC(14:0) [sn2]/PC(MHDA_18:1) | 1.40 | 1.18 | 1.66 | 9.3E−05 |
| LPC(14:0) [sn2]/PC(MHDA_18:2) | 1.46 | 1.21 | 1.75 | 5.4E−05 |
| LPC(14:0) [sn2]/PC(MHDA_22:6) | 1.53 | 1.28 | 1.82 | 2.4E−06 |
| LPC(14:0) [sn2]/PC(17:0_22:6) | 1.37 | 1.16 | 1.61 | 2.1E−04 |
| LPC(14:0) [sn2]/PI(37:6) | 1.55 | 1.30 | 1.84 | 1.0E−06 |
| LPC(14:0) [sn2]/SM(d16:1/19:0) | 1.39 | 1.16 | 1.67 | 4.2E−04 |
| LPC(14:0) [sn2]/SM(d17:1/14:0) | 1.52 | 1.26 | 1.84 | 1.2E−05 |
| LPC(14:0) [sn2]/SM(d17:1/16:0) | 1.39 | 1.16 | 1.65 | 3.0E−04 |
| LPC(14:0) [sn2]/SM(d18:2/18:1) | 1.33 | 1.13 | 1.58 | 7.8E−04 |
| LPC(14:0) [sn2]/SM(d18:2/24:0) | 1.37 | 1.16 | 1.61 | 2.2E−04 |
| LPE(18:0) [sn1]/Cer(d18:2/26:0) | 1.56 | 1.31 | 1.85 | 6.8E−07 |
| LPE(18:0) [sn1]/Cer(d19:1/26:0) | 1.43 | 1.20 | 1.71 | 8.8E−05 |
| LPE(18:0) [sn1]/LPC(17:0) [sn2] | 1.80 | 1.50 | 2.17 | 2.3E−10 |
| LPE(18:0) [sn1]/LPC(MHDA) [sn1] | 1.79 | 1.48 | 2.15 | 7.5E−10 |

TABLE 3-continued

Odds Ratios based on combination biomarker values of Group A and Group B, and Group C and Group D diabetes biomarkers in subjects who developed diabetes during the follow-up as compared to a control group in AusDiab study cohort according to some embodiments of all aspects of the present disclosure. Abbreviations are described in the detailed description of the present disclosure.

| Lipids | OR | CI_LOW | CI_HIGH | p_value |
|---|---|---|---|---|
| LPE(18:0) [sn1]/LPC(MHDA) [sn2] | 1.82 | 1.51 | 2.19 | 2.5E−10 |
| LPE(18:0) [sn1]/LPC(17:0) [sn1] | 1.69 | 1.42 | 2.02 | 4.3E−09 |
| LPE(18:0) [sn1]/LPC(18:2) [sn1] | 1.74 | 1.46 | 2.08 | 1.2E−09 |
| LPE(18:0) [sn1]/LPC(18:2) [sn2] | 1.74 | 1.45 | 2.08 | 1.3E−09 |
| LPE(18:0) [sn1]/LPC(19:0) [sn2] | 1.72 | 1.44 | 2.07 | 4.0E−09 |
| LPE(18:0) [sn1]/LPC(19:0) [sn1] | 1.63 | 1.37 | 1.94 | 3.3E−08 |
| LPE(18:0) [sn1]/LPC(20:0) [sn2] | 1.59 | 1.33 | 1.89 | 1.6E−07 |
| LPE(18:0) [sn1]/LPC(20:1) [sn1] | 1.71 | 1.44 | 2.05 | 2.6E−09 |
| LPE(18:0) [sn1]/LPC(20:1) [sn2] | 1.67 | 1.39 | 1.99 | 2.1E−08 |
| LPE(18:0) [sn1]/LPC(20:2) [sn1] | 1.95 | 1.62 | 2.35 | 1.0E−12 |
| LPE(18:0) [sn1]/LPC(22:0) [sn1] | 1.56 | 1.32 | 1.85 | 2.1E−07 |
| LPE(18:0) [sn1]/LPC(22:1) [sn1] | 1.59 | 1.34 | 1.89 | 1.5E−07 |
| LPE(18:0) [sn1]/LPC(22:1) [sn2] | 1.58 | 1.32 | 1.89 | 6.5E−07 |
| LPE(18:0) [sn1]/LPC(24:0) [sn1] | 1.60 | 1.35 | 1.90 | 5.6E−08 |
| LPE(18:0) [sn1]/LPC(24:0) [sn2] | 1.61 | 1.36 | 1.92 | 6.6E−08 |
| LPE(18:0) [sn1]/LPC(26:0) [sn1] | 1.81 | 1.51 | 2.17 | 1.2E−10 |
| LPE(18:0) [sn1]/LPC(26:0) [sn2] | 1.75 | 1.47 | 2.09 | 4.2E−10 |
| LPE(18:0) [sn1]/LPC(P-16:0) | 1.76 | 1.47 | 2.11 | 1.1E−09 |
| LPE(18:0) [sn1]/LPC(P-17:0) | 1.66 | 1.40 | 1.97 | 6.4E−09 |
| LPE(18:0) [sn1]/LPC(P-18:0) | 1.69 | 1.42 | 2.02 | 5.7E−09 |
| LPE(18:0) [sn1]/LPC(P-18:1) | 1.66 | 1.39 | 1.98 | 1.9E−08 |
| LPE(18:0) [sn1]/LPC(P-20:0) | 1.87 | 1.55 | 2.26 | 8.6E−11 |
| LPE(18:0) [sn1]/LPE(P-20:0) | 1.69 | 1.41 | 2.01 | 8.2E−09 |
| LPE(18:0) [sn1]/PC(MHDA_18:1) | 1.58 | 1.31 | 1.90 | 1.1E−06 |
| LPE(18:0) [sn1]/PC(MHDA_18:2) | 1.68 | 1.37 | 2.06 | 6.5E−07 |
| LPE(18:0) [sn1]/PC(MHDA_22:6) | 1.70 | 1.41 | 2.05 | 3.5E−08 |
| LPE(18:0) [sn1]/PC(17:0_22:6) | 1.49 | 1.25 | 1.77 | 5.9E−06 |
| LPE(18:0) [sn1]/PI(37:6) | 1.71 | 1.41 | 2.08 | 6.0E−08 |
| LPE(18:0) [sn1]/SM(d16:1/19:0) | 1.64 | 1.34 | 2.02 | 2.3E−06 |
| LPE(18:0) [sn1]/SM(d17:1/14:0) | 1.58 | 1.31 | 1.90 | 1.5E−06 |
| LPE(18:0) [sn1]/SM(d17:1/16:0) | 1.59 | 1.32 | 1.93 | 2.0E−06 |
| LPE(18:0) [sn1]/SM(d17:1/24:1) | 1.58 | 1.32 | 1.90 | 9.1E−07 |
| LPE(18:0) [sn1]/SM(d18:2/17:0) | 1.56 | 1.28 | 1.91 | 1.4E−05 |
| LPE(18:0) [sn1]/SM(d18:2/18:1) | 1.51 | 1.25 | 1.82 | 2.0E−05 |
| LPE(18:0) [sn1]/SM(d18:2/23:0) | 1.66 | 1.37 | 2.02 | 3.1E−07 |
| LPE(18:0) [sn1]/SM(d18:2/24:0) | 1.64 | 1.37 | 1.98 | 1.4E−07 |
| LPE(18:0) [sn2]/Cer(d18:2/26:0) | 1.54 | 1.29 | 1.84 | 1.4E−06 |
| LPE(18:0) [sn2]/Cer(d19:1/26:0) | 1.41 | 1.18 | 1.68 | 1.3E−04 |
| LPE(18:0) [sn2]/LPC(17:0) [sn2] | 1.80 | 1.50 | 2.16 | 2.9E−10 |
| LPE(18:0) [sn2]/LPC(MHDA) [sn1] | 1.78 | 1.48 | 2.13 | 9.2E−10 |
| LPE(18:0) [sn2]/LPC(MHDA) [sn2] | 1.82 | 1.51 | 2.19 | 1.9E−10 |
| LPE(18:0) [sn2]/LPC(17:0) [sn1] | 1.68 | 1.41 | 2.00 | 6.8E−09 |
| LPE(18:0) [sn2]/LPC(18:2) [sn1] | 1.75 | 1.46 | 2.09 | 9.1E−10 |
| LPE(18:0) [sn2]/LPC(18:2) [sn2] | 1.74 | 1.46 | 2.08 | 1.1E−09 |
| LPE(18:0) [sn2]/LPC(19:0) [sn2] | 1.73 | 1.45 | 2.07 | 2.7E−09 |
| LPE(18:0) [sn2]/LPC(19:0) [sn1] | 1.63 | 1.37 | 1.94 | 3.1E−08 |
| LPE(18:0) [sn2]/LPC(20:0) [sn2] | 1.60 | 1.35 | 1.90 | 5.7E−08 |
| LPE(18:0) [sn2]/LPC(20:1) [sn1] | 1.71 | 1.43 | 2.03 | 2.4E−09 |
| LPE(18:0) [sn2]/LPC(20:1) [sn2] | 1.67 | 1.40 | 1.99 | 7.9E−09 |
| LPE(18:0) [sn2]/LPC(20:2) [sn1] | 1.92 | 1.60 | 2.30 | 2.6E−12 |
| LPE(18:0) [sn2]/LPC(22:0) [sn1] | 1.56 | 1.31 | 1.84 | 2.7E−07 |
| LPE(18:0) [sn2]/LPC(22:1) [sn1] | 1.59 | 1.34 | 1.89 | 1.4E−07 |
| LPE(18:0) [sn2]/LPC(22:1) [sn2] | 1.58 | 1.33 | 1.89 | 3.4E−07 |
| LPE(18:0) [sn2]/LPC(24:0) [sn1] | 1.57 | 1.33 | 1.86 | 1.6E−07 |
| LPE(18:0) [sn2]/LPC(24:0) [sn2] | 1.61 | 1.35 | 1.92 | 7.7E−08 |
| LPE(18:0) [sn2]/LPC(26:0) [sn1] | 1.75 | 1.47 | 2.09 | 6.0E−10 |
| LPE(18:0) [sn2]/LPC(26:0) [sn2] | 1.74 | 1.46 | 2.08 | 8.3E−10 |
| LPE(18:0) [sn2]/LPC(P-16:0) | 1.74 | 1.45 | 2.08 | 2.2E−09 |
| LPE(18:0) [sn2]/LPC(P-17:0) | 1.66 | 1.40 | 1.97 | 7.2E−09 |
| LPE(18:0) [sn2]/LPC(P-18:0) | 1.68 | 1.41 | 2.01 | 7.9E−09 |
| LPE(18:0) [sn2]/LPC(P-18:1) | 1.65 | 1.38 | 1.96 | 2.1E−08 |
| LPE(18:0) [sn2]/LPC(P-20:0) | 1.85 | 1.54 | 2.23 | 1.2E−10 |
| LPE(18:0) [sn2]/LPE(P-20:0) | 1.68 | 1.41 | 2.00 | 7.0E−09 |
| LPE(18:0) [sn2]/PC(MHDA_18:1) | 1.55 | 1.29 | 1.86 | 2.4E−06 |
| LPE(18:0) [sn2]/PC(MHDA_18:2) | 1.64 | 1.34 | 2.01 | 1.9E−06 |
| LPE(18:0) [sn2]/PC(MHDA_22:6) | 1.69 | 1.40 | 2.04 | 5.8E−08 |
| LPE(18:0) [sn2]/PC(17:0_22:6) | 1.48 | 1.24 | 1.75 | 8.2E−06 |
| LPE(18:0) [sn2]/PI(37:6) | 1.69 | 1.40 | 2.04 | 5.4E−08 |
| LPE(18:0) [sn2]/SM(d16:1/19:0) | 1.62 | 1.31 | 1.99 | 5.3E−06 |
| LPE(18:0) [sn2]/SM(d17:1/14:0) | 1.57 | 1.30 | 1.89 | 2.1E−06 |
| LPE(18:0) [sn2]/SM(d17:1/16:0) | 1.57 | 1.29 | 1.89 | 3.9E−06 |
| LPE(18:0) [sn2]/SM(d17:1/24:1) | 1.55 | 1.29 | 1.86 | 2.4E−06 |

TABLE 3-continued

Odds Ratios based on combination biomarker values of Group A and Group B, and Group C and Group D diabetes biomarkers in subjects who developed diabetes during the follow-up as compared to a control group in AusDiab study cohort according to some embodiments of all aspects of the present disclosure. Abbreviations are described in the detailed description of the present disclosure.

| Lipids | OR | CI_LOW | CI_HIGH | p_value |
|---|---|---|---|---|
| LPE(18:0) [sn2]/SM(d18:2/17:0) | 1.53 | 1.26 | 1.87 | 2.7E−05 |
| LPE(18:0) [sn2]/SM(d18:2/18:1) | 1.49 | 1.23 | 1.80 | 3.2E−05 |
| LPE(18:0) [sn2]/SM(d18:2/23:0) | 1.63 | 1.35 | 1.99 | 7.2E−07 |
| LPE(18:0) [sn2]/SM(d18:2/24:0) | 1.62 | 1.34 | 1.94 | 4.2E−07 |
| LPI(18:0) [sn2]/Cer(d19:1/26:0) | 1.26 | 1.08 | 1.48 | 4.1E−03 |
| LPI(18:0) [sn2]/LPC(17:0) [sn2] | 1.40 | 1.19 | 1.65 | 6.3E−05 |
| LPI(18:0) [sn2]/LPC(MHDA) [sn1] | 1.41 | 1.20 | 1.67 | 4.2E−05 |
| LPI(18:0) [sn2]/LPC(MHDA) [sn2] | 1.42 | 1.21 | 1.68 | 2.7E−05 |
| LPI(18:0) [sn2]/LPC(17:0) [sn1] | 1.35 | 1.14 | 1.58 | 3.7E−04 |
| LPI(18:0) [sn2]/LPC(18:2) [sn2] | 1.39 | 1.18 | 1.63 | 9.0E−05 |
| LPI(18:0) [sn2]/LPC(19:0) [sn2] | 1.38 | 1.17 | 1.62 | 1.2E−04 |
| LPI(18:0) [sn2]/LPC(19:0) [sn1] | 1.35 | 1.15 | 1.59 | 2.7E−04 |
| LPI(18:0) [sn2]/LPC(20:0) [sn2] | 1.32 | 1.12 | 1.55 | 8.6E−04 |
| LPI(18:0) [sn2]/LPC(20:1) [sn1] | 1.39 | 1.18 | 1.64 | 8.5E−05 |
| LPI(18:0) [sn2]/LPC(20:1) [sn2] | 1.37 | 1.16 | 1.61 | 1.5E−04 |
| LPI(18:0) [sn2]/LPC(20:2) [sn1] | 1.38 | 1.17 | 1.62 | 1.3E−04 |
| LPI(18:0) [sn2]/LPC(22:0) [sn1] | 1.33 | 1.13 | 1.56 | 7.4E−04 |
| LPI(18:0) [sn2]/LPC(22:1) [sn1] | 1.38 | 1.17 | 1.62 | 1.3E−04 |
| LPI(18:0) [sn2]/LPC(22:1) [sn2] | 1.37 | 1.16 | 1.62 | 1.8E−04 |
| LPI(18:0) [sn2]/LPC(24:0) [sn1] | 1.32 | 1.12 | 1.56 | 8.1E−04 |
| LPI(18:0) [sn2]/LPC(24:0) [sn2] | 1.36 | 1.15 | 1.59 | 2.4E−04 |
| LPI(18:0) [sn2]/LPC(26:0) [sn2] | 1.49 | 1.25 | 1.76 | 5.1E−06 |
| LPI(18:0) [sn2]/LPC(P-16:0) | 1.34 | 1.14 | 1.58 | 3.7E−04 |
| LPI(18:0) [sn2]/LPC(P-17:0) | 1.36 | 1.16 | 1.61 | 1.8E−04 |
| LPI(18:0) [sn2]/LPC(P-18:0) | 1.36 | 1.15 | 1.61 | 2.6E−04 |
| LPI(18:0) [sn2]/LPC(P-18:1) | 1.39 | 1.17 | 1.64 | 1.2E−04 |
| LPI(18:0) [sn2]/LPE(P-20:0) | 1.41 | 1.19 | 1.66 | 5.1E−05 |
| LPI(18:0) [sn2]/PC(MHDA_18:1) | 1.31 | 1.11 | 1.54 | 1.4E−03 |
| LPI(18:0) [sn2]/PC(MHDA_18:2) | 1.41 | 1.19 | 1.67 | 8.3E−05 |
| LPI(18:0) [sn2]/PC(MHDA_22:6) | 1.51 | 1.27 | 1.79 | 2.7E−06 |
| LPI(18:0) [sn2]/PC(17:0_22:6) | 1.38 | 1.17 | 1.63 | 1.3E−04 |
| LPI(18:0) [sn2]/PI(37:6) | 1.50 | 1.26 | 1.78 | 6.0E−06 |
| LPI(18:0) [sn2]/SM(d16:1/19:0) | 1.39 | 1.17 | 1.64 | 1.3E−04 |
| LPI(18:0) [sn2]/SM(d17:1/14:0) | 1.43 | 1.21 | 1.70 | 2.6E−05 |
| LPI(18:0) [sn2]/SM(d17:1/16:0) | 1.39 | 1.17 | 1.64 | 1.2E−04 |
| LPI(18:0) [sn2]/SM(d18:2/17:0) | 1.40 | 1.17 | 1.67 | 2.9E−04 |
| LPI(18:0) [sn2]/SM(d18:2/18:1) | 1.43 | 1.18 | 1.73 | 2.4E−04 |
| LPI(18:0) [sn2]/SM(d18:2/24:0) | 1.39 | 1.18 | 1.64 | 8.8E−05 |
| LPI(20:4) [sn1]/Cer(d19:1/26:0) | 1.32 | 1.12 | 1.55 | 7.1E−04 |
| LPI(20:4) [sn1]/LPC(17:0) [sn2] | 1.49 | 1.26 | 1.76 | 4.4E−06 |
| LPI(20:4) [sn1]/LPC(MHDA) [sn1] | 1.50 | 1.26 | 1.78 | 4.2E−06 |
| LPI(20:4) [sn1]/LPC(MHDA) [sn2] | 1.51 | 1.27 | 1.79 | 2.5E−06 |
| LPI(20:4) [sn1]/LPC(17:0) [sn1] | 1.41 | 1.20 | 1.66 | 4.3E−05 |
| LPI(20:4) [sn1]/LPC(18:2) [sn1] | 1.58 | 1.33 | 1.87 | 1.5E−07 |
| LPI(20:4) [sn1]/LPC(18:2) [sn2] | 1.58 | 1.33 | 1.87 | 1.3E−07 |
| LPI(20:4) [sn1]/LPC(19:0) [sn2] | 1.46 | 1.24 | 1.73 | 1.0E−05 |
| LPI(20:4) [sn1]/LPC(19:0) [sn1] | 1.41 | 1.19 | 1.67 | 5.1E−05 |
| LPI(20:4) [sn1]/LPC(20:0) [sn2] | 1.42 | 1.20 | 1.67 | 3.3E−05 |
| LPI(20:4) [sn1]/LPC(20:1) [sn1] | 1.46 | 1.23 | 1.72 | 8.5E−06 |
| LPI(20:4) [sn1]/LPC(20:1) [sn2] | 1.44 | 1.22 | 1.69 | 1.5E−05 |
| LPI(20:4) [sn1]/LPC(20:2) [sn1] | 1.51 | 1.28 | 1.78 | 1.1E−06 |
| LPI(20:4) [sn1]/LPC(22:0) [sn1] | 1.39 | 1.18 | 1.63 | 8.6E−05 |
| LPI(20:4) [sn1]/LPC(22:1) [sn1] | 1.42 | 1.21 | 1.68 | 2.7E−05 |
| LPI(20:4) [sn1]/LPC(22:1) [sn2] | 1.44 | 1.22 | 1.69 | 1.4E−05 |
| LPI(20:4) [sn1]/LPC(24:0) [sn1] | 1.42 | 1.21 | 1.67 | 2.8E−05 |
| LPI(20:4) [sn1]/LPC(24:0) [sn2] | 1.46 | 1.23 | 1.72 | 8.2E−06 |
| LPI(20:4) [sn1]/LPC(26:0) [sn1] | 1.56 | 1.31 | 1.84 | 3.1E−07 |
| LPI(20:4) [sn1]/LPC(26:0) [sn2] | 1.53 | 1.30 | 1.81 | 6.5E−07 |
| LPI(20:4) [sn1]/LPC(P-16:0) | 1.47 | 1.24 | 1.73 | 8.1E−06 |
| LPI(20:4) [sn1]/LPC(P-17:0) | 1.43 | 1.21 | 1.68 | 2.3E−05 |
| LPI(20:4) [sn1]/LPC(P-18:0) | 1.45 | 1.23 | 1.71 | 1.1E−05 |
| LPI(20:4) [sn1]/LPC(P-18:1) | 1.42 | 1.20 | 1.69 | 4.1E−05 |
| LPI(20:4) [sn1]/LPC(P-20:0) | 1.60 | 1.35 | 1.89 | 4.3E−08 |
| LPI(20:4) [sn1]/LPE(P-20:0) | 1.53 | 1.27 | 1.84 | 5.3E−06 |
| LPI(20:4) [sn1]/PC(MHDA_18:1) | 1.40 | 1.18 | 1.65 | 7.3E−05 |
| LPI(20:4) [sn1]/PC(MHDA_18:2) | 1.46 | 1.24 | 1.73 | 7.0E−06 |
| LPI(20:4) [sn1]/PC(MHDA_22:6) | 1.53 | 1.29 | 1.81 | 9.9E−07 |
| LPI(20:4) [sn1]/PC(17:0_22:6) | 1.36 | 1.15 | 1.61 | 2.9E−04 |
| LPI(20:4) [sn1]/PI(37:6) | 1.50 | 1.25 | 1.81 | 1.9E−05 |
| LPI(20:4) [sn1]/SM(d16:1/19:0) | 1.41 | 1.20 | 1.67 | 4.4E−05 |
| LPI(20:4) [sn1]/SM(d17:1/14:0) | 1.41 | 1.19 | 1.66 | 5.3E−05 |
| LPI(20:4) [sn1]/SM(d17:1/16:0) | 1.36 | 1.15 | 1.60 | 2.7E−04 |

TABLE 3-continued

Odds Ratios based on combination biomarker values of Group A and Group B, and Group C and Group D diabetes biomarkers in subjects who developed diabetes during the follow-up as compared to a control group in AusDiab study cohort according to some embodiments of all aspects of the present disclosure. Abbreviations are described in the detailed description of the present disclosure.

| Lipids | OR | CI_LOW | CI_HIGH | p_value |
|---|---|---|---|---|
| LPI(20:4) [sn1]/SM(d17:1/24:1) | 1.41 | 1.20 | 1.67 | 4.2E−05 |
| LPI(20:4) [sn1]/SM(d18:2/17:0) | 1.37 | 1.16 | 1.62 | 1.8E−04 |
| LPI(20:4) [sn1]/SM(d18:2/18:1) | 1.36 | 1.16 | 1.61 | 2.2E−04 |
| LPI(20:4) [sn1]/SM(d18:2/24:0) | 1.44 | 1.22 | 1.71 | 1.9E−05 |
| LPI(20:4) [sn2]/Cer(d18:2/26:0) | 1.36 | 1.15 | 1.60 | 2.4E−04 |
| LPI(20:4) [sn2]/Cer(d19:1/26:0) | 1.33 | 1.13 | 1.57 | 6.2E−04 |
| LPI(20:4) [sn2]/LPC(17:0) [sn2] | 1.46 | 1.24 | 1.73 | 6.7E−06 |
| LPI(20:4) [sn2]/LPC(MHDA) [sn1] | 1.47 | 1.24 | 1.74 | 6.4E−06 |
| LPI(20:4) [sn2]/LPC(MHDA) [sn2] | 1.48 | 1.26 | 1.75 | 3.8E−06 |
| LPI(20:4) [sn2]/LPC(17:0) [sn1] | 1.39 | 1.18 | 1.64 | 6.9E−05 |
| LPI(20:4) [sn2]/LPC(18:2) [sn1] | 1.53 | 1.29 | 1.80 | 5.5E−07 |
| LPI(20:4) [sn2]/LPC(18:2) [sn2] | 1.54 | 1.31 | 1.82 | 2.7E−07 |
| LPI(20:4) [sn2]/LPC(19:0) [sn2] | 1.43 | 1.22 | 1.69 | 1.6E−05 |
| LPI(20:4) [sn2]/LPC(19:0) [sn1] | 1.39 | 1.18 | 1.63 | 7.7E−05 |
| LPI(20:4) [sn2]/LPC(20:0) [sn2] | 1.40 | 1.19 | 1.65 | 5.0E−05 |
| LPI(20:4) [sn2]/LPC(20:1) [sn1] | 1.41 | 1.19 | 1.65 | 4.5E−05 |
| LPI(20:4) [sn2]/LPC(20:1) [sn2] | 1.41 | 1.20 | 1.66 | 3.5E−05 |
| LPI(20:4) [sn2]/LPC(20:2) [sn1] | 1.45 | 1.23 | 1.71 | 9.5E−06 |
| LPI(20:4) [sn2]/LPC(22:0) [sn1] | 1.38 | 1.17 | 1.62 | 1.1E−04 |
| LPI(20:4) [sn2]/LPC(22:1) [sn1] | 1.38 | 1.17 | 1.62 | 1.2E−04 |
| LPI(20:4) [sn2]/LPC(22:1) [sn2] | 1.42 | 1.20 | 1.67 | 2.8E−05 |
| LPI(20:4) [sn2]/LPC(24:0) [sn1] | 1.39 | 1.18 | 1.64 | 8.9E−05 |
| LPI(20:4) [sn2]/LPC(24:0) [sn2] | 1.45 | 1.23 | 1.71 | 9.7E−06 |
| LPI(20:4) [sn2]/LPC(26:0) [sn1] | 1.54 | 1.30 | 1.82 | 6.4E−07 |
| LPI(20:4) [sn2]/LPC(26:0) [sn2] | 1.52 | 1.28 | 1.80 | 9.9E−07 |
| LPI(20:4) [sn2]/LPC(P-16:0) | 1.40 | 1.19 | 1.65 | 5.3E−05 |
| LPI(20:4) [sn2]/LPC(P-17:0) | 1.40 | 1.19 | 1.65 | 5.3E−05 |
| LPI(20:4) [sn2]/LPC(P-18:0) | 1.42 | 1.20 | 1.67 | 3.0E−05 |
| LPI(20:4) [sn2]/LPC(P-18:1) | 1.38 | 1.17 | 1.63 | 1.4E−04 |
| LPI(20:4) [sn2]/LPC(P-20:0) | 1.56 | 1.32 | 1.85 | 1.5E−07 |
| LPI(20:4) [sn2]/LPE(P-20:0) | 1.47 | 1.24 | 1.75 | 1.1E−05 |
| LPI(20:4) [sn2]/PC(MHDA_18:1) | 1.38 | 1.17 | 1.62 | 1.2E−04 |
| LPI(20:4) [sn2]/PC(MHDA_18:2) | 1.45 | 1.23 | 1.72 | 1.4E−05 |
| LPI(20:4) [sn2]/PC(MHDA_22:6) | 1.57 | 1.32 | 1.86 | 2.9E−07 |
| LPI(20:4) [sn2]/PC(17:0_22:6) | 1.42 | 1.20 | 1.69 | 5.4E−05 |
| LPI(20:4) [sn2]/PI(37:6) | 1.48 | 1.23 | 1.77 | 2.5E−05 |
| LPI(20:4) [sn2]/SM(d16:1/19:0) | 1.41 | 1.19 | 1.67 | 8.8E−05 |
| LPI(20:4) [sn2]/SM(d17:1/14:0) | 1.41 | 1.19 | 1.67 | 7.7E−05 |
| LPI(20:4) [sn2]/SM(d17:1/16:0) | 1.37 | 1.15 | 1.63 | 3.3E−04 |
| LPI(20:4) [sn2]/SM(d17:1/24:1) | 1.44 | 1.22 | 1.71 | 2.0E−05 |
| LPI(20:4) [sn2]/SM(d18:2/17:0) | 1.41 | 1.19 | 1.67 | 9.2E−05 |
| LPI(20:4) [sn2]/SM(d18:2/18:1) | 1.41 | 1.19 | 1.67 | 7.6E−05 |
| LPI(20:4) [sn2]/SM(d18:2/23:0) | 1.50 | 1.26 | 1.78 | 4.8E−06 |
| LPI(20:4) [sn2]/SM(d18:2/24:0) | 1.48 | 1.25 | 1.75 | 5.6E−06 |
| PC(36:0)/LPC(26:0) [sn1] | 1.87 | 1.55 | 2.25 | 3.8E−11 |
| PC(36:0)/LPC(26:0) [sn2] | 1.83 | 1.52 | 2.20 | 1.3E−10 |
| PC(36:0)/LPC(P-20:0) | 1.87 | 1.55 | 2.25 | 5.1E−11 |
| PC(36:0)/PC(MHDA_22:6) | 1.89 | 1.56 | 2.29 | 1.3E−10 |
| PC(36:0)/PC(17:0_22:6) | 1.81 | 1.51 | 2.16 | 9.0E−11 |
| PC(36:0)/SM(d16:1/19:0) | 1.82 | 1.52 | 2.19 | 1.5E−10 |
| PC(36:0)/SM(d17:1/14:0) | 1.82 | 1.51 | 2.19 | 2.9E−10 |
| PC(36:0)/SM(d17:1/16:0) | 1.84 | 1.53 | 2.21 | 7.4E−11 |
| PC(36:0)/SM(d17:1/24:1) | 1.92 | 1.60 | 2.31 | 3.5E−12 |
| PC(36:0)/SM(d18:2/17:0) | 1.80 | 1.51 | 2.15 | 1.1E−10 |
| PC(36:0)/SM(d18:2/18:1) | 1.79 | 1.49 | 2.14 | 2.4E−10 |
| PC(36:0)/SM(d18:2/23:0) | 1.91 | 1.60 | 2.29 | 2.0E−12 |
| PC(36:0)/SM(d18:2/24:0) | 1.94 | 1.62 | 2.33 | 8.6E−13 |
| SM(d18:0/22:0)/LPC(26:0) [sn1] | 1.84 | 1.52 | 2.21 | 1.4E−10 |
| SM (d18:0/22:0)/LPC(26:0) [sn2] | 1.78 | 1.49 | 2.14 | 4.3E−10 |
| SM(d18:0/22:0)/LPC(P-20:0) | 1.84 | 1.53 | 2.22 | 1.7E−10 |
| SM(d18:0/22:0)/PC(MHDA_22:6) | 1.86 | 1.53 | 2.25 | 3.5E−10 |
| SM(d18:0/22:0)/PC(17:0_22:6) | 1.78 | 1.49 | 2.12 | 2.9E−10 |
| SM(d18:0/22:0)/SM(d17:1/24:1) | 1.89 | 1.57 | 2.27 | 1.8E−11 |
| SM(d18:0/22:0)/SM(d18:2/23:0) | 1.85 | 1.55 | 2.22 | 2.4E−11 |
| SM(d18:0/22:0)/SM(d18:2/24:0) | 1.88 | 1.57 | 2.26 | 1.3E−11 |
| TG(O-50:1)/Cer(d18:2/26:0) | 1.80 | 1.44 | 2.24 | 1.7E−07 |
| TG(O-50:1)/Cer(d19:1/26:0) | 1.58 | 1.30 | 1.92 | 3.9E−06 |
| TG(O-50:1)/LPC(17:0) [sn2] | 1.78 | 1.44 | 2.19 | 7.7E−08 |
| TG(O-50:1)/LPC(MHDA) [sn1] | 1.74 | 1.42 | 2.13 | 7.9E−08 |
| TG(O-50:1)/LPC(MHDA) [sn2] | 1.78 | 1.44 | 2.20 | 1.1E−07 |
| TG(O-50:1)/LPC(17:0) [sn1] | 1.75 | 1.42 | 2.16 | 2.1E−07 |
| TG(O-50:1)/LPC(18:2) [sn1] | 1.87 | 1.49 | 2.34 | 6.7E−08 |

TABLE 3-continued

Odds Ratios based on combination biomarker values of Group A and Group B, and Group C and Group D diabetes biomarkers in subjects who developed diabetes during the follow-up as compared to a control group in AusDiab study cohort according to some embodiments of all aspects of the present disclosure. Abbreviations are described in the detailed description of the present disclosure.

| Lipids | OR | CI_LOW | CI_HIGH | p_value |
|---|---|---|---|---|
| TG(O-50:1)/LPC(18:2) [sn2] | 1.94 | 1.53 | 2.47 | 6.6E−08 |
| TG(O-50:1)/LPC(19:0) [sn2] | 1.82 | 1.46 | 2.27 | 1.0E−07 |
| TG(O-50:1)/LPC(19:0) [sn1] | 1.70 | 1.39 | 2.08 | 3.3E−07 |
| TG(O-50:1)/LPC(20:0) [sn2] | 1.68 | 1.37 | 2.06 | 6.1E−07 |
| TG(O-50:1)/LPC(20:1) [sn1] | 1.72 | 1.39 | 2.12 | 4.5E−07 |
| TG(O-50:1)/LPC(20:1) [sn2] | 1.72 | 1.38 | 2.15 | 1.6E−06 |
| TG(O-50:1)/LPC(20:2) [sn1] | 1.83 | 1.47 | 2.29 | 8.9E−08 |
| TG(O-50:1)/LPC(22:0) [sn1] | 1.68 | 1.37 | 2.06 | 4.8E−07 |
| TG(O-50:1)/LPC(22:1) [sn1] | 1.71 | 1.38 | 2.13 | 1.4E−06 |
| TG(O-50:1)/LPC(22:1) [sn2] | 1.80 | 1.41 | 2.29 | 1.7E−06 |
| TG(O-50:1)/LPC(24:0) [sn1] | 1.81 | 1.43 | 2.29 | 6.6E−07 |
| TG(O-50:1)/LPC(24:0) [sn2] | 1.79 | 1.42 | 2.25 | 5.7E−07 |
| TG(O-50:1)/LPC(26:0) [sn1] | 2.00 | 1.56 | 2.56 | 5.1E−08 |
| TG(O-50:1)/LPC(26:0) [sn2] | 1.99 | 1.53 | 2.57 | 1.9E−07 |
| TG(O-50:1)/LPC(P-16:0) | 1.88 | 1.46 | 2.43 | 9.1E−07 |
| TG(O-50:1)/LPC(P-17:0) | 1.72 | 1.39 | 2.14 | 1.1E−06 |
| TG(O-50:1)/LPC(P-18:0) | 1.87 | 1.46 | 2.39 | 5.7E−07 |
| TG(O-50:1)/LPC(P-18:1) | 1.71 | 1.37 | 2.13 | 2.4E−06 |
| TG(O-50:1)/LPC(P-20:0) | 2.05 | 1.59 | 2.63 | 2.1E−08 |
| TG(O-50:1)/LPE(P-20:0) | 1.90 | 1.50 | 2.41 | 1.2E−07 |
| TG(O-50:1)/PC(MHDA_18:1) | 1.76 | 1.42 | 2.19 | 2.6E−07 |
| TG(O-50:1)/PC(MHDA_18:2) | 1.78 | 1.46 | 2.17 | 8.5E−09 |
| TG(O-50:1)/PC(MHDA_22:6) | 1.85 | 1.48 | 2.31 | 6.3E−08 |
| TG(O-50:1)/PC(17:0_22:6) | 1.67 | 1.35 | 2.06 | 1.8E−06 |
| TG(O-50:1)/PI(37:6) | 2.04 | 1.54 | 2.70 | 7.6E−07 |
| TG(O-50:1)/SM(d16:1/19:0) | 1.73 | 1.40 | 2.12 | 2.7E−07 |
| TG(O-50:1)/SM(d17:1/14:0) | 1.63 | 1.35 | 1.97 | 4.6E−07 |
| TG(O-50:1)/SM(d17:1/16:0) | 1.71 | 1.39 | 2.10 | 3.3E−07 |
| TG(O-50:1)/SM(d17:1/24:1) | 1.82 | 1.44 | 2.30 | 6.9E−07 |
| TG(O-50:1)/SM(d18:2/17:0) | 1.72 | 1.39 | 2.12 | 4.0E−07 |
| TG(O-50:1)/SM(d18:2/18:1) | 1.66 | 1.37 | 2.01 | 2.2E−07 |
| TG(O-50:1)/SM(d18:2/23:0) | 1.90 | 1.50 | 2.41 | 1.4E−07 |
| TG(O-50:1)/SM(d18:2/24:0) | 1.96 | 1.51 | 2.56 | 5.4E−07 |
| TG(O-52:0)/Cer(d18:2/26:0) | 1.62 | 1.34 | 1.96 | 7.0E−07 |
| TG(O-52:0)/Cer(d19:1/26:0) | 1.56 | 1.30 | 1.88 | 2.6E−06 |
| TG(O-52:0)/LPC(17:0) [sn2] | 1.73 | 1.41 | 2.13 | 1.6E−07 |
| TG(O-52:0)/LPC(MHDA) [sn1] | 1.75 | 1.42 | 2.14 | 7.8E−08 |
| TG(O-52:0)/LPC(MHDA) [sn2] | 1.80 | 1.45 | 2.22 | 6.7E−08 |
| TG(O-52:0)/LPC(17:0) [sn1] | 1.64 | 1.34 | 2.01 | 1.7E−06 |
| TG(O-52:0)/LPC(18:2) [sn1] | 1.82 | 1.46 | 2.27 | 9.6E−08 |
| TG(O-52:0)/LPC(18:2) [sn2] | 1.87 | 1.48 | 2.37 | 1.5E−07 |
| TG(O-52:0)/LPC(19:0) [sn2] | 1.71 | 1.38 | 2.11 | 7.5E−07 |
| TG(O-52:0)/LPC(19:0) [sn1] | 1.59 | 1.31 | 1.93 | 3.3E−06 |
| TG(O-52:0)/LPC(20:0) [sn2] | 1.57 | 1.30 | 1.90 | 3.1E−06 |
| TG(O-52:0)/LPC(20:1) [sn1] | 1.60 | 1.32 | 1.95 | 2.3E−06 |
| TG(O-52:0)/LPC(20:1) [sn2] | 1.61 | 1.30 | 1.98 | 8.6E−06 |
| TG(O-52:0)/LPC(20:2) [sn1] | 1.65 | 1.35 | 2.03 | 1.1E−06 |
| TG(O-52:0)/LPC(22:0) [sn1] | 1.56 | 1.29 | 1.88 | 3.3E−06 |
| TG(O-52:0)/LPC(22:1) [sn1] | 1.63 | 1.33 | 1.99 | 2.4E−06 |
| TG(O-52:0)/LPC(22:1) [sn2] | 1.71 | 1.37 | 2.14 | 2.6E−06 |
| TG(O-52:0)/LPC(24:0) [sn1] | 1.56 | 1.28 | 1.90 | 8.5E−06 |
| TG(O-52:0)/LPC(24:0) [sn2] | 1.59 | 1.30 | 1.93 | 4.2E−06 |
| TG(O-52:0)/LPC(26:0) [sn1] | 1.69 | 1.37 | 2.08 | 1.2E−06 |
| TG(O-52:0)/LPC(26:0) [sn2] | 1.71 | 1.36 | 2.14 | 3.7E−06 |
| TG(O-52:0)/LPC(P-16:0) | 1.67 | 1.34 | 2.08 | 4.3E−06 |
| TG(O-52:0)/LPC(P-17:0) | 1.66 | 1.35 | 2.03 | 1.0E−06 |
| TG(O-52:0)/LPC(P-18:0) | 1.69 | 1.36 | 2.10 | 2.0E−06 |
| TG(O-52:0)/LPC(P-18:1) | 1.53 | 1.26 | 1.85 | 1.3E−05 |
| TG(O-52:0)/LPC(P-20:0) | 1.80 | 1.44 | 2.25 | 2.8E−07 |
| TG(O-52:0)/LPE(P-20:0) | 1.78 | 1.43 | 2.23 | 3.4E−07 |
| TG(O-52:0)/PC(MHDA_18:1) | 1.76 | 1.42 | 2.18 | 2.6E−07 |
| TG(O-52:0)/PC(MHDA_18:2) | 1.78 | 1.45 | 2.18 | 2.5E−08 |
| TG(O-52:0)/PC(MHDA_22:6) | 1.80 | 1.45 | 2.25 | 1.6E−07 |
| TG(O-52:0)/PC(17:0_22:6) | 1.58 | 1.29 | 1.94 | 1.2E−05 |
| TG(O-52:0)/SM(d16:1/19:0) | 1.65 | 1.36 | 2.01 | 6.3E−07 |
| TG(O-52:0)/SM(d17:1/14:0) | 1.54 | 1.28 | 1.84 | 3.4E−06 |
| TG(O-52:0)/SM(d17:1/16:0) | 1.58 | 1.30 | 1.91 | 3.5E−06 |
| TG(O-52:0)/SM(d17:1/24:1) | 1.61 | 1.31 | 1.99 | 6.5E−06 |
| TG(O-52:0)/SM(d 18:2/17:0) | 1.58 | 1.30 | 1.92 | 3.6E−06 |
| TG(O-52:0)/SM(d18:2/18:1) | 1.55 | 1.29 | 1.86 | 2.3E−06 |
| TG(O-52:0)/SM(d18:2/23:0) | 1.61 | 1.31 | 1.96 | 3.9E−06 |
| TG(O-52:0)/SM(d18:2/24:0) | 1.60 | 1.30 | 1.98 | 1.3E−05 |

TABLE 3-continued

Odds Ratios based on combination biomarker values of Group A and Group B, and Group C and Group D diabetes biomarkers in subjects who developed diabetes during the follow-up as compared to a control group in AusDiab study cohort according to some embodiments of all aspects of the present disclosure. Abbreviations are described in the detailed description of the present disclosure.

| Lipids | OR | CI_LOW | CI_HIGH | p_value |
|---|---|---|---|---|
| TG(O-52:2)/Cer(d18:2/26:0) | 1.70 | 1.39 | 2.06 | 1.2E-07 |
| TG(O-52:2)/Cer(d19:1/26:0) | 1.51 | 1.27 | 1.80 | 3.1E-06 |
| TG(O-52:2)/LPC(17:0) [sn2] | 1.64 | 1.36 | 1.97 | 2.0E-07 |
| TG(O-52:2)/LPC(MHDA) [sn1] | 1.61 | 1.34 | 1.93 | 3.5E-07 |
| TG(O-52:2)/LPC(MHDA) [sn2] | 1.62 | 1.34 | 1.95 | 4.2E-07 |
| TG(O-52:2)/LPC(17:0) [sn1] | 1.63 | 1.35 | 1.96 | 3.8E-07 |
| TG(O-52:2)/LPC(18:2) [sn1] | 1.78 | 1.45 | 2.18 | 2.4E-08 |
| TG(O-52:2)/LPC(18:2) [sn2] | 1.86 | 1.50 | 2.30 | 1.7E-08 |
| TG(O-52:2)/LPC(19:0) [sn2] | 1.66 | 1.38 | 2.01 | 1.4E-07 |
| TG(O-52:2)/LPC(19:0) [sn1] | 1.60 | 1.34 | 1.92 | 3.4E-07 |
| TG(O-52:2)/LPC(20:0) [sn2] | 1.61 | 1.34 | 1.93 | 2.6E-07 |
| TG(O-52:2)/LPC(20:1) [sn1] | 1.66 | 1.37 | 2.00 | 1.8E-07 |
| TG(O-52:2)/LPC(20:1) [sn2] | 1.65 | 1.36 | 2.01 | 5.4E-07 |
| TG(O-52:2)/LPC(20:2) [sn1] | 1.76 | 1.44 | 2.15 | 2.9E-08 |
| TG(O-52:2)/LPC(22:0) [sn1] | 1.61 | 1.35 | 1.93 | 2.0E-07 |
| TG(O-52:2)/LPC(22:1) [sn1] | 1.65 | 1.36 | 2.00 | 3.8E-07 |
| TG(O-52:2)/LPC(22:1) [sn2] | 1.72 | 1.39 | 2.11 | 4.0E-07 |
| TG(O-52:2)/LPC(24:0) [sn1] | 1.71 | 1.40 | 2.10 | 2.1E-07 |
| TG(O-52:2)/LPC(24:0) [sn2] | 1.70 | 1.40 | 2.08 | 1.5E-07 |
| TG(O-52:2)/LPC(26:0) [sn1] | 1.88 | 1.51 | 2.34 | 1.7E-08 |
| TG(O-52:2)/LPC(26:0) [sn2] | 1.87 | 1.49 | 2.34 | 5.3E-08 |
| TG(O-52:2)/LPC(P-16:0) | 1.70 | 1.38 | 2.10 | 7.4E-07 |
| TG(O-52:2)/LPC(P-17:0) | 1.58 | 1.31 | 1.89 | 1.1E-06 |
| TG(O-52:2)/LPC(P-18:0) | 1.69 | 1.38 | 2.08 | 4.7E-07 |
| TG(O-52:2)/LPC(P-18:1) | 1.63 | 1.34 | 1.98 | 1.1E-06 |
| TG(O-52:2)/LPC(P-20:0) | 1.88 | 1.52 | 2.33 | 7.7E-09 |
| TG(O-52:2)/LPE(P-20:0) | 1.78 | 1.44 | 2.20 | 9.6E-08 |
| TG(O-52:2)/PC(MHDA_18:1) | 1.60 | 1.33 | 1.94 | 9.5E-07 |
| TG(O-52:2)/PC(MHDA_18:2) | 1.72 | 1.43 | 2.07 | 1.3E-08 |
| TG(O-52:2)/PC(MHDA_22:6) | 1.76 | 1.44 | 2.16 | 4.6E-08 |
| TG(O-52:2)/PC(17:0_22:6) | 1.64 | 1.35 | 2.00 | 1.0E-06 |
| TG(O-52:2)/PI(37:6) | 1.98 | 1.53 | 2.57 | 2.3E-07 |
| TG(O-52:2)/SM(d16:1/19:0) | 1.63 | 1.35 | 1.97 | 3.8E-07 |
| TG(O-52:2)/SM(d17:1/14:0) | 1.59 | 1.33 | 1.91 | 4.3E-07 |
| TG(O-52:2)/SM(d17:1/16:0) | 1.64 | 1.36 | 1.98 | 2.6E-07 |
| TG(O-52:2)/SM(d17:1/24:1) | 1.73 | 1.40 | 2.14 | 3.4E-07 |
| TG(O-52:2)/SM(d 18:2/17:0) | 1.66 | 1.37 | 2.02 | 2.6E-07 |
| TG(O-52:2)/SM(d18:2/18:1) | 1.63 | 1.36 | 1.97 | 2.2E-07 |
| TG(O-52:2)/SM(d18:2/23:0) | 1.82 | 1.46 | 2.25 | 6.6E-08 |
| TG(O-52:2)/SM(d18:2/24:0) | 1.84 | 1.46 | 2.32 | 2.4E-07 |

Table 4 shows results of Odds Ratios based on individual diabetes biomarker values from Group A, Group B, Group C and Group D in subjects who developed diabetes during the follow-up as compared to a control group. As can be seen, Odds Ratios based on combination biomarker values of the at least one diabetes biomarker from Group A and the at least one diabetes biomarker from Group B, and combination biomarker values of the at least one diabetes biomarker from Group C and the diabetes biomarker from Group D, shown in Table 3, provide stronger association with incident diabetes than the individual markers in Table 4, improving thus the prognostic and diagnostic performance of the biomarkers.

TABLE 4

Odds Ratios based on Individual diabetes biomarker value from Group A, Group B, Group C and Group D in subjects who developed diabetes during the follow-up as compared to a control group in AusDiab study cohort. Abbreviations are described in the detailed description of the present disclosure.

| Lipids | OR | CI_LOW | CI_HIGH | p_value |
|---|---|---|---|---|
| Cer(d16:1/18:0) | 1.51 | 1.27 | 1.8 | 3.4E-06 |
| Cer(d16:1/20:0) | 1.49 | 1.25 | 1.77 | 6.5E-06 |
| Cer(d16:1/22:0) | 1.41 | 1.18 | 1.67 | 9.4E-05 |
| Cer(d17:1/20:0) | 1.23 | 1.04 | 1.45 | 1.6E-02 |
| Cer(d18:1/16:0) | 1.13 | 0.96 | 1.33 | 1.3E-01 |
| Cer(d18:1/18:0) | 1.51 | 1.27 | 1.79 | 2.3E-06 |
| Cer(d18:1/20:0) | 1.47 | 1.24 | 1.74 | 9.5E-06 |
| Cer(d18:1/21:0) | 1.26 | 1.07 | 1.49 | 5.8E-03 |
| Cer(d18:1/22:0) | 1.46 | 1.23 | 1.73 | 1.5E-05 |
| Cer(d18:2/26:0) | 0.76 | 0.64 | 0.9 | 1.2E-03 |
| Cer(d19:1/18:0) | 1.21 | 1.03 | 1.44 | 2.3E-02 |
| Cer(d19:1/26:0) | 0.82 | 0.69 | 0.96 | 1.6E-02 |
| Cer(d20:1/22:0) | 1.55 | 1.3 | 1.85 | 9.3E-07 |
| Cer(d20:1/23:0) | 1.29 | 1.09 | 1.53 | 2.9E-03 |
| Cer(d20:1/24:0) | 1.38 | 1.17 | 1.64 | 2.0E-04 |
| Cer(d20:1/24:1) | 1.25 | 1.06 | 1.48 | 8.1E-03 |
| LPC(14:0) [sn1] | 1.25 | 1.06 | 1.48 | 7.4E-03 |
| LPC(14:0) [sn2] | 1.24 | 1.05 | 1.46 | 1.2E-02 |
| LPC(17:0) [sn2] | 0.76 | 0.64 | 0.89 | 1.0E-03 |

TABLE 4-continued

Odds Ratios based on Individual diabetes biomarker value from Group A, Group B, Group C and Group D in subjects who developed diabetes during the follow-up as compared to a control group in AusDiab study cohort. Abbreviations are described in the detailed description of the present disclosure.

| Lipids | OR | CI_LOW | CI_HIGH | p_value |
|---|---|---|---|---|
| LPC(MHDA) [sn1] | 0.74 | 0.63 | 0.87 | 3.7E−04 |
| LPC(MHDA) [sn2] | 0.74 | 0.62 | 0.87 | 3.2E−04 |
| LPC(17:0) [sn1] | 0.8 | 0.68 | 0.95 | 9.6E−03 |
| LPC(18:2) [sn1] | 0.7 | 0.59 | 0.83 | 3.8E−05 |
| LPC(18:2) [sn2] | 0.72 | 0.61 | 0.85 | 1.1E−04 |
| LPC(19:0) [sn2] | 0.77 | 0.66 | 0.91 | 2.2E−03 |
| LPC(19:0) [sn1] | 0.79 | 0.67 | 0.93 | 4.1E−03 |
| LPC(20:0) [sn2] | 0.82 | 0.7 | 0.97 | 1.9E−02 |
| LPC(20:1) [sn1] | 0.77 | 0.65 | 0.91 | 2.2E−03 |
| LPC(20:1) [sn2] | 0.78 | 0.66 | 0.92 | 3.9E−03 |
| LPC(20:2) [sn1] | 0.77 | 0.65 | 0.91 | 2.4E−03 |
| LPC(22:0) [sn1] | 0.82 | 0.7 | 0.97 | 2.1E−02 |
| LPC(22:1) [sn1] | 0.79 | 0.66 | 0.93 | 6.2E−03 |
| LPC(22:1) [sn2] | 0.78 | 0.66 | 0.92 | 3.4E−03 |
| LPC(24:0) [sn1] | 0.81 | 0.68 | 0.95 | 1.1E−02 |
| LPC(24:0) [sn2] | 0.8 | 0.67 | 0.94 | 7.9E−03 |
| LPC(26:0) [sn1] | 0.67 | 0.57 | 0.8 | 5.6E−06 |
| LPC(26:0) [sn2] | 0.7 | 0.59 | 0.83 | 4.6E−05 |
| LPC(P-16:0) | 0.78 | 0.66 | 0.92 | 3.5E−03 |
| LPC(P-17:0) | 0.77 | 0.65 | 0.91 | 1.8E−03 |
| LPC(P-18:0) | 0.76 | 0.65 | 0.9 | 1.5E−03 |
| LPC(P-18:1) | 0.78 | 0.66 | 0.92 | 3.5E−03 |
| LPC(P-20:0) | 0.65 | 0.55 | 0.78 | 1.1E−06 |
| LPE(18:0) [sn1] | 1.36 | 1.15 | 1.61 | 2.7E−04 |
| LPE(18:0) [sn2] | 1.33 | 1.12 | 1.57 | 8.6E−04 |
| LPE(P-20:0) | 0.77 | 0.65 | 0.91 | 2.1E−03 |
| LPI(18:0) [sn2] | 1.23 | 1.04 | 1.45 | 1.5E−02 |
| LPI(20:4) [sn1] | 1.32 | 1.12 | 1.56 | 1.1E−03 |
| LPI(20:4) [sn2] | 1.3 | 1.1 | 1.54 | 2.2E−03 |
| PC(MHDA_18:1) | 0.82 | 0.69 | 0.96 | 1.6E−02 |
| PC(MHDA_18:2) | 0.72 | 0.61 | 0.85 | 8.7E−05 |
| PC(MHDA_22:6) | 0.67 | 0.56 | 0.79 | 3.1E−06 |
| PC(17:0_22:6) | 0.74 | 0.62 | 0.87 | 3.2E−04 |
| PC(36:0) | 1.77 | 1.48 | 2.12 | 2.9E−10 |
| PI(37:6) | 0.72 | 0.61 | 0.85 | 1.0E−04 |
| SM(d16:1/19:0) | 0.76 | 0.65 | 0.9 | 1.4E−03 |
| SM(d17:1/14:0) | 0.74 | 0.63 | 0.87 | 4.1E−04 |
| SM(d17:1/16:0) | 0.76 | 0.64 | 0.89 | 1.0E−03 |
| SM(d17:1/24:1) | 0.71 | 0.6 | 0.84 | 6.2E−05 |
| SM(d18:0/22:0) | 1.76 | 1.47 | 2.1 | 4.4E−10 |
| SM(d18:2/17:0) | 0.75 | 0.64 | 0.89 | 6.8E−04 |
| SM(d18:2/18:1) | 0.78 | 0.66 | 0.92 | 3.1E−03 |
| SM(d18:2/23:0) | 0.69 | 0.58 | 0.82 | 1.9E−05 |
| SM(d18:2/24:0) | 0.73 | 0.62 | 0.87 | 3.0E−04 |
| TG(O-50:1) | 1.48 | 1.25 | 1.75 | 7.3E−06 |
| TG(O-52:0) | 1.44 | 1.21 | 1.7 | 2.2E−05 |
| TG(O-52:2) | 1.46 | 1.23 | 1.73 | 1.1E−05 |

Finrisk 2002
Prediction of Incident Diabetes in FINRISK Study

Logistic regression models were constructed to predict the 10-year risk of incident diabetes in the FINRISK 2002 study. The models were constructed separately for men and women.

As an example, the following formula was developed by cross-validation and used in calculating the AUC (area under the curve) values of the models for a specific combination biomarker value based on of a diabetes biomarker from Group C and a diabetes biomarker from Group D, the ceramide ratio Cer(d18:1/18:0)/Cer(d18:1/16:0):

risk=$(\exp(r)/1+\exp(r))*100$, wherein for men $r=-11.66+0.18\times BMI+4.30\times Cer(d18:1/18:0)/Cer(d18:1/16:0)+0.040\times age$; and for women $r=-10.43+0.13\times BMI+4.01\times Cer(d18:1/18:0)/Cer(d18:1/16:0)+0.036\times age$.

As another example, the following formula was developed by cross-validation and used in calculating the AUC (area under the curve) values of the models for a specific combination biomarker value of a diabetes biomarker from Group C and a diabetes biomarker from Group D, the ceramide ratio Cer(d18:1/18:0)/Cer(d18:1/16:0):

risk=$(\exp(r)/1+\exp(r))*100$, wherein for men $r=-18.64+0.15\times BMI+4.55\times Cer(d18:1/18:0)/Cer(d18:1/16:0)+1.60\times glucose$; and for women $r=-18.63+0.07\times BMI+3.35\times Cer(d18:1/18:0)/Cer(d18:1/16:0)+2.11\times glucose$.

In Table 5, the cross-validated results are shown for the ceramide ratio Cer(d18:1/18:0)/Cer(d18:1/16:0). The addition of Cer(d18:1/18:0)/Cer(d18:1/16:0) increased the AUC values in the models incorporating BMI and age or glucose as well. The mean increase of the AUC value incorporating the ceramide ratio is 0.018 on top of BMI and age, and 0.013 on top of BMI and glucose.

TABLE 5

AUC values of logistic regression models for incident diabetes in FINRISK 2002 study. The values show median cross-validated AUC values together with 95% confidence interval. Abbreviations are described in the detailed description of the present disclosure.

| Variables | AUC |
|---|---|
| Cer(d18:1/18:0)/Cer(d18:1/16:0) + Glucose + BMI | 0.866 (0.806-0.914) |
| Glucose + BMI | 0.853 (0.797-0.904) |
| Cer(d18:1/18:0)/Cer(d18:1/16:0) + BMI + Age | 0.825 (0.804-0.846) |
| BMI + Age | 0.807 (0.786-0.828) |

Group A and Group B diabetes biomarkers surprisingly show strong association with fatty liver disease as well. Results for Group A, Group B, Group E and Group F fatty liver biomarkers are presented below in Tables 6, 7 and 8.
Young Finns Study Table 6 shows statistically significant Odds Ratios ($p<0.01$) based on combination biomarker values of at least one biomarker from Group A and at least one biomarker from Group B in subjects, whose liver fat content was determined four years after the lipid measurements, as compared to a control group.

TABLE 6

Odds Ratios (OR) based on combination biomarker values of Group A and Group B biomarkers in subjects, whose liver fat content was determined four years after the lipid measurements, as compared to a control group in Young Finns Study cohort.

| | FL | | NAFLD | | FL (severe) | | NAFLD (severe) | | DM2 | |
|---|---|---|---|---|---|---|---|---|---|---|
| Lipid ratio | OR | p-value | OR | p-value | OR | p-value | OR | p-value | OR | p-value |
| Cer(d16:1/18:0)/SM(d17:1/14:0) | 2.74 | 2.1E−38 | 3.04 | 7.4E−34 | 3.62 | 3.4E−19 | 3.94 | 1.1E−15 | 2.39 | 6.6E−05 |
| Cer(d18:1/22:0)/LPC(22:0) [sn1] | 2.54 | 2.3E−38 | 2.64 | 4.5E−32 | 3.66 | 3.2E−21 | 4.15 | 1.3E−18 | 2.30 | 3.0E−05 |
| Cer(d18:1/22:0)/LPC(20:0) [sn2] | 2.54 | 4.0E−38 | 2.57 | 7.5E−31 | 3.59 | 3.1E−21 | 3.82 | 4.0E−18 | 2.11 | 1.3E−04 |

TABLE 6-continued

Odds Ratios (OR) based on combination biomarker values of Group A and Group B biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| Cer(d18:1/18:0)/LPC(MHDA) [sn1] | 2.49 | 6.5E−38 | 2.58 | 4.2E−32 | 3.43 | 1.2E−21 | 3.42 | 1.9E−17 | 2.55 | 8.6E−08 |
| Cer(d18:1/18:0)/LPC(P-18:1) | 2.52 | 1.4E−37 | 2.58 | 7.1E−31 | 3.20 | 2.1E−19 | 3.08 | 3.1E−15 | 1.97 | 2.2E−04 |
| Cer(d18:1/22:0)/LPC(19:0) [sn1] | 2.52 | 1.7E−37 | 2.50 | 2.0E−29 | 3.54 | 1.2E−20 | 3.73 | 4.7E−17 | 2.23 | 3.1E−05 |
| Cer(d18:1/18:0)/LPC(19:0) [sn1] | 2.48 | 7.0E−37 | 2.55 | 1.9E−30 | 3.45 | 1.0E−20 | 3.53 | 6.1E−17 | 2.48 | 9.6E−07 |
| Cer(d16:1/18:0)/LPC(MHDA) [sn1] | 2.58 | 1.2E−36 | 2.83 | 2.7E−32 | 4.21 | 8.3E−22 | 4.35 | 1.3E−17 | 3.08 | 1.8E−07 |
| Cer(d18:1/18:0)/LPC(MHDA) [sn2] | 2.41 | 1.7E−36 | 2.47 | 2.5E−30 | 3.22 | 8.4E−21 | 3.16 | 1.8E−16 | 2.45 | 2.9E−07 |
| Cer(d16:1/18:0)/LPC(MHDA) [sn2] | 2.54 | 4.8E−36 | 2.75 | 2.3E−31 | 3.99 | 4.1E−21 | 4.10 | 9.4E−17 | 2.96 | 4.7E−07 |
| Cer(d18:1/18:0)/LPC(P-18:0) | 2.40 | 5.6E−36 | 2.48 | 4.5E−30 | 3.30 | 3.2E−20 | 3.16 | 5.6E−16 | 2.27 | 3.0E−06 |
| Cer(d18:1/18:0)/LPC(20:1) [sn1] | 2.52 | 1.2E−35 | 2.71 | 3.3E−31 | 3.79 | 9.4E−20 | 4.10 | 1.3E−16 | 2.24 | 8.6E−05 |
| Cer(d18:1/18:0)/LPC(19:0) [sn2] | 2.36 | 2.4E−35 | 2.46 | 4.3E−30 | 3.05 | 9.9E−21 | 3.12 | 1.9E−17 | 2.14 | 8.9E−06 |
| Cer(d18:1/22:0)/LPC(19:0) [sn2] | 2.36 | 2.8E−35 | 2.39 | 1.2E−28 | 2.97 | 2.7E−20 | 3.07 | 3.7E−17 | 1.87 | 3.1E−04 |
| Cer(d18:1/18:0)/LPC(17:0) [sn1] | 2.42 | 2.9E−35 | 2.44 | 1.5E−28 | 3.28 | 4.4E−20 | 3.27 | 5.2E−16 | 2.24 | 3.9E−06 |
| Cer(d18:1/18:0)/LPC(20:1) [sn2] | 2.47 | 1.2E−34 | 2.65 | 2.5E−30 | 3.53 | 1.3E−18 | 3.79 | 8.3E−16 | 2.15 | 2.0E−04 |
| Cer(d18:1/22:0)/LPC(MHDA) [sn1] | 2.31 | 1.4E−34 | 2.34 | 5.4E−28 | 3.13 | 9.5E−20 | 3.14 | 7.4E−16 | 2.22 | 8.5E−06 |
| Cer(d18:1/22:0)/LPC(24:0) [sn2] | 2.40 | 1.7E−34 | 2.58 | 2.3E−30 | 3.27 | 9.7E−19 | 3.76 | 6.4E−17 | 2.05 | 2.7E−04 |
| Cer(d18:1/18:0)/SM(d17:1/14:0) | 2.35 | 2.0E−34 | 2.42 | 5.4E−29 | 2.81 | 1.8E−17 | 2.81 | 2.0E−14 | 2.03 | 2.4E−04 |
| Cer(d18:1/22:0)/LPC(P-18:0) | 2.32 | 2.3E−34 | 2.31 | 3.7E−27 | 3.07 | 3.4E−19 | 3.01 | 5.4E−15 | 1.98 | 1.8E−04 |
| SM(d18:0/22:0)/LPC(P-18:1) | 2.35 | 3.2E−34 | 2.35 | 1.3E−27 | 3.19 | 6.0E−19 | 3.33 | 5.5E−16 | 1.74 | 6.5E−03 |
| SM(d18:0/22:0)/LPC(20:1) [sn1] | 2.40 | 4.1E−34 | 2.52 | 2.4E−29 | 3.67 | 8.2E−20 | 4.24 | 7.5E−18 | 1.91 | 2.2E−03 |
| Cer(d18:1/22:0)/LPC(20:1) [sn1] | 2.43 | 4.6E−34 | 2.55 | 8.4E−29 | 3.40 | 1.8E−18 | 3.77 | 4.6E−16 | 1.79 | 4.9E−03 |
| Cer(d16:1/18:0)/LPC(19:0) [sn1] | 2.47 | 4.7E−34 | 2.63 | 4.6E−29 | 3.92 | 6.2E−20 | 4.03 | 2.6E−16 | 2.85 | 4.7E−06 |
| Cer(d18:1/18:0)/LPC(22:0) [sn1] | 2.42 | 6.4E−34 | 2.60 | 1.2E−29 | 3.55 | 1.1E−19 | 3.79 | 6.1E−17 | 2.56 | 1.8E−06 |
| Cer(d18:1/18:0)/LPC(20:0) [sn2] | 2.38 | 7.8E−34 | 2.50 | 8.3E−29 | 3.44 | 7.4E−20 | 3.57 | 9.9E−17 | 2.36 | 7.9E−06 |
| Cer(d18:1/18:0)/LPC(17:0) [sn2] | 2.32 | 1.5E−33 | 2.37 | 1.3E−27 | 3.00 | 1.4E−19 | 2.96 | 1.3E−15 | 2.19 | 4.4E−06 |
| Cer(d16:1/18:0)/PC(17:0_22:6) | 2.44 | 1.9E−33 | 2.62 | 3.9E−29 | 3.00 | 5.8E−15 | 3.15 | 1.5E−12 | 2.06 | 1.1E−03 |
| SM(d18:0/22:0)/LPC(20:1) [sn2] | 2.36 | 4.9E−33 | 2.47 | 1.9E−28 | 3.45 | 1.6E−18 | 4.01 | 9.0E−17 | 1.82 | 4.2E−03 |
| SM(d18:0/22:0)/SM(d17:1/14:0) | 2.32 | 5.2E−33 | 2.35 | 5.2E−27 | 3.08 | 1.6E−17 | 3.18 | 3.1E−15 | 1.76 | 5.5E−03 |
| Cer(d18:1/18:0)/LPC(24:0) [sn2] | 2.37 | 7.8E−33 | 2.63 | 3.2E−30 | 3.34 | 8.7E−19 | 3.63 | 1.4E−16 | 2.40 | 5.0E−06 |
| Cer(d18:1/18:0)/LPC(24:0) [sn1] | 2.37 | 8.8E−33 | 2.63 | 2.9E−30 | 3.28 | 6.6E−19 | 3.53 | 1.2E−16 | 2.48 | 2.3E−06 |
| Cer(d18:1/22:0)/LPC(17:0) [sn1] | 2.29 | 9.5E−33 | 2.24 | 5.6E−25 | 3.10 | 1.0E−18 | 3.18 | 4.6E−15 | 1.90 | 6.0E−04 |
| Cer(d18:1/22:0)/LPC(MHDA) [sn2] | 2.23 | 1.0E−32 | 2.22 | 1.1E−25 | 2.85 | 1.8E−18 | 2.79 | 1.6E−14 | 2.09 | 3.0E−05 |
| SM(d18:0/22:0)/LPC(P-18:0) | 2.25 | 1.0E−32 | 2.27 | 8.0E−27 | 3.32 | 6.8E−20 | 3.42 | 9.5E−17 | 2.06 | 3.2E−04 |
| SM(d18:0/22:0)/LPC(20:0) [sn2] | 2.27 | 1.1E−32 | 2.34 | 1.8E−27 | 3.44 | 4.0E−20 | 3.86 | 4.8E−18 | 2.06 | 4.4E−04 |
| Cer(d16:1/18:0)/LPC(19:0) [sn2] | 2.36 | 1.4E−32 | 2.55 | 8.1E−29 | 3.37 | 9.1E−20 | 3.47 | 1.2E−16 | 2.32 | 2.2E−05 |
| Cer(d16:1/22:0)/LPC(17:0) [sn2] | 2.25 | 2.6E−32 | 2.21 | 6.0E−25 | 2.86 | 1.1E−18 | 2.82 | 7.9E−15 | 1.91 | 3.5E−04 |
| Cer(d16:1/18:0)/LPC(17:0) [sn1] | 2.39 | 3.6E−32 | 2.51 | 3.5E−27 | 3.78 | 1.7E−19 | 3.78 | 1.5E−15 | 2.61 | 2.0E−05 |
| SM(d18:0/22:0)/LPC(MHDA) [sn2] | 2.27 | 4.5E−32 | 2.28 | 2.6E−26 | 3.26 | 1.3E−19 | 3.32 | 9.6E−17 | 2.20 | 6.2E−05 |
| Cer(d16:1/18:0)/LPC(P-18:1) | 2.37 | 4.7E−32 | 2.49 | 1.4E−27 | 3.32 | 1.3E−17 | 3.22 | 6.5E−14 | 2.09 | 8.1E−04 |
| Cer(d16:1/18:0)/LPC(P-18:0) | 2.32 | 6.9E−32 | 2.46 | 7.2E−28 | 3.39 | 2.7E−19 | 3.47 | 2.1E−15 | 2.55 | 2.2E−05 |
| SM(d18:0/22:0)/LPC(19:0) [sn2] | 2.23 | 7.7E−32 | 2.30 | 2.8E−27 | 3.15 | 3.5E−20 | 3.47 | 4.5E−18 | 1.93 | 5.6E−04 |
| SM(d18:0/22:0)/LPC(24:0) [sn2] | 2.26 | 1.4E−31 | 2.44 | 2.0E−28 | 3.39 | 3.2E−19 | 4.04 | 3.5E−18 | 2.05 | 4.5E−04 |
| Cer(d16:1/18:0)/LPC(20:1) [sn1] | 2.41 | 2.7E−31 | 2.66 | 2.2E−28 | 3.83 | 4.2E−18 | 4.08 | 2.4E−15 | 2.35 | 3.0E−04 |
| Cer(d16:1/18:0)/LPC(17:0) [sn2] | 2.32 | 3.3E−31 | 2.46 | 5.7E−27 | 3.42 | 3.2E−19 | 3.43 | 1.8E−15 | 2.49 | 1.7E−05 |
| Cer(d18:1/18:0)/LPC(P-16:0) | 2.20 | 8.7E−31 | 2.28 | 3.4E−26 | 2.77 | 2.8E−17 | 2.73 | 3.1E−14 | 1.95 | 5.4E−05 |
| Cer(d18:1/18:0)/LPC(20:2) [sn1] | 2.24 | 1.7E−30 | 2.49 | 1.8E−28 | 3.04 | 1.2E−17 | 3.16 | 8.2E−15 | 2.24 | 1.7E−05 |
| Cer(d16:1/18:0)/LPC(22:0) [sn1] | 2.37 | 1.7E−30 | 2.61 | 1.2E−27 | 3.87 | 1.9E−18 | 4.20 | 8.1E−16 | 2.85 | 1.0E−05 |
| SM(d18:0/22:0)/LPC(17:0) [sn1] | 2.20 | 2.4E−30 | 2.20 | 2.0E−24 | 3.35 | 4.9E−19 | 3.55 | 1.5E−16 | 1.98 | 9.5E−04 |
| Cer(d16:1/18:0)/LPC(20:1) [sn2] | 2.36 | 2.5E−30 | 2.60 | 1.4E−27 | 3.58 | 6.0E−17 | 3.82 | 2.1E−14 | 2.24 | 6.0E−04 |
| Cer(d16:1/18:0)/LPC(20:0) [sn2] | 2.33 | 3.4E−30 | 2.50 | 1.1E−26 | 3.73 | 1.4E−18 | 3.89 | 1.2E−15 | 2.58 | 4.1E−05 |
| Cer(d16:1/18:0)/LPC(24:0) [sn1] | 2.34 | 1.7E−29 | 2.66 | 3.0E−28 | 3.69 | 9.3E−18 | 4.09 | 2.2E−15 | 2.80 | 1.4E−05 |
| Cer(d16:1/18:0)/LPC(24:0) [sn2] | 2.34 | 1.9E−29 | 2.65 | 5.5E−28 | 3.73 | 1.1E−17 | 4.17 | 1.6E−15 | 2.72 | 3.2E−05 |
| Cer(d16:1/22:0)/LPC(19:0) [sn2] | 2.17 | 2.0E−29 | 2.22 | 6.4E−25 | 2.69 | 4.5E−17 | 2.69 | 5.0E−14 | 1.85 | 8.1E−04 |
| Cer(d16:1/22:0)/LPC(MHDA) [sn2] | 2.14 | 8.3E−29 | 2.17 | 1.3E−23 | 2.72 | 5.2E−16 | 2.60 | 5.8E−12 | 2.16 | 6.3E−05 |
| SM(d18:0/22:0)/LPC(P-16:0) | 2.11 | 1.0E−28 | 2.17 | 2.7E−24 | 2.95 | 8.3E−18 | 3.21 | 7.3E−16 | 1.82 | 2.9E−03 |
| SM(d18:0/22:0)/LPC(17:0) [sn2] | 2.13 | 1.1E−28 | 2.16 | 1.3E−23 | 3.03 | 5.9E−18 | 3.22 | 1.7E−15 | 1.93 | 8.4E−04 |
| SM(d18:0/22:0)/LPE(P-20:0) | 2.10 | 1.7E−28 | 2.14 | 6.0E−24 | 3.02 | 3.7E−18 | 3.23 | 9.7E−16 | 1.89 | 1.1E−03 |
| SM(d18:0/22:0)/LPC(20:2) [sn1] | 2.16 | 1.7E−28 | 2.34 | 4.7E−26 | 3.17 | 2.3E−17 | 3.59 | 8.6E−16 | 1.94 | 1.2E−03 |
| Cer(d16:1/20:0)/SM(d17:1/14:0) | 2.21 | 2.5E−28 | 2.40 | 7.2E−26 | 2.55 | 1.2E−12 | 2.46 | 2.0E−09 | 2.41 | 7.6E−05 |
| Cer(d16:1/20:0)/LPC(MHDA) [sn1] | 2.16 | 5.5E−28 | 2.38 | 4.1E−26 | 3.04 | 1.1E−16 | 3.02 | 2.6E−13 | 2.99 | 6.3E−08 |
| Cer(d16:1/22:0)/LPC(19:0) [sn1] | 2.10 | 8.3E−28 | 2.17 | 1.6E−23 | 3.10 | 1.3E−17 | 3.06 | 1.2E−14 | 2.44 | 1.0E−06 |
| Cer(d18:1/22:0)/LPC(P-16:0) | 2.08 | 1.1E−27 | 2.09 | 2.9E−22 | 2.55 | 1.6E−15 | 2.56 | 7.8E−13 | 1.66 | 5.3E−03 |
| Cer(d16:1/18:0)/LPC(P-16:0) | 2.16 | 1.4E−27 | 2.32 | 8.5E−25 | 3.11 | 8.5E−17 | 3.11 | 6.5E−14 | 2.21 | 2.2E−04 |
| Cer(d18:1/22:0)/LPC(20:2) [sn1] | 2.09 | 1.5E−27 | 2.24 | 6.5E−25 | 2.75 | 2.4E−15 | 2.92 | 3.4E−13 | 1.85 | 2.4E−03 |
| Cer(d16:1/22:0)/LPC(19:0) [sn1] | 2.15 | 1.7E−27 | 2.30 | 1.4E−24 | 2.95 | 1.1E−16 | 2.96 | 8.2E−13 | 2.83 | 1.3E−06 |
| Cer(d16:1/18:0)/LPC(20:2) [sn1] | 2.21 | 2.6E−27 | 2.52 | 1.4E−26 | 3.34 | 3.5E−16 | 3.49 | 1.6E−13 | 2.47 | 7.0E−05 |
| Cer(d18:1/22:0)/LPC(18:2) [sn1] | 2.08 | 2.7E−27 | 2.18 | 7.4E−24 | 3.01 | 1.1E−17 | 3.13 | 6.7E−15 | 2.05 | 2.7E−04 |
| Cer(d16:1/20:0)/LPC(MHDA) [sn2] | 2.11 | 3.5E−27 | 2.28 | 9.7E−25 | 2.85 | 7.6E−16 | 2.78 | 2.7E−12 | 2.81 | 2.0E−07 |
| Cer(d18:1/18:0)/LPC(18:2) [sn1] | 2.08 | 4.7E−27 | 2.20 | 5.9E−24 | 3.06 | 5.2E−17 | 3.19 | 2.4E−14 | 1.90 | 1.8E−03 |
| Cer(d16:1/18:0)/LPE(P-20:0) | 2.16 | 5.5E−27 | 2.30 | 5.4E−24 | 3.24 | 4.8E−17 | 3.14 | 8.7E−14 | 2.33 | 7.4E−05 |
| SM(d18:0/22:0)/LPC(18:2) [sn1] | 2.07 | 5.6E−27 | 2.19 | 4.9E−24 | 3.16 | 4.7E−18 | 3.47 | 4.5E−16 | 2.06 | 4.3E−04 |
| LPC(14:0) [sn2]/LPC(19:0) [sn2] | 2.13 | 8.1E−27 | 2.08 | 1.1E−20 | 2.70 | 5.2E−15 | 2.64 | 3.7E−12 | 1.81 | 8.1E−04 |
| SM(d18:0/22:0)/LPC(18:2) [sn2] | 2.07 | 9.9E−27 | 2.20 | 5.6E−24 | 3.22 | 1.9E−17 | 3.57 | 1.3E−15 | 1.94 | 1.5E−03 |
| Cer(d18:1/20:0)/LPC(P-18:1) | 2.06 | 1.1E−26 | 2.12 | 1.4E−22 | 2.58 | 5.5E−15 | 2.51 | 9.9E−12 | 1.84 | 6.9E−04 |

TABLE 6-continued

Odds Ratios (OR) based on combination biomarker values of Group A and Group B biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| Cer(d18:1/22:0)/LPE(P-20:0) | 2.05 | 1.4E−26 | 2.03 | 6.4E−21 | 2.70 | 9.0E−16 | 2.61 | 2.0E−12 | 1.78 | 2.0E−03 |
| LPC(14:0) [sn2]/LPC(MHDA) [sn2] | 2.04 | 2.4E−26 | 1.95 | 2.8E−19 | 2.49 | 1.8E−13 | 2.24 | 1.7E−09 | 2.11 | 3.8E−05 |
| Cer(d18:1/20:0)/LPC(20:1) [sn1] | 2.10 | 2.5E−26 | 2.29 | 1.6E−24 | 3.07 | 1.8E−16 | 3.36 | 1.9E−14 | 2.16 | 1.4E−04 |
| Cer(d16:1/20:0)/LPC(19:0) [sn2] | 2.07 | 3.5E−26 | 2.25 | 1.5E−24 | 2.65 | 6.9E−16 | 2.70 | 1.5E−13 | 2.26 | 9.4E−06 |
| Cer(d18:1/20:0)/LPC(20:0) [sn2] | 2.05 | 5.5E−26 | 2.17 | 4.1E−23 | 2.97 | 2.9E−17 | 3.12 | 5.8E−15 | 2.36 | 4.7E−06 |
| Cer(d18:1/20:0)/LPC(19:0) [sn2] | 2.00 | 5.7E−26 | 2.10 | 4.3E−23 | 2.60 | 1.8E−17 | 2.67 | 4.1E−15 | 2.04 | 1.4E−05 |
| Cer(d16:1/22:0)/LPC(17:0) [sn1] | 2.05 | 7.5E−26 | 2.03 | 3.0E−20 | 2.64 | 1.5E−14 | 2.52 | 9.4E−11 | 1.87 | 2.3E−03 |
| Cer(d18:1/20:0)/LPC(MHDA) [sn1] | 2.01 | 7.5E−26 | 2.11 | 8.3E−23 | 2.83 | 2.1E−17 | 2.84 | 3.2E−14 | 2.48 | 1.6E−07 |
| Cer(d16:1/22:0)/LPC(17:0) [sn2] | 2.02 | 1.4E−25 | 2.03 | 1.4E−20 | 2.48 | 1.3E−14 | 2.35 | 6.7E−11 | 1.85 | 1.2E−03 |
| Cer(d18:1/20:0)/LPC(P-18:0) | 1.99 | 2.5E−25 | 2.06 | 7.7E−22 | 2.74 | 1.5E−16 | 2.66 | 4.0E−13 | 2.18 | 7.0E−06 |
| Cer(d18:1/20:0)/LPC(22:0) [sn1] | 2.06 | 2.7E−25 | 2.25 | 1.6E−23 | 3.13 | 8.0E−17 | 3.43 | 5.1E−15 | 2.68 | 9.4E−07 |
| Cer(d16:1/18:0)/LPC(18:2) [sn1] | 2.10 | 3.0E−25 | 2.31 | 6.6E−24 | 3.33 | 9.6E−17 | 3.40 | 6.1E−14 | 2.53 | 3.5E−05 |
| Cer(d18:1/20:0)/LPC(20:1) [sn2] | 2.05 | 3.1E−25 | 2.24 | 1.7E−23 | 2.86 | 4.4E−15 | 3.13 | 2.2E−13 | 2.05 | 3.8E−04 |
| LPC(14:0) [sn1]/LPC(MHDA) [sn2] | 1.99 | 4.6E−25 | 1.91 | 2.5E−18 | 2.29 | 5.7E−12 | 2.05 | 2.9E−08 | 2.00 | 1.1E−04 |
| Cer(d16:1/16:0)/LPC(19:0) [sn1] | 1.95 | 6.8E−25 | 1.89 | 7.5E−19 | 2.44 | 9.4E−16 | 2.38 | 1.1E−12 | 2.07 | 1.6E−05 |
| Cer(d16:1/18:0)/LPC(18:2) [sn2] | 2.11 | 7.9E−25 | 2.35 | 8.1E−24 | 3.41 | 3.3E−16 | 3.52 | 1.7E−13 | 2.43 | 1.4E−04 |
| Cer(d16:1/20:0)/LPC(20:1) [sn1] | 2.09 | 1.3E−24 | 2.35 | 4.7E−24 | 2.91 | 1.0E−13 | 3.06 | 9.9E−12 | 2.35 | 2.0E−04 |
| Cer(d16:1/20:0)/LPC(20:0) [sn2] | 2.06 | 1.9E−24 | 2.25 | 4.4E−23 | 2.86 | 1.2E−14 | 2.97 | 1.7E−12 | 2.66 | 1.1E−05 |
| Cer(d18:1/20:0)/LPC(MHDA) [sn2] | 1.95 | 3.9E−24 | 2.00 | 1.3E−20 | 2.59 | 5.2E−16 | 2.54 | 8.9E−13 | 2.31 | 7.3E−07 |
| Cer(d16:1/20:0)/LPC(22:0) [sn1] | 2.07 | 4.4E−24 | 2.32 | 1.4E−23 | 2.91 | 2.9E−14 | 3.12 | 1.9E−12 | 2.97 | 2.5E−06 |
| Cer(d16:1/20:0)/LPC(P-18:1) | 2.01 | 6.5E−24 | 2.15 | 1.2E−21 | 2.47 | 2.7E−12 | 2.38 | 2.0E−09 | 1.99 | 9.9E−04 |
| Cer(d16:1/20:0)/LPC(P-18:0) | 1.99 | 1.2E−23 | 2.12 | 8.8E−22 | 2.67 | 3.0E−14 | 2.57 | 4.3E−11 | 2.45 | 1.6E−05 |
| Cer(d16:1/20:0)/LPC(20:1) [sn2] | 2.04 | 1.4E−23 | 2.28 | 4.2E−23 | 2.70 | 2.0E−12 | 2.83 | 1.1E−10 | 2.22 | 4.6E−04 |
| Cer(d18:1/16:0)/LPC(20:1) [sn1] | 1.98 | 2.3E−23 | 2.04 | 4.3E−20 | 2.60 | 3.6E−14 | 2.68 | 3.6E−12 | 1.78 | 4.5E−03 |
| Cer(d16:1/20:0)/LPC(17:0) [sn1] | 1.99 | 2.6E−23 | 2.12 | 7.6E−21 | 2.70 | 6.5E−14 | 2.64 | 7.0E−11 | 2.52 | 1.1E−05 |
| Cer(d18:1/20:0)/LPC(17:0) [sn1] | 1.94 | 3.7E−23 | 1.98 | 3.0E−19 | 2.68 | 7.0E−16 | 2.70 | 8.9E−13 | 2.17 | 1.0E−05 |
| Cer(d16:1/20:0)/LPC(17:0) [sn2] | 1.96 | 6.1E−23 | 2.09 | 6.7E−21 | 2.51 | 6.4E−14 | 2.46 | 6.0E−11 | 2.35 | 8.1E−06 |
| LPC(14:0) [sn2]/LPC(17:0) [sn2] | 1.92 | 7.8E−23 | 1.81 | 4.2E−16 | 2.30 | 1.7E−12 | 2.10 | 7.8E−09 | 1.85 | 1.4E−03 |
| Cer(d18:1/20:0)/LPC(17:0) [sn2] | 1.90 | 1.5E−22 | 1.95 | 3.5E−19 | 2.52 | 1.2E−15 | 2.49 | 1.4E−12 | 2.11 | 1.0E−05 |
| Cer(d18:1/16:0)/LPC(19:0) [sn2] | 1.83 | 2.3E−22 | 1.84 | 2.0E−18 | 2.16 | 2.6E−15 | 2.18 | 4.6E−13 | 1.73 | 4.0E−04 |
| Cer(d18:1/20:0)/LPC(24:0) [sn2] | 1.95 | 3.7E−22 | 2.18 | 2.6E−22 | 2.84 | 7.9E−15 | 3.21 | 7.4E−14 | 2.44 | 6.7E−06 |
| Cer(d20:1/24:1)/LPC(19:0) [sn2] | 1.83 | 4.4E−22 | 1.84 | 3.5E−18 | 2.60 | 1.6E−16 | 2.70 | 9.5E−15 | 1.84 | 1.2E−03 |
| Cer(d18:1/20:0)/LPC(24:0) [sn1] | 1.94 | 5.9E−22 | 2.18 | 2.2E−22 | 2.81 | 7.4E−15 | 3.13 | 8.8E−14 | 2.57 | 2.5E−06 |
| Cer(d20:1/24:1)/LPC(20:1) [sn1] | 1.83 | 8.8E−22 | 1.86 | 2.3E−18 | 2.50 | 4.4E−15 | 2.66 | 1.4E−13 | 1.71 | 5.0E−03 |
| Cer(d16:1/20:0)/LPC(24:0) [sn2] | 1.96 | 1.7E−21 | 2.26 | 1.1E−22 | 2.64 | 1.9E−12 | 2.88 | 2.2E−11 | 2.71 | 1.5E−05 |
| Cer(d16:1/20:0)/LPC(24:0) [sn1] | 1.96 | 1.9E−21 | 2.28 | 6.4E−23 | 2.65 | 1.7E−12 | 2.86 | 3.2E−11 | 2.86 | 6.1E−06 |
| Cer(d20:1/24:1)/LPC(20:1) [sn2] | 1.81 | 2.7E−21 | 1.84 | 6.7E−18 | 2.41 | 3.2E−14 | 2.55 | 7.3E−13 | 1.66 | 8.2E−03 |
| Cer(d18:1/16:0)/LPC(20:0) [sn2] | 1.83 | 4.3E−21 | 1.82 | 6.5E−17 | 2.31 | 2.6E−14 | 2.31 | 3.7E−12 | 1.88 | 2.4E−04 |
| Cer(d18:1/20:0)/SM(d17:1/14:0) | 1.88 | 4.4E−21 | 1.93 | 4.9E−18 | 2.31 | 2.2E−11 | 2.31 | 4.1E−09 | 1.96 | 1.2E−03 |
| Cer(d18:1/16:0)/LPC(22:0) [sn1] | 1.87 | 4.7E−21 | 1.89 | 9.9E−18 | 2.45 | 3.6E−14 | 2.50 | 1.8E−12 | 2.15 | 2.7E−05 |
| Cer(d18:1/16:0)/LPC(P-18:0) | 1.82 | 7.9E−21 | 1.78 | 4.1E−16 | 2.22 | 4.8E−14 | 2.08 | 1.7E−10 | 1.84 | 1.9E−04 |
| Cer(d20:1/24:1)/LPC(MHDA) [sn2] | 1.79 | 8.6E−21 | 1.77 | 3.1E−16 | 2.47 | 2.4E−15 | 2.47 | 1.3E−12 | 2.00 | 1.9E−04 |
| Cer(d18:1/16:0)/LPC(MHDA) [sn1] | 1.81 | 1.2E−20 | 1.81 | 1.6E−16 | 2.32 | 2.9E−14 | 2.22 | 3.6E−11 | 2.12 | 5.3E−06 |
| Cer(d16:1/22:0)/LPC(20:2) [sn1] | 1.87 | 3.5E−20 | 2.02 | 1.7E−19 | 2.33 | 1.2E−10 | 2.29 | 1.8E−08 | 1.77 | 7.7E−03 |
| Cer(d16:1/22:0)/LPE(P-20:0) | 1.85 | 5.6E−20 | 1.86 | 1.3E−16 | 2.33 | 7.1E−12 | 2.18 | 8.0E−09 | 1.73 | 6.9E−03 |
| Cer(d20:1/24:1)/LPC(17:0) [sn2] | 1.74 | 3.7E−19 | 1.72 | 8.2E−15 | 2.43 | 7.2E−15 | 2.46 | 1.8E−12 | 1.84 | 1.3E−03 |
| Cer(d16:1/22:0)/LPC(18:2) [sn2] | 1.84 | 3.7E−19 | 1.97 | 4.4E−18 | 2.54 | 7.3E−12 | 2.49 | 2.0E−09 | 1.81 | 7.4E−03 |
| Cer(d18:1/20:0)/LPC(P-16:0) | 1.78 | 4.2E−19 | 1.86 | 2.7E−17 | 2.25 | 5.1E−13 | 2.25 | 4.6E−11 | 1.85 | 1.9E−04 |
| Cer(d18:1/20:0)/LPC(20:2) [sn1] | 1.80 | 5.3E−19 | 2.03 | 6.7E−20 | 2.49 | 4.7E−13 | 2.64 | 1.8E−11 | 2.21 | 3.9E−05 |
| Cer(d16:1/20:0)/LPC(20:2) [sn1] | 1.86 | 6.0E−19 | 2.16 | 9.1E−21 | 2.45 | 6.3E−11 | 2.52 | 3.3E−09 | 2.48 | 4.6E−05 |
| Cer(d18:1/16:0)/LPC(MHDA) [sn2] | 1.75 | 7.2E−19 | 1.71 | 2.3E−14 | 2.13 | 1.1E−12 | 2.01 | 1.8E−09 | 1.97 | 3.0E−05 |
| Cer(d18:1/20:0)/LPE(P-20:0) | 1.79 | 9.4E−19 | 1.86 | 1.3E−16 | 2.49 | 2.1E−13 | 2.43 | 9.1E−11 | 2.04 | 6.0E−05 |
| Cer(d16:1/20:0)/LPC(P-16:0) | 1.80 | 1.2E−18 | 1.96 | 3.7E−18 | 2.27 | 3.2E−11 | 2.27 | 2.8E−09 | 2.07 | 2.6E−04 |
| Cer(d16:1/20:0)/LPE(P-20:0) | 1.81 | 1.6E−18 | 1.94 | 1.2E−17 | 2.37 | 1.0E−11 | 2.30 | 2.9E−09 | 2.24 | 6.7E−05 |
| Cer(d18:1/20:0)/LPC(18:2) [sn1] | 1.77 | 3.0E−18 | 1.92 | 4.7E−18 | 2.55 | 3.0E−14 | 2.63 | 3.1E−12 | 2.20 | 1.1E−05 |
| Cer(d20:1/24:1)/LPC(17:0) [sn1] | 1.70 | 5.4E−18 | 1.66 | 1.4E−13 | 2.33 | 4.9E−14 | 2.36 | 6.7E−12 | 1.76 | 2.4E−03 |
| LPC(14:0) [sn2]/LPC(20:2) [sn1] | 1.82 | 5.7E−18 | 1.90 | 1.0E−15 | 2.20 | 2.1E−08 | 2.11 | 2.8E−06 | 1.81 | 9.1E−03 |
| Cer(d16:1/20:0)/LPC(18:2) [sn1] | 1.80 | 6.2E−18 | 2.01 | 1.1E−18 | 2.52 | 2.8E−12 | 2.55 | 2.8E−10 | 2.48 | 1.9E−05 |
| Cer(d18:1/16:0)/LPC(17:0) [sn1] | 1.72 | 6.3E−18 | 1.63 | 1.6E−12 | 2.13 | 8.4E−13 | 2.03 | 1.4E−09 | 1.77 | 6.6E−04 |
| Cer(d18:1/20:0)/LPC(18:2) [sn2] | 1.77 | 9.4E−18 | 1.94 | 5.5E−18 | 2.62 | 1.2E−13 | 2.73 | 9.8E−12 | 2.19 | 6.6E−05 |
| Cer(d18:1/16:0)/LPC(24:0) [sn1] | 1.75 | 1.1E−17 | 1.87 | 8.1E−17 | 2.22 | 1.1E−11 | 2.33 | 8.6E−11 | 2.06 | 7.1E−05 |
| Cer(d16:1/20:0)/LPC(18:2) [sn2] | 1.80 | 2.3E−17 | 2.04 | 1.6E−18 | 2.54 | 1.6E−11 | 2.58 | 1.2E−09 | 2.42 | 9.2E−05 |
| Cer(d18:1/16:0)/LPC(24:0) [sn2] | 1.73 | 2.3E−17 | 1.84 | 1.8E−16 | 2.20 | 1.1E−11 | 2.34 | 4.5E−11 | 1.90 | 2.9E−04 |
| Cer(d18:1/16:0)/LPC(17:0) [sn2] | 1.67 | 7.5E−17 | 1.62 | 1.5E−12 | 2.01 | 3.3E−12 | 1.93 | 3.4E−09 | 1.73 | 6.6E−04 |
| Cer(d20:1/24:1)/LPC(P-16:0) | 1.66 | 8.5E−17 | 1.65 | 1.8E−13 | 2.23 | 4.1E−13 | 2.27 | 2.4E−11 | 1.66 | 6.8E−03 |
| Cer(d20:1/24:1)/LPE(P-20:0) | 1.65 | 6.0E−16 | 1.63 | 1.6E−12 | 2.26 | 6.2E−13 | 2.26 | 8.6E−11 | 1.73 | 3.8E−03 |
| Cer(d20:1/24:1)/LPC(18:2) [sn2] | 1.64 | 1.0E−15 | 1.67 | 1.1E−13 | 2.29 | 3.9E−13 | 2.35 | 1.8E−11 | 1.74 | 3.5E−03 |
| Cer(d20:1/24:1)/LPC(20:2) [sn1] | 1.61 | 4.5E−15 | 1.65 | 3.1E−13 | 2.11 | 2.5E−11 | 2.16 | 6.3E−10 | 1.70 | 5.1E−03 |
| Cer(d18:1/16:0)/LPC(P-16:0) | 1.58 | 4.2E−14 | 1.57 | 2.3E−11 | 1.83 | 5.6E−10 | 1.79 | 5.2E−08 | 1.53 | 8.6E−03 |

TABLE 6-continued

Odds Ratios (OR) based on combination biomarker values of Group A and Group B biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| Cer(d18:1/16:0)/LPE(P-20:0) | 1.60 | 5.9E−14 | 1.58 | 8.3E−11 | 2.00 | 1.6E−10 | 1.89 | 7.5E−08 | 1.70 | 2.0E−03 |
| Cer(d18:1/16:0)/LPC(20:2) [sn1] | 1.61 | 1.0E−13 | 1.73 | 9.6E−14 | 2.01 | 3.5E−09 | 2.01 | 1.2E−07 | 1.81 | 2.2E−03 |
| Cer(d18:1/16:0)/LPC(18:2) [sn1] | 1.58 | 2.0E−13 | 1.64 | 1.7E−12 | 2.07 | 2.2E−11 | 2.05 | 1.9E−09 | 1.83 | 3.4E−04 |
| Cer(d18:1/16:0)/LPC(18:2) [sn2] | 1.57 | 1.6E−12 | 1.64 | 5.1E−12 | 2.09 | 2.4E−10 | 2.07 | 1.5E−08 | 1.76 | 2.9E−03 |

FL: subjects with fatty liver disease vs. healthy controls, NAFLD: subjects with non-alcoholic fatty liver disease vs. healthy controls, FL(severe): subjects with severe fatty liver disease vs. healthy controls, NAFLD(severe): subjects with severe non-alcoholic fatty liver disease vs. healthy controls, DM2: subjects who developed type 2 diabetes during the follow-up vs. healthy controls. Other abbreviations are described in the detailed description of the present disclosure.

Table 7 shows statistically significant Odds Ratios (p<0.01) based on combination biomarker values of at least one fatty liver biomarker from Group E and at least one fatty liver biomarker from Group F in subjects, whose liver fat content was determined four years after the lipid measurements, as compared to a control group.

TABLE 7

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| DAG(18:0/18:1)/LPC(MHDA) [sn2] | 3.10 | 5.2E−54 | 3.10 | 1.2E−44 | 3.95 | 2.2E−25 | 3.90 | 3.0E−21 | 2.55 | 2.1E−07 |
| DAG(18:0/18:1)/PC(35:3) | 3.27 | 5.3E−54 | 3.40 | 9.6E−46 | 4.02 | 1.5E−24 | 4.08 | 4.8E−21 | 2.45 | 6.1E−06 |
| DAG(18:0/18:1)/LPC(MHDA) [sn1] | 3.11 | 7.7E−54 | 3.13 | 7.5E−45 | 4.08 | 1.5E−25 | 4.07 | 1.4E−21 | 2.61 | 1.4E−07 |
| DAG(18:0/18:1)/PC(P-36:2) | 3.20 | 2.9E−53 | 3.35 | 3.9E−45 | 4.11 | 4.7E−25 | 4.16 | 2.6E−21 | 2.46 | 3.4E−06 |
| DAG(18:0/18:1)/PC(37:2) | 3.30 | 3.5E−53 | 3.40 | 2.6E−44 | 4.12 | 2.5E−24 | 4.26 | 5.0E−21 | 2.63 | 2.7E−06 |
| DAG(18:0/18:1)/LPC(20:0) [sn2] | 3.17 | 8.1E−53 | 3.23 | 7.2E−44 | 4.14 | 4.4E−25 | 4.25 | 2.9E−21 | 2.57 | 1.9E−06 |
| DAG(18:0/18:1)/LPC(20:0) [sn1] | 3.17 | 1.4E−52 | 3.23 | 1.1E−43 | 4.25 | 3.8E−25 | 4.38 | 2.3E−21 | 2.68 | 1.0E−06 |
| DAG(18:0/18:1)/LPC(19:0) [sn2] | 3.13 | 1.5E−52 | 3.15 | 1.5E−43 | 4.01 | 5.1E−25 | 4.03 | 3.8E−21 | 2.43 | 2.3E−06 |
| DAG(18:0/18:1)/LPC(19:0) [sn1] | 3.16 | 1.5E−52 | 3.18 | 3.0E−43 | 4.18 | 1.9E−24 | 4.25 | 1.2E−20 | 2.65 | 7.6E−07 |
| DAG(18:0/18:1)/PC(P-36:1) | 3.13 | 1.8E−52 | 3.27 | 2.2E−44 | 3.91 | 4.2E−24 | 4.05 | 1.0E−20 | 2.44 | 4.5E−06 |
| DAG(18:0/18:1)/LPC(22:0) [sn2] | 3.13 | 2.8E−52 | 3.26 | 3.6E−44 | 4.13 | 5.4E−25 | 4.27 | 1.8E−21 | 2.62 | 1.7E−06 |
| DAG(18:0/18:1)/LPC(O-24:2) | 3.22 | 2.9E−52 | 3.32 | 1.6E−43 | 4.01 | 1.8E−23 | 4.16 | 4.5E−20 | 2.42 | 7.7E−06 |
| DAG(18:0/18:1)/PC(35:2) | 3.19 | 3.2E−52 | 3.29 | 3.0E−44 | 4.14 | 5.0E−24 | 4.15 | 2.5E−20 | 2.62 | 8.5E−07 |
| DAG(18:0/18:1)/LPC(17:0) [sn1] | 3.05 | 5.6E−52 | 3.04 | 1.7E−42 | 3.92 | 3.1E−24 | 3.92 | 1.7E−20 | 2.42 | 2.6E−06 |
| DAG(18:0/18:1)/LPC(20:2) [sn2] | 3.06 | 6.1E−52 | 3.26 | 9.4E−45 | 3.64 | 4.6E−24 | 3.79 | 1.8E−20 | 2.38 | 5.1E−06 |
| DAG(18:0/18:1)/PC(O-36:2) | 3.07 | 6.5E−52 | 3.20 | 6.3E−44 | 3.88 | 2.3E−24 | 3.88 | 8.5E−21 | 2.44 | 4.0E−06 |
| DAG(18:0/18:1)/LPC(17:0) [sn2] | 3.03 | 6.7E−52 | 3.02 | 1.9E−42 | 3.85 | 2.0E−24 | 3.77 | 2.4E−20 | 2.42 | 1.8E−06 |
| DAG(18:0/18:1)/LPC(20:1) [sn2] | 3.12 | 1.0E−51 | 3.23 | 2.5E−43 | 3.88 | 8.8E−24 | 4.04 | 4.1E−20 | 2.31 | 2.5E−05 |
| DAG(18:0/18:1)/LPC(O-22:1) | 3.13 | 1.2E−51 | 3.20 | 5.6E−43 | 3.99 | 1.5E−23 | 4.11 | 2.0E−20 | 2.41 | 4.5E−06 |
| DAG(18:0/18:1)/LPC(22:0) [sn1] | 3.12 | 1.4E−51 | 3.24 | 1.7E−43 | 4.12 | 1.6E−24 | 4.39 | 3.3E−21 | 2.67 | 1.1E−06 |
| DAG(18:0/18:1)/PC(O-40:6) | 3.13 | 3.7E−51 | 3.23 | 5.2E−43 | 3.66 | 3.8E−22 | 3.73 | 4.6E−19 | 2.39 | 7.9E−06 |
| DAG(18:0/18:1)/LPC(20:1) [sn1] | 3.08 | 4.2E−51 | 3.19 | 7.6E−43 | 3.99 | 5.7E−24 | 4.12 | 2.6E−20 | 2.35 | 1.9E−05 |
| DAG(18:0/18:1)/LPE(16:0) [sn1] | 3.07 | 4.5E−51 | 3.28 | 2.6E−44 | 3.61 | 1.6E−22 | 4.03 | 5.3E−20 | 2.43 | 4.2E−06 |
| DAG(18:0/18:1)/PC(P-34:1) | 3.07 | 5.2E−51 | 3.26 | 4.2E−43 | 3.68 | 6.8E−23 | 3.81 | 1.1E−19 | 2.34 | 1.4E−05 |
| DAG(18:0/18:1)/LPC(24:0) [sn2] | 3.06 | 8.5E−51 | 3.20 | 3.0E−43 | 3.81 | 6.5E−24 | 4.07 | 1.0E−20 | 2.51 | 2.6E−06 |
| DAG(18:0/18:1)/LPC(20:2) [sn1] | 3.02 | 8.7E−51 | 3.19 | 1.7E−43 | 3.71 | 5.2E−24 | 3.83 | 2.7E−20 | 2.42 | 3.3E−06 |
| DAG(18:0/18:1)/LPE(16:0) [sn2] | 3.05 | 8.8E−51 | 3.25 | 3.8E−44 | 3.60 | 1.7E−22 | 3.93 | 7.8E−20 | 2.45 | 3.8E−06 |
| DAG(18:0/18:1)/SM(37:2) | 3.04 | 1.0E−50 | 3.21 | 1.0E−43 | 3.85 | 8.6E−24 | 3.91 | 3.1E−20 | 2.29 | 2.2E−05 |
| DAG(18:0/18:1)/LPC(15:0) [sn2] | 2.95 | 2.2E−50 | 2.96 | 1.3E−41 | 3.60 | 4.0E−23 | 3.55 | 1.8E−19 | 2.19 | 1.5E−05 |
| DAG(18:0/18:1)/PC(33:2) | 2.99 | 2.8E−50 | 3.13 | 9.0E−43 | 3.46 | 4.0E−22 | 3.58 | 2.1E−19 | 2.26 | 2.4E−05 |
| DAG(18:0/18:1)/LPC(24:0) [sn1] | 3.02 | 3.8E−50 | 3.17 | 6.3E−43 | 3.77 | 1.2E−23 | 4.00 | 1.7E−20 | 2.56 | 1.9E−06 |
| DAG(18:0/18:1)/PC(O-34:1) | 3.02 | 4.1E−50 | 3.12 | 3.3E−42 | 3.61 | 8.8E−23 | 3.66 | 1.1E−19 | 2.32 | 1.8E−05 |
| DAG(18:0/18:1)/LPC(O-20:0) | 2.98 | 5.1E−50 | 3.04 | 1.2E−41 | 3.85 | 4.1E−23 | 3.94 | 4.6E−20 | 2.51 | 1.2E−06 |
| DAG(18:0/18:1)/LPC(O-20:1) | 3.02 | 6.1E−50 | 3.07 | 1.3E−41 | 3.88 | 4.0E−23 | 3.90 | 7.4E−20 | 2.37 | 6.9E−06 |
| DAG(18:0/18:1)/PC(O-36:3) | 3.04 | 1.0E−49 | 3.16 | 6.5E−42 | 3.79 | 5.5E−23 | 3.76 | 2.5E−19 | 2.39 | 1.4E−05 |
| DAG(18:0/18:1)/PC(37:1) | 3.03 | 1.3E−49 | 3.08 | 4.5E−41 | 3.45 | 6.1E−22 | 3.52 | 7.2E−19 | 2.37 | 9.9E−06 |
| DAG(18:0/18:1)/SM (d17:1/14:0) | 2.95 | 1.5E−49 | 2.98 | 3.8E−41 | 3.42 | 3.8E−22 | 3.36 | 8.6E−19 | 2.17 | 3.9E−05 |
| DAG(18:0/18:1)/LPC(O-22:0) | 2.95 | 1.6E−49 | 3.03 | 1.2E−41 | 3.67 | 6.0E−23 | 3.82 | 5.2E−20 | 2.42 | 3.0E−06 |
| DAG(18:0/18:1)/LacCer(d18:1/16:0) | 2.98 | 1.6E−49 | 3.08 | 6.7E−42 | 3.36 | 1.1E−21 | 3.40 | 9.5E−19 | 2.25 | 2.5E−05 |
| DAG(18:0/18:1)/LPC( 15:0) [sn1] | 2.89 | 2.4E−49 | 2.92 | 6.0E−41 | 3.54 | 3.4E−23 | 3.56 | 1.2E−19 | 2.32 | 3.8E−06 |
| DAG(18:0/18:1)/LPC(P-18:0) | 2.90 | 3.2E−49 | 2.93 | 1.5E−40 | 3.71 | 1.6E−23 | 3.64 | 1.7E−19 | 2.38 | 3.1E−06 |
| DAG(18:0/18:1)/LPC(O-18:0) | 2.90 | 3.9E−49 | 2.92 | 1.5E−40 | 3.75 | 5.1E−23 | 3.72 | 1.3E−19 | 2.48 | 1.5E−06 |
| DAG(18:0/18:1)/LPC(P-18:1) | 2.95 | 5.5E−49 | 2.95 | 4.6E−40 | 3.51 | 3.2E−22 | 3.42 | 2.8E−18 | 2.11 | 6.4E−05 |
| DAG(18:0/18:1)/LPC(18:2) [sn2] | 2.92 | 6.7E−49 | 3.06 | 1.4E−41 | 3.82 | 3.4E−24 | 3.90 | 3.1E−20 | 2.45 | 4.9E−06 |
| DAG(18:0/18:1)/LPC(O-24:1) | 2.94 | 2.2E−48 | 3.01 | 2.2E−40 | 3.59 | 2.2E−22 | 3.69 | 2.8E−19 | 2.29 | 1.8E−05 |
| DAG(18:0/18:1)/PC(O-34:0) | 2.89 | 2.3E−48 | 2.98 | 1.0E−40 | 3.30 | 3.5E−21 | 3.36 | 2.3E−18 | 2.30 | 1.1E−05 |
| DAG(18:0/18:1)/LPC(18:1) [sn2] | 2.86 | 3.1E−48 | 3.03 | 1.4E−41 | 3.65 | 8.9E−24 | 3.80 | 3.7E−20 | 2.61 | 8.9E−07 |
| DAG(18:0/18:1)/LPE(P-20:0) | 2.86 | 3.2E−48 | 2.90 | 9.2E−40 | 3.65 | 4.2E−23 | 3.59 | 4.7E−19 | 2.30 | 5.8E−06 |
| DAG(18:0/18:1)/LPC(O-18:1) | 2.87 | 7.5E−48 | 2.87 | 3.4E−39 | 3.57 | 3.6E−22 | 3.49 | 1.6E−18 | 2.23 | 2.9E−05 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| DAG(18:0/18:1)/PC(P-40:4) | 2.91 | 1.7E−47 | 2.99 | 8.1E−40 | 3.65 | 4.4E−22 | 3.73 | 3.0E−19 | 2.43 | 4.3E−06 |
| DAG(18:0/18:1)/LPC(18:2) [sn1] | 2.82 | 2.2E−47 | 2.94 | 4.3E−40 | 3.74 | 7.7E−24 | 3.81 | 6.2E−20 | 2.50 | 2.4E−06 |
| Cer(d18:1/18:0)/PC(P-36:1) | 2.98 | 2.2E−47 | 3.25 | 5.3E−41 | 4.29 | 8.8E−24 | 4.56 | 9.0E−20 | 2.73 | 1.3E−06 |
| DAG(18:0/18:1)/PC(39:4) | 2.91 | 2.5E−47 | 2.96 | 3.1E−39 | 3.50 | 2.0E−21 | 3.59 | 1.2E−18 | 2.28 | 2.3E−05 |
| DAG(18:0/18:1)/PC(P-32:0) | 2.88 | 2.6E−47 | 2.99 | 5.1E−40 | 3.43 | 1.9E−21 | 3.56 | 1.8E−18 | 2.28 | 2.5E−05 |
| SM(36:0)/PC(P-36:1) | 2.80 | 3.0E−47 | 2.92 | 4.8E−40 | 4.31 | 3.2E−26 | 4.57 | 3.7E−22 | 3.26 | 1.0E−08 |
| DAG(18:0/18:1)/LPC(O-24:0) | 2.83 | 4.9E−47 | 2.91 | 1.4E−39 | 3.41 | 1.3E−21 | 3.55 | 8.4E−19 | 2.33 | 9.3E−06 |
| DAG(18:0/18:1)/PC(O-34:2) | 2.87 | 5.6E−47 | 2.98 | 9.9E−40 | 3.69 | 1.8E−22 | 3.69 | 8.9E−19 | 2.37 | 1.1E−05 |
| DAG(18:0/18:1)/LPC(18:1) [sn1] | 2.80 | 6.3E−47 | 2.92 | 5.2E−40 | 3.62 | 1.8E−23 | 3.74 | 8.6E−20 | 2.56 | 1.2E−06 |
| DAG(18:0/18:1)/LPC(P-16:0) | 2.80 | 7.3E−47 | 2.84 | 6.1E−39 | 3.39 | 4.0E−22 | 3.40 | 1.2E−18 | 2.20 | 1.8E−05 |
| DAG(18:0/18:1)/LPE(P-18:0) | 2.73 | 2.1E−46 | 2.79 | 7.9E−39 | 3.36 | 4.4E−22 | 3.33 | 2.2E−18 | 2.29 | 1.3E−05 |
| PI(40:5)/PC(P-36:1) | 2.97 | 3.2E−46 | 2.85 | 2.9E−35 | 4.22 | 1.3E−22 | 4.05 | 2.3E−17 | 2.45 | 9.1E−06 |
| Cer(d18:1/18:0)/SM(37:1) | 2.97 | 4.2E−46 | 3.20 | 1.2E−39 | 3.66 | 1.3E−21 | 3.77 | 6.5E−18 | 2.16 | 1.2E−04 |
| SM(36:0)/SM(33:0) | 2.76 | 4.3E−46 | 2.86 | 2.5E−38 | 3.52 | 2.6E−23 | 3.82 | 2.5E−20 | 2.48 | 1.2E−06 |
| Cer(d18:1/18:0)/PC(P-36:2) | 2.93 | 6.5E−46 | 3.17 | 7.1E−40 | 4.27 | 3.7E−24 | 4.30 | 7.3E−20 | 2.62 | 1.7E−06 |
| PG(36:1)/PC(35:3) | 2.95 | 7.1E−46 | 3.17 | 8.0E−40 | 4.07 | 7.7E−23 | 4.12 | 1.0E−18 | 2.38 | 3.2E−05 |
| PC(38:3)/PC(P-36:2) | 2.98 | 8.1E−46 | 3.20 | 2.1E−39 | 5.14 | 5.2E−25 | 5.44 | 1.4E−20 | 2.38 | 4.4E−05 |
| PG(36:1)/PC(P-36:2) | 2.93 | 1.0E−45 | 3.19 | 2.1E−39 | 4.13 | 1.4E−23 | 4.29 | 3.9E−19 | 2.40 | 1.5E−05 |
| PC(38:3)/PC(P-34:1) | 2.93 | 1.1E−45 | 3.27 | 3.0E−40 | 4.59 | 3.1E−23 | 5.46 | 6.6E−20 | 2.25 | 1.8E−04 |
| PG(36:1)/PC(P-36:1) | 2.91 | 1.2E−45 | 3.12 | 3.4E−39 | 4.04 | 5.1E−23 | 4.25 | 5.1E−19 | 2.41 | 1.6E−05 |
| SM(36:0)/PC(P-34:1) | 2.70 | 4.8E−45 | 2.85 | 1.1E−38 | 3.80 | 1.1E−24 | 4.03 | 2.0E−21 | 3.01 | 2.2E−08 |
| DAG(16:0/18:1)/LPC(MHDA) [sn2] | 2.68 | 7.6E−45 | 2.71 | 1.9E−37 | 3.53 | 3.2E−23 | 3.50 | 1.7E−19 | 2.52 | 1.8E−07 |
| DAG(16:0/18:1)/LPC(MHDA) [sn1] | 2.69 | 1.2E−44 | 2.74 | 1.0E−37 | 3.64 | 2.3E−23 | 3.67 | 7.2E−20 | 2.58 | 1.2E−07 |
| PG(36:1)/LPC(O-24:2) | 2.84 | 1.2E−44 | 3.00 | 1.2E−38 | 3.83 | 6.4E−22 | 3.93 | 5.9E−18 | 2.28 | 3.8E−05 |
| SM(36:0)/SM(37:1) | 2.71 | 1.4E−44 | 2.80 | 3.2E−37 | 3.70 | 7.3E−24 | 3.84 | 2.5E−20 | 2.62 | 2.7E−07 |
| SM(36:1)/SM(37:1) | 2.87 | 1.5E−44 | 3.11 | 5.6E−39 | 3.85 | 7.4E−22 | 4.22 | 1.4E−19 | 2.46 | 2.5E−05 |
| DAG(16:0/18:1)/LPC(O-24:2) | 2.76 | 2.0E−44 | 2.86 | 1.6E−37 | 3.48 | 2.3E−21 | 3.62 | 2.0E−18 | 2.38 | 7.8E−06 |
| PC(38:3)/SM(37:1) | 2.93 | 2.3E−44 | 3.14 | 5.1E−38 | 4.21 | 3.9E−22 | 4.60 | 1.0E−18 | 1.82 | 4.7E−03 |
| DAG(16:0/18:1)/PC(P-36:2) | 2.76 | 2.3E−44 | 2.93 | 2.3E−38 | 3.79 | 1.6E−22 | 3.94 | 4.1E−19 | 2.50 | 4.7E−06 |
| PG(36:1)/PC(P-34:1) | 2.85 | 2.4E−44 | 3.08 | 1.9E−38 | 3.80 | 6.6E−22 | 4.00 | 4.9E−18 | 2.30 | 5.4E−05 |
| DAG(16:0/18:1)/PC(35:3) | 2.81 | 2.8E−44 | 3.00 | 1.2E−38 | 3.77 | 5.0E−22 | 3.98 | 5.6E−19 | 2.54 | 5.5E−06 |
| PG(36:1)/PC(O-40:6) | 2.84 | 3.0E−44 | 3.01 | 4.8E−38 | 3.57 | 1.4E−20 | 3.66 | 4.6E−17 | 2.32 | 3.8E−05 |
| Cer(d18:1/18:0)/PC(P-34:1) | 2.82 | 3.4E−44 | 3.08 | 9.1E−39 | 3.68 | 8.6E−22 | 3.83 | 2.0E−18 | 2.45 | 7.4E−06 |
| SM(36:0)/PC(P-36:2) | 2.69 | 3.8E−44 | 2.81 | 1.2E−37 | 4.16 | 3.6E−25 | 4.25 | 4.3E−21 | 3.05 | 2.8E−08 |
| DAG(16:0/16:1)/PC(O-40:6) | 2.80 | 4.0E−44 | 2.84 | 2.7E−36 | 3.52 | 9.6E−21 | 3.73 | 4.9E−18 | 2.47 | 6.8E−06 |
| DAG(18:0/18:2)/LPC(O-24:2) | 2.76 | 4.0E−44 | 2.93 | 3.6E−38 | 3.33 | 3.6E−20 | 3.53 | 1.9E−17 | 2.45 | 5.6E−06 |
| DAG(16:0/18:1)/PC(P-36:1) | 2.72 | 5.7E−44 | 2.88 | 5.6E−38 | 3.64 | 1.0E−21 | 3.85 | 8.4E−19 | 2.47 | 5.2E−06 |
| DAG(16:0/18:1)/PC(O-40:6) | 2.80 | 6.5E−44 | 2.95 | 7.6E−38 | 3.45 | 2.1E−20 | 3.61 | 1.2E−17 | 2.46 | 5.2E−06 |
| PC(38:3)/PC(37:2) | 3.04 | 7.4E−44 | 3.22 | 3.1E−37 | 5.41 | 1.4E−23 | 6.22 | 2.9E−20 | 2.56 | 4.1E−05 |
| PI(40:5)/PC(P-34:1) | 2.85 | 7.4E−44 | 2.74 | 1.7E−33 | 3.69 | 1.5E−21 | 3.53 | 6.4E−16 | 2.25 | 6.2E−05 |
| PG(36:1)/LPC(MHDA) [sn1] | 2.71 | 8.5E−44 | 2.80 | 4.9E−37 | 3.84 | 1.2E−23 | 3.77 | 3.2E−19 | 2.53 | 9.4E−07 |
| PG(36:1)/PC(35:2) | 2.87 | 9.3E−44 | 3.08 | 2.5E−38 | 4.21 | 6.0E−22 | 4.31 | 1.2E−17 | 2.71 | 2.2E−06 |
| DAG(16:0/20:4)/LPC(O-24:2) | 2.74 | 9.6E−44 | 2.77 | 3.1E−36 | 3.25 | 1.2E−20 | 3.31 | 1.1E−17 | 2.11 | 1.6E−04 |
| PI(40:5)/PC(P-36:2) | 2.81 | 1.1E−43 | 2.70 | 3.2E−33 | 4.12 | 3.0E−22 | 3.78 | 1.1E−16 | 2.41 | 2.3E−05 |
| PG(36:1)/LPC(O-22:1) | 2.76 | 1.2E−43 | 2.88 | 8.5E−37 | 3.86 | 4.0E−22 | 3.93 | 2.3E−18 | 2.31 | 2.6E−05 |
| DAG(16:0/18:1)/PC(35:2) | 2.78 | 1.4E−43 | 2.94 | 7.4E−38 | 3.95 | 6.3E−22 | 4.15 | 1.1E−18 | 2.73 | 5.7E−07 |
| PG(36:1)/PC(37:2) | 2.82 | 1.5E−43 | 3.03 | 1.7E−37 | 3.80 | 8.8E−22 | 4.10 | 2.7E−18 | 2.43 | 1.8E−05 |
| DAG(16:0/16:1)/PC(P-36:1) | 2.74 | 1.6E−43 | 2.78 | 1.1E−35 | 3.79 | 2.0E−21 | 4.01 | 1.4E−18 | 2.50 | 8.1E−06 |
| DAG(16:0/18:1)/LPC(19:0) [sn2] | 2.68 | 1.6E−43 | 2.74 | 9.3E−37 | 3.52 | 7.2E−23 | 3.59 | 1.7E−19 | 2.38 | 2.1E−06 |
| PI(40:5)/LPC(O-24:2) | 2.92 | 1.7E−43 | 2.75 | 1.8E−32 | 3.91 | 8.5E−21 | 3.73 | 1.2E−16 | 2.32 | 4.6E−05 |
| DAG(16:0/18:1)/LPC(O-22:1) | 2.68 | 2.3E−43 | 2.76 | 1.1E−36 | 3.50 | 2.8E−21 | 3.64 | 1.4E−18 | 2.37 | 5.1E−06 |
| Cer(d18:1/18:0)/LPC(O-24:2) | 2.89 | 2.6E−43 | 3.05 | 2.2E−36 | 3.99 | 5.7E−22 | 4.18 | 1.5E−18 | 2.46 | 6.9E−06 |
| DAG(16:0/16:1)/PC(P-36:2) | 2.75 | 2.8E−43 | 2.80 | 1.4E−35 | 3.88 | 6.7E−22 | 4.10 | 1.0E−18 | 2.51 | 8.6E−06 |
| PC(34:1)/PC(P-34:1) | 2.86 | 3.0E−43 | 2.91 | 1.4E−35 | 3.74 | 1.0E−19 | 3.80 | 1.7E−16 | 2.15 | 2.7E−04 |
| PG(36:1)/SM(37:2) | 2.77 | 3.1E−43 | 3.05 | 2.2E−38 | 3.83 | 2.5E−22 | 3.99 | 3.8E−18 | 2.19 | 1.1E−04 |
| DAG(16:0/16:1)/PC(P-34:1) | 2.74 | 3.6E−43 | 2.80 | 1.6E−35 | 3.66 | 9.4E−21 | 3.91 | 4.1E−18 | 2.45 | 1.6E−05 |
| PG(36:1)/LPC(19:0) [sn2] | 2.70 | 3.8E−43 | 2.78 | 2.7E−36 | 3.72 | 1.8E−23 | 3.73 | 2.8E−19 | 2.27 | 1.7E−05 |
| PC(38:3)/LPC(O-24:2) | 2.80 | 4.5E−43 | 2.89 | 7.0E−36 | 3.94 | 2.7E−22 | 4.25 | 5.1E−19 | 2.18 | 1.5E−04 |
| DAG(16:0/18:1)/PC(37:2) | 2.78 | 4.8E−43 | 2.92 | 7.9E−37 | 3.68 | 1.9E−21 | 3.99 | 1.5E−18 | 2.66 | 3.1E−06 |
| DAG(16:0/18:1)/LPC(19:0) [sn1] | 2.66 | 4.9E−43 | 2.70 | 8.0E−36 | 3.52 | 3.4E−22 | 3.60 | 8.5E−19 | 2.56 | 8.4E−07 |
| DAG(16:0/16:1)/PC(35:3) | 2.78 | 5.8E−43 | 2.83 | 3.2E−35 | 3.86 | 2.3E−21 | 4.14 | 1.8E−18 | 2.52 | 1.1E−05 |
| PC(38:3)/PC(O-34:1) | 2.83 | 6.5E−43 | 3.06 | 3.2E−37 | 4.42 | 1.2E−22 | 4.98 | 2.5E−19 | 2.15 | 3.6E−04 |
| Cer(d18:1/18:0)/LPC(O-22:1) | 2.78 | 6.7E−43 | 2.91 | 5.6E−36 | 4.01 | 2.6E−22 | 4.15 | 1.3E−18 | 2.51 | 2.8E−06 |
| DAG(16:0/18:1)/LPC(20:1) [sn2] | 2.68 | 7.2E−43 | 2.80 | 7.7E−37 | 3.51 | 1.9E−21 | 3.67 | 2.3E−18 | 2.32 | 2.5E−05 |
| DAG(18:0/18:2)/LPC(19:0) [sn1] | 2.69 | 7.7E−43 | 2.78 | 2.4E−36 | 3.51 | 6.0E−21 | 3.62 | 1.2E−17 | 2.74 | 4.0E−07 |
| PG(36:1)/LPC(19:0) [sn1] | 2.70 | 7.8E−43 | 2.79 | 8.2E−36 | 3.74 | 1.2E−22 | 3.79 | 1.6E−18 | 2.43 | 4.7E−06 |
| DAG(18:0/18:2)/PC(P-36:2) | 2.68 | 8.4E−43 | 2.90 | 6.1E−38 | 3.47 | 6.6E−21 | 3.56 | 1.2E−17 | 2.50 | 4.4E−06 |
| DAG(16:0/16:1)/LPC(O-24:2) | 2.72 | 8.6E−43 | 2.70 | 2.2E−34 | 3.54 | 1.0E−20 | 3.66 | 8.4E−18 | 2.39 | 1.6E−05 |
| PG(36:1)/LPC(MHDA) [sn2] | 2.66 | 1.0E−42 | 2.71 | 1.4E−36 | 3.63 | 5.5E−23 | 3.51 | 2.2E−18 | 2.44 | 2.1E−06 |
| Cer(d18:1/18:0)/PC(O-34:1) | 2.78 | 1.4E−42 | 3.00 | 3.4E−37 | 3.84 | 9.9E−22 | 3.99 | 1.9E−18 | 2.53 | 1.1E−05 |
| PC(38:3)/PC(35:3) | 2.78 | 1.6E−42 | 3.11 | 1.5E−38 | 4.44 | 1.6E−23 | 4.98 | 4.0E−20 | 2.11 | 2.4E−04 |
| DAG(16:0/18:1)/PC(P-34:1) | 2.67 | 1.6E−42 | 2.84 | 4.8E−37 | 3.41 | 1.5E−20 | 3.62 | 6.8E−18 | 2.38 | 1.5E−05 |
| PG(36:1)/SM(37:1) | 2.75 | 2.1E−42 | 2.93 | 2.8E−36 | 3.48 | 1.5E−20 | 3.56 | 1.5E−16 | 2.00 | 5.9E−04 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| DAG(16:0/18:1)/LPC(20:0) [sn2] | 2.63 | 2.2E−42 | 2.70 | 8.0E−36 | 3.47 | 1.6E−22 | 3.57 | 2.9E−19 | 2.49 | 2.4E−06 |
| PI(40:5)/SM(37:2) | 2.82 | 2.2E−42 | 2.78 | 2.6E−33 | 4.04 | 1.1E−21 | 3.71 | 1.8E−16 | 2.16 | 1.7E−04 |
| PG(36:1)/LPC(20:0) [sn1] | 2.72 | 2.6E−42 | 2.84 | 1.1E−35 | 3.95 | 3.1E−23 | 4.01 | 4.9E−19 | 2.48 | 6.9E−06 |
| PG(36:1)/PC(O-34:1) | 2.75 | 2.6E−42 | 2.95 | 1.9E−36 | 3.73 | 2.9E−21 | 3.84 | 1.6E−17 | 2.25 | 9.2E−05 |
| DAG(18:0/18:2)/LPC(19:0) [sn2] | 2.65 | 2.7E−42 | 2.77 | 1.4E−36 | 3.36 | 1.9E−21 | 3.45 | 2.4E−18 | 2.46 | 1.6E−06 |
| PG(36:1)/PC(O-36:2) | 2.72 | 2.8E−42 | 2.92 | 1.9E−36 | 3.77 | 4.3E−22 | 3.82 | 8.6E−18 | 2.32 | 2.7E−05 |
| Cer(d18:1/18:0)/LacCer(d18:1/16:0) | 2.74 | 3.0E−42 | 2.94 | 1.5E−36 | 3.33 | 1.6E−20 | 3.42 | 2.8E−17 | 2.34 | 1.6E−05 |
| SM(d18:0/22:0)/PC(P-34:1) | 2.77 | 3.3E−42 | 2.93 | 3.6E−36 | 4.01 | 8.7E−22 | 4.54 | 2.7E−19 | 2.12 | 3.2E−04 |
| DAG(16:0/16:1)/LPC(MHDA) [sn2] | 2.63 | 3.4E−42 | 2.57 | 2.2E−33 | 3.52 | 5.1E−22 | 3.53 | 1.9E−18 | 2.53 | 8.9E−07 |
| PC(38:3)/PC(O-36:2) | 2.77 | 4.1E−42 | 2.95 | 4.1E−36 | 4.60 | 2.6E−23 | 4.74 | 4.5E−19 | 2.26 | 5.4E−05 |
| PC(38:3)/SM(37:2) | 2.77 | 4.2E−42 | 3.10 | 5.4E−38 | 4.50 | 5.6E−24 | 4.87 | 2.7E−20 | 2.04 | 5.7E−04 |
| PG(36:1)/LPC(20:1) [sn1] | 2.72 | 4.7E−42 | 2.88 | 7.0E−36 | 3.90 | 3.0E−22 | 3.99 | 4.1E−18 | 2.19 | 1.2E−04 |
| DAG(16:0/16:1)/LPE(16:0) [sn2] | 2.75 | 5.0E−42 | 2.85 | 3.4E−35 | 3.69 | 1.9E−20 | 4.22 | 2.1E−18 | 2.67 | 4.7E−06 |
| DAG(16:0/16:1)/LPC(MHDA) [sn1] | 2.63 | 5.2E−42 | 2.60 | 1.4E−33 | 3.62 | 5.2E−22 | 3.69 | 1.2E−18 | 2.58 | 6.6E−07 |
| Cer(d18:1/18:0)/Gb3(d18:1/16:0) | 2.74 | 5.5E−42 | 2.95 | 7.2E−37 | 3.41 | 1.4E−20 | 3.46 | 3.4E−17 | 2.01 | 3.8E−04 |
| DAG(16:0/18:1)/LPC(20:1) [sn1] | 2.64 | 5.9E−42 | 2.75 | 5.0E−36 | 3.55 | 1.4E−21 | 3.68 | 1.7E−18 | 2.34 | 2.1E−05 |
| DAG(16:0/18:1)/PC(O-36:2) | 2.63 | 6.0E−42 | 2.78 | 2.8E−36 | 3.50 | 2.5E−21 | 3.61 | 4.1E−18 | 2.45 | 5.9E−06 |
| DAG(18:0/18:2)/LPC(20:0) [sn2] | 2.64 | 6.3E−42 | 2.81 | 1.6E−36 | 3.41 | 3.5E−21 | 3.61 | 3.2E−18 | 2.62 | 1.4E−06 |
| DAG(16:0/18:1)/LPC(20:0) [sn1] | 2.62 | 6.8E−42 | 2.69 | 2.0E−35 | 3.50 | 1.7E−22 | 3.63 | 2.8E−19 | 2.58 | 1.4E−06 |
| PG(36:1)/LPE(16:0) [sn1] | 2.71 | 7.1E−42 | 3.02 | 1.3E−37 | 3.69 | 3.1E−21 | 4.24 | 2.9E−18 | 2.37 | 3.0E−05 |
| DAG(16:0/18:1)/LPC(17:0) [sn2] | 2.56 | 7.3E−42 | 2.58 | 1.2E−34 | 3.34 | 5.2E−22 | 3.31 | 2.3E−18 | 2.37 | 2.2E−06 |
| DAG(16:0/20:4)/PC(O-40:6) | 2.66 | 7.7E−42 | 2.74 | 1.5E−35 | 3.09 | 1.4E−18 | 3.17 | 4.2E−16 | 2.06 | 1.9E−04 |
| DAG(16:0/16:1)/PC(37:6) | 2.70 | 7.8E−42 | 2.76 | 1.9E−34 | 3.18 | 5.4E−19 | 3.44 | 1.8E−16 | 2.15 | 1.1E−04 |
| SM(36:1)/PC(P-36:1) | 2.71 | 8.2E−42 | 2.95 | 5.3E−37 | 4.40 | 2.2E−23 | 4.91 | 2.3E−20 | 3.29 | 1.0E−07 |
| DAG(18:0/18:2)/LPC(O-22:1) | 2.64 | 8.7E−42 | 2.78 | 3.6E−36 | 3.28 | 1.2E−19 | 3.46 | 3.4E−17 | 2.42 | 4.3E−06 |
| DAG(16:0/16:1)/LPE(16:0) [sn1] | 2.75 | 8.8E−42 | 2.86 | 5.2E−35 | 3.69 | 3.0E−20 | 4.35 | 2.0E−18 | 2.64 | 5.5E−06 |
| DAG(16:0/18:1)/PC(33:2) | 2.63 | 8.8E−42 | 2.80 | 2.4E−36 | 3.21 | 4.1E−20 | 3.43 | 1.1E−17 | 2.30 | 1.9E−05 |
| DAG(16:0/18:1)/LPC(20:2) [sn2] | 2.63 | 9.1E−42 | 2.85 | 2.3E−37 | 3.38 | 3.3E−21 | 3.57 | 2.8E−18 | 2.42 | 4.0E−06 |
| Cer(d16:1/18:0)/PC(P-36:1) | 2.90 | 1.1E−41 | 3.25 | 3.1E−37 | 4.63 | 5.1E−22 | 5.03 | 2.2E−18 | 2.89 | 6.6E−06 |
| PI(32:1)/PC(P-32:1) | 2.63 | 1.2E−41 | 2.52 | 6.9E−32 | 3.47 | 1.9E−22 | 3.36 | 4.6E−16 | 1.96 | 1.0E−03 |
| DAG(16:0/18:1)/LPC(22:0) [sn2] | 2.61 | 1.2E−41 | 2.72 | 5.4E−36 | 3.47 | 2.6E−22 | 3.61 | 2.4E−19 | 2.55 | 2.2E−06 |
| DAG(16:0/22:6)/PC(O-40:6) | 2.78 | 1.2E−41 | 2.81 | 6.5E−34 | 3.81 | 1.3E−20 | 3.83 | 3.8E−17 | 3.40 | 5.5E−09 |
| PG(36:1)/LPC(20:0) [sn2] | 2.68 | 1.3E−41 | 2.79 | 4.6E−35 | 3.83 | 9.2E−23 | 3.85 | 1.1E−18 | 2.36 | 1.8E−05 |
| PG(36:1)/LPC(22:0) [sn1] | 2.72 | 1.3E−41 | 2.91 | 7.0E−36 | 3.94 | 1.0E−22 | 4.19 | 6.0E−19 | 2.55 | 6.9E−06 |
| DAG(16:0/16:1)/SM(37:1) | 2.67 | 1.3E−41 | 2.69 | 1.0E−33 | 3.40 | 9.8E−21 | 3.58 | 4.9E−17 | 2.20 | 9.5E−05 |
| DAG(16:0/18:1)/SM(37:1) | 2.63 | 1.3E−41 | 2.75 | 9.5E−36 | 3.21 | 9.6E−20 | 3.33 | 4.8E−17 | 2.14 | 1.0E−04 |
| DAG(18:0/18:2)/LPC(20:0) [sn1] | 2.64 | 1.4E−41 | 2.80 | 3.2E−36 | 3.49 | 3.5E−21 | 3.72 | 3.1E−18 | 2.74 | 7.1E−07 |
| DAG(16:0/18:1)/LPC(17:0) [sn1] | 2.55 | 1.5E−41 | 2.57 | 3.0E−34 | 3.31 | 9.5E−22 | 3.32 | 2.3E−18 | 2.34 | 3.2E−06 |
| PG(36:1)/LPC(20:1) [sn2] | 2.71 | 1.5E−41 | 2.86 | 2.4E−35 | 3.82 | 1.9E−21 | 3.90 | 2.0E−17 | 2.14 | 2.1E−04 |
| Cer(d18:1/22:0)/SM(37:2) | 2.69 | 1.7E−41 | 2.90 | 4.6E−36 | 3.69 | 3.8E−21 | 3.86 | 1.8E−17 | 1.87 | 2.1E−03 |
| DAG(16:0/16:1)/LPC(O-22:1) | 2.64 | 1.7E−41 | 2.61 | 2.6E−33 | 3.51 | 1.7E−20 | 3.63 | 8.9E−18 | 2.38 | 1.2E−05 |
| DAG(16:0/20:4)/PC(P-34:1) | 2.65 | 1.8E−41 | 2.75 | 2.3E−35 | 3.16 | 3.7E−19 | 3.27 | 1.8E−16 | 2.04 | 3.5E−04 |
| DAG(16:0/18:1)/SM(37:2) | 2.62 | 2.1E−41 | 2.82 | 1.2E−36 | 3.53 | 2.9E−21 | 3.69 | 3.3E−18 | 2.31 | 2.9E−05 |
| Cer(d18:1/18:0)/SM(37:2) | 2.67 | 2.3E−41 | 2.97 | 2.2E−37 | 3.60 | 2.1E−22 | 3.63 | 1.4E−18 | 2.23 | 2.6E−05 |
| DAG(16:0/18:1)/LPE(16:0) [sn2] | 2.63 | 2.3E−41 | 2.87 | 1.5E−37 | 3.34 | 3.4E−20 | 3.78 | 2.1E−18 | 2.52 | 2.8E−06 |
| DAG(18:0/18:2)/PC(37:2) | 2.68 | 2.3E−41 | 2.86 | 3.1E−36 | 3.33 | 4.2E−19 | 3.51 | 1.5E−16 | 2.70 | 2.7E−06 |
| DAG(16:0/18:1)/LPC(O-20:1) | 2.58 | 2.3E−41 | 2.65 | 4.3E−35 | 3.38 | 8.8E−21 | 3.45 | 6.0E−18 | 2.32 | 7.7E−06 |
| DAG(16:0/16:1)/PC(35:2) | 2.72 | 2.4E−41 | 2.77 | 3.0E−34 | 4.00 | 1.5E−21 | 4.32 | 1.9E−18 | 2.68 | 1.9E−06 |
| DAG(18:0/18:2)/LPC(MHDA) [sn2] | 2.58 | 2.6E−41 | 2.65 | 3.5E−35 | 3.26 | 7.9E−21 | 3.24 | 3.1E−17 | 2.60 | 2.0E−07 |
| DAG(16:0/16:1)/SM(37:2) | 2.66 | 2.7E−41 | 2.74 | 2.1E−34 | 3.69 | 6.7E−21 | 3.89 | 5.9E−18 | 2.37 | 3.6E−05 |
| DAG(18:0/18:2)/LPC(MHDA) [sn1] | 2.59 | 2.9E−41 | 2.69 | 1.1E−35 | 3.39 | 4.9E−21 | 3.44 | 9.9E−18 | 2.68 | 1.3E−07 |
| PC(40:5)/LPC(19:0) [sn1] | 2.62 | 2.9E−41 | 2.59 | 8.4E−33 | 3.41 | 7.3E−21 | 3.28 | 1.3E−16 | 2.29 | 3.5E−05 |
| PC(38:3)/Gb3(d18:1/16:0) | 2.72 | 3.1E−41 | 2.95 | 4.4E−36 | 4.01 | 3.0E−21 | 4.40 | 4.6E−18 | 1.73 | 9.1E−03 |
| DAG(16:0/18:1)/PC(O-34:1) | 2.61 | 3.1E−41 | 2.75 | 1.0E−35 | 3.33 | 2.9E−20 | 3.49 | 1.1E−17 | 2.35 | 1.9E−05 |
| DAG(16:0/16:1)/SM (d17:1/14:0) | 2.65 | 3.2E−41 | 2.65 | 4.2E−33 | 3.36 | 1.9E−20 | 3.56 | 4.4E−17 | 2.27 | 3.5E−05 |
| DAG(16:0/16:1)/LPC(19:0) [sn2] | 2.64 | 3.3E−41 | 2.61 | 5.3E−33 | 3.57 | 6.0E−22 | 3.66 | 1.0E−18 | 2.40 | 6.3E−06 |
| DAG(16:O/16:1)/PC(37:2) | 2.74 | 3.4E−41 | 2.77 | 2.9E−33 | 3.77 | 1.3E−20 | 4.17 | 7.0E−18 | 2.62 | 8.2E−06 |
| PC(40:6)/PC(17:0_22:6) | 2.58 | 3.5E−41 | 2.68 | 7.5E−35 | 2.85 | 2.9E−20 | 3.39 | 2.0E−18 | 1.93 | 1.2E−05 |
| PG(36:1)/PC(O-36:3) | 2.71 | 3.5E−41 | 2.88 | 3.0E−35 | 3.72 | 5.1E−20 | 3.66 | 1.5E−16 | 2.26 | 7.8E−05 |
| DAG(16:0/18:1)/LPE(16:0) [sn1] | 2.63 | 3.7E−41 | 2.89 | 2.5E−37 | 3.34 | 4.6E−20 | 3.88 | 1.7E−18 | 2.48 | 3.3E−06 |
| DAG(16:0/20:4)/LPC(19:0) [sn2] | 2.61 | 4.0E−41 | 2.62 | 3.0E−34 | 3.32 | 1.0E−21 | 3.36 | 1.7E−18 | 2.10 | 9.7E−05 |
| PI(32:1)/PC(P-34:1) | 2.59 | 4.0E−41 | 2.40 | 3.5E−30 | 3.55 | 7.6E−21 | 3.32 | 1.2E−16 | 2.18 | 9.0E−05 |
| SM(36:0)/Gb3(d18:1/16:0) | 2.56 | 4.3E−41 | 2.69 | 1.6E−35 | 3.51 | 2.5E−23 | 3.71 | 3.1E−20 | 2.51 | 1.5E−06 |
| PG(36:1)/LPC(22:0) [sn2] | 2.66 | 5.1E−41 | 2.84 | 2.4E−35 | 3.84 | 1.1E−22 | 3.92 | 8.3E−19 | 2.43 | 1.5E−05 |
| PI(40:5)/LPC(O-22:1) | 2.70 | 5.1E−41 | 2.54 | 3.3E−30 | 3.67 | 1.2E−20 | 3.53 | 2.0E−16 | 2.29 | 3.4E−05 |
| DAG(18:0/18:2)/LPC(20:1) [sn2] | 2.60 | 5.1E−41 | 2.79 | 2.4E−36 | 3.17 | 2.3E−19 | 3.34 | 1.1E−16 | 2.30 | 2.6E−05 |
| DAG(16:0/18:1)/LPC(15:0) [sn2] | 2.53 | 5.3E−41 | 2.58 | 2.6E−34 | 3.20 | 6.1E−21 | 3.21 | 1.2E−17 | 2.16 | 1.5E−05 |
| PG(36:1)/LPC(O-20:1) | 2.63 | 5.5E−41 | 2.73 | 1.5E−34 | 3.68 | 2.2E−21 | 3.68 | 2.0E−17 | 2.24 | 5.0E−05 |
| PC(32:1)/PC(P-34:1) | 2.57 | 5.6E−41 | 2.44 | 1.5E−30 | 3.31 | 1.4E−20 | 3.23 | 1.6E−16 | 2.02 | 1.9E−04 |
| DAG(16:0/20:4)/LPC(MHDA) [sn2] | 2.55 | 5.6E−41 | 2.53 | 1.5E−33 | 3.22 | 2.9E−21 | 3.15 | 1.7E−17 | 2.25 | 1.8E−05 |
| PG(36:1)/LPC(24:0) [sn1] | 2.69 | 5.8E−41 | 2.93 | 4.7E−36 | 3.75 | 6.0E−22 | 4.00 | 2.6E−18 | 2.51 | 1.0E−05 |
| DAG(16:0/22:6)/PC(37:6) | 2.71 | 6.0E−41 | 2.75 | 2.7E−33 | 3.54 | 1.4E−19 | 3.59 | 4.0E−16 | 2.87 | 1.6E−07 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| | FL | | NAFLD | | FL (severe) | | NAFLD (severe) | | DM2 | |
|---|---|---|---|---|---|---|---|---|---|---|
| Lipid ratio | OR | p-value | OR | p-value | OR | p-value | OR | p-value | OR | p-value |
| Cer(d16:1/18:0)/PC(P-36:2) | 2.81 | 6.9E−41 | 3.10 | 2.4E−36 | 4.53 | 1.6E−22 | 4.60 | 3.0E−18 | 2.76 | 9.1E−06 |
| DAG(18:0/18:2)/PC(P-36:1) | 2.59 | 7.0E−41 | 2.80 | 2.9E−36 | 3.22 | 2.7E−19 | 3.39 | 1.3E−16 | 2.43 | 7.2E−06 |
| PG(36:1)/LPE(16:0) [sn2] | 2.66 | 7.3E−41 | 2.94 | 1.3E−36 | 3.62 | 9.9E−21 | 3.95 | 1.5E−17 | 2.37 | 3.2E−05 |
| PG(36:1)/LPC(17:0) [sn1] | 2.59 | 7.9E−41 | 2.65 | 1.3E−33 | 3.58 | 4.4E−22 | 3.56 | 8.5E−18 | 2.24 | 2.4E−05 |
| PG(36:1)/LacCer(d18:1/16:0) | 2.65 | 7.9E−41 | 2.83 | 3.5E−35 | 3.36 | 1.4E−19 | 3.43 | 4.8E−17 | 2.15 | 1.7E−04 |
| DAG(16:0/18:1)/LPC(22:0) [sn1] | 2.59 | 8.1E−41 | 2.70 | 3.1E−35 | 3.44 | 9.6E−22 | 3.68 | 4.8E−19 | 2.59 | 1.6E−06 |
| PC(38:3)/SM(d17:1/14:0) | 2.66 | 8.7E−41 | 2.74 | 6.4E−34 | 3.84 | 2.6E−21 | 3.95 | 1.3E−17 | 1.90 | 1.8E−03 |
| DAG(16:0/18:1)/LacCer(d18:1/16:0) | 2.57 | 9.4E−41 | 2.71 | 2.3E−35 | 3.05 | 2.5E−19 | 3.19 | 6.3E−17 | 2.25 | 2.5E−05 |
| DAG(16:0/16:1)/PC(O-36:2) | 2.62 | 9.6E−41 | 2.66 | 2.9E−33 | 3.64 | 9.5E−21 | 3.82 | 1.3E−17 | 2.47 | 1.3E−05 |
| DAG(18:0/18:2)/LPC(22:0) [sn2] | 2.59 | 9.7E−41 | 2.81 | 2.0E−36 | 3.38 | 1.2E−20 | 3.63 | 5.8E−18 | 2.67 | 1.3E−06 |
| PG(36:1)/LPC(24:0) [sn2] | 2.67 | 1.0E−40 | 2.88 | 1.4E−35 | 3.78 | 1.3E−21 | 4.02 | 3.5E−18 | 2.43 | 2.1E−05 |
| SM(36:0)/SM(37:2) | 2.54 | 1.0E−40 | 2.73 | 6.1E−36 | 3.78 | 6.7E−24 | 3.87 | 2.1E−20 | 2.64 | 1.8E−07 |
| DAG(16:0/16:1)/LPC(20:2) [sn2] | 2.65 | 1.1E−40 | 2.72 | 8.1E−34 | 3.63 | 1.0E−20 | 3.88 | 6.4E−18 | 2.46 | 1.0E−05 |
| DAG(16:0/16:1)/PC(33:2) | 2.63 | 1.1E−40 | 2.70 | 1.9E−33 | 3.28 | 7.3E−20 | 3.65 | 1.9E−17 | 2.30 | 2.8E−05 |
| PC(32:1)/PC(P-32:1) | 2.58 | 1.1E−40 | 2.52 | 6.7E−32 | 3.06 | 2.0E−18 | 3.05 | 2.7E−15 | 1.69 | 7.1E−03 |
| DAG(16:0/16:1)/PC(O-34:1) | 2.64 | 1.2E−40 | 2.66 | 4.5E−33 | 3.52 | 6.9E−20 | 3.74 | 2.9E−17 | 2.39 | 2.8E−05 |
| DAG(16:0/20:4)/SM(37:2) | 2.61 | 1.2E−40 | 2.75 | 2.6E−35 | 3.32 | 7.0E−20 | 3.39 | 7.9E−17 | 1.99 | 6.3E−04 |
| DAG(16:0/18:1)/SM(d17:1/14:0) | 2.57 | 1.3E−40 | 2.65 | 2.1E−34 | 3.15 | 9.7E−20 | 3.23 | 7.4E−17 | 2.20 | 4.0E−05 |
| DAG(18:0/18:2)/LPC(20:1) [sn1] | 2.58 | 1.4E−40 | 2.77 | 6.6E−36 | 3.26 | 9.1E−20 | 3.43 | 5.2E−17 | 2.34 | 1.8E−05 |
| SM(36:2)/PC(P-36:1) | 2.66 | 1.4E−40 | 2.92 | 1.8E−36 | 5.07 | 5.2E−24 | 5.34 | 3.5E−20 | 3.13 | 2.4E−07 |
| DAG(16:0/18:1)/LPC(24:0) [sn2] | 2.56 | 1.6E−40 | 2.71 | 1.2E−35 | 3.32 | 3.3E−21 | 3.58 | 1.0E−18 | 2.47 | 3.0E−06 |
| PG(36:1)/LPC(P-18:1) | 2.61 | 1.6E−40 | 2.65 | 3.2E−33 | 3.39 | 1.3E−20 | 3.20 | 5.7E−16 | 1.98 | 4.4E−04 |
| DAG(16:0/16:1)/PC(34:3) | 2.68 | 1.6E−40 | 2.81 | 1.1E−34 | 3.63 | 2.4E−20 | 3.99 | 5.2E−18 | 2.44 | 2.4E−05 |
| Cer(d18:1/18:0)/PC(O-36:2) | 2.63 | 1.8E−40 | 2.81 | 6.0E−35 | 3.50 | 3.2E−22 | 3.46 | 8.8E−18 | 2.36 | 2.9E−06 |
| PG(36:1)/LPC(17:0) [sn2] | 2.57 | 1.8E−40 | 2.63 | 2.7E−33 | 3.52 | 6.2E−22 | 3.42 | 2.7E−17 | 2.24 | 1.8E−05 |
| DAG(16:0/16:1)/LPC(19:0) [sn1] | 2.61 | 2.0E−40 | 2.56 | 6.6E−32 | 3.50 | 4.9E−21 | 3.61 | 7.3E−18 | 2.54 | 3.6E−06 |
| PC(38:3)/LPC(19:0) [sn1] | 2.59 | 2.3E−40 | 2.60 | 5.7E−33 | 4.02 | 1.6E−23 | 4.16 | 1.1E−19 | 2.46 | 1.3E−05 |
| DAG(18:0/18:2)/PC(O-36:2) | 2.55 | 2.5E−40 | 2.74 | 1.0E−35 | 3.18 | 1.1E−19 | 3.22 | 1.3E−16 | 2.45 | 5.2E−06 |
| DAG(18:0/18:2)/LPC(17:0) [sn1] | 2.55 | 2.5E−40 | 2.61 | 6.1E−34 | 3.26 | 5.2E−20 | 3.28 | 1.0E−16 | 2.46 | 2.1E−06 |
| PC(38:3)/PC(35:2) | 2.68 | 2.8E−40 | 2.85 | 3.5E−35 | 4.27 | 4.8E−22 | 4.44 | 1.6E−18 | 2.45 | 1.6E−05 |
| DAG(16:0/20:4)/PC(37:2) | 2.71 | 2.9E−40 | 2.76 | 1.3E−33 | 3.38 | 7.3E−19 | 3.49 | 3.0E−16 | 2.20 | 1.7E−04 |
| DAG(16:0/16:1)/PC(O-32:1) | 2.64 | 2.9E−40 | 2.71 | 1.4E−33 | 3.40 | 8.6E−19 | 3.65 | 1.3E−16 | 2.29 | 1.0E−04 |
| DAG(16:0/16:1)/PC(31:0) | 2.65 | 3.0E−40 | 2.73 | 4.4E−33 | 3.33 | 3.1E−19 | 3.78 | 6.8E−17 | 2.47 | 1.5E−05 |
| DAG(16:0/16:1)/PC(17:0_22:6) | 2.62 | 3.1E−40 | 2.67 | 7.4E−33 | 3.19 | 2.9E−18 | 3.41 | 4.5E−16 | 2.17 | 1.1E−04 |
| PI(32:1)/PC(P-36:2) | 2.55 | 3.2E−40 | 2.39 | 8.6E−30 | 3.68 | 1.1E−21 | 3.41 | 5.0E−17 | 2.23 | 6.1E−05 |
| PG(36:1)/LPC(O-20:0) | 2.58 | 3.2E−40 | 2.69 | 9.3E−34 | 3.65 | 2.5E−21 | 3.69 | 1.6E−17 | 2.40 | 8.8E−06 |
| SM(38:0)/SM(33:0) | 2.62 | 3.5E−40 | 2.63 | 1.0E−32 | 3.25 | 1.7E−18 | 3.41 | 3.6E−16 | 2.17 | 1.5E−04 |
| DAG(16:0/18:1)/LPC(O-20:0) | 2.50 | 3.6E−40 | 2.57 | 5.4E−34 | 3.26 | 2.0E−20 | 3.38 | 7.3E−18 | 2.43 | 1.8E−06 |
| DAG(16:0/18:1)/PC(O-36:3) | 2.60 | 3.6E−40 | 2.74 | 1.4E−34 | 3.45 | 4.7E−20 | 3.52 | 9.0E−17 | 2.41 | 1.9E−05 |
| DAG(16:0/18:1)/LPC(20:2) [sn1] | 2.56 | 3.7E−40 | 2.74 | 1.6E−35 | 3.35 | 6.8E−21 | 3.48 | 7.9E−18 | 2.42 | 3.8E−06 |
| DAG(18:0/18:2)/LPC(22:0) [sn1] | 2.58 | 3.9E−40 | 2.79 | 7.3E−36 | 3.34 | 3.3E−20 | 3.68 | 8.3E−18 | 2.70 | 8.0E−07 |
| SM(36:0)/PC(O-34:1) | 2.50 | 4.0E−40 | 2.61 | 1.4E−34 | 3.64 | 2.3E−23 | 3.85 | 1.5E−20 | 2.99 | 6.6E−08 |
| DAG(16:0/22:6)/PC(17:0_22:6) | 2.67 | 4.1E−40 | 2.66 | 4.5E−32 | 3.42 | 5.2E−19 | 3.53 | 7.0E−16 | 2.98 | 1.3E−07 |
| DAG(16:0/18:1)/LPC(P-18:1) | 2.52 | 4.2E−40 | 2.54 | 3.1E−33 | 3.09 | 6.1E−20 | 3.03 | 2.0E−16 | 2.08 | 8.1E−05 |
| Cer(d18:1/18:0)/SM(34:1) | 2.66 | 4.4E−40 | 2.92 | 1.4E−35 | 3.37 | 1.7E−20 | 3.55 | 4.0E−17 | 2.09 | 1.3E−04 |
| DAG(16:0/16:1)/LPC(20:1) [sn2] | 2.62 | 4.6E−40 | 2.61 | 2.6E−32 | 3.52 | 4.0E−20 | 3.67 | 3.4E−17 | 2.31 | 5.6E−05 |
| DAG(18:0/18:2)/PC(O-40:6) | 2.62 | 4.8E−40 | 2.77 | 4.4E−35 | 3.02 | 2.2E−17 | 3.11 | 5.1E−15 | 2.42 | 9.9E−06 |
| PG(36:1)/PC(33:2) | 2.57 | 5.1E−40 | 2.77 | 5.4E−35 | 3.13 | 2.2E−19 | 3.34 | 4.2E−16 | 2.08 | 2.0E−04 |
| PC(38:3)/LPC(O-22:1) | 2.59 | 5.2E−40 | 2.65 | 2.7E−33 | 3.71 | 5.9E−22 | 3.93 | 7.6E−19 | 2.17 | 1.3E−04 |
| Cer(d16:1/18:0)/SM(37:1) | 2.95 | 5.4E−40 | 3.36 | 1.1E−35 | 4.19 | 9.2E−20 | 4.47 | 4.9E−16 | 2.33 | 3.0E−04 |
| SM(38:0)/PC(P-36:1) | 2.65 | 5.5E−40 | 2.77 | 6.2E−34 | 4.27 | 8.7E−22 | 4.66 | 1.8E−18 | 3.15 | 5.6E−07 |
| PI(40:5)/LPC(19:0) [sn1] | 2.60 | 6.1E−40 | 2.39 | 2.0E−28 | 3.77 | 1.6E−21 | 3.50 | 9.4E−17 | 2.52 | 2.7E−06 |
| DAG(16:0/20:4)/LPC(20:1) [sn2] | 2.59 | 6.3E−40 | 2.65 | 1.2E−33 | 3.23 | 2.2E−19 | 3.32 | 1.4E−16 | 1.95 | 9.6E−04 |
| PG(36:1)/LPC(P-18:0) | 2.55 | 7.2E−40 | 2.62 | 4.9E−33 | 3.51 | 7.8E−22 | 3.35 | 3.8E−17 | 2.27 | 2.2E−05 |
| SM(d18:0/22:0)/LPC(O-24:2) | 2.65 | 7.3E−40 | 2.75 | 2.1E−33 | 3.66 | 5.9E−21 | 4.27 | 1.3E−18 | 2.08 | 3.1E−04 |
| DAG(16:0/16:1)/LacCer(d18:1/16:0) | 2.58 | 7.9E−40 | 2.60 | 2.1E−32 | 3.25 | 5.8E−19 | 3.39 | 1.7E−16 | 2.31 | 4.1E−05 |
| DAG(18:0/18:2)/PC(35:2) | 2.62 | 8.6E−40 | 2.76 | 6.1E−35 | 3.36 | 1.6E−18 | 3.42 | 1.8E−15 | 2.72 | 1.0E−06 |
| DAG(16:0/20:4)/SM(37:1) | 2.58 | 8.6E−40 | 2.63 | 2.6E−33 | 2.94 | 7.1E−18 | 2.97 | 4.2E−15 | 1.80 | 2.8E−03 |
| SM(40:1)/PC(P-36:1) | 2.70 | 8.8E−40 | 2.83 | 2.0E−33 | 3.87 | 3.5E−20 | 4.38 | 2.7E−17 | 2.55 | 2.5E−05 |
| SM(d18:0/22:0)/SM(37:2) | 2.64 | 9.0E−40 | 2.83 | 1.1E−34 | 4.13 | 2.2E−22 | 4.42 | 1.9E−19 | 1.98 | 8.7E−04 |
| DAG(18:0/18:2)/PC(35:3) | 2.58 | 9.2E−40 | 2.80 | 5.7E−36 | 3.16 | 1.8E−18 | 3.26 | 8.1E−16 | 2.44 | 1.0E−05 |
| PG(36:1)/LPC(O-24:1) | 2.59 | 9.5E−40 | 2.70 | 1.4E−33 | 3.53 | 1.2E−20 | 3.55 | 7.3E−17 | 2.18 | 1.1E−04 |
| PC(40:6)/PC(O-40:6) | 2.51 | 9.5E−40 | 2.54 | 5.2E−33 | 3.27 | 1.2E−21 | 3.18 | 1.6E−17 | 2.60 | 1.3E−07 |
| SM(36:0)/LPC(O-24:2) | 2.58 | 1.0E−39 | 2.66 | 3.0E−33 | 3.68 | 1.2E−22 | 4.01 | 7.6E−20 | 2.81 | 2.6E−07 |
| PI(40:5)/SM(37:1) | 2.67 | 1.0E−39 | 2.46 | 3.4E−28 | 3.13 | 4.2E−17 | 2.79 | 4.8E−12 | 1.80 | 4.1E−03 |
| DAG(14:0/18:1)/LPC(MHDA) [sn1] | 2.54 | 1.1E−39 | 2.62 | 1.6E−33 | 3.33 | 6.2E−20 | 3.34 | 1.3E−16 | 2.38 | 7.7E−06 |
| DAG(16:0/20:4)/PC(39:4) | 2.55 | 1.1E−39 | 2.58 | 6.1E−33 | 3.06 | 1.5E−18 | 3.17 | 3.7E−16 | 1.99 | 4.6E−04 |
| DAG(16:0/18:1)/LPC(15:0) [sn1] | 2.48 | 1.1E−39 | 2.54 | 2.3E−33 | 3.18 | 7.7E−21 | 3.26 | 1.1E−17 | 2.31 | 3.6E−06 |
| DAG(16:0/16:1)/LPC(24:0) [sn2] | 2.58 | 1.1E−39 | 2.60 | 2.0E−32 | 3.46 | 2.0E−20 | 3.69 | 7.0E−18 | 2.51 | 7.7E−06 |
| DAG(16:0/20:4)/LPC(20:1) [sn1] | 2.57 | 1.2E−39 | 2.63 | 1.9E−33 | 3.28 | 9.5E−20 | 3.35 | 6.9E−17 | 1.99 | 6.9E−04 |
| DAG(14:0/18:1)/LPC(MHDA) [sn2] | 2.54 | 1.2E−39 | 2.59 | 5.2E−33 | 3.25 | 9.4E−20 | 3.20 | 3.5E−16 | 2.33 | 1.2E−05 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| PG(36:1)/SM(d17:1/14:0) | 2.59 | 1.3E−39 | 2.71 | 7.7E−34 | 3.23 | 1.6E−19 | 3.33 | 6.9E−16 | 2.03 | 3.2E−04 |
| DAG(16:0/16:1)/LPC(20:0) [sn2] | 2.58 | 1.3E−39 | 2.54 | 1.7E−31 | 3.50 | 6.3E−21 | 3.60 | 7.3E−18 | 2.47 | 9.6E−06 |
| SM(36:0)/LacCer(d18:1/16:0) | 2.50 | 1.4E−39 | 2.62 | 5.2E−34 | 3.37 | 3.1E−22 | 3.66 | 7.3E−20 | 2.78 | 7.3E−08 |
| DAG(16:0/18:1)/LPC(24:0) [sn1] | 2.52 | 1.5E−39 | 2.67 | 5.4E−35 | 3.25 | 8.4E−21 | 3.49 | 2.4E−18 | 2.51 | 2.5E−06 |
| PG(36:1)/LPC(O-22:0) | 2.57 | 1.5E−39 | 2.71 | 9.6E−34 | 3.57 | 5.9E−21 | 3.71 | 2.4E−17 | 2.33 | 2.4E−05 |
| DAG(16:0/16:1)/LPC(17:0) [sn2] | 2.53 | 1.5E−39 | 2.47 | 6.5E−31 | 3.38 | 9.0E−21 | 3.39 | 2.6E−17 | 2.39 | 7.4E−06 |
| DAG(16:0/20:4)/LPC(20:0) [sn2] | 2.56 | 1.5E−39 | 2.57 | 1.0E−32 | 3.28 | 2.0E−20 | 3.33 | 2.1E−17 | 2.16 | 1.4E−04 |
| DAG(18:0/18:2)/LPC(O-20:1) | 2.53 | 1.5E−39 | 2.66 | 2.4E−34 | 3.16 | 4.4E−19 | 3.26 | 2.0E−16 | 2.37 | 7.0E−06 |
| PI(40:5)/PC(O-40:6) | 2.51 | 1.5E−39 | 2.43 | 1.2E−30 | 2.80 | 5.1E−17 | 2.66 | 2.7E−13 | 2.08 | 8.4E−05 |
| DAG(16:0/16:1)/LPC(20:1) [sn1] | 2.58 | 1.8E−39 | 2.58 | 7.5E−32 | 3.53 | 2.8E−20 | 3.66 | 2.3E−17 | 2.33 | 4.8E−05 |
| DAG(16:0/20:4)/PC(17:0_22:6) | 2.56 | 1.9E−39 | 2.61 | 4.5E−33 | 2.81 | 1.9E−16 | 2.93 | 2.2E−14 | 1.81 | 2.3E−03 |
| DAG(16:0/16:1)/LPC(15:0) [sn2] | 2.54 | 1.9E−39 | 2.49 | 4.9E−31 | 3.26 | 2.5E−20 | 3.34 | 4.5E−17 | 2.21 | 2.7E−05 |
| DAG(16:0/18:1)/LPC(P-18:0) | 2.46 | 2.2E−39 | 2.49 | 6.2E−33 | 3.20 | 5.7E−21 | 3.16 | 2.2E−17 | 2.32 | 4.9E−06 |
| DAG(16:0/16:1)/LPC(O-20:1) | 2.54 | 2.4E−39 | 2.51 | 1.8E−31 | 3.38 | 7.2E−20 | 3.44 | 5.5E−17 | 2.33 | 2.0E−05 |
| DAG(16:0/16:1)/PC(O-36:3) | 2.60 | 2.4E−39 | 2.62 | 7.0E−32 | 3.55 | 1.2E−19 | 3.69 | 1.8E−16 | 2.40 | 3.1E−05 |
| DAG(14:0/18:1)/LPC(O-24:2) | 2.61 | 2.4E−39 | 2.70 | 5.0E−33 | 3.26 | 5.0E−18 | 3.38 | 2.5E−15 | 2.17 | 2.2E−04 |
| DAG(16:0/20:4)/PC(37:6) | 2.55 | 2.5E−39 | 2.61 | 4.3E−33 | 2.77 | 1.9E−16 | 2.79 | 4.9E−14 | 1.76 | 3.5E−03 |
| DAG(16:0/16:1)/LPC(O-24:1) | 2.50 | 2.6E−39 | 2.59 | 1.4E−31 | 3.17 | 7.5E−20 | 3.30 | 2.9E−17 | 2.26 | 2.1E−05 |
| DAG(16:0/20:4)/LPC(17:0) [sn1] | 2.49 | 2.7E−39 | 2.45 | 1.1E−31 | 3.13 | 3.9E−20 | 3.07 | 9.9E−17 | 2.07 | 1.9E−04 |
| DAG(16:0/16:1)/LPC(20:0) [sn1] | 2.57 | 2.8E−39 | 2.54 | 3.0E−31 | 3.52 | 6.5E−21 | 3.64 | 6.6E−18 | 2.55 | 6.4E−06 |
| DAG(16:0/16:1)/LPC(22:0) [sn2] | 2.57 | 2.8E−39 | 2.56 | 9.5E−32 | 3.49 | 7.9E−21 | 3.62 | 5.8E−18 | 2.52 | 8.0E−06 |
| DAG(16:0/16:1)/LPC(20:2) [sn1] | 2.58 | 2.8E−39 | 2.62 | 2.3E−32 | 3.54 | 2.9E−20 | 3.72 | 2.7E−17 | 2.48 | 1.0E−05 |
| DAG(16:0/20:4)/Gb3(d18:1/16:0) | 2.53 | 2.9E−39 | 2.61 | 2.6E−33 | 2.90 | 4.2E−18 | 2.95 | 2.4E−15 | 1.77 | 3.6E−03 |
| PC(38:3)/LacCer(d18:1/16:0) | 2.65 | 3.0E−39 | 2.81 | 9.0E−34 | 3.66 | 1.1E−19 | 3.91 | 6.5E−17 | 2.00 | 1.1E−03 |
| DAG(14:0/18:1)/LPC(19:0) [sn2] | 2.57 | 3.0E−39 | 2.64 | 5.9E−33 | 3.33 | 7.6E−20 | 3.40 | 1.0E−16 | 2.21 | 7.6E−05 |
| Cer(d18:1/18:0)/LPC(O-20:1) | 2.60 | 3.2E−39 | 2.71 | 4.4E−33 | 3.82 | 2.3E−21 | 3.85 | 1.7E−17 | 2.42 | 6.6E−06 |
| PG(36:1)/PC(P-32:0) | 2.61 | 3.6E−39 | 2.80 | 6.4E−34 | 3.43 | 7.4E−20 | 3.62 | 2.6E−16 | 2.21 | 1.4E−04 |
| PC(38:3)/SM(41:2) | 2.58 | 3.6E−39 | 2.70 | 4.0E−33 | 3.47 | 1.8E−20 | 3.73 | 1.2E−17 | 1.95 | 1.1E−03 |
| DAG(16:0/18:1)/LPC(O-22:0) | 2.46 | 3.8E−39 | 2.56 | 1.1E−33 | 3.14 | 5.0E−20 | 3.32 | 1.2E−17 | 2.36 | 4.4E−06 |
| DAG (16:0/18:2)/LPC(O-24:2) | 2.51 | 3.9E−39 | 2.66 | 2.9E−34 | 3.08 | 1.2E−18 | 3.36 | 1.1E−16 | 2.41 | 8.1E−06 |
| DAG(16:0/20:4)/PC(O-36:2) | 2.55 | 3.9E−39 | 2.61 | 7.3E−33 | 3.17 | 2.9E−19 | 3.15 | 5.8E−16 | 2.09 | 2.1E−04 |
| PG(36:1)/LPC(20:2) [sn1] | 2.57 | 4.0E−39 | 2.78 | 2.7E−34 | 3.52 | 4.4E−21 | 3.52 | 5.5E−17 | 2.28 | 3.6E−05 |
| DAG(16:0/20:4)/LPC(22:0) [sn2] | 2.54 | 4.1E−39 | 2.60 | 4.7E−33 | 3.27 | 3.5E−20 | 3.36 | 2.2E−17 | 2.19 | 1.2E−04 |
| LPC(16:0) [sn1]/LPC(19:0) [sn1] | 2.57 | 4.1E−39 | 2.49 | 3.2E−30 | 3.36 | 6.2E−20 | 3.54 | 1.5E−16 | 2.28 | 2.8E−05 |
| Cer(d18:1/24:1)/PC(P-36:1) | 2.55 | 4.3E−39 | 2.64 | 1.6E−32 | 3.40 | 3.5E−20 | 3.62 | 3.3E−17 | 2.43 | 1.6E−05 |
| DAG(18:0/18:2)/LPC(17:0) [sn2] | 2.49 | 4.4E−39 | 2.57 | 3.7E−33 | 3.13 | 7.3E−21 | 3.11 | 1.9E−16 | 2.44 | 2.1E−06 |
| DAG(14:0/18:1)/PC(O-40:6) | 2.60 | 4.6E−39 | 2.73 | 1.8E−33 | 3.10 | 7.3E−17 | 3.18 | 2.3E−14 | 2.18 | 1.9E−04 |
| PC(38:3)/PC(P-40:2) | 2.58 | 5.0E−39 | 2.78 | 2.0E−34 | 3.44 | 3.7E−20 | 3.68 | 2.0E−17 | 2.05 | 1.3E−04 |
| DAG(16:0/20:4)/LPC(O-20:1) | 2.50 | 5.0E−39 | 2.52 | 2.2E−32 | 3.11 | 2.6E−19 | 3.13 | 2.1E−16 | 2.04 | 2.7E−04 |
| SM(d18:0/22:0)/SM(37:1) | 2.63 | 5.1E−39 | 2.71 | 2.0E−33 | 3.68 | 7.3E−20 | 4.01 | 1.8E−17 | 1.75 | 7.5E−03 |
| PC(38:3)/PC(O-36:3) | 2.66 | 5.3E−39 | 2.84 | 1.2E−33 | 4.43 | 1.2E−21 | 4.52 | 6.2E−18 | 2.11 | 3.8E−04 |
| DAG(16:0/20:4)/PC(35:3) | 2.59 | 5.9E−39 | 2.69 | 1.5E−33 | 3.16 | 1.1E−18 | 3.22 | 4.8E−16 | 2.02 | 5.5E−04 |
| DAG(16:0/20:4)/LPC(17:0) [sn2] | 2.48 | 6.3E−39 | 2.47 | 1.0E−31 | 3.14 | 3.0E−20 | 3.09 | 1.1E−16 | 2.10 | 1.4E−04 |
| DAG(14:0/18:1)/LPC(19:0) [sn1] | 2.56 | 6.4E−39 | 2.61 | 3.9E−33 | 3.30 | 3.6E−19 | 3.35 | 5.6E−16 | 2.36 | 3.2E−05 |
| DAG(16:0/16:1)/LPC(22:0) [sn1] | 2.56 | 6.4E−39 | 2.56 | 2.0E−31 | 3.47 | 1.6E−20 | 3.69 | 7.3E−18 | 2.57 | 6.1E−06 |
| DAG(16:0/20:4)/LPC(P-18:1) | 2.49 | 6.5E−39 | 2.47 | 1.3E−31 | 2.95 | 8.8E−19 | 2.87 | 3.0E−15 | 1.83 | 1.8E−03 |
| PG(36:1)/PC(37:1) | 2.60 | 6.6E−39 | 2.72 | 7.1E−33 | 3.35 | 2.2E−19 | 3.45 | 8.1E−16 | 2.24 | 1.0E−04 |
| DAG(16:0/16:1)/LPC(24:0) [sn1] | 2.55 | 6.8E−39 | 2.58 | 6.4E−32 | 3.41 | 4.5E−20 | 3.64 | 1.5E−17 | 2.56 | 6.8E−06 |
| DAG(18:0/18:2)/PC(O-36:3) | 2.52 | 7.2E−39 | 2.70 | 1.8E−34 | 3.10 | 2.3E−18 | 3.10 | 3.3E−15 | 2.41 | 1.7E−05 |
| DAG(16:0/20:4)/PC(35:2) | 2.59 | 7.3E−39 | 2.66 | 4.6E−33 | 3.27 | 5.5E−19 | 3.29 | 6.7E−16 | 2.31 | 3.5E−05 |
| DAG(18:0/18:2)/SM(37:2) | 2.51 | 8.0E−39 | 2.77 | 1.2E−35 | 3.22 | 6.9E−19 | 3.36 | 4.1E−16 | 2.29 | 4.1E−05 |
| DAG(16:0/20:4)/PC(O-34:1) | 2.54 | 8.0E−39 | 2.60 | 7.3E−33 | 3.02 | 3.0E−18 | 3.10 | 1.2E−15 | 1.98 | 6.5E−04 |
| SM(38:0)/PC(P-36:2) | 2.60 | 8.5E−39 | 2.70 | 5.8E−33 | 4.31 | 2.5E−22 | 4.39 | 1.5E−18 | 3.05 | 1.0E−06 |
| Cer(d16:1/18:0)/PC(P-34:1) | 2.77 | 8.7E−39 | 3.15 | 2.5E−35 | 4.11 | 5.3E−20 | 4.46 | 1.0E−16 | 2.64 | 3.3E−05 |
| PG(36:1)/PC(39:4) | 2.58 | 8.7E−39 | 2.71 | 6.6E−33 | 3.48 | 8.5E−20 | 3.67 | 1.7E−16 | 2.18 | 1.4E−04 |
| DAG(16:0/16:1)/LPC(P-18:1) | 2.52 | 9.0E−39 | 2.46 | 4.0E−31 | 3.20 | 3.3E−19 | 3.15 | 7.6E−16 | 2.14 | 1.2E−04 |
| DAG(16:0/20:4)/SM(d17:1/14:0) | 2.54 | 9.8E−39 | 2.53 | 1.0E−31 | 2.94 | 9.2E−18 | 2.87 | 1.0E−14 | 1.89 | 1.3E−03 |
| DAG(16:0/18:1)/PC(39:4) | 2.51 | 9.9E−39 | 2.60 | 5.9E−33 | 3.18 | 2.8E−19 | 3.35 | 5.1E−17 | 2.30 | 2.0E−05 |
| DAG(16:0/18:1)/LPC(O-18:0) | 2.43 | 1.0E−38 | 2.47 | 2.1E−32 | 3.19 | 3.5E−20 | 3.22 | 3.0E−17 | 2.41 | 2.4E−06 |
| DAG(16:0/20:4)/LPC(20:2) [sn2] | 2.54 | 1.1E−38 | 2.69 | 4.5E−34 | 3.10 | 1.1E−18 | 3.21 | 4.9E−16 | 2.03 | 3.5E−04 |
| PC(38:3)/LPC(20:0) [sn1] | 2.54 | 1.1E−38 | 2.62 | 1.3E−32 | 4.08 | 1.5E−23 | 4.40 | 4.8E−20 | 2.42 | 2.5E−05 |
| DAG(18:0/18:2)/PC(P-34:1) | 2.50 | 1.2E−38 | 2.70 | 1.1E−34 | 2.95 | 1.4E−17 | 3.11 | 3.2E−15 | 2.31 | 2.6E−05 |
| PC(38:3)/LPC(19:0) [sn2] | 2.49 | 1.2E−38 | 2.56 | 1.0E−32 | 3.63 | 1.2E−23 | 3.81 | 2.7E−20 | 2.07 | 7.5E−05 |
| DAG(18:0/18:2)/PC(17:0_22:6) | 2.56 | 1.2E−38 | 2.68 | 3.0E−33 | 2.77 | 1.5E−15 | 2.88 | 1.5E−13 | 2.15 | 1.4E−04 |
| SM(36:2)/SM(37:1) | 2.60 | 1.3E−38 | 2.89 | 3.9E−35 | 4.08 | 2.1E−22 | 4.24 | 5.3E−19 | 2.21 | 1.8E−04 |
| DAG(16:0/16:1)/LPC(O-24:1) | 2.52 | 1.3E−38 | 2.49 | 6.2E−31 | 3.31 | 2.6E−19 | 3.40 | 1.2E−16 | 2.30 | 3.6E−05 |
| PI(40:5)/LPC(24:0) [sn1] | 2.65 | 1.3E−38 | 2.56 | 1.8E−29 | 3.81 | 1.6E−20 | 3.83 | 7.8E−17 | 2.64 | 2.7E−06 |
| DAG(16:0/16:1)/PC(P-32:0) | 2.54 | 1.4E−38 | 2.56 | 2.5E−31 | 3.32 | 7.4E−19 | 3.54 | 1.9E−16 | 2.37 | 3.6E−05 |
| PG(36:1)/LPC(20:2) [sn2] | 2.55 | 1.4E−38 | 2.77 | 4.0E−34 | 3.50 | 2.6E−20 | 3.52 | 1.6E−16 | 2.22 | 8.5E−05 |
| PI(40:5)/Gb3(d18:1/16:0) | 2.58 | 1.5E−38 | 2.43 | 1.5E−28 | 3.04 | 3.3E−17 | 2.76 | 1.1E−12 | 1.76 | 6.3E−03 |
| DAG(16:0/20:4)/LacCer(d18:1/16:0) | 2.50 | 1.5E−38 | 2.56 | 1.3E−32 | 2.78 | 2.3E−17 | 2.83 | 6.8E−15 | 1.90 | 8.8E−04 |
| PE(38:4)/PC(35:3) | 2.75 | 1.5E−38 | 2.92 | 3.0E−33 | 3.95 | 3.8E−19 | 3.91 | 6.0E−16 | 1.84 | 5.8E−03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| Cer(d16:1/18:0)/PC(O-40:6) | 2.67 | 1.5E-38 | 2.95 | 1.2E-34 | 3.57 | 2.6E-18 | 3.72 | 1.6E-15 | 2.58 | 2.5E-05 |
| DAG(16:0/16:1)/LPC(17:0) [sn1] | 2.49 | 1.6E-38 | 2.43 | 5.1E-30 | 3.29 | 3.2E-20 | 3.35 | 5.1E-17 | 2.34 | 1.3E-05 |
| SM(d18:0/22:0)/PC(O-36:2) | 2.54 | 1.6E-38 | 2.60 | 2.2E-32 | 3.88 | 6.2E-22 | 3.95 | 1.7E-18 | 2.15 | 1.9E-04 |
| Cer(d18:1/18:0)/PC(35:2) | 2.68 | 1.7E-38 | 2.87 | 1.0E-33 | 3.89 | 9.6E-21 | 4.03 | 5.2E-17 | 2.95 | 5.0E-07 |
| DAG(16:0/16:1)/PC(P-40:2) | 2.53 | 1.7E-38 | 2.57 | 1.1E-31 | 3.17 | 1.2E-18 | 3.35 | 2.8E-16 | 2.25 | 1.5E-05 |
| PC(36:3)/PC(35:3) | 2.63 | 1.7E-38 | 2.72 | 3.7E-32 | 4.12 | 1.0E-20 | 4.41 | 1.6E-17 | 2.06 | 6.6E-04 |
| PI(32:1)/PC(O-32:1) | 2.49 | 1.7E-38 | 2.32 | 2.9E-28 | 3.38 | 7.1E-19 | 3.19 | 3.8E-15 | 2.00 | 7.3E-04 |
| PC(38:3)/LPC(MHDA) [sn1] | 2.47 | 1.8E-38 | 2.54 | 1.8E-32 | 3.82 | 9.3E-24 | 3.91 | 8.6E-20 | 2.51 | 2.5E-06 |
| DAG(16:0/16:1)/PC(37:1) | 2.58 | 1.9E-38 | 2.57 | 1.4E-30 | 3.38 | 8.8E-19 | 3.64 | 3.1E-16 | 2.45 | 2.3E-05 |
| DAG(14:0/18:1)/PC(37:2) | 2.62 | 1.9E-38 | 2.74 | 1.6E-32 | 3.37 | 1.2E-17 | 3.54 | 5.7E-15 | 2.32 | 1.4E-04 |
| PC(38:3)/PC(O-38:2) | 2.57 | 2.0E-38 | 2.66 | 4.6E-32 | 3.56 | 1.4E-20 | 3.87 | 1.4E-17 | 2.19 | 1.6E-04 |
| DAG(16:0/16:1)/LPC(O-20:0) | 2.48 | 2.1E-38 | 2.45 | 1.3E-30 | 3.28 | 1.3E-19 | 3.38 | 5.8E-17 | 2.44 | 6.1E-06 |
| DAG(16:0/16:1)/LPC(15:0) [sn1] | 2.50 | 2.1E-38 | 2.47 | 2.5E-30 | 3.26 | 3.5E-20 | 3.40 | 4.3E-17 | 2.35 | 9.2E-06 |
| DAG(16:0/18:1)/PC(37:1) | 2.53 | 2.1E-38 | 2.64 | 1.0E-32 | 3.35 | 9.1E-19 | 3.34 | 2.7E-16 | 2.40 | 1.4E-05 |
| SM(40:1)/PC(P-36:2) | 2.59 | 2.1E-38 | 2.68 | 5.4E-32 | 3.93 | 1.2E-20 | 4.09 | 4.8E-17 | 2.43 | 5.1E-05 |
| Cer(d18:1/22:0)/LPC(20:0) [sn1] | 2.54 | 2.2E-38 | 2.57 | 4.8E-31 | 3.75 | 6.6E-22 | 4.00 | 1.4E-18 | 2.25 | 3.6E-05 |
| DAG(16:0/20:4)/LPE(16:0) [sn2] | 2.57 | 2.2E-38 | 2.78 | 3.7E-34 | 3.06 | 1.1E-17 | 3.35 | 7.4E-16 | 2.09 | 2.1E-04 |
| DAG(16:0/20:4)/LPC(24:0) [sn2] | 2.49 | 2.3E-38 | 2.59 | 4.3E-33 | 3.08 | 2.6E-19 | 3.26 | 4.8E-17 | 2.11 | 1.6E-04 |
| DAG(16:0/18:1)/LPC(O-18:1) | 2.43 | 2.4E-38 | 2.46 | 6.5E-31 | 3.10 | 1.3E-19 | 3.07 | 1.9E-16 | 2.19 | 3.6E-05 |
| Cer(d18:1/24:1)/LPC(O-24:2) | 2.58 | 2.5E-38 | 2.66 | 1.7E-31 | 3.27 | 5.5E-19 | 3.62 | 1.4E-16 | 2.24 | 3.5E-05 |
| SM(36:0)/LPC(O-22:1) | 2.43 | 2.5E-38 | 2.49 | 4.2E-32 | 3.54 | 5.9E-23 | 3.90 | 4.4E-20 | 2.81 | 2.2E-07 |
| DAG(16:0/20:4)/LPC(16:0) [sn1] | 2.59 | 2.5E-38 | 2.80 | 4.7E-34 | 3.08 | 1.3E-17 | 3.43 | 5.3E-16 | 2.08 | 2.7E-04 |
| PC(38:3)/LPC(22:0) [sn1] | 2.53 | 2.6E-38 | 2.67 | 3.0E-33 | 4.00 | 3.2E-23 | 4.48 | 2.8E-20 | 2.45 | 1.9E-05 |
| DAG(16:0/20:4)/LPC(20:2) [sn1] | 2.51 | 2.6E-38 | 2.64 | 2.1E-33 | 3.12 | 4.8E-19 | 3.18 | 3.8E-16 | 2.09 | 2.0E-04 |
| DAG(16:0/20:4)/PC(33:2) | 2.51 | 2.7E-38 | 2.57 | 2.3E-32 | 2.86 | 2.4E-17 | 2.90 | 6.7E-15 | 1.92 | 9.9E-04 |
| DAG(18:0/18:2)/PC(33:2) | 2.51 | 2.7E-38 | 2.66 | 1.2E-33 | 2.90 | 9.8E-17 | 2.98 | 2.4E-14 | 2.30 | 3.0E-05 |
| Cer(d16:1/18:0)/LPC(O-24:2) | 2.68 | 2.7E-38 | 2.88 | 3.3E-33 | 3.83 | 4.5E-20 | 4.03 | 6.9E-17 | 2.53 | 3.5E-05 |
| DAG(18:0/18:2)/LPC(P-18:1) | 2.47 | 2.8E-38 | 2.55 | 1.4E-32 | 2.90 | 7.4E-18 | 2.86 | 1.3E-14 | 2.09 | 8.8E-05 |
| PC(38:2)/PC(P-36:2) | 2.57 | 2.9E-38 | 2.64 | 9.0E-32 | 4.23 | 2.9E-22 | 3.97 | 2.1E-17 | 2.55 | 1.0E-05 |
| CE(16:1)/SM(37:2) | 2.49 | 3.0E-38 | 2.42 | 2.6E-29 | 3.40 | 2.9E-20 | 3.39 | 2.2E-16 | 1.88 | 1.5E-03 |
| PI(40:5)/LPC(22:0) [sn1] | 2.64 | 3.0E-38 | 2.50 | 5.4E-28 | 4.14 | 6.2E-21 | 4.08 | 4.9E-17 | 2.70 | 2.9E-06 |
| DAG(16:0/20:4)/LPC(P-18:0) | 2.42 | 3.1E-38 | 2.41 | 2.3E-31 | 3.03 | 6.0E-20 | 2.96 | 2.6E-16 | 2.08 | 1.4E-04 |
| Cer(d18:1/18:0)/PC(O-36:3) | 2.56 | 3.2E-38 | 2.72 | 4.4E-33 | 3.49 | 4.2E-21 | 3.45 | 6.8E-17 | 2.38 | 2.0E-05 |
| DAG(16:0/16:1)/PC(39:4) | 2.53 | 3.2E-38 | 2.52 | 1.6E-30 | 3.34 | 6.0E-19 | 3.57 | 1.2E-16 | 2.34 | 3.4E-05 |
| DAG(16:0/18:1)/PC(31:0) | 2.51 | 3.4E-38 | 2.67 | 1.7E-33 | 3.03 | 2.7E-18 | 3.28 | 4.4E-16 | 2.36 | 1.9E-05 |
| Cer(d18:1/24:1)/PC(P-36:2) | 2.52 | 3.4E-38 | 2.61 | 7.3E-32 | 3.45 | 9.0E-21 | 3.47 | 3.2E-17 | 2.38 | 2.1E-05 |
| PG(36:1)/LPC(O-18:0) | 2.49 | 3.5E-38 | 2.56 | 1.3E-31 | 3.52 | 7.3E-21 | 3.46 | 1.1E-16 | 2.34 | 1.5E-05 |
| PG(36:1)/PC(P-40:4) | 2.56 | 3.5E-38 | 2.71 | 9.5E-33 | 3.72 | 3.0E-20 | 3.87 | 7.3E-17 | 2.37 | 3.0E-05 |
| DAG(18:0/18:2)/LPC(O-20:0) | 2.47 | 3.6E-38 | 2.60 | 3.3E-33 | 3.10 | 1.5E-18 | 3.27 | 3.0E-16 | 2.53 | 1.4E-06 |
| DAG(16:0/18:1)/LPE(P-20:0) | 2.41 | 3.9E-38 | 2.47 | 3.7E-32 | 3.12 | 1.4E-20 | 3.10 | 4.5E-17 | 2.24 | 7.7E-06 |
| DAG(16:0/20:4)/LPC(24:0) [sn1] | 2.47 | 4.0E-38 | 2.58 | 4.6E-33 | 3.05 | 4.2E-19 | 3.21 | 8.9E-17 | 2.16 | 1.1E-04 |
| DAG(16:0/18:1)/SM(41:2) | 2.42 | 4.1E-38 | 2.51 | 1.3E-32 | 2.84 | 1.7E-18 | 2.95 | 3.9E-16 | 2.16 | 4.2E-05 |
| DAG(16:0/16:1)/SM(41:2) | 2.48 | 4.1E-38 | 2.49 | 1.3E-30 | 3.18 | 1.8E-18 | 3.25 | 5.3E-16 | 2.22 | 5.0E-05 |
| DAG(16:0/18:1)/PC(P-32:0) | 2.47 | 4.4E-38 | 2.61 | 3.6E-33 | 3.10 | 5.6E-19 | 3.30 | 1.3E-16 | 2.30 | 2.8E-05 |
| PC(38:4)/PC(39:4) | 2.56 | 4.4E-38 | 2.63 | 1.1E-31 | 3.59 | 5.0E-20 | 3.90 | 7.6E-18 | 2.08 | 5.4E-04 |
| PI(40:5)/LPC(20:1) [sn1] | 2.63 | 4.5E-38 | 2.50 | 3.2E-28 | 3.82 | 9.7E-20 | 3.66 | 2.0E-15 | 2.11 | 3.6E-04 |
| DAG(18:0/18:2)/PC(P-18:0) | 2.44 | 4.5E-38 | 2.54 | 7.6E-33 | 3.10 | 1.9E-19 | 3.10 | 4.2E-16 | 2.41 | 3.3E-06 |
| PC(38:2)/PC(P-36:1) | 2.52 | 4.7E-38 | 2.58 | 2.4E-31 | 3.79 | 5.2E-21 | 3.74 | 6.9E-17 | 2.57 | 1.1E-05 |
| PC(38:3)/PC(39:4) | 2.55 | 4.9E-38 | 2.67 | 2.7E-32 | 3.82 | 5.9E-21 | 4.32 | 1.6E-18 | 2.05 | 6.6E-04 |
| DAG(16:0/18:1)/PC(P-40:4) | 2.47 | 5.3E-38 | 2.59 | 8.4E-33 | 3.27 | 1.6E-19 | 3.46 | 3.1E-17 | 2.44 | 4.7E-06 |
| PI(40:5)/LPC(19:0) [sn2] | 2.51 | 5.4E-38 | 2.35 | 8.6E-28 | 3.84 | 5.9E-21 | 3.02 | 1.5E-16 | 2.09 | 2.0E-05 |
| DAG(16:0/16:1)/PC(O-38:2) | 2.48 | 5.9E-38 | 2.48 | 2.2E-30 | 3.06 | 1.4E-18 | 3.28 | 4.2E-16 | 2.31 | 1.8E-05 |
| DAG(16:1/18:1)/PC(O-40:6) | 2.56 | 5.9E-38 | 2.64 | 8.8E-32 | 3.02 | 9.7E-17 | 3.18 | 1.5E-14 | 2.25 | 8.3E-05 |
| DAG(18:0/18:2)/LPC(24:0) [sn2] | 2.47 | 6.0E-38 | 2.72 | 8.0E-35 | 3.05 | 7.8E-19 | 3.38 | 8.0E-17 | 2.50 | 2.9E-06 |
| DAG(16:0/20:4)/PC(O-36:3) | 2.54 | 6.0E-38 | 2.60 | 7.4E-32 | 3.16 | 3.8E-18 | 3.13 | 6.5E-15 | 2.03 | 5.4E-04 |
| Cer(d18:1/18:0)/PC(O-34:0) | 2.52 | 6.3E-38 | 2.68 | 7.9E-33 | 3.06 | 1.0E-18 | 3.11 | 1.1E-15 | 2.46 | 5.7E-06 |
| PI(40:5)/LPC(20:0) [sn1] | 2.59 | 6.6E-38 | 2.39 | 3.4E-27 | 4.09 | 4.4E-21 | 3.84 | 1.1E-16 | 2.56 | 5.0E-06 |
| PC(38:3)/PC(33:2) | 2.57 | 6.7E-38 | 2.70 | 8.6E-33 | 3.53 | 1.4E-19 | 3.79 | 3.2E-17 | 1.96 | 1.5E-03 |
| PG(36:1)/LPC(O-18:1) | 2.49 | 6.9E-38 | 2.54 | 4.2E-31 | 3.41 | 3.4E-20 | 3.26 | 7.6E-16 | 2.07 | 2.4E-04 |
| DAG(16:0/16:1)/LPC(O-22:0) | 2.46 | 7.2E-38 | 2.45 | 1.9E-30 | 3.39 | 2.9E-19 | 3.36 | 9.1E-17 | 2.39 | 1.3E-05 |
| PI(40:5)/LPC(24:0) [sn2] | 2.63 | 7.2E-38 | 2.53 | 1.1E-28 | 3.84 | 2.2E-20 | 3.86 | 6.5E-17 | 2.47 | 8.3E-06 |
| PI(32:1)/SM(37:2) | 2.46 | 7.5E-38 | 2.33 | 3.5E-28 | 3.48 | 2.1E-20 | 3.26 | 4.3E-16 | 2.08 | 3.0E-04 |
| PI(40:5)/LPC(MHDA) [sn1] | 2.44 | 7.7E-38 | 2.28 | 3.7E-27 | 3.38 | 1.7E-21 | 3.07 | 5.1E-16 | 2.57 | 6.3E-07 |
| DAG(16:0/20:4)/LPC(15:0) [sn2] | 2.45 | 8.5E-38 | 2.44 | 8.1E-31 | 3.02 | 6.5E-19 | 2.95 | 1.1E-15 | 1.90 | 9.5E-04 |
| DAG(18:1/18:1)/LPC(O-24:2) | 2.45 | 8.7E-38 | 2.62 | 2.5E-33 | 2.87 | 1.4E-17 | 3.12 | 8.3E-16 | 2.05 | 2.2E-04 |
| DAG(16:0/18:1)/LPC(18:2) [sn2] | 2.43 | 8.9E-38 | 2.56 | 4.3E-33 | 3.33 | 6.3E-21 | 3.41 | 1.4E-17 | 2.41 | 8.4E-06 |
| Cer(d18:1/22:0)/LPC(22:0) [sn2] | 2.51 | 8.9E-38 | 2.62 | 9.4E-32 | 3.64 | 4.0E-21 | 4.00 | 2.6E-18 | 2.19 | 1.0E-04 |
| DAG(16:0/18:1)/PC(O-38:2) | 2.41 | 9.1E-38 | 2.49 | 4.1E-32 | 2.85 | 1.3E-18 | 2.96 | 3.3E-16 | 2.26 | 1.3E-05 |
| Cer(d18:1/18:0)/LPC(O-20:0) | 2.50 | 9.4E-38 | 2.60 | 1.2E-31 | 3.54 | 9.3E-21 | 3.59 | 3.4E-17 | 2.54 | 3.9E-07 |
| PG(36:1)/LPC(15:0) [sn2] | 2.46 | 9.4E-38 | 2.54 | 1.8E-31 | 3.24 | 3.4E-20 | 3.23 | 3.9E-16 | 2.00 | 2.3E-04 |
| DAG(16:0/16:1)/LPC(P-18:0) | 2.44 | 9.8E-38 | 2.39 | 9.2E-30 | 3.24 | 5.7E-20 | 3.22 | 1.5E-16 | 2.34 | 1.4E-05 |
| PC(38:3)/LPC(24:0) [sn1] | 2.49 | 1.1E-37 | 2.75 | 1.6E-34 | 3.86 | 1.1E-22 | 4.52 | 3.8E-20 | 2.35 | 2.7E-05 |
| DAG(16:0/16:1)/PC(O-32:0) | 2.49 | 1.1E-37 | 2.50 | 1.5E-30 | 3.12 | 5.4E-18 | 3.32 | 8.5E-16 | 2.30 | 4.5E-05 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| DAG(18:0/18:2)/PC(O-34:1) | 2.45 | 1.1E-37 | 2.62 | 1.4E-33 | 2.90 | 3.0E-17 | 3.01 | 6.8E-15 | 2.29 | 3.0E-05 |
| DAG(14:0/18:1)/PC(35:3) | 2.53 | 1.2E-37 | 2.69 | 9.0E-33 | 3.23 | 2.2E-17 | 3.33 | 1.3E-14 | 2.14 | 3.6E-04 |
| PG(36:1)/LPC(15:0) [sn1] | 2.45 | 1.2E-37 | 2.54 | 1.1E-31 | 3.26 | 1.4E-20 | 3.32 | 1.2E-16 | 2.17 | 4.2E-05 |
| DAG(16:0/20:4)/PC(31:0) | 2.51 | 1.3E-37 | 2.60 | 5.2E-32 | 2.82 | 1.4E-16 | 2.91 | 2.5E-14 | 2.00 | 5.6E-04 |
| PC(40:5)/LPC(20:0) [sn2] | 2.54 | 1.4E-37 | 2.55 | 1.9E-30 | 3.39 | 1.4E-19 | 3.27 | 9.3E-16 | 2.07 | 4.7E-04 |
| DAG(16:1/18:1)/LPC(O-24:2) | 2.48 | 1.5E-37 | 2.51 | 9.6E-31 | 3.01 | 1.0E-17 | 3.11 | 2.6E-15 | 2.16 | 1.4E-04 |
| PG(36:1)/LPE(P-20:0) | 2.48 | 1.6E-37 | 2.55 | 3.1E-31 | 3.53 | 7.9E-21 | 3.34 | 3.0E-16 | 2.19 | 5.2E-05 |
| PG(36:1)/LPC(O-24:0) | 2.51 | 1.6E-37 | 2.64 | 6.9E-32 | 3.43 | 8.4E-20 | 3.50 | 3.4E-16 | 2.26 | 6.0E-05 |
| DAG(18:0/18:2)/LPC(20:2) [sn2] | 2.45 | 1.7E-37 | 2.74 | 3.0E-35 | 2.92 | 6.6E-18 | 3.07 | 1.3E-15 | 2.37 | 6.9E-06 |
| DAG(16:0/20:4)/LPC(O-24:1) | 2.43 | 1.7E-37 | 2.47 | 2.3E-31 | 2.89 | 2.4E-18 | 2.96 | 1.0E-15 | 1.95 | 6.2E-04 |
| DAG(18:1/20:4)/PC(O-40:6) | 2.49 | 1.7E-37 | 2.67 | 1.1E-33 | 2.81 | 5.5E-16 | 2.95 | 2.2E-14 | 1.97 | 7.3E-04 |
| PI(40:5)/PC(O-34:1) | 2.56 | 1.8E-37 | 2.38 | 3.5E-27 | 3.26 | 1.7E-17 | 2.99 | 3.9E-13 | 2.13 | 3.2E-04 |
| PC(38:3)/LPC(20:0) [sn2] | 2.48 | 2.1E-37 | 2.57 | 1.2E-31 | 3.84 | 6.6E-23 | 4.12 | 1.2E-19 | 2.23 | 8.8E-05 |
| Cer(d18:1/20:0)/PC(P-36:1) | 2.52 | 2.4E-37 | 2.76 | 2.5E-33 | 3.69 | 1.8E-20 | 4.05 | 2.5E-17 | 2.80 | 2.2E-06 |
| PC(38:3)/LPC(24:0) [sn2] | 2.48 | 2.5E-37 | 2.74 | 2.7E-34 | 3.83 | 1.8E-22 | 4.49 | 3.1E-20 | 2.25 | 7.2E-05 |
| DAG(14:0/18:1)/PC(35:2) | 2.54 | 2.5E-37 | 2.69 | 2.3E-32 | 3.46 | 1.0E-17 | 3.55 | 1.1E-14 | 2.37 | 5.1E-05 |
| Cer(d18:1/18:0)/LacCer(d18:1/24:1) | 2.51 | 2.6E-37 | 2.61 | 1.4E-31 | 3.05 | 9.3E-19 | 3.15 | 1.3E-15 | 2.06 | 2.5E-04 |
| DAG(14:0/18:1)/PC(33:2) | 2.50 | 2.6E-37 | 2.63 | 7.4E-32 | 2.98 | 1.8E-16 | 3.10 | 7.6E-14 | 2.03 | 5.5E-04 |
| Cer(d16:1/18:0)/LPC(O-22:1) | 2.59 | 2.6E-37 | 2.80 | 1.4E-32 | 3.83 | 1.5E-20 | 4.05 | 2.1E-17 | 2.59 | 2.1E-05 |
| PG(36:1)/LPC(P-16:0) | 2.44 | 2.7E-37 | 2.51 | 3.3E-31 | 3.18 | 3.0E-20 | 3.08 | 4.1E-16 | 2.06 | 1.3E-04 |
| PG(36:1)/PC(O-34:2) | 2.50 | 2.7E-37 | 2.65 | 7.9E-32 | 3.30 | 3.6E-20 | 3.47 | 1.1E-15 | 2.22 | 7.9E-05 |
| SM(38:0)/PC(P-34:1) | 2.53 | 2.7E-37 | 2.69 | 1.8E-32 | 3.69 | 9.7E-20 | 4.07 | 2.5E-17 | 2.87 | 2.0E-06 |
| DAG(16:0/16:1)/PC(P-40:4) | 2.49 | 2.7E-37 | 2.48 | 5.1E-30 | 3.38 | 5.1E-19 | 3.56 | 1.3E-16 | 2.46 | 1.2E-05 |
| DAG(18:0/18:2)/LacCer(d18:1/16:0) | 2.45 | 2.8E-37 | 2.62 | 2.6E-33 | 2.73 | 3.1E-16 | 2.84 | 4.3E-14 | 2.23 | 3.9E-05 |
| DAG(18:0/18:2)/LPC(20:2) [sn1] | 2.44 | 2.9E-37 | 2.70 | 1.1E-34 | 3.01 | 2.1E-18 | 3.13 | 7.2E-16 | 2.41 | 4.2E-06 |
| PI(40:5)/LPC(20:0) [sn2] | 2.56 | 3.1E-37 | 2.37 | 1.1E-26 | 3.84 | 1.2E-20 | 3.61 | 2.7E-16 | 2.38 | 1.8E-05 |
| DAG(14:0/18:1)/SM(d17:1/14:0) | 2.49 | 3.1E-37 | 2.57 | 4.2E-31 | 2.99 | 1.5E-16 | 2.98 | 1.6E-13 | 1.98 | 8.2E-04 |
| SM(36:1)/PC(P-34:1) | 2.48 | 3.4E-37 | 2.77 | 1.9E-34 | 3.49 | 5.3E-20 | 3.99 | 1.9E-18 | 2.81 | 9.2E-07 |
| DAG(18:0/18:2)/LPC(24:0) [sn1] | 2.44 | 3.5E-37 | 2.69 | 2.2E-34 | 3.01 | 1.9E-18 | 3.30 | 1.8E-16 | 2.54 | 2.0E-06 |
| DAG(14:0/18:1)/LPC(15:0) [sn2] | 2.45 | 3.6E-37 | 2.49 | 9.1E-31 | 3.00 | 7.3E-18 | 2.96 | 1.4E-14 | 1.98 | 4.2E-04 |
| DAG(14:0/18:1)/LPC(20:0) [sn2] | 2.51 | 3.8E-37 | 2.59 | 3.7E-31 | 3.29 | 1.2E-18 | 3.39 | 1.0E-15 | 2.27 | 1.2E-04 |
| PI(32:1)/SM(37:1) | 2.40 | 4.0E-37 | 2.21 | 2.0E-26 | 3.10 | 1.1E-18 | 2.89 | 1.5E-14 | 1.89 | 1.2E-03 |
| PI(32:1)/PC(35:3) | 2.41 | 4.1E-37 | 2.26 | 4.3E-27 | 3.43 | 4.0E-20 | 3.24 | 5.2E-16 | 2.11 | 1.8E-04 |
| Cer(d18:1/20:0)/PC(P-36:2) | 2.52 | 4.1E-37 | 2.76 | 2.4E-33 | 3.86 | 3.5E-21 | 4.06 | 2.0E-17 | 2.71 | 2.3E-06 |
| Cer(d16:1/18:0)/PC(35:2) | 2.80 | 4.1E-37 | 3.19 | 1.1E-33 | 4.76 | 2.8E-20 | 5.19 | 2.6E-16 | 3.33 | 7.7E-07 |
| DAG(14:0/18:1)/LPC(20:0) [sn1] | 2.51 | 4.1E-37 | 2.59 | 3.5E-31 | 3.33 | 9.3E-19 | 3.45 | 7.3E-16 | 2.35 | 6.9E-05 |
| DAG(14:0/18:1)/PC(O-36:2) | 2.49 | 4.3E-37 | 2.62 | 8.9E-32 | 3.33 | 5.8E-18 | 3.36 | 6.9E-15 | 2.21 | 1.9E-04 |
| DAG(16:0/20:4)/LPC(15:0) [sn1] | 2.42 | 4.4E-37 | 2.42 | 2.5E-30 | 3.01 | 8.0E-19 | 2.97 | 9.0E-16 | 2.04 | 2.5E-04 |
| PC(38:3)/LPC(22:0) [sn2] | 2.49 | 4.4E-37 | 2.63 | 2.1E-32 | 3.82 | 8.5E-23 | 4.14 | 8.2E-20 | 2.29 | 5.4E-05 |
| DAG(16:0/20:4)/PC(P-40:4) | 2.44 | 4.5E-37 | 2.48 | 3.7E-31 | 3.00 | 3.5E-18 | 3.12 | 8.9E-16 | 2.10 | 1.8E-04 |
| DAG(16:0/16:1)/PC(33:3) | 2.54 | 4.6E-37 | 2.57 | 1.0E-29 | 3.37 | 7.3E-19 | 3.86 | 2.5E-16 | 2.33 | 6.5E-05 |
| PC(40:5)/LPC(24:0) [sn2] | 2.51 | 4.6E-37 | 2.70 | 2.7E-33 | 3.19 | 2.6E-18 | 3.31 | 8.6E-16 | 1.99 | 4.3E-04 |
| PI(32:1)/PC(O-40:6) | 2.36 | 4.8E-37 | 2.26 | 5.9E-28 | 2.97 | 1.2E-18 | 2.94 | 3.0E-15 | 2.07 | 1.5E-04 |
| Cer(d16:1/18:0)/SM(37:2) | 2.61 | 5.1E-37 | 2.99 | 1.7E-34 | 4.03 | 8.3E-21 | 4.19 | 4.3E-17 | 2.40 | 9.5E-05 |
| DAG(16:0/20:4)/LPC(O-22:0) | 2.39 | 5.3E-37 | 2.43 | 4.3E-31 | 2.89 | 2.3E-18 | 2.99 | 5.7E-16 | 2.06 | 1.9E-04 |
| SM(d18:0/22:0)/LacCer(d18:1/16:0) | 2.52 | 5.4E-37 | 2.65 | 8.5E-32 | 3.40 | 5.2E-19 | 3.90 | 2.6E-17 | 1.90 | 1.5E-03 |
| SM(36:2)/PC(P-34:1) | 2.49 | 5.4E-37 | 2.82 | 4.7E-35 | 4.10 | 8.6E-22 | 4.54 | 5.1E-19 | 2.76 | 1.6E-06 |
| DAG(16:0/20:4)/PC(P-32:0) | 2.43 | 6.1E-37 | 2.51 | 2.2E-31 | 2.85 | 4.2E-17 | 2.95 | 9.9E-15 | 1.94 | 7.9E-04 |
| DAG(18:1/18:1)/LPC(O-22:1) | 2.40 | 6.2E-37 | 2.55 | 1.2E-32 | 2.89 | 9.4E-18 | 3.18 | 3.7E-16 | 2.06 | 1.3E-04 |
| DAG(14:0/18:1)/PC(37:6) | 2.52 | 6.3E-37 | 2.62 | 2.9E-31 | 2.84 | 3.7E-15 | 2.87 | 1.3E-12 | 1.87 | 2.4E-03 |
| DAG(16:0/18:1)/LPC(P-16:0) | 2.36 | 6.3E-37 | 2.41 | 2.8E-31 | 2.92 | 1.8E-19 | 2.94 | 1.6E-16 | 2.13 | 2.5E-05 |
| PI(32:1)/PC(O-36:2) | 2.41 | 6.6E-37 | 2.24 | 7.0E-27 | 3.47 | 3.5E-20 | 3.20 | 1.0E-15 | 2.16 | 1.0E-04 |
| PI(40:5)/LPC(20:1) [sn2] | 2.60 | 6.7E-37 | 2.45 | 5.3E-27 | 3.61 | 2.3E-18 | 3.42 | 3.3E-14 | 2.03 | 8.5E-04 |
| DAG(18:1/20:4)/LPC(19:0) [sn2] | 2.43 | 6.9E-37 | 2.57 | 1.3E-32 | 3.02 | 3.0E-19 | 3.19 | 8.5E-17 | 1.99 | 3.0E-04 |
| DAG(16:0/16:1)/LPC(O-24:0) | 2.43 | 7.0E-37 | 2.42 | 1.4E-29 | 3.11 | 1.8E-18 | 3.22 | 4.4E-16 | 2.35 | 2.2E-05 |
| DAG(14:0/18:1)/LPC(17:0) [sn2] | 2.43 | 7.0E-37 | 2.47 | 2.0E-30 | 3.08 | 1.6E-18 | 3.03 | 4.1E-15 | 2.17 | 9.7E-05 |
| DAG(16:0/16:1)/LPE(P-20:0) | 2.42 | 7.2E-37 | 2.38 | 4.0E-29 | 3.23 | 1.9E-19 | 3.20 | 2.1E-16 | 2.29 | 2.0E-05 |
| PI(32:1)/PC(31:0) | 2.38 | 7.3E-37 | 2.23 | 1.1E-26 | 3.09 | 8.2E-19 | 3.03 | 6.0E-15 | 2.12 | 1.4E-04 |
| DAG(16:0/20:4)/SM(41:2) | 2.39 | 7.6E-37 | 2.41 | 1.6E-30 | 2.66 | 1.2E-16 | 2.66 | 4.4E-14 | 1.85 | 1.3E-03 |
| LPC(16:0) [sn2]/LPC(19:0) [sn1] | 2.51 | 7.6E-37 | 2.42 | 5.2E-28 | 3.28 | 7.7E-19 | 3.55 | 9.6E-16 | 2.34 | 2.4E-05 |
| SM (36:0)/SM (34:1) | 2.36 | 8.8E-37 | 2.46 | 1.6E-31 | 3.38 | 2.2E-22 | 3.54 | 2.0E-19 | 2.58 | 3.8E-07 |
| SM(36:0)/PC(O-40:6) | 2.43 | 9.0E-37 | 2.60 | 3.9E-32 | 3.19 | 8.3E-19 | 3.66 | 6.9E-17 | 2.53 | 3.5E-07 |
| DAG(18:0/18:2)/LPC(O-22:0) | 2.40 | 9.1E-37 | 2.56 | 9.7E-33 | 2.93 | 7.4E-18 | 3.15 | 8.6E-16 | 2.41 | 4.0E-06 |
| DAG(16:0/16:1)/LPC(O-18:0) | 2.40 | 9.3E-37 | 2.35 | 7.3E-29 | 3.19 | 3.5E-19 | 3.22 | 3.0E-16 | 2.40 | 9.4E-06 |
| SM(36:0)/PC(O-36:2) | 2.35 | 9.6E-37 | 2.43 | 2.1E-31 | 3.34 | 4.1E-22 | 3.38 | 7.7E-19 | 2.67 | 7.2E-08 |
| PC(36:3)/SM(37:2) | 2.53 | 1.0E-36 | 2.65 | 5.2E-31 | 3.85 | 1.2E-20 | 3.99 | 4.7E-17 | 1.93 | 2.0E-03 |
| PG(36:1)/PC(O-38:0) | 2.52 | 1.0E-36 | 2.72 | 6.7E-32 | 3.28 | 9.2E-19 | 3.50 | 1.7E-15 | 2.29 | 5.3E-05 |
| SM(36:0)/PC(P-32:0) | 2.36 | 1.0E-36 | 2.47 | 1.1E-31 | 3.23 | 7.4E-22 | 3.47 | 1.7E-19 | 2.84 | 3.8E-08 |
| DAG(18:0/18:2)/LPC(15:0) [sn2] | 2.42 | 1.0E-36 | 2.50 | 3.1E-31 | 2.97 | 7.8E-18 | 2.95 | 1.1E-14 | 2.20 | 2.6E-05 |
| DAG(18:1/18:1)/LPC(MHDA) [sn1] | 2.39 | 1.0E-36 | 2.53 | 1.9E-32 | 3.07 | 3.2E-19 | 3.29 | 7.7E-17 | 2.31 | 4.6E-06 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

|  | FL | | NAFLD | | FL (severe) | | NAFLD (severe) | | DM2 | |
|---|---|---|---|---|---|---|---|---|---|---|
| Lipid ratio | OR | p-value | OR | p-value | OR | p-value | OR | p-value | OR | p-value |
| DAG(16:1/18:1)/PC(35:3) | 2.53 | 1.0E−36 | 2.64 | 4.4E−31 | 3.24 | 2.4E−17 | 3.46 | 5.8E−15 | 2.27 | 1.5E−04 |
| DAG(16:0/18:1)/LPC(O-24:0) | 2.38 | 1.1E−36 | 2.47 | 1.2E−31 | 2.96 | 1.0E−18 | 3.11 | 1.7E−16 | 2.29 | 1.3E−05 |
| SM(36:1)/PC(P-36:2) | 2.49 | 1.1E−36 | 2.67 | 1.2E−32 | 4.22 | 3.4E−22 | 4.35 | 7.8E−19 | 2.94 | 7.9E−07 |
| DAG(18:0/18:2)/LPC(O-24:1) | 2.41 | 1.1E−36 | 2.56 | 2.2E−32 | 2.89 | 1.5E−17 | 3.04 | 2.8E−15 | 2.26 | 2.4E−05 |
| PI(32:1)/PC(34:3) | 2.42 | 1.2E−36 | 2.32 | 5.9E−28 | 3.62 | 3.1E−20 | 3.46 | 1.6E−16 | 2.11 | 2.7E−04 |
| PC(32:1)/PC(O-32:1) | 2.39 | 1.2E−36 | 2.26 | 4.1E−27 | 2.93 | 4.0E−17 | 2.85 | 8.9E−14 | 1.76 | 4.4E−03 |
| DAG(16:0/20:4)/PC(O-38:2) | 2.38 | 1.2E−36 | 2.39 | 3.9E−30 | 2.68 | 8.0E−17 | 2.69 | 3.4E−14 | 1.95 | 4.2E−04 |
| Cer(d18:1/18:0)/LPC(O-24:1) | 2.48 | 1.3E−36 | 2.60 | 2.3E−31 | 3.41 | 2.3E−20 | 3.49 | 3.5E−17 | 2.28 | 2.4E−05 |
| DAG(16:0/18:2)/PC(P-36:2) | 2.44 | 1.3E−36 | 2.64 | 6.0E−33 | 3.33 | 7.1E−19 | 3.56 | 2.1E−16 | 2.51 | 9.7E−06 |
| Cer(d18:1/18:0)/PC(35:3) | 2.56 | 1.3E−36 | 2.82 | 7.7E−33 | 3.50 | 1.8E−19 | 3.62 | 2.3E−16 | 2.38 | 2.2E−05 |
| PC(32:0)/PC(P-36:1) | 2.44 | 1.3E−36 | 2.39 | 3.0E−28 | 3.59 | 1.6E−20 | 3.56 | 3.3E−16 | 2.33 | 1.9E−05 |
| DAG(16:0/16:1)/PC(O-34:2) | 2.47 | 1.4E−36 | 2.49 | 1.6E−29 | 3.44 | 4.7E−19 | 3.59 | 6.9E−16 | 2.39 | 3.0E−05 |
| Cer(d18:1/24:1)/LPC(O-22:1) | 2.44 | 1.4E−36 | 2.47 | 1.1E−29 | 3.21 | 3.8E−19 | 3.53 | 1.7E−16 | 2.26 | 1.8E−05 |
| DAG(18:1/20:4)/LPC(20:1) [sn2] | 2.42 | 1.5E−36 | 2.61 | 4.6E−33 | 2.94 | 3.2E−17 | 3.16 | 2.5E−15 | 1.83 | 3.2E−03 |
| PC(36:3)/PC(35:2) | 2.48 | 1.5E−36 | 2.49 | 1.1E−29 | 3.98 | 1.6E−20 | 4.05 | 5.8E−17 | 2.49 | 1.9E−05 |
| PI(32:1)/SM(d17:1/14:0) | 2.35 | 1.5E−36 | 2.16 | 8.3E−26 | 3.06 | 4.9E−19 | 2.87 | 1.3E−14 | 1.94 | 4.8E−04 |
| PI(40:5)/LPC(22:0) [sn2] | 2.56 | 1.5E−36 | 2.43 | 6.0E−27 | 3.86 | 2.3E−20 | 3.70 | 2.9E−16 | 2.49 | 1.1E−05 |
| PI(32:1)/PC(O-34:1) | 2.40 | 1.6E−36 | 2.22 | 2.8E−26 | 3.33 | 5.3E−19 | 3.11 | 4.5E−15 | 2.08 | 2.9E−04 |
| DAG(18:0/18:2)/LPC(O-18:0) | 2.39 | 1.6E−36 | 2.49 | 1.9E−31 | 3.04 | 2.9E−18 | 3.11 | 1.4E−15 | 2.51 | 1.9E−06 |
| PC(38:3)/LPC(O-20:1) | 2.44 | 1.6E−36 | 2.49 | 2.1E−30 | 3.58 | 6.9E−21 | 3.69 | 1.2E−17 | 2.09 | 3.2E−04 |
| DAG(16:0/18:2)/LPC(19:0) [sn1] | 2.40 | 1.7E−36 | 2.48 | 2.3E−31 | 3.14 | 3.9E−19 | 3.33 | 1.1E−16 | 2.64 | 8.4E−07 |
| DAG(16:0/18:2)/LPC(19:0) [sn2] | 2.39 | 1.8E−36 | 2.52 | 3.1E−32 | 3.11 | 8.0E−20 | 3.33 | 1.5E−17 | 2.40 | 2.6E−06 |
| DAG(18:1/18:1)/LPC(MHDA) [sn2] | 2.36 | 1.8E−36 | 2.47 | 1.1E−31 | 2.95 | 8.0E−19 | 3.08 | 3.5E−16 | 2.24 | 8.2E−06 |
| PC(38:3)/LPC(17:0) [sn1] | 2.40 | 1.9E−36 | 2.39 | 2.7E−29 | 3.64 | 2.9E−22 | 3.66 | 2.4E−18 | 2.14 | 1.4E−04 |
| DAG(16:0/18:1)/LPC(18:1) [sn2] | 2.37 | 1.9E−36 | 2.53 | 9.4E−33 | 3.19 | 1.5E−20 | 3.34 | 1.2E−17 | 2.57 | 1.4E−06 |
| DAG(18:1/20:4)/LPC(20:1) [sn1] | 2.42 | 1.9E−36 | 2.61 | 7.4E−33 | 3.03 | 1.0E−17 | 3.23 | 1.1E−15 | 1.88 | 2.1E−03 |
| PC(38:3)/PC(O-32:0) | 2.48 | 2.1E−36 | 2.68 | 4.7E−32 | 3.40 | 1.6E−18 | 3.86 | 1.6E−16 | 1.99 | 1.2E−03 |
| DAG(16:1/18:1)/PC(P-34:1) | 2.46 | 2.3E−36 | 2.57 | 9.0E−31 | 3.05 | 8.2E−17 | 3.24 | 1.3E−14 | 2.18 | 2.1E−04 |
| Cer(d18:1/18:0)/LPC(O-22:0) | 2.45 | 2.3E−36 | 2.60 | 2.5E−31 | 3.33 | 2.6E−20 | 3.47 | 3.7E−17 | 2.43 | 1.4E−06 |
| DAG(16:1/18:1)/LPC(MHDA) [sn1] | 2.41 | 2.3E−36 | 2.43 | 1.3E−29 | 3.19 | 4.6E−19 | 3.30 | 5.5E−16 | 2.42 | 5.0E−06 |
| PC(38:3)/LPC(20:1) [sn1] | 2.50 | 2.4E−36 | 2.68 | 1.1E−31 | 3.94 | 3.7E−21 | 4.41 | 2.4E−18 | 1.99 | 1.3E−03 |
| DAG(18:0/18:2)/LPC(O-18:1) | 2.39 | 2.4E−36 | 2.47 | 3.9E−31 | 2.90 | 1.3E−17 | 2.91 | 1.1E−14 | 2.23 | 3.6E−05 |
| PI(32:1)/LPC(O-24:2) | 2.38 | 2.4E−36 | 2.21 | 2.5E−26 | 3.08 | 8.4E−19 | 2.92 | 3.6E−15 | 2.05 | 2.3E−04 |
| SM(38:0)/SM(37:1) | 2.52 | 2.5E−36 | 2.59 | 2.8E−30 | 3.59 | 7.2E−19 | 3.77 | 3.5E−16 | 2.41 | 4.7E−05 |
| PC(38:2)/PC(P-34:1) | 2.48 | 2.5E−36 | 2.59 | 1.5E−30 | 3.54 | 3.3E−19 | 3.60 | 1.1E−15 | 2.40 | 5.1E−05 |
| DAG(16:0/20:4)/LPE(P-20:0) | 2.36 | 2.6E−36 | 2.37 | 5.1E−30 | 2.98 | 3.3E−19 | 2.95 | 7.2E−16 | 2.00 | 3.1E−04 |
| PC(38:3)/LPC(MHDA) [sn2] | 2.38 | 2.6E−36 | 2.41 | 7.3E−30 | 3.41 | 1.3E−21 | 3.37 | 1.7E−17 | 2.23 | 8.8E−06 |
| DAG(16:0/16:1)/LPC(P-16:0) | 2.38 | 2.7E−36 | 2.35 | 8.4E−29 | 3.06 | 5.5E−19 | 3.09 | 4.4E−16 | 2.21 | 4.8E−05 |
| PC(40:5)/LPC(19:0) [sn2] | 2.41 | 2.7E−36 | 2.42 | 1.6E−29 | 2.68 | 1.7E−18 | 2.59 | 6.5E−15 | 1.77 | 4.7E−04 |
| DAG(16:0/20:4)/SM(34:1) | 2.38 | 2.8E−36 | 2.43 | 1.4E−30 | 2.74 | 6.7E−17 | 2.75 | 3.5E−14 | 1.76 | 4.0E−03 |
| DAG(16:1/18:1)/LPC(O-22:1) | 2.42 | 2.8E−36 | 2.44 | 1.2E−29 | 3.02 | 1.2E−17 | 3.14 | 2.5E−15 | 2.17 | 1.0E−04 |
| DAG(14:0/18:1)/LPC(22:0) [sn2] | 2.48 | 2.9E−36 | 2.61 | 3.8E−31 | 3.29 | 3.5E−18 | 3.42 | 1.5E−15 | 2.30 | 1.1E−04 |
| DAG(16:0/20:4)/LPC(O-18:0) | 2.36 | 3.0E−36 | 2.35 | 1.5E−29 | 2.98 | 1.8E−18 | 2.94 | 1.9E−15 | 2.13 | 1.2E−04 |
| DAG(16:0/18:2)/LPC(O-22:1) | 2.39 | 3.0E−36 | 2.51 | 8.9E−32 | 3.02 | 6.4E−18 | 3.30 | 3.6E−16 | 2.37 | 8.1E−06 |
| Cer(d18:1/18:0)/SM(41:2) | 2.43 | 3.2E−36 | 2.59 | 3.8E−31 | 2.71 | 2.2E−17 | 2.83 | 3.7E−14 | 2.09 | 4.1E−05 |
| DAG(16:1/18:1)/LPC(MHDA) [sn2] | 2.40 | 3.2E−36 | 2.39 | 4.9E−29 | 3.09 | 8.6E−19 | 3.13 | 1.8E−15 | 2.36 | 8.1E−06 |
| DAG(16:0/20:4)/LacCer(d18:1/24:1) | 2.40 | 3.3E−36 | 2.43 | 5.1E−30 | 2.75 | 9.8E−17 | 2.79 | 5.3E−14 | 1.80 | 2.9E−03 |
| PC(38:3)/PC(P-32:0) | 2.49 | 3.3E−36 | 2.71 | 4.8E−32 | 3.71 | 1.9E−19 | 4.29 | 4.5E−17 | 2.03 | 1.0E−03 |
| PC(38:3)/LPC(O-20:0) | 2.39 | 3.4E−36 | 2.44 | 4.1E−30 | 3.50 | 4.2E−21 | 3.69 | 4.7E−18 | 2.32 | 2.9E−05 |
| DAG(14:0/18:1)/LPC(15:0) [sn1] | 2.40 | 3.5E−36 | 2.46 | 4.3E−30 | 3.00 | 9.3E−18 | 3.01 | 1.2E−14 | 2.12 | 1.3E−04 |
| SM(36:2)/PC(P-36:2) | 2.48 | 3.6E−36 | 2.69 | 8.1E−33 | 4.71 | 1.9E−23 | 4.71 | 2.7E−19 | 2.87 | 1.4E−06 |
| PC(32:0)/PC(P-34:1) | 2.44 | 3.6E−36 | 2.41 | 2.3E−28 | 3.22 | 3.1E−19 | 3.22 | 2.6E−15 | 2.12 | 9.4E−05 |
| SM(36:0)/LacCer(d18:1/24:1) | 2.35 | 3.7E−36 | 2.38 | 8.2E−30 | 3.09 | 4.5E−21 | 3.24 | 2.5E−18 | 2.44 | 1.8E−06 |
| Cer(d18:1/18:0)/PC(O-40:6) | 2.46 | 3.7E−36 | 2.62 | 6.1E−32 | 2.98 | 8.9E−17 | 3.10 | 1.7E−14 | 2.30 | 4.1E−05 |
| DAG(14:0/18:1)/LPC(17:0) [sn1] | 2.42 | 3.7E−36 | 2.45 | 1.2E−29 | 3.07 | 5.4E−18 | 3.06 | 8.3E−15 | 2.14 | 1.6E−04 |
| DAG(16:0/20:4)/LPC(O-18:1) | 2.38 | 3.8E−36 | 2.36 | 2.2E−29 | 2.91 | 7.2E−18 | 2.87 | 8.9E−15 | 1.90 | 1.2E−03 |
| Cer(d16:1/18:0)/PC(O-36:2) | 2.56 | 3.8E−36 | 2.81 | 4.7E−32 | 3.80 | 1.1E−20 | 3.88 | 1.7E−16 | 2.55 | 1.4E−05 |
| DAG(16:0/18:1)/LPC(18:2) [sn1] | 2.35 | 3.8E−36 | 2.45 | 1.8E−31 | 3.18 | 1.6E−20 | 3.25 | 2.9E−17 | 2.41 | 4.9E−06 |
| DAG(16:0/16:1)/LPC(18:1) [sn2] | 2.42 | 3.9E−36 | 2.44 | 1.3E−29 | 3.38 | 8.8E−20 | 3.50 | 8.4E−17 | 2.63 | 5.3E−06 |
| DAG(14:0/18:1)/LPC(20:1) [sn2] | 2.47 | 4.0E−36 | 2.59 | 6.8E−31 | 3.15 | 5.0E−17 | 3.27 | 2.1E−14 | 2.03 | 9.1E−04 |
| SM(41:0)/PC(P-36:1) | 2.45 | 4.0E−36 | 2.54 | 7.6E−31 | 3.71 | 5.1E−21 | 4.15 | 2.9E−18 | 2.58 | 1.1E−05 |
| DAG(18:0/18:2)/SM(d17:1/14:0) | 2.41 | 4.1E−36 | 2.49 | 7.3E−31 | 2.79 | 4.0E−16 | 2.77 | 3.0E−13 | 2.17 | 8.0E−05 |
| Cer(d18:1/24:1)/SM(37:2) | 2.41 | 4.2E−36 | 2.59 | 8.1E−32 | 3.22 | 9.1E−20 | 3.29 | 9.8E−17 | 2.05 | 1.9E−04 |
| Cer(d18:1/18:0)/PC(P-32:0) | 2.43 | 4.4E−36 | 2.61 | 6.6E−32 | 3.06 | 1.4E−18 | 3.17 | 8.0E−16 | 2.27 | 2.5E−05 |
| DAG(16:0/18:2)/PC(O-40:6) | 2.45 | 4.5E−36 | 2.62 | 3.0E−32 | 2.92 | 2.4E−16 | 3.15 | 1.0E−14 | 2.47 | 1.0E−05 |
| PI(32:1)/Gb3(d18:1/16:0) | 2.36 | 4.6E−36 | 2.21 | 3.4E−26 | 3.17 | 1.7E−18 | 2.96 | 1.3E−14 | 1.87 | 1.7E−03 |
| PC(32:1)/SM(37:2) | 2.37 | 4.6E−36 | 2.31 | 2.1E−27 | 3.20 | 1.1E−19 | 3.17 | 1.6E−15 | 1.90 | 9.6E−04 |
| Cer(d18:1/18:0)/PC(37:2) | 2.51 | 4.6E−36 | 2.65 | 5.7E−31 | 3.25 | 3.2E−19 | 3.48 | 2.2E−16 | 2.44 | 5.9E−06 |
| DAG(18:1/20:4)/LPC(MHDA) [sn2] | 2.37 | 4.8E−36 | 2.46 | 5.0E−31 | 2.99 | 1.0E−18 | 3.02 | 1.4E−15 | 2.19 | 5.4E−05 |
| PI(40:5)/PC(37:2) | 2.46 | 4.9E−36 | 2.31 | 7.1E−26 | 3.08 | 1.7E−17 | 2.99 | 1.5E−13 | 2.26 | 6.5E−05 |
| DAG(16:0/16:1)/LPC(18:2) [sn2] | 2.42 | 5.3E−36 | 2.43 | 2.7E−29 | 3.37 | 1.1E−19 | 3.45 | 1.5E−16 | 2.39 | 2.6E−05 |
| PG(36:1)/LPC(18:2) [sn2] | 2.43 | 5.3E−36 | 2.58 | 2.9E−31 | 3.58 | 1.2E−20 | 3.50 | 1.4E−16 | 2.25 | 7.4E−05 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| LPC(16:0) [sn2]/LPC(20:0) [sn2] | 2.54 | 5.4E−36 | 2.45 | 1.3E−27 | 3.45 | 1.6E−18 | 3.51 | 7.4E−16 | 2.12 | 4.4E−04 |
| DAG(18:0/18:2)/LPC(18:2) [sn2] | 2.38 | 5.6E−36 | 2.60 | 4.4E−33 | 3.11 | 4.2E−19 | 3.24 | 2.9E−16 | 2.47 | 6.6E−06 |
| DAG(18:1/20:4)/SM(37:2) | 2.39 | 5.6E−36 | 2.64 | 2.0E−33 | 2.94 | 3.1E−17 | 3.09 | 6.0E−15 | 1.85 | 2.5E−03 |
| DAG(18:1/20:4)/PC(39:4) | 2.38 | 6.7E−36 | 2.53 | 5.2E−32 | 2.72 | 4.0E−16 | 2.92 | 9.8E−15 | 1.87 | 1.7E−03 |
| DAG(14:0/18:1)/LPC(20:1) [sn1] | 2.45 | 6.8E−36 | 2.57 | 9.4E−31 | 3.19 | 2.0E−17 | 3.30 | 9.0E−15 | 2.06 | 6.9E−04 |
| DAG(18:1/18:1)/PC(O-40:6) | 2.44 | 7.0E−36 | 2.63 | 2.5E−32 | 2.79 | 1.6E−15 | 3.02 | 3.7E−14 | 2.10 | 2.7E−04 |
| DAG(18:1/20:4)/LPC(P-18:1) | 2.36 | 7.2E−36 | 2.44 | 7.2E−31 | 2.76 | 7.7E−17 | 2.76 | 6.5E−14 | 1.73 | 5.8E−03 |
| PG(36:1)/LPC(18:2) [sn1] | 2.40 | 7.5E−36 | 2.52 | 6.6E−31 | 3.47 | 6.4E−21 | 3.39 | 8.4E−17 | 2.33 | 2.5E−05 |
| DAG(18:0/18:2)/LPC(15:0) [sn1] | 2.38 | 7.6E−36 | 2.46 | 1.1E−30 | 2.95 | 6.5E−18 | 2.98 | 6.1E−15 | 2.36 | 4.8E−06 |
| PI(32:1)/PC(P-40:2) | 2.39 | 7.8E−36 | 2.23 | 5.3E−26 | 3.17 | 1.9E−18 | 2.96 | 1.6E−14 | 2.01 | 1.1E−04 |
| PC(38:3)/PC(37:1) | 2.52 | 7.8E−36 | 2.68 | 1.1E−30 | 3.85 | 2.5E−19 | 4.30 | 1.1E−16 | 2.09 | 7.7E−04 |
| Cer(d18:1/22:0)/LPC(O-20:1) | 2.44 | 8.1E−36 | 2.47 | 7.5E−29 | 3.35 | 9.3E−19 | 3.49 | 1.3E−15 | 1.96 | 6.9E−04 |
| DAG(16:0/20:4)/LPC(P-16:0) | 2.32 | 8.5E−36 | 2.33 | 7.8E−30 | 2.78 | 2.2E−18 | 2.79 | 1.8E−15 | 1.90 | 7.5E−04 |
| Cer(d18:1/22:0)/LPC(O-20:0) | 2.41 | 8.6E−36 | 2.42 | 1.5E−28 | 3.30 | 4.9E−19 | 3.58 | 5.6E−16 | 2.20 | 3.4E−05 |
| Cer(d18:1/18:0)/PC(P-40:4) | 2.45 | 8.9E−36 | 2.60 | 6.3E−31 | 3.49 | 2.0E−20 | 3.62 | 2.2E−17 | 2.67 | 1.2E−06 |
| PI(40:5)/LacCer(d18:1/16:0) | 2.49 | 8.9E−36 | 2.32 | 9.1E−26 | 2.93 | 2.0E−15 | 2.67 | 2.5E−11 | 2.02 | 7.6E−04 |
| DAG(16:0/18:1)/PC(34:3) | 2.43 | 9.8E−36 | 2.69 | 1.7E−33 | 3.17 | 1.4E−18 | 3.40 | 1.6E−16 | 2.29 | 6.2E−05 |
| DAG(18:1/20:4)/LPC(20:0) [sn2] | 2.39 | 1.0E−35 | 2.52 | 1.6E−31 | 3.01 | 3.9E−18 | 3.17 | 5.7E−16 | 2.07 | 3.8E−04 |
| PI(32:1)/Gb3(d18:1/22:0) | 2.36 | 1.0E−35 | 2.24 | 1.1E−26 | 2.90 | 4.9E−17 | 2.68 | 5.0E−13 | 1.89 | 1.4E−03 |
| PI(40:5)/LPC(O-20:1) | 2.45 | 1.1E−35 | 2.28 | 1.3E−25 | 3.38 | 1.3E−18 | 3.13 | 2.9E−14 | 2.16 | 1.3E−04 |
| DAG(14:0/18:1)/LPC(O-20:1) | 2.43 | 1.1E−35 | 2.50 | 5.5E−30 | 3.13 | 3.3E−17 | 3.16 | 1.8E−14 | 2.12 | 2.7E−04 |
| DAG(18:1/18:1)/LPC(19:0) [sn2] | 2.34 | 1.1E−35 | 2.49 | 1.3E−31 | 2.90 | 6.9E−19 | 3.10 | 1.2E−16 | 2.05 | 9.4E−05 |
| DAG(18:0/18:2)/LPE(P-20:0) | 2.35 | 1.2E−35 | 2.47 | 4.3E−31 | 2.94 | 1.7E−18 | 2.97 | 2.8E−15 | 2.30 | 6.9E−06 |
| DAG(16:0/20:4)/PC(37:1) | 2.47 | 1.2E−35 | 2.50 | 1.5E−29 | 2.89 | 2.9E−16 | 2.95 | 6.1E−14 | 1.99 | 8.6E−04 |
| DAG(18:1/18:1)/PC(35:3) | 2.42 | 1.2E−35 | 2.70 | 3.3E−33 | 2.94 | 8.0E−17 | 3.25 | 3.5E−15 | 2.08 | 3.9E−04 |
| DAG(16:0/20:4)/PC(O-32:0) | 2.37 | 1.3E−35 | 2.43 | 2.7E−30 | 2.69 | 6.0E−16 | 2.79 | 6.2E−14 | 1.90 | 1.2E−03 |
| SM(d18:0/22:0)/PC(O-36:3) | 2.43 | 1.4E−35 | 2.49 | 6.6E−30 | 3.49 | 5.6E−20 | 3.57 | 9.3E−17 | 1.97 | 8.0E−04 |
| PC(36:3)/PC(O-36:2) | 2.44 | 1.4E−35 | 2.41 | 2.0E−28 | 3.50 | 2.1E−19 | 3.44 | 1.4E−15 | 2.03 | 2.1E−04 |
| DAG(16:1/16:1)/PC(O-40:6) | 2.37 | 1.5E−35 | 2.30 | 3.9E−27 | 2.95 | 5.6E−18 | 2.96 | 9.1E−15 | 2.08 | 1.2E−04 |
| PI(40:5)/LPC(P-18:1) | 2.43 | 1.5E−35 | 2.20 | 2.0E−24 | 3.09 | 2.2E−17 | 2.69 | 4.2E−12 | 1.82 | 2.7E−03 |
| DAG(14:0/18:1)/SM(37:2) | 2.45 | 1.5E−35 | 2.63 | 2.5E−31 | 3.26 | 4.1E−16 | 3.34 | 2.5E−14 | 2.06 | 8.5E−04 |
| PI(40:5)/LPC(P-18:0) | 2.38 | 1.5E−35 | 2.19 | 7.6E−25 | 3.35 | 6.6E−20 | 2.96 | 2.7E−14 | 2.27 | 2.9E−05 |
| PC(38:3)/LPC(20:1) [sn2] | 2.48 | 1.5E−35 | 2.66 | 5.6E−31 | 3.76 | 4.4E−20 | 4.21 | 1.5E−17 | 1.91 | 2.7E−03 |
| PC(32:1)/PC(35:3) | 2.34 | 1.6E−35 | 2.23 | 5.5E−26 | 3.17 | 2.1E−19 | 3.17 | 2.1E−15 | 1.93 | 5.4E−04 |
| DAG(16:0/20:4)/PC(O-34:2) | 2.41 | 1.6E−35 | 2.47 | 8.6E−30 | 3.08 | 9.6E−18 | 3.06 | 1.9E−14 | 2.03 | 4.5E−04 |
| PI(32:1)/PC(37:6) | 2.32 | 1.6E−35 | 2.22 | 2.2E−26 | 2.79 | 3.1E−17 | 2.79 | 7.1E−14 | 1.83 | 1.8E−03 |
| DAG(18:1/20:4)/LPC(O-20:1) | 2.36 | 1.7E−35 | 2.48 | 3.3E−31 | 2.84 | 2.7E−17 | 2.96 | 4.4E−15 | 1.95 | 7.2E−04 |
| SM(41:0)/SM(33:0) | 2.38 | 1.7E−35 | 2.37 | 8.1E−29 | 2.94 | 1.2E−17 | 3.16 | 5.5E−16 | 1.80 | 3.0E−03 |
| DAG(14:0/18:1)/PC(17:0_22:6) | 2.46 | 1.7E−35 | 2.55 | 6.4E−30 | 2.77 | 1.2E−15 | 2.86 | 2.6E−12 | 1.91 | 2.3E−03 |
| DAG(18:1/18:1)/LPC(19:0) [sn1] | 2.34 | 1.8E−35 | 2.46 | 8.2E−31 | 2.91 | 3.4E−18 | 3.12 | 6.4E−16 | 2.21 | 3.1E−05 |
| PI(40:5)/LPC(17:0) [sn2] | 2.40 | 1.8E−35 | 2.18 | 4.4E−24 | 3.31 | 3.7E−20 | 2.98 | 1.2E−14 | 2.25 | 2.7E−05 |
| PI(40:5)/LPC(MHDA) [sn2] | 2.35 | 2.0E−35 | 2.16 | 1.7E−24 | 3.01 | 2.5E−19 | 2.70 | 1.0E−13 | 2.31 | 2.6E−06 |
| DAG(16:1/18:1)/PC(35:2) | 2.48 | 2.1E−35 | 2.59 | 3.9E−30 | 3.46 | 4.9E−18 | 3.77 | 2.2E−15 | 2.55 | 1.4E−05 |
| Cer(d18:1/24:1)/PC(P-34:1) | 2.36 | 2.2E−35 | 2.44 | 7.1E−30 | 2.87 | 2.6E−17 | 2.98 | 3.8E−15 | 2.13 | 1.3E−04 |
| DAG(16:0/18:2)/LPC(20:1) [sn2] | 2.37 | 2.2E−35 | 2.55 | 3.8E−32 | 3.00 | 1.0E−17 | 3.29 | 6.2E−16 | 2.30 | 4.1E−05 |
| PC(38:3)/LPC(O-22:0) | 2.35 | 2.3E−35 | 2.45 | 2.8E−30 | 3.40 | 9.3E−21 | 3.70 | 4.9E−18 | 2.18 | 1.0E−04 |
| PI(32:1)/PC(35:2) | 2.33 | 2.3E−35 | 2.20 | 2.8E−26 | 3.46 | 1.6E−20 | 3.28 | 2.9E−15 | 2.31 | 2.3E−05 |
| DAG(16:0/20:4)/LPC(18:2) [sn2] | 2.36 | 2.4E−35 | 2.45 | 1.3E−30 | 3.08 | 7.3E−19 | 3.13 | 7.4E−16 | 2.05 | 3.8E−04 |
| DAG(14:0/18:1)/PC(33:3) | 2.42 | 2.5E−35 | 2.54 | 1.0E−29 | 2.99 | 1.2E−16 | 3.18 | 6.2E−14 | 2.03 | 8.3E−04 |
| PC(36:4)/PC(P-36:2) | 2.47 | 2.5E−35 | 2.48 | 3.3E−28 | 4.10 | 8.3E−20 | 3.93 | 1.1E−15 | 2.63 | 1.9E−05 |
| DAG(18:1/18:1)/LPC(20:1) [sn2] | 2.36 | 2.6E−35 | 2.58 | 2.6E−32 | 2.87 | 4.3E−17 | 3.17 | 1.8E−15 | 1.93 | 1.0E−03 |
| DAG(16:0/20:4)/LPC(O-24:0) | 2.32 | 2.9E−35 | 2.37 | 9.3E−30 | 2.69 | 3.9E−17 | 2.80 | 6.2E−15 | 1.97 | 4.4E−04 |
| PC(32:1)/SM(37:1) | 2.30 | 3.0E−35 | 2.16 | 3.8E−25 | 2.74 | 3.0E−17 | 2.66 | 2.4E−13 | 1.67 | 6.2E−03 |
| PI(32:1)/PC(33:2) | 2.31 | 3.0E−35 | 2.18 | 1.1E−25 | 3.02 | 1.4E−18 | 2.99 | 7.5E−15 | 1.97 | 4.0E−04 |
| DAG(14:0/18:1)/LPE(16:0) [sn1] | 2.51 | 3.2E−35 | 2.75 | 1.1E−31 | 3.12 | 5.9E−16 | 3.54 | 2.3E−14 | 2.24 | 2.5E−04 |
| PI(40:5)/LPC(O-20:0) | 2.42 | 3.3E−35 | 2.25 | 5.7E−25 | 3.30 | 1.1E−18 | 3.16 | 1.4E−14 | 2.43 | 6.9E−06 |
| PC(38:1)/PC(P-36:1) | 2.42 | 3.3E−35 | 2.53 | 1.4E−29 | 3.66 | 9.1E−20 | 3.79 | 3.8E−16 | 2.87 | 7.9E−07 |
| Cer(d16:1/18:0)/Gb3(d18:1/16:0) | 2.60 | 3.4E−35 | 2.92 | 2.6E−32 | 3.65 | 3.6E−18 | 3.82 | 5.4E−15 | 2.11 | 1.1E−03 |
| DAG(16:1/18:1)/LPC(19:0) [sn2] | 2.39 | 3.5E−35 | 2.41 | 7.8E−29 | 3.06 | 9.3E−19 | 3.16 | 5.5E−16 | 2.16 | 6.5E−05 |
| DAG(18:0/18:2)/PC(O-34:2) | 2.36 | 3.5E−35 | 2.53 | 1.9E−31 | 3.02 | 1.5E−17 | 3.03 | 1.9E−14 | 2.40 | 1.6E−05 |
| CE(16:1)/PC(O-32:1) | 2.37 | 3.5E−35 | 2.27 | 1.5E−26 | 2.85 | 1.6E−16 | 2.86 | 9.2E−14 | 1.68 | 9.6E−03 |
| PC(36:3)/PC(33:2) | 2.46 | 3.5E−35 | 2.47 | 4.2E−28 | 3.26 | 8.2E−18 | 3.58 | 2.5E−15 | 1.86 | 3.0E−03 |
| PI(40:5)/Gb3(d18:1/22:0) | 2.38 | 3.6E−35 | 2.32 | 5.8E−27 | 2.46 | 7.2E−14 | 2.23 | 9.9E−10 | 1.75 | 4.1E−03 |
| PI(40:5)/LPC(17:0) [sn1] | 2.38 | 3.7E−35 | 2.15 | 2.2E−23 | 3.39 | 9.6E−20 | 3.10 | 2.1E−14 | 2.21 | 5.6E−05 |
| PI(40:5)/LPC(O-22:0) | 2.44 | 3.7E−35 | 2.28 | 3.6E−25 | 3.27 | 1.8E−18 | 3.19 | 1.3E−14 | 2.35 | 2.0E−05 |
| DAG(18:0/18:2)/LacCer(d18:1/24:1) | 2.37 | 3.8E−35 | 2.50 | 8.5E−31 | 2.71 | 9.2E−16 | 2.81 | 2.7E−13 | 2.09 | 1.9E−04 |
| SM(41:0)/PC(P-36:2) | 2.42 | 3.8E−35 | 2.50 | 6.8E−30 | 3.76 | 5.9E−21 | 3.98 | 1.1E−17 | 2.52 | 1.7E−05 |
| DAG(16:0/18:2)/LPC(20:0) [sn2] | 2.34 | 3.9E−35 | 2.48 | 3.7E−31 | 3.05 | 4.5E−19 | 3.32 | 4.9E−17 | 2.53 | 3.0E−06 |
| DAG(16:0/18:2)/LPC(MHDA) [sn2] | 2.33 | 4.0E−35 | 2.42 | 2.7E−30 | 2.99 | 7.4E−19 | 3.08 | 4.3E−16 | 2.54 | 3.4E−07 |
| DAG(16:0/18:2)/LPC(MHDA) [sn1] | 2.35 | 4.1E−35 | 2.46 | 7.8E−31 | 3.15 | 3.6E−19 | 3.33 | 1.1E−16 | 2.65 | 2.3E−07 |
| PC(36:4)/PC(P-36:1) | 2.43 | 4.1E−35 | 2.42 | 7.1E−28 | 3.65 | 7.0E−19 | 3.62 | 3.1E−15 | 2.63 | 2.1E−05 |
| DAG(14:0/18:1)/LPE(16:0) [sn2] | 2.49 | 4.2E−35 | 2.72 | 1.2E−31 | 3.10 | 5.8E−16 | 3.44 | 3.3E−14 | 2.25 | 2.2E−04 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| DAG(16:0/18:2)/PC(P-36:1) | 2.38 | 4.6E-35 | 2.57 | 1.3E-31 | 3.09 | 1.9E-17 | 3.39 | 1.5E-15 | 2.45 | 1.4E-05 |
| DAG(14:0/18:1)/LPC(20:2) [sn2] | 2.44 | 4.6E-35 | 2.64 | 2.4E-31 | 3.11 | 1.1E-16 | 3.24 | 3.7E-14 | 2.13 | 3.5E-04 |
| PC(32:1)/PC(34:3) | 2.31 | 4.7E-35 | 2.26 | 3.4E-27 | 3.14 | 2.5E-19 | 3.13 | 5.8E-16 | 1.85 | 1.2E-03 |
| DAG(18:1/20:4)/PC(17:0_22:6) | 2.39 | 4.7E-35 | 2.53 | 6.3E-31 | 2.52 | 1.3E-13 | 2.67 | 2.0E-12 | 1.68 | 9.8E-03 |
| Cer(d18:1/18:0)/PC(O-32:0) | 2.40 | 4.9E-35 | 2.57 | 7.2E-31 | 2.93 | 2.7E-17 | 3.09 | 5.2E-15 | 2.27 | 3.9E-05 |
| DAG(16:0/20:4)/LPC(22:6) [sn1] | 2.37 | 4.9E-35 | 2.48 | 7.5E-31 | 2.80 | 2.8E-16 | 2.86 | 4.5E-14 | 1.80 | 3.1E-03 |
| DAG(14:0/18:1)/PC(31:0) | 2.43 | 4.9E-35 | 2.58 | 2.9E-30 | 2.86 | 4.7E-15 | 2.98 | 9.6E-13 | 2.11 | 4.7E-04 |
| Cer(d18:1/18:0)/LPC(O-18:0) | 2.36 | 5.0E-35 | 2.42 | 6.8E-29 | 3.30 | 7.8E-20 | 3.22 | 6.7E-16 | 2.41 | 6.3E-07 |
| Cer(d18:1/18:0)/PC(O-38:2) | 2.38 | 5.2E-35 | 2.50 | 1.3E-29 | 2.79 | 1.7E-17 | 2.92 | 2.8E-14 | 2.32 | 6.9E-06 |
| SM(36:0)/PC(35:2) | 2.40 | 5.4E-35 | 2.49 | 4.9E-30 | 3.61 | 2.4E-20 | 3.83 | 3.7E-17 | 2.92 | 2.6E-08 |
| Cer(d16:1/18:0)/PC(O-34:1) | 2.61 | 5.8E-35 | 2.91 | 1.2E-31 | 3.94 | 2.1E-18 | 4.20 | 2.0E-15 | 2.55 | 7.2E-05 |
| DAG(18:1/20:4)/LPC(22:0) [sn2] | 2.36 | 5.9E-35 | 2.54 | 1.0E-31 | 2.97 | 8.7E-18 | 3.15 | 7.0E-16 | 2.09 | 3.4E-04 |
| PI(32:1)/LPE(16:0) [sn1] | 2.36 | 5.9E-35 | 2.22 | 2.3E-25 | 3.21 | 1.2E-18 | 3.14 | 2.6E-15 | 2.22 | 1.5E-04 |
| DAG(18:1/20:4)/LPC(17:0) [sn1] | 2.33 | 6.1E-35 | 2.40 | 8.2E-30 | 2.91 | 8.9E-18 | 2.96 | 4.5E-15 | 1.98 | 5.9E-04 |
| DAG(18:1/18:1)/LPC(20:1) [sn1] | 2.34 | 6.2E-35 | 2.55 | 7.1E-32 | 2.94 | 1.4E-17 | 3.23 | 7.6E-16 | 1.97 | 7.1E-04 |
| DAG(18:1/18:1)/PC(35:2) | 2.42 | 6.3E-35 | 2.65 | 5.3E-32 | 3.12 | 4.0E-17 | 3.48 | 3.9E-15 | 2.38 | 2.6E-05 |
| DAG(16:1/18:1)/PC(37:6) | 2.41 | 6.4E-35 | 2.48 | 5.5E-29 | 2.62 | 2.1E-14 | 2.77 | 2.0E-12 | 1.89 | 1.8E-03 |
| DAG(14:0/18:1)/Gb3(d18:1/22:0) | 2.39 | 6.4E-35 | 2.53 | 2.5E-30 | 2.67 | 1.2E-14 | 2.64 | 6.4E-12 | 1.88 | 2.5E-03 |
| PI(32:1)/PC(O-36:3) | 2.35 | 6.4E-35 | 2.19 | 4.4E-25 | 3.31 | 8.1E-19 | 3.05 | 2.2E-14 | 2.07 | 3.1E-04 |
| SM(d18:0/22:0)/PC(P-32:0) | 2.45 | 6.4E-35 | 2.57 | 4.9E-30 | 3.46 | 9.7E-19 | 3.99 | 4.4E-17 | 1.97 | 1.3E-03 |
| DAG(18:0/18:2)/LPE(16:0) [sn1] | 2.38 | 6.5E-35 | 2.68 | 3.9E-33 | 2.76 | 6.2E-16 | 3.13 | 9.2E-15 | 2.36 | 9.0E-06 |
| PC(38:3)/LPC(O-24:1) | 2.35 | 6.7E-35 | 2.46 | 8.5E-30 | 3.36 | 2.8E-20 | 3.60 | 1.8E-17 | 1.94 | 9.0E-04 |
| PC(40:5)/LPC(17:0) [sn1] | 2.35 | 6.7E-35 | 2.30 | 8.8E-27 | 2.91 | 3.1E-18 | 2.79 | 1.5E-13 | 1.87 | 1.3E-03 |
| DAG(14:0/18:1)/LPC(20:2) [sn1] | 2.41 | 6.7E-35 | 2.58 | 6.0E-31 | 3.10 | 4.1E-17 | 3.19 | 2.2E-14 | 2.17 | 2.1E-04 |
| PI(40:5)/PC(O-36:2) | 2.40 | 7.0E-35 | 2.27 | 1.4E-25 | 3.12 | 3.2E-18 | 2.81 | 2.4E-13 | 2.16 | 9.9E-05 |
| PC(38:3)/PC(P-40:4) | 2.42 | 7.1E-35 | 2.53 | 7.7E-30 | 3.76 | 2.1E-20 | 4.10 | 9.4E-18 | 2.28 | 9.1E-05 |
| PC(36:3)/PC(37:2) | 2.48 | 7.2E-35 | 2.42 | 3.7E-27 | 3.53 | 7.9E-19 | 3.71 | 4.0E-16 | 2.18 | 2.9E-04 |
| DAG(18:0/20:4)/LPC(O-24:2) | 2.39 | 7.4E-35 | 2.48 | 1.7E-29 | 2.88 | 2.4E-17 | 3.09 | 1.3E-15 | 2.57 | 4.9E-06 |
| DAG(18:0/18:2)/LPE(16:0) [sn2] | 2.36 | 7.4E-35 | 2.66 | 3.8E-33 | 2.75 | 5.8E-16 | 3.07 | 1.4E-14 | 2.38 | 8.0E-06 |
| SM(d18:0/22:0)/LacCer(d18:1/24:1) | 2.39 | 7.6E-35 | 2.42 | 1.2E-28 | 3.14 | 3.8E-18 | 3.35 | 6.8E-16 | 1.72 | 6.1E-03 |
| SM(38:0)/SM(37:2) | 2.42 | 8.2E-35 | 2.63 | 3.5E-31 | 3.93 | 1.1E-20 | 4.10 | 9.8E-18 | 2.58 | 8.7E-06 |
| PC(38:3)/LPC(17:0) [sn2] | 2.32 | 8.5E-35 | 2.34 | 1.7E-28 | 3.33 | 1.1E-21 | 3.34 | 7.8E-18 | 2.09 | 1.1E-04 |
| PI(32:1)/PC(37:2) | 2.35 | 8.6E-35 | 2.19 | 6.0E-25 | 3.24 | 6.8E-19 | 3.13 | 3.5E-15 | 2.13 | 1.4E-04 |
| DAG(14:0/18:1)/LPC(24:0) [sn2] | 2.42 | 8.7E-35 | 2.57 | 2.1E-30 | 3.12 | 5.7E-17 | 3.34 | 8.8E-15 | 2.23 | 1.9E-04 |
| PI(40:5)/LPC(O-24:1) | 2.44 | 8.7E-35 | 2.26 | 9.8E-25 | 3.27 | 7.1E-18 | 3.05 | 1.3E-13 | 2.08 | 3.2E-04 |
| Cer(d18:1/22:0)/PC(O-36:3) | 2.38 | 8.8E-35 | 2.43 | 1.4E-28 | 3.06 | 1.6E-17 | 2.98 | 9.9E-14 | 1.84 | 2.4E-03 |
| PI(40:5)/PC(35:2) | 2.43 | 9.5E-35 | 2.30 | 1.1E-25 | 3.19 | 5.2E-17 | 2.84 | 8.0E-12 | 2.53 | 9.2E-06 |
| DAG(18:0/18:2)/LPC(18:2) [sn1] | 2.32 | 1.1E-34 | 2.51 | 1.2E-31 | 3.06 | 5.9E-19 | 3.16 | 3.8E-16 | 2.51 | 3.1E-06 |
| DAG(14:0/18:1)/PC(O-36:3) | 2.43 | 1.1E-34 | 2.55 | 1.3E-29 | 3.18 | 3.0E-16 | 3.17 | 3.8E-13 | 2.12 | 6.0E-04 |
| Cer(d18:1/22:0)/PC(37:2) | 2.44 | 1.2E-34 | 2.48 | 3.4E-28 | 3.15 | 3.7E-17 | 3.49 | 6.8E-15 | 1.99 | 8.4E-04 |
| DAG(14:0/18:1)/SM(37:1) | 2.42 | 1.2E-34 | 2.52 | 2.0E-29 | 2.90 | 4.2E-15 | 2.93 | 1.6E-12 | 1.87 | 3.0E-03 |
| DAG(18:0/18:2)/LPC(P-16:0) | 2.31 | 1.2E-34 | 2.42 | 1.7E-30 | 2.78 | 1.8E-17 | 2.84 | 6.8E-15 | 2.18 | 2.5E-05 |
| Cer(d16:1/18:0)/LacCer(d18:1/16:0) | 2.53 | 1.3E-34 | 2.80 | 3.0E-31 | 3.41 | 3.0E-17 | 3.59 | 2.3E-14 | 2.40 | 1.2E-04 |
| Cer(d18:1/16:0)/PC(P-36:2) | 2.43 | 1.3E-34 | 2.53 | 2.6E-29 | 3.46 | 2.8E-19 | 3.41 | 3.6E-15 | 2.32 | 6.4E-05 |
| DAG(16:0/18:2)/LPC(20:1) [sn1] | 2.34 | 1.3E-34 | 2.51 | 2.3E-31 | 3.06 | 5.8E-18 | 3.34 | 4.2E-16 | 2.33 | 3.3E-05 |
| DAG(18:1/18:1)/LPC(20:0) [sn2] | 2.31 | 1.3E-34 | 2.47 | 6.1E-31 | 2.87 | 3.0E-18 | 3.11 | 2.3E-16 | 2.11 | 1.0E-04 |
| DAG(16:1/16:1)/LPC(O-24:2) | 2.31 | 1.3E-34 | 2.20 | 1.0E-25 | 2.91 | 4.3E-18 | 2.88 | 6.6E-15 | 2.01 | 2.4E-04 |
| DAG(18:1/20:4)/PC(37:2) | 2.42 | 1.4E-34 | 2.60 | 7.5E-31 | 2.86 | 1.2E-15 | 3.06 | 4.5E-14 | 2.05 | 8.5E-04 |
| Cer(d18:1/18:0)/LPC(20:0) [sn1] | 2.42 | 1.5E-34 | 2.53 | 2.7E-29 | 3.55 | 1.2E-20 | 3.68 | 2.5E-17 | 2.49 | 2.2E-06 |
| SM(36:0)/PC(O-36:3) | 2.30 | 1.5E-34 | 2.36 | 3.3E-29 | 3.20 | 7.8E-21 | 3.17 | 2.3E-17 | 2.61 | 3.3E-07 |
| SM(38:0)/LPC(O-24:2) | 2.44 | 1.5E-34 | 2.51 | 5.2E-29 | 3.38 | 7.1E-19 | 3.81 | 1.1E-16 | 2.54 | 6.5E-06 |
| DAG(16:1/16:1)/PC(P-34:1) | 2.33 | 1.6E-34 | 2.25 | 3.7E-26 | 3.01 | 5.9E-18 | 3.00 | 7.6E-15 | 2.03 | 2.9E-04 |
| DAG(16:1/18:1)/LPC(19:0) [sn1] | 2.36 | 1.7E-34 | 2.35 | 1.2E-27 | 2.98 | 7.7E-18 | 3.08 | 4.4E-15 | 2.29 | 3.2E-05 |
| DAG(16:0/18:2)/LPC(20:0) [sn1] | 2.33 | 1.7E-34 | 2.46 | 1.4E-30 | 3.09 | 6.0E-19 | 3.37 | 5.7E-17 | 2.63 | 1.8E-06 |
| DAG(16:0/18:2)/PC(37:2) | 2.41 | 1.7E-34 | 2.59 | 6.3E-31 | 3.13 | 6.3E-17 | 3.52 | 2.6E-15 | 2.72 | 6.1E-06 |
| DAG(18:0/18:2)/PC(O-34:0) | 2.32 | 1.8E-34 | 2.47 | 1.4E-30 | 2.61 | 5.4E-15 | 2.71 | 6.7E-13 | 2.28 | 2.4E-05 |
| DAG(18:1/18:1)/LPC(O-20:1) | 2.29 | 1.9E-34 | 2.43 | 1.2E-30 | 2.78 | 5.4E-17 | 3.00 | 3.2E-15 | 2.00 | 2.4E-04 |
| SM(d18:0/22:0)/LPC(O-20:1) | 2.36 | 1.9E-34 | 2.43 | 8.0E-29 | 3.44 | 7.0E-20 | 3.88 | 1.9E-17 | 2.00 | 6.3E-04 |
| DAG(16:0/20:4)/PC(O-38:4) | 2.31 | 1.9E-34 | 2.34 | 1.5E-28 | 2.77 | 2.0E-16 | 2.85 | 4.2E-14 | 2.12 | 1.5E-04 |
| PC(40:5)/LPC(P-18:0) | 2.30 | 1.9E-34 | 2.28 | 3.4E-27 | 3.02 | 2.8E-18 | 2.74 | 3.4E-13 | 1.99 | 5.5E-04 |
| DAG(18:1/18:1)/LPC(20:0) [sn1] | 2.31 | 2.0E-34 | 2.46 | 9.2E-31 | 2.90 | 2.3E-18 | 3.15 | 1.7E-16 | 2.19 | 5.1E-05 |
| Cer(d18:1/20:0)/LPC(O-24:2) | 2.45 | 2.0E-34 | 2.61 | 8.3E-30 | 3.37 | 8.3E-18 | 3.67 | 2.6E-15 | 2.40 | 1.4E-05 |
| DAG(16:0/20:4)/LPC(18:2) [sn1] | 2.30 | 2.0E-34 | 2.37 | 1.2E-29 | 3.00 | 7.7E-19 | 3.04 | 7.6E-16 | 2.11 | 1.7E-04 |
| DAG(18:0/18:2)/PC(39:4) | 2.34 | 2.1E-34 | 2.45 | 6.2E-30 | 2.74 | 9.6E-16 | 2.86 | 9.5E-14 | 2.26 | 3.6E-05 |
| DAG(16:1/18:1)/SM(37:1) | 2.38 | 2.2E-34 | 2.45 | 1.6E-28 | 2.79 | 2.9E-15 | 2.91 | 5.3E-13 | 1.91 | 1.6E-03 |
| PI(32:1)/LPE(16:0) [sn2] | 2.32 | 2.4E-34 | 2.19 | 4.3E-25 | 3.12 | 2.4E-18 | 3.04 | 5.4E-15 | 2.20 | 1.4E-04 |
| SM(36:0)/LPC(O-20:1) | 2.28 | 2.4E-34 | 2.34 | 6.1E-29 | 3.40 | 1.2E-21 | 3.67 | 9.3E-19 | 2.70 | 5.0E-07 |
| SM(40:1)/SM(37:2) | 2.39 | 2.4E-34 | 2.60 | 7.6E-31 | 3.31 | 1.2E-18 | 3.55 | 4.2E-16 | 1.96 | 1.3E-03 |
| SM(d18:0/22:0)/PC(O-40:6) | 2.39 | 2.5E-34 | 2.54 | 6.0E-30 | 2.99 | 4.2E-17 | 3.42 | 8.3E-16 | 1.94 | 7.8E-04 |
| Cer(d18:1/22:0)/PC(O-38:0) | 2.34 | 2.5E-34 | 2.42 | 1.7E-28 | 2.70 | 7.2E-16 | 2.90 | 1.0E-13 | 2.00 | 3.6E-04 |
| DAG(14:0/18:1)/LPC(P-18:0) | 2.34 | 2.7E-34 | 2.39 | 1.2E-28 | 3.00 | 1.5E-17 | 2.95 | 3.1E-14 | 2.14 | 1.7E-04 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| DAG(18:1/20:4)/LPC(P-18:0) | 2.28 | 2.7E-34 | 2.36 | 9.2E-30 | 2.86 | 8.0E-18 | 2.86 | 8.6E-15 | 2.01 | 3.8E-04 |
| DAG(18:0/20:4)/PC(P-36:2) | 2.36 | 2.9E-34 | 2.46 | 1.7E-29 | 3.14 | 2.6E-18 | 3.25 | 1.6E-15 | 2.70 | 2.6E-06 |
| DAG(16:0/18:2)/PC(17:0_22:6) | 2.38 | 3.0E-34 | 2.51 | 5.9E-30 | 2.66 | 2.3E-14 | 2.90 | 4.1E-13 | 2.16 | 1.6E-04 |
| SM(36:0)/PC(O-34:0) | 2.24 | 3.0E-34 | 2.31 | 3.0E-29 | 2.97 | 1.5E-19 | 3.11 | 2.6E-17 | 2.83 | 6.7E-08 |
| CE(16:1)/PC(O-40:6) | 2.25 | 3.1E-34 | 2.23 | 9.6E-27 | 2.62 | 2.1E-16 | 2.72 | 5.9E-14 | 1.84 | 1.1E-03 |
| CE(16:1)/Gb3(d18:1/22:0) | 2.32 | 3.2E-34 | 2.26 | 1.9E-26 | 2.69 | 2.3E-15 | 2.55 | 4.9E-12 | 1.68 | 8.4E-03 |
| DAG(18:1/20:4)/LPC(17:0) [sn2] | 2.31 | 3.3E-34 | 2.41 | 1.3E-29 | 2.90 | 8.4E-18 | 2.97 | 5.4E-15 | 2.00 | 4.5E-04 |
| PE(36:1)/PC(35:3) | 2.26 | 3.5E-34 | 2.28 | 1.9E-28 | 2.75 | 1.7E-16 | 2.59 | 6.8E-13 | 1.93 | 6.3E-04 |
| PC(38:3)/LPC(20:2) [sn1] | 2.38 | 3.7E-34 | 2.70 | 2.8E-32 | 4.00 | 4.2E-21 | 4.57 | 1.8E-18 | 2.17 | 2.2E-04 |
| Cer(d16:1/18:0)/Gb3(d18:1/22:0) | 2.46 | 3.8E-34 | 2.75 | 1.6E-31 | 2.89 | 8.9E-16 | 2.84 | 1.5E-12 | 2.04 | 8.4E-04 |
| DAG(14:0/18:1)/LPC(P-18:1) | 2.36 | 4.1E-34 | 2.40 | 3.6E-28 | 2.87 | 4.2E-16 | 2.80 | 6.1E-13 | 1.88 | 1.9E-03 |
| DAG(16:1/18:1)/SM(37:2) | 2.37 | 4.1E-34 | 2.50 | 2.2E-29 | 3.08 | 7.0E-17 | 3.23 | 2.2E-14 | 2.07 | 5.1E-04 |
| DAG(18:0/20:4)/PC(P-36:1) | 2.34 | 4.3E-34 | 2.46 | 1.6E-29 | 2.98 | 1.8E-17 | 3.23 | 2.2E-15 | 2.67 | 2.6E-06 |
| DAG(16:0/22:6)/LPC(22:6) [sn2] | 2.39 | 4.5E-34 | 2.46 | 2.3E-28 | 3.08 | 2.3E-17 | 3.04 | 5.1E-14 | 2.81 | 8.5E-07 |
| DAG(16:0/18:2)/LPC(22:0) [sn2] | 2.32 | 4.7E-34 | 2.50 | 3.8E-31 | 3.07 | 1.4E-18 | 3.39 | 6.9E-17 | 2.61 | 2.7E-06 |
| DAG(18:1/20:4)/LacCer(d18:1/16:0) | 2.29 | 4.7E-34 | 2.44 | 8.3E-31 | 2.43 | 1.7E-14 | 2.53 | 6.5E-13 | 1.77 | 3.6E-03 |
| DAG(14:0/18:1)/Gb3(d18:1/16:0) | 2.39 | 5.0E-34 | 2.51 | 2.7E-29 | 2.91 | 2.9E-15 | 2.96 | 9.8E-13 | 1.85 | 4.0E-03 |
| PI(32:1)/LacCer(d18:1/16:0) | 2.27 | 5.4E-34 | 2.11 | 2.6E-24 | 2.93 | 3.3E-17 | 2.76 | 1.2E-13 | 1.97 | 6.4E-04 |
| DAG(18:0/18:2)/PC(P-32:0) | 2.32 | 5.5E-34 | 2.49 | 1.4E-30 | 2.70 | 1.6E-15 | 2.85 | 1.8E-13 | 2.24 | 4.7E-05 |
| DAG(18:0/18:2)/PC(P-40:4) | 2.32 | 5.5E-34 | 2.47 | 3.8E-30 | 2.84 | 2.8E-16 | 2.97 | 3.1E-14 | 2.42 | 7.2E-06 |
| Cer(d16:1/20:0)/PC(P-36:1) | 2.48 | 5.6E-34 | 2.81 | 8.8E-32 | 3.48 | 2.4E-17 | 3.66 | 2.9E-14 | 2.95 | 4.9E-06 |
| DAG(14:0/18:1)/LPC(O-22:0) | 2.35 | 5.7E-34 | 2.44 | 5.5E-29 | 2.98 | 2.5E-16 | 3.10 | 4.6E-14 | 2.16 | 2.0E-04 |
| DAG(16:1/18:1)/PC(37:2) | 2.42 | 5.8E-34 | 2.48 | 4.4E-28 | 3.02 | 4.0E-16 | 3.29 | 4.8E-14 | 2.29 | 1.2E-04 |
| Cer(d16:1/20:0)/PC(P-36:2) | 2.44 | 5.9E-34 | 2.74 | 1.0E-31 | 3.56 | 2.6E-18 | 3.53 | 1.2E-14 | 2.87 | 6.0E-06 |
| SM(38:1)/PC(P-36:1) | 2.43 | 6.2E-34 | 2.62 | 4.8E-30 | 3.71 | 1.9E-18 | 4.02 | 8.1E-16 | 2.92 | 4.4E-06 |
| DAG(16:0/20:4)/LPE(P-18:0) | 2.26 | 6.3E-34 | 2.29 | 3.0E-28 | 2.76 | 3.7E-17 | 2.72 | 4.7E-14 | 1.93 | 7.1E-04 |
| DAG(18:0/18:2)/PC(O-38:2) | 2.28 | 6.3E-34 | 2.37 | 2.9E-29 | 2.55 | 3.8E-15 | 2.60 | 9.0E-13 | 2.24 | 1.9E-05 |
| DAG(16:1/18:1)/PC(O-36:2) | 2.35 | 6.3E-34 | 2.42 | 2.7E-28 | 3.02 | 6.8E-17 | 3.09 | 4.7E-14 | 2.19 | 1.5E-04 |
| DAG(16:1/18:1)/LPC(20:1) [sn2] | 2.37 | 6.5E-34 | 2.42 | 3.5E-28 | 2.98 | 1.4E-16 | 3.13 | 2.7E-14 | 2.04 | 6.4E-04 |
| DAG(16:0/18:2)/LPC(O-20:1) | 2.29 | 6.8E-34 | 2.41 | 7.0E-30 | 2.91 | 2.9E-17 | 3.12 | 2.3E-15 | 2.31 | 1.3E-05 |
| DAG(16:1/18:1)/PC(O-34:1) | 2.37 | 6.8E-34 | 2.44 | 2.3E-28 | 2.92 | 8.1E-16 | 3.08 | 1.0E-13 | 2.11 | 3.8E-04 |
| DAG(14:0/18:1)/LacCer(d18:1/16:0) | 2.38 | 7.3E-34 | 2.48 | 4.4E-29 | 2.82 | 8.1E-15 | 2.88 | 1.6E-12 | 2.00 | 1.1E-03 |
| DAG(18:1/20:4)/PC(35:3) | 2.37 | 8.0E-34 | 2.59 | 3.0E-31 | 2.78 | 1.8E-15 | 2.90 | 1.1E-13 | 1.88 | 2.6E-03 |
| SM(41:0)/Gb3(d18:1/23:0) | 2.33 | 8.4E-34 | 2.29 | 1.0E-26 | 2.70 | 1.3E-16 | 2.81 | 3.4E-14 | 1.73 | 6.4E-03 |
| DAG(18:1/20:4)/LPC(24:0) [sn2] | 2.29 | 8.5E-34 | 2.51 | 1.2E-31 | 2.77 | 1.3E-16 | 3.05 | 2.1E-15 | 2.01 | 5.4E-04 |
| DAG(18:1/18:1)/PC(37:2) | 2.33 | 8.6E-34 | 2.53 | 1.3E-30 | 2.79 | 6.4E-16 | 3.13 | 1.4E-14 | 2.15 | 2.4E-04 |
| DAG(14:0/18:1)/LPC(O-24:1) | 2.36 | 8.8E-34 | 2.44 | 1.2E-28 | 2.96 | 5.3E-16 | 3.05 | 1.5E-13 | 2.04 | 6.9E-04 |
| DAG(16:1/16:1)/PC(P-32:1) | 2.34 | 8.9E-34 | 2.32 | 6.1E-27 | 2.93 | 2.1E-16 | 2.99 | 5.5E-14 | 1.85 | 2.7E-03 |
| DAG(16:1/18:1)/PC(17:0_22:6) | 2.37 | 9.0E-34 | 2.43 | 7.7E-28 | 2.59 | 7.4E-14 | 2.79 | 3.3E-12 | 1.92 | 1.5E-03 |
| DAG(18:1/18:1)/PC(O-36:2) | 2.29 | 9.1E-34 | 2.48 | 1.1E-30 | 2.80 | 7.5E-17 | 2.96 | 1.4E-14 | 2.05 | 2.2E-04 |
| SM(d18:0/22:0)/PC(O-38:0) | 2.37 | 9.2E-34 | 2.49 | 5.1E-29 | 3.48 | 2.7E-18 | 3.95 | 1.1E-16 | 2.14 | 3.3E-04 |
| PI(32:1)/PC(P-32:0) | 2.27 | 9.5E-34 | 2.11 | 6.3E-24 | 2.99 | 1.4E-17 | 2.83 | 6.7E-14 | 2.02 | 4.0E-04 |
| DAG(16:1/18:1)/LPC(O-20:1) | 2.32 | 9.6E-34 | 2.33 | 1.6E-27 | 2.90 | 7.9E-17 | 2.97 | 2.5E-14 | 2.11 | 1.8E-04 |
| DAG(16:0/18:2)/PC(37:6) | 2.36 | 9.7E-34 | 2.48 | 1.3E-29 | 2.64 | 2.8E-14 | 2.78 | 1.2E-12 | 2.08 | 3.2E-04 |
| PE(38:4)/PC(P-40:2) | 2.41 | 1.0E-33 | 2.49 | 2.0E-28 | 2.88 | 5.2E-15 | 2.85 | 2.7E-12 | 1.77 | 3.1E-03 |
| PC(38:3)/LPC(P-18:0) | 2.27 | 1.1E-33 | 2.31 | 4.9E-28 | 3.32 | 1.0E-20 | 3.32 | 7.3E-17 | 2.11 | 1.7E-04 |
| DAG(16:1/18:1)/LPC(20:1) [sn1] | 2.35 | 1.1E-33 | 2.41 | 5.1E-28 | 3.02 | 5.7E-17 | 3.16 | 1.2E-14 | 2.07 | 4.8E-04 |
| Cer(d18:1/18:0)/LPC(O-18:1) | 2.36 | 1.1E-33 | 2.41 | 1.2E-27 | 3.30 | 9.8E-19 | 3.23 | 7.2E-15 | 2.13 | 7.8E-05 |
| Cer(d18:1/24:1)/LPC(20:1) [sn1] | 2.35 | 1.2E-33 | 2.44 | 2.3E-28 | 3.36 | 4.5E-19 | 3.71 | 7.7E-17 | 2.09 | 2.7E-04 |
| DAG(16:0/22:6)/LPC(O-24:2) | 2.33 | 1.2E-33 | 2.34 | 8.2E-27 | 3.21 | 4.3E-18 | 3.29 | 5.3E-15 | 2.84 | 7.5E-07 |
| DAG(16:0/20:4)/CE(17:0) | 2.29 | 1.3E-33 | 2.34 | 2.5E-28 | 2.73 | 2.1E-16 | 2.83 | 7.1E-14 | 1.87 | 1.3E-03 |
| DAG(16:1/18:1)/Gb3(d18:1/16:0) | 2.34 | 1.4E-33 | 2.42 | 3.5E-28 | 2.78 | 2.4E-15 | 2.90 | 4.1E-13 | 1.88 | 2.3E-03 |
| Cer(d18:1/24:1)/PC(O-34:1) | 2.27 | 1.4E-33 | 2.34 | 3.5E-28 | 2.71 | 1.2E-16 | 2.84 | 1.0E-14 | 2.09 | 1.7E-04 |
| DAG(16:0/18:2)/PC(35:2) | 2.40 | 1.5E-33 | 2.59 | 2.9E-30 | 3.24 | 7.5E-17 | 3.55 | 8.6E-15 | 2.84 | 1.2E-06 |
| Cer(d16:1/18:0)/LPC(O-20:1) | 2.42 | 1.6E-33 | 2.59 | 1.8E-29 | 3.62 | 3.0E-19 | 3.73 | 6.0E-16 | 2.46 | 5.0E-05 |
| SM(36:0)/PC(O-32:0) | 2.24 | 1.6E-33 | 2.33 | 4.3E-29 | 2.95 | 2.5E-19 | 3.17 | 1.3E-17 | 2.75 | 1.4E-07 |
| PC(38:3)/LPC(15:0) [sn1] | 2.34 | 1.7E-33 | 2.35 | 1.8E-27 | 3.75 | 4.2E-21 | 3.82 | 1.4E-17 | 2.13 | 2.2E-04 |
| Cer(d16:1/18:0)/LPC(O-20:0) | 2.41 | 1.7E-33 | 2.59 | 2.0E-29 | 3.66 | 1.5E-19 | 3.86 | 2.0E-16 | 2.77 | 3.9E-06 |
| SM(d18:0/22:0)/PC(O-34:0) | 2.35 | 1.7E-33 | 2.42 | 3.2E-28 | 3.19 | 3.3E-17 | 3.51 | 1.9E-15 | 2.00 | 9.0E-04 |
| DAG(14:0/18:1)/LPC(O-18:0) | 2.32 | 1.8E-33 | 2.36 | 7.5E-28 | 2.99 | 1.3E-16 | 2.99 | 8.1E-14 | 2.21 | 1.2E-04 |
| PC(38:3)/LPC(O-18:0) | 2.27 | 1.8E-33 | 2.29 | 2.0E-27 | 3.38 | 2.7E-20 | 3.45 | 6.5E-17 | 2.25 | 6.0E-05 |
| PI(32:1)/PC(33:3) | 2.31 | 1.8E-33 | 2.14 | 2.4E-23 | 3.29 | 9.5E-19 | 3.19 | 8.4E-15 | 2.01 | 5.3E-04 |
| PI(40:5)/PC(35:3) | 2.37 | 1.8E-33 | 2.24 | 1.3E-24 | 2.94 | 3.3E-16 | 2.70 | 6.2E-12 | 2.06 | 5.0E-04 |
| DAG(14:0/18:2)/LPC(O-24:2) | 2.34 | 2.0E-33 | 2.46 | 8.1E-29 | 2.75 | 8.7E-15 | 2.88 | 1.0E-12 | 2.30 | 1.0E-04 |
| DAG(18:0/18:2)/LPC(O-24:0) | 2.27 | 2.1E-33 | 2.42 | 5.1E-30 | 2.66 | 5.6E-16 | 2.84 | 3.4E-14 | 2.28 | 1.7E-05 |
| SM(d18:0/22:0)/PC(O-38:2) | 2.35 | 2.1E-33 | 2.38 | 3.2E-27 | 3.28 | 7.8E-18 | 3.60 | 6.5E-16 | 2.04 | 7.3E-04 |
| PC(38:3)/LPC(20:2) [sn2] | 2.36 | 2.2E-33 | 2.70 | 4.1E-32 | 3.85 | 3.8E-20 | 4.46 | 5.6E-18 | 2.04 | 7.1E-04 |
| PC(36:4)/PC(P-34:1) | 2.41 | 2.2E-33 | 2.42 | 1.1E-26 | 3.59 | 3.9E-17 | 3.61 | 5.2E-14 | 2.53 | 6.5E-05 |
| CE(16:1)/PC(35:3) | 2.27 | 2.2E-33 | 2.19 | 5.1E-25 | 2.97 | 1.6E-17 | 3.05 | 2.3E-14 | 1.81 | 2.2E-03 |
| DAG(16:0/18:2)/LPC(17:0) [sn1] | 2.26 | 2.2E-33 | 2.32 | 2.0E-28 | 2.92 | 6.0E-18 | 3.04 | 1.5E-15 | 2.38 | 4.9E-06 |
| DAG(16:1/18:1)/PC(33:2) | 2.33 | 2.3E-33 | 2.41 | 6.1E-28 | 2.68 | 5.8E-15 | 2.90 | 5.1E-13 | 2.03 | 5.1E-04 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| Cer(d18:1/18:0)/PC(39:4) | 2.37 | 2.4E−33 | 2.46 | 4.3E−28 | 3.03 | 8.7E−18 | 3.15 | 2.4E−15 | 2.25 | 4.8E−05 |
| Cer(d18:1/22:0)/LPC(O-18:0) | 2.27 | 2.4E−33 | 2.24 | 7.5E−26 | 3.02 | 1.5E−18 | 3.06 | 5.2E−15 | 2.10 | 6.3E−05 |
| DAG(18:1/20:4)/LPC(O-24:1) | 2.26 | 2.4E−33 | 2.40 | 8.3E−30 | 2.60 | 5.8E−16 | 2.74 | 3.8E−14 | 1.83 | 2.1E−03 |
| PI(32:1)/PC(O-40:3) | 2.27 | 2.4E−33 | 2.17 | 4.7E−25 | 2.91 | 3.6E−17 | 2.89 | 3.6E−14 | 1.92 | 7.1E−04 |
| Cer(d16:1/18:0)/SM(41:2) | 2.52 | 2.5E−33 | 2.79 | 1.8E−29 | 3.21 | 4.6E−17 | 3.42 | 1.1E−13 | 2.35 | 8.3E−05 |
| Cer(d18:1/24:1)/SM(37:1) | 2.28 | 2.5E−33 | 2.29 | 8.6E−27 | 2.57 | 6.4E−15 | 2.58 | 1.7E−12 | 1.71 | 5.9E−03 |
| DAG(16:1/18:1)/SM(d17:1/14:0) | 2.32 | 2.6E−33 | 2.35 | 4.0E−27 | 2.72 | 4.4E−15 | 2.83 | 1.4E−12 | 1.98 | 7.6E−04 |
| PE(36:1)/PC(37:2) | 2.25 | 2.7E−33 | 2.22 | 8.9E−27 | 2.70 | 6.7E−16 | 2.58 | 9.7E−13 | 2.02 | 2.7E−04 |
| Cer(d18:1/20:0)/LPC(O-22:1) | 2.34 | 2.7E−33 | 2.47 | 1.1E−28 | 3.35 | 1.8E−18 | 3.57 | 1.1E−15 | 2.43 | 5.1E−06 |
| SM(38:1)/SM(37:1) | 2.48 | 2.8E−33 | 2.65 | 4.1E−29 | 3.05 | 4.9E−14 | 3.18 | 7.0E−12 | 1.97 | 3.3E−03 |
| DAG(16:0/18:2)/LPC(22:0) [sn1] | 2.30 | 2.9E−33 | 2.47 | 2.3E−30 | 3.03 | 5.1E−18 | 3.42 | 1.3E−16 | 2.64 | 2.0E−06 |
| DAG(16:0/18:2)/PC(35:3) | 2.37 | 2.9E−33 | 2.61 | 4.4E−31 | 3.08 | 1.1E−16 | 3.39 | 4.9E−15 | 2.50 | 1.7E−05 |
| Cer(d18:1/22:0)/PC(O-34:0) | 2.28 | 3.1E−33 | 2.31 | 5.0E−27 | 2.50 | 2.1E−14 | 2.55 | 5.9E−12 | 1.83 | 1.9E−03 |
| DAG(16:0/18:2)/PC(O-36:2) | 2.30 | 3.1E−33 | 2.46 | 7.3E−30 | 2.98 | 2.8E−17 | 3.12 | 6.0E−15 | 2.41 | 1.3E−05 |
| DAG(18:1/18:1)/LPC(17:0) [sn1] | 2.24 | 3.1E−33 | 2.33 | 1.4E−28 | 2.74 | 2.9E−17 | 2.90 | 5.2E−15 | 2.01 | 1.7E−04 |
| DAG(16:1/18:1)/PC(34:3) | 2.38 | 3.2E−33 | 2.59 | 2.8E−30 | 2.96 | 1.1E−15 | 3.24 | 3.9E−14 | 2.14 | 4.8E−04 |
| SM(d18:0/22:0)/SM(41:2) | 2.34 | 3.2E−33 | 2.37 | 2.5E−27 | 3.14 | 1.7E−17 | 3.39 | 1.2E−15 | 1.83 | 3.4E−03 |
| DAG(18:0/18:2)/LPC(O-16:0) | 2.26 | 3.2E−33 | 2.36 | 5.4E−27 | 2.79 | 1.1E−16 | 2.84 | 4.2E−14 | 2.18 | 4.2E−05 |
| DAG(18:1/18:1)/LPC(22:0) [sn2] | 2.27 | 3.3E−33 | 2.47 | 1.2E−30 | 2.85 | 1.3E−17 | 3.12 | 3.9E−16 | 2.15 | 1.1E−04 |
| PI(40:5)/PC(P-32:0) | 2.38 | 3.4E−33 | 2.24 | 1.1E−23 | 2.93 | 2.4E−15 | 2.74 | 2.4E−11 | 2.06 | 4.8E−04 |
| Cer(d16:1/18:0)/PC(O-36:3) | 2.44 | 3.6E−33 | 2.64 | 2.3E−29 | 3.57 | 2.3E−18 | 3.49 | 2.3E−14 | 2.42 | 9.1E−05 |
| SM(41:0)/SM(37:2) | 2.33 | 3.7E−33 | 2.52 | 8.7E−30 | 3.74 | 1.6E−20 | 4.11 | 7.5E−18 | 2.25 | 9.3E−05 |
| SM(36:0)/LPC(O-24:1) | 2.24 | 3.7E−33 | 2.30 | 5.1E−28 | 3.22 | 3.8E−21 | 3.45 | 1.2E−18 | 2.62 | 5.9E−07 |
| SM(41:0)/PC(P-34:1) | 2.33 | 3.7E−33 | 2.46 | 3.1E−29 | 3.28 | 6.5E−19 | 3.75 | 3.8E−17 | 2.35 | 5.1E−05 |
| DAG(16:1/18:1)/LPC(20:0) [sn2] | 2.32 | 3.8E−33 | 2.33 | 5.8E−27 | 2.97 | 1.9E−17 | 3.07 | 5.8E−15 | 2.20 | 1.0E−04 |
| DAG(14:0/18:1)/PC(37:1) | 2.36 | 3.8E−33 | 2.43 | 6.4E−28 | 2.81 | 1.2E−14 | 2.87 | 2.8E−12 | 2.07 | 7.1E−04 |
| SM(d18:0/22:0)/PC(37:2) | 2.35 | 3.8E−33 | 2.42 | 4.5E−28 | 3.32 | 2.1E−18 | 3.70 | 7.7E−17 | 2.05 | 6.6E−04 |
| SM(d18:0/22:0)/PC(33:2) | 2.36 | 3.9E−33 | 2.43 | 4.1E−28 | 3.14 | 3.5E−17 | 3.45 | 9.9E−16 | 1.84 | 3.1E−03 |
| DAG(16:0/18:2)/SM(37:2) | 2.30 | 4.0E−33 | 2.55 | 3.8E−31 | 3.07 | 3.8E−17 | 3.36 | 3.2E−15 | 2.29 | 6.8E−05 |
| DAG(16:1/16:1)/PC(37:6) | 2.28 | 4.0E−33 | 2.21 | 5.4E−25 | 2.65 | 4.2E−16 | 2.71 | 4.2E−13 | 1.81 | 1.7E−03 |
| SM(36:0)/LPC(MHDA) [sn1] | 2.23 | 4.0E−33 | 2.27 | 1.4E−27 | 3.36 | 4.1E−22 | 3.41 | 8.5E−19 | 2.94 | 5.2E−09 |
| DAG(18:1/20:4)/PC(35:2) | 2.37 | 4.1E−33 | 2.56 | 5.0E−30 | 2.89 | 1.5E−15 | 2.99 | 3.1E−13 | 2.24 | 1.5E−04 |
| DAG(16:1/18:1)/Gb3(d18:1/22:0) | 2.30 | 4.2E−33 | 2.39 | 3.6E−28 | 2.54 | 6.0E−14 | 2.54 | 1.6E−11 | 1.89 | 1.9E−03 |
| Cer(d18:1/22:0)/LacCer(d18:1/16:0) | 2.31 | 4.4E−33 | 2.37 | 2.0E−27 | 2.64 | 2.0E−14 | 2.69 | 4.1E−12 | 1.69 | 9.3E−03 |
| DAG(16:1/18:1)/LPC(20:0) [sn1] | 2.32 | 4.6E−33 | 2.33 | 6.6E−27 | 2.99 | 1.5E−17 | 3.10 | 4.4E−15 | 2.28 | 5.9E−05 |
| DAG(18:1/20:4)/PC(O-36:3) | 2.30 | 4.6E−33 | 2.45 | 1.7E−29 | 2.71 | 3.6E−15 | 2.71 | 1.2E−12 | 1.89 | 2.2E−03 |
| DAG(16:1/16:1)/PC(35:3) | 2.29 | 4.8E−33 | 2.20 | 1.0E−24 | 3.08 | 5.7E−18 | 3.06 | 1.2E−14 | 2.05 | 3.0E−04 |
| SM(36:0)/PC(O-32:1) | 2.24 | 5.0E−33 | 2.40 | 3.4E−30 | 2.86 | 8.8E−19 | 3.01 | 3.5E−17 | 2.37 | 2.9E−06 |
| PC(34:1)/SM(37:2) | 2.34 | 5.0E−33 | 2.50 | 8.5E−29 | 3.22 | 6.4E−18 | 3.34 | 1.9E−14 | 1.79 | 4.4E−03 |
| DAG(16:0/18:2)/PC(P-34:1) | 2.30 | 5.1E−33 | 2.50 | 2.6E−30 | 2.85 | 7.0E−16 | 3.13 | 2.1E−14 | 2.33 | 4.5E−05 |
| DAG(18:0/18:2)/LPE(P-18:0) | 2.23 | 5.4E−33 | 2.36 | 2.2E−29 | 2.71 | 1.7E−16 | 2.72 | 1.1E−13 | 2.27 | 1.8E−05 |
| DAG(18:1/18:1)/LPC(17:0) [sn2] | 2.23 | 5.5E−33 | 2.33 | 1.4E−28 | 2.75 | 2.7E−17 | 2.86 | 6.8E−15 | 2.04 | 1.2E−04 |
| Cer(d18:1/16:0)/LPC(O-24:2) | 2.37 | 5.5E−33 | 2.40 | 1.7E−26 | 2.96 | 3.6E−16 | 3.07 | 1.5E−13 | 2.10 | 2.3E−04 |
| DAG(16:0/18:2)/PC(33:2) | 2.32 | 5.9E−33 | 2.49 | 1.8E−29 | 2.82 | 2.7E−15 | 3.06 | 1.1E−13 | 2.34 | 4.2E−05 |
| DAG(16:1/18:1)/LacCer(d18:1/16:0) | 2.31 | 5.9E−33 | 2.37 | 1.6E−27 | 2.68 | 1.1E−14 | 2.79 | 8.9E−13 | 2.03 | 5.7E−04 |
| Cer(d18:1/18:0)/LPC(22:0) [sn2] | 2.39 | 6.0E−33 | 2.56 | 5.5E−29 | 3.50 | 2.1E−19 | 3.64 | 1.4E−16 | 2.44 | 5.6E−06 |
| PI(40:5)/SM(d17:1/14:0) | 2.29 | 6.4E−33 | 2.11 | 1.5E−22 | 2.63 | 5.9E−15 | 2.40 | 4.3E−10 | 1.80 | 2.5E−03 |
| PE(36:1)/SM(37:2) | 2.23 | 6.4E−33 | 2.29 | 5.5E−28 | 2.76 | 1.4E−16 | 2.64 | 5.8E−13 | 1.87 | 1.6E−03 |
| DAG(18:0/20:4)/LPC(O-22:1) | 2.29 | 6.5E−33 | 2.36 | 6.9E−28 | 2.88 | 3.4E−17 | 3.11 | 1.5E−15 | 2.55 | 2.7E−06 |
| PI(40:5)/PC(O-38:0) | 2.38 | 6.5E−33 | 2.25 | 1.7E−23 | 2.90 | 1.2E−15 | 2.79 | 1.2E−11 | 2.30 | 4.3E−05 |
| DAG(16:1/18:1)/LPE(16:0) [sn1] | 2.34 | 6.7E−33 | 2.49 | 9.8E−29 | 2.82 | 3.4E−15 | 3.25 | 4.9E−14 | 2.22 | 1.4E−04 |
| DAG(14:0/18:1)/PC(P-40:2) | 2.32 | 6.7E−33 | 2.44 | 2.0E−28 | 2.74 | 1.1E−14 | 2.81 | 2.5E−12 | 2.00 | 4.3E−04 |
| DAG(18:1/18:1)/SM(37:2) | 2.26 | 6.7E−33 | 2.51 | 4.8E−31 | 2.82 | 1.6E−16 | 3.08 | 1.1E−14 | 1.91 | 1.2E−03 |
| DAG(16:1/18:1)/LPC(17:0) [sn2] | 2.27 | 6.9E−33 | 2.26 | 4.8E−26 | 2.88 | 2.6E−17 | 2.90 | 3.2E−14 | 2.16 | 8.9E−05 |
| DAG(18:1/18:1)/LPC(P-18:1) | 2.24 | 7.1E−33 | 2.34 | 1.4E−28 | 2.62 | 1.1E−15 | 2.67 | 2.8E−13 | 1.77 | 2.7E−03 |
| PC(40:5)/LPC(17:0) [sn2] | 2.25 | 7.2E−33 | 2.19 | 2.7E−25 | 2.67 | 1.5E−17 | 2.46 | 1.2E−12 | 1.87 | 8.8E−04 |
| DAG(16:1/18:1)/LPE(16:0) [sn2] | 2.33 | 7.4E−33 | 2.48 | 9.9E−29 | 2.81 | 3.1E−15 | 3.14 | 6.6E−14 | 2.25 | 1.3E−04 |
| PC(36:3)/SM(d17:1/14:0) | 2.34 | 7.9E−33 | 2.24 | 2.2E−24 | 3.19 | 1.3E−16 | 3.11 | 3.4E−13 | 1.72 | 9.5E−03 |
| PI(32:1)/PI(38:1) | 2.28 | 7.9E−33 | 2.26 | 3.1E−26 | 3.04 | 2.9E−17 | 3.13 | 1.5E−14 | 2.04 | 3.8E−04 |
| Cer(d16:1/18:0)/PC(O-38:2) | 2.47 | 8.0E−33 | 2.69 | 9.5E−29 | 3.26 | 4.8E−17 | 3.45 | 8.4E−14 | 2.58 | 1.5E−05 |
| Cer(d16:1/18:0)/PC(35:3) | 2.54 | 8.2E−33 | 2.90 | 2.2E−30 | 4.00 | 1.1E−17 | 4.19 | 1.8E−14 | 2.58 | 6.9E−05 |
| PC(38:2)/PC(37:2) | 2.35 | 8.6E−33 | 2.34 | 2.4E−25 | 3.53 | 4.9E−19 | 3.49 | 9.8E−16 | 2.77 | 3.7E−06 |
| PC(36:3)/PC(O-36:3) | 2.35 | 8.7E−33 | 2.33 | 5.7E−26 | 3.47 | 5.3E−18 | 3.36 | 3.4E−14 | 1.94 | 1.7E−03 |
| PI(40:5)/PC(17:0_22:6) | 2.24 | 8.8E−33 | 2.18 | 6.8E−25 | 2.27 | 1.3E−12 | 2.32 | 4.7E−10 | 1.66 | 6.4E−03 |
| DAG(16:1/18:1)/LPC(P-18:1) | 2.29 | 9.1E−33 | 2.27 | 3.8E−26 | 2.76 | 8.5E−16 | 2.72 | 7.7E−13 | 1.90 | 1.3E−03 |
| SM(38:0)/LPC(O-22:1) | 2.28 | 9.3E−33 | 2.34 | 1.9E−27 | 3.27 | 1.9E−19 | 3.67 | 8.0E−17 | 2.57 | 5.7E−06 |
| DAG(16:0/18:2)/LPC(17:0) [sn2] | 2.24 | 9.4E−33 | 2.33 | 2.9E−28 | 2.87 | 6.1E−18 | 2.97 | 2.1E−15 | 2.38 | 4.2E−06 |
| SM(36:0)/SM(41:2) | 2.19 | 9.6E−33 | 2.25 | 2.3E−27 | 2.78 | 4.2E−19 | 2.94 | 9.6E−17 | 2.47 | 3.5E−07 |
| PC(40:4)/PC(O-40:4) | 2.22 | 9.6E−33 | 2.23 | 1.2E−26 | 2.52 | 1.9E−14 | 2.47 | 2.7E−11 | 1.71 | 5.7E−03 |
| PI(32:1)/PC(O-32:0) | 2.23 | 9.7E−33 | 2.07 | 3.4E−23 | 2.88 | 1.1E−16 | 2.74 | 2.4E−13 | 1.98 | 5.5E−04 |
| Cer(d16:1/18:0)/PC(37:2) | 2.51 | 9.9E−33 | 2.76 | 5.3E−29 | 3.65 | 1.4E−17 | 3.94 | 1.3E−14 | 2.67 | 2.2E−05 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| SM(36:0)/PC(P-40:4) | 2.23 | 9.9E-33 | 2.32 | 3.7E-28 | 3.39 | 1.7E-21 | 3.78 | 3.2E-19 | 3.13 | 1.1E-08 |
| DAG(14:0/18:1)/LPE(P-20:0) | 2.30 | 1.0E-32 | 2.36 | 1.8E-27 | 2.95 | 9.4E-17 | 2.91 | 1.2E-13 | 2.07 | 3.3E-04 |
| Cer(d16:1/18:0)/PC(33:2) | 2.50 | 1.0E-32 | 2.77 | 4.9E-29 | 3.32 | 1.4E-16 | 3.62 | 1.3E-13 | 2.37 | 1.5E-04 |
| DAG(18:1/18:1)/SM(37:1) | 2.24 | 1.1E-32 | 2.42 | 1.2E-29 | 2.51 | 2.7E-14 | 2.71 | 7.9E-13 | 1.73 | 5.4E-03 |
| Cer(d16:1/18:0)/SM(39:2) | 2.38 | 1.1E-32 | 2.63 | 3.8E-30 | 2.86 | 1.6E-18 | 3.02 | 6.5E-16 | 1.82 | 1.3E-03 |
| DAG(16:1/18:1)/PC(O-36:3) | 2.34 | 1.2E-32 | 2.39 | 4.0E-27 | 2.97 | 1.2E-15 | 3.02 | 7.0E-13 | 2.14 | 4.0E-04 |
| PI(32:1)/PC(O-38:2) | 2.21 | 1.2E-32 | 2.04 | 1.6E-22 | 2.84 | 4.1E-17 | 2.70 | 3.1E-13 | 2.03 | 2.6E-04 |
| PC(40:6)/PC(37:6) | 2.29 | 1.2E-32 | 2.34 | 4.8E-27 | 2.80 | 4.8E-17 | 2.91 | 9.8E-14 | 1.90 | 5.2E-04 |
| Cer(d18:1/22:0)/PC(35:2) | 2.40 | 1.2E-32 | 2.51 | 1.1E-27 | 3.28 | 5.2E-16 | 3.40 | 1.3E-12 | 2.25 | 1.7E-04 |
| Cer(d18:1/20:0)/PC(P-34:1) | 2.32 | 1.2E-32 | 2.56 | 4.8E-30 | 3.13 | 2.3E-17 | 3.36 | 4.4E-15 | 2.47 | 2.0E-05 |
| DAG(16:0/18:2)/LPC(P-18:1) | 2.24 | 1.2E-32 | 2.32 | 3.2E-28 | 2.70 | 2.9E-16 | 2.76 | 8.2E-14 | 2.06 | 1.6E-04 |
| PI(32:1)/PC(O-34:0) | 2.22 | 1.3E-32 | 2.05 | 6.9E-23 | 2.87 | 9.6E-17 | 2.70 | 4.5E-13 | 2.02 | 3.4E-04 |
| Cer(d18:1/20:0)/SM(37:1) | 2.33 | 1.3E-32 | 2.51 | 3.9E-29 | 2.95 | 3.1E-16 | 3.09 | 1.4E-13 | 2.09 | 5.2E-04 |
| PC(36:3)/PC(P-40:2) | 2.31 | 1.3E-32 | 2.32 | 2.2E-26 | 2.87 | 2.7E-16 | 2.97 | 1.0E-13 | 1.83 | 5.5E-04 |
| SM(d18:0/22:0)/LPC(O-24:1) | 2.29 | 1.4E-32 | 2.38 | 1.2E-27 | 3.21 | 1.0E-18 | 3.64 | 8.0E-17 | 1.88 | 1.5E-03 |
| PC(32:1)/PC(O-40:6) | 2.18 | 1.4E-32 | 2.15 | 5.6E-25 | 2.54 | 9.8E-16 | 2.61 | 5.1E-13 | 1.88 | 6.9E-04 |
| SM(38:0)/Gb3(d18:1/16:0) | 2.33 | 1.4E-32 | 2.47 | 1.1E-28 | 3.23 | 1.1E-17 | 3.54 | 2.2E-15 | 2.21 | 2.2E-04 |
| SM(36:0)/LPC(O-20:0) | 2.17 | 1.4E-32 | 2.21 | 2.9E-27 | 3.13 | 3.7E-21 | 3.34 | 1.2E-18 | 2.82 | 4.8E-08 |
| Cer(d18:1/18:0)/PC(O-38:0) | 2.34 | 1.5E-32 | 2.52 | 8.7E-29 | 2.95 | 2.3E-17 | 3.12 | 7.4E-15 | 2.45 | 5.8E-06 |
| PI(32:1)/LPC(MHDA) [sn2] | 2.16 | 1.6E-32 | 2.00 | 1.1E-22 | 2.80 | 6.1E-19 | 2.60 | 1.5E-14 | 2.10 | 4.7E-05 |
| DAG(18:1/18:1)/PC(17:0_22:6) | 2.30 | 1.7E-32 | 2.45 | 7.8E-29 | 2.44 | 8.5E-13 | 2.68 | 6.6E-12 | 1.79 | 4.5E-03 |
| DAG(14:0/18:1)/LPC(18:2) [sn2] | 2.31 | 1.8E-32 | 2.44 | 1.9E-28 | 3.08 | 6.1E-17 | 3.14 | 4.4E-14 | 2.14 | 3.4E-04 |
| SM(36:0)/LPC(20:1) [sn1] | 2.26 | 1.8E-32 | 2.35 | 6.4E-28 | 3.51 | 1.7E-20 | 3.82 | 3.5E-18 | 2.63 | 3.1E-06 |
| PI(32:1)/SM(41:2) | 2.20 | 1.8E-32 | 2.04 | 1.8E-22 | 2.79 | 9.5E-17 | 2.65 | 6.0E-13 | 1.93 | 7.9E-04 |
| SM(d18:0/22:0)/LPC(22:0) [sn2] | 2.29 | 1.9E-32 | 2.39 | 5.2E-28 | 3.47 | 3.9E-20 | 3.96 | 2.8E-18 | 2.10 | 3.0E-04 |
| SM(38:0)/PC(O-34:1) | 2.31 | 2.0E-32 | 2.42 | 3.1E-28 | 3.37 | 3.0E-18 | 3.64 | 3.0E-16 | 2.72 | 6.6E-06 |
| PI(40:5)/LacCer(d18:1/24:1) | 2.34 | 2.1E-32 | 2.13 | 4.3E-22 | 2.86 | 5.5E-15 | 2.57 | 2.1E-10 | 1.78 | 4.7E-03 |
| DAG(14:0/18:1)/PC(O-34:0) | 2.30 | 2.1E-32 | 2.39 | 1.4E-27 | 2.75 | 3.5E-14 | 2.80 | 7.5E-12 | 2.05 | 6.7E-04 |
| DAG(16:1/18:1)/LPC(22:0) [sn2] | 2.30 | 2.3E-32 | 2.34 | 6.2E-27 | 2.96 | 5.0E-17 | 3.08 | 8.5E-15 | 2.24 | 9.4E-05 |
| PC(38:4)/SM(37:2) | 2.27 | 2.3E-32 | 2.46 | 1.4E-29 | 3.14 | 1.4E-18 | 3.20 | 3.0E-15 | 1.78 | 3.9E-03 |
| DAG(14:0/18:1)/PC(O-34:2) | 2.32 | 2.4E-32 | 2.42 | 1.0E-27 | 3.07 | 5.5E-16 | 3.06 | 7.0E-13 | 2.11 | 5.2E-04 |
| Cer(d18:1/24:1)/LPC(20:1) [sn2] | 2.29 | 2.5E-32 | 2.38 | 3.3E-27 | 3.08 | 2.0E-17 | 3.38 | 1.3E-15 | 1.97 | 7.5E-04 |
| DAG(14:0/18:1)/LPC(O-18:1) | 2.28 | 2.6E-32 | 2.32 | 1.1E-26 | 2.86 | 1.4E-15 | 2.81 | 1.0E-12 | 1.96 | 1.2E-03 |
| SM(41:0)/SM(37:1) | 2.29 | 2.6E-32 | 2.35 | 4.0E-27 | 3.13 | 8.9E-18 | 3.45 | 8.7E-16 | 1.97 | 1.0E-03 |
| DAG(14:0/18:1)/PC(O-38:2) | 2.28 | 2.7E-32 | 2.35 | 6.1E-27 | 2.69 | 1.6E-14 | 2.73 | 5.3E-12 | 2.03 | 5.5E-04 |
| DAG(18:0/18:2)/PC(O-38:0) | 2.27 | 2.7E-32 | 2.46 | 3.8E-29 | 2.63 | 7.6E-15 | 2.80 | 6.4E-13 | 2.33 | 1.7E-05 |
| DAG(18:1/18:1)/PC(O-36:3) | 2.26 | 3.0E-32 | 2.45 | 2.4E-29 | 2.74 | 2.0E-15 | 2.88 | 3.2E-13 | 2.00 | 7.4E-04 |
| DAG(14:0/18:1)/SM(41:2) | 2.28 | 3.0E-32 | 2.35 | 4.7E-27 | 2.67 | 3.1E-14 | 2.69 | 9.3E-12 | 1.93 | 1.5E-03 |
| DAG(16:1/18:1)/LPC(17:0) [sn1] | 2.25 | 3.2E-32 | 2.22 | 2.3E-25 | 2.81 | 9.0E-17 | 2.86 | 5.8E-14 | 2.11 | 1.5E-04 |
| DAG(16:1/16:1)/SM(37:2) | 2.25 | 3.2E-32 | 2.19 | 1.2E-24 | 2.99 | 7.3E-18 | 2.97 | 1.8E-14 | 1.96 | 6.8E-04 |
| SM(d18:0/22:0)/PC(O-32:0) | 2.31 | 3.5E-32 | 2.42 | 7.2E-28 | 3.03 | 1.2E-16 | 3.46 | 1.3E-15 | 1.87 | 2.5E-03 |
| DAG(18:1/18:1)/LacCer(d18:1/16:0) | 2.21 | 3.5E-32 | 2.40 | 1.1E-29 | 2.42 | 4.0E-14 | 2.63 | 5.1E-13 | 1.86 | 1.3E-03 |
| DAG(16:1/18:1)/LPC(O-24:1) | 2.26 | 3.6E-32 | 2.28 | 2.3E-26 | 2.77 | 1.1E-15 | 2.85 | 1.5E-13 | 2.04 | 4.1E-04 |
| DAG(16:0/18:2)/PC(O-36:3) | 2.28 | 3.6E-32 | 2.44 | 5.1E-29 | 2.94 | 4.0E-16 | 3.06 | 8.1E-14 | 2.39 | 3.8E-05 |
| DAG(18:1/20:4)/LPC(O-18:1) | 2.22 | 3.8E-32 | 2.31 | 6.2E-28 | 2.64 | 1.6E-15 | 2.68 | 3.6E-13 | 1.78 | 4.0E-03 |
| DAG(16:1/16:1)/SM(37:1) | 2.24 | 3.8E-32 | 2.13 | 1.2E-23 | 2.77 | 2.1E-16 | 2.73 | 3.5E-13 | 1.82 | 1.9E-03 |
| SM(38:1)/PC(P-36:2) | 2.32 | 3.8E-32 | 2.46 | 2.7E-28 | 3.69 | 6.9E-19 | 3.71 | 2.2E-15 | 2.68 | 1.1E-05 |
| SM(36:0)/PC(O-38:2) | 2.18 | 3.9E-32 | 2.22 | 1.3E-26 | 2.83 | 3.0E-19 | 3.00 | 6.2E-17 | 2.69 | 6.0E-08 |
| SM(36:0)/LPC(P-18:0) | 2.16 | 3.9E-32 | 2.18 | 2.1E-26 | 3.18 | 2.5E-21 | 3.18 | 9.8E-18 | 2.66 | 2.5E-07 |
| DAG(14:0/18:1)/PC(39:4) | 2.32 | 3.9E-32 | 2.38 | 5.6E-27 | 2.86 | 1.1E-14 | 2.94 | 1.5E-12 | 2.02 | 1.0E-03 |
| DAG(16:1/16:1)/LPC(MHDA) [sn2] | 2.21 | 3.9E-32 | 2.08 | 4.8E-23 | 2.94 | 1.4E-18 | 2.84 | 1.4E-14 | 2.15 | 3.3E-05 |
| PC(32:1)/PC(35:2) | 2.18 | 4.1E-32 | 2.11 | 4.0E-24 | 3.04 | 4.3E-19 | 3.05 | 4.7E-15 | 2.10 | 6.0E-05 |
| DAG(16:1/16:1)/PC(34:3) | 2.26 | 4.2E-32 | 2.23 | 2.5E-25 | 3.04 | 1.4E-17 | 3.06 | 8.7E-15 | 2.03 | 4.8E-04 |
| DAG(16:1/18:1)/LPC(24:0) [sn2] | 2.28 | 4.3E-32 | 2.36 | 3.3E-27 | 2.89 | 2.9E-16 | 3.09 | 1.7E-14 | 2.22 | 1.1E-04 |
| Cer(d18:1/22:0)/PC(35:3) | 2.34 | 4.4E-32 | 2.48 | 8.9E-28 | 3.06 | 9.1E-16 | 3.23 | 2.5E-13 | 1.79 | 6.1E-03 |
| Cer(d16:1/18:0)/LPC(O-22:0) | 2.37 | 4.5E-32 | 2.59 | 4.3E-29 | 3.54 | 8.3E-19 | 3.84 | 4.0E-16 | 2.66 | 1.3E-05 |
| DAG(16:1/18:1)/PC(O-32:1) | 2.30 | 4.5E-32 | 2.42 | 9.0E-28 | 2.68 | 6.6E-14 | 2.84 | 2.4E-12 | 1.95 | 2.0E-03 |
| DAG(16:1/16:1)/PC(38:7) | 2.24 | 4.5E-32 | 2.21 | 2.2E-25 | 2.93 | 1.5E-17 | 2.92 | 2.2E-14 | 1.81 | 2.6E-03 |
| Cer(d18:1/22:0)/Glc/GalCer(d18:2/22:0) | 2.25 | 4.7E-32 | 2.22 | 6.1E-25 | 2.40 | 1.8E-12 | 2.44 | 2.0E-10 | 1.79 | 4.2E-03 |
| DAG(16:1/16:1)/PC(35:2) | 2.28 | 4.7E-32 | 2.21 | 1.7E-24 | 3.30 | 1.1E-18 | 3.34 | 3.7E-15 | 2.28 | 3.6E-05 |
| DAG(18:1/18:1)/Gb3(d18:1/16:0) | 2.20 | 4.8E-32 | 2.39 | 1.5E-29 | 2.48 | 1.4E-14 | 2.68 | 4.1E-13 | 1.69 | 7.0E-03 |
| PI(40:5)/PC(O-36:3) | 2.30 | 4.9E-32 | 2.16 | 6.2E-23 | 2.91 | 6.7E-16 | 2.55 | 5.0E-11 | 2.02 | 6.2E-04 |
| PI(32:1)/LPC(24:0) [sn1] | 2.21 | 5.1E-32 | 2.07 | 3.9E-23 | 2.92 | 4.0E-18 | 2.80 | 1.3E-14 | 2.12 | 1.1E-04 |
| PC(32:1)/SM(d17:1/14:0) | 2.16 | 5.1E-32 | 2.04 | 1.1E-22 | 2.55 | 2.1E-16 | 2.59 | 1.2E-12 | 1.70 | 3.0E-03 |
| DAG(16:1/18:1)/LPC(20:2) [sn2] | 2.30 | 5.4E-32 | 2.42 | 9.5E-28 | 2.88 | 1.0E-15 | 3.05 | 1.3E-13 | 2.15 | 2.3E-04 |
| DAG(16:0/18:2)/LacCer(d18:1/16:0) | 2.23 | 5.4E-32 | 2.41 | 2.9E-29 | 2.58 | 1.1E-14 | 2.80 | 2.2E-13 | 2.21 | 5.5E-05 |
| DAG(18:1/18:1)/LPC(P-18:0) | 2.20 | 5.5E-32 | 2.30 | 4.8E-28 | 2.75 | 5.4E-17 | 2.84 | 2.0E-14 | 2.03 | 1.5E-04 |
| Cer(d18:1/24:1)/LPC(19:0) [sn1] | 2.22 | 5.5E-32 | 2.18 | 5.3E-25 | 3.02 | 3.1E-19 | 3.10 | 2.6E-16 | 2.38 | 2.7E-06 |
| DAG(14:0/18:1)/LacCer(d18:1/24:1) | 2.29 | 5.7E-32 | 2.36 | 8.6E-27 | 2.74 | 2.6E-14 | 2.77 | 9.5E-12 | 1.87 | 3.1E-03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| SM(d18:0/22:0)/PC(P-40:2) | 2.27 | 5.9E−32 | 2.41 | 7.6E−28 | 2.89 | 2.8E−16 | 3.18 | 9.3E−15 | 1.91 | 8.1E−04 |
| CE(16:1)/SM(d17:1/14:0) | 2.17 | 5.9E−32 | 2.08 | 3.2E−23 | 2.60 | 4.7E−16 | 2.69 | 4.9E−13 | 1.65 | 6.9E−03 |
| DAG(16:0/22:6)/PC(P-36:2) | 2.30 | 6.1E−32 | 2.33 | 9.5E−26 | 3.42 | 2.6E−18 | 3.42 | 1.1E−14 | 2.91 | 6.7E−07 |
| CE(16:1)/CE(18:1) | 2.17 | 6.2E−32 | 2.05 | 4.0E−23 | 2.79 | 1.7E−17 | 2.75 | 4.2E−14 | 1.81 | 1.3E−03 |
| PC(38:5)/PC(O-40:6) | 2.26 | 6.5E−32 | 2.25 | 9.6E−26 | 2.61 | 5.8E−14 | 2.48 | 9.4E−11 | 2.43 | 1.9E−05 |
| DAG(18:1/18:1)/PC(33:2) | 2.23 | 6.5E−32 | 2.41 | 4.3E−29 | 2.49 | 4.7E−14 | 2.72 | 7.3E−13 | 1.89 | 1.5E−03 |
| DAG(16:0/18:2)/PC(O-34:1) | 2.25 | 6.8E−32 | 2.42 | 4.0E−29 | 2.78 | 1.8E−15 | 3.04 | 5.3E−14 | 2.30 | 5.1E−05 |
| PI(32:1)/PC(O-34:2) | 2.22 | 6.8E−32 | 2.07 | 1.7E−22 | 3.18 | 4.8E−18 | 2.95 | 1.3E−13 | 2.07 | 3.3E−04 |
| DAG(16:0/18:2)/SM(37:1) | 2.26 | 6.8E−32 | 2.41 | 1.2E−28 | 2.70 | 1.3E−14 | 2.90 | 5.2E−13 | 2.08 | 3.3E−04 |
| SM(36:0)/LPC(MHDA) [sn2] | 2.19 | 7.0E−32 | 2.19 | 6.2E−26 | 3.18 | 3.1E−21 | 3.18 | 1.0E−17 | 2.80 | 1.7E−08 |
| PI(32:1)/LPC(19:0) [sn2] | 2.18 | 7.1E−32 | 2.03 | 5.7E−23 | 2.86 | 5.1E−19 | 2.75 | 2.9E−15 | 1.97 | 2.3E−04 |
| Cer(d18:1/20:0)/SM(37:2) | 2.29 | 7.1E−32 | 2.59 | 1.4E−30 | 3.32 | 7.9E−19 | 3.48 | 9.4E−16 | 2.28 | 4.2E−05 |
| Cer(d18:1/24:1)/LPC(O-20:1) | 2.24 | 7.3E−32 | 2.26 | 9.0E−26 | 3.00 | 7.1E−18 | 3.17 | 4.0E−15 | 2.16 | 5.8E−05 |
| CE(16:1)/LacCer(d18:1/16:0) | 2.20 | 7.4E−32 | 2.11 | 1.5E−23 | 2.68 | 1.4E−15 | 2.70 | 6.4E−13 | 1.72 | 4.6E−03 |
| SM(38:0)/PC(O-36:2) | 2.25 | 7.6E−32 | 2.32 | 3.9E−27 | 3.32 | 3.4E−19 | 3.35 | 5.0E−16 | 2.63 | 2.2E−06 |
| PC(32:1)/PC(31:0) | 2.17 | 7.6E−32 | 2.10 | 2.3E−23 | 2.49 | 1.8E−15 | 2.67 | 1.0E−12 | 1.85 | 7.1E−04 |
| DAG(16:1/16:1)/LPC(19:0) [sn2] | 2.22 | 7.7E−32 | 2.10 | 2.0E−23 | 2.97 | 6.2E−19 | 2.94 | 1.8E−15 | 2.02 | 1.6E−04 |
| DAG(14:0/18:1)/LPC(18:2) [sn1] | 2.26 | 7.8E−32 | 2.37 | 9.5E−28 | 3.00 | 5.0E−17 | 3.04 | 3.5E−14 | 2.20 | 1.6E−04 |
| SM(36:0)/PC(35:3) | 2.20 | 7.8E−32 | 2.32 | 4.5E−26 | 3.01 | 1.4E−19 | 3.22 | 3.6E−17 | 2.53 | 3.7E−07 |
| DAG(14:0/18:1)/LPC(P-16:0) | 2.25 | 8.2E−32 | 2.31 | 5.7E−27 | 2.77 | 5.9E−16 | 2.78 | 2.6E−13 | 1.97 | 7.9E−04 |
| DAG(16:0/18:2)/LPC(O-20:0) | 2.21 | 8.5E−32 | 2.32 | 5.5E−28 | 2.81 | 1.5E−16 | 3.04 | 5.4E−15 | 2.45 | 3.4E−06 |
| DAG(16:1/18:1)/LPC(15:0) [sn2] | 2.24 | 8.6E−32 | 2.23 | 2.8E−25 | 2.72 | 4.8E−16 | 2.79 | 2.8E−13 | 1.96 | 5.4E−04 |
| DAG(16:0/18:2)/LPC(24:0) [sn2] | 2.23 | 8.9E−32 | 2.45 | 4.0E−30 | 2.86 | 6.8E−17 | 3.28 | 6.5E−16 | 2.48 | 5.3E−06 |
| SM(36:0)/PC(O-38:0) | 2.19 | 9.0E−32 | 2.29 | 1.0E−27 | 3.01 | 9.8E−20 | 3.20 | 6.7E−18 | 2.91 | 4.0E−08 |
| Cer(d16:1/18:0)/PC(O-34:0) | 2.42 | 9.3E−32 | 2.67 | 1.3E−28 | 3.28 | 4.8E−16 | 3.47 | 3.0E−13 | 2.56 | 4.3E−05 |
| SM(d18:0/22:0)/PC(35:3) | 2.31 | 9.4E−32 | 2.44 | 4.2E−28 | 3.27 | 4.4E−18 | 3.64 | 2.3E−16 | 1.88 | 2.2E−03 |
| DAG(16:1/16:1)/PC(O-32:1) | 2.25 | 9.6E−32 | 2.17 | 3.7E−24 | 2.82 | 9.3E−16 | 2.82 | 4.6E−13 | 1.88 | 1.9E−03 |
| DAG(16:0/22:6)/LPC(22:6) [sn1] | 2.27 | 9.7E−32 | 2.32 | 2.3E−26 | 3.03 | 3.9E−17 | 3.01 | 5.1E−14 | 2.85 | 6.5E−07 |
| Cer(d16:1/18:0)/LPC(O-24:1) | 2.36 | 1.0E−31 | 2.54 | 1.9E−28 | 3.44 | 4.4E−18 | 3.56 | 3.4E−15 | 2.36 | 1.3E−04 |
| DAG(14:0/18:2)/LPC(19:0) [sn1] | 2.26 | 1.0E−31 | 2.33 | 9.4E−27 | 2.78 | 2.0E−15 | 2.83 | 7.1E−13 | 2.53 | 1.4E−05 |
| PI(32:1)/PC(37:1) | 2.20 | 1.1E−31 | 2.02 | 7.6E−22 | 2.88 | 5.8E−17 | 2.73 | 2.8E−13 | 1.98 | 4.4E−04 |
| Cer(d18:1/18:0)/LPC(O-24:0) | 2.24 | 1.1E−31 | 2.34 | 1.4E−27 | 2.90 | 8.6E−18 | 2.97 | 2.4E−15 | 2.25 | 1.1E−05 |
| DAG(14:0/18:2)/LPC(19:0) [sn2] | 2.25 | 1.1E−31 | 2.36 | 1.3E−27 | 2.79 | 3.9E−16 | 2.89 | 9.2E−14 | 2.32 | 3.7E−05 |
| AcylCarnitine(16:0)/LPC(P-18:0) | 2.24 | 1.1E−31 | 2.18 | 4.2E−24 | 3.30 | 3.7E−19 | 3.13 | 9.9E−15 | 2.03 | 4.3E−04 |
| PI(32:1)/LPC(O-24:1) | 2.17 | 1.1E−31 | 2.01 | 2.4E−22 | 2.82 | 2.6E−17 | 2.66 | 1.1E−13 | 1.93 | 6.2E−04 |
| DAG(16:0/18:2)/LPC(P-18:0) | 2.19 | 1.1E−31 | 2.28 | 1.1E−27 | 2.81 | 1.9E−17 | 2.89 | 7.3E−15 | 2.34 | 8.5E−06 |
| SM(d18:0/22:0)/PC(P-40:4) | 2.29 | 1.1E−31 | 2.37 | 5.3E−27 | 3.48 | 1.3E−18 | 4.04 | 4.8E−17 | 2.12 | 3.4E−04 |
| DAG(16:1/16:1)/PC(O-34:1) | 2.22 | 1.2E−31 | 2.12 | 2.0E−23 | 2.85 | 1.1E−16 | 2.84 | 1.2E−13 | 1.96 | 6.0E−04 |
| PI(32:1)/LPC(20:2) [sn1] | 2.20 | 1.2E−31 | 2.07 | 5.0E−23 | 2.96 | 4.2E−18 | 2.80 | 3.8E−14 | 2.06 | 2.5E−04 |
| DAG(18:1/20:4)/SM(d17:1/14:0) | 2.26 | 1.2E−31 | 2.36 | 1.7E−27 | 2.55 | 8.7E−14 | 2.57 | 1.2E−11 | 1.72 | 8.7E−03 |
| SM(38:0)/Gb3(d18:1/22:0) | 2.25 | 1.3E−31 | 2.41 | 1.8E−28 | 2.56 | 1.9E−14 | 2.62 | 2.4E−12 | 2.03 | 2.3E−04 |
| DAG(18:1/20:4)/LPC(20:2) [sn1] | 2.24 | 1.3E−31 | 2.48 | 4.3E−30 | 2.69 | 2.4E−15 | 2.83 | 1.6E−13 | 1.94 | 1.1E−03 |
| Cer(d18:1/24:1)/Gb3(d18:1/16:0) | 2.20 | 1.3E−31 | 2.26 | 6.8E−27 | 2.48 | 6.4E−15 | 2.53 | 6.8E−13 | 1.65 | 9.8E−03 |
| DAG(16:1/16:1)/Gb3(d18:1/16:0) | 2.21 | 1.3E−31 | 2.13 | 1.5E−23 | 2.77 | 2.0E−16 | 2.74 | 3.2E−13 | 1.80 | 2.8E−03 |
| PC(38:2)/LPC(O-24:2) | 2.23 | 1.3E−31 | 2.21 | 4.3E−25 | 2.88 | 5.1E−17 | 2.88 | 4.6E−14 | 2.14 | 1.8E−04 |
| DAG(14:0/18:1)/PC(P-32:0) | 2.29 | 1.3E−31 | 2.41 | 2.8E−27 | 2.83 | 2.5E−14 | 2.93 | 3.7E−12 | 2.01 | 1.2E−03 |
| PI(32:1)/LPC(24:0) [sn2] | 2.20 | 1.4E−31 | 2.05 | 8.4E−23 | 2.89 | 6.1E−18 | 2.79 | 1.3E−14 | 2.05 | 1.8E−04 |
| PI(32:1)/PC(36:7) | 2.24 | 1.4E−31 | 2.17 | 3.5E−24 | 3.35 | 7.4E−19 | 3.54 | 3.8E−16 | 2.83 | 7.5E−07 |
| DAG(16:1/16:1)/Gb3(d18:1/22:0) | 2.21 | 1.4E−31 | 2.16 | 3.4E−24 | 2.59 | 3.7E−15 | 2.50 | 7.3E−12 | 1.83 | 2.3E−03 |
| DAG(16:1/18:1)/LPC(24:0) [sn1] | 2.26 | 1.4E−31 | 2.34 | 6.4E−27 | 2.85 | 6.1E−16 | 3.05 | 4.0E−14 | 2.27 | 8.5E−05 |
| PI(40:5)/SM(34:1) | 2.31 | 1.4E−31 | 2.11 | 1.8E−21 | 2.77 | 2.6E−14 | 2.41 | 1.6E−09 | 1.72 | 9.4E−03 |
| SM(36:0)/LPC(O-22:0) | 2.14 | 1.5E−31 | 2.21 | 4.3E−27 | 3.01 | 8.2E−21 | 3.27 | 9.4E−19 | 2.72 | 8.9E−08 |
| DAG(16:1/16:1)/SM(d17:1/14:0) | 2.21 | 1.5E−31 | 2.10 | 8.3E−23 | 2.75 | 1.8E−16 | 2.74 | 5.7E−13 | 1.88 | 8.9E−04 |
| PC(36:4)/PC(O-36:2) | 2.30 | 1.5E−31 | 2.28 | 7.4E−25 | 3.62 | 4.7E−18 | 3.47 | 2.7E−14 | 2.47 | 2.1E−05 |
| PC(38:1)/PC(P-36:2) | 2.26 | 1.6E−31 | 2.33 | 1.4E−26 | 3.45 | 7.5E−20 | 3.32 | 1.8E−15 | 2.57 | 3.4E−06 |
| DAG(16:1/18:1)/LPC(20:2) [sn1] | 2.27 | 1.6E−31 | 2.36 | 4.7E−27 | 2.89 | 6.6E−16 | 3.03 | 1.5E−13 | 2.19 | 1.7E−04 |
| PC(38:2)/PC(O-36:2) | 2.25 | 1.6E−31 | 2.26 | 1.2E−25 | 3.38 | 5.0E−19 | 3.12 | 2.2E−14 | 2.28 | 1.5E−05 |
| PI(32:1)/LPC(O-20:1) | 2.16 | 1.6E−31 | 2.01 | 2.9E−22 | 2.79 | 1.7E−17 | 2.63 | 9.4E−14 | 1.96 | 4.6E−04 |
| DAG(14:0/18:1)/PC(P-40:4) | 2.29 | 1.6E−31 | 2.37 | 8.3E−27 | 2.93 | 4.6E−15 | 3.01 | 8.0E−13 | 2.15 | 3.4E−04 |
| DAG(14:0/18:1)/LPC(O-24:0) | 2.26 | 1.6E−31 | 2.36 | 4.8E−27 | 2.79 | 6.9E−15 | 2.91 | 8.2E−13 | 2.07 | 5.2E−04 |
| DAG(14:0/18:1)/PC(O-40:3) | 2.27 | 1.6E−31 | 2.41 | 8.9E−28 | 2.64 | 5.9E−14 | 2.82 | 3.9E−12 | 1.90 | 1.9E−03 |
| PC(36:3)/LacCer(d18:1/16:0) | 2.30 | 1.7E−31 | 2.26 | 8.8E−25 | 2.85 | 3.3E−15 | 2.89 | 6.5E−13 | 1.80 | 5.9E−03 |
| DAG(14:0/18:2)/PC(O-40:6) | 2.27 | 1.7E−31 | 2.41 | 7.3E−28 | 2.52 | 1.0E−12 | 2.59 | 6.7E−11 | 2.29 | 1.1E−04 |
| PE(36:1)/PC(O-36:3) | 2.19 | 1.7E−31 | 2.18 | 1.4E−25 | 2.68 | 3.2E−15 | 2.45 | 2.6E−11 | 1.92 | 1.0E−03 |
| PC(32:1)/Gb3(d18:1/22:0) | 2.17 | 1.7E−31 | 2.10 | 8.5E−24 | 2.44 | 4.2E−14 | 2.29 | 1.4E−10 | 1.67 | 8.0E−03 |
| DAG(16:1/18:1)/LPC(P-18:0) | 2.22 | 1.7E−31 | 2.21 | 2.6E−25 | 2.84 | 1.1E−16 | 2.83 | 1.3E−13 | 2.13 | 1.4E−04 |
| DAG(18:1/20:4)/PC(33:2) | 2.25 | 1.7E−31 | 2.40 | 3.0E−28 | 2.48 | 1.9E−13 | 2.57 | 6.4E−12 | 1.76 | 6.0E−03 |
| PI(32:1)/LPC(20:2) [sn2] | 2.20 | 1.8E−31 | 2.09 | 5.8E−23 | 2.98 | 8.2E−18 | 2.84 | 4.8E−14 | 2.02 | 4.0E−04 |
| PC(36:4)/LPC(O-24:2) | 2.27 | 1.9E−31 | 2.22 | 2.1E−24 | 3.03 | 1.7E−16 | 3.04 | 1.1E−13 | 2.28 | 1.2E−04 |
| PE(36:1)/PC(35:2) | 2.19 | 2.0E−31 | 2.20 | 4.5E−26 | 2.84 | 3.6E−16 | 2.65 | 2.7E−12 | 2.21 | 4.0E−05 |
| DAG(18:1/20:4)/PC(P-32:0) | 2.20 | 2.0E−31 | 2.37 | 9.6E−29 | 2.48 | 5.6E−14 | 2.64 | 1.4E−12 | 1.79 | 3.7E−03 |
| DAG(16:1/18:1)/PC(P-40:2) | 2.24 | 2.0E−31 | 2.31 | 1.8E−26 | 2.55 | 4.6E−14 | 2.64 | 4.7E−12 | 1.99 | 2.4E−04 |
| PC(40:5)/PC(O-40:6) | 2.19 | 2.0E−31 | 2.25 | 9.6E−27 | 2.16 | 3.1E−11 | 2.09 | 5.6E−09 | 1.68 | 5.8E−03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| PC(38:2)/SM(37:2) | 2.25 | 2.2E−31 | 2.41 | 9.7E−28 | 3.53 | 2.5E−19 | 3.43 | 3.2E−15 | 2.06 | 3.7E−04 |
| PE(40:5)/SM(37:2) | 2.19 | 2.2E−31 | 2.26 | 1.2E−26 | 2.48 | 4.7E−14 | 2.38 | 1.4E−10 | 1.78 | 3.5E−03 |
| SM(36:0)/LPC(19:0) [sn1] | 2.16 | 2.3E−31 | 2.17 | 1.3E−25 | 3.16 | 1.6E−20 | 3.29 | 8.9E−18 | 2.74 | 1.6E−07 |
| DAG(16:0/18:2)/LPC(15:0) [sn2] | 2.21 | 2.3E−31 | 2.30 | 4.4E−27 | 2.79 | 2.1E−16 | 2.90 | 4.0E−14 | 2.18 | 3.5E−05 |
| DAG(16:1/16:1)/PC(17:0_22:6) | 2.20 | 2.4E−31 | 2.12 | 3.4E−23 | 2.58 | 2.8E−15 | 2.64 | 1.3E−12 | 1.82 | 1.7E−03 |
| PC(32:1)/PC(O-36:3) | 2.19 | 2.5E−31 | 2.08 | 1.8E−22 | 2.92 | 5.9E−17 | 2.84 | 9.7E−13 | 1.89 | 1.2E−03 |
| DAG(16:1/16:1)/PC(37:2) | 2.23 | 2.5E−31 | 2.13 | 5.9E−23 | 2.93 | 5.5E−17 | 3.00 | 5.2E−14 | 2.07 | 2.3E−04 |
| DAG(18:1/18:1)/LPC(O-24:1) | 2.18 | 2.5E−31 | 2.32 | 2.7E−28 | 2.55 | 2.5E−15 | 2.77 | 5.5E−14 | 1.90 | 8.3E−04 |
| PI(32:1)/LPC(20:1) [sn1] | 2.20 | 2.6E−31 | 2.06 | 1.5E−22 | 2.91 | 1.3E−17 | 2.78 | 4.5E−14 | 1.92 | 9.7E−04 |
| Cer(d16:1/18:0)/SM(34:1) | 2.46 | 2.6E−31 | 2.77 | 5.4E−29 | 3.51 | 8.7E−17 | 3.64 | 1.2E−13 | 2.18 | 8.0E−04 |
| DAG(16:1/16:1)/LPE(16:0) [sn2] | 2.24 | 2.6E−31 | 2.19 | 5.5E−24 | 2.87 | 1.5E−16 | 3.01 | 4.2E−14 | 2.11 | 1.9E−04 |
| PE(40:6)/PC(O-40:6) | 2.17 | 2.7E−31 | 2.16 | 2.5E−25 | 2.85 | 5.8E−17 | 2.72 | 2.5E−13 | 2.67 | 1.4E−06 |
| CE(16:1)/PC(P-32:0) | 2.18 | 3.0E−31 | 2.07 | 1.1E−22 | 2.67 | 5.8E−16 | 2.72 | 3.7E−13 | 1.76 | 3.2E−03 |
| DAG(18:1/20:4)/LPC(15:0) [sn2] | 2.22 | 3.0E−31 | 2.31 | 3.3E−27 | 2.71 | 1.5E−15 | 2.75 | 3.0E−13 | 1.75 | 5.6E−03 |
| DAG(18:1/20:4)/SM(41:2) | 2.17 | 3.0E−31 | 2.27 | 9.3E−28 | 2.32 | 2.7E−13 | 2.37 | 1.1E−11 | 1.70 | 6.2E−03 |
| PI(32:1)/PC(O-38:0) | 2.19 | 3.1E−31 | 2.04 | 5.9E−22 | 2.89 | 1.3E−16 | 2.73 | 4.1E−13 | 2.08 | 2.5E−04 |
| Cer(d18:1/20:0)/PC(O-36:2) | 2.24 | 3.2E−31 | 2.41 | 6.5E−28 | 3.11 | 1.3E−18 | 3.15 | 7.0E−15 | 2.37 | 3.6E−06 |
| DAG(18:1/20:4)/LPC(P-16:0) | 2.15 | 3.5E−31 | 2.26 | 6.4E−28 | 2.56 | 7.3E−16 | 2.64 | 8.6E−14 | 1.79 | 2.6E−03 |
| DAG(14:0/18:1)/PC(O-32:0) | 2.26 | 3.6E−31 | 2.35 | 8.4E−27 | 2.66 | 1.5E−13 | 2.74 | 1.4E−11 | 1.97 | 1.4E−03 |
| DAG(18:1/18:1)/LPC(24:0) [sn2] | 2.19 | 3.6E−31 | 2.41 | 1.3E−29 | 2.66 | 5.3E−16 | 3.01 | 3.7E−15 | 2.06 | 2.1E−04 |
| LPC(16:0) [sn2]/LPC(19:0) [sn2] | 2.28 | 3.8E−31 | 2.25 | 5.3E−24 | 2.30 | 1.2E−15 | 2.31 | 1.1E−12 | 1.61 | 8.2E−04 |
| PE(40:5)/PC(35:3) | 2.19 | 3.9E−31 | 2.22 | 9.2E−26 | 2.39 | 8.0E−13 | 2.25 | 1.6E−09 | 1.83 | 2.2E−03 |
| Cer(d16:1/18:0)/PC(P-32:0) | 2.41 | 3.9E−31 | 2.70 | 8.6E−29 | 3.51 | 1.6E−16 | 3.77 | 6.2E−14 | 2.49 | 1.3E−04 |
| PC(32:1)/PC(37:2) | 2.22 | 4.0E−31 | 2.09 | 3.5E−22 | 2.93 | 6.2E−17 | 3.04 | 8.9E−14 | 1.96 | 4.4E−04 |
| PI(40:5)/SM(41:2) | 2.23 | 4.0E−31 | 2.06 | 6.0E−21 | 2.47 | 1.8E−13 | 2.29 | 3.5E−09 | 1.86 | 1.6E−03 |
| DAG(18:0/18:2)/LPC(18:1) [sn2] | 2.21 | 4.2E−31 | 2.46 | 6.4E−30 | 2.85 | 5.5E−17 | 3.03 | 6.2E−15 | 2.56 | 2.4E−06 |
| SM(36:0)/PC(39:4) | 2.21 | 4.4E−31 | 2.25 | 6.3E−26 | 3.12 | 1.2E−19 | 3.46 | 7.0E−18 | 2.72 | 2.7E−07 |
| Cer(d18:1/22:0)/LPC(O-24:1) | 2.23 | 4.4E−31 | 2.25 | 2.4E−25 | 2.87 | 2.6E−16 | 3.02 | 7.4E−14 | 1.76 | 4.5E−03 |
| CE(16:1)/PC(O-36:3) | 2.22 | 4.4E−31 | 2.13 | 8.6E−23 | 2.93 | 1.5E−16 | 2.92 | 6.6E−13 | 1.82 | 2.8E−03 |
| DAG(16:1/16:1)/LPE(16:0) [sn1] | 2.24 | 4.9E−31 | 2.19 | 9.1E−24 | 2.88 | 1.7E−16 | 3.09 | 3.2E−14 | 2.09 | 2.2E−04 |
| PC(38:2)/PC(O-34:1) | 2.23 | 5.1E−31 | 2.26 | 1.7E−25 | 3.09 | 2.1E−17 | 3.03 | 6.9E−14 | 2.23 | 1.7E−04 |
| DAG(18:1/20:4)/LPC(20:2) [sn2] | 2.21 | 5.2E−31 | 2.48 | 4.5E−30 | 2.57 | 1.8E−14 | 2.74 | 5.2E−13 | 1.84 | 2.6E−03 |
| Cer(d18:1/16:0)/LPC(O-22:1) | 2.22 | 5.2E−31 | 2.22 | 9.5E−25 | 2.82 | 1.1E−16 | 2.89 | 3.9E−14 | 2.08 | 1.0E−04 |
| DAG(16:0/18:2)/LPC(20:2) [sn2] | 2.21 | 5.3E−31 | 2.49 | 2.4E−30 | 2.78 | 6.4E−16 | 3.08 | 1.1E−14 | 2.39 | 1.2E−05 |
| DAG(16:1/18:1)/LPC(15:0) [sn1] | 2.21 | 5.3E−31 | 2.22 | 8.7E−25 | 2.72 | 5.6E−16 | 2.84 | 2.1E−13 | 2.10 | 1.5E−04 |
| DAG(16:0/22:6)/LPC(O-22:1) | 2.22 | 5.3E−31 | 2.21 | 1.7E−24 | 3.07 | 1.8E−17 | 3.16 | 1.5E−14 | 2.77 | 9.4E−07 |
| Cer(d18:2/18:0)/SM(37:2) | 2.32 | 5.3E−31 | 2.73 | 1.5E−31 | 3.55 | 2.6E−18 | 3.69 | 1.8E−15 | 1.85 | 4.7E−03 |
| DAG(16:0/18:2)/LPC(O-24:1) | 2.19 | 5.4E−31 | 2.32 | 6.1E−28 | 2.69 | 9.8E−16 | 2.93 | 2.7E−14 | 2.23 | 4.3E−05 |
| CE(16:1)/PC(O-38:0) | 2.20 | 5.4E−31 | 2.09 | 1.6E−22 | 2.75 | 5.7E−16 | 2.80 | 3.1E−13 | 1.89 | 8.2E−04 |
| DAG(16:0/22:6)/PC(P-38:6) | 2.27 | 5.5E−31 | 2.30 | 3.1E−25 | 3.20 | 4.0E−17 | 3.23 | 4.7E−14 | 2.69 | 3.9E−06 |
| PI(40:5)/LPC(O-18:0) | 2.23 | 5.6E−31 | 2.03 | 1.1E−20 | 3.09 | 4.5E−17 | 2.80 | 2.1E−12 | 2.34 | 2.4E−05 |
| PI(40:5)/LPC(P-16:0) | 2.22 | 5.7E−31 | 2.05 | 2.2E−21 | 2.85 | 5.4E−17 | 2.60 | 1.6E−12 | 1.96 | 4.9E−04 |
| DAG(16:1/18:1)/LPC(O-22:0) | 2.20 | 5.7E−31 | 2.23 | 1.6E−25 | 2.71 | 1.8E−15 | 2.83 | 1.5E−13 | 2.13 | 1.5E−04 |
| SM(38:0)/LacCer(d18:1/16:0) | 2.26 | 6.2E−31 | 2.37 | 6.1E−27 | 3.03 | 2.6E−16 | 3.37 | 1.2E−14 | 2.48 | 1.1E−05 |
| DAG(18:1/20:4)/PC(O-38:2) | 2.16 | 6.3E−31 | 2.25 | 3.9E−27 | 2.35 | 1.7E−13 | 2.41 | 8.8E−12 | 1.82 | 2.0E−03 |
| SM(36:0)/PC(37:2) | 2.16 | 6.5E−31 | 2.22 | 3.2E−26 | 2.95 | 1.4E−18 | 3.15 | 1.3E−16 | 2.60 | 3.0E−07 |
| SM(41:0)/LPC(O-24:2) | 2.24 | 7.2E−31 | 2.29 | 9.5E−26 | 3.03 | 6.8E−18 | 3.44 | 3.7E−16 | 2.20 | 1.0E−04 |
| PI(40:5)/PC(39:4) | 2.29 | 7.2E−31 | 2.07 | 1.9E−20 | 2.87 | 1.7E−14 | 2.67 | 5.3E−11 | 2.01 | 8.8E−04 |
| Cer(d16:1/18:0)/LacCer(d18:1/24:1) | 2.35 | 7.3E−31 | 2.51 | 4.1E−27 | 3.06 | 9.4E−16 | 3.19 | 5.8E−13 | 2.06 | 8.3E−04 |
| Cer(d16:1/20:0)/LPC(O-24:2) | 2.31 | 7.4E−31 | 2.52 | 6.2E−28 | 2.92 | 3.6E−15 | 3.06 | 6.5E−13 | 2.47 | 3.5E−05 |
| PI(32:1)/LPC(20:1) [sn2] | 2.18 | 7.5E−31 | 2.04 | 4.1E−22 | 2.86 | 5.9E−17 | 2.74 | 1.7E−13 | 1.89 | 1.5E−03 |
| Cer(d18:1/24:1)/PC(O-36:2) | 2.17 | 7.6E−31 | 2.20 | 2.2E−25 | 2.71 | 1.9E−17 | 2.66 | 3.6E−14 | 2.11 | 6.4E−05 |
| Cer(d16:1/18:0)/LPC(20:0) [sn1] | 2.36 | 7.7E−31 | 2.53 | 3.8E−27 | 3.86 | 4.4E−19 | 4.00 | 5.2E−16 | 2.75 | 1.4E−05 |
| DAG(14:0/18:1)/PC(O-38:0) | 2.26 | 7.9E−31 | 2.37 | 1.7E−26 | 2.75 | 4.6E−14 | 2.87 | 7.1E−12 | 2.10 | 5.2E−04 |
| DAG(16:1/18:1)/LacCer(d18:1/24:1) | 2.23 | 8.2E−31 | 2.25 | 6.4E−25 | 2.62 | 4.1E−14 | 2.70 | 7.7E−12 | 1.89 | 2.0E−03 |
| Cer(d18:1/24:1)/LPC(P-18:1) | 2.18 | 8.2E−31 | 2.12 | 1.4E−23 | 2.54 | 3.9E−16 | 2.44 | 1.2E−12 | 1.73 | 2.5E−03 |
| DAG(16:1/16:1)/PC(33:2) | 2.18 | 8.3E−31 | 2.10 | 6.7E−23 | 2.66 | 4.6E−16 | 2.73 | 3.7E−13 | 1.90 | 7.6E−04 |
| SM(36:1)/LPC(O-24:2) | 2.26 | 8.4E−31 | 2.35 | 3.0E−26 | 3.05 | 7.6E−17 | 3.36 | 2.6E−15 | 2.36 | 1.5E−05 |
| DAG(16:1/18:1)/PC(39:4) | 2.24 | 8.5E−31 | 2.27 | 3.9E−25 | 2.74 | 1.6E−14 | 2.92 | 7.8E−13 | 2.05 | 5.5E−04 |
| CE(16:1)/LPC(MHDA) [sn2] | 2.12 | 8.5E−31 | 1.99 | 1.2E−21 | 2.80 | 9.9E−18 | 2.66 | 7.6E−14 | 1.98 | 1.9E−04 |
| DAG(18:1/20:4)/LPE(P-20:0) | 2.16 | 8.7E−31 | 2.28 | 2.1E−27 | 2.67 | 2.3E−16 | 2.74 | 6.0E−14 | 1.88 | 1.2E−03 |
| PI(32:1)/LPC(O-22:0) | 2.13 | 8.8E−31 | 1.97 | 1.1E−21 | 2.73 | 3.2E−17 | 2.61 | 9.0E−14 | 2.01 | 2.4E−04 |
| SM(36:1)/SM(37:2) | 2.20 | 9.8E−31 | 2.49 | 3.0E−30 | 3.30 | 5.3E−20 | 3.53 | 7.5E−18 | 2.30 | 2.4E−05 |
| DAG(16:0/18:2)/LPC(24:0) [sn1] | 2.19 | 9.9E−31 | 2.41 | 2.4E−29 | 2.79 | 2.2E−16 | 3.17 | 2.1E−15 | 2.51 | 4.4E−06 |
| PI(32:1)/PC(39:4) | 2.17 | 1.0E−30 | 2.00 | 2.8E−21 | 2.88 | 1.5E−16 | 2.78 | 2.5E−13 | 1.96 | 7.7E−04 |
| DAG(14:0/18:1)/CE(17:0) | 2.19 | 1.0E−30 | 2.27 | 2.2E−26 | 2.64 | 1.4E−14 | 2.64 | 4.3E−12 | 1.91 | 1.1E−03 |
| DAG(16:1/18:1)/PC(P-32:0) | 2.23 | 1.0E−30 | 2.30 | 1.1E−25 | 2.70 | 3.3E−14 | 2.86 | 2.2E−12 | 2.06 | 6.1E−04 |
| Cer(d18:1/18:0)/PC(O-34:2) | 2.21 | 1.0E−30 | 2.33 | 8.9E−27 | 3.03 | 1.3E−18 | 2.96 | 1.2E−14 | 2.21 | 3.8E−05 |
| PC(38:1)/PC(P-34:1) | 2.20 | 1.1E−30 | 2.30 | 1.5E−26 | 2.88 | 1.1E−16 | 2.92 | 6.1E−14 | 2.40 | 6.1E−06 |
| PC(32:1)/PC(P-40:2) | 2.16 | 1.1E−30 | 2.06 | 2.6E−22 | 2.60 | 1.7E−15 | 2.58 | 3.1E−12 | 1.77 | 5.8E−04 |
| PC(36:4)/SM(37:2) | 2.31 | 1.2E−30 | 2.36 | 2.4E−25 | 3.74 | 2.4E−17 | 3.61 | 7.0E−14 | 2.34 | 2.4E−04 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| DAG(16:0/18:2)/SM(d17:1/14:0) | 2.21 | 1.2E−30 | 2.31 | 1.3E−26 | 2.68 | 1.7E−14 | 2.80 | 1.6E−12 | 2.18 | 1.3E−04 |
| PI(32:1)/PC(P-40:4) | 2.15 | 1.2E−30 | 1.99 | 2.1E−21 | 2.87 | 4.7E−17 | 2.73 | 1.3E−13 | 2.07 | 2.2E−04 |
| DAG(16:1/16:1)/LacCer(d18:1/16:0) | 2.17 | 1.3E−30 | 2.07 | 1.7E−22 | 2.66 | 1.2E−15 | 2.62 | 1.1E−12 | 1.90 | 9.1E−04 |
| PI(32:1)/LPC(P-18:1) | 2.13 | 1.4E−30 | 1.96 | 4.2E−21 | 2.61 | 1.9E−16 | 2.43 | 1.8E−12 | 1.79 | 2.3E−03 |
| SM(d18:0/22:0)/PC(39:4) | 2.27 | 1.5E−30 | 2.32 | 1.8E−25 | 3.15 | 7.1E−17 | 3.64 | 1.2E−15 | 1.86 | 3.0E−03 |
| DAG(14:0/18:1)/LPC(O-16:0) | 2.20 | 1.5E−30 | 2.25 | 1.3E−25 | 2.76 | 3.6E−15 | 2.75 | 1.6E−12 | 1.93 | 1.3E−03 |
| SM(38:0)/PC(O-40:6) | 2.23 | 1.5E−30 | 2.37 | 4.9E−27 | 2.86 | 2.1E−15 | 3.18 | 4.7E−14 | 2.37 | 9.2E−06 |
| DAG(14:0/18:2)/LPC(MHDA) [sn1] | 2.19 | 1.6E−30 | 2.29 | 1.8E−26 | 2.72 | 2.3E−15 | 2.76 | 1.0E−12 | 2.53 | 5.4E−06 |
| Cer(d18:1/20:0)/PC(O-34:1) | 2.24 | 1.6E−30 | 2.44 | 5.6E−28 | 3.10 | 7.1E−17 | 3.33 | 1.4E−14 | 2.49 | 2.3E−05 |
| DAG(18:1/18:1)/LPC(O-22:0) | 2.14 | 1.6E−30 | 2.29 | 6.7E−28 | 2.54 | 2.4E−15 | 2.82 | 2.8E−14 | 2.00 | 2.1E−04 |
| PE(38:4)/LPC(20:2) [sn1] | 2.36 | 1.6E−30 | 2.54 | 7.8E−27 | 3.42 | 4.8E−17 | 3.48 | 6.2E−14 | 1.91 | 3.5E−03 |
| DAG(16:1/16:1)/LPC(20:1) [sn2] | 2.19 | 1.6E−30 | 2.09 | 2.1E−22 | 2.86 | 1.2E−16 | 2.83 | 1.4E−13 | 1.90 | 1.2E−03 |
| DAG(16:1/18:1)/PC(31:0) | 2.24 | 1.6E−30 | 2.32 | 1.4E−25 | 2.57 | 3.0E−13 | 2.80 | 1.6E−11 | 2.10 | 4.8E−04 |
| DAG(18:0/20:4)/LPC(19:0) [sn1] | 2.23 | 1.7E−30 | 2.25 | 4.4E−25 | 3.01 | 1.8E−17 | 3.19 | 3.0E−15 | 2.98 | 2.9E−07 |
| SM(36:1)/Gb3(d18:1/16:0) | 2.20 | 1.7E−30 | 2.42 | 4.4E−29 | 2.89 | 4.2E−17 | 3.17 | 7.9E−16 | 1.93 | 1.2E−03 |
| DAG(18:0/20:4)/PC(P-34:1) | 2.20 | 1.7E−30 | 2.33 | 4.7E−27 | 2.62 | 7.2E−15 | 2.85 | 1.6E−13 | 2.46 | 1.4E−05 |
| Cer(d18:1/22:0)/LPC(O-18:1) | 2.21 | 1.7E−30 | 2.17 | 2.1E−23 | 2.87 | 3.3E−16 | 2.84 | 7.3E−13 | 1.67 | 8.7E−03 |
| DAG(16:1/16:1)/LPC(O-20:1) | 2.16 | 1.7E−30 | 2.04 | 4.3E−22 | 2.78 | 6.0E−17 | 2.71 | 1.1E−13 | 1.96 | 4.0E−04 |
| PC(32:1)/PC(P-32:0) | 2.14 | 1.7E−30 | 2.00 | 2.0E−21 | 2.67 | 1.3E−15 | 2.61 | 2.4E−12 | 1.83 | 1.6E−03 |
| DAG(18:1/20:4)/LPC(15:0) [sn1] | 2.20 | 1.7E−30 | 2.30 | 1.2E−26 | 2.70 | 1.6E−15 | 2.78 | 2.3E−13 | 1.92 | 1.3E−03 |
| CE(16:1)/PC(P-40:2) | 2.16 | 1.8E−30 | 2.09 | 1.4E−22 | 2.62 | 6.3E−15 | 2.66 | 2.9E−12 | 1.77 | 1.6E−03 |
| DAG(14:0/18:1)/LPC(18:1) [sn2] | 2.23 | 1.9E−30 | 2.39 | 2.4E−27 | 2.94 | 4.6E−16 | 3.05 | 1.2E−13 | 2.28 | 1.4E−04 |
| Cer(d16:1/18:0)/LPC(O-18:0) | 2.27 | 1.9E−30 | 2.40 | 2.1E−26 | 3.48 | 2.0E−18 | 3.50 | 6.0E−15 | 2.67 | 8.3E−06 |
| SM(36:2)/LPC(O-24:2) | 2.26 | 2.0E−30 | 2.37 | 1.8E−26 | 3.32 | 4.5E−18 | 3.58 | 7.2E−16 | 2.32 | 2.4E−05 |
| Cer(d18:1/22:0)/Glc/GalCer(d18:1/23:0) | 2.22 | 2.0E−30 | 2.26 | 4.2E−25 | 2.44 | 3.9E−13 | 2.57 | 1.4E−11 | 1.83 | 2.7E−03 |
| DAG(14:0/18:2)/LPC(MHDA) [sn2] | 2.19 | 2.0E−30 | 2.26 | 6.8E−26 | 2.64 | 4.1E−15 | 2.63 | 3.2E−12 | 2.45 | 7.9E−06 |
| CE(16:1)/LPC(O-24:1) | 2.16 | 2.1E−30 | 2.03 | 9.3E−22 | 2.84 | 1.8E−16 | 2.79 | 2.2E−13 | 1.77 | 3.2E−03 |
| SM(d18:0/22:0)/LPC(O-18:0) | 2.17 | 2.1E−30 | 2.19 | 7.9E−25 | 3.14 | 1.2E−18 | 3.36 | 3.5E−16 | 2.10 | 2.3E−04 |
| Cer(d18:1/24:1)/LacCer(d18:1/16:0) | 2.16 | 2.2E−30 | 2.21 | 2.6E−25 | 2.36 | 1.0E−13 | 2.44 | 4.1E−12 | 1.94 | 5.7E−04 |
| DAG(16:1/16:1)/LPC(20:1) [sn1] | 2.18 | 2.3E−30 | 2.08 | 2.3E−22 | 2.87 | 5.5E−17 | 2.84 | 6.9E−14 | 1.92 | 9.0E−04 |
| PI(32:1)/LPC(O-24:0) | 2.12 | 2.3E−30 | 1.96 | 3.6E−21 | 2.67 | 1.3E−16 | 2.54 | 3.0E−13 | 1.97 | 3.6E−04 |
| DAG(16:1/16:1)/PC(O-36:3) | 2.18 | 2.3E−30 | 2.08 | 2.9E−22 | 2.86 | 1.5E−16 | 2.78 | 5.8E−13 | 1.97 | 6.2E−04 |
| DAG(18:1/18:1)/LPC(O-18:1) | 2.13 | 2.3E−30 | 2.23 | 1.2E−26 | 2.55 | 4.4E−15 | 2.65 | 3.9E−13 | 1.84 | 1.5E−03 |
| DAG(18:1/18:1)/LacCer(d18:1/24:1) | 2.16 | 2.5E−30 | 2.30 | 3.2E−27 | 2.41 | 1.2E−13 | 2.63 | 3.7E−12 | 1.75 | 4.3E−03 |
| DAG(18:1/18:1)/LPC(15:0) [sn2] | 2.14 | 2.6E−30 | 2.24 | 1.4E−26 | 2.54 | 2.5E−15 | 2.68 | 2.9E−13 | 1.81 | 1.5E−03 |
| CE(16:1)/LPC(19:0) [sn2] | 2.13 | 2.6E−30 | 2.02 | 3.8E−22 | 2.80 | 6.7E−18 | 2.76 | 9.2E−15 | 1.81 | 1.1E−03 |
| DAG(16:0/18:2)/LPC(20:2) [sn1] | 2.19 | 2.7E−30 | 2.43 | 3.9E−29 | 2.81 | 4.1E−16 | 3.05 | 1.3E−14 | 2.41 | 9.7E−06 |
| Cer(d16:1/20:0)/PC(P-34:1) | 2.31 | 2.7E−30 | 2.64 | 2.4E−29 | 2.98 | 1.3E−14 | 3.10 | 3.2E−12 | 2.63 | 3.1E−05 |
| DAG(18:1/18:1)/LPC(O-18:0) | 2.13 | 2.7E−30 | 2.23 | 1.2E−26 | 2.62 | 9.2E−16 | 2.79 | 5.9E−14 | 2.07 | 1.0E−04 |
| DAG(16:0/18:2)/LPC(O-18:1) | 2.15 | 2.7E−30 | 2.22 | 2.1E−26 | 2.67 | 1.1E−15 | 2.77 | 1.3E−13 | 2.18 | 6.9E−05 |
| PI(32:1)/LPC(20:0) [sn2] | 2.14 | 2.8E−30 | 1.98 | 2.7E−21 | 2.81 | 1.0E−17 | 2.67 | 3.9E−14 | 1.99 | 3.1E−04 |
| PI(32:1)/LPC(22:0) [sn2] | 2.15 | 2.9E−30 | 2.00 | 1.3E−21 | 2.83 | 9.3E−18 | 2.70 | 3.1E−14 | 2.03 | 2.2E−04 |
| CE(16:1)/LPC(20:1) [sn1] | 2.19 | 2.9E−30 | 2.09 | 3.8E−22 | 3.01 | 8.1E−17 | 2.98 | 7.5E−14 | 1.76 | 5.0E−03 |
| DAG(14:0/18:2)/PC(37:6) | 2.24 | 2.9E−30 | 2.33 | 6.5E−26 | 2.37 | 2.7E−11 | 2.36 | 2.7E−09 | 1.97 | 1.4E−03 |
| DAG(18:0/20:4)/LPC(MHDA) [sn2] | 2.21 | 3.0E−30 | 2.23 | 7.1E−25 | 3.03 | 1.3E−17 | 3.09 | 9.8E−15 | 2.99 | 5.0E−08 |
| DAG(16:0/18:2)/LPC(O-22:0) | 2.15 | 3.0E−30 | 2.29 | 2.1E−27 | 2.68 | 9.8E−16 | 2.97 | 1.7E−14 | 2.35 | 9.7E−06 |
| Cer(d18:1/24:1)/LPC(20:0) [sn1] | 2.16 | 3.1E−30 | 2.15 | 3.7E−24 | 2.91 | 3.2E−19 | 3.17 | 7.9E−17 | 2.37 | 5.1E−06 |
| PC(32:1)/LPE(16:0) [sn1] | 2.21 | 3.3E−30 | 2.10 | 8.3E−22 | 2.91 | 1.0E−15 | 3.00 | 3.2E−13 | 2.04 | 7.1E−04 |
| Cer(d18:1/24:1)/PC(O-36:3) | 2.17 | 3.4E−30 | 2.21 | 9.5E−25 | 2.70 | 6.4E−16 | 2.62 | 1.2E−12 | 2.07 | 2.5E−04 |
| DAG(18:1/20:4)/LPE(16:0) [sn1] | 2.20 | 3.4E−30 | 2.50 | 9.9E−30 | 2.49 | 2.1E−13 | 2.86 | 3.1E−13 | 1.87 | 2.4E−03 |
| PE(38:4)/PC(O-40:6) | 2.27 | 3.5E−30 | 2.37 | 4.4E−26 | 2.64 | 2.3E−13 | 2.73 | 1.2E−11 | 1.77 | 6.8E−03 |
| PC(38:2)/SM(37:1) | 2.22 | 3.6E−30 | 2.21 | 1.3E−23 | 2.83 | 3.4E−15 | 2.67 | 2.6E−11 | 1.73 | 8.0E−03 |
| PI(40:5)/LPC(O-24:0) | 2.25 | 3.7E−30 | 2.07 | 1.1E−20 | 2.92 | 2.4E−15 | 2.74 | 1.2E−11 | 2.18 | 1.8E−04 |
| PE(38:4)/PC(O-38:2) | 2.35 | 3.7E−30 | 2.38 | 5.7E−24 | 2.84 | 8.6E−14 | 2.87 | 4.4E−11 | 1.80 | 7.2E−03 |
| Cer(d16:1/20:0)/SM(37:1) | 2.35 | 3.8E−30 | 2.67 | 1.1E−28 | 2.80 | 4.1E−13 | 2.80 | 2.6E−10 | 2.26 | 4.2E−04 |
| PC(40:5)/LPC(MHDA) [sn2] | 2.16 | 3.8E−30 | 2.10 | 3.6E−23 | 2.52 | 1.1E−14 | 2.26 | 2.7E−10 | 1.92 | 1.2E−03 |
| DAG(16:1/16:1)/PC(P-40:2) | 2.17 | 3.9E−30 | 2.09 | 2.0E−22 | 2.67 | 2.0E−15 | 2.65 | 1.5E−12 | 1.91 | 3.6E−04 |
| DAG(16:1/18:1)/SM(41:2) | 2.18 | 3.9E−30 | 2.21 | 1.5E−24 | 2.48 | 1.6E−13 | 2.59 | 1.6E−11 | 1.94 | 9.3E−04 |
| DAG(18:0/20:4)/LPC(MHDA) [sn1] | 2.21 | 3.9E−30 | 2.27 | 1.7E−25 | 3.14 | 5.6E−18 | 3.32 | 1.8E−15 | 3.16 | 3.1E−08 |
| PC(36:4)/PC(37:2) | 2.29 | 4.0E−30 | 2.23 | 4.2E−23 | 3.10 | 1.3E−16 | 3.45 | 1.1E−13 | 2.71 | 1.5E−05 |
| PI(40:5)/PC(O-38:2) | 2.18 | 4.1E−30 | 2.00 | 6.1E−20 | 2.50 | 1.3E−13 | 2.31 | 2.7E−09 | 2.02 | 2.7E−04 |
| CE(16:1)/CE(22:4) | 2.13 | 4.3E−30 | 2.03 | 4.8E−22 | 2.57 | 6.1E−15 | 2.51 | 5.4E−12 | 1.71 | 3.8E−03 |
| DAG(14:0/18:1)/LPC(22:6) [sn1] | 2.24 | 4.4E−30 | 2.39 | 8.9E−27 | 2.70 | 1.3E−13 | 2.75 | 1.4E−11 | 1.87 | 3.6E−03 |
| PC(32:1)/PC(33:2) | 2.08 | 4.4E−30 | 2.02 | 2.3E−22 | 2.39 | 1.7E−15 | 2.60 | 6.8E−13 | 1.70 | 2.5E−03 |
| DAG(18:1/20:4)/LPE(16:0) [sn2] | 2.18 | 4.5E−30 | 2.47 | 1.1E−29 | 2.48 | 2.2E−13 | 2.81 | 5.5E−13 | 1.88 | 2.0E−03 |
| Cer(d16:1/18:0)/PC(P-40:2) | 2.25 | 4.5E−30 | 2.46 | 1.4E−27 | 2.79 | 3.4E−15 | 2.87 | 1.1E−12 | 2.21 | 6.2E−05 |
| DAG(18:1/18:1)/SM (d17:1/14:0) | 2.15 | 4.5E−30 | 2.27 | 1.3E−26 | 2.43 | 1.6E−13 | 2.58 | 7.7E−12 | 1.79 | 3.3E−03 |
| SM(36:0)/LPC(19:0) [sn2] | 2.10 | 4.5E−30 | 2.15 | 1.6E−25 | 2.92 | 3.6E−20 | 3.04 | 9.4E−18 | 2.34 | 8.9E−07 |
| DAG(18:1/18:1)/LPC(20:2) [sn1] | 2.15 | 4.7E−30 | 2.40 | 6.3E−29 | 2.63 | 2.2E−15 | 2.85 | 6.4E−14 | 2.01 | 3.6E−04 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| DAG(18:1/18:1)/LPC(20:2) [sn2] | 2.15 | 4.7E−30 | 2.42 | 1.8E−29 | 2.55 | 8.6E−15 | 2.81 | 1.1E−13 | 1.96 | 6.8E−04 |
| DAG(16:1/18:1)/PC(O-34:0) | 2.19 | 4.8E−30 | 2.24 | 8.2E−25 | 2.56 | 2.0E−13 | 2.68 | 1.8E−11 | 2.06 | 4.4E−04 |
| DAG(16:1/18:1)/PC(O-38:2) | 2.18 | 4.9E−30 | 2.20 | 2.7E−24 | 2.50 | 9.9E−14 | 2.62 | 1.1E−11 | 2.05 | 3.2E−04 |
| DAG(14:0/18:1)/LPC(18:1) [sn1] | 2.20 | 5.0E−30 | 2.33 | 1.4E−26 | 2.90 | 4.1E−16 | 2.98 | 1.4E−13 | 2.24 | 1.5E−04 |
| PE(40:5)/PC(37:2) | 2.17 | 5.0E−30 | 2.17 | 3.5E−24 | 2.36 | 3.2E−12 | 2.30 | 1.6E−09 | 1.93 | 9.3E−04 |
| DAG(14:0/18:1)/LPC(22:1) [sn1] | 2.26 | 5.2E−30 | 2.32 | 2.9E−25 | 2.84 | 4.1E−14 | 2.96 | 3.5E−12 | 1.90 | 3.5E−03 |
| PI(40:5)/PC(P-40:4) | 2.25 | 5.3E−30 | 2.07 | 1.6E−20 | 3.05 | 1.8E−15 | 2.82 | 1.1E−11 | 2.30 | 7.1E−05 |
| DAG(16:0/18:2)/LPC(15:0) [sn1] | 2.16 | 5.4E−30 | 2.25 | 4.8E−26 | 2.78 | 3.1E−16 | 2.93 | 3.8E−14 | 2.36 | 8.1E−06 |
| Cer(d18:1/24:1)/LacCer(d18:1/24:1) | 2.17 | 5.6E−30 | 2.17 | 7.2E−24 | 2.43 | 3.9E−14 | 2.57 | 4.7E−12 | 1.77 | 2.8E−03 |
| Cer(d16:1/20:0)/LPC(O-22:1) | 2.25 | 5.6E−30 | 2.44 | 2.8E−27 | 2.92 | 8.6E−16 | 3.04 | 2.5E−13 | 2.53 | 1.4E−05 |
| PI(32:1)/LPC(15:0) [sn1] | 2.09 | 5.7E−30 | 1.92 | 2.2E−20 | 2.72 | 1.3E−17 | 2.56 | 1.3E−13 | 1.96 | 3.1E−04 |
| DAG(16:1/18:1)/LPC(O-18:0) | 2.16 | 5.8E−30 | 2.15 | 6.4E−24 | 2.72 | 1.6E−15 | 2.75 | 5.1E−13 | 2.16 | 1.0E−04 |
| PE(40:5)/PC(O-40:6) | 2.13 | 5.8E−30 | 2.15 | 7.1E−25 | 2.21 | 3.0E−11 | 2.13 | 6.8E−09 | 1.84 | 1.8E−03 |
| DAG(16:1/18:1)/LPC(O-18:1) | 2.17 | 5.8E−30 | 2.15 | 8.9E−24 | 2.67 | 5.6E−15 | 2.67 | 2.2E−12 | 1.95 | 8.9E−04 |
| SM(36:1)/PC(O-34:1) | 2.19 | 5.8E−30 | 2.38 | 8.4E−28 | 3.15 | 9.1E−18 | 3.54 | 1.2E−16 | 2.68 | 3.3E−06 |
| SM(38:0)/PC(35:2) | 2.25 | 6.0E−30 | 2.33 | 5.8E−26 | 3.40 | 3.6E−17 | 3.53 | 9.6E−15 | 2.96 | 4.6E−07 |
| DAG(14:0/18:1)/LPE(P-18:0) | 2.18 | 6.1E−30 | 2.25 | 1.7E−25 | 2.74 | 8.4E−15 | 2.70 | 5.9E−12 | 2.02 | 8.1E−04 |
| PE(36:1)/PC(33:2) | 2.12 | 6.4E−30 | 2.14 | 1.5E−24 | 2.46 | 1.1E−13 | 2.38 | 1.1E−10 | 1.77 | 2.3E−03 |
| DAG(16:1/18:1)/PC(O-32:0) | 2.19 | 6.6E−30 | 2.24 | 6.3E−25 | 2.52 | 3.2E−13 | 2.65 | 1.1E−11 | 2.00 | 7.7E−04 |
| PC(36:3)/SM(41:2) | 2.20 | 6.7E−30 | 2.12 | 3.5E−22 | 2.74 | 9.2E−15 | 2.74 | 4.0E−12 | 1.74 | 8.1E−03 |
| PC(32:1)/LacCer(d18:1/16:0) | 2.11 | 6.8E−30 | 1.99 | 2.7E−21 | 2.55 | 1.2E−14 | 2.48 | 1.4E−11 | 1.76 | 3.3E−03 |
| PC(36:4)/PC(35:3) | 2.25 | 7.1E−30 | 2.26 | 2.6E−24 | 3.42 | 7.7E−17 | 3.40 | 1.1E−13 | 2.48 | 5.2E−05 |
| DAG(16:1/18:1)/PC(P-40:4) | 2.20 | 7.3E−30 | 2.23 | 1.2E−24 | 2.78 | 9.9E−15 | 2.92 | 6.8E−13 | 2.18 | 1.7E−04 |
| DAG(16:1/16:1)/LPC(P-18:1) | 2.14 | 7.4E−30 | 2.00 | 4.5E−21 | 2.67 | 4.1E−16 | 2.53 | 1.8E−12 | 1.80 | 2.0E−03 |
| Cer(d18:1/24:1)/LPC(20:0) [sn2] | 2.15 | 7.6E−30 | 2.15 | 6.2E−24 | 2.96 | 1.4E−18 | 3.07 | 2.4E−16 | 2.23 | 2.1E−05 |
| DAG(16:0/18:2)/LPC(O-18:0) | 2.13 | 7.7E−30 | 2.22 | 5.4E−26 | 2.75 | 4.8E−16 | 2.89 | 3.9E−14 | 2.42 | 5.1E−06 |
| SM(d18:0/22:0)/PC(O-34:2) | 2.18 | 7.9E−30 | 2.22 | 6.0E−25 | 3.09 | 2.6E−18 | 3.13 | 3.0E−15 | 1.91 | 1.1E−03 |
| DAG(14:0/18:2)/PC(37:2) | 2.23 | 8.0E−30 | 2.36 | 4.2E−26 | 2.65 | 5.9E−13 | 2.76 | 4.2E−11 | 2.45 | 8.2E−05 |
| SM(36:2)/SM(37:2) | 2.17 | 8.0E−30 | 2.49 | 3.3E−30 | 3.52 | 2.4E−21 | 3.66 | 2.8E−18 | 2.23 | 4.7E−05 |
| DAG(16:0/22:6)/PC(P-34:1) | 2.22 | 8.1E−30 | 2.25 | 3.3E−24 | 3.05 | 2.5E−16 | 3.13 | 1.9E−13 | 2.83 | 1.7E−06 |
| Cer(d18:1/24:1)/LPC(19:0) [sn2] | 2.11 | 8.3E−30 | 2.11 | 2.7E−24 | 2.61 | 1.1E−18 | 2.68 | 3.5E−16 | 1.95 | 3.9E−05 |
| DAG(16:0/18:2)/LacCer(d18:1/24:1) | 2.16 | 8.4E−30 | 2.29 | 1.4E−26 | 2.52 | 4.7E−14 | 2.72 | 2.1E−12 | 2.06 | 2.8E−04 |
| PI(32:1)/LPC(15:0) [sn2] | 2.09 | 8.6E−30 | 1.92 | 3.0E−20 | 2.68 | 3.5E−17 | 2.50 | 3.5E−13 | 1.84 | 1.1E−03 |
| PI(40:5)/LPC(20:2) [sn1] | 2.24 | 8.7E−30 | 2.16 | 2.8E−22 | 2.99 | 1.5E−15 | 2.74 | 1.9E−11 | 2.21 | 1.7E−04 |
| PC(36:3)/PC(O-40:6) | 2.20 | 8.7E−30 | 2.26 | 5.4E−25 | 2.67 | 2.9E−14 | 2.84 | 1.1E−12 | 1.89 | 2.0E−03 |
| PI(32:1)/LPC(17:0) [sn2] | 2.08 | 8.7E−30 | 1.92 | 2.2E−20 | 2.70 | 1.3E−17 | 2.53 | 1.6E−13 | 1.96 | 3.2E−04 |
| DAG(16:1/16:1)/LPC(20:0) [sn2] | 2.14 | 8.9E−30 | 2.02 | 2.2E−21 | 2.84 | 2.2E−17 | 2.80 | 3.8E−14 | 2.02 | 2.6E−04 |
| DAG(16:1/18:1)/PC(O-40:3) | 2.18 | 9.3E−30 | 2.27 | 1.2E−25 | 2.47 | 4.2E−13 | 2.69 | 8.7E−12 | 1.91 | 1.3E−03 |
| DAG(16:1/18:1)/LPE(P-20:0) | 2.15 | 9.7E−30 | 2.15 | 4.7E−24 | 2.68 | 6.6E−16 | 2.67 | 4.1E−13 | 2.03 | 2.5E−04 |
| DAG(16:1/16:1)/LPC(24:0) [sn2] | 2.14 | 9.8E−30 | 2.05 | 4.7E−22 | 2.80 | 7.0E−17 | 2.82 | 4.0E−14 | 2.04 | 2.3E−04 |
| DAG(16:1/16:1)/PC(31:0) | 2.17 | 9.8E−30 | 2.10 | 5.9E−22 | 2.68 | 3.0E−15 | 2.79 | 2.0E−12 | 1.99 | 5.0E−04 |
| Cer(d18:1/22:0)/PC(O-38:2) | 2.12 | 1.0E−29 | 2.10 | 6.2E−23 | 2.42 | 1.7E−13 | 2.46 | 8.2E−11 | 1.79 | 3.0E−03 |
| Cer(d16:1/18:0)/PC(P-40:4) | 2.33 | 1.0E−29 | 2.54 | 6.4E−27 | 3.55 | 2.1E−17 | 3.77 | 9.3E−15 | 2.75 | 1.7E−05 |
| DAG(18:0/20:4)/LPC(19:0) [sn2] | 2.20 | 1.0E−29 | 2.27 | 2.0E−25 | 2.85 | 2.5E−17 | 3.00 | 2.7E−15 | 2.36 | 1.4E−06 |
| SM(36:0)/LPC(22:0) [sn1] | 2.13 | 1.0E−29 | 2.20 | 1.4E−25 | 3.15 | 3.3E−20 | 3.42 | 2.9E−18 | 2.81 | 1.0E−07 |
| PI(40:5)/PC(37:1) | 2.23 | 1.1E−29 | 2.01 | 2.7E−19 | 2.60 | 4.0E−13 | 2.36 | 4.1E−09 | 2.02 | 6.6E−04 |
| PI(40:5)/LPC(O-18:1) | 2.21 | 1.1E−29 | 1.98 | 2.4E−19 | 2.93 | 1.8E−15 | 2.57 | 9.1E−11 | 1.90 | 1.7E−03 |
| DAG(16:1/16:1)/LPC(O-24:1) | 2.13 | 1.2E−29 | 2.01 | 1.9E−21 | 2.72 | 2.7E−16 | 2.67 | 3.1E−13 | 1.92 | 7.0E−04 |
| DAG(16:1/18:1)/PC(37:1) | 2.22 | 1.2E−29 | 2.24 | 5.2E−24 | 2.62 | 1.7E−13 | 2.76 | 1.5E−11 | 2.08 | 5.3E−04 |
| PI(40:5)/PC(O-34:0) | 2.21 | 1.2E−29 | 2.04 | 2.5E−20 | 2.49 | 9.6E−13 | 2.27 | 6.4E−09 | 2.03 | 4.6E−04 |
| SM(36:0)/LPC(20:0) [sn1] | 2.10 | 1.2E−29 | 2.14 | 7.4E−25 | 3.13 | 2.6E−20 | 3.31 | 5.8E−18 | 2.72 | 2.3E−07 |
| CE(16:1)/LPC(20:1) [sn2] | 2.17 | 1.3E−29 | 2.06 | 1.6E−21 | 2.89 | 5.5E−16 | 2.87 | 3.9E−13 | 1.71 | 7.8E−03 |
| SM(41:0)/Gb3(d18:1/22:0) | 2.16 | 1.3E−29 | 2.29 | 2.0E−26 | 2.51 | 2.6E−14 | 2.61 | 1.5E−12 | 1.83 | 1.6E−03 |
| PI(40:5)/LPC(15:0) [sn2] | 2.18 | 1.4E−29 | 1.99 | 2.4E−19 | 2.82 | 6.0E−15 | 2.60 | 3.4E−11 | 1.84 | 2.0E−03 |
| DAG(18:0/20:4)/LPC(20:1) [sn2] | 2.21 | 1.4E−29 | 2.34 | 5.2E−26 | 2.80 | 1.6E−15 | 3.07 | 3.3E−14 | 2.43 | 3.4E−05 |
| Cer(d16:1/18:0)/LPC(22:0) [sn2] | 2.33 | 1.4E−29 | 2.58 | 5.4E−27 | 3.81 | 3.3E−18 | 4.08 | 1.9E−15 | 2.70 | 2.8E−05 |
| PE(36:1)/Gb3(d18:1/22:0) | 2.10 | 1.5E−29 | 2.12 | 8.8E−25 | 2.23 | 4.5E−12 | 2.09 | 5.2E−09 | 1.66 | 9.2E−03 |
| CE(16:2)/PC(O-40:6) | 2.15 | 1.5E−29 | 2.18 | 7.2E−24 | 2.82 | 4.5E−16 | 2.75 | 1.2E−12 | 1.91 | 1.0E−03 |
| PI(32:1)/LPC(P-18:0) | 2.07 | 1.5E−29 | 1.92 | 1.4E−20 | 2.65 | 2.9E−17 | 2.47 | 3.7E−13 | 1.95 | 3.3E−04 |
| DAG(18:0/20:4)/LPC(O-20:1) | 2.17 | 1.5E−29 | 2.22 | 4.6E−25 | 2.75 | 4.6E−16 | 2.92 | 3.3E−14 | 2.50 | 5.3E−06 |
| DAG(16:0/18:2)/PC(39:4) | 2.16 | 1.5E−29 | 2.29 | 2.1E−26 | 2.65 | 1.7E−14 | 2.92 | 2.0E−13 | 2.28 | 4.5E−05 |
| DAG(14:0/18:1)/PC(34:3) | 2.21 | 1.5E−29 | 2.43 | 1.6E−27 | 2.73 | 8.3E−14 | 2.89 | 5.3E−12 | 1.91 | 2.5E−03 |
| DAG(16:0/22:6)/LPC(19:0) [sn2] | 2.18 | 1.5E−29 | 2.17 | 1.8E−23 | 3.27 | 1.7E−18 | 3.30 | 3.3E−15 | 2.85 | 4.5E−07 |
| DAG(18:0/20:4)/PC(O-40:6) | 2.21 | 1.6E−29 | 2.32 | 4.5E−26 | 2.63 | 4.5E−13 | 2.84 | 4.3E−12 | 2.56 | 1.2E−05 |
| SM(d18:0/22:0)/LPC(O-18:1) | 2.17 | 1.6E−29 | 2.19 | 5.7E−24 | 3.13 | 1.6E−17 | 3.34 | 3.8E−15 | 1.79 | 4.8E−03 |
| CE(18:0)/LPC(P-18:0) | 2.17 | 1.7E−29 | 2.26 | 1.4E−25 | 2.77 | 5.9E−14 | 2.70 | 9.6E−13 | 2.08 | 2.2E−04 |
| PI(40:5)/LPC(15:0) [sn1] | 2.17 | 1.7E−29 | 1.99 | 2.3E−19 | 2.88 | 1.2E−16 | 2.71 | 6.0E−12 | 2.11 | 1.5E−04 |
| PC(36:3)/PC(O-38:2) | 2.18 | 1.8E−29 | 2.09 | 1.6E−21 | 2.82 | 4.2E−15 | 2.80 | 2.5E−12 | 1.97 | 1.2E−03 |
| DAG(14:0/18:1)/LPE(20:1) [sn1] | 2.25 | 1.8E−29 | 2.44 | 6.5E−27 | 2.84 | 1.9E−14 | 3.16 | 2.2E−13 | 2.04 | 1.3E−03 |
| PC(38:1)/LPC(O-24:2) | 2.17 | 1.8E−29 | 2.18 | 7.1E−24 | 2.84 | 2.5E−16 | 2.96 | 5.9E−14 | 2.35 | 3.1E−05 |
| PC(36:4)/SM(d17:1/14:0) | 2.18 | 1.9E−29 | 2.10 | 8.5E−22 | 2.92 | 2.8E−15 | 2.77 | 1.4E−11 | 2.13 | 3.3E−04 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| Cer(d16:1/18:0)/PC(39:4) | 2.35 | 2.0E−29 | 2.55 | 5.9E−26 | 3.36 | 3.9E−16 | 3.53 | 1.0E−13 | 2.42 | 1.5E−04 |
| DAG(18:1/18:1)/PC(39:4) | 2.13 | 2.0E−29 | 2.27 | 1.5E−26 | 2.46 | 9.7E−14 | 2.71 | 6.8E−13 | 1.88 | 1.4E−03 |
| DAG(16:1/18:1)/LPC(P-16:0) | 2.13 | 2.0E−29 | 2.14 | 6.3E−24 | 2.61 | 3.3E−15 | 2.65 | 7.8E−13 | 1.96 | 6.0E−04 |
| CE(18:0)/LPC(MHDA) [sn1] | 2.13 | 2.0E−29 | 2.27 | 2.1E−26 | 2.68 | 7.4E−16 | 2.74 | 2.0E−13 | 2.33 | 8.8E−06 |
| DAG(18:1/18:1)/LPC(15:0) [sn1] | 2.11 | 2.1E−29 | 2.22 | 6.2E−26 | 2.53 | 2.3E−15 | 2.72 | 1.6E−13 | 1.95 | 3.4E−04 |
| DAG(16:1/16:1)/LPC(17:0) [sn2] | 2.12 | 2.1E−29 | 1.98 | 1.4E−20 | 2.79 | 2.6E−17 | 2.69 | 1.5E−13 | 2.00 | 2.3E−04 |
| PC(32:1)/LPE(16:0) [sn2] | 2.17 | 2.2E−29 | 2.08 | 2.2E−21 | 2.83 | 2.4E−15 | 2.88 | 9.5E−13 | 2.04 | 6.7E−04 |
| DAG(18:1/20:4)/PC(O-34:2) | 2.15 | 2.2E−29 | 2.28 | 2.7E−26 | 2.60 | 2.2E−14 | 2.59 | 7.4E−12 | 1.87 | 2.3E−03 |
| DAG(14:0/18:2)/LPC(20:0) [sn2] | 2.19 | 2.3E−29 | 2.29 | 1.5E−25 | 2.71 | 1.6E−14 | 2.82 | 2.1E−12 | 2.40 | 6.2E−05 |
| Cer(d16:1/18:0)/PC(O-32:0) | 2.33 | 2.3E−29 | 2.59 | 5.1E−27 | 3.10 | 8.4E−15 | 3.36 | 1.3E−12 | 2.37 | 1.9E−04 |
| SM(36:0)/LPC(24:0) [sn1] | 2.11 | 2.5E−29 | 2.24 | 1.7E−26 | 3.02 | 6.1E−20 | 3.31 | 2.4E−18 | 2.79 | 6.8E−08 |
| PE(36:1)/PC(O-40:6) | 2.13 | 2.6E−29 | 2.17 | 1.4E−24 | 2.41 | 6.4E−13 | 2.37 | 1.4E−10 | 1.90 | 1.3E−03 |
| SM(36:1)/LPC(O-22:1) | 2.14 | 2.6E−29 | 2.20 | 7.6E−25 | 2.99 | 9.4E−18 | 3.26 | 6.1E−16 | 2.42 | 7.2E−06 |
| DAG(16:1/18:1)/LPC(O-24:0) | 2.15 | 2.6E−29 | 2.17 | 3.8E−24 | 2.56 | 3.2E−14 | 2.66 | 1.8E−12 | 2.06 | 3.2E−04 |
| PI(40:5)/PC(O-32:0) | 2.21 | 2.6E−29 | 2.05 | 2.7E−20 | 2.53 | 3.5E−12 | 2.34 | 5.9E−09 | 1.96 | 1.5E−03 |
| SM(36:0)/LPC(O-18:0) | 2.06 | 2.8E−29 | 2.07 | 6.7E−24 | 2.95 | 6.6E−20 | 3.03 | 5.0E−17 | 2.68 | 8.3E−08 |
| DAG(16:0/22:6)/LPC(19:0) [sn1] | 2.18 | 2.8E−29 | 2.13 | 2.1E−22 | 3.20 | 1.2E−17 | 3.19 | 3.6E−14 | 3.07 | 2.0E−07 |
| LPC(20:3) [sn2]/LPC(19:0) [sn2] | 2.20 | 2.8E−29 | 2.13 | 9.1E−23 | 2.79 | 7.2E−18 | 2.95 | 5.8E−16 | 1.76 | 1.1E−03 |
| DAG(16:1/16:1)/LPC(22:0) [sn2] | 2.13 | 2.9E−29 | 2.03 | 2.0E−21 | 2.82 | 3.5E−17 | 2.79 | 4.1E−14 | 2.04 | 2.2E−04 |
| DAG(16:0/18:2)/LPE(16:0) [sn2] | 2.17 | 2.9E−29 | 2.46 | 4.0E−29 | 2.65 | 2.1E−14 | 3.13 | 4.1E−14 | 2.42 | 1.1E−05 |
| SM(36:2)/Gb3(d18:1/16:0) | 2.16 | 3.0E−29 | 2.41 | 7.0E−29 | 3.17 | 1.2E−18 | 3.34 | 3.6E−16 | 1.83 | 2.4E−03 |
| DAG(14:0/18:2)/LPC(20:0) [sn1] | 2.19 | 3.1E−29 | 2.29 | 1.9E−25 | 2.74 | 1.5E−14 | 2.86 | 1.9E−12 | 2.49 | 3.7E−05 |
| PC(38:2)/PC(35:3) | 2.15 | 3.1E−29 | 2.25 | 8.8E−26 | 3.10 | 4.6E−18 | 2.97 | 1.7E−14 | 2.24 | 7.8E−05 |
| DAG(16:0/18:2)/LPE(P-20:0) | 2.11 | 3.1E−29 | 2.22 | 4.6E−26 | 2.69 | 2.0E−16 | 2.79 | 3.6E−14 | 2.26 | 1.7E−05 |
| Cer(d16:1/20:0)/PC(O-36:2) | 2.22 | 3.1E−29 | 2.46 | 2.1E−27 | 2.95 | 3.7E−16 | 2.89 | 1.5E−12 | 2.54 | 5.8E−06 |
| Cer(d16:1/18:0)/LPC(O-24:0) | 2.24 | 3.2E−29 | 2.42 | 9.9E−27 | 3.20 | 7.4E−17 | 3.37 | 1.9E−14 | 2.47 | 4.9E−05 |
| SM(36:0)/LPC(20:0) [sn2] | 2.09 | 3.3E−29 | 2.13 | 1.4E−24 | 3.08 | 8.7E−20 | 3.27 | 1.6E−17 | 2.59 | 7.2E−07 |
| DAG(16:1/16:1)/LPC(20:2) [sn2] | 2.15 | 3.4E−29 | 2.08 | 5.8E−22 | 2.89 | 1.4E−16 | 2.87 | 1.8E−13 | 1.99 | 4.2E−04 |
| PI(40:5)/LPE(P-20:0) | 2.18 | 3.4E−29 | 1.99 | 1.0E−19 | 2.93 | 1.0E−16 | 2.55 | 5.4E−12 | 2.06 | 1.8E−04 |
| DAG(18:0/20:4)/LPC(20:1) [sn1] | 2.19 | 3.5E−29 | 2.31 | 1.1E−25 | 2.88 | 4.5E−16 | 3.14 | 1.2E−14 | 2.48 | 2.3E−05 |
| SM(d18:0/22:0)/LPC(O-24:0) | 2.15 | 3.5E−29 | 2.23 | 4.2E−25 | 2.90 | 4.9E−17 | 3.30 | 6.3E−16 | 1.89 | 9.6E−04 |
| DAG(14:0/18:2)/PC(17:0_22:6) | 2.20 | 3.5E−29 | 2.29 | 4.1E−25 | 2.32 | 1.0E−10 | 2.37 | 3.8E−09 | 2.02 | 1.2E−03 |
| DAG(16:0/22:6)/LPC(20:1) [sn2] | 2.20 | 3.6E−29 | 2.21 | 2.7E−23 | 3.17 | 9.7E−17 | 3.22 | 9.0E−14 | 2.84 | 3.5E−06 |
| DAG(18:1/20:4)/LPC(18:2) [sn2] | 2.13 | 3.7E−29 | 2.32 | 1.8E−27 | 2.72 | 1.4E−15 | 2.84 | 1.3E−13 | 1.91 | 1.6E−03 |
| PI(40:5)/PC(33:2) | 2.14 | 3.8E−29 | 2.04 | 9.2E−21 | 2.39 | 7.5E−13 | 2.29 | 2.7E−09 | 1.82 | 2.6E−03 |
| PE(40:6)/PC(37:6) | 2.11 | 3.8E−29 | 2.08 | 6.4E−23 | 2.64 | 5.5E−15 | 2.50 | 2.1E−11 | 2.19 | 7.4E−05 |
| DAG(18:1/20:4)/LPC(O-24:0) | 2.10 | 4.2E−29 | 2.24 | 1.4E−26 | 2.36 | 8.1E−14 | 2.53 | 1.2E−12 | 1.82 | 2.0E−03 |
| DAG(18:1/18:1)/LPE(P-20:0) | 2.09 | 4.2E−29 | 2.21 | 5.1E−26 | 2.55 | 8.0E−16 | 2.64 | 1.3E−13 | 1.92 | 4.1E−04 |
| Cer(d16:1/18:0)/PC(O-38:0) | 2.30 | 4.4E−29 | 2.57 | 5.2E−27 | 3.21 | 1.1E−15 | 3.52 | 2.3E−13 | 2.61 | 3.3E−05 |
| PC(38:2)/PC(O-36:3) | 2.17 | 4.5E−29 | 2.18 | 1.3E−23 | 3.28 | 2.2E−17 | 2.91 | 1.1E−12 | 2.24 | 1.6E−04 |
| PC(36:4)/LPC(O-22:1) | 2.14 | 4.5E−29 | 2.09 | 2.7E−22 | 2.84 | 2.1E−16 | 2.84 | 1.8E−13 | 2.24 | 1.0E−04 |
| Cer(d18:1/24:1)/LPC(O-24:1) | 2.12 | 4.5E−29 | 2.13 | 1.5E−23 | 2.71 | 4.0E−16 | 2.88 | 4.7E−14 | 2.03 | 2.7E−04 |
| DAG(18:0/20:4)/LPC(P-18:1) | 2.16 | 4.6E−29 | 2.17 | 7.0E−24 | 2.85 | 3.8E−15 | 2.68 | 1.3E−12 | 2.17 | 1.1E−04 |
| SM(36:0)/LPC(24:0) [sn2] | 2.10 | 4.6E−29 | 2.23 | 3.6E−26 | 3.07 | 9.2E−20 | 3.39 | 2.7E−18 | 2.65 | 1.7E−07 |
| DAG(14:0/18:2)/PC(33:2) | 2.18 | 4.7E−29 | 2.29 | 3.6E−25 | 2.43 | 7.4E−12 | 2.46 | 8.8E−10 | 2.16 | 3.2E−04 |
| DAG(14:0/18:2)/PC(O-36:2) | 2.17 | 4.9E−29 | 2.29 | 1.5E−25 | 2.68 | 1.0E−13 | 2.69 | 3.4E−11 | 2.27 | 1.4E−04 |
| PC(36:3)/PC(P-32:0) | 2.18 | 4.9E−29 | 2.18 | 3.9E−23 | 2.85 | 4.0E−15 | 3.00 | 4.0E−13 | 1.83 | 4.6E−03 |
| SM(36:0)/LPC(O-24:0) | 2.07 | 5.1E−29 | 2.12 | 8.9E−25 | 2.88 | 2.7E−19 | 3.07 | 1.6E−17 | 2.62 | 1.7E−07 |
| SM(41:0)/Gb3(d18:1/16:0) | 2.14 | 5.2E−29 | 2.26 | 9.6E−26 | 2.90 | 5.6E−17 | 3.28 | 2.0E−15 | 1.84 | 2.7E−03 |
| DAG(16:0/22:6)/LPC(MHDA) [sn1] | 2.17 | 5.5E−29 | 2.14 | 1.4E−22 | 3.19 | 4.4E−18 | 3.18 | 2.0E−14 | 3.11 | 3.8E−08 |
| DAG(16:0/22:6)/LPC(MHDA) [sn2] | 2.16 | 5.5E−29 | 2.12 | 3.3E−22 | 3.12 | 6.5E−18 | 3.06 | 4.8E−14 | 3.04 | 5.6E−08 |
| Cer(d18:1/20:0)/LPC(O-20:1) | 2.16 | 5.6E−29 | 2.27 | 3.3E−25 | 3.12 | 2.3E−17 | 3.22 | 1.9E−14 | 2.33 | 1.3E−05 |
| DAG(16:0/22:6)/LPC(20:1) [sn1] | 2.19 | 5.7E−29 | 2.18 | 3.9E−23 | 3.19 | 5.6E−17 | 3.23 | 5.6E−14 | 2.84 | 3.0E−06 |
| DAG(16:1/16:1)/PC(P-32:0) | 2.12 | 5.8E−29 | 2.03 | 2.9E−21 | 2.68 | 2.2E−15 | 2.67 | 1.4E−12 | 1.93 | 8.4E−04 |
| DAG(16:0/18:2)/LPE(16:0) [sn1] | 2.17 | 5.8E−29 | 2.47 | 9.2E−29 | 2.64 | 3.0E−14 | 3.18 | 3.3E−14 | 2.38 | 1.4E−05 |
| Cer(d18:1/24:1)/LPC(MHDA) [sn1] | 2.11 | 6.0E−29 | 2.09 | 4.6E−23 | 2.89 | 2.8E−18 | 2.87 | 5.5E−15 | 2.45 | 7.0E−07 |
| CE(16:1)/SM(41:2) | 2.07 | 6.1E−29 | 1.97 | 1.5E−20 | 2.42 | 3.1E−14 | 2.48 | 1.2E−11 | 1.66 | 7.5E−03 |
| SM(36:0)/LPC(17:0) [sn1] | 2.08 | 6.1E−29 | 2.06 | 4.4E−23 | 3.08 | 4.9E−20 | 3.15 | 4.7E−17 | 2.59 | 5.1E−07 |
| PI(32:1)/LPC(17:0) [sn1] | 2.05 | 6.4E−29 | 1.89 | 1.4E−19 | 2.64 | 5.4E−17 | 2.49 | 3.9E−13 | 1.92 | 5.2E−04 |
| PC(36:4)/PC(O-40:6) | 2.12 | 6.5E−29 | 2.15 | 6.1E−24 | 2.51 | 5.1E−14 | 2.57 | 6.4E−12 | 2.16 | 1.1E−04 |
| DAG(16:0/18:2)/LPC(18:2) [sn2] | 2.13 | 6.6E−29 | 2.31 | 2.7E−27 | 2.86 | 1.3E−16 | 3.07 | 1.1E−14 | 2.42 | 1.8E−05 |
| SM(36:0)/LPC(22:0) [sn2] | 2.10 | 6.7E−29 | 2.18 | 5.2E−25 | 3.10 | 6.1E−20 | 3.33 | 7.6E−18 | 2.68 | 3.0E−07 |
| Cer(d16:1/20:0)/SM(37:2) | 2.22 | 6.7E−29 | 2.59 | 4.4E−29 | 3.11 | 1.2E−15 | 3.14 | 1.0E−12 | 2.41 | 8.8E−05 |
| DAG(16:1/16:1)/PC(O-34:2) | 2.18 | 6.7E−29 | 2.22 | 7.7E−24 | 2.84 | 1.2E−15 | 2.87 | 6.4E−12 | 2.11 | 4.7E−04 |
| DAG(18:1/18:1)/PC(P-40:4) | 2.11 | 7.1E−29 | 2.27 | 1.6E−26 | 2.54 | 2.7E−14 | 2.81 | 2.6E−13 | 2.03 | 3.0E−04 |
| DAG(16:1/16:1)/PC(O-40:3) | 2.13 | 7.4E−29 | 2.07 | 4.1E−22 | 2.58 | 1.4E−14 | 2.68 | 2.0E−12 | 1.84 | 1.4E−03 |
| PC(36:4)/PC(35:2) | 2.17 | 7.4E−29 | 2.15 | 4.3E−23 | 3.19 | 1.4E−16 | 3.11 | 3.6E−13 | 2.61 | 1.2E−05 |
| PE(40:4)/PC(P-40:2) | 2.10 | 7.4E−29 | 2.10 | 1.8E−23 | 2.28 | 4.4E−12 | 2.17 | 9.2E−09 | 1.63 | 9.7E−03 |
| CE(16:1)/LPC(20:2) [sn1] | 2.12 | 7.5E−29 | 2.04 | 2.6E−21 | 2.88 | 3.6E−16 | 2.84 | 6.7E−13 | 1.85 | 1.9E−03 |
| DAG(18:0/20:4)/SM(37:2) | 2.13 | 7.5E−29 | 2.29 | 2.4E−26 | 2.75 | 1.2E−15 | 2.90 | 8.9E−14 | 2.33 | 4.5E−05 |
| DAG(18:1/18:1)/LPE(16:0) [sn1] | 2.12 | 7.7E−29 | 2.41 | 1.0E−28 | 2.44 | 2.1E−13 | 2.93 | 1.5E−13 | 1.95 | 6.5E−04 |
| DAG(16:0/22:6)/SM(37:2) | 2.18 | 9.1E−29 | 2.24 | 8.1E−24 | 3.15 | 9.0E−17 | 3.17 | 1.5E−13 | 2.70 | 3.4E−06 |
| CE(16:1)/PC(33:2) | 2.07 | 9.3E−29 | 2.03 | 8.9E−22 | 2.42 | 3.2E−14 | 2.65 | 3.6E−12 | 1.66 | 7.0E−03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| | FL | | NAFLD | | FL (severe) | | NAFLD (severe) | | DM2 | |
|---|---|---|---|---|---|---|---|---|---|---|
| Lipid ratio | OR | p-value | OR | p-value | OR | p-value | OR | p-value | OR | p-value |
| CE(16:1)/PC(31:0) | 2.09 | 9.3E-29 | 2.02 | 2.7E-21 | 2.40 | 1.1E-13 | 2.53 | 1.7E-11 | 1.74 | 4.0E-03 |
| DAG(16:1/16:1)/LPC(15:0) [sn2] | 2.10 | 9.4E-29 | 1.97 | 4.2E-20 | 2.67 | 1.5E-16 | 2.61 | 6.1E-13 | 1.85 | 9.3E-04 |
| Cer(d16:1/18:0)/LPC(15:0) [sn1] | 2.26 | 9.4E-29 | 2.43 | 6.0E-25 | 3.49 | 1.1E-17 | 3.67 | 3.0E-14 | 2.51 | 2.9E-05 |
| PC(36:5)/PC(O-40:6) | 2.13 | 9.5E-29 | 2.05 | 2.2E-21 | 2.42 | 3.3E-12 | 2.31 | 2.9E-09 | 2.58 | 5.3E-06 |
| DAG(18:1/18:1)/LPE(16:0) [sn2] | 2.11 | 9.6E-29 | 2.39 | 1.1E-28 | 2.45 | 2.2E-13 | 2.86 | 2.9E-13 | 1.98 | 5.7E-04 |
| CE(16:1)/PC(O-34:0) | 2.09 | 1.0E-28 | 1.98 | 1.7E-20 | 2.51 | 4.2E-14 | 2.52 | 1.9E-11 | 1.76 | 3.0E-03 |
| Cer(d16:1/18:0)/LPC(15:0) [sn2] | 2.25 | 1.0E-28 | 2.41 | 7.1E-25 | 3.36 | 3.7E-17 | 3.44 | 1.2E-13 | 2.19 | 3.1E-04 |
| PE(38:3)/PC(35:3) | 2.14 | 1.0E-28 | 2.24 | 4.2E-25 | 2.87 | 2.2E-15 | 2.87 | 1.6E-12 | 1.99 | 1.1E-03 |
| Cer(d18:1/24:1)/Gb3(d18:1/22:0) | 2.08 | 1.0E-28 | 2.17 | 4.6E-25 | 2.11 | 1.7E-11 | 2.08 | 2.3E-09 | 1.66 | 7.1E-03 |
| DAG(18:1/20:4)/LPC(18:2) [sn1] | 2.10 | 1.1E-28 | 2.27 | 7.9E-27 | 2.71 | 7.6E-16 | 2.83 | 8.1E-14 | 2.00 | 6.2E-04 |
| SM(38:0)/SM(d 17:1/14:0) | 2.13 | 1.1E-28 | 2.13 | 2.7E-23 | 2.73 | 7.2E-16 | 2.73 | 1.8E-13 | 2.24 | 4.0E-05 |
| SM(38:0)/PC(O-36:3) | 2.15 | 1.1E-28 | 2.21 | 2.3E-24 | 3.06 | 3.9E-17 | 3.03 | 3.7E-14 | 2.46 | 1.5E-05 |
| SM(41:0)/PC(O-40:6) | 2.14 | 1.1E-28 | 2.29 | 9.6E-26 | 2.77 | 1.1E-15 | 3.18 | 9.8E-15 | 2.13 | 8.7E-05 |
| DAG(16:1/16:1)/LPC(20:2) [sn1] | 2.12 | 1.2E-28 | 2.05 | 1.9E-21 | 2.85 | 1.6E-16 | 2.81 | 2.5E-13 | 2.03 | 3.3E-04 |
| PC(36:3)/PC(O-32:0) | 2.16 | 1.2E-28 | 2.13 | 1.4E-22 | 2.64 | 9.5E-14 | 2.74 | 3.9E-12 | 1.78 | 6.1E-03 |
| PC(36:3)/PC(O-34:0) | 2.13 | 1.2E-28 | 2.08 | 6.2E-22 | 2.60 | 7.1E-14 | 2.61 | 1.6E-11 | 1.89 | 2.4E-03 |
| CE(16:1)/PC(O-32:0) | 2.09 | 1.3E-28 | 1.99 | 1.2E-20 | 2.49 | 5.8E-14 | 2.55 | 1.1E-11 | 1.70 | 5.9E-03 |
| PC(36:4)/PC(O-34:1) | 2.21 | 1.3E-28 | 2.17 | 2.7E-22 | 3.21 | 4.2E-15 | 3.14 | 3.4E-12 | 2.36 | 2.1E-04 |
| CE(16:1)/LPC(O-24:0) | 2.08 | 1.4E-28 | 1.95 | 3.4E-20 | 2.61 | 1.7E-15 | 2.59 | 8.2E-13 | 1.80 | 1.9E-03 |
| Cer(d18:1/24:1)/PC(37:2) | 2.12 | 1.4E-28 | 2.14 | 2.6E-23 | 2.66 | 7.4E-15 | 2.87 | 1.4E-13 | 2.21 | 7.2E-05 |
| DAG(16:1/16:1)/LacCer(d18:1/24:1) | 2.10 | 1.4E-28 | 1.98 | 2.8E-20 | 2.59 | 7.5E-15 | 2.53 | 1.0E-11 | 1.80 | 2.7E-03 |
| PC(36:4)/PC(O-36:3) | 2.22 | 1.4E-28 | 2.19 | 3.4E-22 | 3.49 | 6.3E-16 | 3.23 | 5.6E-12 | 2.39 | 1.5E-04 |
| PI(36:4)/PC(35:3) | 2.11 | 1.5E-28 | 2.14 | 1.4E-23 | 3.14 | 1.9E-18 | 2.94 | 3.7E-14 | 1.71 | 8.3E-03 |
| DAG(16:0/18:2)/LPC(P-16:0) | 2.07 | 1.5E-28 | 2.18 | 1.2E-25 | 2.53 | 1.6E-15 | 2.67 | 8.2E-14 | 2.12 | 5.4E-05 |
| DAG(18:1/18:1)/LPC(P-16:0) | 2.06 | 1.5E-28 | 2.18 | 1.0E-25 | 2.44 | 7.1E-15 | 2.57 | 3.6E-13 | 1.82 | 1.1E-03 |
| DAG(18:1/18:1)/PC(P-32:0) | 2.09 | 1.5E-28 | 2.27 | 1.3E-26 | 2.41 | 2.7E-13 | 2.65 | 2.5E-12 | 1.86 | 1.8E-03 |
| DAG(18:0/20:4)/LPC(20:0) [sn2] | 2.16 | 1.6E-28 | 2.23 | 2.7E-24 | 2.87 | 7.7E-17 | 3.09 | 3.4E-15 | 2.73 | 1.3E-06 |
| CE(16:1)/PC(O-38:2) | 2.06 | 1.6E-28 | 1.95 | 4.3E-20 | 2.44 | 2.5E-14 | 2.51 | 9.8E-12 | 1.76 | 2.5E-03 |
| DAG(16:0/22:6)/PC(38:7) | 2.17 | 1.6E-28 | 2.28 | 3.1E-25 | 2.86 | 4.3E-16 | 2.87 | 2.0E-13 | 2.58 | 5.9E-06 |
| DAG(16:0/18:2)/PC(O-38:2) | 2.10 | 1.7E-28 | 2.20 | 4.5E-25 | 2.46 | 1.4E-13 | 2.63 | 4.2E-12 | 2.25 | 3.1E-05 |
| PI(40:5)/PC(P-40:5) | 2.25 | 1.7E-28 | 2.02 | 9.5E-19 | 3.15 | 1.0E-15 | 2.68 | 1.4E-10 | 1.99 | 9.4E-04 |
| DAG(14:0/18:2)/LPC(20:1) [sn2] | 2.15 | 1.7E-28 | 2.29 | 1.5E-25 | 2.56 | 6.3E-13 | 2.68 | 3.5E-11 | 2.12 | 5.7E-04 |
| PC(32:1)/LPC(MHDA) [sn2] | 2.02 | 1.7E-28 | 1.88 | 2.0E-19 | 2.55 | 3.5E-17 | 2.39 | 6.2E-13 | 1.97 | 1.0E-04 |
| Cer(d18:1/20:0)/Gb3(d18:1/16:0) | 2.16 | 1.7E-28 | 2.38 | 9.5E-27 | 2.77 | 3.7E-15 | 2.91 | 5.8E-13 | 1.91 | 1.9E-03 |
| PC(32:1)/PC(O-32:0) | 2.06 | 1.7E-28 | 1.94 | 6.1E-20 | 2.47 | 5.2E-14 | 2.44 | 2.8E-11 | 1.76 | 2.7E-03 |
| SM(36:2)/PC(O-34:1) | 2.16 | 1.7E-28 | 2.38 | 2.2E-27 | 3.51 | 1.3E-19 | 3.75 | 1.9E-17 | 2.56 | 9.2E-06 |
| DAG(16:1/16:1)/PC(39:4) | 2.11 | 1.8E-28 | 1.99 | 3.0E-20 | 2.70 | 2.2E-15 | 2.70 | 1.2E-12 | 1.91 | 9.0E-04 |
| DAG(16:1/16:1)/LPC(P-18:0) | 2.07 | 1.8E-28 | 1.95 | 3.3E-20 | 2.71 | 9.8E-17 | 2.60 | 4.8E-13 | 1.98 | 3.3E-04 |
| DAG(14:0/18:2)/LPC(O-20:1) | 2.14 | 1.8E-28 | 2.23 | 1.2E-24 | 2.57 | 2.5E-13 | 2.63 | 3.3E-11 | 2.20 | 1.8E-04 |
| SM(38:0)/LPC(O-20:1) | 2.12 | 1.9E-28 | 2.18 | 6.1E-24 | 3.09 | 1.7E-17 | 3.39 | 3.8E-15 | 2.45 | 1.7E-05 |
| DAG(18:0/20:4)/LPC(P-18:0) | 2.10 | 2.0E-28 | 2.13 | 1.2E-23 | 2.83 | 5.5E-17 | 2.88 | 3.7E-14 | 2.62 | 1.8E-06 |
| DAG(18:1/18:1)/LPC(18:2) [sn2] | 2.10 | 2.0E-28 | 2.29 | 6.5E-27 | 2.71 | 7.9E-16 | 2.89 | 5.2E-14 | 2.01 | 4.8E-04 |
| DAG(14:0/18:2)/LPC(20:1) [sn1] | 2.15 | 2.1E-28 | 2.28 | 1.7E-25 | 2.60 | 2.3E-13 | 2.72 | 1.5E-11 | 2.15 | 4.3E-04 |
| DAG(16:1/16:1)/LPC(17:0) [sn1] | 2.08 | 2.1E-28 | 1.94 | 1.2E-19 | 2.69 | 1.1E-16 | 2.62 | 3.7E-13 | 1.95 | 3.9E-04 |
| SM(38:1)/PC(P-34:1) | 2.19 | 2.1E-28 | 2.41 | 1.1E-26 | 2.87 | 2.3E-14 | 3.17 | 3.5E-13 | 2.45 | 7.1E-05 |
| PE(40:5)/LPC(19:0) [sn2] | 2.02 | 2.2E-28 | 2.00 | 1.4E-22 | 2.29 | 3.1E-14 | 2.21 | 3.3E-11 | 1.81 | 1.1E-03 |
| DAG(14:0/18:2)/LPC(22:0) [sn2] | 2.17 | 2.2E-28 | 2.31 | 2.0E-25 | 2.70 | 5.5E-14 | 2.85 | 3.9E-12 | 2.45 | 5.9E-05 |
| PI(40:5)/Glc/GalCer(d18:1/23:0) | 2.19 | 2.2E-28 | 2.05 | 4.7E-20 | 2.48 | 3.2E-12 | 2.37 | 3.7E-09 | 2.05 | 4.4E-04 |
| DAG(16:1/16:1)/PC(O-38:2) | 2.09 | 2.2E-28 | 1.98 | 3.5E-20 | 2.53 | 6.7E-15 | 2.53 | 7.1E-12 | 1.92 | 5.0E-04 |
| CE(16:1)/PC(34:3) | 2.10 | 2.3E-28 | 2.08 | 3.2E-22 | 2.71 | 3.9E-15 | 2.77 | 8.8E-13 | 1.68 | 9.5E-03 |
| PC(36:4)/PC(33:2) | 2.13 | 2.3E-28 | 2.11 | 4.7E-21 | 2.78 | 1.2E-14 | 2.83 | 8.8E-12 | 2.19 | 2.1E-04 |
| DAG(14:0/18:2)/PC(35:2) | 2.18 | 2.4E-28 | 2.32 | 3.2E-25 | 2.63 | 1.4E-12 | 2.69 | 2.4E-10 | 2.50 | 4.1E-05 |
| DAG(18:0/20:4)/PC(O-36:2) | 2.11 | 2.4E-28 | 2.18 | 3.4E-24 | 2.60 | 2.6E-15 | 2.65 | 7.8E-13 | 2.44 | 6.2E-06 |
| DAG(16:0/18:2)/PC(P-32:0) | 2.11 | 2.5E-28 | 2.28 | 3.1E-26 | 2.57 | 8.5E-14 | 2.83 | 1.1E-12 | 2.24 | 8.3E-05 |
| DAG(16:1/16:1)/SM(41:2) | 2.08 | 2.6E-28 | 1.97 | 3.4E-20 | 2.50 | 1.0E-14 | 2.49 | 9.9E-12 | 1.84 | 1.3E-03 |
| PE(40:5)/PC(O-36:3) | 2.10 | 2.7E-28 | 2.10 | 1.1E-22 | 2.34 | 4.9E-12 | 2.15 | 1.9E-08 | 1.80 | 3.3E-03 |
| DAG(16:0/18:2)/PC(P-40:4) | 2.11 | 2.7E-28 | 2.26 | 9.4E-26 | 2.68 | 1.2E-14 | 2.96 | 1.8E-13 | 2.42 | 1.3E-05 |
| SM(36:2)/LPC(O-22:1) | 2.11 | 2.7E-28 | 2.20 | 1.5E-24 | 3.18 | 1.3E-18 | 3.40 | 3.5E-16 | 2.34 | 1.3E-05 |
| Cer(d18:1/24:1)/LPC(O-20:0) | 2.09 | 2.8E-28 | 2.08 | 2.1E-22 | 2.79 | 1.2E-16 | 2.96 | 2.0E-14 | 2.34 | 5.7E-06 |
| SM(38:0)/LPC(MHDA) [sn1] | 2.11 | 2.9E-28 | 2.15 | 1.1E-23 | 3.25 | 3.4E-19 | 3.33 | 2.6E-16 | 2.95 | 9.8E-08 |
| Cer(d18:1/24:1)/LPC(22:0) [sn1] | 2.13 | 2.9E-28 | 2.17 | 1.8E-23 | 3.02 | 9.2E-18 | 3.29 | 3.2E-16 | 2.46 | 5.7E-06 |
| PC(36:4)/SM(37:1) | 2.20 | 3.0E-28 | 2.14 | 1.9E-21 | 2.91 | 7.2E-14 | 2.80 | 8.9E-11 | 1.98 | 2.3E-03 |
| Cer(d18:1/16:0)/SM(37:2) | 2.14 | 3.1E-28 | 2.32 | 7.3E-26 | 2.86 | 3.5E-16 | 2.87 | 7.3E-13 | 1.84 | 2.5E-03 |
| Cer(d16:1/18:0)/PC(O-34:2) | 2.19 | 3.1E-28 | 2.34 | 3.9E-25 | 3.20 | 4.2E-17 | 3.09 | 3.5E-13 | 2.31 | 1.1E-04 |
| PE(36:2)/PC(35:3) | 2.07 | 3.1E-28 | 2.12 | 3.9E-24 | 2.41 | 1.8E-13 | 2.36 | 7.5E-11 | 1.96 | 7.5E-04 |
| SM(41:0)/LPC(O-22:1) | 2.09 | 3.1E-28 | 2.14 | 1.3E-23 | 2.95 | 1.0E-17 | 3.29 | 5.1E-16 | 2.20 | 1.1E-04 |
| PE(38:3)/SM(37:2) | 2.11 | 3.2E-28 | 2.21 | 7.8E-25 | 2.77 | 1.7E-15 | 2.77 | 1.6E-12 | 1.88 | 2.5E-03 |
| DAG(16:1/16:1)/PC(O-32:0) | 2.09 | 3.2E-28 | 1.99 | 1.6E-20 | 2.54 | 1.7E-14 | 2.54 | 6.6E-12 | 1.88 | 1.1E-03 |
| DAG(16:1/18:1)/LPC(18:2) [sn2] | 2.14 | 3.4E-28 | 2.20 | 7.8E-24 | 2.82 | 2.3E-15 | 2.89 | 6.3E-13 | 2.12 | 3.7E-04 |
| PE(36:1)/LPC(19:0) [sn2] | 1.99 | 3.4E-28 | 1.97 | 1.7E-22 | 2.35 | 8.6E-16 | 2.28 | 1.1E-12 | 1.80 | 7.6E-04 |
| DAG(14:0/18:2)/LPC(17:0) [sn2] | 2.11 | 3.5E-28 | 2.17 | 6.3E-24 | 2.55 | 4.3E-14 | 2.55 | 1.9E-11 | 2.28 | 6.5E-05 |
| DAG(16:0/22:6)/ | 2.14 | 3.6E-28 | 2.15 | 1.5E-22 | 2.79 | 4.3E-15 | 2.84 | 2.6E-12 | 2.72 | 2.0E-06 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| LacCer(d18:1/16:0) PE(36:1)/LPC(20:1) [sn1] | 2.03 | 3.6E−28 | 2.02 | 6.4E−23 | 2.39 | 1.8E−14 | 2.32 | 1.4E−11 | 1.74 | 3.4E−03 |
| PE(38:4)/PC(O-34:2) | 2.22 | 3.7E−28 | 2.26 | 6.1E−23 | 3.27 | 1.2E−15 | 3.09 | 9.8E−12 | 1.79 | 7.6E−03 |
| PC(32:1)/LPC(19:0) [sn2] | 2.04 | 3.9E−28 | 1.92 | 5.3E−20 | 2.63 | 2.3E−17 | 2.55 | 5.6E−14 | 1.82 | 7.6E−04 |
| DAG(16:1/16:1)/LPC(15:0) [sn1] | 2.08 | 3.9E−28 | 1.95 | 1.1E−19 | 2.67 | 1.9E−16 | 2.65 | 5.0E−13 | 1.95 | 3.3E−04 |
| DAG(16:0/18:2)/PC(O-34:2) | 2.12 | 4.0E−28 | 2.27 | 1.6E−25 | 2.82 | 4.2E−15 | 2.93 | 7.7E−13 | 2.35 | 4.3E−05 |
| PC(32:1)/PC(O-34:0) | 2.04 | 4.1E−28 | 1.91 | 2.1E−19 | 2.45 | 5.3E−14 | 2.39 | 8.1E−11 | 1.81 | 1.5E−03 |
| Cer(d16:1/18:0)/CE(17:0) | 2.21 | 4.2E−28 | 2.49 | 1.9E−26 | 2.90 | 4.4E−16 | 3.17 | 1.9E−13 | 2.18 | 1.4E−04 |
| DAG(16:0/22:6)/LPC(22:1) [sn1] | 2.13 | 4.2E−28 | 2.10 | 5.2E−22 | 2.94 | 7.2E−16 | 2.99 | 2.8E−13 | 2.61 | 6.6E−06 |
| Cer(d16:1/18:0)/LPC(O-18:1) | 2.21 | 4.3E−28 | 2.32 | 3.3E−24 | 3.27 | 1.6E−16 | 3.22 | 3.4E−13 | 2.21 | 4.6E−04 |
| PC(38:5)/PC(17:0_22:6) | 2.09 | 4.3E−28 | 2.07 | 1.0E−21 | 2.18 | 7.0E−11 | 2.16 | 3.1E−08 | 1.88 | 1.1E−03 |
| PI(40:5)/LPC(22:6) [sn1] | 2.17 | 4.3E−28 | 2.13 | 7.6E−22 | 2.62 | 6.3E−13 | 2.44 | 9.8E−10 | 1.75 | 7.5E−03 |
| DAG(16:1/16:1)/PC(O-34:0) | 2.08 | 4.5E−28 | 1.98 | 3.3E−20 | 2.56 | 1.9E−14 | 2.54 | 1.4E−11 | 1.92 | 7.4E−04 |
| PC(32:1)/LPC(O-24:1) | 2.04 | 4.6E−28 | 1.90 | 2.0E−19 | 2.54 | 2.0E−15 | 2.44 | 3.9E−12 | 1.77 | 2.5E−03 |
| DAG(18:0/20:4)/LPC(20:0) [sn1] | 2.14 | 4.7E−28 | 2.20 | 7.8E−24 | 2.88 | 9.8E−17 | 3.11 | 4.7E−15 | 2.86 | 6.0E−07 |
| SM(36:0)/LPC(17:0) [sn2] | 2.04 | 4.7E−28 | 2.05 | 8.8E−23 | 2.87 | 2.2E−19 | 2.92 | 2.4E−16 | 2.45 | 5.0E−07 |
| DAG(16:0/22:6)/LPC(O-20:1) | 2.11 | 4.7E−28 | 2.09 | 5.6E−22 | 2.93 | 2.2E−16 | 2.95 | 2.5E−13 | 2.67 | 1.9E−06 |
| PI(40:5)/LPC(22:1) [sn1] | 2.29 | 4.8E−28 | 2.15 | 4.5E−20 | 3.08 | 4.3E−14 | 3.04 | 2.3E−11 | 1.83 | 5.7E−03 |
| DAG(16:0/22:6)/SM(37:1) | 2.15 | 5.1E−28 | 2.15 | 5.4E−22 | 2.87 | 5.3E−15 | 2.85 | 6.2E−12 | 2.55 | 1.1E−05 |
| Cer(d18:1/24:1)/LPC(P-18:0) | 2.06 | 5.5E−28 | 2.02 | 1.0E−21 | 2.71 | 2.5E−17 | 2.61 | 9.9E−14 | 2.11 | 3.0E−05 |
| Cer(d18:1/20:0)/Gb3(d18:1/22:0) | 2.07 | 5.6E−28 | 2.27 | 1.4E−26 | 2.25 | 2.4E−12 | 2.25 | 4.6E−10 | 1.84 | 1.5E−03 |
| SM(38:0)/PC(P-32:0) | 2.14 | 5.7E−28 | 2.26 | 1.3E−24 | 2.98 | 6.7E−16 | 3.32 | 1.7E−14 | 2.67 | 7.3E−06 |
| PC(32:1)/LPC(24:0) [sn2] | 2.07 | 5.8E−28 | 1.95 | 5.2E−20 | 2.69 | 3.5E−16 | 2.63 | 2.2E−13 | 1.91 | 4.8E−04 |
| DAG(14:0/18:2)/LPC(17:0) [sn1] | 2.11 | 5.8E−28 | 2.16 | 1.9E−23 | 2.55 | 1.1E−13 | 2.55 | 3.5E−11 | 2.26 | 9.4E−05 |
| Cer(d16:1/24:1)/LPC(MHDA) [sn2] | 2.12 | 5.8E−28 | 2.15 | 1.0E−22 | 2.62 | 1.0E−14 | 2.52 | 4.3E−11 | 2.14 | 1.4E−04 |
| Cer(d18:1/20:0)/PC(O-36:3) | 2.14 | 6.2E−28 | 2.30 | 2.9E−25 | 2.99 | 1.7E−16 | 3.00 | 4.2E−13 | 2.36 | 3.5E−05 |
| DAG(16:1/16:1)/PC(37:1) | 2.10 | 6.3E−28 | 1.98 | 1.3E−19 | 2.66 | 7.9E−15 | 2.66 | 7.6E−12 | 1.94 | 8.0E−04 |
| CE(16:1)/LPC(17:0) [sn2] | 2.03 | 6.8E−28 | 1.90 | 3.4E−19 | 2.68 | 1.8E−16 | 2.57 | 6.4E−13 | 1.81 | 1.5E−03 |
| Cer(d18:1/22:0)/PC(O-40:6) | 2.12 | 6.9E−28 | 2.21 | 7.9E−24 | 2.45 | 6.7E−12 | 2.54 | 2.2E−10 | 1.79 | 5.9E−03 |
| PC(36:3)/LPC(MHDA) [sn2] | 2.02 | 6.9E−28 | 1.94 | 7.2E−21 | 2.51 | 4.0E−17 | 2.43 | 1.3E−13 | 1.97 | 6.0E−05 |
| SM(41:0)/PC(O-34:1) | 2.11 | 7.0E−28 | 2.19 | 2.0E−24 | 2.97 | 4.0E−17 | 3.31 | 8.8E−16 | 2.19 | 1.7E−04 |
| DAG(14:0/18:2)/LPC(15:0) [sn2] | 2.11 | 7.1E−28 | 2.16 | 1.9E−23 | 2.46 | 4.3E−13 | 2.44 | 1.7E−10 | 2.10 | 2.8E−04 |
| DAG(16:0/22:6)/Gb3(d18:1/16:0) | 2.13 | 7.3E−28 | 2.16 | 2.1E−22 | 2.82 | 3.0E−15 | 2.86 | 3.0E−12 | 2.50 | 1.6E−05 |
| SM(40:1)/PC(O-36:2) | 2.12 | 7.5E−28 | 2.15 | 7.9E−23 | 2.73 | 1.5E−15 | 2.72 | 1.2E−12 | 2.00 | 2.1E−04 |
| SM(38:0)/SM(31:0) | 2.09 | 7.8E−28 | 2.12 | 6.0E−23 | 2.61 | 1.0E−15 | 2.71 | 3.4E−13 | 2.04 | 2.1E−04 |
| PC(36:3)/LPC(19:0) [sn2] | 2.01 | 8.2E−28 | 1.97 | 5.4E−22 | 2.51 | 8.6E−18 | 2.55 | 3.3E−15 | 1.76 | 9.4E−04 |
| CE(16:1)/Glc/GalCer(d18:1/23:0) | 2.06 | 8.2E−28 | 1.96 | 5.1E−20 | 2.51 | 7.4E−14 | 2.56 | 1.2E−11 | 1.76 | 3.1E−03 |
| SM(38:0)/LPC(P-18:1) | 2.11 | 8.2E−28 | 2.11 | 1.9E−22 | 2.84 | 2.6E−16 | 2.87 | 2.0E−13 | 2.10 | 3.2E−04 |
| DAG(14:0/18:2)/SM(d17:1/14:0) | 2.12 | 8.4E−28 | 2.19 | 1.6E−23 | 2.37 | 1.7E−11 | 2.34 | 3.9E−09 | 2.05 | 6.6E−04 |
| PC(38:4)/LPC(20:1) [sn1] | 2.18 | 8.4E−28 | 2.29 | 2.8E−24 | 3.26 | 8.8E−17 | 3.39 | 1.6E−14 | 1.80 | 6.8E−03 |
| PC(36:3)/LPC(20:1) [sn1] | 2.10 | 8.5E−28 | 2.09 | 2.5E−22 | 2.71 | 1.7E−16 | 2.82 | 3.3E−14 | 1.72 | 7.2E−03 |
| PC(36:4)/PC(P-40:2) | 2.15 | 8.6E−28 | 2.14 | 4.4E−22 | 2.81 | 6.6E−14 | 2.77 | 4.7E−11 | 2.31 | 4.8E−05 |
| SM(36:0)/LPC(P-16:0) | 2.02 | 8.6E−28 | 2.05 | 2.5E−23 | 2.80 | 5.7E−19 | 2.89 | 1.7E−16 | 2.35 | 2.3E−06 |
| Cer(d16:1/18:0)/PC(37:1) | 2.29 | 8.8E−28 | 2.51 | 5.4E−26 | 3.08 | 1.3E−14 | 3.19 | 4.6E−12 | 2.43 | 1.2E−04 |
| Cer(d18:1/24:1)/PC(35:3) | 2.14 | 9.1E−28 | 2.20 | 8.0E−24 | 2.74 | 2.1E−14 | 2.81 | 1.4E−12 | 2.13 | 4.2E−04 |
| CE(16:1)/LPE(16:0) [sn1] | 2.09 | 1.0E−27 | 2.01 | 2.1E−20 | 2.61 | 3.2E−14 | 2.71 | 2.6E−12 | 1.81 | 3.5E−03 |
| DAG(16:0/22:6)/LPC(20:0) [sn2] | 2.13 | 1.0E−27 | 2.10 | 1.5E−21 | 3.11 | 3.8E−17 | 3.15 | 5.4E−14 | 2.94 | 6.3E−07 |
| Cer(d18:2/18:0)/PC(O-36:3) | 2.20 | 1.0E−27 | 2.48 | 1.1E−26 | 3.24 | 3.5E−16 | 3.25 | 5.8E−13 | 1.90 | 4.1E−03 |
| DAG(16:1/16:1)/PC(P-40:4) | 2.07 | 1.1E−27 | 1.96 | 7.6E−20 | 2.71 | 1.7E−15 | 2.68 | 1.1E−12 | 2.00 | 3.4E−04 |
| DAG(16:0/18:2)/LPC(18:2) [sn1] | 2.07 | 1.1E−27 | 2.22 | 6.7E−26 | 2.77 | 2.0E−16 | 2.94 | 1.6E−14 | 2.43 | 9.9E−06 |
| Cer(d18:1/20:0)/ LacCer(d18:1/16:0) | 2.12 | 1.1E−27 | 2.29 | 1.8E−25 | 2.63 | 2.9E−14 | 2.75 | 2.3E−12 | 2.28 | 8.6E−05 |
| SM(41:0)/PC(O-36:2) | 2.08 | 1.1E−27 | 2.13 | 1.8E−23 | 2.97 | 7.2E−18 | 3.06 | 4.0E−15 | 2.26 | 6.1E−05 |
| LPC(20:3) [sn2]/LPC(20:2) [sn1] | 2.19 | 1.1E−27 | 2.32 | 6.6E−24 | 3.25 | 5.9E−16 | 3.81 | 9.2E−15 | 1.93 | 2.8E−03 |
| DAG(16:0/18:2)/LPC(22:6) [sn1] | 2.11 | 1.1E−27 | 2.32 | 1.5E−26 | 2.54 | 2.2E−13 | 2.74 | 2.7E−12 | 2.09 | 3.2E−04 |
| DAG(16:0/22:6)/LPC(P-18:1) | 2.11 | 1.1E−27 | 2.06 | 4.5E−21 | 2.84 | 1.0E−15 | 2.75 | 3.3E−12 | 2.47 | 1.2E−05 |
| PI(36:4)/PC(O-40:6) | 2.05 | 1.2E−27 | 2.07 | 9.4E−23 | 2.58 | 6.3E−15 | 2.52 | 5.4E−12 | 1.73 | 4.6E−03 |
| PE(36:1)/LPC(20:1) [sn2] | 2.02 | 1.2E−27 | 2.01 | 1.9E−22 | 2.34 | 1.1E−13 | 2.27 | 6.7E−11 | 1.70 | 5.4E−03 |
| SM(38:0)/LacCer(d18:1/24:1) | 2.10 | 1.2E−27 | 2.13 | 9.0E−23 | 2.67 | 3.5E−15 | 2.78 | 4.6E−13 | 2.09 | 1.8E−04 |
| CE(16:1)/LPC(20:2) [sn2] | 2.08 | 1.2E−27 | 2.00 | 1.8E−20 | 2.74 | 3.8E−15 | 2.73 | 2.8E−12 | 1.76 | 4.2E−03 |
| LPC(20:3) [sn2]/LPC(MHDA) [sn2] | 2.09 | 1.2E−27 | 2.00 | 3.5E−20 | 2.71 | 1.2E−15 | 2.70 | 9.9E−13 | 1.98 | 9.8E−05 |
| DAG(16:1/18:1)/LPC(18:2) [sn1] | 2.10 | 1.2E−27 | 2.15 | 3.1E−23 | 2.77 | 1.9E−15 | 2.84 | 5.0E−13 | 2.17 | 1.8E−04 |
| DAG(18:1/18:1)/PC(O-34:2) | 2.09 | 1.3E−27 | 2.24 | 3.2E−25 | 2.61 | 2.6E−14 | 2.71 | 4.0E−12 | 1.96 | 9.3E−04 |
| PE(32:1)/Gb3(d18:1/23:0) | 2.04 | 1.3E−27 | 1.90 | 3.2E−19 | 2.33 | 1.8E−13 | 2.15 | 7.5E−10 | 1.65 | 9.1E−03 |
| DAG(14:0/18:2)/Gb3(d18:1/22:0) | 2.11 | 1.3E−27 | 2.25 | 8.6E−25 | 2.22 | 1.4E−10 | 2.22 | 1.3E−08 | 1.91 | 2.1E−03 |
| SM(38:0)/LPC(19:0) [sn1] | 2.09 | 1.3E−27 | 2.09 | 2.0E−22 | 3.09 | 6.9E−18 | 3.22 | 1.7E−15 | 2.71 | 2.0E−06 |
| DAG(14:0/18:2)/PC(35:3) | 2.12 | 1.4E−27 | 2.29 | 2.9E−25 | 2.47 | 3.6E−12 | 2.55 | 2.2E−10 | 2.20 | 2.8E−04 |
| DAG(18:1/18:1)/LPC(18:2) [sn1] | 2.05 | 1.4E−27 | 2.22 | 7.6E−26 | 2.66 | 7.6E−16 | 2.82 | 5.2E−14 | 2.07 | 2.0E−04 |
| SM(36:1)/LacCer(d18:1/16:0) | 2.09 | 1.4E−27 | 2.26 | 1.1E−25 | 2.74 | 1.2E−14 | 3.07 | 2.9E−14 | 2.45 | 1.6E−05 |
| PC(36:4)/LPC(19:0) [sn1] | 2.09 | 1.5E−27 | 2.00 | 2.1E−20 | 2.94 | 7.4E−17 | 2.86 | 1.5E−13 | 2.48 | 1.3E−05 |
| CE(16:1)/LPE(16:0) [sn2] | 2.09 | 1.6E−27 | 2.02 | 1.9E−20 | 2.63 | 3.7E−14 | 2.73 | 3.9E−12 | 1.83 | 2.9E−03 |
| PC(32:1)/LPC(20:1) [sn1] | 2.07 | 1.6E−27 | 1.95 | 1.4E−19 | 2.72 | 1.2E−15 | 2.63 | 1.6E−12 | 1.76 | 4.2E−03 |
| Cer(d16:1/20:0)/PC(35:2) | 2.23 | 1.6E−27 | 2.56 | 3.6E−27 | 3.12 | 2.1E−14 | 3.13 | 2.3E−11 | 3.73 | 2.6E−07 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| Cer(d18:2/18:0)/LacCer(d18:1/16:0) | 2.21 | 1.7E−27 | 2.51 | 3.0E−27 | 2.98 | 3.8E−14 | 3.18 | 3.2E−12 | 1.78 | 9.5E−03 |
| PE(38:3)/PC(37:2) | 2.10 | 1.8E−27 | 2.14 | 6.6E−23 | 2.74 | 1.9E−14 | 2.75 | 5.5E−12 | 2.06 | 6.2E−04 |
| PE(36:2)/PC(37:2) | 2.06 | 1.9E−27 | 2.06 | 2.4E−22 | 2.39 | 7.0E−13 | 2.37 | 1.2E−10 | 2.06 | 3.5E−04 |
| CE(18:0)/LPC(19:0) [sn2] | 2.07 | 1.9E−27 | 2.17 | 2.8E−24 | 2.27 | 1.1E−14 | 2.34 | 4.0E−13 | 1.74 | 6.8E−04 |
| Cer(d18:1/24:1)/LPC(22:0) [sn2] | 2.10 | 1.9E−27 | 2.15 | 4.6E−23 | 3.00 | 1.4E−17 | 3.19 | 7.2E−16 | 2.36 | 2.3E−05 |
| DAG(16:1/18:1)/LPC(18:1) [sn2] | 2.11 | 2.0E−27 | 2.18 | 1.3E−23 | 2.77 | 4.0E−15 | 2.89 | 5.8E−13 | 2.31 | 9.1E−05 |
| DAG(16:0/22:6)/LPC(P-18:0) | 2.08 | 2.0E−27 | 2.04 | 4.1E−21 | 2.97 | 5.9E−17 | 2.90 | 2.8E−13 | 2.75 | 8.4E−07 |
| PE(36:1)/LPE(16:0) [sn1] | 2.08 | 2.0E−27 | 2.16 | 1.1E−23 | 2.49 | 1.1E−12 | 2.58 | 9.3E−11 | 1.98 | 1.2E−03 |
| DAG(16:0/22:6)/LPC(20:0) [sn1] | 2.12 | 2.0E−27 | 2.09 | 2.7E−21 | 3.13 | 5.5E−17 | 3.17 | 6.9E−14 | 3.04 | 4.0E−07 |
| PC(32:1)/PC(O-38:2) | 2.01 | 2.0E−27 | 1.88 | 1.5E−18 | 2.37 | 4.7E−14 | 2.38 | 8.2E−11 | 1.81 | 1.2E−03 |
| PC(32:1)/PC(O-40:3) | 2.03 | 2.1E−27 | 1.99 | 3.1E−21 | 2.31 | 2.7E−13 | 2.47 | 1.1E−11 | 1.66 | 4.9E−03 |
| PE(36:2)/SM(37:2) | 2.04 | 2.1E−27 | 2.12 | 1.0E−23 | 2.45 | 7.8E−14 | 2.39 | 4.9E−11 | 1.85 | 2.2E−03 |
| CE(18:0)/LPC(MHDA) [sn2] | 2.07 | 2.1E−27 | 2.16 | 9.0E−24 | 2.44 | 3.4E−14 | 2.45 | 1.8E−11 | 2.11 | 3.3E−05 |
| CE(16:2)/SM(37:2) | 2.13 | 2.2E−27 | 2.13 | 9.6E−23 | 3.23 | 5.8E−17 | 2.97 | 1.2E−12 | 1.77 | 4.1E−03 |
| DAG(16:0/22:6)/LPC(22:0) [sn1] | 2.12 | 2.3E−27 | 2.11 | 9.4E−22 | 3.09 | 9.0E−17 | 3.23 | 5.9E−14 | 3.09 | 2.9E−07 |
| Cer(d18:1/22:0)/PC(P-40:2) | 2.06 | 2.3E−27 | 2.09 | 1.6E−22 | 2.24 | 7.2E−12 | 2.21 | 1.1E−09 | 1.73 | 3.9E−03 |
| PC(32:1)/LPC(20:2) [sn1] | 2.06 | 2.4E−27 | 1.96 | 1.1E−19 | 2.74 | 7.3E−16 | 2.62 | 3.2E−12 | 1.91 | 8.5E−04 |
| DAG(16:0/22:6)/LPC(22:0) [sn2] | 2.12 | 2.5E−27 | 2.12 | 9.1E−22 | 3.11 | 5.7E−17 | 3.19 | 5.6E−14 | 3.02 | 4.2E−07 |
| DAG(16:1/16:1)/LPE(P-20:0) | 2.04 | 2.5E−27 | 1.92 | 2.1E−19 | 2.65 | 3.6E−16 | 2.52 | 1.1E−12 | 1.92 | 5.3E−04 |
| DAG(16:0/22:6)/LPC(O-24:1) | 2.08 | 2.6E−27 | 2.07 | 1.3E−21 | 2.81 | 8.2E−16 | 2.87 | 5.5E−13 | 2.67 | 2.6E−06 |
| PC(32:1)/SM(41:2) | 2.00 | 2.6E−27 | 1.89 | 1.3E−18 | 2.32 | 1.2E−13 | 2.32 | 1.7E−10 | 1.69 | 4.7E−03 |
| Cer(d18:2/18:0)/PC(O-40:6) | 2.15 | 2.6E−27 | 2.42 | 9.9E−27 | 2.69 | 3.1E−13 | 2.83 | 9.8E−12 | 1.87 | 3.4E−03 |
| PE(32:1)/PC(P-32:1) | 2.04 | 2.6E−27 | 1.99 | 4.2E−21 | 2.43 | 1.1E−13 | 2.33 | 6.6E−11 | 1.72 | 5.8E−03 |
| DAG(18:0/20:4)/LPC(O-20:0) | 2.07 | 2.7E−27 | 2.11 | 5.1E−23 | 2.63 | 2.8E−15 | 2.82 | 8.1E−14 | 2.67 | 7.4E−07 |
| SM(38:0)/LPC(O-20:0) | 2.05 | 3.0E−27 | 2.09 | 8.0E−23 | 2.93 | 2.4E−17 | 3.21 | 2.4E−15 | 2.71 | 1.4E−06 |
| DAG(16:1/16:1)/PC(33:3) | 2.09 | 3.1E−27 | 1.99 | 2.2E−19 | 2.70 | 3.0E−15 | 2.80 | 2.7E−12 | 1.90 | 1.5E−03 |
| PI(40:5)/LPE(16:0) [sn1] | 2.15 | 3.2E−27 | 2.05 | 5.5E−20 | 2.53 | 2.2E−12 | 2.53 | 5.1E−10 | 2.07 | 6.0E−04 |
| DAG(16:1/16:1)/LPC(O-24:0) | 2.05 | 3.2E−27 | 1.94 | 1.6E−19 | 2.56 | 4.6E−15 | 2.51 | 2.5E−12 | 1.94 | 5.7E−04 |
| Cer(d18:1/16:0)/PC(O-36:2) | 2.08 | 3.4E−27 | 2.12 | 1.6E−22 | 2.62 | 1.7E−15 | 2.50 | 1.3E−11 | 1.99 | 1.4E−04 |
| Cer(d18:1/24:1)/PC(35:2) | 2.17 | 3.5E−27 | 2.21 | 9.3E−23 | 2.92 | 5.9E−14 | 2.92 | 3.2E−11 | 2.84 | 5.1E−06 |
| PC(36:3)/PC(39:4) | 2.08 | 3.5E−27 | 2.02 | 2.0E−20 | 2.67 | 9.6E−15 | 2.82 | 4.7E−13 | 1.75 | 6.1E−03 |
| DAG(16:0/22:6)/SM(d17:1/14:0) | 2.11 | 3.5E−27 | 2.08 | 9.7E−21 | 2.83 | 4.9E−15 | 2.77 | 1.2E−11 | 2.67 | 3.6E−06 |
| PC(32:0)/SM(37:2) | 2.09 | 3.5E−27 | 2.15 | 9.0E−23 | 3.04 | 5.2E−18 | 3.01 | 9.2E−14 | 1.82 | 2.6E−03 |
| SM(38:0)/LPC(20:1) [sn1] | 2.12 | 3.5E−27 | 2.22 | 8.5E−24 | 3.23 | 7.6E−17 | 3.60 | 3.7E−15 | 2.36 | 7.9E−05 |
| CE(16:1)/CE(17:0) | 2.02 | 3.7E−27 | 1.93 | 1.8E−19 | 2.55 | 9.3E−15 | 2.52 | 1.2E−11 | 1.69 | 5.7E−03 |
| DAG(16:0/18:2)/LPC(O-24:0) | 2.04 | 3.7E−27 | 2.18 | 5.6E−25 | 2.47 | 6.4E−14 | 2.72 | 5.5E−13 | 2.25 | 3.6E−05 |
| DAG(18:0/20:4)/LPC(17:0) [sn1] | 2.09 | 3.8E−27 | 2.08 | 8.7E−22 | 2.82 | 4.6E−16 | 2.93 | 9.3E−14 | 2.69 | 2.1E−06 |
| DAG(16:0/22:6)/LPC(24:0) [sn2] | 2.11 | 3.8E−27 | 2.13 | 4.3E−22 | 3.03 | 1.4E−16 | 3.21 | 5.5E−14 | 3.00 | 3.2E−07 |
| DAG(16:1/16:1)/PC(O-34:2) | 2.06 | 4.0E−27 | 1.96 | 1.7E−19 | 2.78 | 1.2E−15 | 2.70 | 4.0E−12 | 1.96 | 7.0E−04 |
| CE(16:1)/PC(O-34:2) | 2.05 | 4.0E−27 | 1.95 | 3.2E−19 | 2.72 | 2.2E−15 | 2.66 | 1.0E−11 | 1.79 | 3.3E−03 |
| Cer(d18:1/20:0)/LPC(O-20:0) | 2.08 | 4.1E−27 | 2.17 | 2.1E−23 | 2.96 | 7.6E−17 | 3.09 | 3.3E−14 | 2.51 | 6.0E−07 |
| DAG(18:1/18:1)/LPC(O-24:0) | 2.02 | 4.1E−27 | 2.16 | 5.6E−25 | 2.34 | 2.5E−13 | 2.55 | 1.7E−12 | 1.90 | 8.1E−04 |
| DAG(16:0/22:6)/PC(35:2) | 2.16 | 4.1E−27 | 2.16 | 2.0E−21 | 3.10 | 2.0E−15 | 3.10 | 3.9E−12 | 3.25 | 1.8E−07 |
| PC(38:4)/LPC(P-18:0) | 2.02 | 4.1E−27 | 2.00 | 1.2E−21 | 2.82 | 7.8E−18 | 2.67 | 1.3E−13 | 2.01 | 3.5E−04 |
| Cer(d18:1/24:1)/LPC(MHDA) [sn2] | 2.03 | 4.2E−27 | 1.99 | 8.4E−21 | 2.63 | 8.1E−17 | 2.56 | 2.2E−13 | 2.27 | 3.1E−06 |
| PC(36:4)/Gb3(d18:1/22:0) | 2.08 | 4.2E−27 | 2.12 | 2.2E−22 | 2.43 | 3.2E−12 | 2.34 | 1.9E−09 | 1.87 | 2.9E−03 |
| DAG(18:0/20:4)/SM(37:1) | 2.08 | 4.2E−27 | 2.14 | 3.9E−23 | 2.37 | 2.8E−12 | 2.48 | 8.0E−11 | 2.09 | 3.4E−04 |
| PE(36:1)/PC(O-34:2) | 2.02 | 4.3E−27 | 2.01 | 8.6E−22 | 2.50 | 3.5E−14 | 2.29 | 2.5E−10 | 1.89 | 1.2E−03 |
| PE(38:3)/PC(35:2) | 2.09 | 4.4E−27 | 2.16 | 2.5E−23 | 2.88 | 4.8E−15 | 2.81 | 7.6E−12 | 2.25 | 1.7E−04 |
| DAG(14:0/18:2)/PC(O-36:3) | 2.11 | 4.5E−27 | 2.23 | 6.8E−24 | 2.53 | 4.0E−12 | 2.51 | 1.0E−09 | 2.18 | 3.9E−04 |
| DAG(18:0/20:4)/LPC(22:0) [sn2] | 2.11 | 4.5E−27 | 2.22 | 7.2E−24 | 2.81 | 3.7E−16 | 3.06 | 8.0E−15 | 2.77 | 9.8E−07 |
| PC(32:1)/PC(37:1) | 2.03 | 4.6E−27 | 1.87 | 7.4E−18 | 2.49 | 2.8E−14 | 2.45 | 5.7E−11 | 1.77 | 2.3E−03 |
| CE(16:1)/PC(37:1) | 2.02 | 4.7E−27 | 1.89 | 1.3E−18 | 2.47 | 9.7E−14 | 2.46 | 3.7E−11 | 1.70 | 6.0E−03 |
| PE(38:3)/PC(O-40:6) | 2.09 | 4.7E−27 | 2.17 | 2.5E−23 | 2.54 | 6.3E−13 | 2.57 | 6.0E−11 | 1.96 | 1.4E−03 |
| PE(40:6)/PC(17:0_22:6) | 2.02 | 4.8E−27 | 1.98 | 7.8E−21 | 2.49 | 1.2E−13 | 2.38 | 1.2E−10 | 2.20 | 8.5E−05 |
| PC(36:4)/LPC(MHDA) [sn1] | 2.03 | 4.9E−27 | 1.99 | 6.8E−21 | 2.87 | 3.3E−17 | 2.78 | 1.1E−13 | 2.55 | 2.3E−06 |
| CE(18:0)/LPC(O-18:0) | 2.10 | 5.2E−27 | 2.18 | 4.1E−23 | 2.64 | 6.8E−14 | 2.70 | 1.3E−11 | 2.26 | 8.4E−05 |
| PE(36:1)/LPC(MHDA) [sn2] | 1.97 | 5.4E−27 | 1.92 | 6.8E−21 | 2.32 | 5.5E−15 | 2.18 | 3.3E−11 | 1.93 | 1.5E−04 |
| AcylCarnitine(16:0)/LPC(MHDA) [sn2] | 2.06 | 5.5E−27 | 2.00 | 6.6E−20 | 2.67 | 3.7E−15 | 2.53 | 3.5E−11 | 1.95 | 9.1E−05 |
| PC(32:1)/LPC(20:1) [sn2] | 2.06 | 5.5E−27 | 1.93 | 4.9E−19 | 2.65 | 8.2E−15 | 2.56 | 8.9E−12 | 1.72 | 6.8E−03 |
| DAG(18:0/20:4)/PC(O-34:1) | 2.07 | 5.5E−27 | 2.16 | 1.1E−23 | 2.44 | 2.4E−13 | 2.62 | 4.0E−12 | 2.39 | 2.9E−05 |
| DAG(16:1/16:1)/LPC(O-18:1) | 2.03 | 5.5E−27 | 1.90 | 1.2E−18 | 2.58 | 3.4E−15 | 2.47 | 7.1E−12 | 1.83 | 1.7E−03 |
| PE(40:5)/PC(33:2) | 2.02 | 5.5E−27 | 2.05 | 5.9E−22 | 2.07 | 3.6E−10 | 1.99 | 1.7E−07 | 1.66 | 7.0E−03 |
| DAG(16:0/22:6)/PC(37:2) | 2.13 | 5.6E−27 | 2.13 | 3.9E−22 | 2.99 | 3.0E−15 | 3.06 | 1.8E−12 | 3.04 | 8.6E−07 |
| PE(38:4)/LPC(15:0) [sn1] | 2.13 | 5.7E−27 | 2.11 | 3.7E−21 | 2.88 | 1.3E−15 | 2.80 | 2.0E−12 | 1.76 | 6.1E−03 |
| PC(38:5)/PC(37:6) | 2.10 | 5.8E−27 | 2.09 | 7.6E−21 | 2.25 | 1.6E−10 | 2.11 | 2.0E−07 | 1.85 | 3.2E−03 |
| DAG(16:1/16:1)/LPC(O-18:0) | 2.03 | 6.0E−27 | 1.90 | 8.7E−19 | 2.62 | 1.2E−15 | 2.54 | 2.0E−12 | 1.99 | 2.7E−04 |
| Cer(d18:2/18:0)/LPC(P-18:0) | 2.12 | 6.1E−27 | 2.31 | 3.2E−25 | 3.17 | 3.6E−17 | 3.11 | 7.7E−14 | 2.00 | 5.4E−04 |
| AcylCarnitine(16:0)/LPC(O-18:0) | 2.07 | 6.1E−27 | 1.99 | 8.2E−20 | 2.83 | 1.6E−16 | 2.83 | 2.9E−13 | 2.06 | 2.4E−04 |
| DAG(18:0/20:4)/LPC(22:0) [sn1] | 2.10 | 6.1E−27 | 2.20 | 9.9E−24 | 2.77 | 7.3E−16 | 3.10 | 9.4E−15 | 2.83 | 5.6E−07 |
| SM(38:0)/LPC(MHDA) [sn2] | 2.06 | 6.4E−27 | 2.06 | 7.6E−22 | 2.99 | 7.4E−18 | 2.97 | 8.5E−15 | 2.68 | 3.1E−07 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| PC(34:1)/PC(35:3) | 2.10 | 6.5E-27 | 2.16 | 7.6E-23 | 2.57 | 1.6E-13 | 2.61 | 2.7E-11 | 1.73 | 5.6E-03 |
| SM(41:0)/LacCer(d18:1/16:0) | 2.07 | 6.8E-27 | 2.15 | 1.8E-23 | 2.74 | 2.9E-15 | 3.10 | 2.7E-14 | 2.07 | 3.1E-04 |
| PC(36:4)/PC(37:6) | 2.06 | 7.1E-27 | 2.05 | 3.0E-21 | 2.33 | 5.4E-12 | 2.34 | 1.2E-09 | 1.79 | 4.0E-03 |
| DAG(14:0/18:2)/LPC(15:0) [sn1] | 2.07 | 7.1E-27 | 2.13 | 1.0E-22 | 2.47 | 6.5E-13 | 2.47 | 1.8E-10 | 2.27 | 8.2E-05 |
| DAG(16:1/16:1)/PC(O-38:0) | 2.06 | 7.2E-27 | 1.97 | 1.9E-19 | 2.57 | 2.9E-14 | 2.59 | 1.5E-11 | 1.96 | 6.0E-04 |
| SM(36:1)/SM(34:1) | 2.12 | 7.4E-27 | 2.45 | 1.4E-27 | 3.45 | 7.3E-18 | 4.25 | 3.5E-17 | 2.37 | 5.9E-05 |
| DAG(16:0/18:2)/LPC(O-16:0) | 2.03 | 7.6E-27 | 2.11 | 7.3E-24 | 2.54 | 1.4E-14 | 2.67 | 7.2E-13 | 2.11 | 9.1E-05 |
| DAG(14:0/18:2)/LPC(P-18:0) | 2.06 | 7.8E-27 | 2.13 | 3.6E-23 | 2.51 | 1.3E-13 | 2.50 | 5.2E-11 | 2.23 | 1.2E-04 |
| PC(36:4)/LPC(19:0) [sn2] | 2.04 | 7.9E-27 | 2.00 | 6.2E-21 | 2.84 | 2.0E-17 | 2.82 | 2.1E-14 | 2.15 | 5.7E-05 |
| CE(16:1)/PC(39:4) | 2.03 | 8.0E-27 | 1.91 | 1.0E-18 | 2.50 | 4.6E-14 | 2.59 | 7.5E-12 | 1.69 | 7.0E-03 |
| DAG(14:0/18:2)/LPC(P-18:1) | 2.07 | 8.1E-27 | 2.13 | 5.9E-23 | 2.37 | 3.7E-12 | 2.35 | 9.0E-10 | 1.93 | 1.4E-03 |
| DAG(16:0/22:6)/PE(P-40:6) | 2.11 | 8.1E-27 | 2.10 | 2.6E-21 | 2.90 | 1.2E-14 | 2.77 | 2.6E-11 | 2.73 | 6.2E-06 |
| DAG(16:0/22:6)/PC(O-36:2) | 2.09 | 8.1E-27 | 2.09 | 3.0E-21 | 2.90 | 7.9E-16 | 2.88 | 1.8E-12 | 2.71 | 2.3E-06 |
| DAG(16:0/22:6)/LPC(17:0) [sn2] | 2.08 | 8.4E-27 | 2.03 | 2.3E-20 | 2.98 | 6.8E-17 | 2.93 | 2.9E-13 | 2.80 | 5.6E-07 |
| DAG(18:0/20:4)/LPC(17:0) [sn2] | 2.07 | 8.5E-27 | 2.09 | 5.8E-22 | 2.71 | 4.1E-16 | 2.77 | 1.1E-13 | 2.57 | 1.4E-06 |
| PE(38:3)/PC(33:2) | 2.07 | 8.6E-27 | 2.12 | 2.3E-22 | 2.58 | 2.3E-13 | 2.55 | 7.5E-11 | 1.86 | 2.8E-03 |
| SM(38:0)/PC(O-34:0) | 2.07 | 8.6E-27 | 2.13 | 7.5E-23 | 2.69 | 2.9E-14 | 2.85 | 1.3E-12 | 2.64 | 6.6E-06 |
| PE(36:2)/PC(O-36:3) | 2.03 | 8.7E-27 | 2.04 | 6.1E-22 | 2.44 | 7.0E-13 | 2.27 | 1.2E-09 | 1.93 | 1.3E-03 |
| PE(38:3)/PC(O-36:3) | 2.06 | 8.7E-27 | 2.10 | 2.0E-21 | 2.73 | 2.7E-14 | 2.58 | 5.4E-11 | 1.92 | 1.9E-03 |
| SM(d18:0/22:0)/LPC(20:2) [sn2] | 2.09 | 8.8E-27 | 2.27 | 7.8E-25 | 2.98 | 6.8E-16 | 3.45 | 7.8E-15 | 1.82 | 3.5E-03 |
| SM(38:0)/PC(33:2) | 2.06 | 8.9E-27 | 2.10 | 9.1E-23 | 2.66 | 1.4E-14 | 2.79 | 3.1E-13 | 2.30 | 4.0E-05 |
| PE(36:1)/SM(d17:1/14:0) | 2.02 | 8.9E-27 | 1.99 | 8.7E-21 | 2.38 | 3.1E-12 | 2.20 | 6.1E-09 | 1.69 | 7.2E-03 |
| DAG(16:1/16:1)/LPC(P-16:0) | 2.02 | 9.0E-27 | 1.90 | 5.0E-19 | 2.56 | 1.3E-15 | 2.49 | 1.8E-12 | 1.85 | 1.1E-03 |
| PE(36:1)/LacCer(d18:1/16:0) | 2.03 | 9.1E-27 | 2.03 | 8.9E-22 | 2.29 | 8.4E-12 | 2.20 | 3.1E-09 | 1.76 | 4.9E-03 |
| PI(40:5)/LPC(20:2) [sn2] | 2.13 | 9.3E-27 | 2.05 | 8.2E-20 | 2.68 | 2.3E-13 | 2.47 | 1.0E-09 | 2.04 | 8.7E-04 |
| Cer(d18:1/20:0)/LPC(20:0) [sn1] | 2.08 | 9.6E-27 | 2.20 | 1.1E-23 | 3.08 | 4.2E-18 | 3.24 | 1.3E-15 | 2.52 | 9.1E-07 |
| SM(41:0)/PC(35:2) | 2.09 | 9.6E-27 | 2.18 | 1.6E-23 | 3.12 | 3.9E-16 | 3.39 | 3.2E-14 | 2.48 | 1.9E-05 |
| DAG(18:2/20:4)/PC(O-40:6) | 2.08 | 9.8E-27 | 2.28 | 1.6E-25 | 2.25 | 6.6E-11 | 2.48 | 1.5E-10 | 1.91 | 1.4E-03 |
| PC(36:4)/Gb3(d18:1/16:0) | 2.12 | 1.0E-26 | 2.12 | 2.8E-21 | 2.85 | 6.7E-14 | 2.81 | 4.0E-11 | 1.88 | 4.1E-03 |
| Cer(d18:1/24:1)/LPC(24:0) [sn2] | 2.06 | 1.0E-26 | 2.16 | 2.4E-23 | 2.76 | 3.0E-16 | 3.06 | 1.9E-15 | 2.28 | 2.4E-05 |
| DAG(16:0/22:6)/LPC(17:0) [sn1] | 2.07 | 1.1E-26 | 2.01 | 6.1E-20 | 2.98 | 1.4E-16 | 2.92 | 4.7E-13 | 2.79 | 7.1E-07 |
| DAG(16:0/22:6)/PC(O-34:1) | 2.10 | 1.1E-26 | 2.10 | 3.1E-21 | 2.84 | 6.5E-15 | 2.89 | 3.8E-12 | 2.72 | 3.8E-06 |
| PI(40:5)/LPC(18:2) [sn1] | 2.10 | 1.2E-26 | 2.02 | 7.2E-20 | 3.06 | 1.0E-16 | 2.85 | 1.2E-12 | 2.29 | 6.9E-05 |
| SM(38:0)/PC(37:2) | 2.08 | 1.2E-26 | 2.13 | 8.2E-23 | 2.88 | 8.8E-16 | 3.10 | 1.9E-14 | 2.63 | 6.4E-06 |
| SM(38:0)/SM(34:1) | 2.10 | 1.3E-26 | 2.19 | 2.5E-23 | 2.94 | 9.9E-16 | 3.14 | 8.8E-14 | 2.23 | 1.2E-04 |
| DAG(16:0/22:6)/LPC(24:0) [sn1] | 2.08 | 1.3E-26 | 2.12 | 7.5E-22 | 2.97 | 3.3E-16 | 3.14 | 1.3E-13 | 3.05 | 2.9E-07 |
| PI(40:5)/LPE(16:0) [sn2] | 2.13 | 1.3E-26 | 2.05 | 9.3E-20 | 2.50 | 3.4E-12 | 2.46 | 1.1E-09 | 2.10 | 5.1E-04 |
| PE(36:1)/LPE(16:0) [sn2] | 2.04 | 1.3E-26 | 2.11 | 4.2E-23 | 2.42 | 2.4E-12 | 2.47 | 2.5E-10 | 1.96 | 1.1E-03 |
| Cer(d16:1/20:0)/PC(O-40:6) | 2.10 | 1.3E-26 | 2.33 | 1.2E-25 | 2.43 | 3.0E-11 | 2.49 | 1.2E-09 | 2.41 | 7.1E-05 |
| Cer(d18:1/24:1)/LPC(17:0) [sn1] | 2.02 | 1.4E-26 | 1.95 | 1.0E-19 | 2.70 | 6.1E-17 | 2.72 | 6.7E-14 | 2.08 | 5.9E-05 |
| PC(32:1)/LPC(20:2) [sn2] | 2.04 | 1.4E-26 | 1.95 | 3.3E-19 | 2.69 | 3.8E-15 | 2.62 | 8.2E-12 | 1.82 | 1.9E-03 |
| Cer(d18:1/22:0)/PC(O-34:2) | 2.05 | 1.4E-26 | 2.07 | 1.5E-21 | 2.73 | 4.2E-15 | 2.62 | 1.7E-11 | 1.77 | 4.4E-03 |
| Cer(d16:1/20:0)/PC(O-34:1) | 2.18 | 1.5E-26 | 2.45 | 8.0E-26 | 2.79 | 5.0E-13 | 2.85 | 1.1E-10 | 2.55 | 5.8E-05 |
| DAG(16:0/22:6)/LPC(O-20:0) | 2.05 | 1.7E-26 | 2.03 | 1.3E-20 | 2.85 | 7.6E-16 | 2.90 | 5.2E-13 | 2.81 | 5.7E-07 |
| DAG(18:2/20:4)/LPC(19:0) [sn2] | 2.06 | 1.7E-26 | 2.25 | 3.5E-25 | 2.53 | 1.4E-14 | 2.84 | 1.0E-13 | 1.97 | 5.3E-04 |
| PC(36:4)/PC(33:3) | 2.07 | 2.0E-26 | 1.98 | 3.6E-19 | 2.93 | 1.1E-15 | 2.88 | 2.9E-12 | 2.18 | 2.3E-04 |
| PC(32:1)/PC(O-34:2) | 2.02 | 2.0E-26 | 1.90 | 2.9E-18 | 2.76 | 2.4E-15 | 2.66 | 3.4E-11 | 1.87 | 1.6E-03 |
| DAG(16:0/22:6)/PC(33:2) | 2.08 | 2.1E-26 | 2.07 | 1.3E-20 | 2.72 | 2.2E-14 | 2.72 | 1.6E-11 | 2.70 | 3.3E-06 |
| DAG(16:1/16:1)/LPC(22:6) [sn1] | 2.04 | 2.1E-26 | 1.98 | 6.4E-20 | 2.56 | 2.8E-14 | 2.51 | 1.4E-11 | 1.81 | 2.9E-03 |
| CE(16:1)/LPE(P-20:0) | 1.99 | 2.1E-26 | 1.86 | 3.1E-18 | 2.61 | 1.0E-15 | 2.47 | 3.0E-12 | 1.75 | 2.6E-03 |
| CE(18:0)/LPC(17:0) [sn1] | 2.06 | 2.1E-26 | 2.12 | 4.0E-22 | 2.58 | 7.1E-14 | 2.63 | 1.6E-11 | 1.94 | 1.1E-03 |
| DAG(18:0/20:4)/PC(35:2) | 2.12 | 2.1E-26 | 2.20 | 4.6E-23 | 2.77 | 8.6E-14 | 2.94 | 4.2E-12 | 3.12 | 5.3E-07 |
| PE(36:1)/PC(P-40:2) | 2.03 | 2.2E-26 | 2.05 | 1.7E-21 | 2.30 | 6.0E-12 | 2.21 | 3.6E-09 | 1.79 | 1.3E-03 |
| Cer(d18:1/24:1)/PC(O-40:6) | 2.05 | 2.3E-26 | 2.12 | 1.9E-21 | 2.34 | 2.0E-11 | 2.48 | 2.7E-10 | 2.03 | 7.3E-04 |
| PC(32:1)/PC(O-38:0) | 2.01 | 2.4E-26 | 1.89 | 3.3E-18 | 2.47 | 7.3E-14 | 2.43 | 6.7E-11 | 1.88 | 9.5E-04 |
| PE(32:1)/PC(O-40:6) | 2.00 | 2.4E-26 | 1.94 | 7.1E-20 | 2.42 | 1.2E-13 | 2.33 | 7.8E-11 | 1.90 | 8.8E-04 |
| CE(16:1)/LPC(P-16:0) | 1.99 | 2.4E-26 | 1.86 | 2.6E-18 | 2.51 | 3.7E-15 | 2.42 | 4.2E-12 | 1.68 | 5.6E-03 |
| PE(38:1)/PC(O-40:6) | 2.04 | 2.5E-26 | 2.06 | 1.2E-21 | 2.33 | 5.5E-12 | 2.25 | 3.5E-09 | 2.36 | 2.4E-05 |
| PE(36:2)/PC(35:2) | 2.02 | 2.6E-26 | 2.05 | 3.6E-22 | 2.45 | 2.9E-13 | 2.35 | 3.0E-10 | 2.17 | 9.2E-05 |
| DAG(18:0/20:4)/PC(O-36:3) | 2.05 | 2.6E-26 | 2.12 | 1.3E-22 | 2.46 | 1.6E-13 | 2.47 | 2.6E-11 | 2.37 | 2.9E-05 |
| SM(38:0)/SM(41:2) | 2.06 | 2.6E-26 | 2.08 | 1.2E-21 | 2.69 | 1.9E-14 | 2.79 | 9.9E-13 | 2.41 | 2.8E-05 |
| PC(38:4)/LPC(19:0) [sn2] | 2.02 | 2.7E-26 | 2.06 | 2.8E-22 | 2.59 | 4.6E-17 | 2.65 | 1.5E-14 | 1.77 | 5.8E-04 |
| SM(38:0)/LPC(O-24:1) | 2.05 | 2.8E-26 | 2.12 | 1.6E-22 | 2.88 | 2.6E-16 | 3.17 | 1.5E-14 | 2.32 | 3.0E-05 |
| PC(38:4)/PC(O-40:6) | 2.05 | 2.8E-26 | 2.15 | 3.4E-23 | 2.29 | 7.6E-12 | 2.34 | 2.3E-10 | 1.78 | 2.8E-03 |
| Cer(d18:2/18:0)/LPC(MHDA) [sn2] | 2.09 | 2.8E-26 | 2.27 | 2.0E-24 | 3.06 | 5.8E-17 | 3.06 | 1.0E-13 | 2.19 | 1.1E-04 |
| PI(40:5)/PC(O-34:2) | 2.08 | 2.9E-26 | 1.94 | 3.4E-18 | 2.71 | 2.8E-14 | 2.38 | 1.6E-09 | 2.00 | 8.3E-04 |
| Cer(d18:1/24:1)/LPC(O-22:0) | 2.02 | 2.9E-26 | 2.04 | 1.8E-21 | 2.66 | 1.7E-15 | 2.91 | 6.8E-14 | 2.24 | 3.2E-05 |
| DAG(16:0/22:6)/LacCer(d18:1/24:1) | 2.06 | 2.9E-26 | 2.04 | 1.9E-20 | 2.70 | 2.3E-14 | 2.72 | 1.9E-11 | 2.50 | 1.4E-05 |
| PI(34:2)/SM(37:2) | 2.04 | 3.0E-26 | 2.05 | 3.0E-21 | 3.00 | 3.7E-17 | 2.78 | 6.0E-13 | 1.84 | 2.6E-03 |
| SM(38:1)/SM(37:2) | 2.06 | 3.0E-26 | 2.32 | 4.2E-26 | 2.99 | 3.9E-16 | 3.11 | 6.2E-14 | 2.11 | 3.6E-04 |
| PE(38:5)/PC(O-40:6) | 2.00 | 3.1E-26 | 2.00 | 5.3E-21 | 2.38 | 1.1E-12 | 2.31 | 5.5E-10 | 2.07 | 1.4E-04 |
| PC(36:3)/LPC(O-24:1) | 1.99 | 3.2E-26 | 1.95 | 2.2E-20 | 2.46 | 3.6E-15 | 2.51 | 7.1E-13 | 1.70 | 5.7E-03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| PC(38:2)/PC(35:2) | 2.02 | 3.2E-26 | 2.05 | 4.4E-22 | 2.81 | 5.0E-16 | 2.63 | 2.5E-12 | 2.49 | 5.9E-06 |
| Cer(d18:1/24:1)/SM(34:1) | 1.98 | 3.3E-26 | 2.01 | 1.4E-21 | 2.25 | 4.9E-13 | 2.28 | 5.2E-11 | 1.63 | 9.8E-03 |
| DAG(14:0/18:2)/LPC(24:0) [sn2] | 2.08 | 3.3E-26 | 2.25 | 2.8E-24 | 2.50 | 2.0E-12 | 2.71 | 3.4E-11 | 2.33 | 1.2E-04 |
| DAG(18:0/20:4)/PC(17:0_22:6) | 2.07 | 3.4E-26 | 2.14 | 1.9E-22 | 2.22 | 2.1E-10 | 2.46 | 8.3E-10 | 2.07 | 4.4E-04 |
| DAG(18:0/20:4)/PC(37:2) | 2.07 | 3.9E-26 | 2.14 | 1.6E-22 | 2.54 | 3.7E-13 | 2.75 | 3.0E-12 | 2.67 | 6.0E-06 |
| SM(38:0)/LPC(19:0) [sn2] | 2.02 | 4.2E-26 | 2.07 | 1.9E-22 | 2.83 | 1.1E-17 | 2.99 | 1.1E-15 | 2.22 | 1.1E-05 |
| SM(38:0)/LPC(20:1) [sn2] | 2.08 | 4.3E-26 | 2.18 | 7.5E-23 | 3.01 | 1.2E-15 | 3.36 | 3.7E-14 | 2.25 | 1.9E-04 |
| SM(38:0)/LPC(P-18:0) | 2.01 | 4.3E-26 | 2.03 | 2.0E-21 | 2.93 | 2.2E-17 | 2.95 | 2.7E-14 | 2.49 | 8.0E-06 |
| SM(40:1)/LacCer(d18:1/16:0) | 2.07 | 4.5E-26 | 2.11 | 1.0E-21 | 2.30 | 1.0E-10 | 2.44 | 7.3E-10 | 1.79 | 5.4E-03 |
| SM(36:1)/PC(O-36:2) | 2.03 | 4.5E-26 | 2.13 | 2.7E-23 | 2.84 | 7.7E-17 | 2.90 | 2.4E-14 | 2.27 | 4.6E-06 |
| PC(36:4)/LPC(MHDA) [sn2] | 2.00 | 4.7E-26 | 1.93 | 1.8E-19 | 2.71 | 2.3E-16 | 2.58 | 1.2E-12 | 2.41 | 5.7E-06 |
| PE(34:1)/SM(37:2) | 1.97 | 4.7E-26 | 1.95 | 5.7E-21 | 2.35 | 3.8E-14 | 2.22 | 8.5E-11 | 1.74 | 3.6E-03 |
| Cer(d18:1/24:1)/LPC(24:0) [sn1] | 2.03 | 4.8E-26 | 2.14 | 4.3E-23 | 2.70 | 5.3E-16 | 2.99 | 4.2E-15 | 2.36 | 1.1E-05 |
| SM(38:0)/LPC(22:0) [sn1] | 2.06 | 4.8E-26 | 2.15 | 1.5E-17 | 3.14 | 1.5E-17 | 3.51 | 4.0E-16 | 2.83 | 1.2E-06 |
| DAG(16:0/18:2)/LPE(P-18:0) | 2.00 | 4.8E-26 | 2.11 | 9.2E-24 | 2.49 | 4.0E-14 | 2.59 | 3.1E-12 | 2.22 | 4.8E-05 |
| PE(38:4)/LPC(O-24:0) | 2.11 | 5.0E-26 | 2.12 | 3.7E-21 | 2.64 | 1.5E-13 | 2.67 | 1.8E-11 | 1.74 | 9.1E-03 |
| Cer(d16:1/20:0)/PC(37:2) | 2.16 | 5.1E-26 | 2.40 | 8.6E-25 | 2.74 | 4.7E-13 | 2.85 | 4.5E-11 | 2.88 | 6.7E-06 |
| DAG(16:0/22:6)/LPC(O-22:0) | 2.03 | 5.1E-26 | 2.03 | 1.5E-20 | 2.80 | 1.5E-15 | 2.90 | 7.0E-13 | 2.77 | 8.0E-07 |
| PE(32:1)/PC(35:3) | 1.98 | 5.3E-26 | 1.89 | 6.1E-19 | 2.52 | 8.7E-15 | 2.36 | 2.6E-11 | 1.87 | 9.8E-04 |
| DAG(14:0/18:2)/PC(O-34:1) | 2.06 | 5.4E-26 | 2.18 | 3.5E-23 | 2.38 | 3.5E-11 | 2.44 | 1.7E-09 | 2.09 | 6.7E-04 |
| PC(38:2)/LPC(19:0) [sn1] | 1.95 | 5.6E-26 | 1.89 | 1.5E-19 | 2.67 | 1.8E-17 | 2.56 | 9.4E-14 | 2.25 | 1.2E-05 |
| DAG(18:1/18:2)/LPC(19:0) [sn2] | 2.00 | 5.7E-26 | 2.19 | 7.7E-25 | 2.46 | 1.8E-14 | 2.69 | 2.3E-13 | 1.95 | 4.6E-04 |
| SM(38:0)/LPC(20:0) [sn1] | 2.03 | 5.7E-26 | 2.07 | 6.0E-22 | 3.08 | 1.1E-17 | 3.33 | 8.5E-16 | 2.68 | 3.1E-06 |
| PI(40:5)/LPC(O-16:0) | 2.07 | 5.8E-26 | 1.87 | 1.2E-16 | 2.78 | 1.7E-14 | 2.47 | 4.0E-10 | 1.88 | 2.2E-03 |
| DAG(16:0/22:6)/PC(35:3) | 2.09 | 5.9E-26 | 2.12 | 6.3E-21 | 2.92 | 7.3E-15 | 2.94 | 4.6E-12 | 2.90 | 2.1E-06 |
| PE(38:4)/SM(37:2) | 2.00 | 6.1E-26 | 2.08 | 8.6E-23 | 2.46 | 3.3E-14 | 2.40 | 4.2E-11 | 1.83 | 2.2E-03 |
| DAG(14:0/18:2)/PC(33:3) | 2.07 | 6.2E-26 | 2.16 | 3.7E-22 | 2.40 | 1.2E-11 | 2.43 | 1.3E-09 | 2.12 | 5.6E-04 |
| DAG(16:0/22:6)/PC(O-36:3) | 2.07 | 6.2E-26 | 2.07 | 1.7E-20 | 2.83 | 1.0E-14 | 2.74 | 1.8E-11 | 2.68 | 4.6E-06 |
| SM(38:0)/PC(O-38:2) | 2.04 | 6.3E-26 | 2.06 | 4.6E-21 | 2.74 | 1.4E-14 | 2.87 | 8.3E-13 | 2.72 | 4.0E-06 |
| PI(40:5)/LPC(18:2) [sn2] | 2.10 | 6.3E-26 | 2.02 | 2.8E-19 | 3.02 | 9.1E-16 | 2.80 | 1.1E-11 | 2.13 | 3.9E-04 |
| DAG(14:0/18:2)/SM(37:1) | 2.06 | 6.4E-26 | 2.16 | 9.5E-23 | 2.28 | 1.8E-10 | 2.31 | 1.1E-08 | 1.90 | 2.7E-03 |
| DAG(16:0/22:6)/LPE(22:6) [sn1] | 2.07 | 6.6E-26 | 2.13 | 9.3E-22 | 2.61 | 1.7E-13 | 2.79 | 5.7E-12 | 2.69 | 3.8E-06 |
| PE(36:1)/PC(O-34:0) | 1.99 | 6.6E-26 | 1.97 | 1.4E-20 | 2.24 | 2.0E-11 | 2.15 | 1.1E-08 | 1.81 | 2.1E-03 |
| DAG(14:0/18:2)/LPC(O-24:1) | 2.05 | 6.8E-26 | 2.16 | 6.6E-23 | 2.39 | 8.3E-12 | 2.49 | 4.1E-10 | 2.10 | 4.9E-04 |
| PE(40:5)/LPE(16:0) [sn1] | 2.04 | 6.9E-26 | 2.12 | 2.5E-22 | 2.13 | 1.2E-09 | 2.15 | 5.2E-08 | 1.87 | 2.5E-03 |
| SM(38:0)/PC(O-38:0) | 2.06 | 7.0E-26 | 2.17 | 7.1E-23 | 2.89 | 3.5E-15 | 3.17 | 5.3E-14 | 2.89 | 1.7E-06 |
| Cer(d16:1/20:0)/LPC(O-20:1) | 2.09 | 7.1E-26 | 2.26 | 6.2E-24 | 2.75 | 2.5E-14 | 2.80 | 9.5E-12 | 2.43 | 4.0E-05 |
| DAG(18:0/20:4)/LPC(O-24:1) | 2.02 | 7.1E-26 | 2.09 | 2.0E-22 | 2.46 | 7.1E-14 | 2.65 | 1.3E-12 | 2.33 | 2.6E-05 |
| PC(36:4)/LPC(20:0) [sn1] | 2.04 | 7.3E-26 | 1.98 | 1.4E-19 | 2.96 | 1.1E-16 | 2.94 | 1.1E-13 | 2.46 | 2.4E-05 |
| PC(32:1)/PC(33:3) | 1.99 | 7.4E-26 | 1.86 | 3.2E-17 | 2.51 | 1.5E-14 | 2.59 | 2.6E-11 | 1.71 | 5.8E-03 |
| Cer(d18:1/24:1)/LPC(O-18:1) | 2.00 | 7.5E-26 | 1.95 | 1.9E-19 | 2.52 | 3.8E-15 | 2.48 | 2.7E-12 | 1.86 | 9.0E-04 |
| DAG(18:0/20:4)/LacCer(d18:1/16:0) | 2.03 | 7.9E-26 | 2.11 | 1.4E-22 | 2.25 | 8.9E-12 | 2.40 | 9.2E-11 | 2.28 | 4.7E-05 |
| Cer(d18:1/22:0)/LPC(15:0) [sn1] | 2.02 | 8.2E-26 | 1.98 | 1.0E-19 | 2.67 | 8.8E-15 | 2.70 | 8.5E-12 | 1.79 | 2.7E-03 |
| PE(32:1)/Gb3(d18:1/22:0) | 1.97 | 8.2E-26 | 1.89 | 2.9E-19 | 2.27 | 1.5E-12 | 2.10 | 2.9E-09 | 1.72 | 4.7E-03 |
| DAG(14:0/18:2)/Gb3(d18:1/16:0) | 2.05 | 8.4E-26 | 2.19 | 3.0E-23 | 2.31 | 7.4E-11 | 2.37 | 3.9E-09 | 1.88 | 3.3E-03 |
| Cer(d20:1/24:1)/SM(37:2) | 1.97 | 8.5E-26 | 2.02 | 3.5E-22 | 2.73 | 3.5E-17 | 2.77 | 1.2E-14 | 1.79 | 2.3E-03 |
| Cer(d18:1/24:1)/LPC(17:0) [sn2] | 1.99 | 8.6E-26 | 1.94 | 1.4E-19 | 2.53 | 1.8E-16 | 2.51 | 2.2E-13 | 2.03 | 4.1E-05 |
| PC(40:5)/LPC(20:2) [sn1] | 2.07 | 8.6E-26 | 2.24 | 8.8E-24 | 2.51 | 3.1E-12 | 2.39 | 2.7E-09 | 1.75 | 7.6E-03 |
| LPC(16:0) [sn2]/LPC(17:0) [sn2] | 2.04 | 9.0E-26 | 1.88 | 2.2E-17 | 2.04 | 9.3E-13 | 1.88 | 2.4E-09 | 1.61 | 1.4E-03 |
| DAG(14:0/18:2)/LacCer(d18:1/16:0) | 2.05 | 9.6E-26 | 2.17 | 5.5E-23 | 2.25 | 1.9E-10 | 2.31 | 6.8E-09 | 2.05 | 8.1E-04 |
| CE(16:1)/LPC(15:0) [sn1] | 1.96 | 1.0E-25 | 1.84 | 1.2E-17 | 2.52 | 4.5E-15 | 2.54 | 4.2E-12 | 1.74 | 2.9E-03 |
| DAG(18:1/18:1)/LPC(18:1) [sn2] | 2.00 | 1.0E-25 | 2.22 | 1.1E-25 | 2.54 | 8.5E-15 | 2.78 | 1.2E-13 | 2.13 | 1.4E-04 |
| DAG(14:0/18:2)/LPC(24:0) [sn1] | 2.06 | 1.0E-25 | 2.23 | 5.8E-24 | 2.47 | 3.9E-12 | 2.65 | 7.7E-11 | 2.37 | 9.5E-05 |
| SM(38:0)/PC(35:3) | 2.05 | 1.1E-25 | 2.17 | 2.8E-22 | 2.87 | 1.1E-15 | 3.09 | 4.3E-14 | 2.43 | 2.1E-05 |
| DAG(18:2/20:4)/LPC(20:1) [sn1] | 2.03 | 1.1E-25 | 2.27 | 4.1E-22 | 2.44 | 9.7E-13 | 2.77 | 2.5E-12 | 1.83 | 3.3E-03 |
| SM(38:0)/LPC(O-22:0) | 2.00 | 1.1E-25 | 2.08 | 2.6E-22 | 2.83 | 1.4E-16 | 3.18 | 3.7E-15 | 2.59 | 3.3E-06 |
| DAG(16:0/22:6)/PC(31:0) | 2.07 | 1.1E-25 | 2.08 | 2.4E-20 | 2.76 | 8.0E-14 | 2.81 | 3.9E-11 | 2.97 | 1.2E-06 |
| PC(32:1)/LPC(17:0) [sn2] | 1.94 | 1.1E-25 | 1.79 | 5.9E-17 | 2.47 | 8.8E-16 | 2.31 | 7.2E-12 | 1.81 | 1.0E-03 |
| Cer(d16:1/20:0)/Gb3(d18:1/22:0) | 2.05 | 1.2E-25 | 2.31 | 2.8E-23 | 2.18 | 2.6E-10 | 2.12 | 5.6E-08 | 1.93 | 1.5E-03 |
| Cer(d14:0/18:2)/LPC(20:2) [sn1] | 2.05 | 1.2E-25 | 2.24 | 3.6E-24 | 2.45 | 4.3E-12 | 2.55 | 2.4E-10 | 2.25 | 1.6E-04 |
| Cer(d16:1/22:0)/PC(O-40:6) | 2.05 | 1.3E-25 | 2.15 | 2.4E-22 | 2.24 | 4.1E-10 | 2.23 | 3.7E-08 | 1.77 | 7.3E-03 |
| PC(36:4)/LPC(20:1) [sn1] | 2.06 | 1.3E-25 | 2.05 | 3.1E-20 | 2.89 | 2.7E-15 | 2.91 | 1.1E-12 | 2.12 | 6.0E-04 |
| Cer(d16:1/18:0)/LPC(20:2) [sn2] | 2.15 | 1.3E-25 | 2.47 | 2.4E-25 | 3.09 | 8.5E-15 | 3.29 | 1.7E-12 | 2.33 | 2.0E-04 |
| PC(40:5)/LPE(P-20:0) | 2.01 | 1.3E-25 | 2.00 | 2.4E-20 | 2.49 | 3.8E-14 | 2.28 | 3.8E-10 | 1.72 | 6.0E-03 |
| PC(32:1)/PC(39:4) | 1.97 | 1.4E-25 | 1.84 | 3.4E-17 | 2.46 | 1.1E-13 | 2.47 | 4.4E-11 | 1.73 | 4.2E-03 |
| Cer(d16:1/20:0)/PC(O-36:3) | 2.10 | 1.4E-25 | 2.31 | 3.7E-24 | 2.75 | 2.1E-13 | 2.61 | 4.6E-10 | 2.44 | 6.2E-05 |
| DAG(14:0/18:2)/LPC(O-22:0) | 2.04 | 1.4E-25 | 2.15 | 1.0E-22 | 2.41 | 6.0E-12 | 2.53 | 2.2E-10 | 2.24 | 1.5E-04 |
| DAG(18:1/18:1)/LPC(18:1) [sn1] | 1.98 | 1.4E-25 | 2.17 | 7.8E-25 | 2.53 | 5.5E-15 | 2.73 | 1.2E-13 | 2.09 | 1.5E-04 |
| DAG(18:0/20:4)/LPC(24:0) [sn2] | 2.04 | 1.4E-25 | 2.20 | 1.1E-23 | 2.61 | 1.4E-14 | 3.01 | 3.7E-14 | 2.69 | 1.6E-06 |
| PE(32:1)/PC(O-32:1) | 1.98 | 1.5E-25 | 1.89 | 8.8E-19 | 2.41 | 3.1E-13 | 2.27 | 2.9E-10 | 1.76 | 4.0E-03 |
| PE(38:3)/PC(P-40:2) | 2.01 | 1.5E-25 | 2.07 | 1.2E-21 | 2.42 | 1.1E-12 | 2.38 | 3.6E-10 | 1.89 | 1.1E-03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| PC(38:4)/LPC(20:0) [sn2] | 2.03 | 1.5E−25 | 2.06 | 3.1E−21 | 2.94 | 5.6E−17 | 3.01 | 1.5E−14 | 2.00 | 6.4E−04 |
| Cer(d18:1/20:0)/PC(37:2) | 2.07 | 1.5E−25 | 2.22 | 3.5E−23 | 2.84 | 4.0E−15 | 3.18 | 2.0E−13 | 2.55 | 9.5E−06 |
| SM(41:0)/PC(37:6) | 2.04 | 1.6E−25 | 2.15 | 1.9E−22 | 2.47 | 6.5E−13 | 2.87 | 4.4E−12 | 1.75 | 5.9E−03 |
| PC(36:2)/PC(37:2) | 2.03 | 1.7E−25 | 2.01 | 6.8E−20 | 2.42 | 1.8E−12 | 2.36 | 9.5E−10 | 2.07 | 3.6E−04 |
| Cer(d16:1/20:0)/LPC(O-20:0) | 2.07 | 1.8E−25 | 2.24 | 1.2E−23 | 2.72 | 2.2E−14 | 2.82 | 4.6E−12 | 2.74 | 1.8E−06 |
| SM(40:1)/SM(41:2) | 2.01 | 1.8E−25 | 1.98 | 1.2E−19 | 2.11 | 2.7E−10 | 2.24 | 4.7E−09 | 1.73 | 5.0E−03 |
| PE(36:1)/LPC(20:2) [sn1] | 1.94 | 1.8E−25 | 1.97 | 1.5E−21 | 2.25 | 2.4E−13 | 2.16 | 2.3E−10 | 1.81 | 1.2E−03 |
| SM(38:0)/LPC(20:0) [sn2] | 2.00 | 2.1E−25 | 2.05 | 1.5E−21 | 3.01 | 4.0E−17 | 3.26 | 2.5E−15 | 2.51 | 1.1E−05 |
| PC(36:3)/LPC(20:2) [sn1] | 1.99 | 2.1E−25 | 2.06 | 5.9E−22 | 2.64 | 1.1E−15 | 2.75 | 1.9E−13 | 1.87 | 1.6E−03 |
| DAG(18:1/18:1)/PC(34:3) | 2.02 | 2.1E−25 | 2.32 | 1.2E−26 | 2.40 | 2.9E−12 | 2.66 | 6.7E−12 | 1.79 | 5.1E−03 |
| PE(32:1)/SM(37:1) | 1.96 | 2.1E−25 | 1.85 | 6.9E−18 | 2.38 | 2.6E−13 | 2.21 | 5.9E−10 | 1.72 | 5.2E−03 |
| SM(38:0)/PC(P-40:2) | 2.00 | 2.1E−25 | 2.12 | 8.1E−23 | 2.47 | 1.6E−13 | 2.64 | 3.1E−12 | 2.25 | 1.3E−05 |
| PE(36:2)/PC(33:2) | 1.97 | 2.1E−25 | 2.00 | 6.4E−21 | 2.21 | 4.6E−11 | 2.17 | 7.9E−09 | 1.80 | 2.6E−03 |
| DAG(16:0/22:6)/LPC(15:0) [sn2] | 2.04 | 2.2E−25 | 2.00 | 3.9E−19 | 2.89 | 9.8E−16 | 2.84 | 3.1E−12 | 2.61 | 2.6E−06 |
| DAG(16:0/22:6)/PC(P-32:0) | 2.04 | 2.3E−25 | 2.05 | 3.1E−20 | 2.77 | 3.0E−14 | 2.81 | 1.3E−11 | 2.79 | 2.7E−06 |
| Cer(d18:2/18:0)/LPC(O-24:1) | 2.12 | 2.3E−25 | 2.35 | 9.7E−25 | 3.11 | 2.2E−15 | 3.27 | 2.4E−13 | 1.83 | 5.8E−03 |
| SM(41:0)/LacCer(d18:1/24:1) | 2.00 | 2.5E−25 | 2.02 | 5.5E−21 | 2.60 | 4.7E−15 | 2.81 | 1.3E−13 | 1.84 | 1.8E−03 |
| PC(32:1)/LPC(O-24:0) | 1.94 | 2.5E−25 | 1.81 | 3.5E−17 | 2.35 | 6.3E−14 | 2.28 | 4.1E−11 | 1.80 | 1.6E−03 |
| PE(40:5)/LPC(17:0) [sn2] | 1.92 | 2.6E−25 | 1.87 | 4.0E−19 | 2.17 | 2.1E−12 | 2.03 | 7.1E−09 | 1.80 | 1.5E−03 |
| PC(34:1)/PC(35:2) | 2.01 | 2.6E−25 | 2.05 | 3.3E−21 | 2.70 | 2.8E−14 | 2.74 | 1.4E−11 | 2.20 | 6.7E−05 |
| DAG(18:2/20:4)/LPC(20:1) [sn2] | 2.02 | 2.6E−25 | 2.26 | 6.6E−25 | 2.36 | 5.1E−12 | 2.68 | 8.9E−12 | 1.78 | 5.3E−03 |
| PE(40:4)/PC(O-40:4) | 1.96 | 2.7E−25 | 1.93 | 9.8E−20 | 2.17 | 6.9E−11 | 2.05 | 4.4E−08 | 1.70 | 5.7E−03 |
| DAG(16:0/22:6)/PC(39:4) | 2.05 | 2.7E−25 | 2.02 | 2.1E−19 | 2.87 | 2.0E−14 | 2.94 | 8.0E−12 | 2.79 | 2.1E−06 |
| PI(34:2)/PC(37:2) | 1.97 | 2.8E−25 | 1.88 | 1.4E−18 | 2.69 | 2.3E−16 | 2.56 | 1.1E−12 | 1.98 | 3.4E−04 |
| DAG(18:1/18:2)/PC(O-40:6) | 2.04 | 2.8E−25 | 2.23 | 3.4E−24 | 2.18 | 3.8E−10 | 2.35 | 1.6E−09 | 1.92 | 1.5E−03 |
| Cer(d18:1/16:0)/LPC(O-20:1) | 2.00 | 2.9E−25 | 1.99 | 4.8E−20 | 2.59 | 6.2E−15 | 2.57 | 4.5E−12 | 1.94 | 4.2E−04 |
| PC(36:4)/LPC(22:0) [sn1] | 2.04 | 2.9E−25 | 2.01 | 1.2E−19 | 2.97 | 4.2E−16 | 3.01 | 1.6E−13 | 2.55 | 1.7E−05 |
| SM(36:2)/LacCer(d18:1/16:0) | 2.04 | 2.9E−25 | 2.23 | 2.3E−24 | 2.99 | 6.9E−16 | 3.23 | 2.1E−14 | 2.35 | 5.3E−05 |
| DAG(18:2/20:4)/LPC(P-18:1) | 2.00 | 2.9E−25 | 2.14 | 3.1E−23 | 2.30 | 7.2E−12 | 2.44 | 1.7E−10 | 1.69 | 9.7E−03 |
| Cer(d16:1/20:0)/LPC(20:0) [sn1] | 2.09 | 2.9E−25 | 2.29 | 1.0E−23 | 3.00 | 2.3E−15 | 3.10 | 5.3E−13 | 2.89 | 2.7E−06 |
| DAG(14:0/18:2)/LPC(20:2) [sn2] | 2.04 | 3.0E−25 | 2.25 | 4.0E−24 | 2.39 | 2.0E−11 | 2.51 | 6.4E−10 | 2.20 | 2.5E−04 |
| PC(38:4)/PC(P-40:4) | 2.02 | 3.4E−25 | 2.07 | 3.9E−21 | 2.85 | 2.7E−15 | 2.98 | 4.0E−13 | 2.15 | 2.5E−04 |
| SM(41:0)/PC(O-36:3) | 2.01 | 3.4E−25 | 2.05 | 2.1E−21 | 2.80 | 5.6E−16 | 2.86 | 1.6E−13 | 2.11 | 2.6E−04 |
| PE(34:1)/PC(35:3) | 1.93 | 3.8E−25 | 1.90 | 9.1E−20 | 2.28 | 2.3E−13 | 2.15 | 3.6E−10 | 1.77 | 2.3E−03 |
| CE(16:1)/LacCer(d18:1/24:0) | 1.97 | 3.8E−25 | 1.86 | 8.3E−18 | 2.43 | 2.7E−13 | 2.45 | 1.9E−11 | 1.78 | 2.2E−03 |
| DAG(14:0/18:2)/LPC(O-18:0) | 2.01 | 3.9E−25 | 2.08 | 1.6E−21 | 2.43 | 3.5E−12 | 2.45 | 4.7E−10 | 2.30 | 9.1E−05 |
| SM(38:0)/LPC(22:0) [sn2] | 2.02 | 3.9E−25 | 2.11 | 4.2E−22 | 3.08 | 2.8E−17 | 3.39 | 1.1E−15 | 2.63 | 4.3E−06 |
| PI(34:2)/PC(O-36:3) | 1.98 | 4.0E−25 | 1.91 | 1.0E−18 | 2.90 | 2.8E−16 | 2.57 | 2.7E−11 | 1.89 | 1.4E−03 |
| Cer(d16:1/20:0)/Gb3(d18:1/16:0) | 2.08 | 4.0E−25 | 2.37 | 5.4E−25 | 2.49 | 9.6E−12 | 2.52 | 1.5E−09 | 1.98 | 2.2E−03 |
| SM(38:0)/PC(O-32:0) | 2.02 | 4.3E−25 | 2.11 | 3.5E−22 | 2.59 | 1.7E−13 | 2.86 | 1.0E−12 | 2.48 | 2.1E−05 |
| PC(32:1)/PC(36:7) | 2.02 | 4.5E−25 | 2.00 | 1.7E−19 | 2.90 | 1.8E−15 | 3.14 | 7.5E−14 | 2.90 | 1.6E−07 |
| SM(41:0)/SM(d17:1/14:0) | 1.98 | 4.7E−25 | 1.98 | 2.7E−20 | 2.53 | 4.9E−15 | 2.61 | 3.6E−13 | 1.90 | 8.3E−04 |
| CE(16:1)/LPC(18:2) [sn2] | 1.98 | 4.7E−25 | 1.90 | 2.6E−18 | 2.74 | 2.6E−15 | 2.66 | 3.1E−12 | 1.79 | 3.2E−03 |
| DAG(18:0/20:4)/LPC(O-22:0) | 1.98 | 4.9E−25 | 2.06 | 6.9E−22 | 2.46 | 5.8E−14 | 2.70 | 5.2E−13 | 2.52 | 3.0E−06 |
| PE(40:5)/LPE(16:0) [sn2] | 2.00 | 5.0E−25 | 2.08 | 1.2E−21 | 2.09 | 2.4E−09 | 2.08 | 1.3E−07 | 1.87 | 2.4E−03 |
| PE(36:1)/PC(31:0) | 1.98 | 5.1E−25 | 2.00 | 1.6E−20 | 2.20 | 9.8E−11 | 2.14 | 2.2E−08 | 1.81 | 3.2E−03 |
| PE(36:1)/PC(P-32:0) | 1.97 | 5.2E−25 | 1.97 | 2.4E−20 | 2.28 | 1.3E−11 | 2.21 | 4.0E−09 | 1.78 | 4.3E−03 |
| PC(36:4)/LPC(20:0) [sn2] | 2.01 | 5.3E−25 | 1.95 | 5.9E−19 | 2.81 | 5.8E−16 | 2.80 | 4.1E−13 | 2.27 | 7.2E−05 |
| PC(36:3)/PC(O-34:2) | 2.02 | 5.3E−25 | 2.00 | 1.8E−19 | 2.95 | 1.6E−15 | 2.86 | 5.6E−12 | 1.85 | 2.9E−03 |
| Cer(d18:1/22:0)/LPC(O-24:0) | 2.00 | 5.4E−25 | 2.02 | 2.3E−20 | 2.48 | 4.7E−13 | 2.64 | 2.0E−11 | 1.77 | 4.4E−03 |
| PE(36:1)/LPC(17:0) [sn2] | 1.90 | 5.6E−25 | 1.84 | 4.5E−19 | 2.21 | 5.5E−14 | 2.09 | 1.7E−10 | 1.77 | 1.0E−03 |
| PE(32:1)/PC(O-36:3) | 1.95 | 5.6E−25 | 1.85 | 6.9E−18 | 2.49 | 5.4E−14 | 2.29 | 2.6E−10 | 1.86 | 1.5E−03 |
| PE(38:3)/LPC(19:0) [sn2] | 1.93 | 5.8E−25 | 1.94 | 1.1E−20 | 2.43 | 3.8E−15 | 2.43 | 1.6E−12 | 1.84 | 1.1E−03 |
| DAG(16:0/22:6)/SM(41:2) | 2.02 | 6.1E−25 | 1.99 | 5.2E−19 | 2.64 | 1.1E−13 | 2.62 | 9.2E−11 | 2.61 | 3.7E−06 |
| Cer(d18:1/24:1)/PC(P-32:0) | 1.95 | 6.3E−25 | 1.99 | 9.8E−21 | 2.26 | 2.4E−12 | 2.35 | 4.3E−11 | 1.91 | 7.5E−04 |
| SM(36:1)/Gb3(d18:1/22:0) | 1.95 | 6.5E−25 | 2.12 | 7.4E−24 | 2.04 | 1.1E−10 | 2.10 | 2.7E−09 | 1.74 | 2.5E−03 |
| DAG(16:0/22:6)/PC(O-38:2) | 2.02 | 6.5E−25 | 1.98 | 8.5E−19 | 2.67 | 6.9E−14 | 2.66 | 7.0E−11 | 2.74 | 1.2E−06 |
| SM(41:0)/LPC(MHDA) [sn1] | 1.97 | 6.8E−25 | 2.00 | 6.7E−21 | 2.99 | 4.4E−18 | 3.14 | 8.7E−16 | 2.52 | 3.2E−06 |
| PE(32:1)/PC(P-40:2) | 1.96 | 7.5E−25 | 1.86 | 6.9E−18 | 2.41 | 3.1E−13 | 2.25 | 5.1E−10 | 1.83 | 8.0E−04 |
| PE(36:1)/LPC(O-24:1) | 1.93 | 7.9E−25 | 1.91 | 9.2E−20 | 2.26 | 2.2E−12 | 2.19 | 9.7E−10 | 1.74 | 4.2E−03 |
| PC(36:4)/PC(O-40:3) | 2.00 | 8.1E−25 | 2.03 | 1.6E−20 | 2.35 | 1.8E−12 | 2.43 | 1.2E−10 | 1.94 | 8.0E−04 |
| PC(36:4)/LPC(O-20:1) | 1.99 | 8.1E−25 | 1.94 | 8.1E−19 | 2.68 | 1.1E−14 | 2.63 | 1.0E−11 | 2.14 | 3.0E−04 |
| DAG(16:0/22:6)/LPE(P-20:0) | 1.99 | 8.2E−25 | 1.95 | 3.4E−19 | 2.78 | 8.4E−16 | 2.72 | 1.8E−12 | 2.66 | 1.7E−06 |
| Cer(d18:1/20:0)/PC(O-34:0) | 2.00 | 8.2E−25 | 2.13 | 2.0E−22 | 2.42 | 7.2E−13 | 2.52 | 6.7E−11 | 2.44 | 1.6E−05 |
| PE(38:3)/SM(d17:1/14:0) | 1.99 | 8.2E−25 | 1.98 | 7.8E−20 | 2.48 | 2.2E−12 | 2.37 | 1.8E−09 | 1.76 | 6.7E−03 |
| SM(41:0)/SM(41:2) | 1.98 | 8.3E−25 | 1.98 | 2.8E−20 | 2.57 | 1.1E−14 | 2.74 | 2.5E−13 | 2.02 | 3.8E−04 |
| DAG(18:1/18:2)/LPC(20:1) [sn1] | 1.98 | 8.4E−25 | 2.21 | 9.2E−25 | 2.40 | 1.5E−12 | 2.67 | 5.6E−12 | 1.82 | 3.3E−03 |
| PC(38:1)/PC(O-34:1) | 1.95 | 8.9E−25 | 2.01 | 3.2E−21 | 2.41 | 1.7E−14 | 2.46 | 4.5E−12 | 2.21 | 1.3E−05 |
| DAG(18:1/18:2)/LPC(20:1) [sn2] | 1.98 | 9.0E−25 | 2.21 | 6.5E−25 | 2.32 | 6.6E−12 | 2.59 | 1.9E−11 | 1.77 | 5.1E−03 |
| PI(40:5)/CE(17:0) | 2.00 | 9.2E−25 | 1.88 | 3.0E−17 | 2.39 | 9.6E−13 | 2.22 | 9.2E−09 | 1.82 | 2.4E−03 |
| SM(41:0)/LPC(19:0) [sn1] | 1.96 | 9.2E−25 | 1.95 | 5.3E−20 | 2.82 | 3.6E−17 | 2.99 | 3.5E−15 | 2.30 | 2.8E−05 |
| DAG(14:0/18:2)/PC(31:0) | 2.03 | 9.4E−25 | 2.16 | 4.0E−22 | 2.20 | 1.0E−09 | 2.25 | 3.3E−08 | 2.17 | 4.2E−04 |
| DAG(18:0/20:4)/LPC(O-18:0) | 1.98 | 9.7E−25 | 1.99 | 2.7E−20 | 2.55 | 2.1E−14 | 2.66 | 1.8E−12 | 2.66 | 1.2E−06 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| PC(36:4)/LPC(20:1) [sn2] | 2.04 | 9.7E−25 | 2.02 | 2.0E−19 | 2.76 | 3.5E−14 | 2.78 | 1.0E−11 | 2.04 | 1.2E−03 |
| Cer(d18:1/20:0)/LPC(O-24:1) | 2.01 | 9.7E−25 | 2.12 | 2.9E−22 | 2.75 | 3.9E−15 | 2.88 | 4.7E−13 | 2.18 | 7.8E−05 |
| PC(36:3)/PC(O-38:0) | 2.03 | 1.0E−24 | 2.01 | 1.9E−19 | 2.58 | 3.2E−13 | 2.68 | 2.0E−11 | 1.96 | 1.6E−03 |
| PC(36:3)/LPC(17:0) [sn1] | 1.90 | 1.0E−24 | 1.79 | 1.4E−17 | 2.35 | 7.2E−16 | 2.30 | 1.0E−12 | 1.74 | 2.0E−03 |
| PC(36:4)/PC(31:0) | 2.01 | 1.1E−24 | 1.99 | 2.9E−19 | 2.48 | 2.4E−12 | 2.49 | 6.2E−10 | 2.28 | 1.2E−04 |
| PE(36:1)/PC(37:1) | 1.94 | 1.1E−24 | 1.91 | 3.2E−19 | 2.18 | 3.8E−11 | 2.08 | 1.8E−08 | 1.78 | 3.5E−03 |
| DAG(16:0/22:6)/LPC(15:0) [sn1] | 2.01 | 1.1E−24 | 1.97 | 1.4E−18 | 2.87 | 1.5E−15 | 2.85 | 3.2E−12 | 2.79 | 6.7E−07 |
| PC(36:4)/LacCer(d18:1/16:0) | 2.04 | 1.2E−24 | 2.00 | 3.4E−19 | 2.56 | 1.7E−12 | 2.53 | 4.3E−10 | 2.10 | 7.4E−04 |
| DAG(16:0/22:6)/LPC(O-24:0) | 1.98 | 1.2E−24 | 1.98 | 1.5E−19 | 2.65 | 1.5E−14 | 2.70 | 4.6E−12 | 2.74 | 1.4E−06 |
| PE(36:1)/PC(O-40:3) | 1.96 | 1.2E−24 | 2.00 | 5.5E−21 | 2.14 | 7.2E−11 | 2.17 | 5.0E−09 | 1.67 | 7.4E−03 |
| PC(38:4)/LPC(O-24:1) | 1.98 | 1.2E−24 | 2.01 | 1.4E−20 | 2.59 | 1.3E−14 | 2.62 | 2.4E−12 | 1.74 | 5.8E−03 |
| PC(34:1)/PC(P-32:0) | 2.01 | 1.3E−24 | 2.00 | 1.6E−19 | 2.36 | 5.0E−11 | 2.41 | 2.4E−09 | 1.72 | 9.4E−03 |
| Cer(d18:1/20:0)/LacCer(d18:1/24:1) | 1.98 | 1.3E−24 | 2.08 | 1.5E−21 | 2.43 | 3.7E−13 | 2.53 | 6.0E−11 | 1.93 | 1.2E−03 |
| PC(36:3)/LPC(20:2) [sn2] | 1.99 | 1.3E−24 | 2.09 | 1.3E−21 | 2.66 | 8.2E−15 | 2.82 | 5.0E−13 | 1.79 | 4.6E−03 |
| PC(38:4)/PC(P-32:0) | 1.98 | 1.3E−24 | 2.06 | 1.7E−21 | 2.50 | 7.5E−13 | 2.58 | 4.9E−11 | 1.74 | 7.9E−03 |
| PE(40:5)/LPC(O-24:1) | 1.93 | 1.3E−24 | 1.92 | 2.0E−19 | 2.13 | 1.3E−10 | 2.04 | 4.6E−08 | 1.70 | 7.0E−03 |
| SM(36:2)/PC(O-36:2) | 2.00 | 1.3E−24 | 2.13 | 1.4E−22 | 2.98 | 6.7E−17 | 2.98 | 3.7E−14 | 2.11 | 1.2E−05 |
| PC(36:5)/PC(37:6) | 1.99 | 1.4E−24 | 1.92 | 2.0E−17 | 2.11 | 2.5E−09 | 2.00 | 1.8E−06 | 2.00 | 7.0E−04 |
| PE(36:1)/LPC(17:0) [sn1] | 1.89 | 1.4E−24 | 1.82 | 2.0E−18 | 2.20 | 1.5E−13 | 2.07 | 3.6E−10 | 1.75 | 1.6E−03 |
| SM(38:0)/PC(P-40:4) | 2.01 | 1.4E−24 | 2.09 | 3.0E−21 | 3.02 | 5.0E−16 | 3.44 | 1.3E−14 | 2.89 | 1.5E−06 |
| Cer(d18:1/16:0)/LacCer(d18:1/16:0) | 2.00 | 1.4E−24 | 2.05 | 1.4E−20 | 2.17 | 2.3E−10 | 2.18 | 2.6E−08 | 1.78 | 4.5E−03 |
| DAG(16:0/22:6)/LPE(16:0) [sn2] | 2.04 | 1.5E−24 | 2.11 | 1.2E−20 | 2.80 | 3.0E−14 | 3.03 | 3.0E−12 | 3.05 | 5.6E−07 |
| DAG(18:0/20:4)/PC(35:3) | 2.01 | 1.6E−24 | 2.14 | 3.0E−22 | 2.47 | 1.3E−12 | 2.63 | 1.8E−11 | 2.45 | 2.9E−05 |
| PE(32:1)/PC(33:2) | 1.92 | 1.6E−24 | 1.84 | 1.1E−17 | 2.37 | 2.1E−13 | 2.27 | 2.6E−10 | 1.79 | 1.9E−03 |
| Cer(d18:2/18:0)/LPC(17:0) [sn1] | 2.07 | 1.6E−24 | 2.23 | 2.2E−22 | 3.13 | 2.9E−16 | 3.19 | 3.6E−13 | 1.92 | 1.8E−03 |
| PE(36:1)/LPC(20:2) [sn2] | 1.93 | 1.6E−24 | 1.97 | 5.8E−21 | 2.24 | 2.7E−12 | 2.16 | 1.3E−09 | 1.77 | 2.8E−03 |
| Cer(d18:2/18:0)/Glc/GalCer(d18:2/22:0) | 2.07 | 1.7E−24 | 2.27 | 2.7E−23 | 2.46 | 1.5E−11 | 2.53 | 6.4E−10 | 1.82 | 6.6E−03 |
| CE(18:0)/LPC(17:0) [sn2] | 1.96 | 1.7E−24 | 2.02 | 5.2E−21 | 2.26 | 2.6E−13 | 2.25 | 5.8E−11 | 1.84 | 8.4E−04 |
| DAG(18:0/20:4)/LPC(24:0) [sn1] | 2.00 | 1.7E−24 | 2.16 | 5.7E−23 | 2.56 | 4.3E−14 | 2.91 | 1.4E−13 | 2.73 | 1.2E−06 |
| SM(40:1)/LPC(22:0) [sn1] | 1.96 | 1.7E−24 | 2.00 | 6.7E−21 | 2.62 | 1.2E−15 | 2.93 | 5.2E−15 | 2.28 | 2.5E−05 |
| DAG(16:0/22:6)/LPC(20:2) [sn1] | 2.01 | 1.7E−24 | 2.05 | 3.6E−20 | 2.83 | 7.9E−15 | 2.83 | 5.2E−12 | 2.88 | 1.3E−06 |
| DAG(14:0/18:2)/LPE(16:0) [sn1] | 2.04 | 1.7E−24 | 2.27 | 1.3E−23 | 2.32 | 1.7E−10 | 2.58 | 7.4E−10 | 2.27 | 2.2E−04 |
| PE(32:1)/Gb3(d18:1/16:0) | 1.93 | 1.8E−24 | 1.84 | 9.4E−18 | 2.38 | 4.0E−13 | 2.23 | 5.4E−10 | 1.69 | 7.4E−03 |
| DAG(14:0/18:2)/LPC(O-18:1) | 1.99 | 1.8E−24 | 2.05 | 6.2E−21 | 2.33 | 2.5E−11 | 2.33 | 3.0E−09 | 2.03 | 8.9E−04 |
| PC(38:6)/PC(O-40:6) | 1.95 | 1.8E−24 | 1.88 | 3.6E−18 | 2.47 | 5.0E−15 | 2.41 | 9.7E−12 | 2.32 | 2.1E−06 |
| PC(38:5)/LPC(19:0) [sn1] | 2.00 | 1.8E−24 | 1.92 | 9.6E−18 | 2.74 | 7.1E−15 | 2.64 | 3.8E−11 | 2.55 | 8.2E−06 |
| DAG(14:0/18:2)/LPE(16:0) [sn2] | 2.04 | 1.9E−24 | 2.26 | 1.3E−23 | 2.31 | 1.6E−10 | 2.54 | 9.8E−10 | 2.28 | 1.9E−04 |
| Cer(d18:1/24:1)/LPC(O-18:0) | 1.94 | 1.9E−24 | 1.89 | 1.8E−18 | 2.56 | 2.4E−15 | 2.55 | 1.1E−12 | 2.22 | 1.5E−05 |
| PC(38:2)/PC(O-40:6) | 1.94 | 1.9E−24 | 2.00 | 4.7E−21 | 2.22 | 8.5E−12 | 2.22 | 6.6E−10 | 1.91 | 5.0E−04 |
| PE(32:1)/PC(37:6) | 1.94 | 2.0E−24 | 1.88 | 6.4E−18 | 2.29 | 4.4E−12 | 2.21 | 2.5E−09 | 1.69 | 7.5E−03 |
| SM(41:0)/PC(P-32:0) | 1.99 | 2.0E−24 | 2.08 | 8.5E−22 | 2.71 | 6.0E−15 | 3.09 | 3.5E−14 | 2.16 | 2.0E−04 |
| CE(20:3)/PC(O-40:6) | 1.98 | 2.0E−24 | 2.05 | 4.3E−21 | 2.76 | 5.1E−15 | 3.09 | 4.3E−14 | 1.77 | 5.4E−03 |
| DAG(14:0/18:2)/LPE(P-20:0) | 1.98 | 2.1E−24 | 2.07 | 1.8E−21 | 2.41 | 2.1E−12 | 2.41 | 3.4E−10 | 2.15 | 2.6E−04 |
| PE(40:5)/PC(39:4) | 1.94 | 2.1E−24 | 1.92 | 5.2E−19 | 2.06 | 1.6E−09 | 1.98 | 2.6E−07 | 1.69 | 7.6E−03 |
| PC(32:1)/LPC(15:0) [sn1] | 1.89 | 2.1E−24 | 1.75 | 6.1E−16 | 2.35 | 5.3E−15 | 2.28 | 1.8E−11 | 1.75 | 1.4E−03 |
| DAG(18:1/18:3)/LPC(20:1) [sn2] | 2.02 | 2.1E−24 | 2.26 | 2.5E−24 | 2.12 | 3.4E−09 | 2.48 | 1.2E−09 | 2.18 | 2.7E−04 |
| DAG(16:0/22:6)/LPE(16:0) [sn1] | 2.03 | 2.2E−24 | 2.10 | 1.7E−20 | 2.78 | 3.5E−14 | 3.05 | 2.5E−12 | 2.98 | 6.6E−07 |
| PC(32:1)/LPC(15:0) [sn2] | 1.89 | 2.2E−24 | 1.75 | 7.0E−16 | 2.33 | 1.4E−14 | 2.22 | 6.4E−11 | 1.62 | 6.9E−03 |
| DAG(18:0/20:4)/LPC(O-18:1) | 1.99 | 2.2E−24 | 2.00 | 5.8E−20 | 2.50 | 1.7E−13 | 2.58 | 1.5E−11 | 2.33 | 5.1E−05 |
| DAG(16:0/22:6)/LPC(P-16:0) | 1.97 | 2.2E−24 | 1.95 | 5.6E−19 | 2.69 | 4.0E−15 | 2.68 | 3.7E−12 | 2.54 | 4.4E−06 |
| DAG(18:1/18:2)/LPC(20:0) [sn2] | 1.96 | 2.2E−24 | 2.14 | 1.2E−23 | 2.40 | 3.0E−13 | 2.66 | 1.7E−12 | 1.99 | 5.5E−04 |
| PC(38:1)/SM(37:2) | 1.96 | 2.2E−24 | 2.11 | 9.3E−23 | 2.79 | 1.4E−16 | 2.75 | 2.6E−13 | 2.00 | 1.6E−04 |
| DAG(16:0/22:6)/LPC(20:2) [sn2] | 2.01 | 2.3E−24 | 2.06 | 3.6E−20 | 2.79 | 1.6E−14 | 2.82 | 7.2E−12 | 2.91 | 1.4E−06 |
| PE(32:1)/PC(37:2) | 1.94 | 2.3E−24 | 1.84 | 2.5E−17 | 2.44 | 9.5E−14 | 2.33 | 1.0E−10 | 1.89 | 8.3E−04 |
| DAG(18:1/18:3)/PC(O-40:6) | 2.03 | 2.3E−24 | 2.21 | 2.6E−23 | 1.97 | 7.5E−08 | 2.22 | 4.6E−08 | 2.24 | 1.3E−04 |
| Cer(d16:1/20:0)/PC(35:3) | 2.10 | 2.3E−24 | 2.45 | 3.2E−25 | 2.73 | 2.0E−12 | 2.76 | 2.9E−10 | 2.66 | 4.2E−05 |
| SM(41:0)/LPC(O-20:1) | 1.96 | 2.3E−24 | 2.00 | 2.0E−20 | 2.80 | 3.1E−16 | 3.07 | 1.8E−14 | 2.10 | 2.7E−04 |
| Cer(d18:1/20:0)/LPC(O-22:0) | 2.00 | 2.3E−24 | 2.13 | 3.7E−22 | 2.83 | 1.5E−15 | 3.03 | 1.4E−13 | 2.44 | 3.1E−06 |
| PI(36:4)/PC(O-38:2) | 1.95 | 2.4E−24 | 1.86 | 1.4E−17 | 2.70 | 5.7E−15 | 2.46 | 9.0E−11 | 1.73 | 6.7E−03 |
| PC(38:4)/LPC(24:0) [sn2] | 2.00 | 2.5E−24 | 2.17 | 2.9E−23 | 2.85 | 4.1E−16 | 3.14 | 3.9E−15 | 1.97 | 4.7E−04 |
| SM(41:0)/PC(P-18:1) | 1.96 | 2.5E−24 | 1.96 | 1.3E−19 | 2.58 | 1.7E−15 | 2.66 | 3.0E−13 | 1.80 | 2.9E−03 |
| SM(38:0)/LPC(24:0) [sn1] | 2.00 | 2.5E−24 | 2.15 | 9.3E−23 | 2.95 | 2.1E−16 | 3.35 | 1.5E−15 | 2.78 | 1.6E−06 |
| DAG(14:0/18:2)/PC(O-34:2) | 2.01 | 2.6E−24 | 2.11 | 1.4E−21 | 2.46 | 1.3E−11 | 2.43 | 3.0E−09 | 2.18 | 3.6E−04 |
| PE(36:1)/PC(O-32:0) | 1.93 | 2.7E−24 | 1.93 | 1.1E−19 | 2.17 | 1.4E−10 | 2.10 | 2.3E−08 | 1.73 | 5.4E−03 |
| Cer(d18:1/20:0)/PC(35:2) | 2.06 | 2.8E−24 | 2.25 | 7.7E−23 | 3.06 | 1.1E−14 | 3.25 | 5.5E−12 | 3.04 | 1.2E−06 |
| DAG(14:0/18:2)/PC(P-40:2) | 1.99 | 2.8E−24 | 2.11 | 9.4E−22 | 2.19 | 4.8E−10 | 2.23 | 2.0E−08 | 2.04 | 4.0E−04 |
| DAG(14:0/18:2)/LacCer(d18:1/24:1) | 1.99 | 2.9E−24 | 2.08 | 3.9E−21 | 2.22 | 3.7E−10 | 2.24 | 2.2E−08 | 1.91 | 2.4E−03 |
| SM(41:0)/SM(39:2) | 1.95 | 2.9E−24 | 2.02 | 1.3E−21 | 2.30 | 2.0E−15 | 2.46 | 2.3E−14 | 1.60 | 6.2E−03 |
| PE(38:4)/PC(O-40:6) | 1.98 | 2.9E−24 | 2.04 | 8.8E−21 | 2.28 | 7.5E−11 | 2.28 | 5.4E−09 | 1.95 | 1.3E−03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| Cer(d18:1/20:0)/LPC(22:0) [sn2] | 2.02 | 3.0E−24 | 2.20 | 9.5E−23 | 3.06 | 1.9E−16 | 3.27 | 1.5E−14 | 2.53 | 4.2E−06 |
| PC(38:4)/LPC(17:0) [sn1] | 1.97 | 3.0E−24 | 1.91 | 2.0E−18 | 2.85 | 1.1E−16 | 2.75 | 4.2E−13 | 1.92 | 1.2E−03 |
| PC(38:2)/LPC(19:0) [sn2] | 1.88 | 3.0E−24 | 1.87 | 1.3E−19 | 2.44 | 1.8E−17 | 2.43 | 2.0E−14 | 1.89 | 1.3E−04 |
| PE(40:5)/PC(P-32:0) | 1.94 | 3.1E−24 | 1.95 | 1.7E−19 | 2.05 | 2.9E−09 | 1.97 | 6.4E−07 | 1.70 | 8.3E−03 |
| PC(36:4)/LPC(22:0) [sn2] | 2.00 | 3.2E−24 | 1.97 | 5.4E−19 | 2.83 | 1.1E−15 | 2.84 | 5.3E−13 | 2.36 | 4.5E−05 |
| PE(36:1)/SM(41:2) | 1.92 | 3.3E−24 | 1.89 | 9.7E−19 | 2.16 | 7.9E−11 | 2.04 | 5.3E−08 | 1.68 | 7.3E−03 |
| PC(32:1)/LPC(17:0) [sn1] | 1.89 | 3.3E−24 | 1.74 | 1.0E−15 | 2.38 | 8.8E−15 | 2.27 | 3.0E−11 | 1.75 | 2.0E−03 |
| Cer(d18:1/23:0)/PC(O-38:0) | 1.97 | 3.5E−24 | 2.01 | 5.1E−20 | 2.61 | 9.8E−14 | 2.89 | 8.5E−13 | 1.80 | 3.8E−03 |
| DAG(14:0/18:2)/LPC(18:2) [sn2] | 2.00 | 3.5E−24 | 2.15 | 2.0E−22 | 2.49 | 1.9E−12 | 2.58 | 1.6E−10 | 2.24 | 2.4E−04 |
| DAG(18:0/20:4)/LacCer(d18:1/24:1) | 1.98 | 3.5E−24 | 2.03 | 2.3E−20 | 2.25 | 1.6E−11 | 2.39 | 4.5E−10 | 2.08 | 3.4E−04 |
| DAG(16:0/22:6)/SM(34:1) | 1.99 | 3.7E−24 | 1.99 | 6.4E−19 | 2.66 | 1.1E−13 | 2.63 | 8.7E−11 | 2.54 | 1.4E−05 |
| PC(36:3)/LPC(17:0) [sn2] | 1.88 | 3.8E−24 | 1.81 | 8.5E−18 | 2.32 | 1.0E−15 | 2.28 | 1.4E−12 | 1.75 | 1.4E−03 |
| SM(41:0)/PC(37:2) | 1.97 | 3.8E−24 | 2.02 | 1.0E−20 | 2.73 | 2.0E−15 | 3.03 | 1.4E−14 | 2.23 | 9.9E−05 |
| PE(40:5)/PC(P-40:2) | 1.94 | 3.8E−24 | 1.95 | 1.7E−19 | 1.98 | 3.8E−09 | 1.88 | 1.1E−06 | 1.72 | 3.8E−03 |
| SM(38:0)/LPC(24:0) [sn2] | 1.99 | 3.9E−24 | 2.15 | 1.8E−22 | 3.00 | 2.3E−16 | 3.47 | 1.0E−15 | 2.62 | 4.5E−06 |
| DAG(16:0/22:6)/LPC(O-18:1) | 1.98 | 3.9E−24 | 1.93 | 3.7E−18 | 2.71 | 2.1E−14 | 2.65 | 2.7E−11 | 2.54 | 9.4E−06 |
| PE(36:1)/PC(39:4) | 1.93 | 4.0E−24 | 1.91 | 6.6E−19 | 2.23 | 1.8E−11 | 2.17 | 3.6E−09 | 1.74 | 4.8E−03 |
| PC(38:2)/LPC(20:1) [sn1] | 1.95 | 4.2E−24 | 1.97 | 4.5E−20 | 2.64 | 1.3E−15 | 2.65 | 6.6E−13 | 1.89 | 1.6E−03 |
| PC(36:4)/LPC(24:0) [sn1] | 2.00 | 4.2E−24 | 2.01 | 1.0E−19 | 2.85 | 5.0E−15 | 2.93 | 8.0E−13 | 2.52 | 2.2E−05 |
| Cer(d18:1/20:0)/PC(35:3) | 2.03 | 4.2E−24 | 2.29 | 6.3E−24 | 2.92 | 1.8E−14 | 3.15 | 1.4E−12 | 2.43 | 6.7E−05 |
| DAG(16:0/22:6)/PC(P-40:4) | 1.99 | 4.2E−24 | 1.98 | 7.1E−19 | 2.77 | 2.1E−14 | 2.85 | 7.9E−12 | 2.86 | 1.1E−06 |
| PC(36:4)/LPC(24:0) [sn2] | 1.99 | 4.3E−24 | 2.00 | 1.4E−19 | 2.81 | 5.7E−15 | 2.93 | 5.8E−13 | 2.38 | 4.7E−05 |
| PE(34:1)/PC(O-36:3) | 1.91 | 4.3E−24 | 1.85 | 2.0E−18 | 2.29 | 1.1E−12 | 2.10 | 3.7E−09 | 1.77 | 3.2E−03 |
| DAG(18:0/20:4)/PC(39:4) | 1.99 | 4.4E−24 | 2.04 | 2.4E−20 | 2.41 | 4.9E−12 | 2.66 | 2.2E−11 | 2.51 | 2.0E−05 |
| PE(36:1)/PC(33:3) | 1.95 | 4.5E−24 | 1.93 | 1.3E−18 | 2.35 | 4.4E−12 | 2.26 | 3.2E−09 | 1.72 | 7.7E−03 |
| PE(32:1)/SM(39:2) | 1.90 | 4.5E−24 | 1.82 | 1.6E−17 | 2.33 | 1.4E−13 | 2.22 | 1.2E−10 | 1.65 | 8.8E−03 |
| DAG(18:0/20:4)/LPE(P-20:0) | 1.95 | 4.5E−24 | 1.99 | 1.9E−20 | 2.56 | 6.8E−15 | 2.64 | 9.1E−13 | 2.44 | 5.8E−06 |
| PE(32:1)/SM(d17:1/14:0) | 1.91 | 4.7E−24 | 1.79 | 1.4E−16 | 2.35 | 4.2E−13 | 2.17 | 1.3E−09 | 1.75 | 3.1E−03 |
| PE(34:1)/PC(O-40:6) | 1.93 | 4.7E−24 | 1.93 | 2.4E−19 | 2.21 | 2.2E−11 | 2.14 | 3.7E−09 | 1.81 | 2.5E−03 |
| CE(16:1)/LPC(18:1) [sn1] | 1.93 | 4.8E−24 | 1.83 | 4.6E−17 | 2.65 | 2.5E−15 | 2.58 | 3.0E−12 | 1.91 | 9.0E−04 |
| PE(32:1)/LPE(16:0) [sn1] | 1.94 | 5.0E−24 | 1.85 | 1.9E−17 | 2.43 | 2.2E−13 | 2.35 | 1.1E−10 | 1.95 | 8.3E−04 |
| Cer(d18:1/24:1)/PC(O-34:0) | 1.94 | 5.0E−24 | 1.94 | 3.5E−19 | 2.12 | 7.2E−11 | 2.16 | 2.7E−09 | 1.99 | 3.8E−04 |
| DAG(16:0/22:6)/LPC(O-18:0) | 1.97 | 5.1E−24 | 1.93 | 3.5E−18 | 2.75 | 7.4E−15 | 2.73 | 9.1E−12 | 2.76 | 1.1E−06 |
| PC(38:4)/LPC(MHDA) [sn2] | 1.97 | 5.5E−24 | 1.95 | 6.6E−19 | 2.64 | 8.8E−15 | 2.48 | 2.4E−11 | 2.01 | 5.6E−05 |
| PE(36:1)/PC(O-38:2) | 1.92 | 5.5E−24 | 1.88 | 2.0E−18 | 2.18 | 5.0E−11 | 2.06 | 3.5E−08 | 1.79 | 2.5E−03 |
| Cer(d16:1/20:0)/PC(33:2) | 2.06 | 5.6E−24 | 2.29 | 7.7E−23 | 2.40 | 1.2E−10 | 2.42 | 1.8E−08 | 2.42 | 1.4E−04 |
| PI(36:4)/PC(P-40:2) | 1.95 | 5.6E−24 | 1.93 | 5.0E−19 | 2.58 | 7.1E−14 | 2.42 | 2.0E−10 | 1.66 | 6.5E−03 |
| Cer(d18:1/24:1)/PC(O-38:0) | 1.94 | 5.8E−24 | 1.99 | 5.5E−20 | 2.27 | 4.4E−12 | 2.44 | 5.6E−11 | 2.17 | 6.9E−05 |
| SM(41:0)/PC(33:2) | 1.95 | 6.0E−24 | 2.00 | 1.6E−20 | 2.53 | 3.4E−14 | 2.73 | 3.1E−13 | 1.98 | 5.7E−04 |
| Cer(d16:1/20:0)/LacCer(d18:1/16:0) | 2.03 | 6.1E−24 | 2.27 | 2.1E−23 | 2.33 | 1.4E−10 | 2.35 | 1.0E−08 | 2.27 | 2.0E−04 |
| PE(34:1)/PC(35:2) | 1.91 | 6.2E−24 | 1.88 | 5.9E−19 | 2.39 | 7.4E−14 | 2.23 | 2.5E−10 | 2.01 | 1.8E−04 |
| SM(41:0)/LPC(19:0) [sn2] | 1.92 | 6.2E−24 | 1.97 | 1.3E−20 | 2.67 | 2.3E−17 | 2.89 | 8.8E−16 | 1.99 | 1.3E−04 |
| PE(32:1)/PC(O-40:3) | 1.93 | 6.3E−24 | 1.86 | 8.5E−18 | 2.34 | 1.5E−12 | 2.28 | 5.5E−10 | 1.77 | 3.1E−03 |
| SM(41:0)/PC(O-38:0) | 1.97 | 6.3E−24 | 2.05 | 4.8E−21 | 2.74 | 3.4E−15 | 3.08 | 1.7E−14 | 2.40 | 3.2E−05 |
| SM(41:0)/PC(O-38:2) | 1.95 | 6.3E−24 | 1.95 | 2.2E−19 | 2.60 | 1.4E−14 | 2.79 | 3.0E−13 | 2.24 | 7.4E−05 |
| Cer(d18:2/18:0)/PC(O-34:0) | 2.05 | 6.5E−24 | 2.26 | 1.7E−23 | 2.65 | 1.9E−12 | 2.71 | 1.6E−10 | 1.86 | 5.2E−03 |
| PC(34:5)/PC(O-40:6) | 1.99 | 6.7E−24 | 1.96 | 1.6E−18 | 2.11 | 4.8E−09 | 2.00 | 9.2E−07 | 2.10 | 6.0E−04 |
| PE(36:1)/PC(O-38:0) | 1.92 | 6.8E−24 | 1.93 | 2.7E−19 | 2.23 | 4.1E−11 | 2.16 | 1.1E−08 | 1.85 | 1.6E−03 |
| DAG(18:1/18:2)/LPC(MHDA) [sn2] | 1.95 | 7.0E−24 | 2.08 | 6.7E−22 | 2.34 | 1.2E−12 | 2.44 | 9.1E−11 | 2.06 | 8.3E−05 |
| PE(40:5)/PC(O-34:2) | 1.94 | 7.3E−24 | 1.93 | 7.6E−19 | 2.21 | 6.7E−11 | 2.02 | 2.0E−07 | 1.78 | 3.8E−03 |
| PI(36:4)/LPE(16:0) [sn1] | 1.97 | 7.5E−24 | 2.07 | 6.6E−21 | 2.90 | 1.1E−15 | 3.05 | 3.1E−13 | 1.74 | 7.3E−03 |
| DAG(14:0/18:2)/LPC(P-16:0) | 1.96 | 7.6E−24 | 2.04 | 3.5E−21 | 2.30 | 1.0E−11 | 2.34 | 6.5E−10 | 2.03 | 6.0E−04 |
| PC(36:5)/PC(17:0_22:6) | 1.92 | 7.6E−24 | 1.84 | 8.6E−17 | 1.98 | 5.8E−09 | 1.95 | 1.2E−06 | 1.94 | 4.2E−04 |
| PE(40:5)/PC(31:0) | 1.94 | 7.7E−24 | 1.96 | 1.9E−19 | 1.91 | 4.2E−08 | 1.84 | 6.6E−06 | 1.72 | 6.2E−03 |
| DAG(16:0/22:6)/PC(O-34:2) | 1.99 | 7.8E−24 | 1.98 | 9.2E−19 | 2.80 | 1.7E−14 | 2.71 | 3.3E−11 | 2.70 | 3.2E−06 |
| SM(36:2)/Gb3(d18:1/22:0) | 1.93 | 7.9E−24 | 2.10 | 3.3E−23 | 2.15 | 1.7E−11 | 2.14 | 1.7E−09 | 1.70 | 4.2E−03 |
| DAG(14:0/18:2)/LPC(18:2) [sn1] | 1.97 | 7.9E−24 | 2.10 | 6.2E−22 | 2.47 | 1.0E−12 | 2.54 | 8.7E−11 | 2.29 | 1.2E−04 |
| CE(20:3)/CE(22:4) | 1.93 | 8.1E−24 | 1.99 | 2.1E−20 | 2.78 | 2.4E−16 | 3.14 | 2.9E−15 | 1.67 | 9.0E−03 |
| PC(38:2)/LacCer(d18:1/16:0) | 1.96 | 8.5E−24 | 1.97 | 2.2E−19 | 2.36 | 2.7E−12 | 2.30 | 9.7E−10 | 1.92 | 1.7E−03 |
| PE(38:3)/PC(O-40:3) | 1.94 | 8.5E−24 | 2.01 | 9.8E−21 | 2.25 | 1.4E−11 | 2.31 | 6.2E−10 | 1.73 | 6.7E−03 |
| DAG(14:0/18:2)/PC(O-38:2) | 1.96 | 8.6E−24 | 2.03 | 3.0E−20 | 2.17 | 6.9E−10 | 2.17 | 4.9E−08 | 2.10 | 4.1E−04 |
| PE(32:1)/LPE(16:0) [sn2] | 1.93 | 8.7E−24 | 1.85 | 2.2E−17 | 2.40 | 3.0E−13 | 2.31 | 1.7E−10 | 1.95 | 7.8E−04 |
| PC(36:4)/LPC(20:2) [sn1] | 2.03 | 8.8E−24 | 2.07 | 6.2E−20 | 3.06 | 6.7E−15 | 3.05 | 4.3E−12 | 2.51 | 6.0E−05 |
| PI(36:4)/LPC(20:2) [sn1] | 1.92 | 8.9E−24 | 1.97 | 2.1E−20 | 2.75 | 4.6E−17 | 2.64 | 5.5E−13 | 1.74 | 4.4E−03 |
| PE(32:1)/PC(34:3) | 1.91 | 9.4E−24 | 1.87 | 2.9E−18 | 2.45 | 6.3E−14 | 2.33 | 6.4E−11 | 1.82 | 1.9E−03 |
| PC(36:4)/LPC(O-24:1) | 1.96 | 9.4E−24 | 1.92 | 3.0E−18 | 2.60 | 7.0E−14 | 2.57 | 2.7E−11 | 2.07 | 5.4E−04 |
| SM(38:0)/PC(39:4) | 2.00 | 1.0E−23 | 2.04 | 7.7E−20 | 2.78 | 2.1E−14 | 3.11 | 1.8E−13 | 2.46 | 2.7E−05 |
| PE(36:1)/LPC(18:2) [sn2] | 1.86 | 1.1E−23 | 1.87 | 1.1E−19 | 2.20 | 1.4E−13 | 2.12 | 1.8E−10 | 1.76 | 1.6E−03 |
| DAG(18:0/20:4)/LPC(P-16:0) | 1.93 | 1.1E−23 | 1.99 | 1.9E−20 | 2.45 | 3.7E−14 | 2.58 | 1.4E−12 | 2.28 | 2.4E−05 |
| PE(40:5)/PC(O-34:0) | 1.92 | 1.1E−23 | 1.90 | 1.4E−18 | 1.96 | 1.3E−08 | 1.85 | 3.6E−06 | 1.72 | 5.4E−03 |
| DAG(14:0/18:2)/SM(41:2) | 1.96 | 1.1E−23 | 2.03 | 2.5E−20 | 2.15 | 1.3E−09 | 2.15 | 7.8E−08 | 1.98 | 1.1E−03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| PC(36:4)/PC(17:0_22:6) | 1.95 | 1.1E-23 | 1.95 | 7.5E-19 | 2.14 | 1.9E-10 | 2.25 | 4.8E-09 | 1.75 | 3.9E-03 |
| PE(38:3)/LacCer(d18:1/16:0) | 1.95 | 1.1E-23 | 1.99 | 7.1E-20 | 2.33 | 1.6E-11 | 2.30 | 2.1E-09 | 1.78 | 5.9E-03 |
| DAG(18:2/20:4)/LPC(MHDA) [sn2] | 1.96 | 1.2E-23 | 2.09 | 1.3E-21 | 2.36 | 1.2E-12 | 2.50 | 4.2E-11 | 2.08 | 1.6E-04 |
| PE(38:4)/PC(35:3) | 1.96 | 1.2E-23 | 2.03 | 2.1E-20 | 2.42 | 2.0E-12 | 2.34 | 1.0E-09 | 1.95 | 1.4E-03 |
| Cer(d18:2/18:0)/PC(O-38:2) | 2.05 | 1.2E-23 | 2.25 | 1.9E-22 | 2.69 | 6.8E-13 | 2.79 | 1.2E-10 | 1.88 | 4.0E-03 |
| PC(40:5)/LPC(15:0) [sn1] | 1.95 | 1.2E-23 | 1.93 | 3.6E-18 | 2.29 | 5.5E-12 | 2.18 | 2.2E-08 | 1.67 | 1.0E-02 |
| DAG(14:0/18:2)/PC(39:4) | 1.98 | 1.3E-23 | 2.06 | 1.5E-20 | 2.25 | 4.1E-10 | 2.33 | 9.7E-09 | 2.08 | 7.5E-04 |
| SM(41:0)/LPC(MHDA) [sn2] | 1.92 | 1.3E-23 | 1.92 | 3.4E-19 | 2.76 | 1.2E-16 | 2.81 | 3.7E-14 | 2.30 | 8.5E-06 |
| PE(40:5)/LPC(20:2) [sn1] | 1.91 | 1.3E-23 | 1.95 | 6.6E-20 | 2.12 | 2.0E-10 | 2.01 | 1.0E-07 | 1.79 | 3.1E-03 |
| SM(38:0)/LPC(17:0) [sn1] | 1.95 | 1.5E-23 | 1.93 | 1.3E-18 | 2.96 | 2.2E-16 | 3.02 | 7.5E-14 | 2.48 | 1.6E-05 |
| SM(40:1)/PC(O-36:3) | 1.97 | 1.5E-23 | 1.99 | 1.7E-19 | 2.44 | 1.3E-12 | 2.42 | 4.1E-10 | 1.84 | 2.9E-03 |
| SM(41:0)/SM(31:0) | 1.95 | 1.6E-23 | 1.96 | 3.0E-19 | 2.53 | 1.4E-14 | 2.64 | 8.9E-13 | 1.75 | 4.5E-03 |
| DAG(16:0/22:6)/PC(O-38:0) | 1.98 | 1.6E-23 | 1.98 | 1.2E-18 | 2.63 | 2.3E-13 | 2.70 | 6.7E-11 | 2.77 | 2.0E-06 |
| PE(32:1)/PC(31:0) | 1.91 | 1.6E-23 | 1.82 | 9.0E-17 | 2.31 | 1.6E-12 | 2.20 | 1.5E-09 | 1.87 | 1.3E-03 |
| PE(38:1)/PC(37:6) | 1.94 | 1.7E-23 | 1.94 | 1.5E-18 | 2.12 | 1.0E-09 | 2.00 | 6.5E-07 | 1.95 | 1.2E-03 |
| DAG(14:0/18:2)/PC(O-34:0) | 1.97 | 1.7E-23 | 2.06 | 1.0E-20 | 2.15 | 1.7E-09 | 2.19 | 6.4E-08 | 2.08 | 6.2E-04 |
| PE(36:2)/PC(O-40:6) | 1.93 | 1.7E-23 | 1.98 | 5.6E-20 | 2.11 | 5.5E-10 | 2.10 | 2.0E-08 | 1.86 | 2.1E-03 |
| PC(38:2)/LPC(20:0) [sn1] | 1.89 | 1.8E-23 | 1.86 | 2.1E-18 | 2.67 | 4.8E-17 | 2.63 | 7.1E-14 | 2.23 | 2.6E-05 |
| PC(36:3)/LPC(15:0) [sn1] | 1.90 | 1.8E-23 | 1.80 | 9.0E-17 | 2.46 | 3.0E-15 | 2.38 | 2.4E-12 | 1.77 | 1.9E-03 |
| Cer(d18:2/18:0)/LPC(17:0) [sn2] | 2.00 | 1.8E-23 | 2.17 | 5.7E-22 | 2.85 | 8.0E-16 | 2.89 | 5.7E-13 | 1.89 | 1.5E-03 |
| SM(36:1)/LPC(O-20:1) | 1.93 | 1.9E-23 | 1.98 | 3.6E-20 | 2.74 | 1.0E-15 | 2.93 | 5.9E-14 | 2.29 | 3.2E-05 |
| PC(38:5)/LPC(19:0) [sn2] | 1.94 | 2.0E-23 | 1.91 | 3.6E-18 | 2.65 | 2.7E-15 | 2.62 | 4.6E-12 | 2.15 | 5.7E-05 |
| PC(38:1)/SM(37:1) | 1.91 | 2.2E-23 | 1.89 | 2.4E-18 | 2.22 | 1.3E-11 | 2.12 | 1.4E-08 | 1.70 | 4.6E-03 |
| Cer(d18:1/20:0)/Glc/GalCer(d18:2/22:0) | 1.94 | 2.2E-23 | 2.01 | 3.6E-20 | 2.18 | 9.3E-11 | 2.25 | 3.3E-09 | 2.24 | 5.5E-05 |
| PE(36:2)/LPC(19:0) [sn2] | 1.86 | 2.2E-23 | 1.85 | 6.4E-19 | 2.18 | 2.6E-13 | 2.16 | 5.4E-11 | 1.80 | 9.5E-04 |
| PC(32:1)/LPE(P-20:0) | 1.88 | 2.3E-23 | 1.74 | 1.4E-15 | 2.38 | 1.8E-14 | 2.21 | 7.2E-11 | 1.74 | 2.1E-03 |
| PE(38:3)/LPC(20:1) [sn1] | 1.92 | 2.3E-23 | 1.96 | 7.2E-20 | 2.40 | 2.8E-13 | 2.42 | 4.7E-11 | 1.75 | 5.6E-03 |
| SM(38:0)/LPC(O-18:0) | 1.91 | 2.3E-23 | 1.92 | 5.6E-19 | 2.72 | 8.6E-16 | 2.83 | 1.9E-13 | 2.56 | 3.4E-06 |
| DAG(16:0/22:6)/PC(O-32:0) | 1.97 | 2.3E-23 | 1.97 | 1.6E-18 | 2.53 | 1.0E-12 | 2.58 | 1.9E-10 | 2.63 | 6.4E-06 |
| SM(41:0)/PC(17:0_22:6) | 1.95 | 2.4E-23 | 2.05 | 1.3E-20 | 2.30 | 8.1E-12 | 2.76 | 1.2E-11 | 1.74 | 4.8E-03 |
| DAG(14:0/18:2)/PC(O-40:3) | 1.96 | 2.4E-23 | 2.08 | 2.7E-21 | 2.13 | 1.4E-09 | 2.23 | 2.0E-08 | 1.92 | 1.7E-03 |
| Cer(d18:1/20:0)/LPC(O-18:0) | 1.92 | 2.4E-23 | 1.97 | 8.3E-20 | 2.66 | 1.2E-15 | 2.64 | 8.9E-13 | 2.34 | 1.2E-06 |
| Cer(d18:1/16:0)/PC(O-36:3) | 1.96 | 2.4E-23 | 2.00 | 2.2E-19 | 2.46 | 1.2E-12 | 2.29 | 4.6E-09 | 1.90 | 2.0E-03 |
| PE(36:1)/LPC(18:2) [sn1] | 1.83 | 2.5E-23 | 1.84 | 2.8E-19 | 2.15 | 8.0E-14 | 2.08 | 9.4E-11 | 1.79 | 6.1E-04 |
| PC(38:5)/LPC(22:1) [sn1] | 2.00 | 2.5E-23 | 1.96 | 1.2E-17 | 2.59 | 1.6E-12 | 2.56 | 5.1E-10 | 2.00 | 1.1E-03 |
| PC(36:4)/PC(O-34:2) | 1.99 | 2.5E-23 | 1.96 | 7.1E-18 | 3.12 | 1.6E-14 | 2.87 | 9.6E-11 | 2.33 | 1.9E-04 |
| PE(36:1)/PI(38:1) | 1.94 | 2.5E-23 | 2.09 | 3.3E-22 | 2.12 | 4.5E-10 | 2.20 | 6.1E-09 | 1.75 | 5.6E-03 |
| DAG(18:0/20:4)/LPC(20:2) [sn1] | 1.95 | 2.7E-23 | 2.11 | 4.5E-22 | 2.46 | 3.9E-13 | 2.64 | 6.0E-12 | 2.53 | 6.0E-06 |
| PC(36:4)/PC(O-32:1) | 2.00 | 2.7E-23 | 2.03 | 2.0E-19 | 2.48 | 2.3E-11 | 2.48 | 1.6E-09 | 1.90 | 3.4E-03 |
| DAG(18:2/20:4)/LPC(17:0) [sn1] | 1.95 | 2.7E-23 | 2.07 | 4.0E-21 | 2.37 | 2.8E-12 | 2.56 | 4.0E-11 | 1.94 | 1.2E-03 |
| SM(41:0)/LPC(20:1) [sn1] | 1.95 | 2.7E-23 | 2.03 | 1.6E-20 | 2.86 | 6.1E-16 | 3.22 | 7.6E-15 | 1.99 | 9.8E-04 |
| DAG(16:0/22:6)/CE(17:0) | 1.95 | 2.9E-23 | 1.94 | 3.9E-18 | 2.61 | 9.3E-14 | 2.62 | 7.6E-11 | 2.51 | 4.5E-06 |
| LPC(20:3) [sn2]/LPC(18:2) [sn2] | 1.97 | 2.9E-23 | 2.01 | 1.4E-19 | 2.88 | 1.2E-15 | 3.11 | 5.1E-14 | 1.83 | 4.4E-03 |
| PC(38:5)/LPC(20:1) [sn1] | 2.01 | 3.0E-23 | 1.99 | 4.0E-18 | 2.74 | 2.4E-13 | 2.65 | 2.7E-10 | 2.16 | 5.2E-04 |
| SM(42:1)/PC(O-38:0) | 1.96 | 3.0E-23 | 1.90 | 2.5E-17 | 2.15 | 1.6E-09 | 2.41 | 3.0E-09 | 1.91 | 2.3E-03 |
| Cer(d18:1/24:1)/PC(P-40:4) | 1.92 | 3.0E-23 | 1.93 | 1.5E-18 | 2.45 | 1.9E-13 | 2.60 | 4.4E-12 | 2.21 | 3.9E-05 |
| DAG(18:0/20:4)/PC(P-40:4) | 1.95 | 3.1E-23 | 2.01 | 4.4E-20 | 2.42 | 1.0E-12 | 2.64 | 8.7E-12 | 2.68 | 2.6E-06 |
| DAG(18:0/20:4)/PC(33:2) | 1.94 | 3.2E-23 | 2.00 | 5.7E-20 | 2.22 | 9.9E-11 | 2.33 | 1.0E-09 | 2.23 | 1.2E-04 |
| PE(40:5)/PC(O-38:2) | 1.89 | 3.2E-23 | 1.86 | 1.1E-17 | 1.94 | 1.2E-08 | 1.82 | 5.3E-06 | 1.72 | 4.6E-03 |
| PC(36:4)/PC(O-34:0) | 1.97 | 3.2E-23 | 1.93 | 1.5E-17 | 2.52 | 1.0E-11 | 2.47 | 3.2E-09 | 2.26 | 2.8E-04 |
| PC(36:4)/PC(P-32:0) | 1.99 | 3.3E-23 | 1.97 | 5.3E-18 | 2.72 | 2.7E-12 | 2.72 | 5.7E-10 | 2.25 | 5.1E-04 |
| DAG(14:0/18:2)/LPC(22:1) [sn1] | 1.99 | 3.3E-23 | 2.08 | 1.7E-20 | 2.33 | 2.2E-10 | 2.45 | 2.8E-09 | 1.96 | 2.5E-03 |
| CE(16:2)/LPC(20:1) [sn1] | 1.98 | 3.4E-23 | 1.94 | 7.9E-18 | 3.07 | 1.2E-15 | 2.95 | 3.2E-12 | 1.73 | 9.1E-03 |
| Cer(d18:1/20:0)/PC(O-40:6) | 1.95 | 3.7E-23 | 2.10 | 1.2E-21 | 2.34 | 3.1E-11 | 2.46 | 4.4E-10 | 2.17 | 2.8E-04 |
| PC(38:1)/Gb3(d18:1/16:0) | 1.91 | 3.7E-23 | 1.99 | 2.3E-20 | 2.31 | 1.4E-12 | 2.29 | 4.6E-10 | 1.66 | 7.6E-03 |
| PG(34:1)/PC(O-40:6) | 1.93 | 3.8E-23 | 1.97 | 2.3E-19 | 2.18 | 1.1E-10 | 2.15 | 1.2E-08 | 1.99 | 3.8E-04 |
| DAG(18:2/20:4)/PC(O-36:3) | 1.94 | 3.8E-23 | 2.11 | 3.7E-22 | 2.23 | 8.6E-11 | 2.34 | 1.4E-09 | 1.84 | 3.8E-03 |
| DAG(18:1/18:3)/LPC(MHDA) [sn2] | 1.98 | 3.8E-23 | 2.12 | 2.2E-21 | 2.16 | 7.3E-10 | 2.38 | 3.0E-09 | 2.42 | 7.1E-06 |
| Cer(d18:1/16:0)/LPC(O-20:0) | 1.92 | 3.9E-23 | 1.89 | 5.6E-18 | 2.43 | 2.5E-14 | 2.44 | 7.0E-12 | 2.12 | 1.3E-05 |
| DAG(18:0/20:4)/SM(d17:1/14:0) | 1.95 | 4.0E-23 | 1.96 | 6.5E-19 | 2.26 | 5.9E-11 | 2.30 | 2.7E-09 | 2.17 | 1.9E-04 |
| PE(38:4)/PC(35:2) | 1.95 | 4.0E-23 | 2.00 | 1.1E-19 | 2.50 | 1.3E-12 | 2.38 | 2.4E-09 | 2.36 | 5.2E-05 |
| PE(40:5)/PC(37:1) | 1.91 | 4.1E-23 | 1.88 | 1.0E-17 | 1.93 | 3.1E-08 | 1.82 | 7.9E-06 | 1.70 | 8.0E-03 |
| DAG(16:0/22:6)/PC(37:1) | 1.98 | 4.2E-23 | 1.96 | 1.1E-17 | 2.66 | 4.5E-13 | 2.69 | 1.8E-10 | 2.83 | 2.5E-06 |
| PC(38:2)/SM(d17:1/14:0) | 1.92 | 4.4E-23 | 1.87 | 3.6E-17 | 2.42 | 8.2E-13 | 2.24 | 5.2E-09 | 1.76 | 3.7E-03 |
| PI(36:4)/PC(O-34:2) | 1.92 | 4.4E-23 | 1.89 | 4.5E-18 | 3.01 | 3.2E-16 | 2.68 | 1.8E-11 | 1.72 | 7.2E-03 |
| PI(34:2)/PC(33:2) | 1.90 | 4.7E-23 | 1.81 | 2.2E-16 | 2.54 | 3.3E-14 | 2.33 | 3.4E-10 | 1.75 | 4.2E-03 |
| DAG(14:0/18:2)/PC(P-40:4) | 1.96 | 4.7E-23 | 2.06 | 2.0E-20 | 2.16 | 1.6E-10 | 2.37 | 4.9E-09 | 2.21 | 2.6E-04 |
| Cer(d16:1/20:0)/LPC(O-22:0) | 1.99 | 4.7E-23 | 2.20 | 1.7E-22 | 2.59 | 5.4E-13 | 2.74 | 3.5E-11 | 2.66 | 8.8E-06 |
| PC(32:1)/LPC(P-16:0) | 1.86 | 4.9E-23 | 1.73 | 1.6E-15 | 2.25 | 9.9E-14 | 2.15 | 1.4E-10 | 1.66 | 5.2E-03 |
| SM(40:1)/LPC(22:0) [sn2] | 1.91 | 5.0E-23 | 1.97 | 6.0E-20 | 2.56 | 3.3E-15 | 2.82 | 2.3E-14 | 2.11 | 1.3E-04 |
| DAG(18:0/20:4)/PC(P-32:0) | 1.92 | 5.0E-23 | 2.01 | 1.9E-20 | 2.25 | 2.0E-11 | 2.43 | 1.2E-10 | 2.30 | 4.0E-05 |
| PE(34:1)/PC(33:2) | 1.87 | 5.0E-23 | 1.83 | 1.1E-17 | 2.18 | 1.7E-11 | 2.07 | 9.4E-09 | 1.69 | 5.7E-03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| Cer(d16:1/20:0)/LPC(22:0) [sn2] | 2.02 | 5.0E−23 | 2.27 | 7.6E−23 | 2.84 | 7.5E−14 | 2.99 | 5.8E−12 | 2.76 | 9.1E−06 |
| Cer(d18:1/20:0)/SM(34:1) | 1.95 | 5.0E−23 | 2.14 | 3.2E−22 | 2.56 | 1.7E−13 | 2.70 | 2.0E−11 | 1.97 | 1.1E−03 |
| SM(41:0)/PC(O-34:0) | 1.92 | 5.3E−23 | 1.97 | 1.4E−19 | 2.47 | 2.5E−13 | 2.68 | 2.7E−12 | 2.17 | 1.7E−04 |
| PE(38:3)/LPC(20:1) [sn2] | 1.91 | 5.4E−23 | 1.95 | 1.6E−19 | 2.34 | 1.4E−12 | 2.36 | 1.7E−10 | 1.70 | 8.2E−03 |
| DAG(14:0/18:2)/PC(P-32:0) | 1.96 | 5.4E−23 | 2.08 | 7.3E−21 | 2.21 | 9.4E−10 | 2.30 | 2.0E−08 | 2.05 | 1.0E−03 |
| PC(36:4)/PC(O-38:2) | 1.98 | 5.5E−23 | 1.90 | 1.8E−16 | 2.60 | 3.7E−12 | 2.52 | 2.8E−09 | 2.36 | 1.5E−04 |
| SM(41:0)/LPC(O-20:0) | 1.89 | 5.7E−23 | 1.92 | 3.9E−19 | 2.65 | 7.6E−16 | 2.89 | 2.0E−14 | 2.28 | 3.5E−05 |
| Cer(d18:1/24:1)/SM(41:2) | 1.87 | 5.8E−23 | 1.86 | 8.0E−18 | 2.02 | 1.6E−10 | 2.06 | 6.3E−09 | 1.74 | 2.6E−03 |
| PC(36:4)/LPC(P-18:1) | 1.94 | 5.9E−23 | 1.87 | 5.1E−17 | 2.45 | 6.0E−13 | 2.34 | 7.4E−10 | 1.83 | 3.6E−03 |
| PE(32:1)/LacCer(d18:1/16:0) | 1.88 | 6.1E−23 | 1.79 | 2.4E−16 | 2.28 | 4.3E−12 | 2.15 | 3.0E−09 | 1.77 | 3.4E−03 |
| SM(41:0)/SM(34:1) | 1.91 | 6.1E−23 | 1.99 | 2.9E−20 | 2.56 | 1.3E−14 | 2.80 | 1.9E−13 | 1.80 | 2.9E−03 |
| PC(38:2)/LPC(O-20:1) | 1.88 | 6.1E−23 | 1.85 | 7.0E−18 | 2.48 | 9.4E−15 | 2.41 | 1.3E−11 | 1.96 | 5.6E−04 |
| PC(38:2)/LPC(20:1) [sn2] | 1.92 | 6.2E−23 | 1.94 | 5.3E−19 | 2.52 | 4.1E−14 | 2.54 | 1.2E−11 | 1.80 | 4.0E−03 |
| PE(32:1)/PC(33:3) | 1.90 | 6.4E−23 | 1.80 | 9.1E−16 | 2.50 | 1.7E−13 | 2.37 | 3.2E−10 | 1.81 | 2.6E−03 |
| SM(38:0)/LPC(17:0) [sn2] | 1.91 | 6.4E−23 | 1.92 | 1.3E−18 | 2.66 | 1.0E−15 | 2.72 | 3.7E−13 | 2.27 | 1.2E−05 |
| SM(41:0)/PC(35:3) | 1.93 | 6.4E−23 | 2.04 | 3.4E−21 | 2.69 | 4.1E−15 | 2.98 | 3.6E−14 | 2.05 | 3.6E−04 |
| PC(36:4)/LPC(O-22:0) | 1.92 | 6.5E−23 | 1.89 | 1.2E−17 | 2.57 | 6.3E−14 | 2.58 | 1.4E−11 | 2.27 | 9.6E−05 |
| PC(36:4)/LPC(17:0) [sn2] | 1.89 | 7.0E−23 | 1.82 | 9.3E−17 | 2.54 | 5.6E−15 | 2.43 | 1.4E−11 | 2.13 | 1.0E−04 |
| PC(32:1)/LPC(18:2) [sn1] | 1.88 | 7.3E−23 | 1.78 | 2.9E−16 | 2.47 | 5.7E−15 | 2.36 | 1.3E−11 | 1.87 | 7.6E−04 |
| PC(31:1)/PC(O-40:6) | 1.89 | 7.3E−23 | 1.85 | 1.1E−17 | 2.21 | 3.4E−11 | 2.22 | 1.9E−09 | 1.72 | 5.6E−03 |
| DAG(14:0/18:2)/LPC(O-24:0) | 1.94 | 8.4E−23 | 2.06 | 1.4E−20 | 2.22 | 3.0E−10 | 2.34 | 5.0E−09 | 2.13 | 4.3E−04 |
| DAG(16:0/22:6)/LPE(20:1) [sn1] | 2.00 | 8.4E−23 | 2.06 | 2.4E−19 | 2.75 | 1.5E−13 | 3.03 | 3.0E−12 | 2.79 | 1.2E−05 |
| PC(36:5)/Gb3(d18:1/23:0) | 1.92 | 8.8E−23 | 1.77 | 7.8E−15 | 2.04 | 2.9E−09 | 1.86 | 5.4E−06 | 1.74 | 6.4E−03 |
| PE(38:5)/PC(37:6) | 1.88 | 8.8E−23 | 1.87 | 1.3E−17 | 2.10 | 4.4E−10 | 2.04 | 1.7E−07 | 1.72 | 4.9E−03 |
| DAG(18:0/20:4)/LPC(15:0) [sn2] | 1.93 | 8.9E−23 | 1.95 | 9.6E−19 | 2.47 | 4.4E−13 | 2.56 | 2.8E−11 | 2.24 | 6.4E−05 |
| PC(38:4)/LPC(17:0) [sn2] | 1.90 | 9.4E−23 | 1.89 | 4.7E−18 | 2.60 | 9.6E−16 | 2.57 | 1.7E−12 | 1.88 | 9.5E−04 |
| CE(20:3)/PC(P-40:2) | 1.93 | 9.6E−23 | 1.95 | 6.7E−19 | 2.82 | 8.3E−15 | 3.11 | 1.5E−13 | 1.75 | 5.1E−03 |
| PC(38:2)/LPC(MHDA) [sn1] | 1.86 | 9.7E−23 | 1.84 | 4.4E−18 | 2.61 | 7.8E−17 | 2.50 | 4.9E−13 | 2.33 | 2.7E−06 |
| SM(41:0)/LPC(P-18:0) | 1.88 | 1.0E−22 | 1.89 | 1.1E−18 | 2.65 | 2.3E−16 | 2.71 | 7.5E−14 | 2.11 | 1.1E−04 |
| CE(20:3)/PC(O-38:0) | 1.95 | 1.0E−22 | 1.96 | 1.8E−20 | 3.10 | 1.3E−16 | 3.50 | 2.0E−15 | 1.90 | 2.2E−03 |
| Cer(d18:2/22:0)/LPC(19:0) [sn2] | 1.90 | 1.0E−22 | 2.01 | 1.1E−20 | 2.58 | 4.7E−15 | 2.73 | 2.4E−13 | 1.91 | 5.9E−04 |
| CE(18:0)/PC(O-40:6) | 1.93 | 1.0E−22 | 2.08 | 2.2E−21 | 1.95 | 7.0E−08 | 2.06 | 2.7E−07 | 1.73 | 8.8E−03 |
| Cer(d18:1/24:1)/LPC(20:2) [sn1] | 1.90 | 1.0E−22 | 2.00 | 1.9E−20 | 2.47 | 7.9E−14 | 2.57 | 4.1E−12 | 2.10 | 1.8E−04 |
| SM(40:1)/LPC(20:0) [sn2] | 1.88 | 1.0E−22 | 1.89 | 1.6E−18 | 2.47 | 7.4E−15 | 2.65 | 1.1E−13 | 1.97 | 3.4E−04 |
| PE(P-38:6)/PC(O-40:6) | 1.90 | 1.0E−22 | 1.95 | 3.2E−19 | 2.32 | 1.6E−12 | 2.54 | 2.7E−11 | 2.32 | 9.4E−06 |
| PC(36:1)/LPC(20:2) [sn1] | 1.91 | 1.1E−22 | 2.04 | 5.7E−21 | 2.57 | 5.5E−14 | 2.58 | 2.3E−11 | 1.71 | 7.4E−03 |
| SM(40:1)/LPC(20:1) [sn1] | 1.94 | 1.1E−22 | 2.03 | 5.5E−20 | 2.58 | 2.3E−13 | 2.90 | 1.1E−12 | 1.74 | 8.4E−03 |
| PC(38:4)/PC(O-38:2) | 1.90 | 1.1E−22 | 1.88 | 9.1E−18 | 2.26 | 2.4E−11 | 2.24 | 5.5E−09 | 1.83 | 3.1E−03 |
| Cer(d18:1/24:1)/PC(O-32:0) | 1.87 | 1.2E−22 | 1.90 | 9.5E−19 | 2.04 | 5.0E−10 | 2.14 | 2.6E−09 | 1.84 | 1.6E−03 |
| PI(36:4)/LPE(16:0) [sn2] | 1.91 | 1.2E−22 | 2.02 | 4.8E−21 | 2.73 | 4.8E−15 | 2.81 | 1.7E−12 | 1.73 | 6.9E−03 |
| DAG(18:1/18:3)/PC(17:0_22:6) | 1.96 | 1.2E−22 | 2.11 | 3.7E−21 | 1.81 | 2.7E−06 | 2.02 | 1.4E−06 | 1.98 | 1.4E−03 |
| SM(41:0)/LPC(20:1) [sn2] | 1.93 | 1.2E−22 | 2.01 | 6.0E−20 | 2.74 | 8.2E−15 | 3.10 | 6.8E−14 | 1.91 | 1.9E−03 |
| DAG(14:0/18:2)/PC(37:1) | 1.95 | 1.2E−22 | 2.04 | 6.4E−20 | 2.14 | 2.8E−09 | 2.18 | 7.5E−08 | 2.10 | 7.0E−04 |
| PC(38:2)/LPC(22:0) [sn1] | 1.88 | 1.2E−22 | 1.89 | 1.3E−18 | 2.67 | 2.3E−16 | 2.71 | 8.2E−14 | 2.32 | 1.9E−05 |
| Cer(d16:1/20:0)/PC(O-34:0) | 1.99 | 1.2E−22 | 2.22 | 5.0E−22 | 2.29 | 5.3E−10 | 2.32 | 5.4E−08 | 2.56 | 3.6E−05 |
| PE(38:3)/PC(O-34:0) | 1.90 | 1.3E−22 | 1.93 | 1.2E−18 | 2.27 | 4.1E−11 | 2.22 | 7.2E−09 | 1.85 | 3.0E−03 |
| PE(38:1)/PC(17:0_22:6) | 1.91 | 1.3E−22 | 1.89 | 1.3E−17 | 2.04 | 4.0E−09 | 1.95 | 8.7E−07 | 1.98 | 9.4E−04 |
| Cer(d16:1/20:0)/LPC(O-24:1) | 1.97 | 1.3E−22 | 2.14 | 1.2E−21 | 2.49 | 3.2E−12 | 2.55 | 3.2E−10 | 2.28 | 1.6E−04 |
| PE(38:4)/PC(O-36:3) | 1.90 | 1.4E−22 | 1.91 | 1.7E−18 | 2.30 | 8.2E−12 | 2.14 | 1.4E−08 | 1.85 | 2.3E−03 |
| DAG(14:0/18:2)/PC(O-38:0) | 1.95 | 1.4E−22 | 2.07 | 3.1E−20 | 2.19 | 1.4E−09 | 2.27 | 3.4E−08 | 2.16 | 4.2E−04 |
| SM(36:2)/LPC(O-20:1) | 1.91 | 1.5E−22 | 1.99 | 5.4E−20 | 2.90 | 8.6E−17 | 3.05 | 2.2E−14 | 2.20 | 5.5E−05 |
| Cer(d18:1/24:1)/LPC(P-16:0) | 1.87 | 1.5E−22 | 1.84 | 8.6E−18 | 2.26 | 4.8E−14 | 2.25 | 7.0E−12 | 1.78 | 7.0E−04 |
| PE(36:1)/LPC(15:0) [sn2] | 1.84 | 1.5E−22 | 1.79 | 4.1E−17 | 2.15 | 4.8E−12 | 2.01 | 6.6E−09 | 1.62 | 8.5E−03 |
| PE(36:1)/LPC(O-18:1) | 1.83 | 1.6E−22 | 1.78 | 4.1E−17 | 2.10 | 1.3E−11 | 1.98 | 1.3E−08 | 1.63 | 8.7E−03 |
| DAG(14:0/18:2)/LPC(22:6) [sn1] | 1.95 | 1.6E−22 | 2.11 | 2.7E−21 | 2.18 | 1.7E−09 | 2.26 | 2.6E−08 | 1.93 | 2.7E−03 |
| DAG(18:2/20:4)/LacCer(d18:1/16:0) | 1.90 | 1.6E−22 | 2.08 | 4.0E−22 | 2.00 | 3.1E−09 | 2.19 | 4.6E−09 | 1.71 | 7.2E−03 |
| DAG(14:0/18:2)/PC(O-32:0) | 1.93 | 1.7E−22 | 2.03 | 3.2E−20 | 2.10 | 5.4E−09 | 2.17 | 8.3E−08 | 2.01 | 1.2E−03 |
| PE(40:5)/LPC(20:2) [sn2] | 1.89 | 1.8E−22 | 1.93 | 3.7E−19 | 2.03 | 3.4E−09 | 1.93 | 7.9E−07 | 1.71 | 6.9E−03 |
| DAG(16:0/22:6)/PC(P-40:5) | 1.95 | 1.9E−22 | 1.92 | 2.4E−17 | 2.78 | 7.8E−14 | 2.75 | 7.2E−11 | 2.78 | 5.5E−06 |
| SM(40:1)/LPC(19:0) [sn2] | 1.85 | 2.0E−22 | 1.88 | 5.5E−19 | 2.28 | 3.2E−15 | 2.41 | 5.8E−14 | 1.76 | 6.4E−04 |
| PC(36:4)/SM(41:2) | 1.96 | 2.1E−22 | 1.89 | 2.9E−16 | 2.50 | 1.6E−11 | 2.41 | 8.0E−09 | 2.09 | 9.0E−04 |
| PE(36:1)/LPC(15:0) [sn1] | 1.83 | 2.1E−22 | 1.78 | 5.0E−17 | 2.16 | 2.6E−12 | 2.03 | 3.1E−09 | 1.74 | 2.1E−03 |
| DAG(18:2/20:4)/LPC(O-24:1) | 1.89 | 2.2E−22 | 2.06 | 9.5E−22 | 2.14 | 8.4E−11 | 2.37 | 1.7E−10 | 1.77 | 4.1E−03 |
| SM(41:0)/LPC(22:0) [sn1] | 1.90 | 2.2E−22 | 1.96 | 1.3E−19 | 2.77 | 1.7E−16 | 3.11 | 1.5E−15 | 2.31 | 3.1E−05 |
| PC(36:4)/LPC(P-18:0) | 1.89 | 2.3E−22 | 1.84 | 7.7E−17 | 2.57 | 2.2E−14 | 2.44 | 4.6E−11 | 2.14 | 1.7E−04 |
| Cer(d16:1/20:0)/SM(41:2) | 1.96 | 2.3E−22 | 2.15 | 3.9E−21 | 2.17 | 7.3E−10 | 2.13 | 1.4E−07 | 2.26 | 1.3E−04 |
| PC(36:4)/LPC(20:2) [sn2] | 1.98 | 2.4E−22 | 2.03 | 7.0E−19 | 2.89 | 1.3E−13 | 2.92 | 3.4E−11 | 2.38 | 1.6E−04 |
| DAG(16:0/22:6)/LPC(18:2) [sn2] | 1.93 | 2.5E−22 | 1.95 | 3.8E−18 | 2.76 | 1.6E−14 | 2.76 | 9.8E−12 | 2.73 | 4.7E−06 |
| DAG(18:0/20:4)/LPC(18:2) [sn2] | 1.92 | 2.5E−22 | 2.05 | 9.0E−21 | 2.59 | 3.1E−14 | 2.76 | 9.9E−13 | 2.51 | 9.9E−06 |
| PE(32:1)/PC(17:0_22:6) | 1.87 | 2.5E−22 | 1.80 | 3.1E−16 | 2.17 | 5.1E−11 | 2.12 | 1.1E−08 | 1.67 | 8.4E−03 |
| CE(18:0)/PC(O-34:0) | 1.95 | 2.5E−22 | 2.09 | 3.4E−20 | 1.88 | 4.9E−07 | 1.95 | 4.6E−06 | 1.76 | 7.3E−03 |
| PC(36:4)/LPC(17:0) [sn1] | 1.89 | 2.5E−22 | 1.80 | 6.2E−16 | 2.59 | 1.6E−14 | 2.48 | 2.5E−11 | 2.15 | 1.7E−04 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| Cer(d20:1/24:1)/PC(O-40:6) | 1.88 | 2.6E−22 | 1.94 | 4.0E−19 | 2.32 | 2.0E−12 | 2.51 | 3.6E−11 | 1.81 | 2.4E−03 |
| PE(36:2)/PC(P-40:2) | 1.89 | 2.6E−22 | 1.92 | 1.9E−18 | 2.07 | 1.0E−09 | 2.02 | 1.2E−07 | 1.81 | 1.4E−03 |
| SM(38:0)/LPC(O-18:1) | 1.91 | 2.6E−22 | 1.91 | 5.1E−18 | 2.69 | 1.6E−14 | 2.78 | 2.9E−12 | 2.19 | 1.9E−04 |
| DAG(18:2/20:4)/LPC(17:0) [sn2] | 1.92 | 2.6E−22 | 2.06 | 1.1E−20 | 2.35 | 4.5E−12 | 2.53 | 6.9E−11 | 1.94 | 1.1E−03 |
| PC(38:2)/LPC(20:0) [sn2] | 1.85 | 2.6E−22 | 1.82 | 1.5E−17 | 2.52 | 4.7E−16 | 2.49 | 4.2E−13 | 2.05 | 1.3E−04 |
| DAG(18:1/18:3)/PC(37:6) | 1.94 | 2.7E−22 | 2.07 | 9.6E−21 | 1.80 | 2.6E−06 | 1.96 | 2.7E−06 | 1.90 | 2.4E−03 |
| PC(38:1)/LPC(20:1) [sn1] | 1.87 | 2.7E−22 | 1.92 | 2.1E−18 | 2.55 | 1.3E−15 | 2.61 | 1.8E−13 | 2.04 | 1.9E−04 |
| SM(41:0)/LPC(O-24:1) | 1.89 | 2.8E−22 | 1.95 | 3.3E−19 | 2.61 | 5.0E−15 | 2.87 | 6.0E−14 | 1.98 | 5.9E−04 |
| PE(38:4)/PC(37:2) | 1.90 | 2.8E−22 | 1.91 | 2.9E−18 | 2.27 | 1.8E−11 | 2.26 | 2.4E−09 | 1.97 | 6.9E−04 |
| SM(36:2)/LPC(P-18:1) | 1.88 | 2.9E−22 | 1.93 | 2.9E−19 | 2.49 | 3.5E−15 | 2.45 | 2.9E−12 | 1.72 | 2.1E−03 |
| Cer(d18:1/22:0)/LPC(18:1) [sn1] | 1.89 | 2.9E−22 | 2.00 | 2.0E−20 | 2.71 | 1.2E−15 | 2.85 | 1.1E−13 | 2.02 | 3.3E−04 |
| PE(32:1)/PC(O-34:0) | 1.85 | 2.9E−22 | 1.74 | 1.9E−15 | 2.22 | 7.0E−12 | 2.09 | 6.5E−09 | 1.81 | 1.9E−03 |
| SM(38:1)/PC(O-36:2) | 1.91 | 2.9E−22 | 1.98 | 1.9E−19 | 2.52 | 1.4E−13 | 2.50 | 7.7E−11 | 2.05 | 5.1E−05 |
| Cer(d18:1/16:0)/LPC(20:0) [sn1] | 1.87 | 2.9E−22 | 1.86 | 1.1E−17 | 2.41 | 2.4E−15 | 2.40 | 6.4E−13 | 2.02 | 3.6E−05 |
| SM(36:2)/SM(41:2) | 1.88 | 3.0E−22 | 2.03 | 7.0E−21 | 2.45 | 4.0E−15 | 2.72 | 1.2E−13 | 2.17 | 1.9E−05 |
| DAG(18:2/20:4)/PC(39:4) | 1.91 | 3.1E−22 | 2.09 | 1.3E−21 | 2.11 | 7.3E−10 | 2.39 | 4.7E−10 | 1.80 | 4.0E−03 |
| DAG(18:1/18:2)/LPC(17:0) [sn1] | 1.88 | 3.1E−22 | 1.99 | 2.8E−20 | 2.28 | 5.5E−12 | 2.42 | 1.3E−10 | 1.90 | 1.1E−03 |
| PE(40:5)/PC(O-38:0) | 1.88 | 3.1E−22 | 1.89 | 7.7E−18 | 1.96 | 1.4E−08 | 1.90 | 2.0E−06 | 1.77 | 3.6E−03 |
| LPC(14:0) [sn2]/LPC(15:0) [sn1] | 1.88 | 3.3E−22 | 1.79 | 2.1E−15 | 2.22 | 2.9E−11 | 2.07 | 1.0E−07 | 1.82 | 1.9E−03 |
| DAG(16:0/22:6)/LPC(18:2) [sn1] | 1.91 | 3.3E−22 | 1.92 | 5.5E−18 | 2.73 | 1.0E−14 | 2.73 | 6.2E−12 | 2.76 | 2.6E−06 |
| PE(36:1)/LPE(P-20:0) | 1.83 | 3.5E−22 | 1.80 | 2.8E−17 | 2.17 | 1.6E−12 | 2.04 | 2.3E−09 | 1.73 | 2.7E−03 |
| SM(40:1)/PC(O-38:2) | 1.90 | 3.5E−22 | 1.86 | 1.9E−16 | 2.16 | 8.4E−10 | 2.29 | 1.9E−08 | 2.03 | 4.2E−04 |
| SM(41:0)/LPC(20:0) [sn1] | 1.87 | 3.6E−22 | 1.91 | 8.9E−19 | 2.73 | 1.5E−16 | 2.97 | 3.4E−15 | 2.22 | 5.7E−05 |
| SM(44:2)/SM(44:3) | 1.90 | 3.6E−22 | 1.96 | 2.1E−19 | 2.26 | 1.7E−11 | 2.54 | 8.5E−12 | 1.75 | 4.0E−03 |
| PE(32:1)/PI(38:1) | 1.92 | 3.6E−22 | 1.91 | 9.6E−18 | 2.42 | 7.8E−12 | 2.45 | 1.0E−09 | 1.86 | 2.4E−03 |
| DAG(16:0/22:6)/LPC(O-16:0) | 1.91 | 3.6E−22 | 1.86 | 7.9E−17 | 2.63 | 6.0E−14 | 2.58 | 5.0E−11 | 2.50 | 8.6E−06 |
| DAG(14:0/18:2)/LPC(O-16:0) | 1.90 | 3.7E−22 | 1.97 | 2.5E−19 | 2.25 | 1.0E−10 | 2.27 | 7.0E−09 | 2.00 | 1.0E−03 |
| LPC(14:0) [sn1]/LPC(15:0) [sn1] | 1.87 | 3.9E−22 | 1.78 | 2.7E−15 | 2.08 | 5.7E−10 | 1.89 | 2.1E−06 | 1.75 | 4.2E−03 |
| PE(32:1)/PC(P-32:0) | 1.85 | 4.0E−22 | 1.76 | 1.3E−15 | 2.26 | 3.7E−12 | 2.14 | 2.7E−09 | 1.79 | 2.7E−03 |
| SM(40:1)/LPC(P-18:0) | 1.84 | 4.2E−22 | 1.81 | 2.2E−17 | 2.30 | 2.5E−14 | 2.27 | 1.2E−11 | 1.89 | 3.0E−04 |
| DAG(18:0/20:4)/PC(O-34:0) | 1.90 | 4.2E−22 | 1.95 | 7.1E−19 | 2.13 | 4.4E−10 | 2.24 | 5.2E−09 | 2.34 | 3.7E−05 |
| PE(34:1)/PC(P-40:2) | 1.87 | 4.2E−22 | 1.82 | 6.1E−17 | 2.15 | 1.0E−10 | 2.02 | 5.1E−08 | 1.72 | 2.4E−03 |
| PE(38:3)/PC(O-34:2) | 1.89 | 4.2E−22 | 1.92 | 2.2E−18 | 2.53 | 6.5E−13 | 2.39 | 8.9E−10 | 1.88 | 2.6E−03 |
| SM(41:0)/LPC(20:0) [sn2] | 1.87 | 4.3E−22 | 1.91 | 9.6E−19 | 2.71 | 2.9E−16 | 2.97 | 5.6E−15 | 2.13 | 1.5E−04 |
| DAG(18:1/18:3)/PC(37:2) | 1.94 | 4.4E−22 | 2.14 | 1.7E−21 | 1.98 | 9.2E−08 | 2.31 | 3.3E−08 | 2.36 | 8.7E−05 |
| PI(34:2)/PC(35:3) | 1.87 | 4.4E−22 | 1.86 | 1.3E−17 | 2.68 | 4.2E−15 | 2.53 | 1.6E−11 | 1.83 | 2.5E−03 |
| PC(38:5)/LPC(20:1) [sn2] | 1.96 | 4.5E−22 | 1.94 | 3.9E−17 | 2.58 | 4.8E−12 | 2.49 | 3.2E−09 | 2.05 | 1.2E−03 |
| PC(36:3)/LPC(O-24:0) | 1.85 | 4.8E−22 | 1.81 | 4.2E−17 | 2.21 | 5.5E−13 | 2.28 | 2.0E−11 | 1.72 | 3.8E−03 |
| PE(32:1)/PC(O-34:2) | 1.86 | 4.8E−22 | 1.76 | 1.9E−15 | 2.40 | 4.4E−13 | 2.21 | 1.7E−09 | 1.85 | 1.7E−03 |
| SM(38:0)/PC(O-34:2) | 1.90 | 4.8E−22 | 1.94 | 1.2E−18 | 2.70 | 6.2E−15 | 2.66 | 4.0E−12 | 2.32 | 3.0E−05 |
| Cer(d18:1/24:1)/PC(O-38:2) | 1.84 | 4.8E−22 | 1.81 | 1.3E−16 | 2.06 | 1.4E−10 | 2.09 | 7.2E−09 | 1.93 | 4.1E−04 |
| Cer(d18:1/20:0)/LPC(O-18:1) | 1.89 | 4.9E−22 | 1.95 | 1.0E−18 | 2.55 | 4.5E−14 | 2.52 | 2.5E−11 | 1.99 | 2.2E−04 |
| PE(40:5)/LPC(15:0) [sn1] | 1.84 | 5.0E−22 | 1.79 | 1.4E−16 | 2.03 | 3.1E−10 | 1.90 | 2.9E−07 | 1.72 | 3.6E−03 |
| DAG(18:1/18:2)/PC(O-36:3) | 1.90 | 5.2E−22 | 2.07 | 1.8E−21 | 2.21 | 2.0E−10 | 2.29 | 5.7E−09 | 1.83 | 4.0E−03 |
| Cer(d18:2/18:0)/PC(P-40:2) | 1.95 | 5.3E−22 | 2.14 | 1.2E−21 | 2.40 | 2.0E−11 | 2.41 | 1.1E−09 | 1.77 | 5.7E−03 |
| DAG(18:0/20:4)/PC(O-34:2) | 1.89 | 5.3E−22 | 1.95 | 7.0E−19 | 2.36 | 1.7E−12 | 2.37 | 2.7E−10 | 2.32 | 2.7E−05 |
| PC(36:4)/PC(O-32:0) | 1.95 | 5.3E−22 | 1.92 | 5.3E−17 | 2.48 | 5.3E−11 | 2.48 | 4.2E−09 | 2.17 | 7.1E−04 |
| PC(36:4)/LPC(15:0) [sn1] | 1.88 | 5.4E−22 | 1.80 | 8.3E−16 | 2.57 | 2.3E−14 | 2.47 | 3.8E−11 | 2.19 | 8.0E−05 |
| CE(16:2)/LPC(O-24:1) | 1.91 | 5.5E−22 | 1.85 | 3.0E−16 | 2.78 | 2.0E−14 | 2.64 | 6.1E−11 | 1.72 | 6.6E−03 |
| SM(41:0)/Glc/GalCer(d18:1/23:0) | 1.88 | 5.5E−22 | 1.94 | 1.9E−19 | 2.39 | 5.6E−13 | 2.69 | 9.1E−13 | 2.12 | 1.4E−04 |
| Cer(d16:1/20:0)/PC(O-38:2) | 1.95 | 5.5E−22 | 2.10 | 2.9E−20 | 2.23 | 1.1E−07 | 2.53 | 1.8E−05 | | |
| DAG(16:0/22:6)/LPE(P-18:0) | 1.90 | 5.6E−22 | 1.87 | 7.9E−17 | 2.62 | 1.1E−13 | 2.55 | 1.5E−10 | 2.66 | 3.7E−06 |
| DAG(14:0/18:2)/CE(17:0) | 1.89 | 5.6E−22 | 1.98 | 1.3E−19 | 2.12 | 5.7E−10 | 2.15 | 3.3E−08 | 1.95 | 9.6E−04 |
| PE(38:3)/LPE(16:0) [sn1] | 1.92 | 5.6E−22 | 2.05 | 3.9E−20 | 2.45 | 9.8E−12 | 2.64 | 1.6E−10 | 1.96 | 2.2E−03 |
| SM(41:0)/PC(O-32:1) | 1.91 | 5.8E−22 | 2.07 | 1.5E−21 | 2.43 | 1.1E−12 | 2.78 | 9.4E−13 | 1.78 | 4.9E−03 |
| PE(32:1)/LPC(20:1) [sn1] | 1.85 | 5.9E−22 | 1.76 | 7.6E−16 | 2.29 | 6.3E−13 | 2.19 | 4.6E−10 | 1.73 | 4.0E−03 |
| DAG(18:0/20:4)/LPC(20:2) [sn2] | 1.91 | 5.9E−22 | 2.09 | 2.9E−21 | 2.31 | 8.6E−12 | 2.50 | 4.3E−11 | 2.45 | 1.3E−05 |
| SM(41:0)/PC(P-40:2) | 1.89 | 6.1E−22 | 1.98 | 1.5E−19 | 2.32 | 1.9E−12 | 2.50 | 1.4E−11 | 1.94 | 2.4E−04 |
| PE(38:1)/PC(37:2) | 1.84 | 6.3E−22 | 1.81 | 4.1E−17 | 2.13 | 2.0E−11 | 2.03 | 1.5E−08 | 2.19 | 2.1E−05 |
| SM(36:1)/PC(O-36:3) | 1.89 | 6.7E−22 | 2.00 | 4.8E−20 | 2.59 | 2.3E−14 | 2.65 | 3.2E−12 | 2.22 | 7.1E−05 |
| PE(38:3)/LPC(17:0) [sn2] | 1.83 | 6.8E−22 | 1.81 | 2.1E−17 | 2.27 | 2.2E−13 | 2.19 | 1.9E−10 | 1.81 | 1.5E−03 |
| Cer(d16:1/20:0)/PC(P-40:2) | 1.92 | 6.9E−22 | 2.12 | 1.5E−21 | 2.12 | 9.7E−10 | 2.12 | 6.7E−08 | 2.15 | 5.6E−05 |
| Cer(d18:1/24:1)/PC(39:4) | 1.88 | 7.1E−22 | 1.86 | 7.5E−17 | 2.22 | 3.2E−11 | 2.38 | 2.0E−10 | 1.87 | 1.4E−03 |
| DAG(14:0/18:2)/Glc/GalCer(d18:1/23:0) | 1.93 | 7.1E−22 | 2.05 | 1.1E−19 | 2.12 | 8.0E−09 | 2.21 | 1.1E−07 | 2.10 | 7.8E−04 |
| PE(38:3)/SM(41:2) | 1.88 | 7.2E−22 | 1.89 | 1.4E−17 | 2.24 | 8.0E−11 | 2.18 | 1.8E−08 | 1.74 | 7.7E−03 |
| Cer(d16:1/20:0)/LPC(O-18:0) | 1.92 | 7.7E−22 | 2.05 | 4.3E−20 | 2.56 | 5.6E−13 | 2.54 | 2.3E−10 | 2.64 | 4.5E−06 |
| DAG(18:0/20:4)/LPC(18:2) [sn1] | 1.88 | 7.7E−22 | 2.00 | 4.1E−20 | 2.58 | 1.8E−14 | 2.74 | 6.6E−13 | 2.58 | 4.1E−06 |
| PC(36:4)/PC(37:1) | 1.93 | 7.9E−22 | 1.87 | 4.3E−16 | 2.53 | 8.6E−12 | 2.51 | 2.2E−09 | 2.24 | 2.5E−04 |
| DAG(18:0/20:4)/SM(41:2) | 1.88 | 7.9E−22 | 1.90 | 3.3E−18 | 2.11 | 4.3E−10 | 2.19 | 6.5E−09 | 2.17 | 1.1E−04 |
| SM(40:1)/PC(37:2) | 1.90 | 8.0E−22 | 1.93 | 3.3E−18 | 2.32 | 1.9E−11 | 2.62 | 3.9E−11 | 1.97 | 8.5E−04 |
| PE(38:1)/PC(O-36:2) | 1.83 | 8.2E−22 | 1.81 | 2.9E−17 | 2.22 | 2.0E−12 | 2.06 | 8.9E−09 | 2.09 | 6.9E−05 |
| PC(38:2)/PC(33:2) | 1.86 | 8.2E−22 | 1.88 | 5.2E−18 | 2.23 | 7.3E−12 | 2.25 | 1.7E−09 | 1.81 | 2.1E−03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| DAG(18:1/18:3)/Gb3(d18:1/22:0) | 1.90 | 8.3E−22 | 2.09 | 1.6E−21 | 1.80 | 1.0E−06 | 1.93 | 1.8E−06 | 1.87 | 2.2E−03 |
| SM(41:0)/LPC(22:0) [sn2] | 1.88 | 8.3E−22 | 1.95 | 2.8E−19 | 2.77 | 3.0E−16 | 3.08 | 3.6E−15 | 2.20 | 8.8E−05 |
| Cer(d18:1/24:1)/Glc/GalCer(d18:1/23:0) | 1.87 | 8.5E−22 | 1.90 | 2.9E−18 | 2.06 | 6.7E−10 | 2.19 | 2.5E−09 | 1.97 | 3.8E−04 |
| Cer(d18:1/20:0)/SM(41:2) | 1.89 | 8.5E−22 | 1.99 | 2.7E−19 | 2.22 | 1.3E−11 | 2.29 | 1.2E−09 | 2.07 | 2.1E−04 |
| PC(34:1)/PC(O-34:0) | 1.86 | 8.6E−22 | 1.83 | 1.4E−16 | 1.98 | 1.2E−08 | 1.97 | 7.7E−07 | 1.72 | 5.7E−03 |
| DAG(18:0/20:4)/PC(O-38:2) | 1.87 | 8.6E−22 | 1.89 | 6.9E−18 | 2.12 | 2.0E−10 | 2.22 | 3.9E−09 | 2.34 | 1.9E−05 |
| PE(38:3)/LPC(O-24:1) | 1.85 | 8.7E−22 | 1.87 | 5.0E−18 | 2.26 | 4.8E−12 | 2.25 | 7.4E−10 | 1.74 | 5.4E−03 |
| PC(38:5)/LPC(P-18:1) | 1.89 | 8.7E−22 | 1.81 | 1.4E−15 | 2.31 | 1.2E−11 | 2.13 | 6.8E−08 | 1.83 | 3.2E−03 |
| Cer(d16:1/22:0)/LPC(15:0) [sn1] | 1.91 | 8.8E−22 | 1.90 | 4.1E−17 | 2.39 | 5.0E−12 | 2.24 | 1.2E−08 | 1.79 | 4.5E−03 |
| PC(36:4)/PC(O-38:0) | 1.94 | 9.0E−22 | 1.91 | 1.1E−16 | 2.60 | 6.5E−12 | 2.57 | 1.3E−09 | 2.42 | 1.3E−04 |
| PE(36:2)/LPC(MHDA) [sn2] | 1.82 | 9.0E−22 | 1.79 | 6.4E−17 | 2.11 | 3.0E−12 | 2.01 | 2.6E−09 | 1.93 | 1.9E−04 |
| PE(38:3)/PC(O-38:2) | 1.88 | 9.2E−22 | 1.88 | 2.3E−17 | 2.28 | 4.9E−11 | 2.22 | 1.2E−08 | 1.87 | 2.7E−03 |
| SM(36:1)/LPC(P-18:1) | 1.86 | 9.3E−22 | 1.88 | 3.3E−18 | 2.25 | 2.2E−13 | 2.26 | 2.4E−11 | 1.73 | 1.7E−03 |
| PC(36:4)/LPC(15:0) [sn2] | 1.87 | 9.4E−22 | 1.79 | 1.3E−15 | 2.51 | 1.1E−13 | 2.38 | 1.9E−10 | 1.94 | 8.2E−04 |
| PE(38:1)/Gb3(d18:1/22:0) | 1.84 | 9.7E−22 | 1.85 | 4.2E−18 | 1.96 | 2.9E−09 | 1.82 | 2.0E−06 | 1.82 | 1.6E−03 |
| DAG(18:0/20:4)/LPC(15:0) [sn1] | 1.89 | 9.8E−22 | 1.92 | 6.4E−18 | 2.45 | 5.2E−13 | 2.57 | 2.2E−11 | 2.49 | 6.7E−06 |
| Cer(d18:1/16:0)/PC(37:2) | 1.90 | 1.0E−21 | 1.90 | 1.4E−17 | 2.26 | 1.8E−11 | 2.29 | 8.6E−10 | 2.01 | 4.1E−04 |
| SM(38:0)/LPC(O-24:0) | 1.88 | 1.0E−21 | 1.95 | 5.4E−18 | 2.57 | 5.5E−14 | 2.83 | 4.2E−13 | 2.37 | 1.1E−05 |
| PI(34:2)/PC(O-40:6) | 1.85 | 1.0E−21 | 1.84 | 2.7E−17 | 2.23 | 6.5E−12 | 2.19 | 1.9E−09 | 1.80 | 2.7E−03 |
| SM(36:2)/PC(O-36:3) | 1.90 | 1.0E−21 | 2.03 | 1.5E−20 | 2.81 | 4.5E−16 | 2.80 | 4.4E−13 | 2.20 | 1.1E−04 |
| PE(32:1)/LPC(O-24:1) | 1.83 | 1.0E−21 | 1.73 | 3.0E−15 | 2.24 | 1.7E−12 | 2.12 | 1.5E−09 | 1.75 | 3.2E−03 |
| PC(38:5)/LPC(20:0) [sn1] | 1.90 | 1.1E−21 | 1.85 | 4.0E−16 | 2.61 | 6.1E−14 | 2.57 | 9.6E−11 | 2.40 | 1.9E−05 |
| PE(32:1)/LPC(20:1) [sn2] | 1.84 | 1.1E−21 | 1.76 | 1.4E−15 | 2.26 | 1.9E−12 | 2.16 | 1.2E−09 | 1.71 | 5.4E−03 |
| LPE(P-16:0)/LPC(19:0) [sn1] | 1.87 | 1.1E−21 | 1.83 | 2.3E−16 | 2.55 | 1.4E−14 | 2.68 | 9.9E−13 | 2.39 | 1.0E−05 |
| CE(20:3)/CE(18:1) | 1.89 | 1.1E−21 | 1.96 | 7.5E−19 | 3.20 | 2.8E−18 | 3.90 | 5.9E−17 | 1.79 | 5.3E−03 |
| PE(38:5)/Gb3(d18:1/22:0) | 1.86 | 1.1E−21 | 1.83 | 6.6E−17 | 2.05 | 1.4E−09 | 1.89 | 9.5E−07 | 1.72 | 5.2E−03 |
| PE(32:1)/LacCer(d18:1/24:1) | 1.83 | 1.2E−21 | 1.72 | 7.5E−15 | 2.21 | 1.1E−11 | 2.07 | 1.1E−08 | 1.67 | 8.0E−03 |
| PE(36:2)/SM(d17:1/14:0) | 1.86 | 1.2E−21 | 1.83 | 1.1E−16 | 2.09 | 1.6E−09 | 1.97 | 5.3E−07 | 1.69 | 9.6E−03 |
| SM(40:1)/PC(O-34:0) | 1.91 | 1.3E−21 | 1.91 | 2.8E−17 | 2.07 | 1.2E−08 | 2.18 | 8.3E−08 | 1.98 | 1.4E−03 |
| PE(32:1)/PC(O-32:0) | 1.83 | 1.3E−21 | 1.74 | 3.4E−15 | 2.20 | 1.7E−11 | 2.08 | 7.3E−09 | 1.76 | 3.2E−03 |
| Cer(d18:1/20:0)/PC(P-32:0) | 1.89 | 1.3E−21 | 2.05 | 1.4E−20 | 2.43 | 1.9E−12 | 2.57 | 4.1E−11 | 2.21 | 1.4E−04 |
| SM(36:1)/PC(O-40:6) | 1.87 | 1.4E−21 | 2.03 | 7.4E−21 | 2.20 | 1.1E−10 | 2.47 | 1.1E−10 | 2.13 | 1.5E−04 |
| SM(40:1)/PC(O-38:0) | 1.94 | 1.4E−21 | 1.98 | 3.2E−18 | 2.29 | 5.1E−10 | 2.60 | 1.0E−09 | 2.34 | 1.8E−04 |
| PC(34:1)/PC(O-40:6) | 1.85 | 1.4E−21 | 1.90 | 1.5E−18 | 1.97 | 8.3E−09 | 2.06 | 6.7E−08 | 1.68 | 8.7E−03 |
| PE(36:1)/PE(P-36:2) | 1.83 | 1.4E−21 | 1.80 | 7.4E−17 | 2.40 | 2.1E−13 | 2.23 | 9.1E−10 | 1.97 | 3.9E−04 |
| PC(36:4)/LacCer(d18:1/24:1) | 1.90 | 1.5E−21 | 1.84 | 7.4E−16 | 2.40 | 1.9E−11 | 2.30 | 8.1E−09 | 1.82 | 4.7E−03 |
| PE(38:3)/PC(39:4) | 1.87 | 1.5E−21 | 1.89 | 1.1E−17 | 2.32 | 2.0E−11 | 2.34 | 1.3E−09 | 1.78 | 5.4E−03 |
| DAG(18:1/18:2)/LPC(17:0) [sn2] | 1.86 | 1.5E−21 | 1.99 | 4.6E−20 | 2.26 | 6.2E−12 | 2.37 | 1.8E−10 | 1.91 | 9.2E−04 |
| PE(36:2)/LPC(20:1) [sn2] | 1.84 | 1.5E−21 | 1.86 | 7.2E−18 | 2.10 | 1.1E−10 | 2.09 | 7.3E−09 | 1.67 | 8.8E−03 |
| PE(38:3)/PC(P-32:0) | 1.88 | 1.5E−21 | 1.93 | 2.3E−18 | 2.31 | 3.7E−11 | 2.31 | 3.2E−09 | 1.79 | 5.7E−03 |
| PE(38:3)/PC(31:0) | 1.89 | 1.5E−21 | 1.95 | 2.4E−18 | 2.24 | 1.9E−10 | 2.26 | 1.5E−08 | 1.85 | 4.1E−03 |
| Cer(d18:2/18:0)/PC(P-16:0) | 1.93 | 1.6E−21 | 2.13 | 2.4E−21 | 2.68 | 3.7E−14 | 2.71 | 4.3E−12 | 1.70 | 8.2E−03 |
| PE(36:1)/LPC(O-24:0) | 1.83 | 1.6E−21 | 1.82 | 3.5E−17 | 2.11 | 9.9E−11 | 2.07 | 1.4E−08 | 1.76 | 3.5E−03 |
| CE(16:2)/PC(O-38:0) | 1.91 | 1.6E−21 | 1.85 | 7.8E−16 | 2.67 | 8.9E−14 | 2.54 | 2.8E−10 | 1.88 | 1.6E−03 |
| PE(38:3)/LPE(16:0) [sn2] | 1.90 | 1.7E−21 | 2.02 | 8.9E−20 | 2.38 | 1.7E−11 | 2.51 | 3.7E−10 | 1.94 | 2.1E−03 |
| SM(36:1)/SM(41:2) | 1.85 | 1.7E−21 | 1.96 | 2.4E−19 | 2.13 | 7.8E−12 | 2.39 | 1.4E−11 | 2.13 | 1.3E−05 |
| SM(38:0)/LPC(P-16:0) | 1.85 | 1.7E−21 | 1.90 | 2.5E−18 | 2.54 | 9.2E−15 | 2.67 | 5.9E−13 | 2.15 | 9.7E−05 |
| PE(32:1)/LPC(P-18:1) | 1.81 | 1.7E−21 | 1.70 | 9.0E−15 | 2.13 | 4.0E−12 | 1.99 | 7.1E−09 | 1.63 | 8.0E−03 |
| Cer(d18:2/18:0)/PC(O-34:2) | 1.92 | 1.8E−21 | 2.12 | 3.4E−21 | 2.78 | 5.2E−14 | 2.72 | 4.6E−11 | 1.81 | 6.4E−03 |
| PC(38:5)/LPC(P-18:0) | 1.87 | 1.8E−21 | 1.81 | 9.9E−16 | 2.54 | 9.3E−14 | 2.38 | 1.2E−09 | 2.27 | 6.6E−05 |
| PE(38:3)/PC(O-32:0) | 1.87 | 1.8E−21 | 1.91 | 3.7E−18 | 2.21 | 1.8E−10 | 2.21 | 1.0E−08 | 1.76 | 6.4E−03 |
| PE(40:5)/LPE(P-20:0) | 1.83 | 1.9E−21 | 1.79 | 1.6E−16 | 2.06 | 1.4E−10 | 1.92 | 1.5E−07 | 1.71 | 4.7E−03 |
| DAG(18:1/18:2)/PC(35:3) | 1.91 | 1.9E−21 | 2.17 | 2.3E−22 | 2.21 | 6.4E−10 | 2.43 | 2.1E−09 | 1.85 | 4.1E−03 |
| PC(38:5)/Gb3(d18:1/22:0) | 1.86 | 1.9E−21 | 1.87 | 2.8E−17 | 1.97 | 1.0E−08 | 1.84 | 5.6E−06 | 1.71 | 6.5E−03 |
| SM(41:0)/PC(O-32:0) | 1.87 | 2.0E−21 | 1.95 | 4.8E−19 | 2.38 | 1.2E−12 | 2.69 | 2.0E−12 | 2.02 | 5.3E−04 |
| PI(36:4)/LPC(O-24:0) | 1.83 | 2.0E−21 | 1.81 | 9.0E−17 | 2.46 | 1.0E−14 | 2.40 | 1.3E−11 | 1.67 | 7.8E−03 |
| PC(38:4)/LPC(P-16:0) | 1.83 | 2.1E−21 | 1.85 | 6.2E−18 | 2.41 | 1.8E−14 | 2.41 | 6.9E−12 | 1.67 | 8.4E−03 |
| DAG(18:1/18:3)/LPC(17:0) [sn1] | 1.91 | 2.2E−21 | 2.04 | 8.5E−20 | 2.08 | 8.4E−09 | 2.35 | 1.2E−08 | 2.28 | 7.6E−05 |
| Cer(d16:1/20:0)/LacCer(d18:1/24:1) | 1.92 | 2.2E−21 | 2.07 | 5.6E−20 | 2.22 | 5.6E−10 | 2.22 | 7.4E−08 | 1.96 | 1.7E−03 |
| DAG(18:1/18:3)/LPC(17:0) [sn2] | 1.90 | 2.2E−21 | 2.05 | 4.6E−20 | 2.10 | 4.2E−09 | 2.34 | 8.4E−09 | 2.30 | 6.4E−05 |
| Cer(d18:1/24:1)/PC(O-34:2) | 1.86 | 2.2E−21 | 1.86 | 3.8E−17 | 2.39 | 4.2E−13 | 2.30 | 4.3E−10 | 1.95 | 6.6E−04 |
| DAG(14:0/18:2)/LPE(20:1) [sn1] | 1.92 | 2.3E−21 | 2.11 | 4.7E−21 | 2.25 | 4.0E−10 | 2.51 | 6.4E−10 | 1.96 | 2.5E−03 |
| DAG(14:0/18:2)/LPE(P-18:0) | 1.88 | 2.3E−21 | 1.96 | 4.5E−19 | 2.19 | 4.4E−10 | 2.18 | 3.8E−08 | 2.08 | 6.3E−04 |
| PC(36:5)/LPC(22:1) [sn1] | 1.91 | 2.3E−21 | 1.78 | 2.4E−14 | 2.35 | 5.0E−11 | 2.29 | 1.4E−08 | 2.18 | 2.7E−04 |
| PI(34:2)/PC(35:2) | 1.85 | 2.4E−21 | 1.81 | 2.0E−16 | 2.67 | 3.8E−15 | 2.50 | 2.5E−11 | 2.13 | 1.3E−04 |
| PI(34:2)/LPC(20:1) [sn1] | 1.81 | 2.4E−21 | 1.77 | 1.5E−16 | 2.32 | 1.4E−14 | 2.27 | 1.2E−11 | 1.66 | 5.8E−03 |
| Cer(d18:2/22:0)/LPC(20:0) [sn2] | 1.88 | 2.5E−21 | 2.00 | 1.6E−19 | 2.63 | 1.2E−13 | 2.88 | 3.1E−12 | 2.06 | 5.1E−04 |
| Cer(d18:1/20:0)/PC(P-40:2) | 1.87 | 2.5E−21 | 1.98 | 1.5E−19 | 2.18 | 4.2E−11 | 2.19 | 2.3E−09 | 2.01 | 8.0E−05 |
| PE(36:2)/PC(O-34:2) | 1.85 | 2.6E−21 | 1.85 | 2.9E−17 | 2.25 | 2.7E−11 | 2.10 | 2.9E−08 | 1.88 | 1.9E−03 |
| PC(40:6)/LPC(22:6) [sn2] | 1.89 | 2.6E−21 | 2.07 | 6.5E−21 | 2.72 | 4.5E−14 | 2.64 | 4.1E−11 | 1.79 | 4.4E−03 |
| DAG(18:2/20:4)/LPC(O-18:1) | 1.87 | 2.7E−21 | 1.99 | 6.6E−20 | 2.16 | 2.0E−10 | 2.32 | 1.3E−09 | 1.74 | 7.2E−03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| PE(38:3)/LPC(17:0) [sn1] | 1.81 | 2.7E−21 | 1.78 | 1.5E−16 | 2.24 | 7.7E−13 | 2.16 | 5.0E−10 | 1.78 | 2.4E−03 |
| PC(38:2)/LPC(22:0) [sn2] | 1.83 | 2.7E−21 | 1.85 | 1.1E−17 | 2.57 | 7.9E−16 | 2.57 | 4.1E−13 | 2.15 | 7.6E−05 |
| PE(32:1)/PC(O-38:2) | 1.82 | 2.8E−21 | 1.71 | 2.1E−14 | 2.21 | 1.2E−11 | 2.07 | 1.3E−08 | 1.81 | 1.9E−03 |
| PE(32:1)/SM(41:2) | 1.82 | 2.8E−21 | 1.71 | 1.9E−14 | 2.18 | 1.9E−11 | 2.04 | 1.8E−08 | 1.73 | 4.2E−03 |
| SM(41:0)/LPC(O-22:0) | 1.84 | 2.8E−21 | 1.89 | 1.8E−18 | 2.54 | 5.1E−15 | 2.83 | 3.5E−14 | 2.15 | 9.5E−05 |
| PE(40:5)/LPC(O-24:0) | 1.83 | 2.9E−21 | 1.82 | 9.0E−17 | 1.96 | 7.8E−09 | 1.90 | 8.6E−07 | 1.73 | 5.7E−03 |
| SM(40:1)/LPC(24:0) [sn1] | 1.87 | 2.9E−21 | 2.03 | 1.1E−20 | 2.44 | 2.1E−13 | 2.86 | 6.2E−14 | 2.23 | 5.5E−05 |
| PC(38:5)/LPC(MHDA) [sn1] | 1.86 | 2.9E−21 | 1.82 | 6.5E−16 | 2.53 | 1.1E−13 | 2.40 | 6.6E−10 | 2.55 | 4.9E−06 |
| Cer(d18:1/20:0)/PC(P-40:4) | 1.89 | 2.9E−21 | 2.01 | 2.5E−19 | 2.68 | 3.9E−14 | 2.83 | 1.8E−12 | 2.62 | 4.1E−06 |
| SM(41:0)/LPC(24:0) [sn2] | 1.86 | 2.9E−21 | 1.98 | 6.5E−20 | 2.70 | 1.3E−15 | 3.15 | 1.9E−15 | 2.17 | 9.5E−05 |
| SM(36:1)/LPC(19:0) [sn1] | 1.84 | 3.0E−21 | 1.86 | 8.8E−18 | 2.60 | 1.6E−15 | 2.73 | 5.9E−14 | 2.41 | 2.9E−06 |
| SM(36:1)/LPC(O-20:0) | 1.83 | 3.1E−21 | 1.87 | 3.8E−18 | 2.53 | 3.7E−15 | 2.71 | 7.6E−14 | 2.47 | 9.5E−07 |
| PE(32:1)/PC(O-38:0) | 1.82 | 3.2E−21 | 1.72 | 7.9E−15 | 2.21 | 9.9E−12 | 2.09 | 6.0E−09 | 1.84 | 1.5E−03 |
| PC(38:5)/LPC(20:0) [sn2] | 1.89 | 3.2E−21 | 1.83 | 9.1E−16 | 2.55 | 1.8E−13 | 2.51 | 2.3E−10 | 2.26 | 6.2E−05 |
| PE(34:1)/LPE(16:0) [sn1] | 1.82 | 3.4E−21 | 1.81 | 5.0E−17 | 2.09 | 5.4E−11 | 2.07 | 5.0E−09 | 1.79 | 2.5E−03 |
| SM(41:0)/PC(39:4) | 1.89 | 3.6E−21 | 1.93 | 6.2E−18 | 2.60 | 7.4E−14 | 3.02 | 2.3E−13 | 2.05 | 4.7E−04 |
| DAG(18:1/18:3)/PC(35:2) | 1.94 | 3.6E−21 | 2.13 | 2.0E−20 | 1.98 | 3.0E−07 | 2.23 | 4.6E−07 | 2.54 | 2.3E−05 |
| Cer(d18:1/24:1)/LPE(P-20:0) | 1.85 | 3.6E−21 | 1.81 | 2.7E−16 | 2.46 | 3.7E−14 | 2.40 | 2.2E−11 | 1.95 | 2.7E−04 |
| Cer(d18:1/24:1)/PC(33:2) | 1.87 | 3.8E−21 | 1.90 | 2.5E−17 | 2.11 | 9.2E−10 | 2.25 | 1.5E−08 | 1.76 | 5.3E−03 |
| LPE(P-16:0)/LPC(P-18:0) | 1.84 | 3.8E−21 | 1.80 | 3.9E−16 | 2.53 | 8.8E−15 | 2.40 | 2.1E−11 | 2.14 | 4.2E−05 |
| PC(38:5)/LPC(22:0) [sn1] | 1.89 | 3.8E−21 | 1.86 | 3.0E−16 | 2.53 | 2.7E−13 | 2.55 | 1.6E−10 | 2.44 | 1.3E−05 |
| PE(38:5)/PC(17:0_22:6) | 1.82 | 3.8E−21 | 1.80 | 4.1E−16 | 2.01 | 2.8E−09 | 2.00 | 3.5E−07 | 1.72 | 4.7E−03 |
| DAG(18:1/18:3)/PC(35:3) | 1.92 | 3.9E−21 | 2.16 | 1.8E−21 | 1.94 | 2.2E−07 | 2.23 | 1.0E−07 | 2.22 | 2.0E−04 |
| Cer(d16:1/16:0)/PC(O-40:6) | 1.88 | 4.0E−21 | 2.01 | 1.5E−19 | 2.16 | 2.7E−09 | 2.33 | 7.9E−09 | 1.86 | 3.5E−03 |
| SM(41:0)/LPC(24:0) [sn1] | 1.85 | 4.1E−21 | 1.97 | 7.1E−20 | 2.61 | 2.0E−15 | 2.98 | 4.5E−15 | 2.24 | 4.3E−05 |
| PE(36:1)/LPC(P-16:0) | 1.78 | 4.1E−21 | 1.76 | 1.1E−16 | 2.02 | 1.4E−11 | 1.95 | 6.0E−09 | 1.62 | 6.6E−03 |
| PC(38:2)/PC(O-34:0) | 1.86 | 4.1E−21 | 1.84 | 1.7E−16 | 2.25 | 5.6E−11 | 2.19 | 2.7E−08 | 2.09 | 3.8E−04 |
| PE(36:2)/PC(O-40:3) | 1.84 | 4.3E−21 | 1.89 | 3.1E−18 | 1.96 | 6.5E−09 | 2.00 | 1.3E−07 | 1.67 | 8.6E−03 |
| PE(36:2)/LacCer(d18:1/16:0) | 1.85 | 4.4E−21 | 1.86 | 2.5E−17 | 2.01 | 6.0E−09 | 1.97 | 3.2E−07 | 1.73 | 7.5E−03 |
| SM(36:1)/LacCer(d18:1/24:1) | 1.84 | 4.4E−21 | 1.89 | 3.4E−18 | 2.26 | 3.4E−12 | 2.39 | 5.2E−11 | 1.83 | 1.6E−03 |
| PC(34:1)/LPC(MHDA) [sn2] | 1.80 | 4.4E−21 | 1.74 | 1.9E−15 | 2.21 | 2.0E−13 | 2.09 | 3.5E−10 | 1.92 | 1.2E−04 |
| PC(38:2)/PC(P-40:2) | 1.87 | 4.5E−21 | 1.90 | 1.5E−18 | 2.24 | 4.7E−11 | 2.21 | 1.5E−08 | 1.93 | 3.3E−04 |
| PI(34:2)/LacCer(d18:1/16:0) | 1.84 | 4.6E−21 | 1.78 | 1.0E−15 | 2.36 | 2.7E−12 | 2.24 | 3.0E−09 | 1.72 | 7.5E−03 |
| PE(38:1)/PC(35:3) | 1.82 | 4.7E−21 | 1.83 | 2.6E−17 | 2.14 | 3.0E−11 | 2.01 | 3.8E−08 | 2.12 | 5.1E−05 |
| SM(36:1)/PC(P-32:0) | 1.84 | 4.8E−21 | 2.02 | 3.7E−21 | 2.42 | 2.8E−13 | 2.78 | 1.3E−13 | 2.41 | 1.1E−05 |
| PE(38:1)/SM(37:1) | 1.82 | 5.0E−21 | 1.79 | 3.4E−16 | 2.04 | 8.1E−10 | 1.89 | 9.2E−07 | 1.86 | 1.2E−03 |
| SM(40:1)/LPC(24:0) [sn2] | 1.87 | 5.0E−21 | 2.04 | 1.5E−20 | 2.46 | 1.6E−13 | 2.95 | 2.2E−14 | 2.01 | 1.8E−04 |
| PE(38:4)/LPC(19:0) [sn2] | 1.78 | 5.2E−21 | 1.78 | 3.9E−17 | 2.14 | 3.9E−13 | 2.12 | 1.0E−10 | 1.76 | 1.2E−03 |
| PE(32:1)/LPC(20:2) [sn1] | 1.82 | 5.4E−21 | 1.74 | 2.9E−15 | 2.25 | 1.4E−12 | 2.12 | 1.7E−09 | 1.81 | 1.6E−03 |
| PE(38:3)/LPC(20:2) [sn1] | 1.84 | 5.5E−21 | 1.92 | 8.4E−19 | 2.32 | 3.2E−12 | 2.31 | 5.4E−10 | 1.85 | 2.3E−03 |
| DAG(18:0/20:4)/PC(O-32:0) | 1.85 | 5.7E−21 | 1.92 | 1.3E−18 | 2.06 | 1.6E−09 | 2.23 | 4.2E−09 | 2.22 | 9.3E−05 |
| PI(36:4)/LPC(15:0) [sn1] | 1.82 | 5.7E−21 | 1.74 | 4.0E−15 | 2.57 | 6.5E−16 | 2.36 | 1.3E−11 | 1.67 | 6.5E−03 |
| PE(38:3)/PC(34:3) | 1.87 | 5.8E−21 | 2.07 | 3.7E−21 | 2.44 | 6.4E−12 | 2.59 | 1.8E−10 | 1.75 | 7.8E−03 |
| Cer(d16:1/20:0)/Glc/GalCer(d18:2/22:0) | 1.91 | 6.0E−21 | 2.05 | 1.9E−19 | 2.02 | 3.8E−08 | 2.04 | 1.2E−06 | 2.27 | 1.4E−04 |
| PE(38:1)/PC(35:2) | 1.85 | 6.0E−21 | 1.84 | 7.1E−17 | 2.25 | 2.0E−11 | 2.08 | 6.2E−08 | 2.53 | 1.6E−06 |
| Cer(d18:1/24:1)/LPC(18:2) [sn1] | 1.85 | 6.1E−21 | 1.91 | 2.8E−18 | 2.63 | 2.3E−15 | 2.71 | 3.2E−13 | 2.21 | 4.3E−05 |
| DAG(18:0/20:4)/LPC(O-24:0) | 1.83 | 6.2E−21 | 1.90 | 1.6E−18 | 2.18 | 3.0E−11 | 2.38 | 1.1E−10 | 2.33 | 2.1E−05 |
| PE(38:1)/PC(O-36:3) | 1.81 | 6.3E−21 | 1.79 | 1.7E−16 | 2.15 | 4.1E−11 | 1.95 | 1.5E−07 | 2.05 | 1.6E−04 |
| SM(40:1)/PC(35:2) | 1.89 | 6.4E−21 | 1.98 | 2.1E−18 | 2.39 | 1.4E−10 | 2.55 | 2.9E−09 | 2.23 | 1.5E−04 |
| SM(38:0)/LPE(P-20:0) | 1.84 | 6.7E−21 | 1.88 | 1.2E−17 | 2.67 | 6.0E−15 | 2.77 | 1.2E−12 | 2.30 | 3.6E−05 |
| Cer(d18:1/16:0)/LPC(O-24:1) | 1.85 | 6.7E−21 | 1.85 | 5.8E−17 | 2.29 | 4.9E−12 | 2.31 | 5.8E−10 | 1.79 | 3.1E−03 |
| PI(34:2)/LPC(19:0) [sn2] | 1.77 | 6.9E−21 | 1.72 | 6.1E−16 | 2.25 | 1.2E−15 | 2.21 | 1.8E−12 | 1.71 | 1.2E−03 |
| PE(32:1)/PE(O-34:2) | 1.83 | 7.0E−21 | 1.74 | 7.1E−15 | 2.41 | 7.6E−13 | 2.22 | 2.6E−09 | 1.68 | 9.1E−03 |
| PC(38:2)/LPC(24:0) [sn1] | 1.81 | 7.1E−21 | 1.89 | 8.7E−19 | 2.49 | 4.9E−15 | 2.59 | 5.0E−13 | 2.26 | 2.3E−05 |
| PI(36:4)/LPE(P-20:0) | 1.80 | 7.1E−21 | 1.76 | 5.5E−16 | 2.48 | 9.8E−16 | 2.30 | 1.1E−11 | 1.64 | 7.1E−03 |
| Cer(d18:2/18:0)/PC(O-38:0) | 1.93 | 7.4E−21 | 2.18 | 2.0E−21 | 2.60 | 7.2E−12 | 2.79 | 1.6E−10 | 1.90 | 4.0E−03 |
| DAG(18:1/18:2)/LacCer(d18:1/16:0) | 1.83 | 7.5E−21 | 2.02 | 6.5E−21 | 1.93 | 1.5E−08 | 2.09 | 3.5E−08 | 1.69 | 8.3E−03 |
| PE(32:1)/LPC(17:0) [sn2] | 1.78 | 7.6E−21 | 1.67 | 3.8E−14 | 2.18 | 5.1E−13 | 2.05 | 1.2E−09 | 1.77 | 1.6E−03 |
| AcylCarnitine(16:0)/LPE(P-20:0) | 1.87 | 7.7E−21 | 1.81 | 1.8E−15 | 2.55 | 9.8E−14 | 2.37 | 1.3E−10 | 1.70 | 7.9E−03 |
| LPE(P-16:0)/LPC(O-20:1) | 1.86 | 7.8E−21 | 1.84 | 3.6E−16 | 2.39 | 2.2E−12 | 2.44 | 1.9E−10 | 1.98 | 8.2E−04 |
| PC(38:2)/LPC(O-24:1) | 1.82 | 7.8E−21 | 1.80 | 1.6E−16 | 2.36 | 2.0E−13 | 2.33 | 9.2E−11 | 1.86 | 1.6E−03 |
| SM(41:0)/PC(P-40:4) | 1.86 | 8.0E−21 | 1.92 | 3.7E−18 | 2.70 | 9.2E−15 | 3.08 | 4.0E−14 | 2.32 | 6.3E−05 |
| SM(38:0)/LPC(15:0) [sn2] | 1.85 | 8.1E−21 | 1.85 | 7.3E−17 | 2.64 | 1.4E−14 | 2.70 | 1.8E−12 | 2.10 | 2.2E−04 |
| Cer(d18:1/20:0)/PC(O-38:2) | 1.85 | 8.1E−21 | 1.92 | 6.6E−18 | 2.27 | 1.3E−11 | 2.34 | 1.5E−09 | 2.31 | 3.3E−05 |
| PC(31:1)/PC(31:0) | 1.85 | 8.2E−21 | 1.75 | 2.4E−14 | 2.23 | 2.1E−10 | 2.20 | 3.2E−08 | 1.72 | 8.5E−03 |
| DAG(18:1/18:2)/LPC(O-24:1) | 1.83 | 8.3E−21 | 1.99 | 1.7E−20 | 2.08 | 3.7E−10 | 2.27 | 1.2E−09 | 1.75 | 4.8E−03 |
| Cer(d18:1/20:0)/PC(O-38:0) | 1.88 | 8.3E−21 | 2.03 | 1.2E−20 | 2.38 | 4.8E−12 | 2.57 | 1.1E−10 | 2.46 | 1.1E−05 |
| PC(38:2)/PC(P-32:0) | 1.87 | 8.4E−21 | 1.88 | 4.9E−17 | 2.43 | 4.5E−12 | 2.40 | 1.1E−09 | 2.00 | 1.0E−03 |
| DAG(18:2/20:4)/PC(35:3) | 1.89 | 9.3E−21 | 2.14 | 2.2E−21 | 2.17 | 1.9E−09 | 2.41 | 2.6E−09 | 1.80 | 6.4E−03 |
| PE(34:1)/LPE(16:0) [sn2] | 1.80 | 9.6E−21 | 1.80 | 8.4E−17 | 2.06 | 9.7E−11 | 2.02 | 1.1E−08 | 1.79 | 2.3E−03 |
| SM(38:0)/LPC(20:2) [sn1] | 1.87 | 9.8E−21 | 2.02 | 7.9E−20 | 2.74 | 6.2E−14 | 2.99 | 1.2E−12 | 2.46 | 2.4E−05 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| PC(38:2)/LPC(24:0) [sn2] | 1.81 | 1.0E-20 | 1.88 | 1.8E-18 | 2.46 | 6.7E-15 | 2.59 | 3.7E-13 | 2.12 | 7.6E-05 |
| PE(36:2)/PC(O-34:0) | 1.82 | 1.0E-20 | 1.82 | 1.5E-16 | 1.98 | 8.8E-09 | 1.92 | 7.7E-07 | 1.82 | 2.9E-03 |
| PE(38:1)/LPC(20:1) [sn2] | 1.78 | 1.1E-20 | 1.77 | 1.0E-16 | 2.05 | 4.7E-11 | 1.98 | 2.0E-08 | 1.89 | 5.4E-04 |
| SM(40:1)/PC(O-40:6) | 1.83 | 1.2E-20 | 1.92 | 1.4E-18 | 1.97 | 1.1E-08 | 2.11 | 2.2E-08 | 1.75 | 4.5E-03 |
| PE(32:1)/PC(37:1) | 1.81 | 1.2E-20 | 1.70 | 5.5E-14 | 2.20 | 1.5E-11 | 2.07 | 1.3E-08 | 1.77 | 2.8E-03 |
| SM(38:0)/LPC(15:0) [sn1] | 1.84 | 1.2E-20 | 1.84 | 9.1E-17 | 2.69 | 5.3E-15 | 2.77 | 4.8E-13 | 2.39 | 1.5E-05 |
| PE(40:5)/LPC(18:2) [sn2] | 1.81 | 1.2E-20 | 1.83 | 3.3E-17 | 2.08 | 2.1E-10 | 1.99 | 9.1E-08 | 1.73 | 4.9E-03 |
| PC(38:1)/LPC(20:1) [sn2] | 1.83 | 1.2E-20 | 1.88 | 5.2E-18 | 2.42 | 1.7E-13 | 2.50 | 1.0E-11 | 1.95 | 7.7E-04 |
| LPE(P-16:0)/LPC(20:1) [sn1] | 1.87 | 1.2E-20 | 1.94 | 6.2E-18 | 2.43 | 1.4E-12 | 2.69 | 9.3E-12 | 1.77 | 5.8E-03 |
| PI(34:2)/PC(P-40:2) | 1.85 | 1.2E-20 | 1.80 | 1.7E-15 | 2.40 | 5.7E-12 | 2.26 | 8.9E-09 | 1.74 | 1.5E-03 |
| SM(41:0)/LPC(17:0) [sn2] | 1.82 | 1.2E-20 | 1.82 | 8.2E-17 | 2.54 | 2.2E-15 | 2.66 | 2.5E-13 | 2.03 | 1.7E-04 |
| SM(36:2)/LPC(19:0) [sn1] | 1.82 | 1.3E-20 | 1.87 | 1.0E-17 | 2.82 | 1.4E-16 | 2.92 | 2.9E-14 | 2.37 | 5.7E-06 |
| PC(38:2)/LPC(20:2) [sn1] | 1.84 | 1.3E-20 | 1.96 | 2.7E-19 | 2.71 | 5.7E-15 | 2.69 | 5.2E-12 | 2.28 | 9.2E-05 |
| PC(38:4)/PC(O-34:0) | 1.87 | 1.3E-20 | 1.89 | 5.3E-17 | 2.20 | 9.6E-10 | 2.19 | 7.5E-08 | 1.77 | 7.7E-03 |
| PC(38:5)/LPC(MHDA) [sn2] | 1.84 | 1.4E-20 | 1.77 | 9.6E-15 | 2.44 | 5.9E-13 | 2.25 | 6.0E-09 | 2.44 | 1.3E-05 |
| PE(38:3)/PC(O-38:0) | 1.84 | 1.4E-20 | 1.87 | 2.3E-17 | 2.22 | 1.1E-10 | 2.22 | 8.4E-09 | 1.88 | 2.4E-03 |
| PE(38:4)/PC(33:2) | 1.83 | 1.5E-20 | 1.86 | 7.0E-17 | 2.08 | 8.6E-10 | 2.05 | 1.5E-07 | 1.73 | 5.3E-03 |
| PE(32:1)/LPC(20:2) [sn2] | 1.81 | 1.5E-20 | 1.74 | 6.0E-15 | 2.25 | 3.9E-12 | 2.13 | 3.3E-09 | 1.78 | 2.5E-03 |
| PE(32:1)/PC(39:4) | 1.80 | 1.6E-20 | 1.70 | 4.2E-14 | 2.22 | 1.2E-11 | 2.12 | 4.6E-09 | 1.75 | 3.8E-03 |
| Cer(d18:1/20:0)/PC(33:2) | 1.88 | 1.6E-20 | 2.02 | 7.4E-19 | 2.31 | 7.5E-11 | 2.49 | 2.0E-09 | 2.06 | 6.8E-04 |
| PE(38:3)/PC(33:3) | 1.86 | 1.7E-20 | 1.87 | 1.6E-16 | 2.36 | 1.7E-11 | 2.38 | 3.2E-09 | 1.73 | 9.5E-03 |
| DAG(18:0/20:4)/LPC(O-16:0) | 1.83 | 1.7E-20 | 1.86 | 3.3E-17 | 2.32 | 2.3E-12 | 2.43 | 8.3E-11 | 2.22 | 6.7E-05 |
| DAG(18:1/18:2)/PC(33:2) | 1.86 | 1.7E-20 | 2.01 | 1.3E-19 | 2.00 | 2.2E-08 | 2.13 | 1.2E-07 | 1.73 | 9.1E-03 |
| PC(38:2)/LPC(MHDA) [sn2] | 1.79 | 1.7E-20 | 1.75 | 1.8E-15 | 2.35 | 3.3E-14 | 2.19 | 1.6E-10 | 2.04 | 1.7E-05 |
| SM(36:1)/LPC(MHDA) [sn1] | 1.82 | 1.7E-20 | 1.89 | 2.9E-18 | 2.60 | 3.2E-16 | 2.69 | 2.6E-14 | 2.55 | 9.8E-08 |
| PC(36:4)/LPC(O-18:0) | 1.83 | 1.7E-20 | 1.77 | 6.0E-15 | 2.47 | 4.3E-13 | 2.40 | 2.8E-10 | 2.25 | 1.1E-04 |
| PG(34:1)/Gb3(d18:1/22:0) | 1.82 | 1.8E-20 | 1.84 | 4.4E-17 | 1.95 | 9.5E-09 | 1.83 | 2.8E-06 | 1.68 | 8.1E-03 |
| SM(41:0)/LPC(17:0) [sn1] | 1.82 | 1.8E-20 | 1.80 | 3.8E-16 | 2.64 | 1.9E-15 | 2.76 | 1.6E-13 | 2.07 | 2.6E-04 |
| SM(36:1)/PC(O-34:0) | 1.83 | 1.8E-20 | 1.92 | 1.3E-18 | 2.25 | 4.1E-11 | 2.43 | 1.3E-10 | 2.58 | 4.6E-06 |
| SM(36:2)/PC(O-40:6) | 1.84 | 1.9E-20 | 2.00 | 4.8E-20 | 2.28 | 2.2E-11 | 2.48 | 1.0E-10 | 2.03 | 2.8E-04 |
| DAG(18:0/20:4)/LPE(P-18:0) | 1.83 | 2.0E-20 | 1.88 | 1.6E-17 | 2.29 | 6.3E-12 | 2.35 | 4.9E-10 | 2.42 | 1.6E-05 |
| PE(38:3)/LPC(15:0) [sn2] | 1.80 | 2.0E-20 | 1.78 | 4.5E-16 | 2.22 | 5.8E-12 | 2.12 | 2.9E-09 | 1.66 | 8.7E-03 |
| PE(38:4)/LacCer(d18:1/16:0) | 1.82 | 2.1E-20 | 1.83 | 9.3E-17 | 2.03 | 2.5E-09 | 1.97 | 2.9E-07 | 1.73 | 6.7E-03 |
| PE(40:6)/Gb3(d18:1/22:0) | 1.81 | 2.1E-20 | 1.82 | 8.9E-17 | 2.13 | 1.1E-10 | 1.99 | 9.6E-08 | 1.90 | 9.8E-04 |
| DAG(14:0/18:2)/LPC(18:1) [sn1] | 1.85 | 2.1E-20 | 2.00 | 1.8E-19 | 2.28 | 6.9E-11 | 2.38 | 1.7E-09 | 2.28 | 1.6E-04 |
| PE(36:2)/LPE(16:0) [sn1] | 1.85 | 2.2E-20 | 1.94 | 2.4E-18 | 2.11 | 2.3E-09 | 2.23 | 1.7E-08 | 1.95 | 1.7E-03 |
| PE(38:3)/PC(37:1) | 1.84 | 2.2E-20 | 1.86 | 1.0E-16 | 2.23 | 2.0E-10 | 2.21 | 2.0E-08 | 1.80 | 5.4E-03 |
| Cer(d18:1/20:0)/PC(O-32:0) | 1.85 | 2.2E-20 | 1.99 | 3.0E-19 | 2.23 | 1.3E-10 | 2.38 | 1.3E-09 | 2.15 | 2.2E-04 |
| PE(38:3)/LPC(20:2) [sn2] | 1.83 | 2.3E-20 | 1.92 | 1.7E-18 | 2.29 | 1.7E-11 | 2.30 | 1.7E-09 | 1.80 | 4.3E-03 |
| Cer(d16:1/20:0)/PC(P-32:0) | 1.90 | 2.3E-20 | 2.13 | 1.6E-20 | 2.28 | 1.1E-09 | 2.34 | 3.4E-08 | 2.34 | 2.1E-04 |
| DAG(18:1/18:3)/PC(33:2) | 1.88 | 2.4E-20 | 2.03 | 2.4E-19 | 1.82 | 2.1E-06 | 2.02 | 2.0E-06 | 2.09 | 5.4E-04 |
| PC(38:2)/PC(O-38:2) | 1.83 | 2.5E-20 | 1.77 | 1.3E-14 | 2.26 | 1.7E-11 | 2.15 | 2.7E-08 | 2.13 | 1.6E-04 |
| PC(38:1)/LacCer(d18:1/16:0) | 1.83 | 2.5E-20 | 1.87 | 3.0E-17 | 2.10 | 2.2E-10 | 2.14 | 1.7E-08 | 2.09 | 1.2E-04 |
| Cer(d18:2/18:0)/LPC(O-24:0) | 1.91 | 2.5E-20 | 2.12 | 8.7E-21 | 2.64 | 9.6E-13 | 2.78 | 1.8E-11 | 1.81 | 5.3E-03 |
| PE(38:5)/LPC(19:0) [sn2] | 1.79 | 2.6E-20 | 1.73 | 4.0E-15 | 2.28 | 3.9E-13 | 2.20 | 2.8E-10 | 1.91 | 4.0E-04 |
| PC(38:1)/PC(O-36:2) | 1.80 | 2.6E-20 | 1.81 | 1.1E-16 | 2.35 | 7.5E-14 | 2.24 | 1.6E-10 | 2.05 | 3.8E-05 |
| CE(16:2)/CE(18:1) | 1.84 | 2.8E-20 | 1.80 | 3.2E-15 | 2.68 | 9.5E-15 | 2.46 | 1.3E-10 | 1.80 | 3.9E-03 |
| Cer(d18:1/24:1)/LPC(18:2) [sn2] | 1.84 | 2.8E-20 | 1.91 | 5.9E-18 | 2.67 | 1.8E-14 | 2.75 | 1.7E-12 | 2.10 | 3.4E-04 |
| SM(36:1)/PC(35:2) | 1.87 | 2.8E-20 | 2.04 | 1.3E-19 | 2.73 | 1.4E-13 | 3.13 | 1.4E-12 | 2.92 | 7.8E-07 |
| PE(38:4)/LPC(MHDA) [sn2] | 1.77 | 2.8E-20 | 1.74 | 1.2E-15 | 2.14 | 1.6E-12 | 2.02 | 3.4E-09 | 1.96 | 1.7E-04 |
| DAG(18:2/20:4)/LPC(P-16:0) | 1.82 | 3.0E-20 | 1.97 | 7.5E-20 | 2.10 | 1.2E-10 | 2.33 | 3.8E-10 | 1.74 | 5.4E-03 |
| DAG(14:0/18:2)/LPC(18:1) [sn2] | 1.86 | 3.2E-20 | 2.02 | 8.9E-20 | 2.27 | 1.4E-10 | 2.39 | 2.5E-09 | 2.31 | 1.5E-04 |
| PC(38:5)/LPC(22:6) [sn1] | 1.86 | 3.4E-20 | 1.91 | 3.4E-17 | 2.22 | 6.8E-10 | 2.11 | 2.2E-07 | 1.96 | 2.0E-03 |
| SM(36:1)/LPC(P-18:0) | 1.78 | 3.6E-20 | 1.81 | 2.5E-17 | 2.38 | 4.0E-15 | 2.37 | 1.0E-12 | 2.08 | 9.4E-06 |
| PC(38:1)/Gb3(d18:1/22:0) | 1.79 | 3.6E-20 | 1.87 | 4.1E-18 | 1.84 | 3.4E-08 | 1.76 | 3.8E-06 | 1.60 | 9.3E-03 |
| Cer(d18:1/16:0)/LPC(O-22:0) | 1.82 | 3.6E-20 | 1.83 | 2.2E-16 | 2.30 | 1.6E-12 | 2.35 | 1.1E-10 | 2.00 | 1.0E-04 |
| PC(38:5)/LPC(22:0) [sn2] | 1.85 | 3.7E-20 | 1.83 | 1.3E-15 | 2.46 | 6.5E-13 | 2.43 | 4.4E-10 | 2.28 | 4.4E-05 |
| PC(38:5)/SM(37:1) | 1.81 | 3.7E-20 | 1.75 | 1.2E-14 | 2.00 | 5.2E-09 | 1.86 | 4.6E-06 | 1.69 | 8.5E-03 |
| CE(20:3)/PC(O-38:2) | 1.82 | 3.8E-20 | 1.77 | 4.1E-15 | 2.68 | 1.6E-14 | 2.86 | 4.9E-13 | 1.72 | 8.5E-03 |
| Cer(d16:1/20:0)/PC(O-38:0) | 1.90 | 3.9E-20 | 2.14 | 2.6E-20 | 2.28 | 9.6E-10 | 2.37 | 3.5E-08 | 2.64 | 2.5E-05 |
| SM(36:2)/PC(O-38:2) | 1.83 | 3.9E-20 | 1.91 | 9.0E-18 | 2.57 | 1.4E-14 | 2.78 | 1.2E-12 | 2.65 | 1.0E-06 |
| PE(38:3)/LPC(15:0) [sn1] | 1.79 | 4.1E-20 | 1.77 | 7.2E-16 | 2.23 | 3.7E-12 | 2.15 | 1.6E-09 | 1.80 | 2.4E-03 |
| Cer(d18:2/18:0)/LPE(P-20:0) | 1.89 | 4.3E-20 | 2.07 | 1.4E-19 | 2.72 | 6.6E-14 | 2.68 | 1.8E-11 | 1.79 | 4.2E-03 |
| PE(34:1)/PC(O-34:0) | 1.77 | 4.4E-20 | 1.71 | 7.4E-15 | 1.99 | 1.1E-09 | 1.87 | 3.6E-07 | 1.70 | 5.0E-03 |
| SM(36:1)/LPC(20:1) [sn1] | 1.85 | 4.7E-20 | 2.01 | 3.0E-19 | 2.74 | 3.5E-14 | 3.18 | 1.0E-13 | 2.09 | 5.1E-04 |
| PE(32:1)/LPC(15:0) [sn2] | 1.76 | 4.7E-20 | 1.65 | 2.0E-13 | 2.14 | 3.3E-12 | 1.99 | 5.5E-09 | 1.67 | 5.0E-03 |
| PE(32:1)/PC(36:7) | 1.82 | 4.9E-20 | 1.78 | 2.2E-15 | 2.34 | 8.6E-13 | 2.34 | 1.0E-10 | 2.30 | 1.3E-05 |
| SM(40:1)/LPC(O-24:1) | 1.82 | 5.0E-20 | 1.84 | 1.7E-16 | 2.26 | 3.1E-11 | 2.41 | 2.4E-10 | 1.74 | 6.7E-03 |
| Cer(d18:1/24:1)/LPC(O-24:0) | 1.81 | 5.0E-20 | 1.81 | 5.4E-16 | 2.26 | 2.3E-11 | 2.39 | 2.5E-10 | 2.02 | 4.5E-04 |
| PE(34:1)/PC(O-34:2) | 1.78 | 5.2E-20 | 1.72 | 5.0E-15 | 2.16 | 1.7E-11 | 1.99 | 4.0E-08 | 1.74 | 4.1E-03 |
| PC(38:2)/LPC(P-18:0) | 1.77 | 5.3E-20 | 1.73 | 2.5E-15 | 2.34 | 2.0E-14 | 2.20 | 1.2E-10 | 1.95 | 2.7E-04 |
| PC(38:2)/PC(O-34:2) | 1.83 | 5.5E-20 | 1.82 | 6.0E-16 | 2.75 | 2.4E-14 | 2.46 | 5.5E-10 | 2.07 | 3.8E-04 |
| SM(36:1)/LPC(O-24:1) | 1.81 | 5.6E-20 | 1.89 | 4.5E-18 | 2.49 | 8.4E-14 | 2.73 | 5.4E-13 | 2.12 | 1.1E-04 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| Cer(d20:1/24:1)/LPC(O-24:1) | 1.76 | 5.7E−20 | 1.77 | 3.1E−16 | 2.32 | 1.1E−13 | 2.42 | 4.1E−12 | 1.72 | 4.1E−03 |
| PC(38:2)/PC(37:1) | 1.83 | 5.9E−20 | 1.77 | 8.2E−15 | 2.32 | 1.7E−11 | 2.18 | 1.1E−08 | 2.07 | 2.2E−04 |
| PC(34:1)/PC(P-40:2) | 1.81 | 5.9E−20 | 1.81 | 5.0E−16 | 1.94 | 2.9E−08 | 1.92 | 1.2E−06 | 1.62 | 5.7E−03 |
| PC(36:4)/LPC(O-24:0) | 1.83 | 6.2E−20 | 1.79 | 2.4E−15 | 2.37 | 6.5E−12 | 2.38 | 5.4E−10 | 2.14 | 3.1E−04 |
| PC(36:4)/PC(P-40:4) | 1.85 | 6.7E−20 | 1.80 | 5.1E−15 | 2.53 | 4.5E−12 | 2.53 | 6.4E−10 | 2.31 | 1.9E−04 |
| DAG(18:1/18:2)/LPC(O-18:1) | 1.80 | 6.8E−20 | 1.92 | 6.9E−19 | 2.08 | 6.1E−10 | 2.19 | 6.6E−09 | 1.70 | 8.0E−03 |
| PE(38:1)/Gb3(d18:1/16:0) | 1.78 | 7.0E−20 | 1.78 | 3.9E−16 | 2.01 | 9.4E−10 | 1.90 | 5.2E−07 | 1.80 | 2.4E−03 |
| PE(38:5)/SM(37:1) | 1.80 | 7.0E−20 | 1.73 | 2.8E−14 | 2.10 | 7.5E−10 | 1.95 | 5.9E−07 | 1.71 | 6.6E−03 |
| PE(36:2)/LPE(16:0) [sn2] | 1.82 | 7.5E−20 | 1.91 | 5.3E−18 | 2.06 | 4.1E−09 | 2.15 | 4.1E−08 | 1.93 | 1.7E−03 |
| PC(36:4)/LPE(16:0) [sn1] | 1.88 | 7.9E−20 | 1.93 | 7.9E−17 | 2.55 | 3.0E−11 | 2.75 | 3.1E−10 | 2.33 | 2.7E−04 |
| Cer(d16:1/20:0)/SM(34:1) | 1.89 | 8.2E−20 | 2.14 | 2.0E−20 | 2.25 | 2.2E−09 | 2.21 | 2.6E−07 | 2.04 | 1.6E−03 |
| Cer(d16:1/20:0)/LPC(15:0) [sn2] | 1.87 | 8.4E−20 | 2.01 | 3.5E−18 | 2.42 | 3.2E−11 | 2.33 | 1.4E−08 | 2.15 | 2.8E−04 |
| PE(32:1)/LPC(17:0) [sn1] | 1.75 | 8.4E−20 | 1.64 | 3.0E−13 | 2.14 | 2.8E−12 | 2.01 | 3.8E−09 | 1.73 | 2.6E−03 |
| PE(32:1)/LPC(15:0) [sn1] | 1.75 | 8.8E−20 | 1.64 | 3.0E−13 | 2.15 | 2.7E−12 | 2.01 | 3.8E−09 | 1.75 | 2.0E−03 |
| SM(36:2)/LPC(O-20:0) | 1.79 | 8.8E−20 | 1.85 | 2.1E−17 | 2.65 | 5.2E−16 | 2.78 | 5.0E−14 | 2.38 | 2.5E−06 |
| SM(36:2)/LPC(P-18:0) | 1.77 | 8.9E−20 | 1.82 | 1.8E−17 | 2.56 | 2.1E−16 | 2.50 | 2.9E−13 | 2.06 | 1.7E−05 |
| PE(38:1)/PC(33:2) | 1.80 | 9.0E−20 | 1.76 | 3.4E−15 | 2.05 | 1.2E−09 | 1.90 | 1.0E−06 | 2.06 | 1.9E−04 |
| PE(32:1)/LPC(O-24:0) | 1.76 | 9.2E−20 | 1.67 | 1.0E−13 | 2.13 | 1.9E−11 | 2.03 | 8.1E−09 | 1.77 | 2.5E−03 |
| DAG(18:1/18:3)/Glc/GalCer(d18:2/20:0) | 1.83 | 9.3E−20 | 1.93 | 5.3E−18 | 1.68 | 3.2E−05 | 1.90 | 7.4E−06 | 1.88 | 2.5E−03 |
| PC(36:5)/SM(44:3) | 1.82 | 9.3E−20 | 1.76 | 1.7E−14 | 1.91 | 1.0E−07 | 1.86 | 6.8E−06 | 1.74 | 7.3E−03 |
| PE(40:6)/SM(37:1) | 1.80 | 9.4E−20 | 1.76 | 4.5E−15 | 2.33 | 7.3E−12 | 2.18 | 1.2E−08 | 1.99 | 6.9E−04 |
| SM(36:2)/SM(34:1) | 1.84 | 9.6E−20 | 2.11 | 1.3E−21 | 3.10 | 3.6E−17 | 3.31 | 4.4E−15 | 1.96 | 1.3E−03 |
| DAG(18:0/20:4)/PC(O-38:0) | 1.84 | 9.9E−20 | 1.93 | 1.6E−17 | 2.15 | 8.0E−10 | 2.35 | 3.5E−09 | 2.41 | 2.7E−05 |
| SM(41:0)/LPC(O-18:0) | 1.78 | 1.0E−19 | 1.78 | 6.1E−16 | 2.48 | 1.7E−14 | 2.60 | 9.3E−13 | 2.17 | 8.1E−05 |
| SM(38:0)/LPC(18:2) [sn1] | 1.81 | 1.0E−19 | 1.91 | 4.2E−18 | 2.71 | 6.2E−15 | 2.90 | 3.3E−13 | 2.45 | 1.3E−05 |
| Cer(d18:2/24:1)/LPC(19:0) [sn2] | 1.79 | 1.0E−19 | 1.84 | 3.9E−17 | 2.47 | 2.8E−15 | 2.49 | 6.6E−13 | 1.81 | 8.1E−04 |
| Cer(d16:1/20:0)/PC(O-34:2) | 1.85 | 1.0E−19 | 2.00 | 8.0E−19 | 2.42 | 1.5E−11 | 2.28 | 1.9E−08 | 2.28 | 1.1E−04 |
| SM(36:2)/PC(P-32:0) | 1.81 | 1.1E−19 | 2.01 | 8.4E−21 | 2.64 | 3.3E−15 | 2.90 | 2.4E−14 | 2.31 | 3.2E−05 |
| PC(38:5)/LPC(O-24:1) | 1.80 | 1.1E−19 | 1.77 | 7.6E−15 | 2.20 | 4.8E−11 | 2.15 | 2.9E−08 | 1.97 | 7.1E−04 |
| Cer(d18:1/16:0)/PC(35:2) | 1.87 | 1.1E−19 | 1.93 | 8.0E−17 | 2.50 | 4.8E−11 | 2.43 | 2.2E−08 | 2.43 | 6.3E−05 |
| Cer(d18:1/20:0)/PC(O-34:2) | 1.83 | 1.1E−19 | 1.94 | 6.1E−18 | 2.62 | 1.4E−13 | 2.57 | 1.6E−10 | 2.21 | 1.1E−04 |
| SM(40:1)/PC(P-32:0) | 1.84 | 1.1E−19 | 1.92 | 2.5E−17 | 2.14 | 4.2E−09 | 2.39 | 4.9E−09 | 1.79 | 7.0E−03 |
| PE(34:1)/PC(31:0) | 1.78 | 1.2E−19 | 1.75 | 4.5E−15 | 1.99 | 2.1E−09 | 1.91 | 3.8E−07 | 1.72 | 5.8E−03 |
| Cer(d16:1/20:0)/LPC(O-18:1) | 1.87 | 1.2E−19 | 1.99 | 4.5E−18 | 2.41 | 5.1E−11 | 2.35 | 1.4E−08 | 2.16 | 4.9E−04 |
| PE(32:1)/Glc/GalCer(d18:1/23:0) | 1.77 | 1.2E−19 | 1.68 | 9.1E−14 | 2.13 | 1.3E−10 | 2.03 | 3.7E−08 | 1.76 | 3.1E−03 |
| PC(38:2)/SM(41:2) | 1.80 | 1.2E−19 | 1.76 | 1.8E−14 | 2.15 | 1.4E−10 | 2.05 | 1.2E−07 | 1.80 | 2.7E−03 |
| DAG(18:2/20:4)/LPE(P-20:0) | 1.81 | 1.2E−19 | 1.96 | 4.4E−19 | 2.19 | 7.9E−11 | 2.37 | 5.1E−10 | 1.83 | 2.8E−03 |
| DAG(18:1/18:3)/LPC(22:1) [sn1] | 1.87 | 1.3E−19 | 2.04 | 3.8E−19 | 1.97 | 3.2E−07 | 2.28 | 7.1E−08 | 2.01 | 1.7E−03 |
| PC(38:1)/LPC(19:0) [sn1] | 1.75 | 1.3E−19 | 1.71 | 7.5E−15 | 2.37 | 6.4E−15 | 2.31 | 4.1E−12 | 2.27 | 3.1E−06 |
| PE(36:2)/LPC(O-24:1) | 1.78 | 1.3E−19 | 1.77 | 8.3E−16 | 2.03 | 8.5E−10 | 2.00 | 5.8E−08 | 1.71 | 6.3E−03 |
| Cer(d16:1/20:0)/LPC(15:0) [sn1] | 1.87 | 1.3E−19 | 2.01 | 4.0E−18 | 2.48 | 1.1E−11 | 2.43 | 4.3E−09 | 2.50 | 1.6E−05 |
| PC(38:5)/LPC(24:0) [sn1] | 1.81 | 1.4E−19 | 1.83 | 4.0E−16 | 2.29 | 6.3E−12 | 2.33 | 1.4E−09 | 2.30 | 2.1E−05 |
| PC(38:1)/LPC(O-20:1) | 1.77 | 1.4E−19 | 1.76 | 1.5E−15 | 2.38 | 1.4E−13 | 2.40 | 5.8E−11 | 2.08 | 1.2E−04 |
| PE(36:2)/LPC(17:0) [sn2] | 1.75 | 1.4E−19 | 1.71 | 5.2E−15 | 2.02 | 3.5E−11 | 1.94 | 1.5E−08 | 1.76 | 1.5E−03 |
| DAG(18:2/20:4)/LPC(20:2) [sn1] | 1.83 | 1.4E−19 | 2.09 | 5.7E−21 | 2.13 | 9.3E−10 | 2.37 | 1.3E−09 | 1.86 | 2.7E−03 |
| PE(38:1)/LPC(MHDA) [sn1] | 1.74 | 1.5E−19 | 1.71 | 3.4E−15 | 2.12 | 2.9E−12 | 2.00 | 7.0E−09 | 2.19 | 7.3E−06 |
| PC(40:5)/LPC(18:1) | 1.83 | 1.5E−19 | 1.96 | 2.1E−18 | 2.44 | 2.9E−12 | 2.38 | 1.1E−09 | 1.96 | 1.2E−03 |
| PC(38:5)/LPC(24:0) [sn2] | 1.81 | 1.5E−19 | 1.82 | 7.3E−16 | 2.31 | 6.3E−12 | 2.36 | 9.1E−10 | 2.21 | 4.9E−05 |
| PE(32:1)/LPE(20:1) [sn1] | 1.82 | 1.6E−19 | 1.78 | 9.6E−15 | 2.33 | 1.0E−11 | 2.34 | 7.1E−10 | 1.76 | 6.1E−03 |
| DAG(18:1/18:3)/LPC(24:0) [sn2] | 1.84 | 1.6E−19 | 2.07 | 2.2E−20 | 1.95 | 1.2E−07 | 2.34 | 1.5E−08 | 2.28 | 1.1E−04 |
| PG(34:1)/PC(35:2) | 1.83 | 1.6E−19 | 1.86 | 2.3E−16 | 2.37 | 1.9E−11 | 2.21 | 2.5E−08 | 2.39 | 3.3E−05 |
| Cer(d16:1/20:0)/PC(P-40:4) | 1.88 | 1.7E−19 | 2.07 | 3.6E−19 | 2.42 | 8.6E−11 | 2.48 | 3.7E−09 | 2.70 | 1.7E−05 |
| Cer(d18:1/16:0)/LPC(22:0) [sn2] | 1.81 | 1.7E−19 | 1.84 | 1.2E−16 | 2.37 | 1.5E−13 | 2.38 | 1.1E−11 | 1.99 | 1.7E−04 |
| SM(36:1)/PC(O-38:2) | 1.79 | 1.7E−19 | 1.84 | 1.2E−16 | 2.21 | 1.3E−11 | 2.43 | 5.1E−11 | 2.58 | 9.5E−07 |
| DAG(18:2/20:4)/PC(O-34:2) | 1.81 | 1.8E−19 | 1.96 | 6.7E−19 | 2.14 | 7.4E−10 | 2.22 | 1.1E−08 | 1.82 | 4.4E−03 |
| DAG(18:1/18:3)/LacCer(d18:1/16:0) | 1.83 | 1.9E−19 | 2.01 | 2.9E−19 | 1.76 | 3.4E−06 | 1.97 | 1.6E−06 | 2.00 | 7.7E−04 |
| DAG(18:1/18:3)/SM(37:1) | 1.83 | 1.9E−19 | 1.99 | 9.7E−19 | 1.78 | 3.6E−06 | 1.96 | 3.5E−06 | 1.86 | 3.1E−03 |
| Cer(d16:1/20:0)/PC(O-40:3) | 1.80 | 1.9E−19 | 1.99 | 6.6E−20 | 1.88 | 1.7E−08 | 1.98 | 1.1E−07 | 1.83 | 1.2E−03 |
| Cer(d18:1/16:0)/PC(O-34:0) | 1.81 | 2.0E−19 | 1.81 | 2.6E−16 | 1.94 | 4.8E−08 | 1.88 | 6.0E−06 | 1.91 | 1.4E−03 |
| PG(34:1)/PC(O-36:3) | 1.81 | 2.0E−19 | 1.80 | 1.6E−15 | 2.23 | 1.2E−10 | 2.04 | 1.4E−07 | 1.93 | 1.3E−03 |
| SM(44:2)/Gb3(d18:1/24:1) | 1.85 | 2.1E−19 | 1.83 | 5.1E−15 | 2.41 | 5.2E−11 | 2.63 | 2.7E−10 | 1.75 | 9.5E−03 |
| PC(38:2)/LPC(O-22:0) | 1.76 | 2.2E−19 | 1.76 | 1.6E−15 | 2.33 | 2.0E−13 | 2.35 | 4.4E−11 | 2.06 | 1.6E−04 |
| PE(34:1)/PC(P-32:0) | 1.76 | 2.3E−19 | 1.71 | 9.3E−15 | 2.00 | 6.8E−10 | 1.91 | 1.4E−07 | 1.66 | 8.5E−03 |
| SM(40:1)/LPC(MHDA) [sn2] | 1.78 | 2.4E−19 | 1.76 | 3.4E−15 | 2.20 | 2.1E−12 | 2.17 | 3.2E−10 | 1.97 | 5.6E−05 |
| PC(36:4)/LPC(O-18:1) | 1.81 | 2.4E−19 | 1.74 | 6.6E−14 | 2.38 | 7.4E−12 | 2.28 | 4.2E−09 | 1.90 | 2.3E−03 |
| DAG(18:1/18:3)/LacCer(d18:1/24:1) | 1.81 | 2.5E−19 | 1.96 | 1.6E−18 | 1.78 | 1.9E−06 | 1.96 | 1.9E−06 | 1.88 | 2.0E−03 |
| DAG(18:2/20:4)/PC(P-32:0) | 1.80 | 2.5E−19 | 1.99 | 1.5E−19 | 1.98 | 2.0E−08 | 2.20 | 1.8E−08 | 1.71 | 8.9E−03 |
| PI(36:4)/LPC(18:2) [sn2] | 1.76 | 2.5E−19 | 1.79 | 2.4E−16 | 2.50 | 2.3E−15 | 2.41 | 9.7E−12 | 1.65 | 8.8E−03 |
| PE(36:2)/LPC(20:2) [sn1] | 1.77 | 2.5E−19 | 1.82 | 5.7E−17 | 2.04 | 3.4E−10 | 2.01 | 3.2E−08 | 1.82 | 2.0E−03 |
| PG(34:1)/SM(37:1) | 1.81 | 2.6E−19 | 1.79 | 4.6E−15 | 2.08 | 3.3E−09 | 1.95 | 1.2E−06 | 1.69 | 9.9E−03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| SM(41:0)/LacCer(d18:1/22:0) | 1.80 | 2.6E-19 | 1.83 | 2.0E-16 | 2.37 | 3.3E-12 | 2.60 | 1.5E-11 | 1.86 | 2.0E-03 |
| SM(41:0)/PC(O-34:2) | 1.80 | 2.6E-19 | 1.83 | 2.5E-16 | 2.51 | 6.7E-14 | 2.52 | 1.2E-11 | 2.02 | 4.4E-04 |
| CE(18:0)/LPE(P-20:0) | 1.81 | 2.7E-19 | 1.90 | 1.5E-17 | 2.19 | 7.9E-11 | 2.20 | 5.2E-09 | 1.76 | 4.6E-03 |
| PG(34:1)/PC(35:3) | 1.81 | 2.7E-19 | 1.84 | 4.2E-16 | 2.22 | 1.2E-10 | 2.11 | 4.3E-08 | 1.99 | 8.4E-04 |
| CE(20:3)/LPC(O-24:0) | 1.78 | 2.8E-19 | 1.79 | 6.5E-16 | 2.62 | 2.5E-15 | 2.92 | 1.7E-14 | 1.70 | 6.5E-03 |
| CE(16:2)/PC(O-38:2) | 1.80 | 2.8E-19 | 1.69 | 6.0E-13 | 2.40 | 4.3E-12 | 2.19 | 2.2E-08 | 1.73 | 6.2E-03 |
| PC(36:4)/LPE(16:0) [sn2] | 1.85 | 2.9E-19 | 1.91 | 1.4E-16 | 2.47 | 5.9E-11 | 2.62 | 7.6E-10 | 2.30 | 2.7E-04 |
| Cer(d18:1/24:1)/LPC(O-16:0) | 1.76 | 3.0E-19 | 1.72 | 1.6E-14 | 2.21 | 1.3E-12 | 2.19 | 1.9E-10 | 1.74 | 2.2E-03 |
| PE(32:1)/PC(O-40:4) | 1.76 | 3.0E-19 | 1.65 | 7.3E-13 | 2.16 | 5.5E-11 | 2.04 | 3.3E-08 | 1.87 | 1.1E-03 |
| PE(32:1)/LPE(P-20:0) | 1.74 | 3.0E-19 | 1.64 | 3.2E-13 | 2.14 | 4.0E-12 | 2.00 | 5.8E-09 | 1.73 | 2.7E-03 |
| SM(36:2)/LPC(20:1) [sn1] | 1.83 | 3.0E-19 | 2.00 | 5.1E-19 | 3.00 | 2.8E-15 | 3.41 | 5.2E-14 | 2.03 | 9.4E-04 |
| PC(38:2)/PC(O-32:0) | 1.81 | 3.1E-19 | 1.82 | 9.3E-16 | 2.16 | 5.1E-10 | 2.18 | 3.1E-08 | 1.93 | 1.6E-03 |
| PC(36:5)/LPC(20:1) [sn2] | 1.84 | 3.1E-19 | 1.75 | 2.3E-13 | 2.30 | 3.3E-10 | 2.21 | 1.2E-07 | 2.15 | 4.6E-04 |
| SM(36:1)/LPC(19:0) [sn2] | 1.74 | 3.2E-19 | 1.82 | 1.5E-17 | 2.25 | 6.0E-15 | 2.40 | 5.7E-14 | 1.89 | 5.4E-05 |
| DAG(18:2/20:4)/PC(O-38:2) | 1.80 | 3.3E-19 | 1.91 | 5.5E-18 | 1.93 | 4.0E-08 | 2.05 | 1.2E-07 | 1.77 | 4.6E-03 |
| DAG(18:1/18:3)/LPC(O-18:1) | 1.82 | 3.3E-19 | 1.96 | 3.1E-18 | 1.90 | 2.5E-07 | 2.11 | 3.2E-07 | 2.05 | 6.6E-04 |
| PE(32:1)/PE(O-36:1) | 1.77 | 3.3E-19 | 1.67 | 2.9E-13 | 2.28 | 1.1E-11 | 2.14 | 7.5E-09 | 1.67 | 9.6E-03 |
| SM(38:0)/LPC(18:2) [sn2] | 1.81 | 3.4E-19 | 1.92 | 8.1E-18 | 2.76 | 2.9E-14 | 2.97 | 1.2E-12 | 2.37 | 5.8E-05 |
| PE(38:4)/PC(39:4) | 1.78 | 3.6E-19 | 1.78 | 3.3E-15 | 2.11 | 8.2E-10 | 2.09 | 5.5E-08 | 1.79 | 4.0E-03 |
| PC(38:1)/PC(O-40:6) | 1.77 | 3.6E-19 | 1.85 | 3.0E-17 | 1.94 | 6.3E-09 | 2.00 | 8.3E-08 | 1.95 | 2.3E-04 |
| Cer(d18:2/18:0)/LPC(20:2) [sn1] | 1.87 | 3.7E-19 | 2.19 | 2.4E-21 | 2.70 | 9.9E-13 | 2.85 | 3.6E-11 | 1.81 | 6.4E-03 |
| SM(36:2)/LacCer(d18:1/24:1) | 1.79 | 3.7E-19 | 1.85 | 4.3E-17 | 2.40 | 4.7E-13 | 2.45 | 3.9E-11 | 1.76 | 4.0E-03 |
| PE(36:2)/PC(P-32:0) | 1.78 | 3.7E-19 | 1.80 | 7.0E-16 | 1.99 | 1.1E-08 | 1.97 | 4.4E-07 | 1.75 | 6.7E-03 |
| PC(38:2)/LPC(17:0) [sn1] | 1.74 | 3.8E-19 | 1.66 | 1.6E-13 | 2.36 | 1.9E-14 | 2.21 | 9.3E-11 | 1.94 | 3.3E-04 |
| PC(36:4)/LPC(18:2) [sn1] | 1.80 | 3.8E-19 | 1.81 | 1.0E-15 | 2.57 | 7.3E-14 | 2.56 | 2.9E-11 | 2.24 | 1.1E-04 |
| PC(36:4)/LPE(P-20:0) | 1.79 | 3.8E-19 | 1.73 | 2.5E-14 | 2.40 | 4.5E-13 | 2.30 | 3.8E-10 | 2.00 | 4.2E-04 |
| PE(38:5)/PC(37:2) | 1.78 | 4.4E-19 | 1.72 | 5.9E-14 | 2.19 | 1.4E-10 | 2.11 | 4.1E-08 | 1.99 | 4.3E-04 |
| SM(38:1)/LPC(19:0) [sn1] | 1.75 | 4.4E-19 | 1.75 | 1.5E-15 | 2.29 | 2.0E-13 | 2.34 | 1.3E-11 | 2.22 | 1.3E-05 |
| PC(40:6)/LPC(22:6) [sn1] | 1.80 | 4.5E-19 | 1.94 | 1.3E-18 | 2.68 | 9.2E-15 | 2.69 | 3.2E-12 | 2.01 | 6.6E-04 |
| PC(36:4)/LPC(P-16:0) | 1.78 | 4.6E-19 | 1.75 | 1.4E-14 | 2.33 | 2.5E-12 | 2.30 | 6.3E-10 | 1.92 | 1.2E-03 |
| SM(36:2)/LPC(MHDA) [sn1] | 1.77 | 4.6E-19 | 1.86 | 1.7E-17 | 2.73 | 9.3E-17 | 2.79 | 3.3E-14 | 2.48 | 4.4E-07 |
| PC(36:4)/PC(39:4) | 1.82 | 4.8E-19 | 1.76 | 5.0E-14 | 2.35 | 1.2E-10 | 2.38 | 6.7E-09 | 2.01 | 1.4E-03 |
| PI(34:2)/LPC(O-24:1) | 1.74 | 4.9E-19 | 1.69 | 4.3E-14 | 2.25 | 6.8E-13 | 2.17 | 6.3E-10 | 1.68 | 5.9E-03 |
| Cer(d16:1/20:0)/PC(O-32:0) | 1.85 | 4.9E-19 | 2.06 | 3.4E-19 | 2.08 | 3.1E-08 | 2.14 | 4.9E-07 | 2.27 | 3.1E-04 |
| PG(34:1)/PC(17:0_22:6) | 1.78 | 4.9E-19 | 1.79 | 3.2E-15 | 1.89 | 7.9E-08 | 1.89 | 2.9E-06 | 1.66 | 9.6E-03 |
| Cer(d18:1/24:1)/LPC(15:0) [sn2] | 1.78 | 5.3E-19 | 1.73 | 4.4E-14 | 2.28 | 6.6E-12 | 2.28 | 1.0E-09 | 1.70 | 6.1E-03 |
| PE(36:2)/LPC(17:0) [sn1] | 1.73 | 5.3E-19 | 1.68 | 3.2E-14 | 2.00 | 1.2E-10 | 1.92 | 3.8E-08 | 1.74 | 2.5E-03 |
| Cer(d20:1/24:1)/LacCer(d18:1/16:0) | 1.73 | 5.5E-19 | 1.73 | 1.4E-15 | 2.08 | 2.0E-11 | 2.12 | 4.7E-10 | 1.62 | 9.2E-03 |
| DAG(18:0/20:4)/LPE(16:0) [sn2] | 1.80 | 5.8E-19 | 1.96 | 7.1E-19 | 2.09 | 1.3E-09 | 2.38 | 5.0E-10 | 2.34 | 2.7E-05 |
| Cer(d16:1/20:0)/PC(39:4) | 1.85 | 5.8E-19 | 2.00 | 4.1E-18 | 2.18 | 2.9E-09 | 2.22 | 5.4E-08 | 2.26 | 2.3E-04 |
| PE(32:1)/LPC(O-18:1) | 1.73 | 5.8E-19 | 1.63 | 9.8E-13 | 2.08 | 3.0E-11 | 1.95 | 2.8E-08 | 1.65 | 7.1E-03 |
| PE(32:1)/CE(17:0) | 1.74 | 5.9E-19 | 1.65 | 3.5E-13 | 2.11 | 3.4E-11 | 1.99 | 3.0E-08 | 1.69 | 4.9E-03 |
| LPE(P-16:0)/LPC(19:0) [sn2] | 1.76 | 6.1E-19 | 1.78 | 6.3E-16 | 2.11 | 1.3E-13 | 2.20 | 3.5E-12 | 1.71 | 3.0E-04 |
| Cer(d18:1/20:0)/Glc/GalCer(d18:1/23:0) | 1.81 | 6.1E-19 | 1.96 | 4.7E-18 | 2.22 | 4.9E-10 | 2.40 | 3.5E-09 | 2.29 | 6.8E-05 |
| Cer(d18:1/24:1)/LPC(20:2) [sn2] | 1.78 | 6.2E-19 | 1.87 | 2.2E-17 | 2.21 | 7.3E-11 | 2.30 | 7.3E-10 | 1.92 | 1.3E-03 |
| PE(32:1)/LPC(18:2) [sn2] | 1.74 | 6.2E-19 | 1.67 | 1.2E-13 | 2.16 | 3.7E-12 | 2.05 | 3.5E-09 | 1.74 | 2.7E-03 |
| SM(36:2)/LPC(O-24:1) | 1.79 | 6.6E-19 | 1.90 | 9.0E-18 | 2.67 | 7.0E-15 | 2.86 | 2.6E-13 | 2.05 | 2.2E-04 |
| PC(38:2)/LPC(17:0) [sn2] | 1.72 | 6.7E-19 | 1.67 | 5.2E-14 | 2.25 | 2.1E-14 | 2.14 | 9.4E-11 | 1.90 | 2.4E-04 |
| PC(36:5)/LPC(P-18:1) | 1.78 | 7.2E-19 | 1.65 | 4.2E-12 | 2.10 | 8.0E-10 | 1.93 | 1.7E-06 | 1.91 | 1.3E-03 |
| PC(38:5)/LPC(17:0) [sn2] | 1.78 | 7.5E-19 | 1.70 | 2.5E-13 | 2.33 | 2.3E-12 | 2.19 | 1.2E-08 | 2.13 | 1.2E-04 |
| Cer(d18:1/24:1)/LPC(15:0) [sn1] | 1.77 | 7.9E-19 | 1.72 | 5.7E-14 | 2.32 | 1.9E-12 | 2.35 | 2.1E-10 | 1.95 | 4.4E-04 |
| PE(38:3)/LPC(O-24:0) | 1.76 | 8.2E-19 | 1.78 | 1.0E-15 | 2.11 | 1.6E-10 | 2.12 | 8.4E-09 | 1.76 | 4.4E-03 |
| PG(34:1)/PC(37:2) | 1.78 | 8.4E-19 | 1.77 | 6.0E-15 | 2.13 | 3.2E-10 | 2.07 | 4.2E-08 | 1.98 | 4.6E-04 |
| DAG(18:2/20:4)/LPC(15:0) [sn1] | 1.82 | 8.5E-19 | 1.94 | 1.6E-17 | 2.18 | 9.7E-10 | 2.36 | 5.4E-09 | 1.88 | 3.1E-03 |
| PE(38:3)/LPE(P-20:0) | 1.75 | 8.7E-19 | 1.75 | 2.6E-13 | 2.16 | 8.4E-12 | 2.09 | 3.3E-09 | 1.73 | 4.0E-03 |
| Cer(d20:1/24:1)/PC(O-38:0) | 1.75 | 8.7E-19 | 1.76 | 1.8E-15 | 2.27 | 1.7E-12 | 2.37 | 2.5E-11 | 1.89 | 1.1E-03 |
| PC(38:6)/PC(17:0_22:6) | 1.74 | 8.8E-19 | 1.64 | 1.9E-12 | 1.92 | 6.7E-10 | 2.05 | 1.1E-08 | 1.56 | 2.8E-03 |
| DAG(18:0/20:4)/LPE(16:0) [sn1] | 1.79 | 8.9E-19 | 1.95 | 1.5E-18 | 2.07 | 1.5E-09 | 2.38 | 3.8E-10 | 2.28 | 3.3E-05 |
| DAG(18:1/18:3)/LPC(O-18:0) | 1.81 | 9.4E-19 | 1.94 | 1.1E-18 | 1.96 | 1.0E-07 | 2.20 | 1.4E-07 | 2.28 | 8.5E-05 |
| PE(36:2)/PC(O-32:0) | 1.76 | 9.4E-19 | 1.77 | 2.1E-15 | 1.89 | 8.1E-08 | 1.87 | 1.9E-06 | 1.71 | 7.9E-03 |
| PE(38:4)/PC(P-40:2) | 1.77 | 9.6E-19 | 1.78 | 1.9E-15 | 1.96 | 8.7E-09 | 1.89 | 1.1E-06 | 1.75 | 2.5E-03 |
| Cer(d18:1/20:0)/PC(39:4) | 1.81 | 9.6E-19 | 1.88 | 1.5E-16 | 2.32 | 2.8E-11 | 2.45 | 3.2E-10 | 2.12 | 2.7E-04 |
| Cer(d18:2/18:0)/LPC(15:0) [sn1] | 1.83 | 1.0E-18 | 1.98 | 7.9E-18 | 2.63 | 6.0E-13 | 2.67 | 1.1E-10 | 1.78 | 6.6E-03 |
| CE(16:2)/PC(P-40:2) | 1.78 | 1.0E-18 | 1.73 | 4.1E-14 | 2.21 | 4.6E-11 | 2.09 | 4.3E-08 | 1.67 | 7.7E-03 |
| SM(41:0)/LPC(O-18:1) | 1.77 | 1.0E-18 | 1.76 | 4.1E-15 | 2.43 | 1.8E-13 | 2.55 | 7.9E-12 | 1.85 | 2.3E-03 |
| Cer(d18:1/24:1)/PC(P-40:5) | 1.79 | 1.0E-18 | 1.79 | 9.7E-15 | 2.36 | 5.3E-12 | 2.41 | 6.9E-10 | 1.87 | 1.9E-03 |
| PC(36:4)/LPC(18:2) [sn2] | 1.80 | 1.1E-18 | 1.81 | 2.0E-15 | 2.60 | 3.7E-13 | 2.58 | 1.2E-10 | 2.14 | 4.2E-04 |
| SM(36:1)/LPC(MHDA) [sn2] | 1.75 | 1.1E-18 | 1.79 | 6.3E-16 | 2.38 | 2.0E-14 | 2.41 | 2.5E-12 | 2.33 | 7.7E-07 |
| CE(20:3)/LPC(20:2) [sn1] | 1.78 | 1.2E-18 | 1.87 | 5.1E-17 | 2.91 | 1.6E-15 | 3.30 | 2.0E-14 | 1.73 | 8.1E-03 |
| PE(38:5)/PC(O-36:3) | 1.77 | 1.2E-18 | 1.72 | 1.0E-13 | 2.18 | 2.5E-10 | 1.99 | 3.3E-07 | 1.89 | 1.6E-03 |
| PE(38:5)/LPC(20:1) [sn2] | 1.76 | 1.2E-18 | 1.72 | 4.8E-14 | 2.16 | 1.5E-10 | 2.08 | 3.9E-08 | 1.77 | 3.5E-03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| CE(16:2)/Glc/GalCer(d18:1/23:0) | 1.79 | 1.2E-18 | 1.74 | 7.5E-14 | 2.36 | 1.5E-11 | 2.25 | 9.3E-09 | 1.71 | 7.0E-03 |
| DAG(18:1/18:3)/LPC(18:2) [sn1] | 1.80 | 1.2E-18 | 2.01 | 3.1E-19 | 2.06 | 1.2E-08 | 2.34 | 9.6E-09 | 2.36 | 7.7E-05 |
| DAG(18:1/18:3)/LPC(18:2) [sn2] | 1.81 | 1.2E-18 | 2.04 | 2.0E-19 | 2.03 | 3.8E-08 | 2.32 | 2.6E-08 | 2.29 | 1.8E-04 |
| DAG(18:1/18:3)/LPC(20:2) [sn1] | 1.82 | 1.2E-18 | 2.07 | 6.7E-20 | 1.91 | 3.7E-07 | 2.19 | 1.4E-07 | 2.24 | 1.6E-04 |
| SM(41:0)/LPC(15:0) [sn2] | 1.77 | 1.2E-18 | 1.77 | 4.0E-15 | 2.52 | 4.6E-14 | 2.63 | 2.1E-12 | 1.85 | 2.2E-03 |
| PE(38:1)/LPC(MHDA) [sn2] | 1.71 | 1.2E-18 | 1.67 | 5.2E-14 | 2.04 | 1.9E-11 | 1.90 | 5.2E-08 | 2.10 | 1.9E-05 |
| DAG(18:2/20:4)/LPC(18:2) [sn2] | 1.79 | 1.2E-18 | 2.01 | 1.3E-19 | 2.21 | 1.9E-10 | 2.45 | 4.5E-10 | 1.85 | 3.3E-03 |
| PE(38:5)/LPC(MHDA) [sn2] | 1.73 | 1.2E-18 | 1.66 | 4.2E-13 | 2.17 | 7.4E-12 | 2.01 | 2.1E-08 | 2.05 | 1.1E-04 |
| PE(36:5)/PC(O-40:6) | 1.74 | 1.3E-18 | 1.69 | 1.2E-13 | 1.99 | 3.7E-09 | 1.85 | 1.9E-06 | 2.08 | 1.2E-04 |
| PC(40:6)/Gb3(d18:1/22:0) | 1.78 | 1.3E-18 | 1.83 | 6.0E-16 | 2.19 | 3.3E-10 | 2.05 | 1.7E-07 | 1.71 | 8.4E-03 |
| CE(16:2)/LPC(O-24:0) | 1.79 | 1.3E-18 | 1.74 | 1.2E-13 | 2.56 | 5.3E-13 | 2.46 | 6.0E-10 | 1.77 | 5.1E-03 |
| PE(32:1)/LPC(P-16:0) | 1.71 | 1.3E-18 | 1.62 | 6.8E-13 | 2.04 | 1.9E-11 | 1.94 | 1.2E-08 | 1.65 | 5.3E-03 |
| PE(38:1)/LacCer(d18:1/16:0) | 1.75 | 1.3E-18 | 1.74 | 9.4E-15 | 1.95 | 8.5E-09 | 1.85 | 2.5E-06 | 1.97 | 4.8E-04 |
| DAG(18:1/18:3)/LPC(15:0) [sn2] | 1.81 | 1.3E-18 | 1.94 | 1.9E-17 | 1.89 | 4.4E-07 | 2.09 | 6.6E-07 | 2.04 | 6.5E-04 |
| PC(40:6)/LPC(19:0) [sn1] | 1.79 | 1.3E-18 | 1.75 | 7.3E-14 | 3.02 | 3.7E-16 | 2.95 | 1.0E-12 | 2.52 | 1.6E-05 |
| SM(36:1)/LPC(O-22:0) | 1.75 | 1.3E-18 | 1.83 | 3.9E-17 | 2.42 | 6.6E-14 | 2.67 | 1.8E-13 | 2.35 | 3.2E-06 |
| PC(36:5)/LPC(P-18:0) | 1.76 | 1.3E-18 | 1.65 | 3.0E-12 | 2.26 | 1.3E-11 | 2.10 | 5.8E-08 | 2.26 | 3.5E-05 |
| SM(41:0)/CE(17:0) | 1.78 | 1.4E-18 | 1.84 | 3.3E-16 | 2.46 | 6.5E-13 | 2.64 | 1.6E-11 | 1.93 | 1.1E-03 |
| SM(36:1)/LPC(20:1) [sn2] | 1.80 | 1.4E-18 | 1.95 | 6.1E-18 | 2.54 | 2.2E-12 | 2.94 | 3.0E-12 | 1.97 | 1.7E-03 |
| CE(20:3)/LPE(P-20:0) | 1.76 | 1.4E-18 | 1.75 | 6.9E-15 | 2.76 | 6.7E-16 | 2.89 | 6.9E-14 | 1.68 | 6.8E-03 |
| PI(34:2)/PC(O-34:2) | 1.76 | 1.4E-18 | 1.70 | 1.5E-13 | 2.57 | 7.3E-14 | 2.29 | 2.4E-09 | 1.83 | 2.6E-03 |
| PC(38:5)/LPC(17:0) [sn1] | 1.77 | 1.4E-18 | 1.68 | 1.4E-12 | 2.32 | 5.8E-12 | 2.17 | 2.6E-08 | 2.12 | 1.7E-04 |
| PE(36:2)/PC(O-38:2) | 1.76 | 1.5E-18 | 1.73 | 3.5E-14 | 1.93 | 3.4E-08 | 1.85 | 3.4E-06 | 1.79 | 3.6E-03 |
| PC(38:4)/LPE(P-20:0) | 1.78 | 1.5E-18 | 1.79 | 2.7E-15 | 2.54 | 8.5E-14 | 2.47 | 6.8E-11 | 1.78 | 4.0E-03 |
| PE(34:1)/PC(O-38:2) | 1.72 | 1.6E-18 | 1.65 | 3.5E-13 | 1.96 | 2.5E-09 | 1.83 | 9.8E-07 | 1.69 | 5.7E-03 |
| PI(34:2)/PC(P-32:0) | 1.75 | 1.6E-18 | 1.71 | 8.7E-14 | 2.30 | 7.1E-12 | 2.20 | 6.3E-09 | 1.74 | 6.1E-03 |
| DAG(18:0/20:4)/CE(17:0) | 1.78 | 1.6E-18 | 1.84 | 3.0E-16 | 2.14 | 3.9E-10 | 2.29 | 6.5E-09 | 2.11 | 1.4E-04 |
| PC(34:1)/PC(O-38:2) | 1.75 | 1.6E-18 | 1.68 | 5.9E-13 | 1.87 | 6.3E-08 | 1.86 | 5.6E-06 | 1.68 | 6.7E-03 |
| SM(40:1)/Glc/GalCer(d18:2/22:0) | 1.78 | 1.8E-18 | 1.74 | 5.3E-14 | 1.77 | 3.4E-06 | 1.86 | 6.8E-06 | 1.75 | 7.0E-03 |
| CE(18:0)/LPC(20:2) [sn1] | 1.80 | 2.0E-18 | 2.06 | 3.4E-20 | 2.11 | 1.0E-08 | 2.27 | 3.9E-08 | 1.76 | 7.3E-03 |
| PC(38:5)/LacCer(d18:1/16:0) | 1.77 | 2.0E-18 | 1.74 | 6.1E-14 | 1.99 | 1.7E-08 | 1.89 | 4.7E-06 | 1.89 | 2.0E-03 |
| PE(38:4)/LPC(O-24:1) | 1.73 | 2.1E-18 | 1.72 | 8.7E-15 | 2.03 | 4.5E-10 | 1.99 | 5.8E-08 | 1.70 | 6.3E-03 |
| PE(36:2)/Glc/GalCer(d18:2/22:0) | 1.75 | 2.1E-18 | 1.73 | 3.4E-14 | 1.83 | 4.6E-07 | 1.79 | 1.4E-05 | 1.72 | 7.4E-03 |
| PE(36:2)/PC(O-38:0) | 1.76 | 2.1E-18 | 1.76 | 5.3E-15 | 1.95 | 2.3E-08 | 1.92 | 9.3E-07 | 1.84 | 2.4E-03 |
| SM(40:1)/LPC(O-18:0) | 1.73 | 2.1E-18 | 1.69 | 1.0E-13 | 2.20 | 5.5E-12 | 2.23 | 3.6E-10 | 2.02 | 1.7E-04 |
| PE(38:5)/PC(35:3) | 1.75 | 2.1E-18 | 1.72 | 6.3E-14 | 2.13 | 2.6E-10 | 2.01 | 1.4E-07 | 1.91 | 1.1E-03 |
| PC(38:4)/PC(O-38:0) | 1.81 | 2.2E-18 | 1.88 | 4.4E-16 | 2.24 | 6.3E-10 | 2.36 | 1.2E-08 | 1.88 | 3.8E-03 |
| PC(38:1)/LPC(P-18:1) | 1.72 | 2.2E-18 | 1.66 | 9.5E-14 | 2.01 | 1.4E-11 | 1.89 | 2.2E-08 | 1.63 | 5.4E-03 |
| PC(38:5)/PC(37:2) | 1.77 | 2.2E-18 | 1.72 | 1.0E-13 | 2.09 | 1.0E-09 | 2.02 | 2.3E-07 | 2.05 | 3.0E-04 |
| PC(38:2)/LPC(20:2) [sn2] | 1.78 | 2.2E-18 | 1.92 | 8.1E-18 | 2.61 | 3.3E-13 | 2.60 | 9.4E-11 | 2.14 | 3.6E-04 |
| Cer(d16:1/16:0)/LPC(MHDA) [sn2] | 1.78 | 2.3E-18 | 1.82 | 1.4E-15 | 2.43 | 1.4E-12 | 2.46 | 1.5E-10 | 2.19 | 1.1E-04 |
| PE(36:2)/PC(31:0) | 1.76 | 2.4E-18 | 1.78 | 3.4E-15 | 1.88 | 1.7E-07 | 1.85 | 5.3E-06 | 1.77 | 5.6E-03 |
| SM(36:2)/LPC(19:0) [sn2] | 1.72 | 2.4E-18 | 1.81 | 3.1E-17 | 2.36 | 1.0E-15 | 2.48 | 3.7E-14 | 1.86 | 1.1E-04 |
| Glc/GalCer(d16:1/18:0)/PC(O-40:6) | 1.82 | 2.6E-18 | 1.90 | 4.7E-16 | 2.33 | 4.7E-10 | 2.48 | 5.1E-09 | 1.95 | 2.6E-03 |
| PE(38:3)/LPC(P-16:0) | 1.72 | 2.6E-18 | 1.73 | 3.7E-15 | 2.05 | 4.5E-11 | 2.03 | 6.0E-09 | 1.64 | 8.8E-03 |
| PC(38:1)/PC(O-36:3) | 1.74 | 2.6E-18 | 1.76 | 3.2E-15 | 2.24 | 6.4E-12 | 2.08 | 1.5E-08 | 2.02 | 2.3E-04 |
| Cer(d16:1/20:0)/LPC(O-24:0) | 1.81 | 2.7E-18 | 1.98 | 2.6E-18 | 2.22 | 7.3E-10 | 2.30 | 1.5E-08 | 2.37 | 7.7E-05 |
| SM(36:1)/LPC(20:0) [sn1] | 1.75 | 2.7E-18 | 1.82 | 2.0E-16 | 2.54 | 5.1E-15 | 2.78 | 3.6E-14 | 2.35 | 6.7E-06 |
| DAG(18:1/18:3)/SM(d17:1/14:0) | 1.80 | 2.8E-18 | 1.91 | 5.9E-17 | 1.76 | 6.3E-06 | 1.90 | 1.1E-05 | 1.94 | 1.6E-03 |
| Cer(d16:1/16:0)/PC(O-40:6) | 1.76 | 2.8E-18 | 1.81 | 5.3E-16 | 1.88 | 1.3E-07 | 1.91 | 1.4E-06 | 1.74 | 6.3E-03 |
| PE(38:4)/PC(P-32:0) | 1.75 | 2.9E-18 | 1.77 | 3.3E-15 | 2.02 | 4.5E-09 | 1.97 | 3.7E-07 | 1.75 | 5.6E-03 |
| SM(41:0)/LPC(P-16:0) | 1.73 | 2.9E-18 | 1.77 | 1.1E-15 | 2.34 | 8.6E-14 | 2.50 | 1.4E-12 | 1.85 | 1.2E-03 |
| PE(34:1)/LPC(20:2) [sn1] | 1.70 | 3.0E-18 | 1.69 | 1.4E-14 | 1.96 | 1.5E-10 | 1.88 | 5.3E-08 | 1.67 | 4.3E-03 |
| CE(16:2)/LPE(P-20:0) | 1.77 | 3.0E-18 | 1.70 | 3.3E-13 | 2.68 | 2.9E-14 | 2.46 | 2.3E-10 | 1.74 | 5.5E-03 |
| DAG(18:1/18:2)/LPE(P-20:0) | 1.75 | 3.0E-18 | 1.89 | 6.1E-18 | 2.09 | 2.1E-10 | 2.20 | 2.5E-09 | 1.79 | 2.9E-03 |
| PE(38:1)/LPC(P-18:1) | 1.70 | 3.0E-18 | 1.65 | 1.2E-13 | 1.91 | 1.0E-09 | 1.78 | 1.2E-06 | 1.73 | 2.4E-03 |
| PE(38:3)/LPC(18:2) [sn2] | 1.73 | 3.1E-18 | 1.78 | 4.2E-16 | 2.19 | 1.0E-11 | 2.18 | 1.6E-09 | 1.75 | 4.1E-03 |
| SM(36:1)/PC(37:2) | 1.76 | 3.1E-18 | 1.86 | 5.5E-17 | 2.33 | 4.2E-12 | 2.66 | 3.3E-12 | 2.30 | 2.1E-05 |
| Cer(d18:2/22:0)/LPC(MHDA) [sn2] | 1.75 | 3.2E-18 | 1.80 | 8.1E-16 | 2.27 | 1.2E-11 | 2.24 | 2.8E-09 | 2.03 | 1.4E-04 |
| PE(38:4)/PC(O-34:0) | 1.74 | 3.2E-18 | 1.73 | 1.8E-14 | 1.93 | 2.0E-08 | 1.85 | 2.8E-06 | 1.78 | 3.4E-03 |
| PE(40:6)/PC(35:2) | 1.78 | 3.2E-18 | 1.77 | 1.9E-14 | 2.55 | 2.3E-12 | 2.37 | 6.5E-09 | 2.77 | 5.6E-06 |
| SM(36:1)/SM(d17:1/14:0) | 1.75 | 3.3E-18 | 1.79 | 1.8E-15 | 2.08 | 1.5E-10 | 2.17 | 2.7E-09 | 1.87 | 8.8E-04 |
| DAG(18:1/18:2)/LPC(P-16:0) | 1.74 | 3.3E-18 | 1.88 | 4.1E-18 | 2.03 | 7.2E-10 | 2.16 | 3.4E-09 | 1.69 | 6.7E-03 |
| DAG(18:1/18:3)/LPE(P-20:0) | 1.79 | 3.3E-18 | 1.95 | 8.8E-18 | 1.95 | 7.5E-08 | 2.17 | 1.0E-07 | 2.16 | 2.4E-04 |
| Cer(d18:1/16:0)/LPC(O-18:0) | 1.73 | 3.3E-18 | 1.67 | 2.5E-13 | 2.15 | 2.0E-12 | 2.05 | 1.8E-09 | 1.94 | 4.9E-05 |
| PE(38:5)/PC(35:2) | 1.77 | 3.4E-18 | 1.73 | 8.0E-14 | 2.17 | 8.6E-10 | 1.96 | 1.9E-06 | 2.19 | 1.4E-04 |
| SM(38:1)/LacCer(d18:1/16:0) | 1.78 | 3.4E-18 | 1.88 | 5.7E-17 | 2.02 | 2.7E-08 | 2.14 | 1.0E-07 | 1.96 | 1.6E-03 |
| PE(36:2)/LPC(20:2) [sn2] | 1.74 | 3.5E-18 | 1.81 | 3.1E-16 | 1.98 | 4.3E-09 | 1.97 | 1.9E-07 | 1.76 | 4.4E-03 |
| Cer(d18:2/18:0)/LPC(18:2) [sn2] | 1.84 | 3.6E-18 | 2.11 | 9.4E-20 | 2.86 | 2.3E-13 | 3.01 | 1.4E-11 | 1.82 | 6.3E-03 |
| DAG(18:1/18:2)/LPC(20:2) [sn1] | 1.77 | 3.7E-18 | 2.01 | 5.3E-20 | 2.08 | 2.4E-09 | 2.26 | 5.1E-09 | 1.84 | 2.9E-03 |
| PI(34:2)/PC(O-34:0) | 1.74 | 3.8E-18 | 1.66 | 8.1E-13 | 2.20 | 8.5E-11 | 2.05 | 9.8E-08 | 1.77 | 4.0E-03 |
| PC(36:5)/LPC(MHDA) [sn2] | 1.75 | 3.8E-18 | 1.63 | 1.2E-11 | 2.22 | 3.7E-11 | 2.04 | 1.6E-07 | 2.45 | 6.5E-06 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| SM(41:0)/LPC(O-24:0) | 1.75 | 3.9E−18 | 1.80 | 6.0E−16 | 2.32 | 9.5E−13 | 2.57 | 2.1E−12 | 2.00 | 3.3E−04 |
| PE(34:1)/PC(O-38:0) | 1.72 | 3.9E−18 | 1.67 | 1.2E−13 | 1.96 | 2.8E−09 | 1.88 | 4.3E−07 | 1.72 | 4.3E−03 |
| Cer(d16:1/20:0)/PC(37:1) | 1.83 | 3.9E−18 | 2.02 | 5.0E−18 | 2.08 | 2.8E−08 | 2.09 | 8.5E−07 | 2.43 | 9.9E−05 |
| DAG(18:2/20:4)/LPC(20:2) [sn2] | 1.78 | 3.9E−18 | 2.05 | 4.2E−20 | 2.01 | 1.6E−08 | 2.26 | 8.8E−09 | 1.76 | 6.5E−03 |
| PC(36:4)/PC(34:3) | 1.80 | 4.0E−18 | 1.93 | 2.7E−17 | 2.49 | 3.3E−11 | 2.62 | 6.8E−10 | 2.02 | 1.6E−03 |
| PC(36:5)/LPC(22:6) [sn1] | 1.78 | 4.2E−18 | 1.73 | 1.8E−13 | 2.02 | 1.9E−08 | 1.90 | 4.1E−06 | 2.11 | 4.4E−04 |
| PE(38:1)/Glc/GalCer(d18:2/20:0) | 1.72 | 4.3E−18 | 1.67 | 3.4E−13 | 1.74 | 2.0E−06 | 1.69 | 5.7E−05 | 1.79 | 2.3E−03 |
| PE(40:6)/LacCer(d18:1/16:0) | 1.74 | 4.4E−18 | 1.71 | 4.2E−14 | 2.20 | 5.7E−11 | 2.10 | 2.8E−08 | 2.10 | 2.4E−04 |
| SM(41:0)/LPC(15:0) [sn1] | 1.75 | 4.4E−18 | 1.75 | 1.1E−14 | 2.53 | 2.8E−14 | 2.66 | 8.7E−13 | 2.06 | 2.7E−04 |
| DAG(18:2/20:4)/PC(P-40:2) | 1.76 | 4.5E−18 | 1.91 | 8.4E−18 | 1.88 | 1.8E−07 | 2.00 | 3.5E−07 | 1.71 | 7.4E−03 |
| DAG(18:1/18:3)/PC(O-34:2) | 1.78 | 4.7E−18 | 1.93 | 1.4E−17 | 1.91 | 3.4E−07 | 2.06 | 1.1E−06 | 2.13 | 4.2E−04 |
| PC(38:5)/LPC(O-22:0) | 1.75 | 4.8E−18 | 1.72 | 1.1E−13 | 2.16 | 9.0E−11 | 2.16 | 2.6E−08 | 2.14 | 1.3E−04 |
| Cer(d18:2/22:0)/LPC(17:0) [sn2] | 1.75 | 4.8E−18 | 1.80 | 1.5E−15 | 2.30 | 5.0E−12 | 2.29 | 1.1E−09 | 1.91 | 9.2E−04 |
| PE(40:6)/PC(O-36:3) | 1.75 | 4.8E−18 | 1.73 | 4.5E−14 | 2.37 | 7.1E−12 | 2.17 | 1.6E−08 | 2.16 | 2.1E−04 |
| PE(38:1)/SM(d17:1/14:0) | 1.73 | 4.9E−18 | 1.67 | 4.1E−13 | 1.98 | 6.7E−09 | 1.79 | 9.2E−06 | 1.92 | 7.6E−04 |
| SM(38:1)/PC(O-36:3) | 1.77 | 5.2E−18 | 1.84 | 3.8E−16 | 2.27 | 7.3E−11 | 2.21 | 1.7E−08 | 2.00 | 8.5E−04 |
| DAG(18:1/18:3)/LPC(P-16:0) | 1.77 | 5.4E−18 | 1.93 | 8.0E−18 | 1.89 | 2.0E−07 | 2.12 | 1.3E−07 | 2.03 | 6.0E−04 |
| SM(40:1)/LPC(17:0) [sn1] | 1.73 | 5.5E−18 | 1.67 | 4.6E−13 | 2.26 | 2.1E−12 | 2.27 | 1.8E−10 | 1.83 | 1.6E−03 |
| DAG(18:1/18:2)/Glc/GalCer(d18:2/22:0) | 1.74 | 5.5E−18 | 1.87 | 2.6E−17 | 1.78 | 1.1E−06 | 1.91 | 2.0E−06 | 1.70 | 8.7E−03 |
| SM(36:2)/PC(35:2) | 1.79 | 5.6E−18 | 1.96 | 7.2E−18 | 2.76 | 7.8E−14 | 2.99 | 5.3E−12 | 2.78 | 2.8E−06 |
| Cer(d16:1/20:0)/Glc/GalCer(d18:1/23:0) | 1.81 | 5.6E−18 | 2.01 | 2.6E−18 | 2.01 | 9.5E−08 | 2.10 | 9.2E−07 | 2.33 | 1.4E−04 |
| SM(41:0)/PC(37:1) | 1.76 | 5.7E−18 | 1.80 | 1.2E−15 | 2.32 | 1.1E−11 | 2.55 | 2.8E−11 | 1.98 | 6.9E−04 |
| PC(34:2)/PC(37:2) | 1.76 | 6.0E−18 | 1.66 | 3.0E−12 | 2.08 | 1.5E−09 | 1.97 | 4.0E−07 | 1.94 | 9.8E−04 |
| DAG(18:1/18:2)/PC(39:4) | 1.75 | 6.2E−18 | 1.89 | 1.3E−17 | 1.92 | 5.3E−08 | 2.10 | 6.4E−08 | 1.70 | 9.1E−03 |
| Cer(d18:1/20:0)/LPC(O-24:0) | 1.76 | 6.3E−18 | 1.87 | 9.1E−17 | 2.31 | 1.3E−11 | 2.44 | 1.6E−10 | 2.18 | 6.5E−05 |
| DAG(18:1/18:3)/LPC(15:0) [sn1] | 1.78 | 6.9E−18 | 1.91 | 7.5E−17 | 1.89 | 5.0E−07 | 2.11 | 5.7E−07 | 2.20 | 1.8E−04 |
| PE(38:5)/LPC(P-18:1) | 1.72 | 6.9E−18 | 1.64 | 1.5E−12 | 2.03 | 5.6E−10 | 1.88 | 5.6E−07 | 1.66 | 7.7E−03 |
| PC(38:2)/PC(O-38:0) | 1.78 | 7.1E−18 | 1.79 | 1.7E−14 | 2.29 | 8.5E−12 | 2.29 | 1.4E−08 | 2.22 | 2.1E−04 |
| CE(16:2)/PC(O-34:2) | 1.76 | 7.2E−18 | 1.71 | 4.1E−13 | 2.52 | 8.5E−13 | 2.30 | 8.1E−09 | 1.71 | 8.5E−03 |
| PC(36:5)/LPC(22:6) [sn2] | 1.76 | 7.5E−18 | 1.71 | 2.9E−13 | 1.86 | 5.2E−07 | 1.72 | 8.6E−05 | 1.87 | 2.6E−03 |
| SM(36:1)/LPC(22:0) [sn1] | 1.76 | 7.6E−18 | 1.88 | 4.9E−17 | 2.61 | 1.6E−14 | 2.99 | 2.2E−14 | 2.55 | 2.5E−06 |
| PC(36:4)/CE(17:0) | 1.75 | 7.7E−18 | 1.73 | 7.0E−14 | 2.24 | 9.2E−11 | 2.20 | 2.4E−08 | 1.91 | 1.8E−03 |
| DAG(18:2/20:4)/LPC(O-24:0) | 1.74 | 8.0E−18 | 1.90 | 5.5E−18 | 1.93 | 2.1E−08 | 2.16 | 1.3E−08 | 1.75 | 5.0E−03 |
| PC(38:4)/PC(O-34:2) | 1.75 | 8.0E−18 | 1.77 | 4.4E−15 | 2.30 | 9.5E−12 | 2.17 | 1.0E−08 | 1.69 | 9.2E−03 |
| PE(38:4)/LPC(17:0) [sn2] | 1.69 | 8.1E−18 | 1.66 | 1.4E−13 | 2.03 | 2.8E−11 | 1.94 | 2.2E−08 | 1.76 | 1.6E−03 |
| PC(38:2)/PC(39:4) | 1.75 | 8.2E−18 | 1.70 | 2.9E−13 | 2.25 | 6.5E−11 | 2.23 | 5.1E−09 | 1.89 | 1.9E−03 |
| SM(41:1)/PC(O-38:2) | 1.75 | 8.4E−18 | 1.70 | 3.4E−13 | 2.10 | 2.0E−09 | 2.24 | 7.0E−09 | 1.74 | 5.5E−03 |
| PE(40:6)/PC(37:2) | 1.74 | 8.5E−18 | 1.72 | 1.0E−13 | 2.36 | 8.3E−12 | 2.29 | 3.3E−09 | 2.33 | 5.4E−05 |
| PE(40:6)/LPC(19:0) [sn2] | 1.69 | 8.6E−18 | 1.67 | 6.0E−14 | 2.24 | 2.8E−13 | 2.19 | 1.7E−10 | 2.00 | 1.2E−04 |
| PE(36:2)/LPC(18:2) [sn2] | 1.70 | 8.8E−18 | 1.73 | 2.7E−15 | 2.01 | 1.4E−10 | 1.98 | 1.9E−08 | 1.75 | 2.7E−03 |
| PI(34:2)/PC(O-38:2) | 1.73 | 8.9E−18 | 1.61 | 1.8E−11 | 2.25 | 2.5E−11 | 2.03 | 1.1E−07 | 1.82 | 2.9E−03 |
| CE(18:0)/LPC(15:0) [sn1] | 1.77 | 9.1E−18 | 1.83 | 2.0E−15 | 2.08 | 4.1E−09 | 2.15 | 1.3E−07 | 1.75 | 6.5E−03 |
| CE(16:2)/LPC(20:2) [sn1] | 1.76 | 9.2E−18 | 1.76 | 3.4E−14 | 2.54 | 7.6E−13 | 2.40 | 1.4E−09 | 1.74 | 6.3E−03 |
| PC(38:2)/PC(P-40:4) | 1.75 | 9.4E−18 | 1.72 | 8.0E−14 | 2.41 | 1.9E−12 | 2.37 | 4.4E−10 | 2.25 | 1.0E−04 |
| SM(41:0)/LPE(P-20:0) | 1.72 | 9.5E−18 | 1.75 | 4.5E−15 | 2.44 | 4.6E−14 | 2.56 | 2.4E−12 | 1.94 | 5.0E−04 |
| DAG(18:1/18:3)/Glc/GalCer(d18:2/22:0) | 1.77 | 9.5E−18 | 1.89 | 5.3E−17 | 1.66 | 4.2E−05 | 1.84 | 2.1E−05 | 2.03 | 8.2E−04 |
| DAG(18:1/18:3)/PC(P-40:2) | 1.76 | 9.6E−18 | 1.91 | 2.2E−17 | 1.71 | 9.4E−06 | 1.87 | 8.4E−06 | 1.99 | 5.8E−04 |
| DAG(18:1/18:2)/PC(P-40:2) | 1.73 | 9.6E−18 | 1.88 | 1.3E−17 | 1.83 | 2.2E−07 | 1.92 | 7.8E−07 | 1.70 | 5.8E−03 |
| PE(38:5)/SM(d17:1/14:0) | 1.73 | 1.0E−17 | 1.64 | 4.3E−12 | 2.03 | 2.8E−09 | 1.86 | 3.1E−06 | 1.75 | 3.6E−03 |
| PE(38:1)/LPC(22:1) [sn1] | 1.69 | 1.0E−17 | 1.67 | 5.0E−14 | 1.90 | 3.1E−09 | 1.86 | 2.2E−07 | 1.77 | 2.0E−03 |
| PC(38:4)/LPC(20:2) [sn1] | 1.78 | 1.0E−17 | 1.93 | 1.9E−17 | 2.45 | 8.9E−12 | 2.50 | 4.3E−10 | 1.81 | 5.3E−03 |
| PG(34:1)/LPC(MHDA) [sn2] | 1.70 | 1.1E−17 | 1.66 | 2.5E−13 | 2.03 | 2.9E−11 | 1.90 | 3.6E−08 | 1.94 | 1.1E−04 |
| DAG(18:1/18:2)/LPC(18:2) [sn2] | 1.75 | 1.1E−17 | 1.96 | 6.1E−19 | 2.19 | 2.7E−10 | 2.38 | 1.2E−09 | 1.86 | 3.1E−03 |
| SM(41:0)/LPC(20:2) [sn1] | 1.75 | 1.2E−17 | 1.87 | 5.8E−17 | 2.48 | 5.8E−13 | 2.73 | 3.1E−12 | 2.05 | 4.7E−04 |
| PC(38:5)/PC(O-36:3) | 1.74 | 1.2E−17 | 1.70 | 2.4E−13 | 2.07 | 1.4E−09 | 1.90 | 2.2E−06 | 1.89 | 1.7E−03 |
| PE(40:6)/PC(33:2) | 1.75 | 1.2E−17 | 1.71 | 2.8E−13 | 2.31 | 3.9E−11 | 2.17 | 3.2E−08 | 2.19 | 1.7E−04 |
| PE(34:1)/PC(37:1) | 1.70 | 1.2E−17 | 1.63 | 9.3E−13 | 1.91 | 5.7E−09 | 1.81 | 1.2E−06 | 1.63 | 9.5E−03 |
| PE(40:6)/LPC(MHDA) [sn1] | 1.70 | 1.2E−17 | 1.66 | 2.0E−13 | 2.29 | 2.6E−13 | 2.17 | 6.3E−10 | 2.28 | 8.8E−06 |
| SM(36:2)/LPC(20:1) [sn2] | 1.77 | 1.2E−17 | 1.94 | 1.3E−17 | 2.73 | 2.3E−13 | 3.11 | 1.7E−12 | 1.90 | 2.9E−03 |
| PC(32:0)/PC(P-32:0) | 1.72 | 1.2E−17 | 1.64 | 3.8E−12 | 2.12 | 1.6E−10 | 2.09 | 7.3E−08 | 1.74 | 3.5E−03 |
| PC(40:6)/LPC(19:0) [sn2] | 1.74 | 1.3E−17 | 1.74 | 2.1E−14 | 2.72 | 4.1E−16 | 2.73 | 2.2E−13 | 2.04 | 1.3E−04 |
| PC(36:1)/LPC(18:1) [sn1] | 1.70 | 1.3E−17 | 1.78 | 3.5E−16 | 2.38 | 1.6E−14 | 2.38 | 6.9E−12 | 1.89 | 7.7E−04 |
| PI(34:2)/PC(O-32:0) | 1.72 | 1.3E−17 | 1.66 | 7.3E−13 | 2.16 | 1.4E−10 | 2.07 | 5.0E−08 | 1.69 | 8.3E−03 |
| PG(34:1)/LPC(20:1) [sn2] | 1.72 | 1.3E−17 | 1.72 | 2.3E−14 | 2.01 | 6.6E−10 | 1.97 | 6.8E−08 | 1.70 | 5.2E−03 |
| Cer(d18:2/18:0)/PC(O-38:4) | 1.79 | 1.3E−17 | 1.94 | 1.9E−17 | 2.37 | 1.0E−10 | 2.43 | 2.9E−09 | 1.99 | 1.8E−03 |
| DAG(18:1/18:2)/LPC(15:0) [sn1] | 1.74 | 1.3E−17 | 1.85 | 1.6E−16 | 2.07 | 2.2E−09 | 2.20 | 2.3E−08 | 1.82 | 3.0E−03 |
| PC(32:0)/PC(O-40:6) | 1.71 | 1.4E−17 | 1.72 | 2.6E−14 | 1.86 | 3.0E−08 | 1.87 | 7.7E−07 | 1.68 | 5.3E−03 |
| PE(40:6)/PC(35:3) | 1.74 | 1.4E−17 | 1.75 | 3.2E−14 | 2.42 | 4.7E−12 | 2.30 | 3.9E−09 | 2.31 | 8.9E−05 |
| CE(16:2)/LPC(15:0) [sn1] | 1.73 | 1.5E−17 | 1.65 | 5.9E−12 | 2.55 | 1.5E−13 | 2.38 | 1.1E−09 | 1.73 | 5.4E−03 |
| Cer(d20:1/24:1)/LPC(O-18:1) | 1.69 | 1.5E−17 | 1.66 | 2.1E−13 | 2.24 | 9.1E−13 | 2.25 | 9.4E−11 | 1.64 | 9.7E−03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| PG(34:1)/PC(33:2) | 1.74 | 1.5E-17 | 1.74 | 7.8E-14 | 2.02 | 9.1E-09 | 1.93 | 1.6E-06 | 1.82 | 2.7E-03 |
| SM(36:2)/LPC(20:0) [sn1] | 1.73 | 1.5E-17 | 1.82 | 2.8E-16 | 2.74 | 3.3E-16 | 2.96 | 1.4E-14 | 2.32 | 1.5E-05 |
| DAG(18:1/18:2)/PC(O-34:2) | 1.74 | 1.5E-17 | 1.89 | 2.8E-17 | 2.09 | 3.5E-09 | 2.14 | 8.8E-08 | 1.79 | 5.6E-03 |
| CE(18:0)/LPC(18:2) [sn2] | 1.76 | 1.6E-17 | 1.98 | 1.6E-18 | 2.25 | 2.8E-10 | 2.41 | 2.2E-09 | 1.78 | 6.6E-03 |
| PC(38:5)/SM(d17:1/14:0) | 1.73 | 1.6E-17 | 1.64 | 5.7E-12 | 1.94 | 2.3E-08 | 1.76 | 3.0E-05 | 1.78 | 3.8E-03 |
| SM(36:1)/LPC(20:0) [sn2] | 1.72 | 1.6E-17 | 1.79 | 7.5E-16 | 2.44 | 3.9E-14 | 2.68 | 1.8E-13 | 2.18 | 3.9E-05 |
| PE(36:2)/PC(37:1) | 1.73 | 1.6E-17 | 1.71 | 9.1E-14 | 1.86 | 1.3E-07 | 1.82 | 5.1E-06 | 1.74 | 6.5E-03 |
| DAG(18:1/18:3)/LPC(20:2) [sn2] | 1.78 | 1.7E-17 | 2.03 | 3.8E-19 | 1.79 | 3.7E-06 | 2.07 | 8.7E-07 | 2.16 | 3.2E-04 |
| CE(20:3)/LPC(15:0) [sn1] | 1.75 | 1.7E-17 | 1.71 | 2.3E-13 | 2.93 | 2.5E-15 | 3.16 | 1.3E-13 | 1.72 | 8.4E-03 |
| PE(34:1)/LPC(20:2) [sn2] | 1.69 | 1.7E-17 | 1.68 | 4.5E-14 | 1.94 | 8.3E-10 | 1.86 | 1.8E-07 | 1.63 | 7.9E-03 |
| PC(38:1)/LPC(19:0) [sn2] | 1.67 | 1.8E-17 | 1.68 | 8.8E-15 | 2.11 | 2.6E-14 | 2.13 | 2.5E-12 | 1.83 | 8.8E-05 |
| SM(38:1)/PC(O-40:6) | 1.73 | 1.8E-17 | 1.85 | 6.8E-17 | 1.90 | 9.6E-08 | 2.04 | 1.7E-07 | 1.90 | 1.3E-03 |
| PE(38:5)/LacCer(d18:1/16:0) | 1.73 | 1.8E-17 | 1.68 | 7.1E-13 | 2.02 | 1.1E-08 | 1.91 | 2.0E-06 | 1.82 | 3.2E-03 |
| PE(36:2)/PC(39:4) | 1.72 | 1.8E-17 | 1.71 | 9.1E-14 | 1.91 | 3.9E-08 | 1.90 | 8.7E-07 | 1.69 | 9.1E-03 |
| PE(40:6)/SM(39:2) | 1.70 | 1.8E-17 | 1.70 | 5.4E-14 | 2.17 | 7.3E-12 | 2.11 | 2.7E-09 | 1.77 | 2.4E-03 |
| SM(40:1)/LPC(17:0) [sn2] | 1.71 | 1.9E-17 | 1.68 | 1.7E-13 | 2.11 | 4.2E-12 | 2.14 | 3.1E-10 | 1.77 | 1.0E-03 |
| SM(36:2)/PC(O-34:0) | 1.74 | 1.9E-17 | 1.84 | 1.9E-16 | 2.30 | 1.3E-11 | 2.39 | 3.4E-10 | 2.31 | 3.7E-05 |
| PG(34:1)/LacCer(d18:1/16:0) | 1.74 | 2.0E-17 | 1.73 | 6.0E-14 | 1.99 | 2.3E-08 | 1.90 | 2.3E-06 | 1.81 | 3.7E-03 |
| SM(36:2)/LPC(MHDA) [sn2] | 1.71 | 2.1E-17 | 1.77 | 3.0E-15 | 2.49 | 6.2E-15 | 2.48 | 2.9E-12 | 2.27 | 2.8E-06 |
| PE(38:4)/PC(O-34:2) | 1.72 | 2.1E-17 | 1.72 | 4.5E-14 | 2.13 | 2.9E-10 | 1.98 | 2.9E-07 | 1.80 | 3.3E-03 |
| Cer(d18:1/16:0)/PC(P-32:0) | 1.74 | 2.2E-17 | 1.78 | 9.2E-15 | 1.97 | 1.8E-08 | 1.96 | 5.9E-07 | 1.73 | 6.8E-03 |
| PE(40:6)/PC(P-32:1) | 1.72 | 2.3E-17 | 1.80 | 5.8E-16 | 2.13 | 5.1E-10 | 2.14 | 2.4E-08 | 1.83 | 2.5E-03 |
| PE(38:5)/LPC(24:0) [sn2] | 1.71 | 2.4E-17 | 1.68 | 3.2E-13 | 2.11 | 1.3E-10 | 2.07 | 1.6E-08 | 1.96 | 4.2E-04 |
| DAG(18:0/20:4)/LPC(18:1) [sn1] | 1.74 | 2.4E-17 | 1.87 | 7.3E-17 | 2.37 | 3.4E-12 | 2.59 | 2.0E-11 | 2.64 | 3.0E-06 |
| PC(38:1)/LacCer(d18:1/24:1) | 1.71 | 2.4E-17 | 1.67 | 3.7E-13 | 1.98 | 1.1E-09 | 1.91 | 3.0E-07 | 1.68 | 4.7E-03 |
| PC(36:5)/PC(P-38:6) | 1.74 | 2.5E-17 | 1.65 | 4.7E-12 | 1.99 | 3.0E-08 | 1.86 | 7.6E-06 | 1.82 | 4.2E-03 |
| PC(38:4)/PC(O-38:4) | 1.74 | 2.5E-17 | 1.74 | 8.3E-14 | 2.17 | 5.1E-10 | 2.22 | 2.9E-08 | 2.09 | 2.6E-04 |
| PC(34:1)/LPC(20:2) [sn1] | 1.73 | 2.6E-17 | 1.80 | 1.6E-15 | 2.19 | 1.6E-10 | 2.21 | 9.4E-09 | 1.76 | 5.1E-03 |
| Cer(d18:2/22:0)/PC(O-40:6) | 1.74 | 2.6E-17 | 1.85 | 2.4E-16 | 1.90 | 3.1E-07 | 1.98 | 1.8E-06 | 1.73 | 9.7E-03 |
| PC(40:2)/PC(O-40:6) | 1.74 | 2.8E-17 | 1.78 | 1.9E-14 | 1.97 | 2.0E-08 | 2.14 | 6.1E-08 | 2.07 | 2.0E-04 |
| LPE(P-16:0)/LPC(20:0) [sn2] | 1.72 | 2.8E-17 | 1.72 | 6.8E-14 | 2.29 | 1.7E-12 | 2.50 | 1.2E-11 | 2.00 | 2.9E-04 |
| SM(36:2)/PC(37:2) | 1.73 | 2.8E-17 | 1.86 | 1.0E-16 | 2.50 | 2.3E-13 | 2.79 | 1.2E-12 | 2.23 | 5.1E-05 |
| PE(P-38:6)/PC(17:0_22:6) | 1.71 | 2.9E-17 | 1.70 | 1.8E-13 | 1.87 | 2.0E-08 | 2.06 | 9.7E-08 | 1.71 | 2.4E-03 |
| PC(32:0)/PC(37:2) | 1.73 | 2.9E-17 | 1.65 | 6.4E-12 | 2.21 | 3.5E-11 | 2.23 | 3.9E-09 | 1.90 | 7.8E-04 |
| SM(38:1)/LPC(19:0) [sn2] | 1.67 | 3.0E-17 | 1.73 | 9.8E-15 | 2.08 | 2.4E-13 | 2.17 | 2.7E-12 | 1.79 | 2.3E-04 |
| PE(P-38:6)/PC(37:6) | 1.72 | 3.1E-17 | 1.71 | 2.3E-14 | 1.93 | 1.7E-08 | 2.05 | 5.0E-07 | 1.69 | 6.4E-03 |
| PC(38:4)/LPC(O-24:0) | 1.73 | 3.2E-17 | 1.76 | 8.7E-15 | 2.16 | 1.2E-10 | 2.25 | 2.0E-09 | 1.72 | 6.5E-03 |
| PE(40:6)/SM(d17:1/14:0) | 1.72 | 3.3E-17 | 1.65 | 2.4E-12 | 2.24 | 5.9E-11 | 2.05 | 1.3E-07 | 2.06 | 4.0E-04 |
| Cer(d18:1/20:0)/LPC(15:0) [sn2] | 1.73 | 3.3E-17 | 1.78 | 9.1E-15 | 2.30 | 8.4E-12 | 2.29 | 1.8E-09 | 1.84 | 1.0E-03 |
| DAG(18:1/18:2)/PC(O-34:0) | 1.72 | 3.4E-17 | 1.86 | 5.2E-17 | 1.82 | 4.7E-07 | 1.94 | 1.5E-06 | 1.72 | 7.7E-03 |
| PC(38:5)/LacCer(d18:1/24:1) | 1.73 | 3.4E-17 | 1.67 | 2.6E-12 | 1.98 | 2.1E-08 | 1.85 | 9.8E-06 | 1.71 | 8.7E-03 |
| SM(38:1)/SM(41:2) | 1.71 | 3.4E-17 | 1.75 | 1.7E-14 | 1.83 | 8.9E-08 | 1.88 | 1.6E-06 | 1.94 | 3.5E-04 |
| Cer(d18:1/16:0)/PC(35:3) | 1.76 | 3.5E-17 | 1.85 | 8.8E-16 | 2.15 | 2.4E-09 | 2.13 | 1.4E-07 | 1.75 | 8.1E-03 |
| PE(38:1)/LPC(O-24:1) | 1.68 | 3.8E-17 | 1.66 | 2.3E-13 | 1.94 | 1.9E-09 | 1.87 | 5.1E-07 | 1.89 | 6.8E-04 |
| PE(38:5)/LPC(O-24:1) | 1.70 | 3.8E-17 | 1.65 | 1.9E-12 | 2.08 | 8.2E-10 | 1.99 | 2.1E-07 | 1.82 | 2.5E-03 |
| PE(38:5)/LPC(17:0) [sn2] | 1.69 | 3.8E-17 | 1.61 | 8.1E-12 | 2.11 | 3.6E-11 | 1.97 | 5.6E-08 | 1.89 | 6.2E-04 |
| PE(38:5)/Glc/GalCer(d18:2/20:0) | 1.71 | 3.9E-17 | 1.63 | 8.1E-12 | 1.77 | 1.4E-06 | 1.73 | 3.7E-05 | 1.65 | 8.7E-03 |
| PE(38:1)/LacCer(d18:1/24:1) | 1.69 | 4.0E-17 | 1.66 | 6.1E-13 | 1.88 | 2.1E-08 | 1.78 | 7.6E-06 | 1.78 | 2.4E-03 |
| PE(38:4)/PC(O-38:2) | 1.70 | 4.0E-17 | 1.67 | 5.8E-13 | 1.91 | 2.7E-08 | 1.82 | 5.3E-06 | 1.78 | 3.1E-03 |
| SM(36:2)/LPC(22:0) [sn1] | 1.74 | 4.3E-17 | 1.87 | 6.9E-17 | 2.80 | 7.1E-16 | 3.12 | 6.6E-15 | 2.50 | 6.0E-06 |
| PE(38:5)/LPC(22:1) [sn1] | 1.70 | 4.4E-17 | 1.65 | 1.5E-12 | 2.01 | 2.2E-09 | 1.98 | 1.5E-07 | 1.69 | 7.1E-03 |
| SM(40:1)/PC(P-40:2) | 1.73 | 4.5E-17 | 1.76 | 1.6E-14 | 1.84 | 4.8E-07 | 1.88 | 2.5E-06 | 1.70 | 4.5E-03 |
| Cer(d20:1/24:1)/Glc/GalCer(d18:1/23:0) | 1.69 | 4.5E-17 | 1.71 | 4.0E-14 | 2.11 | 7.6E-11 | 2.22 | 4.8E-10 | 1.76 | 3.5E-03 |
| DAG(18:1/18:3)/LPC(22:6) [sn1] | 1.76 | 4.6E-17 | 1.97 | 3.5E-18 | 1.74 | 1.4E-05 | 1.97 | 3.9E-06 | 1.92 | 2.8E-03 |
| PE(36:2)/PI(38:1) | 1.73 | 4.7E-17 | 1.87 | 5.4E-17 | 1.84 | 5.5E-07 | 1.95 | 1.5E-06 | 1.67 | 1.0E-02 |
| PE(38:5)/PC(33:2) | 1.70 | 4.7E-17 | 1.65 | 2.7E-12 | 1.97 | 8.6E-09 | 1.87 | 2.5E-06 | 1.78 | 2.9E-03 |
| SM(36:2)/LPC(O-22:0) | 1.71 | 4.7E-17 | 1.81 | 2.5E-16 | 2.54 | 7.2E-15 | 2.75 | 1.2E-13 | 2.27 | 9.8E-06 |
| DAG(18:2/20:4)/LPE(16:0) [sn2] | 1.75 | 4.8E-17 | 2.02 | 2.8E-19 | 1.92 | 1.8E-07 | 2.27 | 2.1E-08 | 1.78 | 6.2E-03 |
| PE(40:6)/LPC(MHDA) [sn2] | 1.68 | 4.8E-17 | 1.63 | 1.4E-12 | 2.22 | 1.2E-12 | 2.08 | 3.7E-09 | 2.21 | 1.9E-05 |
| PE(38:4)/PC(O-32:0) | 1.70 | 4.9E-17 | 1.72 | 4.8E-14 | 1.88 | 9.8E-08 | 1.85 | 3.7E-06 | 1.69 | 8.3E-03 |
| PC(38:2)/LPC(O-18:0) | 1.68 | 4.9E-17 | 1.63 | 1.8E-12 | 2.24 | 1.4E-12 | 2.14 | 1.7E-09 | 2.05 | 1.4E-04 |
| DAG(18:2/20:4)/LPE(16:0) [sn1] | 1.75 | 5.0E-17 | 2.03 | 3.2E-19 | 1.92 | 2.0E-07 | 2.31 | 1.6E-08 | 1.76 | 7.4E-03 |
| SM(38:1)/LPC(MHDA) [sn1] | 1.70 | 5.0E-17 | 1.75 | 4.0E-15 | 2.28 | 2.1E-13 | 2.30 | 1.9E-11 | 2.33 | 1.1E-06 |
| PE(36:2)/LPC(15:0) [sn1] | 1.68 | 5.1E-17 | 1.64 | 7.1E-13 | 1.94 | 1.8E-09 | 1.86 | 3.2E-07 | 1.73 | 3.0E-03 |
| PC(40:6)/LPC(P-18:1) | 1.73 | 5.3E-17 | 1.69 | 8.9E-13 | 2.58 | 3.2E-13 | 2.40 | 1.2E-09 | 1.77 | 5.9E-03 |
| PE(38:1)/LPC(17:0) [sn2] | 1.65 | 5.4E-17 | 1.61 | 1.4E-12 | 1.96 | 1.1E-10 | 1.84 | 1.7E-07 | 1.92 | 1.4E-04 |
| PE(38:1)/LPC(24:0) [sn2] | 1.66 | 5.4E-17 | 1.67 | 4.0E-14 | 1.95 | 5.8E-10 | 1.93 | 6.4E-08 | 2.00 | 9.9E-05 |
| SM(32:1)/PC(35:2) | 1.74 | 5.4E-17 | 1.86 | 3.0E-16 | 2.19 | 1.3E-09 | 2.31 | 1.1E-08 | 2.43 | 3.6E-05 |
| PC(38:5)/PC(35:2) | 1.73 | 5.5E-17 | 1.70 | 5.9E-13 | 2.04 | 7.2E-09 | 1.90 | 5.1E-06 | 2.19 | 1.4E-04 |
| DAG(18:1/18:2)/LPC(20:2) [sn2] | 1.73 | 5.5E-17 | 1.99 | 2.1E-19 | 1.96 | 3.3E-08 | 2.16 | 3.2E-08 | 1.75 | 6.5E-03 |
| SM(38:1)/LPC(20:1) [sn1] | 1.73 | 5.6E-17 | 1.85 | 2.2E-16 | 2.28 | 2.4E-11 | 2.51 | 7.3E-11 | 1.84 | 3.3E-03 |
| DAG(18:1/18:3)/PC(O-40:3) | 1.73 | 5.7E-17 | 1.88 | 6.2E-17 | 1.67 | 1.6E-05 | 1.86 | 6.6E-06 | 1.85 | 2.3E-03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| | FL | | NAFLD | | FL (severe) | | NAFLD (severe) | | DM2 | |
|---|---|---|---|---|---|---|---|---|---|---|
| Lipid ratio | OR | p-value | OR | p-value | OR | p-value | OR | p-value | OR | p-value |
| PE(38:1)/PC(P-40:2) | 1.70 | 5.8E-17 | 1.70 | 1.1E-13 | 1.89 | 4.2E-08 | 1.79 | 9.1E-06 | 1.99 | 2.7E-04 |
| LPE(P-16:0)/LPC(20:0) [sn1] | 1.72 | 5.8E-17 | 1.71 | 1.7E-13 | 2.35 | 1.2E-12 | 2.56 | 1.0E-11 | 2.16 | 6.8E-05 |
| PC(38:2)/PC(O-40:3) | 1.69 | 5.9E-17 | 1.75 | 1.7E-15 | 1.82 | 1.1E-08 | 1.92 | 6.4E-08 | 1.57 | 9.8E-03 |
| PC(38:1)/PC(37:2) | 1.70 | 5.9E-17 | 1.71 | 4.3E-14 | 2.16 | 3.6E-11 | 2.23 | 7.0E-10 | 2.25 | 1.7E-05 |
| PC(34:1)/PC(O-38:0) | 1.76 | 6.0E-17 | 1.76 | 3.1E-13 | 2.03 | 8.9E-08 | 2.10 | 1.4E-06 | 1.86 | 4.3E-03 |
| PE(36:2)/LPE(P-20:0) | 1.68 | 6.0E-17 | 1.66 | 2.2E-13 | 1.96 | 7.4E-10 | 1.88 | 1.6E-07 | 1.71 | 4.0E-03 |
| DAG(18:1/18:2)/PC(O-38:2) | 1.71 | 6.2E-17 | 1.81 | 5.5E-16 | 1.82 | 3.4E-07 | 1.91 | 1.7E-06 | 1.72 | 6.3E-03 |
| Cer(d16:1/20:0)/CE(17:0) | 1.74 | 6.2E-17 | 1.94 | 1.7E-17 | 2.06 | 4.4E-09 | 2.10 | 2.9E-07 | 2.06 | 4.1E-04 |
| PE(38:5)/LacCer(d18:1/24:1) | 1.71 | 6.4E-17 | 1.64 | 7.4E-12 | 2.03 | 9.4E-09 | 1.89 | 3.4E-06 | 1.70 | 8.7E-03 |
| Cer(d18:1/20:0)/LPC(15:0) [sn1] | 1.72 | 6.5E-17 | 1.77 | 1.5E-14 | 2.34 | 2.5E-12 | 2.37 | 4.5E-10 | 2.09 | 5.9E-05 |
| SM(32:1)/LPC(MHDA) [sn1] | 1.70 | 6.5E-17 | 1.74 | 1.0E-14 | 2.32 | 4.9E-13 | 2.36 | 3.2E-11 | 2.31 | 4.4E-06 |
| SM(38:1)/LPC(O-20:0) | 1.69 | 6.7E-17 | 1.71 | 4.1E-14 | 2.16 | 1.3E-11 | 2.27 | 2.5E-10 | 2.23 | 1.9E-05 |
| PC(38:1)/LPC(20:0) [sn1] | 1.67 | 6.9E-17 | 1.66 | 1.6E-13 | 2.28 | 2.3E-14 | 2.30 | 3.4E-12 | 2.16 | 5.6E-06 |
| SM(38:1)/PC(35:2) | 1.75 | 7.0E-17 | 1.88 | 2.1E-16 | 2.30 | 7.4E-10 | 2.43 | 1.5E-08 | 2.75 | 5.9E-06 |
| SM(36:1)/PC(O-32:0) | 1.72 | 7.2E-17 | 1.86 | 9.6E-17 | 2.08 | 2.4E-09 | 2.41 | 3.4E-10 | 2.28 | 5.9E-05 |
| SM(36:1)/PC(P-40:4) | 1.73 | 7.3E-17 | 1.83 | 8.1E-16 | 2.61 | 2.5E-13 | 3.05 | 2.3E-13 | 3.08 | 6.0E-07 |
| PI(34:2)/PC(31:0) | 1.72 | 7.5E-17 | 1.67 | 3.5E-12 | 2.21 | 4.2E-10 | 2.06 | 3.2E-07 | 1.78 | 5.8E-03 |
| PE(38:1)/PC(O-34:2) | 1.68 | 7.7E-17 | 1.66 | 4.4E-13 | 2.04 | 5.1E-10 | 1.85 | 1.3E-06 | 2.01 | 2.1E-04 |
| DAG(18:1/18:3)/PC(39:4) | 1.74 | 7.9E-17 | 1.87 | 2.8E-16 | 1.72 | 1.3E-05 | 1.94 | 4.1E-06 | 2.00 | 9.2E-04 |
| SM(38:1)/LPC(20:0) [sn1] | 1.68 | 8.3E-17 | 1.73 | 7.8E-15 | 2.24 | 3.8E-13 | 2.37 | 4.5E-12 | 2.16 | 2.2E-05 |
| PE(40:6)/LPC(20:1) [sn2] | 1.68 | 8.4E-17 | 1.68 | 2.0E-13 | 2.17 | 3.0E-11 | 2.12 | 7.6E-09 | 1.93 | 8.4E-04 |
| PE(38:1)/LPC(24:0) [sn1] | 1.66 | 9.0E-17 | 1.67 | 4.6E-14 | 1.93 | 6.7E-10 | 1.90 | 1.0E-07 | 2.02 | 5.9E-05 |
| DAG(18:1/18:3)/PC(O-34:0) | 1.73 | 9.1E-17 | 1.87 | 2.5E-16 | 1.67 | 2.8E-05 | 1.84 | 2.1E-05 | 2.02 | 7.8E-04 |
| DAG(18:1/18:3)/PC(33:3) | 1.75 | 9.2E-17 | 1.86 | 1.2E-15 | 1.77 | 6.3E-06 | 1.93 | 7.0E-06 | 2.01 | 1.5E-03 |
| PC(36:5)/LPC(24:0) [sn2] | 1.72 | 9.3E-17 | 1.65 | 7.5E-12 | 2.10 | 6.5E-10 | 2.10 | 7.3E-08 | 2.26 | 1.9E-05 |
| PI(32:0)/PC(O-40:6) | 1.67 | 9.5E-17 | 1.59 | 1.6E-11 | 2.07 | 2.4E-11 | 2.01 | 7.3E-09 | 1.63 | 8.1E-03 |
| PI(34:2)/LPC(20:2) [sn1] | 1.68 | 9.9E-17 | 1.69 | 5.3E-14 | 2.22 | 8.1E-13 | 2.14 | 7.9E-10 | 1.76 | 2.4E-03 |
| PE(40:6)/PC(38:7) | 1.69 | 1.0E-16 | 1.80 | 2.7E-16 | 2.13 | 1.9E-11 | 2.12 | 2.7E-09 | 1.81 | 1.6E-03 |
| PE(40:6)/PC(P-38:6) | 1.70 | 1.0E-16 | 1.71 | 8.0E-14 | 2.21 | 5.0E-11 | 2.13 | 1.7E-08 | 1.86 | 2.3E-03 |
| PE(38:4)/LPE(16:0) [sn1] | 1.71 | 1.0E-16 | 1.80 | 2.2E-15 | 2.01 | 1.6E-08 | 2.10 | 1.2E-07 | 1.88 | 2.8E-03 |
| PG(34:1)/LPC(O-24:1) | 1.69 | 1.1E-16 | 1.67 | 4.4E-13 | 2.00 | 1.7E-09 | 1.93 | 2.3E-07 | 1.77 | 2.8E-03 |
| SM(38:1)/LPC(22:0) [sn1] | 1.70 | 1.1E-16 | 1.79 | 9.1E-16 | 2.28 | 8.3E-13 | 2.50 | 1.9E-12 | 2.35 | 7.2E-06 |
| PE(40:6)/LPC(P-18:1) | 1.66 | 1.1E-16 | 1.62 | 2.3E-12 | 2.06 | 6.5E-11 | 1.94 | 7.7E-08 | 1.79 | 1.8E-03 |
| PI(34:2)/LPE(16:0) [sn1] | 1.70 | 1.2E-16 | 1.73 | 3.9E-14 | 2.30 | 9.7E-12 | 2.38 | 4.0E-10 | 1.83 | 2.7E-03 |
| SM(41:0)/LPC(18:2) [sn1] | 1.70 | 1.2E-16 | 1.78 | 2.2E-15 | 2.48 | 5.3E-14 | 2.69 | 8.9E-13 | 2.08 | 2.1E-04 |
| SM(36:2)/LPC(20:0) [sn2] | 1.70 | 1.2E-16 | 1.79 | 1.4E-15 | 2.62 | 4.1E-15 | 2.84 | 9.9E-14 | 2.15 | 8.8E-05 |
| PC(38:5)/PC(39:4) | 1.69 | 1.2E-16 | 1.61 | 1.6E-11 | 1.95 | 1.6E-08 | 1.87 | 3.1E-06 | 1.92 | 1.0E-03 |
| DAG(18:1/18:3)/PC(P-32:0) | 1.73 | 1.2E-16 | 1.89 | 9.2E-17 | 1.71 | 1.5E-05 | 1.92 | 6.3E-06 | 1.98 | 1.2E-03 |
| PC(36:4)/LPE(20:1) [sn1] | 1.78 | 1.2E-16 | 1.85 | 1.1E-14 | 2.47 | 8.9E-11 | 2.82 | 1.4E-10 | 2.05 | 1.7E-03 |
| Cer(d20:1/24:1)/Glc/GalCer(d18:2/22:0) | 1.67 | 1.3E-16 | 1.64 | 9.2E-13 | 1.96 | 2.3E-09 | 2.00 | 3.1E-08 | 1.65 | 8.2E-03 |
| PC(38:1)/LPC(O-24:1) | 1.68 | 1.4E-16 | 1.68 | 1.7E-13 | 2.21 | 1.1E-11 | 2.24 | 1.0E-09 | 2.00 | 3.4E-04 |
| SM(38:1)/SM(d17:1/14:0) | 1.71 | 1.4E-16 | 1.70 | 4.2E-13 | 1.92 | 4.6E-08 | 1.86 | 4.0E-06 | 1.75 | 5.2E-03 |
| PE(38:1)/PC(39:4) | 1.68 | 1.4E-16 | 1.64 | 1.9E-12 | 1.94 | 1.1E-08 | 1.85 | 2.0E-06 | 2.00 | 3.1E-04 |
| PE(34:1)/LPC(18:2) [sn2] | 1.64 | 1.6E-16 | 1.62 | 4.7E-13 | 1.92 | 1.6E-10 | 1.85 | 5.5E-08 | 1.61 | 6.2E-03 |
| DAG(18:1/18:3)/PC(O-38:2) | 1.73 | 1.6E-16 | 1.84 | 1.5E-15 | 1.68 | 2.6E-05 | 1.83 | 2.6E-05 | 2.03 | 5.6E-04 |
| SM(36:1)/LPC(22:0) [sn2] | 1.71 | 1.6E-16 | 1.84 | 4.5E-16 | 2.53 | 5.1E-14 | 2.84 | 1.0E-13 | 2.36 | 1.6E-05 |
| DAG(18:1/18:3)/PC(P-40:4) | 1.73 | 1.6E-16 | 1.88 | 3.2E-16 | 1.78 | 4.1E-06 | 2.01 | 1.8E-06 | 2.15 | 2.8E-04 |
| Cer(d18:2/24:1)/PC(O-40:6) | 1.72 | 1.7E-16 | 1.78 | 1.3E-14 | 1.98 | 6.7E-08 | 1.99 | 1.6E-06 | 1.73 | 9.5E-03 |
| PC(38:5)/LPC(P-16:0) | 1.70 | 1.8E-16 | 1.66 | 3.2E-12 | 2.18 | 1.7E-10 | 2.08 | 1.3E-07 | 1.95 | 1.1E-03 |
| Cer(d18:2/22:0)/LPC(17:0) [sn1] | 1.70 | 1.8E-16 | 1.73 | 8.6E-14 | 2.26 | 8.4E-11 | 2.28 | 9.2E-09 | 1.85 | 2.5E-03 |
| PI(34:2)/PC(O-38:0) | 1.71 | 1.8E-16 | 1.65 | 5.3E-12 | 2.25 | 8.2E-11 | 2.14 | 4.3E-08 | 1.87 | 2.3E-03 |
| PE(36:2)/Glc/GalCer(d18:1/23:0) | 1.70 | 1.8E-16 | 1.71 | 1.7E-13 | 1.84 | 5.7E-07 | 1.84 | 8.8E-06 | 1.73 | 6.9E-03 |
| SM(36:1)/LPC(O-18:0) | 1.66 | 1.9E-16 | 1.68 | 9.9E-14 | 2.27 | 3.3E-13 | 2.33 | 1.2E-11 | 2.25 | 2.9E-06 |
| Cer(d16:1/20:0)/LPC(20:2) [sn2] | 1.77 | 1.9E-16 | 2.06 | 8.6E-19 | 2.20 | 5.5E-09 | 2.27 | 9.4E-08 | 2.31 | 1.9E-04 |
| PE(34:1)/LPE(P-20:0) | 1.64 | 1.9E-16 | 1.58 | 4.6E-12 | 1.90 | 3.0E-10 | 1.80 | 1.7E-07 | 1.60 | 7.1E-03 |
| SM(38:1)/PC(37:2) | 1.71 | 1.9E-16 | 1.79 | 4.5E-15 | 2.15 | 7.6E-10 | 2.38 | 1.4E-09 | 2.21 | 9.1E-05 |
| PC(40:6)/LacCer(d18:1/16:0) | 1.72 | 2.0E-16 | 1.73 | 2.4E-13 | 2.51 | 8.9E-12 | 2.45 | 3.3E-09 | 2.03 | 1.0E-03 |
| PE(34:1)/LPC(15:0) [sn1] | 1.64 | 2.1E-16 | 1.57 | 1.4E-11 | 1.89 | 5.1E-10 | 1.78 | 2.4E-07 | 1.61 | 5.9E-03 |
| PG(34:1)/PC(P-40:2) | 1.71 | 2.1E-16 | 1.71 | 3.9E-13 | 1.96 | 5.1E-08 | 1.85 | 6.2E-06 | 1.84 | 1.3E-03 |
| DAG(18:1/18:3)/SM(41:2) | 1.72 | 2.1E-16 | 1.84 | 1.1E-15 | 1.65 | 4.4E-05 | 1.80 | 3.8E-05 | 1.92 | 1.6E-03 |
| SM(41:0)/LPC(18:2) [sn2] | 1.70 | 2.1E-16 | 1.79 | 2.9E-15 | 2.52 | 2.1E-13 | 2.75 | 2.5E-12 | 2.00 | 7.5E-04 |
| PE(38:4)/Glc/GalCer(d18:2/22:0) | 1.68 | 2.1E-16 | 1.65 | 1.6E-12 | 1.76 | 8.8E-07 | 1.70 | 3.7E-05 | 1.67 | 8.4E-03 |
| PC(38:5)/PC(P-32:0) | 1.69 | 2.2E-16 | 1.65 | 2.6E-12 | 1.92 | 3.5E-08 | 1.82 | 7.3E-06 | 1.89 | 1.4E-03 |
| PG(34:1)/SM(d17:1/14:0) | 1.70 | 2.2E-16 | 1.66 | 4.1E-12 | 1.99 | 2.7E-08 | 1.83 | 1.1E-05 | 1.73 | 6.4E-03 |
| Cer(d20:1/24:1)/PC(O-34:0) | 1.65 | 2.2E-16 | 1.64 | 5.4E-13 | 1.98 | 4.8E-10 | 2.00 | 1.1E-08 | 1.67 | 6.1E-03 |
| LPC(20:3) [sn2]/LPC(18:1) [sn1] | 1.69 | 2.3E-16 | 1.74 | 2.5E-14 | 2.41 | 4.9E-13 | 2.67 | 1.7E-12 | 1.93 | 1.3E-03 |
| PC(36:5)/LacCer(d18:2/24:1) | 1.69 | 2.4E-16 | 1.54 | 1.2E-09 | 1.76 | 2.9E-06 | 1.66 | 1.8E-04 | 1.70 | 7.5E-03 |
| PE(38:1)/LPC(17:0) [sn1] | 1.64 | 2.4E-16 | 1.57 | 1.1E-11 | 1.92 | 4.4E-10 | 1.80 | 5.1E-07 | 1.89 | 2.3E-04 |
| PE(38:5)/PC(O-38:0) | 1.69 | 2.4E-16 | 1.64 | 9.5E-12 | 2.02 | 9.1E-09 | 1.92 | 1.9E-06 | 1.98 | 5.9E-04 |
| PE(38:1)/PC(O-40:3) | 1.68 | 2.5E-16 | 1.69 | 2.1E-13 | 1.83 | 1.0E-07 | 1.79 | 6.3E-06 | 1.83 | 1.6E-03 |
| PE(34:1)/LPC(O-24:0) | 1.65 | 2.5E-16 | 1.60 | 3.6E-12 | 1.88 | 5.5E-09 | 1.82 | 5.3E-07 | 1.63 | 7.9E-03 |
| PE(36:2)/LPC(O-24:0) | 1.67 | 2.8E-16 | 1.67 | 3.2E-13 | 1.88 | 4.5E-08 | 1.87 | 9.7E-07 | 1.73 | 5.2E-03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| PG(34:1)/LPE(16:0) [sn1] | 1.71 | 2.8E−16 | 1.77 | 2.5E−14 | 2.05 | 9.5E−09 | 2.07 | 1.6E−07 | 2.08 | 5.0E−04 |
| SM(32:1)/PC(O-40:6) | 1.69 | 2.8E−16 | 1.78 | 1.8E−15 | 1.78 | 1.8E−06 | 1.92 | 1.8E−06 | 1.72 | 7.2E−03 |
| Cer(d18:1/20:0)/LPC(O-16:0) | 1.69 | 2.9E−16 | 1.75 | 2.1E−14 | 2.23 | 7.2E−12 | 2.22 | 8.3E−10 | 1.84 | 5.0E−04 |
| PE(38:4)/LPE(16:0) [sn2] | 1.70 | 3.0E−16 | 1.78 | 4.7E−15 | 1.98 | 2.7E−08 | 2.03 | 3.0E−07 | 1.87 | 2.6E−03 |
| PC(38:1)/LPC(20:0) [sn2] | 1.65 | 3.1E−16 | 1.64 | 4.1E−13 | 2.20 | 1.6E−13 | 2.23 | 1.6E−11 | 2.03 | 3.7E−05 |
| PC(34:5)/SM(d17:1/14:0) | 1.72 | 3.1E−16 | 1.62 | 8.9E−11 | 1.81 | 2.0E−06 | 1.62 | 6.2E−04 | 1.72 | 9.8E−03 |
| PC(38:2)/LPC(O-18:1) | 1.66 | 3.1E−16 | 1.60 | 9.9E−12 | 2.11 | 2.8E−11 | 1.99 | 2.9E−08 | 1.68 | 7.5E−03 |
| PC(40:6)/LPC(P-18:0) | 1.69 | 3.1E−16 | 1.67 | 1.6E−12 | 2.72 | 5.8E−15 | 2.57 | 4.2E−11 | 2.19 | 1.3E−04 |
| PC(36:5)/LPC(17:0) [sn2] | 1.68 | 3.3E−16 | 1.56 | 3.9E−10 | 2.11 | 2.5E−10 | 1.97 | 4.8E−07 | 2.15 | 6.3E−05 |
| Cer(d18:1/16:0)/PC(P-40:4) | 1.71 | 3.4E−16 | 1.70 | 8.9E−13 | 2.20 | 4.5E−10 | 2.23 | 2.1E−08 | 2.14 | 2.2E−04 |
| PE(40:6)/LPC(O-24:1) | 1.65 | 3.4E−16 | 1.63 | 1.7E−12 | 2.11 | 4.4E−11 | 2.04 | 1.5E−08 | 1.96 | 4.3E−04 |
| CE(16:2)/LPC(18:2) [sn2] | 1.71 | 3.6E−16 | 1.70 | 8.5E−13 | 2.56 | 5.8E−13 | 2.42 | 9.1E−10 | 1.71 | 7.9E−03 |
| PE(38:1)/PC(P-32:0) | 1.66 | 4.1E−16 | 1.65 | 8.0E−13 | 1.88 | 3.4E−08 | 1.79 | 5.9E−06 | 1.95 | 5.0E−04 |
| PE(36:5)/PC(37:6) | 1.66 | 4.1E−16 | 1.59 | 4.9E−11 | 1.80 | 3.6E−07 | 1.64 | 1.5E−04 | 1.74 | 3.5E−03 |
| DAG(18:2/20:4)/LPE(P-18:0) | 1.69 | 4.2E−16 | 1.83 | 3.1E−16 | 1.93 | 4.2E−08 | 2.06 | 1.5E−07 | 1.72 | 8.2E−03 |
| LPC(20:5) [sn2]/LPC(22:1) [sn1] | 1.74 | 4.2E−16 | 1.62 | 1.5E−10 | 1.92 | 1.1E−06 | 1.93 | 1.7E−05 | 1.93 | 3.0E−03 |
| PE(40:6)/LPC(22:6) [sn2] | 1.66 | 4.3E−16 | 1.69 | 8.0E−14 | 1.98 | 2.7E−09 | 1.90 | 5.4E−07 | 1.81 | 2.4E−03 |
| SM(38:1)/LPC(20:0) [sn2] | 1.66 | 4.5E−16 | 1.71 | 2.7E−14 | 2.17 | 2.5E−12 | 2.30 | 1.9E−11 | 2.01 | 1.3E−04 |
| Cer(d18:2/24:1)/LPC(MHDA) [sn2] | 1.68 | 4.6E−16 | 1.69 | 6.3E−13 | 2.35 | 2.6E−12 | 2.24 | 3.8E−09 | 2.04 | 1.5E−04 |
| DAG(18:1/18:3)/PC(O-38:0) | 1.71 | 4.6E−16 | 1.87 | 4.3E−16 | 1.69 | 2.2E−05 | 1.89 | 1.1E−05 | 2.08 | 5.1E−04 |
| SM(41:0)/LPC(20:2) [sn2] | 1.70 | 4.7E−16 | 1.82 | 8.7E−16 | 2.34 | 1.4E−11 | 2.61 | 2.6E−11 | 1.94 | 1.3E−03 |
| SM(38:1)/LPC(P-18:0) | 1.64 | 4.8E−16 | 1.66 | 1.4E−13 | 2.07 | 4.9E−12 | 2.04 | 1.1E−09 | 1.91 | 1.4E−04 |
| PE(38:4)/PC(O-38:0) | 1.68 | 4.8E−16 | 1.69 | 3.5E−13 | 1.91 | 4.9E−08 | 1.88 | 2.5E−06 | 1.83 | 2.7E−03 |
| DAG(18:1/18:3)/LPC(O-24:0) | 1.71 | 4.9E−16 | 1.86 | 3.9E−16 | 1.73 | 8.5E−06 | 1.98 | 2.5E−06 | 2.05 | 5.7E−04 |
| PE(40:6)/LacCer(d18:1/24:1) | 1.66 | 5.0E−16 | 1.63 | 5.5E−12 | 2.07 | 5.2E−10 | 1.97 | 2.5E−07 | 1.87 | 1.5E−03 |
| DAG(18:1/18:3)/LPC(O-16:0) | 1.71 | 5.0E−16 | 1.84 | 1.1E−15 | 1.80 | 2.4E−06 | 2.01 | 1.9E−06 | 1.98 | 1.1E−03 |
| LPC(20:3) [sn2]/LPC(18:1) [sn2] | 1.69 | 5.0E−16 | 1.79 | 5.3E−15 | 2.43 | 1.3E−12 | 2.79 | 1.4E−12 | 1.96 | 1.2E−03 |
| PC(38:4)/LPC(15:0) [sn1] | 1.70 | 5.1E−16 | 1.69 | 1.9E−12 | 2.37 | 9.1E−12 | 2.35 | 2.4E−09 | 1.74 | 7.1E−03 |
| Cer(d20:1/24:1)/Glc/GalCer(d18:2/23:0) | 1.66 | 5.1E−16 | 1.62 | 6.0E−12 | 1.89 | 2.3E−08 | 1.97 | 1.1E−07 | 1.66 | 8.2E−03 |
| SM(36:1)/LPC(17:0) [sn1] | 1.66 | 5.3E−16 | 1.66 | 6.3E−13 | 2.34 | 1.7E−13 | 2.40 | 8.0E−12 | 2.11 | 3.3E−05 |
| DAG(18:1/18:2)/LPC(O-24:0) | 1.67 | 5.3E−16 | 1.82 | 2.3E−16 | 1.86 | 1.0E−07 | 2.04 | 1.1E−07 | 1.72 | 6.2E−03 |
| PE(38:1)/LPE(20:1) [sn1] | 1.69 | 5.4E−16 | 1.74 | 2.9E−14 | 2.03 | 2.5E−09 | 2.10 | 2.7E−08 | 2.01 | 9.2E−04 |
| PE(40:6)/LPC(20:0) [sn2] | 1.65 | 5.5E−16 | 1.62 | 3.1E−12 | 2.15 | 5.9E−12 | 2.10 | 2.4E−09 | 2.02 | 1.5E−04 |
| DAG(18:1/18:3)/PC(O-32:0) | 1.70 | 5.6E−16 | 1.85 | 5.0E−16 | 1.62 | 7.5E−05 | 1.81 | 2.6E−05 | 1.94 | 1.5E−03 |
| PE(38:1)/SM(41:2) | 1.66 | 5.6E−16 | 1.60 | 1.2E−11 | 1.83 | 1.1E−07 | 1.68 | 4.6E−05 | 1.89 | 6.8E−04 |
| PE(38:5)/PC(P-40:2) | 1.67 | 5.8E−16 | 1.63 | 8.3E−12 | 1.90 | 6.2E−08 | 1.79 | 9.7E−06 | 1.82 | 1.9E−03 |
| PC(36:1)/LPC(18:1) [sn2] | 1.66 | 6.0E−16 | 1.77 | 1.3E−15 | 2.35 | 4.2E−13 | 2.39 | 6.0E−11 | 1.88 | 1.4E−03 |
| PC(38:1)/LPC(P-18:0) | 1.64 | 6.5E−16 | 1.61 | 2.7E−12 | 2.14 | 6.6E−13 | 2.03 | 1.4E−09 | 1.98 | 5.6E−05 |
| PE(40:6)/LPC(P-18:0) | 1.63 | 6.5E−16 | 1.60 | 5.7E−12 | 2.12 | 6.8E−12 | 2.00 | 1.2E−08 | 1.99 | 1.8E−04 |
| PE(38:1)/PC(O-34:0) | 1.65 | 6.6E−16 | 1.63 | 3.6E−12 | 1.82 | 1.4E−07 | 1.71 | 2.9E−05 | 1.96 | 3.7E−04 |
| PE(34:1)/PC(O-40:4) | 1.65 | 6.6E−16 | 1.58 | 2.8E−11 | 1.91 | 1.8E−08 | 1.81 | 3.2E−06 | 1.77 | 2.8E−03 |
| PE(38:1)/PC(O-38:2) | 1.65 | 7.2E−16 | 1.60 | 1.9E−11 | 1.85 | 6.7E−08 | 1.71 | 3.2E−05 | 2.01 | 2.0E−04 |
| Cer(d16:1/20:0)/LPC(O-16:0) | 1.71 | 7.3E−16 | 1.82 | 3.0E−15 | 2.16 | 9.9E−10 | 2.13 | 9.4E−08 | 2.02 | 6.9E−04 |
| PC(36:5)/SM(39:2) | 1.65 | 7.3E−16 | 1.59 | 2.9E−11 | 1.85 | 1.7E−08 | 1.84 | 2.0E−06 | 1.63 | 8.2E−03 |
| Cer(d18:1/20:0)/LPC(20:2) [sn2] | 1.69 | 7.4E−16 | 1.91 | 2.1E−17 | 2.25 | 1.3E−10 | 2.41 | 1.1E−09 | 2.10 | 2.9E−04 |
| PC(38:4)/LPC(18:2) [sn2] | 1.70 | 7.5E−16 | 1.80 | 3.8E−15 | 2.47 | 2.6E−12 | 2.51 | 2.3E−10 | 1.76 | 7.4E−03 |
| PE(38:5)/LPC(17:0) [sn1] | 1.65 | 7.6E−16 | 1.56 | 1.4E−10 | 2.04 | 3.5E−10 | 1.91 | 2.8E−07 | 1.83 | 1.3E−03 |
| Cer(d20:1/24:1)/PC(P-40:2) | 1.64 | 7.8E−16 | 1.65 | 4.5E−13 | 1.93 | 2.6E−09 | 1.95 | 4.6E−08 | 1.67 | 7.1E−03 |
| PI(34:2)/LPE(16:0) [sn2] | 1.67 | 8.1E−16 | 1.70 | 1.4E−13 | 2.20 | 3.9E−11 | 2.23 | 2.1E−09 | 1.81 | 2.9E−03 |
| PE(38:5)/PC(31:0) | 1.67 | 8.7E−16 | 1.62 | 2.1E−11 | 1.89 | 9.6E−08 | 1.78 | 1.5E−05 | 1.87 | 1.6E−03 |
| Cer(d18:1/16:0)/Glc/GalCer(d18:2/22:0) | 1.67 | 8.9E−16 | 1.62 | 1.3E−11 | 1.67 | 1.8E−05 | 1.62 | 3.3E−04 | 1.69 | 8.8E−03 |
| PE(38:1)/PC(O-32:1) | 1.66 | 8.9E−16 | 1.70 | 1.4E−13 | 1.83 | 2.5E−07 | 1.77 | 1.6E−05 | 1.82 | 3.2E−03 |
| PE(38:5)/PC(P-32:0) | 1.67 | 9.0E−16 | 1.63 | 1.5E−11 | 1.98 | 1.8E−08 | 1.88 | 2.7E−06 | 1.82 | 2.6E−03 |
| PE(36:2)/PE(P-36:2) | 1.66 | 9.4E−16 | 1.65 | 1.6E−12 | 2.11 | 3.1E−10 | 2.02 | 1.8E−07 | 1.96 | 6.3E−04 |
| SM(36:1)/LPC(24:0) [sn1] | 1.68 | 9.7E−16 | 1.90 | 1.7E−17 | 2.41 | 3.6E−13 | 2.87 | 5.8E−14 | 2.50 | 2.1E−06 |
| PG(34:1)/LPE(16:0) [sn2] | 1.69 | 9.7E−16 | 1.74 | 5.8E−14 | 2.00 | 1.7E−08 | 2.00 | 3.9E−07 | 2.05 | 5.1E−04 |
| PC(40:6)/LPC(20:1) [sn2] | 1.72 | 9.8E−16 | 1.75 | 2.7E−13 | 2.79 | 1.0E−12 | 2.84 | 1.5E−10 | 1.94 | 3.4E−03 |
| Cer(d20:1/24:1)/PC(O-34:2) | 1.64 | 9.8E−16 | 1.63 | 1.3E−12 | 2.14 | 8.5E−12 | 2.09 | 1.7E−09 | 1.67 | 6.3E−03 |
| PE(38:4)/LPC(20:2) [sn1] | 1.65 | 1.0E−15 | 1.71 | 4.8E−14 | 1.97 | 2.9E−09 | 1.93 | 2.9E−07 | 1.76 | 3.5E−03 |
| SM(36:2)/LPC(22:0) [sn2] | 1.69 | 1.0E−15 | 1.83 | 7.5E−16 | 2.71 | 3.4E−15 | 3.00 | 4.0E−14 | 2.32 | 4.0E−05 |
| PC(38:5)/LPC(O-18:0) | 1.67 | 1.1E−15 | 1.61 | 5.9E−11 | 2.13 | 5.5E−10 | 2.03 | 5.0E−07 | 2.15 | 1.6E−04 |
| PC(40:6)/LPC(MHDA) [sn1] | 1.69 | 1.1E−15 | 1.68 | 2.6E−12 | 2.86 | 8.6E−15 | 2.75 | 2.2E−11 | 2.61 | 7.4E−05 |
| PC(38:1)/LPC(22:0) [sn1] | 1.66 | 1.1E−15 | 1.68 | 2.0E−13 | 2.31 | 2.1E−13 | 2.40 | 5.6E−12 | 2.31 | 2.9E−06 |
| SM(38:1)/LPC(20:1) [sn2] | 1.68 | 1.1E−15 | 1.80 | 3.3E−15 | 2.13 | 1.1E−09 | 2.35 | 2.0E−09 | 1.73 | 9.0E−03 |
| PC(40:6)/LPC(O-24:1) | 1.68 | 1.2E−15 | 1.68 | 1.3E−12 | 2.60 | 2.7E−13 | 2.59 | 8.9E−11 | 2.02 | 7.3E−04 |
| CE(16:2)/Glc/GalCer(d18:2/24:0) | 1.69 | 1.2E−15 | 1.60 | 1.2E−10 | 2.30 | 1.1E−10 | 2.08 | 2.5E−07 | 1.91 | 1.7E−03 |
| PE(40:6)/LPC(22:0) [sn2] | 1.64 | 1.2E−15 | 1.63 | 2.1E−12 | 2.17 | 6.8E−12 | 2.11 | 2.3E−09 | 2.07 | 9.5E−05 |
| SM(36:1)/PC(35:3) | 1.68 | 1.2E−15 | 1.88 | 6.4E−17 | 2.27 | 4.1E−11 | 2.62 | 2.7E−11 | 2.09 | 2.4E−04 |
| SM(36:1)/PC(O-38:0) | 1.70 | 1.3E−15 | 1.83 | 2.4E−15 | 2.26 | 4.2E−10 | 2.59 | 2.1E−10 | 2.68 | 4.4E−06 |
| PC(38:5)/PC(O-38:2) | 1.66 | 1.3E−15 | 1.57 | 2.7E−10 | 1.86 | 1.7E−07 | 1.69 | 9.5E−05 | 1.98 | 6.4E−04 |
| SM(44:2)/PC(O-40:6) | 1.68 | 1.3E−15 | 1.71 | 3.4E−13 | 2.01 | 8.7E−09 | 2.20 | 2.1E−08 | 2.13 | 1.0E−04 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| PC(40:6)/LPC(20:0) [sn1] | 1.70 | 1.3E−15 | 1.69 | 2.6E−12 | 2.94 | 5.5E−15 | 2.97 | 2.7E−12 | 2.41 | 4.7E−05 |
| PE(40:6)/PC(O-32:1) | 1.67 | 1.3E−15 | 1.70 | 2.8E−13 | 2.11 | 1.8E−09 | 2.06 | 1.8E−07 | 1.97 | 1.5E−03 |
| PE(38:5)/LPE(16:0) [sn1] | 1.68 | 1.4E−15 | 1.66 | 4.2E−12 | 2.00 | 1.7E−08 | 1.98 | 6.6E−07 | 2.00 | 8.0E−04 |
| DAG(18:1/18:3)/LPE(16:0) [sn2] | 1.71 | 1.4E−15 | 1.94 | 2.9E−17 | 1.68 | 4.1E−05 | 1.98 | 4.0E−06 | 2.10 | 5.1E−04 |
| SM(36:2)/PC(P-40:4) | 1.69 | 1.4E−15 | 1.81 | 2.5E−15 | 2.73 | 1.0E−14 | 3.03 | 9.3E−14 | 2.72 | 1.9E−06 |
| PE(38:5)/LPE(16:0) [sn2] | 1.68 | 1.4E−15 | 1.67 | 3.0E−12 | 2.00 | 2.0E−08 | 1.97 | 9.1E−07 | 2.03 | 6.9E−04 |
| Cer(d18:1/16:0)/PC(P-40:2) | 1.67 | 1.5E−15 | 1.70 | 5.7E−13 | 1.78 | 1.2E−06 | 1.72 | 4.2E−05 | 1.65 | 4.3E−03 |
| PE(38:1)/PC(31:0) | 1.66 | 1.5E−15 | 1.65 | 3.6E−12 | 1.83 | 3.5E−07 | 1.71 | 5.3E−05 | 2.09 | 2.7E−04 |
| DAG(18:1/18:3)/LPE(16:0) [sn1] | 1.71 | 1.5E−15 | 1.94 | 4.0E−17 | 1.67 | 4.4E−05 | 2.00 | 3.4E−06 | 2.08 | 5.8E−04 |
| SM(41:0)/PC(P-40:5) | 1.68 | 1.5E−15 | 1.73 | 1.0E−13 | 2.43 | 1.5E−12 | 2.60 | 1.8E−11 | 1.88 | 2.0E−03 |
| PC(38:5)/LPE(P-20:0) | 1.67 | 1.7E−15 | 1.62 | 2.4E−11 | 2.15 | 1.6E−10 | 2.02 | 2.1E−07 | 1.98 | 5.2E−04 |
| DAG(18:1/18:3)/Glc/GalCer(d18:1/23:0) | 1.69 | 1.7E−15 | 1.85 | 9.6E−16 | 1.62 | 9.4E−05 | 1.84 | 2.8E−05 | 2.00 | 9.2E−04 |
| PG(34:1)/LPC(17:0) [sn2] | 1.63 | 1.7E−15 | 1.59 | 1.7E−11 | 1.95 | 3.6E−10 | 1.84 | 2.0E−07 | 1.78 | 9.8E−04 |
| PE(40:6)/PC(P-32:0) | 1.65 | 1.8E−15 | 1.64 | 3.4E−12 | 2.14 | 3.4E−10 | 2.06 | 8.7E−08 | 2.11 | 2.7E−04 |
| PE(38:1)/Glc/GalCer(d18:2/22:0) | 1.64 | 1.8E−15 | 1.60 | 2.0E−11 | 1.74 | 1.3E−06 | 1.64 | 1.2E−04 | 1.90 | 7.7E−04 |
| DAG(18:2/18:2)/PC(O-40:6) | 1.68 | 1.8E−15 | 1.83 | 1.4E−15 | 1.68 | 1.7E−05 | 1.82 | 1.2E−05 | 1.92 | 9.8E−04 |
| PE(38:4)/PC(31:0) | 1.67 | 1.9E−15 | 1.70 | 7.6E−13 | 1.82 | 6.6E−07 | 1.79 | 2.5E−05 | 1.73 | 7.4E−03 |
| SM(36:2)/PC(O-32:0) | 1.67 | 1.9E−15 | 1.83 | 3.6E−16 | 2.24 | 6.9E−11 | 2.47 | 8.8E−11 | 2.15 | 2.0E−04 |
| SM(36:1)/LPC(24:0) [sn2] | 1.67 | 1.9E−15 | 1.88 | 4.4E−17 | 2.40 | 5.2E−13 | 2.90 | 4.8E−14 | 2.26 | 9.9E−06 |
| PC(34:2)/PC(35:2) | 1.68 | 2.0E−15 | 1.63 | 2.8E−11 | 2.17 | 2.9E−09 | 1.94 | 6.2E−06 | 2.24 | 1.1E−04 |
| CE(16:2)/LacCer(d18:1/24:0) | 1.68 | 2.0E−15 | 1.65 | 1.0E−11 | 2.07 | 7.5E−11 | 2.23 | 1.3E−08 | 1.73 | 5.1E−03 |
| PE(38:5)/PC(O-34:2) | 1.66 | 2.0E−15 | 1.60 | 4.6E−11 | 2.07 | 1.9E−09 | 1.88 | 2.0E−06 | 1.87 | 1.8E−03 |
| PC(36:5)/LPC(17:0) [sn1] | 1.66 | 2.0E−15 | 1.52 | 3.3E−09 | 2.06 | 1.2E−09 | 1.92 | 1.5E−06 | 2.11 | 1.1E−04 |
| SM(32:1)/LPC(MHDA) [sn2] | 1.65 | 2.0E−15 | 1.65 | 1.4E−12 | 2.12 | 1.9E−11 | 2.10 | 2.4E−09 | 2.10 | 2.6E−05 |
| PE(38:1)/LPC(20:2) [sn1] | 1.63 | 2.1E−15 | 1.65 | 3.6E−13 | 1.90 | 4.6E−09 | 1.81 | 1.2E−06 | 1.96 | 1.9E−04 |
| DAG(18:1/18:2)/LPE(16:0) [sn2] | 1.68 | 2.1E−15 | 1.92 | 6.9E−18 | 1.83 | 6.1E−07 | 2.10 | 1.3E−07 | 1.74 | 7.0E−03 |
| PC(38:5)/LPC(O-18:1) | 1.67 | 2.1E−15 | 1.59 | 1.4E−10 | 2.07 | 4.2E−09 | 1.92 | 3.6E−06 | 1.83 | 3.4E−03 |
| PC(38:4)/PC(P-38:4) | 1.68 | 2.3E−15 | 1.70 | 1.8E−12 | 2.37 | 2.8E−11 | 2.28 | 2.3E−08 | 1.95 | 1.7E−03 |
| DAG(18:1/18:2)/LPE(16:0) [sn1] | 1.68 | 2.3E−15 | 1.93 | 8.1E−18 | 1.83 | 6.4E−07 | 2.14 | 8.9E−08 | 1.72 | 8.1E−03 |
| PE(40:6)/PC(P-40:2) | 1.66 | 2.3E−15 | 1.65 | 3.5E−12 | 2.07 | 1.9E−09 | 1.98 | 4.5E−07 | 2.02 | 2.2E−04 |
| SM(36:1)/LPC(17:0) [sn2] | 1.63 | 2.4E−15 | 1.66 | 4.5E−13 | 2.14 | 7.4E−13 | 2.21 | 3.1E−11 | 1.95 | 3.8E−05 |
| CE(20:3)/LacCer(d18:1/24:0) | 1.66 | 2.4E−15 | 1.71 | 1.8E−13 | 2.46 | 1.4E−12 | 2.90 | 7.1E−13 | 1.71 | 8.5E−03 |
| SM(38:1)/LPC(22:0) [sn2] | 1.65 | 2.4E−15 | 1.75 | 7.8E−15 | 2.23 | 2.8E−12 | 2.41 | 9.7E−12 | 2.16 | 4.7E−05 |
| PE(38:5)/PC(O-40:3) | 1.65 | 2.5E−15 | 1.63 | 7.3E−12 | 1.82 | 1.5E−07 | 1.79 | 6.3E−06 | 1.68 | 7.5E−03 |
| PE(38:5)/SM(41:2) | 1.65 | 2.6E−15 | 1.57 | 2.8E−10 | 1.89 | 8.3E−08 | 1.75 | 2.7E−05 | 1.75 | 4.2E−03 |
| PE(40:6)/LPC(24:0) [sn2] | 1.63 | 2.6E−15 | 1.64 | 1.2E−12 | 2.13 | 2.1E−11 | 2.12 | 2.6E−09 | 2.09 | 8.2E−05 |
| SM(38:1)/LPC(MHDA) [sn2] | 1.64 | 2.6E−15 | 1.66 | 7.9E−13 | 2.08 | 2.1E−11 | 2.04 | 2.8E−09 | 2.08 | 8.9E−06 |
| PE(38:1)/PC(O-38:0) | 1.64 | 2.6E−15 | 1.62 | 4.8E−12 | 1.85 | 7.9E−08 | 1.77 | 1.1E−05 | 2.05 | 2.0E−04 |
| PC(38:5)/SM(41:2) | 1.65 | 2.6E−15 | 1.56 | 2.6E−10 | 1.80 | 4.7E−07 | 1.64 | 1.8E−04 | 1.79 | 3.2E−03 |
| PE(38:1)/PI(38:1) | 1.66 | 2.8E−15 | 1.77 | 5.4E−15 | 1.81 | 4.9E−07 | 1.82 | 7.1E−06 | 2.01 | 3.8E−04 |
| PE(38:1)/PC(P-40:4) | 1.64 | 2.8E−15 | 1.62 | 8.0E−12 | 1.95 | 9.2E−09 | 1.87 | 1.7E−06 | 2.09 | 1.2E−04 |
| PE(40:6)/LPC(24:0) [sn1] | 1.63 | 2.9E−15 | 1.64 | 1.2E−12 | 2.13 | 2.0E−11 | 2.11 | 3.6E−09 | 2.15 | 4.8E−05 |
| SM(32:1)/PC(37:2) | 1.67 | 2.9E−15 | 1.73 | 1.1E−13 | 1.98 | 1.9E−08 | 2.18 | 1.4E−08 | 1.92 | 1.1E−03 |
| PE(38:5)/PC(39:4) | 1.65 | 2.9E−15 | 1.58 | 1.4E−10 | 1.99 | 1.9E−08 | 1.91 | 2.0E−06 | 1.81 | 2.7E−03 |
| PC(36:5)/SM(d17:1/14:0) | 1.66 | 3.0E−15 | 1.52 | 4.6E−09 | 1.83 | 4.5E−07 | 1.64 | 2.7E−04 | 1.89 | 1.3E−03 |
| PC(40:6)/LPC(22:0) [sn1] | 1.69 | 3.2E−15 | 1.71 | 1.2E−12 | 2.93 | 9.8E−15 | 3.04 | 1.6E−12 | 2.51 | 2.5E−05 |
| PC(40:6)/LPC(20:0) [sn2] | 1.68 | 3.2E−15 | 1.68 | 4.6E−12 | 2.84 | 1.7E−14 | 2.86 | 7.0E−12 | 2.24 | 1.7E−04 |
| PC(38:1)/LPC(MHDA) [sn1] | 1.63 | 3.2E−15 | 1.63 | 2.3E−12 | 2.25 | 4.5E−13 | 2.18 | 2.8E−10 | 2.33 | 1.4E−06 |
| SM(38:1)/PC(O-38:2) | 1.66 | 3.3E−15 | 1.65 | 5.3E−12 | 1.90 | 1.3E−07 | 1.91 | 3.6E−06 | 2.35 | 2.3E−05 |
| SM(36:2)/LPC(O-18:0) | 1.63 | 3.3E−15 | 1.66 | 3.5E−13 | 2.37 | 4.0E−14 | 2.40 | 7.1E−12 | 2.18 | 8.6E−06 |
| PG(34:1)/PC(P-32:0) | 1.66 | 3.4E−15 | 1.67 | 2.9E−12 | 1.94 | 5.6E−08 | 1.87 | 4.0E−06 | 1.82 | 3.2E−03 |
| SM(36:2)/LPC(17:0) [sn1] | 1.64 | 3.4E−15 | 1.66 | 1.1E−12 | 2.53 | 1.4E−14 | 2.54 | 4.4E−12 | 2.06 | 8.0E−05 |
| DAG(18:1/18:3)/LPE(20:1) [sn1] | 1.70 | 3.5E−15 | 1.93 | 4.6E−17 | 1.76 | 7.8E−06 | 2.13 | 2.1E−07 | 1.98 | 1.8E−03 |
| PC(36:5)/LacCer(d18:1/24:1) | 1.66 | 3.7E−15 | 1.55 | 1.4E−09 | 1.85 | 3.4E−07 | 1.71 | 8.8E−05 | 1.81 | 3.4E−03 |
| PE(40:6)/PC(39:4) | 1.65 | 3.8E−15 | 1.61 | 3.6E−11 | 2.22 | 2.1E−10 | 2.14 | 5.0E−08 | 2.14 | 2.3E−04 |
| PE(38:5)/PC(O-38:2) | 1.64 | 3.8E−15 | 1.56 | 4.4E−10 | 1.91 | 5.6E−08 | 1.77 | 1.9E−05 | 1.85 | 1.5E−03 |
| PG(34:1)/PC(O-34:2) | 1.66 | 3.9E−15 | 1.64 | 6.5E−12 | 2.08 | 2.5E−09 | 1.91 | 1.8E−06 | 1.89 | 1.9E−03 |
| PG(34:1)/PC(O-34:0) | 1.66 | 4.3E−15 | 1.63 | 1.2E−11 | 1.88 | 2.4E−07 | 1.78 | 2.3E−05 | 1.85 | 2.2E−03 |
| PE(40:6)/PC(31:0) | 1.66 | 4.3E−15 | 1.64 | 1.2E−11 | 2.12 | 2.0E−09 | 2.02 | 5.3E−07 | 2.27 | 1.2E−04 |
| PE(34:1)/PE(P-36:2) | 1.61 | 4.3E−15 | 1.56 | 5.9E−11 | 2.01 | 1.8E−10 | 1.88 | 1.9E−07 | 1.76 | 1.8E−03 |
| PE(38:5)/PC(O-34:0) | 1.65 | 4.5E−15 | 1.58 | 1.4E−10 | 1.88 | 1.3E−07 | 1.76 | 2.1E−05 | 1.83 | 2.4E−03 |
| SM(36:1)/PC(33:2) | 1.65 | 4.6E−15 | 1.73 | 5.4E−14 | 1.96 | 1.0E−08 | 2.19 | 1.1E−08 | 1.89 | 1.3E−03 |
| PE(38:1)/PC(O-32:2) | 1.63 | 4.7E−15 | 1.61 | 7.8E−12 | 1.79 | 4.2E−07 | 1.70 | 3.7E−05 | 1.91 | 7.4E−04 |
| PE(38:4)/LPE(P-20:0) | 1.62 | 4.8E−15 | 1.60 | 7.9E−12 | 1.95 | 8.1E−10 | 1.86 | 3.0E−07 | 1.69 | 4.5E−03 |
| PG(34:1)/LPC(17:0) [sn1] | 1.61 | 4.8E−15 | 1.56 | 7.8E−11 | 1.92 | 1.0E−09 | 1.81 | 4.3E−07 | 1.75 | 1.5E−03 |
| PE(40:6)/SM(41:2) | 1.64 | 5.0E−15 | 1.59 | 9.1E−11 | 2.07 | 1.3E−09 | 1.93 | 9.0E−07 | 2.03 | 3.9E−04 |
| PE(40:6)/LPC(17:0) [sn2] | 1.61 | 5.1E−15 | 1.56 | 5.7E−11 | 2.11 | 1.3E−11 | 2.00 | 1.8E−08 | 2.00 | 1.6E−04 |
| PC(36:5)/PC(35:2) | 1.67 | 5.1E−15 | 1.58 | 3.5E−10 | 1.94 | 8.8E−08 | 1.79 | 4.0E−05 | 2.31 | 4.6E−05 |
| PC(38:5)/PC(35:3) | 1.65 | 5.1E−15 | 1.64 | 8.1E−12 | 1.91 | 4.8E−08 | 1.81 | 8.9E−06 | 1.82 | 2.6E−03 |
| SM(36:2)/LPC(24:0) [sn1] | 1.66 | 5.2E−15 | 1.90 | 2.0E−17 | 2.66 | 1.0E−14 | 3.12 | 1.3E−14 | 2.49 | 5.8E−06 |
| PE(40:6)/PC(O-38:2) | 1.64 | 5.3E−15 | 1.58 | 1.3E−10 | 2.10 | 8.4E−10 | 1.95 | 6.4E−07 | 2.17 | 1.2E−04 |
| PE(40:6)/LPC(22:6) [sn1] | 1.62 | 5.4E−15 | 1.65 | 7.3E−13 | 1.98 | 1.3E−09 | 1.93 | 1.8E−07 | 1.86 | 1.2E−03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| | FL | | NAFLD | | FL (severe) | | NAFLD (severe) | | DM2 | |
|---|---|---|---|---|---|---|---|---|---|---|
| Lipid ratio | OR | p-value | OR | p-value | OR | p-value | OR | p-value | OR | p-value |
| PC(32:0)/PC(35:2) | 1.66 | 5.6E-15 | 1.63 | 2.6E-11 | 2.30 | 1.4E-10 | 2.17 | 1.4E-07 | 2.25 | 6.9E-05 |
| DAG(18:1/18:3)/CE(17:0) | 1.66 | 5.7E-15 | 1.80 | 6.0E-15 | 1.68 | 2.0E-05 | 1.84 | 1.9E-05 | 1.88 | 1.6E-03 |
| PE(38:5)/Glc/GalCer(d18:2/23:0) | 1.65 | 5.8E-15 | 1.55 | 8.0E-10 | 1.76 | 2.5E-06 | 1.68 | 1.2E-04 | 1.81 | 3.0E-03 |
| Cer(d20:1/24:1)/LacCer(d18:1/24:0) | 1.64 | 6.7E-15 | 1.69 | 5.6E-13 | 2.20 | 7.3E-11 | 2.43 | 9.8E-11 | 1.89 | 1.4E-03 |
| PC(38:5)/LPC(O-24:0) | 1.64 | 6.8E-15 | 1.60 | 3.5E-11 | 1.93 | 1.8E-08 | 1.88 | 2.0E-06 | 1.97 | 5.5E-04 |
| PG(34:1)/PC(O-40:3) | 1.64 | 7.0E-15 | 1.67 | 1.3E-12 | 1.81 | 2.7E-07 | 1.82 | 6.2E-06 | 1.67 | 8.4E-03 |
| PE(38:1)/LPE(16:0) [sn1] | 1.64 | 7.1E-15 | 1.68 | 5.2E-13 | 1.87 | 7.2E-08 | 1.86 | 2.2E-06 | 2.10 | 1.3E-04 |
| PC(40:6)/LPC(MHDA) [sn2] | 1.66 | 7.4E-15 | 1.62 | 4.4E-11 | 2.66 | 1.0E-13 | 2.49 | 3.9E-10 | 2.43 | 2.4E-05 |
| AcylCarnitine(16:0)/LPC(18:1) [sn1] | 1.67 | 7.5E-15 | 1.75 | 1.5E-13 | 2.59 | 1.6E-12 | 2.73 | 7.1E-11 | 2.00 | 1.5E-03 |
| PE(40:6)/LPC(O-22:0) | 1.61 | 7.5E-15 | 1.58 | 1.8E-11 | 2.06 | 9.7E-11 | 2.02 | 2.1E-08 | 2.03 | 1.6E-04 |
| SM(40:1)/PC(O-34:2) | 1.66 | 7.6E-15 | 1.67 | 3.4E-12 | 2.12 | 1.4E-09 | 2.07 | 1.9E-07 | 1.74 | 7.0E-03 |
| Cer(d18:1/16:0)/PC(O-38:0) | 1.69 | 7.9E-15 | 1.71 | 2.6E-12 | 1.94 | 2.7E-07 | 1.96 | 6.5E-06 | 2.03 | 1.1E-03 |
| Cer(d18:2/24:1)/LPC(17:0) [sn2] | 1.65 | 7.9E-15 | 1.64 | 8.4E-12 | 2.35 | 2.2E-12 | 2.26 | 2.7E-09 | 1.86 | 1.7E-03 |
| PE(38:5)/Glc/GalCer(d18:2/22:0) | 1.64 | 8.2E-15 | 1.56 | 4.1E-10 | 1.79 | 9.5E-07 | 1.69 | 7.4E-05 | 1.78 | 3.8E-03 |
| PE(36:5)/PC(17:0_22:6) | 1.62 | 8.3E-15 | 1.55 | 4.8E-10 | 1.73 | 1.5E-06 | 1.63 | 2.1E-04 | 1.73 | 3.4E-03 |
| DAG(18:1/18:3)/LPE(P-18:0) | 1.67 | 8.4E-15 | 1.82 | 8.0E-15 | 1.73 | 1.3E-05 | 1.89 | 1.5E-05 | 2.06 | 7.8E-04 |
| PC(38:2)/LPC(P-16:0) | 1.60 | 8.6E-15 | 1.59 | 9.3E-12 | 2.02 | 2.9E-11 | 1.98 | 7.4E-09 | 1.66 | 4.7E-03 |
| PC(38:5)/PC(P-40:4) | 1.63 | 8.8E-15 | 1.58 | 1.1E-10 | 1.94 | 1.3E-08 | 1.88 | 2.6E-06 | 2.03 | 3.1E-04 |
| PI(34:2)/LPC(20:2) [sn2] | 1.63 | 9.0E-15 | 1.66 | 1.4E-12 | 2.18 | 2.7E-11 | 2.11 | 9.2E-09 | 1.69 | 7.2E-03 |
| PC(34:5)/PC(33:2) | 1.66 | 9.2E-15 | 1.59 | 3.0E-10 | 1.74 | 8.3E-06 | 1.60 | 7.8E-04 | 1.73 | 1.0E-02 |
| PC(38:5)/Glc/GalCer(d18:2/22:0) | 1.65 | 9.8E-15 | 1.58 | 2.8E-10 | 1.73 | 5.0E-06 | 1.64 | 3.4E-04 | 1.85 | 2.9E-03 |
| PE(40:6)/LPC(22:1) [sn1] | 1.61 | 1.0E-14 | 1.60 | 1.6E-11 | 2.00 | 1.2E-09 | 1.99 | 6.8E-08 | 1.79 | 2.4E-03 |
| PI(34:2)/LPE(P-20:0) | 1.59 | 1.0E-14 | 1.54 | 1.2E-10 | 2.06 | 5.4E-12 | 1.94 | 9.2E-09 | 1.64 | 5.0E-03 |
| SM(36:1)/LPC(O-18:1) | 1.63 | 1.1E-14 | 1.65 | 2.5E-12 | 2.18 | 3.0E-11 | 2.24 | 6.2E-10 | 1.87 | 9.8E-04 |
| PE(38:1)/LPE(16:0) [sn2] | 1.63 | 1.1E-14 | 1.67 | 5.8E-13 | 1.86 | 9.6E-08 | 1.83 | 3.6E-06 | 2.10 | 1.4E-04 |
| PE(38:1)/LPC(O-18:1) | 1.59 | 1.1E-14 | 1.54 | 9.3E-11 | 1.82 | 2.0E-08 | 1.71 | 8.0E-06 | 1.75 | 1.7E-03 |
| PE(38:5)/LPC(15:0) [sn2] | 1.62 | 1.2E-14 | 1.53 | 9.7E-10 | 1.99 | 3.6E-09 | 1.83 | 2.5E-06 | 1.72 | 5.0E-03 |
| PE(38:1)/LPC(O-18:0) | 1.59 | 1.2E-14 | 1.55 | 8.9E-11 | 1.87 | 6.2E-09 | 1.77 | 2.5E-06 | 1.94 | 2.0E-04 |
| DAG(18:2/18:2)/PC(17:0_22:6) | 1.65 | 1.3E-14 | 1.76 | 5.1E-14 | 1.56 | 3.0E-04 | 1.69 | 2.0E-04 | 1.73 | 9.1E-03 |
| PE(40:6)/PC(O-34:2) | 1.63 | 1.3E-14 | 1.61 | 2.9E-11 | 2.24 | 8.0E-11 | 2.05 | 1.3E-07 | 2.11 | 2.7E-04 |
| Cer(d20:1/24:1)/LPC(O-24:0) | 1.60 | 1.3E-14 | 1.60 | 8.1E-12 | 2.05 | 1.2E-10 | 2.13 | 1.2E-09 | 1.69 | 5.8E-03 |
| PI(34:2)/LPC(O-24:0) | 1.61 | 1.3E-14 | 1.56 | 9.6E-11 | 2.03 | 1.5E-10 | 1.99 | 2.8E-08 | 1.69 | 5.0E-03 |
| PE(38:4)/PC(37:1) | 1.63 | 1.3E-14 | 1.62 | 2.1E-11 | 1.82 | 4.5E-07 | 1.76 | 2.4E-05 | 1.70 | 8.8E-03 |
| PE(38:1)/PC(37:1) | 1.61 | 1.4E-14 | 1.57 | 7.2E-11 | 1.80 | 2.8E-07 | 1.68 | 5.1E-05 | 1.97 | 3.0E-04 |
| PC(38:1)/PC(P-32:0) | 1.62 | 1.4E-14 | 1.65 | 1.4E-12 | 1.95 | 4.9E-09 | 1.97 | 1.5E-07 | 2.04 | 1.1E-04 |
| DAG(18:1/18:3)/LPC(18:1) [sn1] | 1.67 | 1.4E-14 | 1.87 | 6.6E-16 | 1.85 | 1.4E-06 | 2.12 | 4.2E-07 | 2.30 | 1.3E-04 |
| PE(38:1)/LPC(15:0) [sn2] | 1.60 | 1.5E-14 | 1.54 | 1.8E-10 | 1.88 | 9.0E-09 | 1.73 | 6.8E-06 | 1.80 | 1.2E-03 |
| PE(40:6)/LPC(17:0) [sn1] | 1.60 | 1.5E-14 | 1.54 | 2.9E-10 | 2.08 | 3.8E-11 | 1.96 | 4.2E-08 | 1.97 | 2.4E-04 |
| SM(38:1)/LPC(O-24:1) | 1.63 | 1.5E-14 | 1.68 | 3.9E-13 | 2.02 | 2.1E-09 | 2.14 | 1.1E-08 | 1.82 | 2.5E-03 |
| PC(38:5)/PC(O-38:0) | 1.64 | 1.5E-14 | 1.61 | 7.4E-11 | 1.87 | 2.0E-07 | 1.80 | 2.4E-05 | 2.02 | 5.7E-04 |
| PC(34:5)/PC(33:9) | 1.65 | 1.5E-14 | 1.55 | 2.0E-09 | 1.80 | 1.6E-06 | 1.64 | 3.6E-04 | 1.73 | 8.6E-03 |
| PE(40:6)/PC(O-40:3) | 1.63 | 1.5E-14 | 1.64 | 4.9E-12 | 1.95 | 7.6E-09 | 1.95 | 4.0E-07 | 1.87 | 1.4E-03 |
| CE(18:0)/PC(O-38:4) | 1.66 | 1.5E-14 | 1.71 | 7.6E-13 | 1.69 | 2.8E-05 | 1.74 | 1.0E-04 | 1.94 | 1.7E-03 |
| SM(36:2)/LPC(24:0) [sn2] | 1.64 | 1.6E-14 | 1.87 | 8.7E-17 | 2.59 | 3.2E-14 | 3.07 | 2.1E-14 | 2.22 | 2.7E-05 |
| PC(40:2)/LacCer(d18:1/24:1) | 1.65 | 1.6E-14 | 1.57 | 7.6E-10 | 2.02 | 1.1E-08 | 2.04 | 3.2E-07 | 1.81 | 3.3E-03 |
| SM(33:2)/PC(O-40:6) | 1.63 | 1.6E-14 | 1.81 | 5.2E-16 | 2.17 | 2.5E-10 | 2.48 | 1.1E-10 | 2.00 | 3.9E-04 |
| PE(38:4)/LPC(O-24:0) | 1.61 | 1.6E-14 | 1.61 | 1.0E-11 | 1.86 | 4.5E-08 | 1.83 | 1.6E-06 | 1.71 | 5.2E-03 |
| SM(36:1)/PC(39:4) | 1.66 | 1.6E-14 | 1.72 | 4.9E-13 | 2.19 | 4.5E-10 | 2.54 | 8.2E-11 | 2.23 | 1.5E-04 |
| PC(36:5)/PC(P-32:0) | 1.63 | 1.7E-14 | 1.53 | 2.0E-09 | 1.81 | 5.5E-07 | 1.70 | 7.5E-05 | 2.02 | 4.4E-04 |
| PC(38:1)/PC(35:2) | 1.64 | 1.7E-14 | 1.68 | 1.5E-12 | 2.14 | 2.0E-09 | 2.07 | 2.8E-07 | 2.60 | 5.4E-06 |
| SM(36:2)/PC(35:3) | 1.65 | 1.7E-14 | 1.86 | 2.9E-16 | 2.43 | 3.5E-12 | 2.70 | 1.7E-11 | 2.01 | 6.2E-04 |
| LPE(P-16:0)/LPC(MHDA) [sn2] | 1.63 | 1.7E-14 | 1.59 | 7.2E-11 | 2.06 | 5.9E-10 | 1.99 | 1.2E-07 | 2.01 | 4.5E-05 |
| PC(38:1)/LPC(22:0) [sn2] | 1.62 | 1.7E-14 | 1.65 | 1.1E-12 | 2.23 | 7.2E-13 | 2.28 | 2.9E-11 | 2.14 | 1.9E-05 |
| PC(38:2)/LPC(15:0) [sn1] | 1.62 | 1.7E-14 | 1.56 | 5.2E-10 | 2.27 | 5.2E-12 | 2.15 | 7.0E-09 | 1.90 | 6.5E-04 |
| Cer(d18:1/16:0)/PC(O-38:2) | 1.62 | 1.8E-14 | 1.56 | 4.6E-10 | 1.76 | 1.1E-06 | 1.67 | 1.5E-04 | 1.76 | 3.2E-03 |
| PG(34:1)/PC(39:4) | 1.63 | 1.8E-14 | 1.60 | 5.4E-11 | 1.91 | 8.2E-08 | 1.86 | 3.6E-06 | 1.78 | 3.7E-03 |
| SM(40:2)/PC(O-40:6) | 1.62 | 1.8E-14 | 1.67 | 4.8E-13 | 1.65 | 1.0E-05 | 1.76 | 7.5E-06 | 1.71 | 3.6E-03 |
| PC(38:5)/PC(33:2) | 1.62 | 1.9E-14 | 1.57 | 2.3E-10 | 1.79 | 7.3E-07 | 1.67 | 1.2E-04 | 1.74 | 6.0E-03 |
| PE(34:2)/PC(O-40:6) | 1.62 | 1.9E-14 | 1.62 | 1.1E-10 | 1.83 | 1.6E-07 | 1.82 | 3.3E-06 | 1.77 | 3.7E-03 |
| PE(38:5)/LPC(20:2) [sn1] | 1.62 | 1.9E-14 | 1.60 | 3.3E-11 | 1.97 | 8.0E-09 | 1.87 | 1.6E-06 | 1.87 | 1.6E-03 |
| PE(38:4)/LPC(15:0) [sn1] | 1.60 | 1.9E-14 | 1.57 | 8.5E-11 | 1.93 | 4.1E-09 | 1.84 | 9.9E-07 | 1.71 | 4.1E-03 |
| PC(38:5)/PC(O-34:2) | 1.63 | 1.9E-14 | 1.59 | 1.1E-10 | 2.00 | 7.7E-09 | 1.82 | 1.0E-05 | 1.90 | 1.6E-03 |
| PC(38:2)/LPE(P-20:0) | 1.60 | 2.1E-14 | 1.57 | 4.2E-11 | 2.12 | 8.8E-12 | 2.02 | 8.8E-09 | 1.78 | 1.5E-03 |
| SM(38:1)/PC(O-34:0) | 1.64 | 2.2E-14 | 1.70 | 9.6E-13 | 1.82 | 1.7E-06 | 1.89 | 9.6E-06 | 2.19 | 2.8E-04 |
| DAG(18:1/18:2)/LPE(P-18:0) | 1.63 | 2.2E-14 | 1.76 | 9.5E-15 | 1.87 | 1.5E-07 | 1.95 | 9.8E-07 | 1.69 | 9.6E-03 |
| SM(36:2)/LPC(O-18:1) | 1.62 | 2.2E-14 | 1.66 | 1.3E-12 | 2.36 | 1.1E-12 | 2.37 | 1.3E-10 | 1.83 | 1.6E-03 |
| PC(34:1)/LPC(18:2) [sn2] | 1.61 | 2.2E-14 | 1.65 | 1.8E-12 | 2.12 | 1.0E-10 | 2.12 | 8.9E-09 | 1.66 | 9.2E-03 |
| PE(40:6)/LPE(16:0) [sn1] | 1.63 | 2.3E-14 | 1.67 | 2.4E-12 | 2.20 | 3.6E-10 | 2.22 | 1.6E-08 | 2.36 | 7.4E-05 |
| PE(38:5)/Glc/GalCer(d18:1/23:0) | 1.63 | 2.3E-14 | 1.58 | 2.0E-10 | 1.86 | 2.7E-07 | 1.79 | 1.7E-05 | 1.84 | 1.9E-03 |
| SM(36:2)/LPC(17:0) [sn2] | 1.60 | 2.4E-14 | 1.65 | 1.2E-12 | 2.25 | 1.4E-13 | 2.28 | 2.4E-11 | 1.92 | 1.0E-04 |
| SM(33:2)/SM(d17:1/14:0) | 1.64 | 2.5E-14 | 1.76 | 4.8E-14 | 2.89 | 6.4E-16 | 3.13 | 7.1E-14 | 2.14 | 1.6E-04 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| PC(36:5)/LPC(P-16:0) | 1.62 | 2.5E-14 | 1.53 | 2.7E-09 | 1.98 | 8.0E-09 | 1.88 | 3.0E-06 | 2.01 | 4.5E-04 |
| PE(40:6)/PC(O-34:0) | 1.62 | 2.5E-14 | 1.59 | 8.0E-11 | 2.02 | 5.5E-09 | 1.92 | 1.3E-06 | 2.07 | 3.3E-04 |
| DAG(18:1/18:3)/PC(P-40:5) | 1.66 | 2.6E-14 | 1.79 | 2.1E-14 | 1.69 | 3.0E-05 | 1.86 | 2.2E-05 | 1.97 | 1.7E-03 |
| SM(40:1)/Glc/GalCer(d18:1/23:0) | 1.64 | 2.8E-14 | 1.69 | 1.7E-12 | 1.75 | 8.5E-06 | 1.94 | 3.3E-06 | 1.76 | 7.1E-03 |
| PE(38:5)/PC(O-32:0) | 1.62 | 2.8E-14 | 1.57 | 2.7E-10 | 1.85 | 3.9E-07 | 1.76 | 2.6E-05 | 1.77 | 4.5E-03 |
| PC(40:6)/LPC(22:0) [sn2] | 1.65 | 2.8E-14 | 1.68 | 4.8E-12 | 2.83 | 3.4E-14 | 2.87 | 6.5E-12 | 2.32 | 9.9E-05 |
| PC(38:2)/LPC(18:2) [sn1] | 1.60 | 2.8E-14 | 1.65 | 8.4E-13 | 2.24 | 1.2E-12 | 2.23 | 3.1E-10 | 1.98 | 3.4E-04 |
| PE(38:1)/SM(34:1) | 1.60 | 2.9E-14 | 1.58 | 5.1E-11 | 1.79 | 3.0E-07 | 1.66 | 7.8E-05 | 1.74 | 3.5E-03 |
| PE(38:4)/LPC(20:2) [sn2] | 1.62 | 2.9E-14 | 1.68 | 5.3E-13 | 1.90 | 4.9E-08 | 1.86 | 2.3E-06 | 1.69 | 8.1E-03 |
| PI(34:2)/LPC(18:2) [sn2] | 1.58 | 3.0E-14 | 1.58 | 1.1E-11 | 2.08 | 3.5E-12 | 2.03 | 2.4E-09 | 1.66 | 4.8E-03 |
| PE(38:4)/LPC(18:2) [sn2] | 1.60 | 3.1E-14 | 1.63 | 1.9E-12 | 1.96 | 1.3E-09 | 1.91 | 1.7E-07 | 1.70 | 5.0E-03 |
| PE(38:5)/LPE(P-20:0) | 1.60 | 3.1E-14 | 1.54 | 5.1E-10 | 1.99 | 1.6E-09 | 1.86 | 8.9E-07 | 1.79 | 2.0E-03 |
| Cer(d20:1/22:0)/PE(P-36:2) | 1.60 | 3.1E-14 | 1.58 | 5.0E-11 | 2.19 | 7.6E-12 | 2.21 | 8.2E-10 | 1.66 | 8.2E-03 |
| Cer(d18:1/16:0)/PC(O-34:2) | 1.63 | 3.1E-14 | 1.64 | 1.4E-11 | 2.10 | 2.0E-09 | 1.93 | 2.2E-06 | 1.76 | 5.6E-03 |
| PC(38:5)/LPC(15:0) [sn2] | 1.63 | 3.3E-14 | 1.55 | 1.4E-09 | 2.02 | 7.3E-09 | 1.86 | 7.9E-06 | 1.79 | 4.2E-03 |
| PG(34:1)/PC(O-38:0) | 1.63 | 3.3E-14 | 1.62 | 2.8E-11 | 1.89 | 1.7E-07 | 1.82 | 1.0E-05 | 1.91 | 1.3E-03 |
| PG(34:1)/PC(O-32:0) | 1.63 | 3.3E-14 | 1.62 | 2.8E-11 | 1.83 | 7.5E-07 | 1.76 | 2.7E-05 | 1.77 | 4.6E-03 |
| PC(38:2)/LPC(O-24:0) | 1.62 | 3.4E-14 | 1.61 | 2.1E-11 | 2.06 | 6.9E-10 | 2.08 | 3.1E-08 | 1.89 | 1.3E-03 |
| PE(40:6)/PC(P-40:4) | 1.61 | 3.4E-14 | 1.59 | 8.0E-11 | 2.18 | 1.9E-10 | 2.11 | 4.5E-08 | 2.21 | 9.5E-05 |
| PE(38:1)/LPC(20:2) [sn2] | 1.60 | 3.6E-14 | 1.62 | 3.2E-12 | 1.85 | 5.3E-08 | 1.76 | 7.5E-06 | 1.94 | 3.7E-04 |
| PI(34:2)/LPC(15:0) [sn1] | 1.59 | 3.6E-14 | 1.50 | 3.2E-09 | 2.09 | 1.4E-11 | 1.93 | 3.2E-08 | 1.67 | 3.8E-03 |
| PE(40:6)/PE(P-40:6) | 1.62 | 3.6E-14 | 1.61 | 2.8E-11 | 2.05 | 3.0E-09 | 1.89 | 2.1E-06 | 1.88 | 1.8E-03 |
| PG(34:1)/SM(41:2) | 1.62 | 3.6E-14 | 1.58 | 2.0E-10 | 1.83 | 5.5E-07 | 1.71 | 7.1E-05 | 1.72 | 6.6E-03 |
| PE(38:5)/LPC(O-18:1) | 1.60 | 3.7E-14 | 1.53 | 1.4E-09 | 1.93 | 1.7E-08 | 1.80 | 5.7E-06 | 1.69 | 6.9E-03 |
| PC(38:5)/LPC(20:2) [sn1] | 1.63 | 3.7E-14 | 1.65 | 9.7E-12 | 1.99 | 1.5E-08 | 1.90 | 3.3E-06 | 1.99 | 8.1E-04 |
| PC(38:5)/PC(31:0) | 1.63 | 3.7E-14 | 1.59 | 2.2E-10 | 1.76 | 3.4E-06 | 1.64 | 3.7E-04 | 1.94 | 1.7E-03 |
| PE(38:1)/LPC(15:0) [sn1] | 1.59 | 3.7E-14 | 1.53 | 3.6E-10 | 1.88 | 7.1E-09 | 1.75 | 4.7E-06 | 1.93 | 2.4E-04 |
| PG(34:1)/PC(O-38:2) | 1.62 | 3.7E-14 | 1.58 | 2.8E-10 | 1.86 | 3.2E-07 | 1.73 | 4.6E-05 | 1.85 | 2.0E-03 |
| PE(38:1)/LPE(P-20:0) | 1.58 | 3.8E-14 | 1.55 | 8.6E-11 | 1.88 | 3.9E-09 | 1.77 | 2.1E-06 | 1.85 | 5.5E-04 |
| PG(34:1)/Glc/GalCer(d18:2/22:0) | 1.62 | 3.9E-14 | 1.58 | 1.5E-10 | 1.74 | 3.4E-06 | 1.67 | 1.3E-04 | 1.75 | 4.9E-03 |
| PG(34:1)/PC(31:0) | 1.64 | 3.9E-14 | 1.64 | 2.7E-11 | 1.84 | 1.2E-06 | 1.77 | 5.8E-05 | 1.89 | 2.8E-03 |
| PE(40:6)/PC(O-38:0) | 1.61 | 4.0E-14 | 1.59 | 5.3E-11 | 2.05 | 1.8E-09 | 1.98 | 3.3E-07 | 2.14 | 1.4E-04 |
| PC(38:5)/LPC(18:2) [sn1] | 1.63 | 4.1E-14 | 1.64 | 1.4E-11 | 2.17 | 2.3E-10 | 2.11 | 7.4E-08 | 2.11 | 2.7E-04 |
| PE(40:6)/LPE(16:0) [sn2] | 1.62 | 4.3E-14 | 1.66 | 3.2E-12 | 2.16 | 6.0E-10 | 2.15 | 3.3E-08 | 2.33 | 7.5E-05 |
| PE(38:5)/PC(37:1) | 1.61 | 4.3E-14 | 1.54 | 1.7E-09 | 1.88 | 1.7E-07 | 1.76 | 2.7E-05 | 1.82 | 2.3E-03 |
| LPC(16:0) [sn1]/LPC(18:1) [sn1] | 1.64 | 4.4E-14 | 1.75 | 8.5E-14 | 2.24 | 1.5E-10 | 2.29 | 6.9E-09 | 2.02 | 7.7E-04 |
| PE(38:1)/PC(33:3) | 1.62 | 4.4E-14 | 1.57 | 3.1E-10 | 1.92 | 5.1E-08 | 1.78 | 1.6E-05 | 1.91 | 1.4E-03 |
| PE(38:5)/LPC(15:0) [sn1] | 1.60 | 4.5E-14 | 1.51 | 2.6E-09 | 1.98 | 3.9E-09 | 1.84 | 2.1E-06 | 1.85 | 1.4E-03 |
| SM(36:2)/PC(39:4) | 1.63 | 4.8E-14 | 1.72 | 2.9E-13 | 2.38 | 5.7E-13 | 2.63 | 1.2E-11 | 2.11 | 2.8E-04 |
| SM(40:1)/LPE(P-20:0) | 1.61 | 5.1E-14 | 1.60 | 2.4E-11 | 2.05 | 2.5E-10 | 2.08 | 8.7E-09 | 1.71 | 4.2E-03 |
| DAG(18:1/18:3)/LPC(18:1) [sn2] | 1.65 | 5.1E-14 | 1.88 | 8.0E-16 | 1.80 | 4.2E-06 | 2.09 | 9.6E-07 | 2.32 | 1.4E-04 |
| PE(40:6)/PC(O-32:0) | 1.61 | 5.2E-14 | 1.59 | 6.6E-11 | 2.02 | 8.1E-09 | 1.95 | 8.8E-07 | 2.04 | 4.9E-04 |
| PC(32:0)/LPC(24:0) [sn1] | 1.60 | 5.3E-14 | 1.59 | 3.7E-11 | 2.14 | 5.4E-12 | 2.16 | 3.3E-10 | 1.98 | 1.2E-04 |
| PC(38:5)/LPC(15:0) [sn1] | 1.62 | 5.3E-14 | 1.54 | 2.4E-09 | 2.03 | 3.6E-09 | 1.88 | 3.9E-06 | 2.00 | 5.3E-04 |
| PC(40:6)/PC(37:2) | 1.65 | 5.5E-14 | 1.65 | 4.6E-11 | 2.53 | 1.5E-11 | 2.55 | 1.7E-09 | 2.24 | 3.2E-04 |
| PE(38:1)/LPC(18:2) [sn1] | 1.56 | 5.8E-14 | 1.57 | 1.2E-11 | 1.87 | 1.4E-09 | 1.80 | 3.6E-07 | 1.88 | 2.1E-04 |
| PE(38:5)/LPC(P-16:0) | 1.59 | 6.2E-14 | 1.53 | 5.9E-10 | 1.90 | 6.0E-09 | 1.81 | 1.3E-06 | 1.70 | 4.4E-03 |
| PE(38:5)/LPC(O-24:0) | 1.60 | 6.3E-14 | 1.55 | 5.7E-10 | 1.91 | 4.3E-08 | 1.84 | 3.6E-06 | 1.84 | 2.0E-03 |
| SM(38:1)/LPC(O-22:0) | 1.60 | 6.4E-14 | 1.66 | 1.1E-12 | 2.03 | 6.1E-10 | 2.19 | 1.8E-09 | 2.10 | 9.5E-05 |
| PE(38:1)/Glc/GalCer(d18:1/23:0) | 1.59 | 6.5E-14 | 1.58 | 5.0E-11 | 1.74 | 1.2E-06 | 1.67 | 6.7E-05 | 1.92 | 5.5E-04 |
| PG(34:1)/LPC(20:2) [sn1] | 1.60 | 6.8E-14 | 1.63 | 5.2E-12 | 1.90 | 1.5E-08 | 1.84 | 1.6E-06 | 1.82 | 1.6E-03 |
| PE(40:6)/LPE(22:6) [sn1] | 1.60 | 6.8E-14 | 1.62 | 7.4E-12 | 1.88 | 2.5E-08 | 1.90 | 3.5E-07 | 1.89 | 9.3E-04 |
| Cer(d16:1/16:0)/PC(P-40:2) | 1.63 | 6.9E-14 | 1.70 | 7.7E-13 | 1.82 | 1.4E-06 | 1.90 | 6.0E-06 | 1.68 | 9.8E-03 |
| PC(34:5)/PC(35:3) | 1.64 | 7.0E-14 | 1.60 | 1.8E-10 | 1.78 | 4.2E-06 | 1.67 | 2.7E-04 | 1.76 | 8.2E-03 |
| PC(38:5)/PC(P-40:2) | 1.60 | 8.6E-14 | 1.58 | 1.5E-10 | 1.74 | 2.5E-06 | 1.65 | 1.9E-04 | 1.80 | 3.3E-03 |
| Glc/GalCer(d16:1/18:0)/PC(P-40:2) | 1.64 | 8.7E-14 | 1.66 | 1.4E-11 | 2.06 | 2.5E-08 | 2.09 | 4.1E-07 | 1.85 | 3.9E-03 |
| PG(34:1)/LPC(O-18:1) | 1.58 | 9.6E-14 | 1.53 | 4.3E-10 | 1.82 | 3.3E-08 | 1.72 | 6.5E-06 | 1.62 | 8.3E-03 |
| PE(38:1)/LPC(18:2) [sn2] | 1.56 | 9.8E-14 | 1.57 | 1.7E-11 | 1.86 | 4.3E-09 | 1.79 | 1.0E-06 | 1.85 | 5.0E-04 |
| PE(38:1)/LPC(P-16:0) | 1.56 | 1.0E-13 | 1.53 | 1.2E-10 | 1.78 | 1.7E-08 | 1.71 | 3.4E-06 | 1.73 | 1.4E-03 |
| PC(36:5)/PC(39:4) | 1.60 | 1.1E-13 | 1.48 | 3.7E-08 | 1.80 | 8.2E-07 | 1.71 | 7.3E-05 | 2.00 | 4.8E-04 |
| PC(32:0)/LPC(MHDA) [sn2] | 1.58 | 1.2E-13 | 1.49 | 6.2E-09 | 2.00 | 7.8E-11 | 1.85 | 1.3E-07 | 1.83 | 1.6E-04 |
| PC(36:5)/LPE(P-20:0) | 1.60 | 1.3E-13 | 1.50 | 1.0E-08 | 1.98 | 6.6E-09 | 1.85 | 4.2E-06 | 2.04 | 2.4E-04 |
| PC(38:2)/LPC(18:2) [sn2] | 1.60 | 1.3E-13 | 1.65 | 2.1E-12 | 2.27 | 8.4E-12 | 2.25 | 1.8E-09 | 1.88 | 1.7E-03 |
| SM(32:0)/PC(O-40:6) | 1.60 | 1.3E-13 | 1.66 | 1.9E-12 | 1.72 | 6.0E-06 | 1.81 | 1.3E-05 | 1.73 | 5.1E-03 |
| PE(38:4)/PC(O-38:4) | 1.59 | 1.4E-13 | 1.56 | 2.5E-10 | 1.83 | 3.0E-07 | 1.77 | 1.9E-05 | 1.91 | 1.1E-03 |
| SM(40:1)/LPC(20:2) [sn1] | 1.61 | 1.4E-13 | 1.75 | 4.5E-14 | 2.06 | 1.3E-08 | 2.26 | 1.8E-08 | 1.80 | 5.1E-03 |
| PC(38:1)/LPC(MHDA) [sn2] | 1.58 | 1.5E-13 | 1.55 | 2.8E-10 | 2.03 | 9.0E-11 | 1.92 | 4.8E-08 | 2.02 | 1.5E-05 |
| PE(34:2)/PC(35:3) | 1.58 | 1.5E-13 | 1.56 | 9.7E-11 | 1.89 | 9.1E-09 | 1.83 | 9.3E-07 | 1.75 | 2.7E-03 |
| PC(38:5)/PC(O-34:0) | 1.59 | 1.6E-13 | 1.54 | 1.0E-09 | 1.74 | 2.6E-06 | 1.63 | 2.7E-04 | 1.81 | 2.7E-03 |
| DAG(18:1/18:2)/LPC(18:1) [sn1] | 1.61 | 1.6E-13 | 1.80 | 1.9E-15 | 1.99 | 1.5E-08 | 2.18 | 1.8E-08 | 1.90 | 1.9E-03 |
| PC(36:5)/PC(35:3) | 1.60 | 1.6E-13 | 1.53 | 2.8E-09 | 1.83 | 5.5E-07 | 1.72 | 7.2E-05 | 1.96 | 8.2E-04 |
| Cer(d16:1/16:0)/PC(O-38:2) | 1.63 | 1.7E-13 | 1.63 | 6.1E-11 | 1.88 | 6.5E-07 | 1.93 | 6.4E-06 | 1.78 | 6.9E-03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| PC(40:6)/LPC(O-22:0) | 1.61 | 1.7E−13 | 1.62 | 6.2E−11 | 2.53 | 1.3E−12 | 2.61 | 1.8E−10 | 2.21 | 1.3E−04 |
| PC(36:5)/PC(O-38:2) | 1.59 | 1.8E−13 | 1.45 | 1.2E−07 | 1.75 | 2.9E−06 | 1.58 | 7.4E−04 | 2.09 | 2.6E−04 |
| PC(40:6)/LPC(24:0) [sn1] | 1.62 | 1.8E−13 | 1.71 | 1.4E−12 | 2.81 | 1.1E−13 | 2.99 | 4.7E−12 | 2.49 | 3.2E−05 |
| PC(36:5)/LPC(O-18:0) | 1.59 | 1.8E−13 | 1.48 | 2.7E−08 | 1.93 | 2.8E−08 | 1.82 | 1.0E−05 | 2.14 | 1.0E−04 |
| PG(34:1)/LPE(P-20:0) | 1.57 | 1.8E−13 | 1.54 | 2.4E−10 | 1.88 | 4.7E−09 | 1.78 | 1.3E−06 | 1.72 | 2.3E−03 |
| PE(40:6)/SM(34:1) | 1.59 | 1.9E−13 | 1.56 | 2.7E−10 | 2.03 | 3.4E−09 | 1.90 | 1.4E−06 | 1.86 | 1.9E−03 |
| SM(36:2)/PC(O-38:0) | 1.63 | 1.9E−13 | 1.76 | 9.5E−14 | 2.34 | 1.4E−10 | 2.55 | 4.8E−10 | 2.48 | 3.6E−05 |
| PC(40:6)/LPC(24:0) [sn2] | 1.62 | 2.0E−13 | 1.70 | 2.2E−12 | 2.80 | 1.6E−13 | 3.02 | 4.4E−12 | 2.29 | 8.5E−05 |
| PE(38:5)/PC(33:3) | 1.59 | 2.0E−13 | 1.51 | 5.8E−09 | 1.91 | 7.1E−08 | 1.79 | 1.6E−05 | 1.70 | 7.9E−03 |
| PC(32:0)/LPC(24:0) [sn2] | 1.58 | 2.0E−13 | 1.57 | 9.0E−11 | 2.09 | 1.3E−11 | 2.16 | 2.5E−10 | 1.79 | 6.1E−03 |
| PC(40:6)/LPC(22:1) [sn1] | 1.63 | 2.0E−13 | 1.64 | 5.9E−11 | 2.40 | 1.4E−10 | 2.50 | 2.8E−09 | 1.74 | 9.9E−03 |
| SM(36:1)/LPC(P-16:0) | 1.56 | 2.3E−13 | 1.62 | 1.6E−12 | 1.96 | 3.5E−11 | 2.05 | 1.8E−10 | 1.74 | 4.8E−04 |
| PE(38:1)/LPC(O-24:0) | 1.57 | 2.3E−13 | 1.55 | 2.1E−10 | 1.80 | 1.7E−07 | 1.74 | 1.3E−05 | 1.91 | 5.9E−04 |
| PC(40:6)/PC(35:2) | 1.64 | 2.4E−13 | 1.65 | 7.6E−11 | 2.49 | 1.5E−10 | 2.37 | 6.2E−08 | 2.52 | 7.3E−05 |
| LPE(P-16:0)/LPC(P-16:0) | 1.57 | 2.5E−13 | 1.57 | 1.0E−10 | 1.97 | 5.2E−10 | 2.00 | 1.0E−08 | 1.68 | 4.2E−03 |
| PE(38:4)/PC(O-40:4) | 1.58 | 2.6E−13 | 1.56 | 4.5E−10 | 1.81 | 5.6E−07 | 1.73 | 3.7E−05 | 1.88 | 1.4E−03 |
| SM(38:1)/LPC(24:0) [sn2] | 1.59 | 2.7E−13 | 1.77 | 5.0E−15 | 2.10 | 1.8E−10 | 2.43 | 1.7E−11 | 2.11 | 5.6E−05 |
| PE(38:5)/LPC(18:2) [sn2] | 1.58 | 2.7E−13 | 1.56 | 3.3E−10 | 1.99 | 4.0E−09 | 1.90 | 8.4E−07 | 1.80 | 2.4E−03 |
| SM(38:1)/LPC(24:0) [sn1] | 1.59 | 2.7E−13 | 1.77 | 3.3E−15 | 2.10 | 1.9E−10 | 2.39 | 3.7E−11 | 2.31 | 1.4E−05 |
| SM(40:1)/LPC(O-24:0) | 1.60 | 2.7E−13 | 1.62 | 2.8E−11 | 1.90 | 1.3E−07 | 2.09 | 1.0E−07 | 1.77 | 5.6E−03 |
| PE(40:6)/LPC(O-24:0) | 1.56 | 2.8E−13 | 1.54 | 2.9E−10 | 1.97 | 1.4E−09 | 1.92 | 1.8E−07 | 1.99 | 2.6E−04 |
| LPE(P-16:0)/LPE(P-20:0) | 1.58 | 2.9E−13 | 1.55 | 4.8E−10 | 2.09 | 8.5E−11 | 2.03 | 1.8E−08 | 1.80 | 3.8E−04 |
| SM(36:2)/LPC(P-16:0) | 1.56 | 3.0E−13 | 1.64 | 5.8E−13 | 2.12 | 1.4E−12 | 2.19 | 3.6E−11 | 1.74 | 7.1E−04 |
| PC(36:6)/PC(O-40:6) | 1.57 | 3.0E−13 | 1.60 | 2.1E−11 | 1.97 | 6.4E−09 | 1.95 | 3.8E−07 | 1.72 | 5.8E−03 |
| PE(40:6)/LPC(O-18:0) | 1.56 | 3.1E−13 | 1.51 | 1.3E−09 | 2.01 | 5.0E−10 | 1.92 | 2.1E−07 | 2.01 | 2.1E−04 |
| PG(34:1)/LPC(O-24:0) | 1.58 | 3.1E−13 | 1.56 | 2.1E−10 | 1.84 | 1.1E−07 | 1.79 | 4.7E−06 | 1.79 | 2.3E−03 |
| SM(36:1)/PC(O-34:2) | 1.59 | 3.1E−13 | 1.66 | 2.3E−12 | 2.21 | 8.1E−11 | 2.24 | 4.6E−09 | 2.04 | 3.3E−04 |
| PE(38:5)/LPC(20:2) [sn2] | 1.58 | 3.2E−13 | 1.57 | 2.8E−10 | 1.89 | 8.0E−08 | 1.80 | 8.7E−06 | 1.80 | 3.2E−03 |
| PC(38:5)/PC(O-32:0) | 1.58 | 3.2E−13 | 1.55 | 7.8E−10 | 1.72 | 4.8E−06 | 1.64 | 2.2E−04 | 1.77 | 4.6E−03 |
| PC(36:5)/LPC(O-18:1) | 1.59 | 3.4E−13 | 1.47 | 6.0E−08 | 1.88 | 1.6E−07 | 1.74 | 5.3E−05 | 1.89 | 1.6E−03 |
| PC(40:6)/LPC(17:0) [sn1] | 1.61 | 3.5E−13 | 1.54 | 4.4E−09 | 2.70 | 1.7E−13 | 2.56 | 5.4E−10 | 2.17 | 3.0E−04 |
| PE(38:5)/PI(38:1) | 1.59 | 3.5E−13 | 1.63 | 2.0E−11 | 1.77 | 2.3E−06 | 1.77 | 2.6E−05 | 1.73 | 5.4E−03 |
| PE(34:2)/PC(33:2) | 1.57 | 3.6E−13 | 1.52 | 1.5E−09 | 1.84 | 1.3E−07 | 1.76 | 1.1E−05 | 1.70 | 6.0E−03 |
| PC(38:1)/LPC(24:0) [sn2] | 1.56 | 3.7E−13 | 1.65 | 5.2E−13 | 2.10 | 1.4E−11 | 2.28 | 2.8E−11 | 2.10 | 1.6E−05 |
| PC(34:5)/PC(O-34:2) | 1.62 | 3.8E−13 | 1.56 | 2.2E−09 | 1.86 | 1.6E−06 | 1.67 | 3.7E−04 | 1.81 | 6.4E−03 |
| SM(44:2)/LacCer(d18:1/24:1) | 1.60 | 3.9E−13 | 1.53 | 5.7E−09 | 2.11 | 1.8E−09 | 2.17 | 4.0E−08 | 1.93 | 1.1E−03 |
| PE(40:6)/LPC(15:0) [sn2] | 1.57 | 3.9E−13 | 1.51 | 2.8E−09 | 2.05 | 4.1E−10 | 1.91 | 3.5E−07 | 1.87 | 9.8E−04 |
| Cer(d20:1/24:1)/LPC(15:0) [sn1] | 1.56 | 4.0E−13 | 1.53 | 7.2E−10 | 2.08 | 9.6E−11 | 2.11 | 3.7E−09 | 1.67 | 7.7E−03 |
| Glc/GalCer(d16:1/18:0)/ Glc/GalCer(d18:2/23:0) | 1.64 | 4.1E−13 | 1.59 | 1.6E−09 | 1.91 | 1.5E−06 | 1.99 | 7.7E−06 | 1.88 | 5.6E−03 |
| PC(40:6)/LPC(17:0) [sn2] | 1.60 | 4.1E−13 | 1.56 | 1.2E−09 | 2.53 | 3.0E−13 | 2.41 | 6.2E−10 | 2.09 | 2.4E−04 |
| PC(36:5)/PC(33:2) | 1.58 | 4.1E−13 | 1.48 | 3.0E−08 | 1.73 | 4.8E−06 | 1.60 | 5.3E−04 | 1.86 | 2.0E−03 |
| PE(40:6)/PC(O-18:1) | 1.56 | 4.2E−13 | 1.51 | 1.7E−09 | 1.97 | 1.7E−09 | 1.86 | 6.9E−07 | 1.82 | 1.6E−03 |
| PE(38:5)/LPE(20:1) [sn1] | 1.60 | 4.3E−13 | 1.61 | 1.6E−10 | 1.96 | 5.5E−08 | 2.04 | 4.0E−07 | 1.77 | 6.9E−03 |
| PC(34:5)/LPC(15:0) [sn1] | 1.61 | 4.4E−13 | 1.52 | 1.5E−08 | 1.84 | 1.0E−06 | 1.69 | 2.2E−04 | 1.87 | 3.0E−03 |
| PE(38:5)/CE(17:0) | 1.57 | 4.5E−13 | 1.52 | 2.3E−09 | 1.86 | 9.8E−08 | 1.75 | 2.2E−05 | 1.72 | 5.5E−03 |
| PC(36:5)/PC(O-34:2) | 1.58 | 4.6E−13 | 1.50 | 1.7E−08 | 1.90 | 1.1E−07 | 1.71 | 7.8E−05 | 2.01 | 6.3E−04 |
| PC(38:5)/LPC(18:2) [sn2] | 1.59 | 4.7E−13 | 1.60 | 1.0E−10 | 2.06 | 3.0E−09 | 1.98 | 6.9E−07 | 1.94 | 1.2E−03 |
| PC(38:5)/PC(P-40:5) | 1.59 | 4.7E−13 | 1.54 | 2.8E−09 | 1.98 | 2.8E−08 | 1.82 | 2.2E−05 | 1.89 | 2.2E−03 |
| PG(34:1)/LPC(15:0) [sn2] | 1.57 | 4.8E−13 | 1.52 | 2.0E−09 | 1.85 | 3.3E−08 | 1.73 | 8.1E−06 | 1.63 | 8.5E−03 |
| LPE(P-16:0)/LPC(O-18:0) | 1.59 | 5.1E−13 | 1.52 | 5.8E−09 | 2.08 | 2.9E−09 | 2.07 | 2.0E−07 | 2.23 | 1.1E−04 |
| PG(34:1)/LPC(P-16:0) | 1.55 | 5.2E−13 | 1.52 | 3.7E−10 | 1.78 | 2.2E−08 | 1.72 | 2.2E−06 | 1.61 | 5.8E−03 |
| PE(40:6)/LPE(P-20:0) | 1.55 | 6.1E−13 | 1.52 | 8.6E−10 | 2.03 | 2.1E−10 | 1.92 | 1.3E−07 | 1.92 | 4.4E−04 |
| PC(38:1)/LPC(24:0) [sn1] | 1.56 | 6.3E−13 | 1.66 | 5.2E−13 | 2.09 | 1.8E−11 | 2.23 | 6.6E−11 | 2.23 | 3.3E−06 |
| PC(38:1)/LPC(O-22:0) | 1.56 | 6.3E−13 | 1.57 | 1.2E−10 | 2.05 | 2.8E−10 | 2.13 | 6.1E−09 | 2.13 | 4.4E−05 |
| PC(36:5)/LPC(O-24:0) | 1.57 | 6.3E−13 | 1.48 | 2.4E−08 | 1.79 | 4.8E−07 | 1.73 | 3.4E−05 | 2.05 | 2.3E−04 |
| PG(34:1)/LPC(15:0) [sn1] | 1.56 | 6.5E−13 | 1.51 | 2.5E−09 | 1.87 | 1.8E−08 | 1.75 | 4.1E−06 | 1.76 | 1.8E−03 |
| PE(40:6)/LPC(20:2) [sn1] | 1.57 | 6.6E−13 | 1.59 | 6.7E−11 | 2.05 | 1.0E−09 | 1.98 | 2.0E−07 | 2.05 | 3.1E−04 |
| SM(36:2)/PC(O-34:2) | 1.58 | 6.6E−13 | 1.67 | 1.5E−12 | 2.35 | 3.5E−12 | 2.31 | 1.1E−09 | 2.00 | 5.5E−04 |
| PE(34:2)/PC(P-40:2) | 1.57 | 7.2E−13 | 1.54 | 9.5E−10 | 1.81 | 5.2E−07 | 1.73 | 3.0E−05 | 1.71 | 2.7E−03 |
| Cer(d18:1/16:0)/LPC(O-24:0) | 1.58 | 7.7E−13 | 1.59 | 1.5E−10 | 1.89 | 1.1E−07 | 1.94 | 1.1E−06 | 1.79 | 3.0E−03 |
| PE(38:1)/CE(17:0) | 1.55 | 7.9E−13 | 1.54 | 4.7E−10 | 1.78 | 2.7E−07 | 1.68 | 5.3E−05 | 1.81 | 1.5E−03 |
| SM(38:1)/PC(P-40:2) | 1.57 | 8.1E−13 | 1.64 | 6.6E−12 | 1.70 | 8.3E−06 | 1.74 | 3.9E−05 | 1.78 | 1.3E−03 |
| PE(40:6)/LPC(15:0) [sn1] | 1.55 | 8.1E−13 | 1.50 | 4.8E−09 | 2.05 | 3.0E−10 | 1.93 | 2.2E−07 | 2.02 | 2.2E−04 |
| PC(36:5)/PC(O-38:0) | 1.58 | 8.1E−13 | 1.49 | 2.9E−08 | 1.76 | 2.8E−06 | 1.67 | 2.2E−04 | 2.11 | 2.2E−04 |
| SM(38:1)/PC(33:2) | 1.58 | 8.5E−13 | 1.63 | 2.2E−11 | 1.77 | 2.8E−06 | 1.85 | 1.5E−05 | 1.76 | 6.9E−03 |
| PE(38:5)/PC(P-40:5) | 1.57 | 8.5E−13 | 1.51 | 7.1E−09 | 1.95 | 3.9E−08 | 1.80 | 1.3E−05 | 1.74 | 4.6E−03 |
| Cer(d20:1/24:1)/CE(18:1) | 1.56 | 8.8E−13 | 1.58 | 6.6E−11 | 1.95 | 6.5E−10 | 2.04 | 7.4E−09 | 1.65 | 8.7E−03 |
| PC(O-38:6)/PC(O-40:6) | 1.57 | 9.1E−13 | 1.62 | 2.5E−10 | 1.84 | 1.9E−07 | 1.93 | 1.6E−06 | 2.06 | 9.1E−05 |
| SM(40:1)/LPC(18:2) [sn2] | 1.58 | 9.2E−13 | 1.68 | 1.4E−12 | 2.16 | 4.8E−10 | 2.33 | 2.0E−09 | 1.77 | 5.8E−03 |
| Glc/GalCer(d16:1/18:0)/ PC(O-34:0) | 1.62 | 1.0E−12 | 1.62 | 3.6E−10 | 2.12 | 5.9E−08 | 2.15 | 1.0E−06 | 1.90 | 5.5E−03 |
| LPE(P-16:0)/LPC(17:0) [sn1] | 1.57 | 1.0E−12 | 1.49 | 1.9E−08 | 2.10 | 3.5E−10 | 2.09 | 3.5E−08 | 1.87 | 1.3E−03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

|  | FL | | NAFLD | | FL (severe) | | NAFLD (severe) | | DM2 | |
|---|---|---|---|---|---|---|---|---|---|---|
| Lipid ratio | OR | p-value | OR | p-value | OR | p-value | OR | p-value | OR | p-value |
| PE(40:6)/PC(37:1) | 1.57 | 1.1E−12 | 1.53 | 2.6E−09 | 2.01 | 1.1E−08 | 1.91 | 2.2E−06 | 2.10 | 3.1E−04 |
| Cer(d20:1/24:1)/Glc/GalCer(d18:2/24:0) | 1.55 | 1.1E−12 | 1.52 | 1.4E−09 | 1.97 | 5.8E−09 | 1.96 | 2.1E−07 | 1.85 | 1.7E−03 |
| PC(36:5)/LPC(20:2) [sn1] | 1.58 | 1.1E−12 | 1.53 | 4.0E−09 | 1.87 | 2.5E−07 | 1.77 | 3.6E−05 | 2.10 | 2.9E−04 |
| PE(40:6)/LPC(P-16:0) | 1.53 | 1.1E−12 | 1.51 | 9.5E−10 | 1.92 | 9.3E−10 | 1.86 | 2.1E−07 | 1.80 | 1.1E−03 |
| SM(38:1)/PC(P-32:0) | 1.59 | 1.1E−12 | 1.71 | 7.0E−13 | 1.88 | 6.5E−07 | 2.06 | 5.9E−07 | 1.97 | 1.7E−03 |
| PC(36:5)/PC(P-40:4) | 1.56 | 1.1E−12 | 1.46 | 6.2E−08 | 1.81 | 4.0E−07 | 1.74 | 4.3E−05 | 2.10 | 1.5E−04 |
| PC(38:5)/CE(17:0) | 1.57 | 1.2E−12 | 1.54 | 1.8E−09 | 1.84 | 2.8E−07 | 1.72 | 7.2E−05 | 1.77 | 4.1E−03 |
| LPE(P-16:0)/LPC(17:0) [sn2] | 1.55 | 1.2E−12 | 1.51 | 2.8E−09 | 1.91 | 5.4E−10 | 1.89 | 4.7E−08 | 1.74 | 7.7E−04 |
| PC(40:6)/SM(d17:1/14:0) | 1.59 | 1.2E−12 | 1.53 | 8.1E−09 | 2.20 | 9.1E−10 | 2.01 | 1.2E−06 | 1.80 | 6.6E−03 |
| CE(18:0)/LPC(18:1) [sn1] | 1.59 | 1.5E−12 | 1.80 | 8.1E−15 | 2.06 | 1.7E−08 | 2.25 | 2.2E−08 | 1.93 | 1.9E−03 |
| SM(36:1)/LPC(O-24:0) | 1.56 | 1.5E−12 | 1.64 | 2.9E−12 | 2.05 | 9.2E−10 | 2.30 | 3.6E−10 | 2.11 | 5.6E−05 |
| PG(34:1)/LPC(20:2) [sn2] | 1.57 | 1.5E−12 | 1.61 | 4.5E−11 | 1.84 | 1.8E−07 | 1.79 | 9.2E−06 | 1.77 | 3.5E−03 |
| SM(32:2)/PC(O-40:6) | 1.56 | 1.5E−12 | 1.68 | 4.1E−13 | 1.88 | 7.2E−08 | 1.98 | 2.5E−07 | 1.86 | 1.3E−03 |
| PC(36:5)/PC(P-40:2) | 1.56 | 1.6E−12 | 1.50 | 1.5E−08 | 1.68 | 1.4E−05 | 1.58 | 7.6E−04 | 1.90 | 1.5E−03 |
| SM(32:0)/PC(35:2) | 1.58 | 1.6E−12 | 1.63 | 3.7E−11 | 2.01 | 8.4E−08 | 2.02 | 2.0E−06 | 2.20 | 1.7E−04 |
| SM(38:1)/LPC(17:0) [sn2] | 1.54 | 1.6E−12 | 1.55 | 1.9E−10 | 1.92 | 2.5E−10 | 1.93 | 1.3E−08 | 1.81 | 3.1E−04 |
| PC(38:5)/LPC(O-16:0) | 1.57 | 1.6E−12 | 1.51 | 1.1E−08 | 1.98 | 3.1E−08 | 1.85 | 1.2E−05 | 1.81 | 4.3E−03 |
| PC(38:5)/PC(37:1) | 1.56 | 1.6E−12 | 1.50 | 1.4E−08 | 1.72 | 3.9E−06 | 1.62 | 4.0E−04 | 1.83 | 2.3E−03 |
| SM(36:1)/LPE(P-20:0) | 1.55 | 1.7E−12 | 1.60 | 2.1E−11 | 2.13 | 2.0E−11 | 2.19 | 4.7E−10 | 1.94 | 1.5E−04 |
| PC(36:5)/LPC(15:0) [sn2] | 1.56 | 1.7E−12 | 1.44 | 2.9E−07 | 1.87 | 1.7E−07 | 1.72 | 8.2E−05 | 1.87 | 1.5E−03 |
| PC(34:5)/LPC(20:2) [sn1] | 1.60 | 1.7E−12 | 1.59 | 8.6E−10 | 1.80 | 4.8E−06 | 1.70 | 2.5E−04 | 1.85 | 5.3E−03 |
| SM(38:1)/LPC(17:0) [sn1] | 1.54 | 1.8E−12 | 1.52 | 1.0E−09 | 2.00 | 2.4E−10 | 1.99 | 1.5E−08 | 1.89 | 4.2E−04 |
| Glc/GalCer(d16:1/18:0)/Glc/GalCer(d18:2/22:0) | 1.62 | 1.9E−12 | 1.59 | 1.9E−09 | 1.98 | 7.4E−07 | 2.01 | 6.9E−06 | 1.83 | 9.2E−03 |
| Cer(d18:2/22:0)/LPE(P-20:0) | 1.57 | 1.9E−12 | 1.63 | 2.2E−11 | 2.03 | 1.1E−08 | 2.01 | 4.4E−07 | 1.72 | 8.1E−03 |
| SM(38:1)/PC(35:3) | 1.58 | 2.1E−12 | 1.76 | 6.7E−14 | 1.99 | 6.1E−08 | 2.17 | 9.5E−08 | 1.90 | 2.2E−03 |
| PC(36:5)/PC(O-32:1) | 1.57 | 2.1E−12 | 1.52 | 6.1E−09 | 1.66 | 2.5E−05 | 1.58 | 7.1E−04 | 1.73 | 7.5E−03 |
| SM(38:1)/PC(O-38:0) | 1.59 | 2.2E−12 | 1.68 | 5.2E−12 | 1.90 | 7.8E−07 | 2.08 | 1.1E−06 | 2.44 | 6.2E−05 |
| SM(38:1)/LPC(O-18:0) | 1.53 | 2.2E−12 | 1.53 | 5.0E−10 | 1.94 | 1.2E−09 | 1.96 | 4.1E−08 | 2.04 | 6.8E−05 |
| PE(40:6)/PC(33:3) | 1.57 | 2.2E−12 | 1.53 | 6.8E−09 | 2.09 | 4.7E−09 | 1.99 | 1.2E−06 | 2.00 | 1.4E−03 |
| LPC(16:0) [sn2]/LPC(18:1) [sn1] | 1.58 | 2.4E−12 | 1.67 | 7.8E−12 | 2.16 | 3.8E−09 | 2.20 | 8.2E−08 | 2.08 | 8.0E−04 |
| PG(34:1)/PC(37:1) | 1.56 | 2.4E−12 | 1.54 | 2.7E−09 | 1.78 | 2.1E−06 | 1.69 | 1.0E−04 | 1.78 | 4.4E−03 |
| PG(34:1)/LPC(18:2) [sn2] | 1.54 | 2.6E−12 | 1.56 | 1.8E−10 | 1.89 | 1.2E−08 | 1.83 | 1.2E−06 | 1.73 | 3.2E−03 |
| PG(34:1)/Glc/GalCer(d18:1/23:0) | 1.56 | 2.7E−12 | 1.56 | 7.5E−10 | 1.75 | 4.4E−06 | 1.71 | 9.0E−05 | 1.76 | 4.4E−03 |
| SM(32:2)/SM(d17:1/14:0) | 1.56 | 2.9E−12 | 1.60 | 1.3E−10 | 2.31 | 1.2E−11 | 2.14 | 4.8E−08 | 1.98 | 7.7E−04 |
| PC(36:5)/LPC(15:0) [sn1] | 1.55 | 3.5E−12 | 1.43 | 5.3E−07 | 1.88 | 1.1E−07 | 1.73 | 5.3E−05 | 2.06 | 2.2E−04 |
| PE(40:6)/CE(17:0) | 1.54 | 3.8E−12 | 1.52 | 2.3E−09 | 1.96 | 6.9E−09 | 1.88 | 2.0E−06 | 1.91 | 9.5E−04 |
| PE(36:5)/LPC(22:1) [sn1] | 1.54 | 3.8E−12 | 1.47 | 4.7E−08 | 1.81 | 4.3E−07 | 1.72 | 3.7E−05 | 1.75 | 5.0E−03 |
| PC(38:5)/Glc/GalCer(d18:1/23:0) | 1.56 | 4.2E−12 | 1.53 | 3.7E−09 | 1.71 | 1.1E−05 | 1.65 | 3.3E−04 | 1.85 | 3.1E−03 |
| Cer(d18:2/22:0)/LPC(18:2) [sn2] | 1.56 | 4.3E−12 | 1.71 | 5.5E−13 | 2.12 | 6.2E−09 | 2.23 | 6.0E−08 | 1.77 | 7.4E−03 |
| SM(40:1)/LPC(15:0) [sn1] | 1.55 | 4.6E−12 | 1.51 | 8.8E−09 | 2.01 | 7.6E−09 | 2.04 | 1.3E−07 | 1.74 | 5.7E−03 |
| SM(38:1)/Glc/GalCer(d18:2/22:0) | 1.55 | 4.7E−12 | 1.57 | 4.8E−10 | 1.55 | 2.6E−04 | 1.62 | 4.3E−04 | 1.84 | 2.5E−03 |
| PC(40:6)/PC(P-32:0) | 1.57 | 4.9E−12 | 1.59 | 4.3E−10 | 2.34 | 4.7E−10 | 2.31 | 4.6E−08 | 2.02 | 1.6E−03 |
| PE(40:6)/LPC(20:2) [sn2] | 1.54 | 5.3E−12 | 1.57 | 3.1E−10 | 2.02 | 5.5E−09 | 1.95 | 6.7E−07 | 2.04 | 4.9E−04 |
| SM(33:2)/PC(35:2) | 1.56 | 5.4E−12 | 1.76 | 3.0E−14 | 2.64 | 9.0E−14 | 3.02 | 2.3E−13 | 2.69 | 9.0E−07 |
| Cer(d20:1/24:1)/LPC(18:1) [sn1] | 1.52 | 5.7E−12 | 1.55 | 1.4E−10 | 2.12 | 1.5E−11 | 2.19 | 2.5E−10 | 1.78 | 1.8E−03 |
| PE(38:1)/PC(P-40:5) | 1.53 | 6.3E−12 | 1.50 | 4.0E−09 | 1.79 | 3.1E−07 | 1.67 | 6.8E−05 | 1.82 | 1.6E−03 |
| PC(34:5)/LPC(O-24:0) | 1.57 | 6.5E−12 | 1.52 | 1.3E−08 | 1.70 | 1.9E−05 | 1.64 | 4.7E−04 | 1.79 | 6.6E−03 |
| PE(38:5)/LPC(O-16:0) | 1.53 | 6.9E−12 | 1.46 | 4.8E−08 | 1.84 | 1.0E−07 | 1.73 | 1.7E−05 | 1.66 | 8.8E−03 |
| PC(38:1)/LPC(17:0) [sn1] | 1.52 | 7.1E−12 | 1.45 | 3.8E−08 | 2.06 | 4.7E−11 | 1.96 | 2.7E−08 | 1.94 | 1.8E−04 |
| PC(36:5)/LPC(18:2) [sn2] | 1.54 | 7.3E−12 | 1.50 | 1.7E−08 | 1.92 | 4.5E−08 | 1.83 | 7.7E−06 | 2.01 | 4.7E−04 |
| SM(39:1)/PC(35:2) | 1.57 | 7.3E−12 | 1.73 | 4.0E−13 | 1.98 | 2.8E−07 | 2.28 | 9.8E−08 | 2.30 | 1.7E−04 |
| SM(40:2)/PC(35:2) | 1.56 | 7.3E−12 | 1.60 | 1.4E−10 | 1.83 | 1.0E−06 | 1.95 | 2.7E−06 | 2.29 | 2.7E−05 |
| PC(38:1)/LPC(17:0) [sn2] | 1.51 | 7.3E−12 | 1.48 | 7.3E−09 | 1.96 | 6.3E−11 | 1.90 | 2.7E−08 | 1.87 | 1.7E−04 |
| PE(40:6)/LPC(18:2) [sn1] | 1.52 | 8.6E−12 | 1.53 | 9.0E−10 | 2.01 | 5.3E−10 | 1.95 | 9.6E−08 | 1.96 | 3.4E−04 |
| Glc/GalCer(d16:1/18:0)/PC(O-38:0) | 1.60 | 8.7E−12 | 1.61 | 8.7E−10 | 2.20 | 2.7E−08 | 2.29 | 2.4E−07 | 2.04 | 2.5E−03 |
| PC(38:1)/PC(35:3) | 1.53 | 9.0E−12 | 1.61 | 2.4E−11 | 1.95 | 1.8E−08 | 1.95 | 4.7E−07 | 1.89 | 8.9E−04 |
| PC(38:1)/PC(O-34:0) | 1.53 | 9.0E−12 | 1.52 | 3.4E−09 | 1.70 | 3.6E−06 | 1.67 | 1.2E−04 | 1.95 | 2.6E−04 |
| SM(44:2)/PC(17:0_22:6) | 1.53 | 1.0E−11 | 1.52 | 5.2E−09 | 1.66 | 9.2E−06 | 1.86 | 9.5E−06 | 1.64 | 8.8E−03 |
| PE(38:1)/PC(34:3) | 1.53 | 1.2E−11 | 1.61 | 1.9E−11 | 1.77 | 8.5E−07 | 1.73 | 2.8E−05 | 1.87 | 1.4E−03 |
| SM(36:2)/LPE(P-20:0) | 1.53 | 1.2E−11 | 1.60 | 4.0E−11 | 2.27 | 3.6E−12 | 2.28 | 3.2E−10 | 1.90 | 3.4E−04 |
| SM(32:1)/PC(O-38:2) | 1.53 | 1.3E−11 | 1.49 | 2.4E−08 | 1.60 | 7.0E−05 | 1.59 | 5.7E−04 | 1.85 | 1.6E−03 |
| PC(36:5)/PC(O-40:3) | 1.53 | 1.3E−11 | 1.49 | 1.8E−08 | 1.62 | 2.5E−05 | 1.59 | 4.7E−04 | 1.69 | 6.5E−03 |
| PC(38:5)/LPC(20:2) [sn2] | 1.54 | 1.6E−11 | 1.55 | 1.2E−09 | 1.79 | 1.2E−06 | 1.71 | 7.8E−05 | 1.81 | 3.4E−03 |
| PE(40:6)/LPC(18:2) [sn2] | 1.52 | 1.6E−11 | 1.53 | 1.4E−09 | 2.01 | 1.4E−09 | 1.95 | 2.4E−07 | 1.93 | 7.5E−04 |
| PC(38:1)/PC(O-38:2) | 1.51 | 1.8E−11 | 1.45 | 8.9E−08 | 1.75 | 6.6E−07 | 1.66 | 8.2E−05 | 2.09 | 4.8E−05 |
| SM(36:1)/LPC(18:2) [sn1] | 1.52 | 1.8E−11 | 1.65 | 2.7E−12 | 2.19 | 1.1E−11 | 2.37 | 4.1E−11 | 2.11 | 5.2E−05 |
| PE(38:5)/LacCer(d18:1/24:0) | 1.53 | 1.8E−11 | 1.49 | 1.7E−08 | 1.77 | 1.9E−06 | 1.74 | 3.8E−05 | 1.86 | 2.0E−03 |
| SM(36:1)/LPC(20:2) [sn1] | 1.54 | 1.9E−11 | 1.73 | 1.7E−13 | 2.15 | 1.2E−09 | 2.43 | 7.5E−10 | 2.17 | 1.9E−04 |
| PC(38:1)/PC(P-40:2) | 1.52 | 1.9E−11 | 1.53 | 1.0E−09 | 1.66 | 1.0E−05 | 1.63 | 1.8E−04 | 1.77 | 1.2E−03 |
| PC(O-36:5)/LPC(22:1) [sn1] | 1.53 | 1.9E−11 | 1.46 | 1.3E−07 | 1.70 | 1.2E−05 | 1.67 | 1.8E−04 | 1.83 | 2.4E−03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| SM(36:2)/LPC(O-24:0) | 1.53 | 2.1E−11 | 1.63 | 1.0E−11 | 2.13 | 1.2E−10 | 2.32 | 2.7E−10 | 2.01 | 1.7E−04 |
| PE(40:6)/PC(P-40:5) | 1.51 | 2.6E−11 | 1.48 | 1.5E−08 | 1.99 | 4.9E−09 | 1.87 | 1.6E−06 | 1.92 | 9.3E−04 |
| Cer(d18:2/22:0)/LPC(15:0) [sn1] | 1.53 | 2.7E−11 | 1.55 | 1.4E−09 | 1.92 | 1.8E−07 | 1.90 | 5.8E−06 | 1.72 | 9.1E−03 |
| PC(36:5)/CE(17:0) | 1.52 | 2.7E−11 | 1.44 | 3.0E−07 | 1.74 | 3.1E−06 | 1.61 | 4.8E−04 | 1.88 | 1.5E−03 |
| SM(31:2)/SM(d17:1/14:0) | 1.56 | 3.0E−11 | 1.70 | 5.6E−12 | 2.63 | 7.1E−13 | 2.74 | 4.8E−11 | 2.78 | 2.8E−06 |
| PE(40:6)/PC(34:3) | 1.53 | 3.0E−11 | 1.60 | 8.5E−11 | 2.05 | 7.6E−09 | 2.03 | 3.8E−07 | 2.05 | 6.6E−04 |
| PG(34:1)/PC(34:3) | 1.54 | 3.1E−11 | 1.63 | 2.9E−11 | 1.83 | 1.1E−06 | 1.82 | 1.7E−05 | 1.74 | 9.1E−03 |
| Glc/GalCer(d16:1/18:0)/PC(O-38:2) | 1.57 | 3.3E−11 | 1.52 | 3.8E−08 | 2.08 | 1.4E−07 | 2.05 | 3.9E−06 | 1.89 | 5.5E−03 |
| PC(38:1)/LPC(O-18:1) | 1.49 | 3.4E−11 | 1.45 | 5.5E−08 | 1.89 | 5.7E−09 | 1.81 | 1.3E−06 | 1.71 | 3.5E−03 |
| SM(32:1)/PC(O-34:0) | 1.53 | 3.7E−11 | 1.55 | 1.4E−09 | 1.58 | 2.4E−04 | 1.63 | 5.4E−04 | 1.74 | 7.9E−03 |
| PC(36:5)/PC(P-40:5) | 1.52 | 3.7E−11 | 1.41 | 1.3E−06 | 1.81 | 1.0E−06 | 1.64 | 3.0E−04 | 1.97 | 7.6E−04 |
| PC(40:6)/LPC(O-18:0) | 1.52 | 3.8E−11 | 1.49 | 4.0E−08 | 2.35 | 6.0E−11 | 2.27 | 2.9E−08 | 2.15 | 2.6E−04 |
| PC(38:1)/PC(P-40:4) | 1.51 | 3.9E−11 | 1.51 | 7.1E−09 | 2.03 | 2.1E−09 | 2.10 | 4.8E−08 | 2.39 | 5.8E−06 |
| PE(38:5)/PC(34:3) | 1.51 | 4.1E−11 | 1.53 | 1.6E−09 | 1.76 | 1.1E−06 | 1.72 | 3.5E−05 | 1.67 | 9.8E−03 |
| PE(34:2)/PC(O-34:2) | 1.50 | 4.1E−11 | 1.46 | 3.5E−08 | 1.86 | 6.5E−08 | 1.72 | 1.7E−05 | 1.73 | 4.8E−03 |
| PC(38:5)/LPE(16:0) [sn1] | 1.53 | 4.1E−11 | 1.54 | 2.4E−09 | 1.73 | 7.7E−06 | 1.75 | 7.4E−05 | 1.85 | 2.8E−03 |
| PC(40:6)/PC(39:4) | 1.55 | 4.1E−11 | 1.50 | 4.7E−08 | 2.42 | 5.5E−10 | 2.40 | 4.6E−08 | 2.04 | 1.6E−03 |
| Cer(d20:1/24:1)/PE(P-36:2) | 1.49 | 4.1E−11 | 1.48 | 1.1E−08 | 2.02 | 1.3E−10 | 2.01 | 9.8E−09 | 1.75 | 2.4E−03 |
| PE(38:5)/LPC(18:1) [sn1] | 1.50 | 4.7E−11 | 1.47 | 2.1E−08 | 1.86 | 3.1E−08 | 1.80 | 3.5E−06 | 1.86 | 9.4E−04 |
| Cer(d16:1/16:0)/LPC(15:0) [sn1] | 1.54 | 4.7E−11 | 1.54 | 5.3E−09 | 2.06 | 3.1E−08 | 2.11 | 4.3E−07 | 1.77 | 8.1E−03 |
| PC(38:5)/LPE(16:0) [sn2] | 1.52 | 4.8E−11 | 1.55 | 2.0E−09 | 1.72 | 8.4E−06 | 1.72 | 1.0E−04 | 1.86 | 2.4E−03 |
| SM(36:2)/LPC(18:2) [sn1] | 1.51 | 4.9E−11 | 1.65 | 2.4E−12 | 2.32 | 9.1E−13 | 2.48 | 1.3E−11 | 2.10 | 1.0E−04 |
| PC(40:6)/LPC(P-16:0) | 1.51 | 5.5E−11 | 1.51 | 7.3E−09 | 2.29 | 2.3E−11 | 2.24 | 5.4E−09 | 1.84 | 2.5E−03 |
| PC(40:6)/PC(O-38:2) | 1.53 | 5.7E−11 | 1.46 | 2.4E−07 | 2.14 | 5.0E−09 | 1.99 | 2.9E−06 | 2.10 | 6.1E−04 |
| PE(P-38:6)/LacCer(d18:1/24:1) | 1.52 | 5.8E−11 | 1.47 | 9.4E−08 | 1.87 | 1.4E−07 | 1.86 | 5.2E−06 | 1.69 | 9.1E−03 |
| Glc/GalCer(d16:1/18:0)/Glc/GalCer(d18:1/23:0) | 1.56 | 6.0E−11 | 1.58 | 3.1E−09 | 2.03 | 3.2E−07 | 2.15 | 1.3E−06 | 1.90 | 6.2E−03 |
| PC(38:1)/LPC(O-18:0) | 1.49 | 6.0E−11 | 1.44 | 6.5E−08 | 1.96 | 1.7E−09 | 1.90 | 3.0E−07 | 2.06 | 5.8E−05 |
| PC(38:1)/PC(39:4) | 1.51 | 6.3E−11 | 1.47 | 4.5E−08 | 1.87 | 1.2E−07 | 1.92 | 7.9E−07 | 2.00 | 3.5E−04 |
| DAG(18:2/18:2)/PC(33:2) | 1.53 | 6.5E−11 | 1.63 | 6.9E−11 | 1.53 | 6.4E−04 | 1.62 | 7.4E−04 | 1.80 | 6.4E−03 |
| PC(40:6)/LPC(O-18:1) | 1.52 | 6.6E−11 | 1.48 | 7.2E−08 | 2.30 | 2.7E−10 | 2.17 | 1.3E−07 | 1.80 | 5.9E−03 |
| PC(38:1)/SM(41:2) | 1.49 | 6.6E−11 | 1.44 | 1.0E−07 | 1.66 | 4.5E−06 | 1.59 | 3.1E−04 | 1.76 | 1.6E−03 |
| PC(38:5)/LPE(P-18:0) | 1.51 | 7.0E−11 | 1.46 | 1.0E−07 | 1.83 | 6.0E−07 | 1.67 | 2.0E−04 | 1.85 | 2.6E−03 |
| Cer(d20:1/24:1)/LPC(18:1) [sn2] | 1.48 | 7.3E−11 | 1.52 | 5.9E−10 | 2.04 | 1.6E−10 | 2.12 | 1.4E−09 | 1.75 | 2.7E−03 |
| PC(36:5)/LPC(O-16:0) | 1.51 | 7.7E−11 | 1.40 | 1.9E−06 | 1.81 | 8.0E−07 | 1.68 | 1.5E−04 | 1.88 | 1.9E−03 |
| PC(38:5)/LPE(20:1) [sn1] | 1.53 | 7.9E−11 | 1.56 | 2.6E−09 | 1.83 | 1.3E−06 | 1.94 | 3.8E−06 | 1.76 | 9.0E−03 |
| SM(38:1)/PC(P-40:4) | 1.53 | 7.9E−11 | 1.59 | 5.3E−10 | 2.03 | 5.9E−08 | 2.24 | 8.3E−08 | 2.46 | 8.3E−05 |
| PC(40:6)/Glc/GalCer(d18:2/22:0) | 1.52 | 8.1E−11 | 1.48 | 5.8E−08 | 1.88 | 4.8E−07 | 1.82 | 2.0E−05 | 1.84 | 3.4E−03 |
| PC(38:1)/PC(O-32:0) | 1.49 | 8.1E−11 | 1.52 | 2.7E−09 | 1.66 | 1.3E−05 | 1.70 | 6.1E−05 | 1.93 | 6.7E−04 |
| PC(40:6)/PC(33:2) | 1.52 | 8.2E−11 | 1.49 | 4.8E−08 | 2.00 | 4.1E−08 | 1.90 | 5.1E−06 | 1.76 | 7.9E−03 |
| PC(38:1)/PC(O-38:0) | 1.51 | 8.9E−11 | 1.53 | 3.6E−09 | 1.81 | 5.5E−07 | 1.85 | 7.0E−06 | 2.25 | 3.5E−05 |
| PC(40:6)/PC(P-40:2) | 1.51 | 9.0E−11 | 1.52 | 6.4E−09 | 1.91 | 2.4E−07 | 1.85 | 1.2E−05 | 1.80 | 3.2E−03 |
| PC(40:6)/SM(41:2) | 1.52 | 9.7E−11 | 1.47 | 1.9E−07 | 2.08 | 1.3E−08 | 1.94 | 5.3E−06 | 1.83 | 4.1E−03 |
| Cer(d18:1/16:0)/LPC(15:0) [sn1] | 1.49 | 1.0E−10 | 1.44 | 2.0E−07 | 1.87 | 2.8E−08 | 1.78 | 5.0E−06 | 1.68 | 5.1E−03 |
| PC(40:6)/PC(35:3) | 1.53 | 1.1E−10 | 1.56 | 2.4E−09 | 2.24 | 2.1E−09 | 2.20 | 2.0E−07 | 1.89 | 3.7E−03 |
| LPE(P-16:0)/LPC(18:2) [sn1] | 1.49 | 1.2E−10 | 1.58 | 1.2E−10 | 2.08 | 2.0E−09 | 2.21 | 1.7E−09 | 2.03 | 2.2E−04 |
| SM(36:1)/LPC(18:2) [sn2] | 1.50 | 1.4E−10 | 1.65 | 8.5E−12 | 2.23 | 1.0E−10 | 2.46 | 2.3E−10 | 2.06 | 4.0E−04 |
| SM(36:2)/LPC(20:2) [sn1] | 1.51 | 1.4E−10 | 1.71 | 4.9E−13 | 2.25 | 1.6E−10 | 2.46 | 5.0E−10 | 2.08 | 5.1E−04 |
| SM(44:2)/LPC(22:1) [sn1] | 1.53 | 1.5E−10 | 1.52 | 3.9E−08 | 2.17 | 3.0E−08 | 2.49 | 1.9E−08 | 1.86 | 4.4E−03 |
| CE(18:0)/LPC(18:1) [sn2] | 1.52 | 1.5E−10 | 1.75 | 1.7E−13 | 1.90 | 6.6E−07 | 2.11 | 3.7E−07 | 1.85 | 4.2E−03 |
| PC(36:5)/LPE(20:1) [sn1] | 1.52 | 1.6E−10 | 1.49 | 9.6E−08 | 1.78 | 4.9E−06 | 1.86 | 1.9E−05 | 1.96 | 2.6E−03 |
| PE(36:5)/PC(O-40:3) | 1.49 | 1.6E−10 | 1.44 | 2.1E−07 | 1.64 | 1.9E−05 | 1.55 | 9.2E−04 | 1.71 | 6.1E−03 |
| PE(34:2)/PC(O-34:0) | 1.48 | 1.7E−10 | 1.43 | 1.7E−07 | 1.67 | 6.7E−06 | 1.60 | 2.2E−04 | 1.68 | 6.9E−03 |
| PC(40:6)/PC(O-38:0) | 1.52 | 1.9E−10 | 1.52 | 1.7E−08 | 2.19 | 5.8E−09 | 2.19 | 4.0E−07 | 2.14 | 5.1E−04 |
| PE(36:5)/PC(O-34:2) | 1.50 | 2.0E−10 | 1.41 | 1.2E−06 | 1.84 | 5.7E−07 | 1.61 | 4.4E−04 | 1.94 | 1.3E−03 |
| PC(36:5)/LPC(20:2) [sn2] | 1.50 | 2.2E−10 | 1.45 | 2.2E−07 | 1.70 | 1.0E−05 | 1.61 | 5.0E−04 | 1.94 | 1.1E−03 |
| PE(P-36:4)/PE(P-36:2) | 1.49 | 2.2E−10 | 1.46 | 8.0E−08 | 1.89 | 1.6E−07 | 2.00 | 5.8E−07 | 1.74 | 5.4E−03 |
| PC(36:5)/LPE(16:0) [sn1] | 1.50 | 2.4E−10 | 1.45 | 2.5E−07 | 1.66 | 3.6E−05 | 1.64 | 3.9E−04 | 2.00 | 7.4E−04 |
| PC(36:5)/LPE(16:0) [sn2] | 1.50 | 2.5E−10 | 1.46 | 4.8E−07 | 1.66 | 3.7E−05 | 1.63 | 4.7E−04 | 2.02 | 6.4E−04 |
| PC(40:6)/PC(P-40:4) | 1.50 | 2.5E−10 | 1.49 | 4.7E−08 | 2.35 | 3.2E−10 | 2.34 | 2.9E−08 | 2.23 | 3.1E−04 |
| SM(38:1)/PC(O-32:0) | 1.50 | 2.5E−10 | 1.59 | 3.0E−10 | 1.62 | 1.3E−04 | 1.77 | 7.1E−05 | 1.86 | 4.4E−03 |
| SM(36:1)/LPC(15:0) [sn2] | 1.48 | 2.6E−10 | 1.50 | 9.4E−09 | 1.99 | 3.1E−09 | 2.06 | 2.9E−08 | 1.72 | 4.5E−03 |
| PC(40:6)/LPE(P-20:0) | 1.50 | 2.7E−10 | 1.48 | 4.3E−08 | 2.33 | 2.3E−11 | 2.22 | 1.3E−08 | 1.94 | 1.2E−03 |
| PC(38:1)/PC(O-34:2) | 1.48 | 2.9E−10 | 1.49 | 2.3E−08 | 1.97 | 1.1E−08 | 1.81 | 6.9E−06 | 1.90 | 9.2E−04 |
| Glc/GalCer(d16:1/18:0)/LPE(P-20:0) | 1.51 | 3.0E−10 | 1.51 | 2.8E−08 | 2.10 | 4.6E−09 | 2.08 | 1.8E−07 | 1.74 | 7.4E−03 |
| PC(38:5)/LPC(18:1) [sn1] | 1.49 | 3.0E−10 | 1.50 | 1.4E−08 | 1.93 | 3.4E−08 | 1.89 | 3.1E−06 | 2.05 | 2.8E−04 |
| PC(32:0)/PC(O-38:0) | 1.51 | 3.4E−10 | 1.43 | 1.2E−06 | 1.82 | 2.0E−06 | 1.77 | 1.0E−04 | 1.87 | 2.9E−03 |
| PE(P-38:6)/PC(O-34:2) | 1.49 | 3.7E−10 | 1.45 | 1.9E−07 | 2.14 | 8.0E−10 | 2.00 | 5.3E−07 | 2.14 | 2.7E−04 |
| SM(38:1)/PC(O-34:2) | 1.49 | 3.8E−10 | 1.53 | 3.3E−09 | 1.94 | 8.2E−08 | 1.87 | 6.7E−06 | 1.85 | 2.9E−03 |
| PC(38:1)/PC(33:2) | 1.47 | 4.0E−10 | 1.46 | 4.7E−08 | 1.67 | 9.5E−06 | 1.63 | 1.8E−04 | 1.68 | 7.6E−03 |
| PE(36:5)/LPE(16:0) [sn1] | 1.49 | 4.0E−10 | 1.43 | 6.5E−07 | 1.76 | 5.4E−06 | 1.65 | 3.5E−04 | 2.19 | 2.7E−04 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| SM(36:1)/LPC(15:0) [sn1] | 1.48 | 4.2E-10 | 1.49 | 1.5E-08 | 2.07 | 7.4E-10 | 2.15 | 5.5E-09 | 2.03 | 1.7E-04 |
| PC(40:6)/LPC(0-24:0) | 1.49 | 4.3E-10 | 1.50 | 2.6E-08 | 2.23 | 6.1E-10 | 2.25 | 2.6E-08 | 2.05 | 7.1E-04 |
| SM(36:2)/LPC(18:2) [sn2] | 1.49 | 4.5E-10 | 1.65 | 9.7E-12 | 2.38 | 1.1E-11 | 2.58 | 9.9E-11 | 2.02 | 7.9E-04 |
| PC(40:6)/PC(O-34:2) | 1.49 | 4.6E-10 | 1.49 | 4.8E-08 | 2.24 | 8.9E-10 | 2.05 | 7.7E-07 | 1.90 | 2.6E-03 |
| PE(36:5)/LPE(16:0) [sn2] | 1.49 | 5.2E-10 | 1.43 | 5.6E-07 | 1.75 | 6.8E-06 | 1.63 | 4.6E-04 | 2.19 | 2.8E-04 |
| PC(40:6)/PC(0-34:0) | 1.49 | 5.2E-10 | 1.48 | 1.1E-07 | 1.98 | 1.9E-07 | 1.90 | 1.4E-05 | 1.90 | 2.9E-03 |
| LPC(16:0) [sn2]/LPC(18:1) [sn2] | 1.51 | 6.0E-10 | 1.65 | 4.5E-11 | 1.95 | 4.8E-07 | 2.04 | 2.2E-06 | 2.05 | 1.5E-03 |
| SM(38:1)/PC(39:4) | 1.49 | 6.4E-10 | 1.52 | 1.0E-08 | 1.75 | 5.6E-06 | 1.93 | 2.8E-06 | 1.86 | 3.7E-03 |
| LPC(14:0) [sn2]/LPC(18:1) [sn2] | 1.50 | 7.5E-10 | 1.57 | 2.7E-09 | 1.89 | 2.1E-06 | 1.87 | 3.7E-05 | 1.90 | 5.2E-03 |
| PE(34:2)/LPE(16:0) [sn1] | 1.45 | 1.1E-09 | 1.46 | 4.1E-08 | 1.69 | 2.3E-06 | 1.72 | 1.3E-05 | 1.74 | 3.2E-03 |
| PC(38:1)/LPC(P-16:0) | 1.43 | 1.2E-09 | 1.43 | 6.1E-08 | 1.77 | 7.6E-09 | 1.75 | 3.5E-07 | 1.64 | 2.4E-03 |
| LPC(16:0) [sn1]/LPC(18:1) [sn2] | 1.48 | 1.2E-09 | 1.62 | 6.7E-11 | 1.89 | 5.2E-07 | 1.95 | 3.0E-06 | 1.84 | 4.4E-03 |
| SM(38:1)/LPC(P-16:0) | 1.43 | 1.4E-09 | 1.48 | 5.3E-09 | 1.73 | 6.7E-08 | 1.78 | 3.2E-07 | 1.59 | 6.3E-03 |
| PE(34:2)/LPE(16:0) [sn2] | 1.45 | 1.6E-09 | 1.46 | 4.1E-08 | 1.68 | 3.1E-06 | 1.69 | 2.1E-05 | 1.74 | 3.1E-03 |
| Glc/GalCer(d16:1/18:0)/LPC(O-24:0) | 1.49 | 1.6E-09 | 1.50 | 5.4E-08 | 2.00 | 1.5E-07 | 2.10 | 6.1E-07 | 1.77 | 9.2E-03 |
| PC(40:6)/PC(0-32:0) | 1.48 | 1.7E-09 | 1.48 | 1.0E-07 | 2.00 | 2.1E-07 | 1.98 | 5.3E-06 | 1.87 | 5.1E-03 |
| LPE(P-16:0)/LPC(18:2) [sn2] | 1.46 | 2.0E-09 | 1.55 | 7.8E-10 | 1.97 | 6.3E-09 | 2.10 | 3.1E-08 | 1.79 | 2.6E-03 |
| PE(34:2)/LPC(20:2) [sn1] | 1.43 | 2.4E-09 | 1.44 | 8.9E-08 | 1.68 | 8.5E-07 | 1.65 | 2.6E-05 | 1.63 | 5.7E-03 |
| SM(36:1)/LPC(0-16:0) | 1.44 | 2.5E-09 | 1.47 | 1.8E-08 | 1.90 | 4.2E-09 | 1.98 | 1.9E-08 | 1.71 | 2.3E-03 |
| SM(33:2)/PC(O-38:2) | 1.46 | 2.5E-09 | 1.53 | 2.7E-09 | 2.46 | 1.0E-12 | 2.66 | 7.5E-12 | 2.60 | 1.4E-06 |
| Glc/GalCer(d16:1/18:0)/LPC(15:0) [sn1] | 1.48 | 2.7E-09 | 1.45 | 7.5E-07 | 2.11 | 2.5E-08 | 2.09 | 8.7E-07 | 1.78 | 7.9E-03 |
| PC(36:5)/LPC(18:1) [sn1] | 1.45 | 2.7E-09 | 1.40 | 1.5E-06 | 1.80 | 5.0E-07 | 1.74 | 3.7E-05 | 2.11 | 1.1E-04 |
| DAG(18:2/18:2)/LPC(15:0) [sn2] | 1.46 | 3.4E-09 | 1.55 | 4.6E-09 | 1.60 | 2.1E-04 | 1.68 | 3.3E-04 | 1.75 | 9.2E-03 |
| PC(32:0)/LPC(20:2) [sn1] | 1.45 | 3.7E-09 | 1.46 | 9.4E-08 | 1.89 | 7.2E-08 | 1.83 | 6.4E-06 | 1.71 | 7.6E-03 |
| PE(P-38:6)/PE(P-40:6) | 1.45 | 3.8E-09 | 1.44 | 3.6E-07 | 1.89 | 3.3E-07 | 1.77 | 5.3E-05 | 1.78 | 5.7E-03 |
| SM(33:2)/SM(41:2) | 1.44 | 4.2E-09 | 1.56 | 5.2E-10 | 2.29 | 2.8E-12 | 2.55 | 6.7E-12 | 2.12 | 9.5E-05 |
| PE(34:2)/PC(O-38:2) | 1.44 | 4.3E-09 | 1.37 | 5.1E-06 | 1.64 | 1.7E-05 | 1.55 | 6.6E-04 | 1.67 | 8.3E-03 |
| PC(40:6)/LPC(18:2) [sn1] | 1.46 | 4.5E-09 | 1.50 | 2.9E-08 | 2.29 | 1.4E-10 | 2.29 | 1.2E-08 | 2.05 | 7.5E-04 |
| PE(P-38:6)/SM(d17:1/14:0) | 1.45 | 4.6E-09 | 1.37 | 1.1E-05 | 1.81 | 9.0E-07 | 1.74 | 7.4E-05 | 1.75 | 6.6E-03 |
| PE(36:5)/LPC(O-24:0) | 1.44 | 5.0E-09 | 1.36 | 1.1E-05 | 1.68 | 9.9E-06 | 1.56 | 7.7E-04 | 1.89 | 1.4E-03 |
| SM(38:1)/LPE(P-20:0) | 1.43 | 5.0E-09 | 1.46 | 3.9E-08 | 1.84 | 3.6E-08 | 1.85 | 7.0E-07 | 1.76 | 2.1E-03 |
| PC(38:1)/LPC(20:2) [sn1] | 1.44 | 5.0E-09 | 1.54 | 1.3E-09 | 1.91 | 5.0E-08 | 1.93 | 8.4E-07 | 2.02 | 3.6E-04 |
| PC(40:6)/LPC(20:2) [sn1] | 1.46 | 5.4E-09 | 1.53 | 1.4E-08 | 2.22 | 3.5E-09 | 2.21 | 1.9E-07 | 2.01 | 1.8E-03 |
| PE(34:2)/PC(31:0) | 1.44 | 5.5E-09 | 1.41 | 1.1E-06 | 1.61 | 4.3E-05 | 1.56 | 6.9E-04 | 1.67 | 9.9E-03 |
| SM(33:2)/PC(33:2) | 1.45 | 5.9E-09 | 1.56 | 1.0E-09 | 2.14 | 8.7E-10 | 2.36 | 1.3E-09 | 1.89 | 1.6E-03 |
| PC(38:1)/LPE(P-20:0) | 1.42 | 6.1E-09 | 1.41 | 4.4E-07 | 1.90 | 4.5E-09 | 1.83 | 7.5E-07 | 1.82 | 8.2E-04 |
| SM(38:1)/LPC(18:2) [sn1] | 1.43 | 6.4E-09 | 1.53 | 1.0E-09 | 1.92 | 4.6E-09 | 2.02 | 2.0E-08 | 1.92 | 4.5E-04 |
| PE(P-38:6)/LPC(22:6) [sn1] | 1.45 | 6.4E-09 | 1.51 | 1.2E-08 | 1.82 | 7.4E-07 | 1.90 | 2.5E-06 | 1.74 | 7.1E-03 |
| Cer(d18:1/26:1)/Glc/GalCer(d18:1/23:0) | 1.44 | 7.5E-09 | 1.31 | 1.5E-04 | 1.72 | 4.5E-06 | 1.67 | 1.1E-04 | 1.76 | 5.1E-03 |
| PE(34:2)/LPC(18:2) [sn2] | 1.40 | 8.6E-09 | 1.40 | 3.4E-07 | 1.69 | 3.0E-07 | 1.65 | 1.2E-05 | 1.59 | 7.7E-03 |
| PC(40:6)/LPC(15:0) [sn1] | 1.45 | 9.5E-09 | 1.39 | 6.0E-06 | 2.32 | 3.6E-10 | 2.17 | 2.4E-07 | 2.05 | 1.1E-03 |
| PC(38:1)/LPC(18:2) [sn1] | 1.42 | 1.0E-08 | 1.47 | 1.5E-08 | 1.94 | 1.2E-09 | 1.96 | 3.6E-08 | 1.95 | 2.0E-04 |
| PE(36:5)/LPC(15:0) [sn1] | 1.42 | 1.1E-08 | 1.32 | 6.4E-05 | 1.73 | 2.4E-06 | 1.55 | 8.1E-04 | 1.86 | 1.1E-03 |
| SM(32:1)/PC(0-38:0) | 1.46 | 1.1E-08 | 1.52 | 3.0E-08 | 1.63 | 2.5E-04 | 1.77 | 1.8E-04 | 1.95 | 3.9E-03 |
| PC(40:6)/PC(31:0) | 1.45 | 1.1E-08 | 1.45 | 6.9E-07 | 1.92 | 9.2E-07 | 1.85 | 4.4E-05 | 1.95 | 3.4E-03 |
| LPE(P-16:0)/LPE(P-18:0) | 1.43 | 1.2E-08 | 1.40 | 2.7E-06 | 1.84 | 6.6E-07 | 1.69 | 1.5E-04 | 2.04 | 5.8E-04 |
| PE(36:5)/LPE(20:1) [sn1] | 1.45 | 1.2E-08 | 1.41 | 2.5E-06 | 1.74 | 9.8E-06 | 1.72 | 1.2E-04 | 1.86 | 4.9E-03 |
| PE(P-38:6)/PC(33:2) | 1.43 | 1.3E-08 | 1.39 | 5.4E-06 | 1.74 | 3.3E-06 | 1.75 | 5.9E-05 | 1.78 | 4.2E-03 |
| SM(39:1)/PC(O-38:2) | 1.43 | 1.5E-08 | 1.44 | 6.1E-07 | 1.56 | 3.8E-04 | 1.68 | 2.7E-04 | 1.95 | 1.5E-03 |
| SM(38:1)/LPC(20:2) [sn1] | 1.43 | 1.6E-08 | 1.59 | 1.8E-10 | 1.84 | 1.1E-06 | 1.98 | 1.3E-06 | 1.91 | 1.9E-03 |
| LPE(P-16:0)/LPC(20:2) [sn1] | 1.43 | 1.8E-08 | 1.54 | 3.3E-09 | 1.72 | 7.7E-06 | 1.83 | 2.0E-05 | 1.75 | 5.2E-03 |
| Glc/GalCer(d16:1/18:0)/Glc/GalCer(d18:2/24:0) | 1.44 | 2.8E-08 | 1.42 | 2.4E-06 | 1.87 | 2.9E-06 | 1.85 | 4.3E-05 | 2.04 | 1.9E-03 |
| PC(40:6)/Glc/GalCer(d18:1/23:0) | 1.43 | 3.1E-08 | 1.43 | 8.2E-07 | 1.88 | 1.3E-06 | 1.88 | 2.0E-05 | 1.88 | 3.7E-03 |
| PC(36:5)/LPC(18:1) [sn2] | 1.41 | 3.1E-08 | 1.38 | 5.6E-06 | 1.71 | 3.8E-06 | 1.66 | 1.5E-04 | 2.05 | 1.9E-04 |
| PC(40:2)/PC(O-38:0) | 1.43 | 3.2E-08 | 1.39 | 6.1E-06 | 1.75 | 1.1E-05 | 1.84 | 2.2E-05 | 2.23 | 1.3E-04 |
| PC(40:6)/LPC(18:2) [sn2] | 1.43 | 3.2E-08 | 1.47 | 1.4E-07 | 2.24 | 1.5E-09 | 2.23 | 1.0E-07 | 1.91 | 3.4E-03 |
| Cer(d18:1/26:1)/LPC(O-24:0) | 1.40 | 3.7E-08 | 1.28 | 3.3E-04 | 1.71 | 1.4E-06 | 1.67 | 4.2E-05 | 1.67 | 7.3E-03 |
| SM(38:1)/Glc/GalCer(d18:1/23:0) | 1.42 | 4.5E-08 | 1.50 | 2.8E-08 | 1.52 | 8.5E-04 | 1.66 | 3.6E-04 | 1.87 | 2.8E-03 |
| DAG(18:2/18:2)/LPC(O-16:0) | 1.41 | 4.8E-08 | 1.51 | 1.5E-08 | 1.55 | 3.9E-04 | 1.66 | 3.1E-04 | 1.72 | 1.0E-02 |
| Glc/GalCer(d16:1/18:0)/Glc/GalCer(d16:1/23:0) | 1.42 | 4.8E-08 | 1.42 | 1.6E-06 | 1.95 | 2.8E-07 | 2.15 | 4.3E-07 | 1.78 | 4.8E-03 |
| SM(38:1)/LPC(18:2) [sn2] | 1.41 | 4.8E-08 | 1.52 | 3.7E-09 | 1.91 | 5.5E-08 | 2.03 | 1.6E-07 | 1.83 | 2.8E-03 |
| SM(38:1)/LPC(O-24:0) | 1.40 | 5.7E-08 | 1.46 | 8.2E-08 | 1.68 | 1.2E-05 | 1.83 | 7.3E-06 | 1.84 | 2.1E-03 |
| PE(34:2)/LPC(15:0) [sn1] | 1.38 | 5.8E-08 | 1.32 | 2.6E-05 | 1.64 | 2.4E-06 | 1.56 | 1.2E-04 | 1.58 | 8.3E-03 |
| PC(40:6)/CE(17:0) | 1.42 | 6.4E-08 | 1.42 | 2.0E-06 | 2.04 | 7.3E-08 | 1.96 | 9.6E-06 | 1.76 | 8.5E-03 |
| PE(P-38:6)/Glc/GalCer(d18:2/22:0) | 1.40 | 6.7E-08 | 1.35 | 2.5E-05 | 1.57 | 1.4E-04 | 1.57 | 7.7E-04 | 1.80 | 2.9E-03 |
| Cer(d18:2/22:0)/PE(P-36:2) | 1.40 | 6.9E-08 | 1.46 | 1.5E-07 | 1.84 | 7.5E-07 | 1.81 | 1.8E-05 | 1.82 | 3.1E-03 |
| PE(P-38:6)/PC(O-38:2) | 1.41 | 7.2E-08 | 1.32 | 1.3E-04 | 1.76 | 3.0E-06 | 1.70 | 1.2E-04 | 2.07 | 3.5E-04 |
| PE(P-38:6)/SM(41:2) | 1.40 | 7.9E-08 | 1.32 | 9.4E-05 | 1.72 | 6.5E-06 | 1.66 | 2.1E-04 | 1.84 | 2.5E-03 |

TABLE 7-continued

Odds Ratios (OR) based on combination biomarker values of Group E and Group F biomarkers in subjects, whose liver fat content was determined four years after the lipid measurements, as compared to a control group in Young Finns Study cohort.

| Lipid ratio | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| PE(P-38:6)/LPE(P-20:0) | 1.39 | 9.7E−08 | 1.35 | 1.4E−05 | 1.94 | 1.2E−08 | 1.89 | 8.5E−07 | 1.90 | 8.5E−04 |
| PC(38:1)/LPC(18:2) [sn2] | 1.39 | 9.8E−08 | 1.45 | 8.2E−08 | 1.92 | 1.7E−08 | 1.94 | 3.8E−07 | 1.86 | 1.5E−03 |
| SM(38:1)/LPC(15:0) [sn1] | 1.39 | 1.2E−07 | 1.38 | 4.1E−06 | 1.83 | 2.9E−07 | 1.83 | 4.5E−06 | 1.88 | 1.1E−03 |
| PE(P-38:6)/PC(O-38:0) | 1.40 | 1.3E−07 | 1.37 | 1.1E−05 | 1.77 | 3.3E−06 | 1.81 | 2.3E−05 | 2.11 | 3.3E−04 |
| Cer(d18:1/16:0)/LPC(18:1) [sn1] | 1.38 | 1.3E−07 | 1.46 | 4.2E−08 | 1.85 | 1.7E−08 | 1.87 | 1.8E−07 | 1.84 | 4.9E−04 |
| PC(38:1)/LPC(O-24:0) | 1.39 | 1.4E−07 | 1.40 | 2.2E−06 | 1.74 | 3.5E−06 | 1.79 | 1.6E−05 | 1.95 | 8.5E−04 |
| Glc/GalCer(d16:1/18:0)/PC(O-40:4) | 1.41 | 1.7E−07 | 1.38 | 1.1E−05 | 1.79 | 1.0E−05 | 1.81 | 6.3E−05 | 1.89 | 4.6E−03 |
| PC(40:6)/PC(P-40:5) | 1.40 | 1.8E−07 | 1.39 | 8.0E−06 | 2.33 | 1.8E−09 | 2.19 | 6.7E−07 | 1.92 | 4.6E−03 |
| PC(40:6)/PC(37:1) | 1.41 | 1.9E−07 | 1.38 | 1.7E−05 | 2.02 | 4.1E−07 | 1.95 | 2.3E−05 | 1.95 | 3.8E−03 |
| PE(P-38:6)/PC(39:4) | 1.40 | 2.2E−07 | 1.33 | 8.4E−05 | 1.87 | 1.4E−06 | 1.93 | 7.0E−06 | 2.00 | 1.4E−03 |
| SM(44:2)/LPC(22:6) [sn1] | 1.39 | 2.6E−07 | 1.45 | 3.8E−07 | 1.79 | 5.3E−06 | 1.97 | 3.6E−06 | 1.80 | 6.7E−03 |
| SM(33:2)/Glc/GalCer(d18:2/22:0) | 1.37 | 4.8E−07 | 1.45 | 1.8E−07 | 1.72 | 5.7E−06 | 1.90 | 1.7E−06 | 1.85 | 2.2E−03 |
| Cer(d18:2/22:0)/LPC(18:1) [sn2] | 1.38 | 5.1E−07 | 1.53 | 4.7E−09 | 1.80 | 4.0E−06 | 1.93 | 5.1E−06 | 1.85 | 4.6E−03 |
| Glc/GalCer(d16:1/18:0)/LacCer(d18:1/24:0) | 1.39 | 6.0E−07 | 1.43 | 1.9E−06 | 1.77 | 1.5E−05 | 1.93 | 1.1E−05 | 1.79 | 9.5E−03 |
| PC(40:6)/LPC(20:2) [sn2] | 1.38 | 6.3E−07 | 1.44 | 7.6E−07 | 2.00 | 2.2E−07 | 2.00 | 4.6E−06 | 1.84 | 6.5E−03 |
| PE(34:2)/PE(P-36:2) | 1.35 | 6.6E−07 | 1.32 | 6.0E−05 | 1.72 | 1.2E−06 | 1.63 | 8.7E−05 | 1.75 | 2.4E−03 |
| Glc/GalCer(d16:1/18:0)/PE(P-36:2) | 1.37 | 6.8E−07 | 1.37 | 1.2E−05 | 1.96 | 1.5E−07 | 1.95 | 3.5E−06 | 1.85 | 4.1E−03 |
| PC(40:6)/LPE(16:0) [sn1] | 1.38 | 7.3E−07 | 1.44 | 7.6E−07 | 1.94 | 6.3E−07 | 2.08 | 1.3E−06 | 1.91 | 4.0E−03 |
| PC(40:6)/LPE(16:0) [sn2] | 1.38 | 7.6E−07 | 1.45 | 6.4E−07 | 1.92 | 8.2E−07 | 2.03 | 2.7E−06 | 1.92 | 3.5E−03 |
| PE(P-38:6)/LPC(O-24:0) | 1.36 | 8.2E−07 | 1.33 | 4.1E−05 | 1.77 | 1.3E−06 | 1.82 | 6.1E−06 | 1.98 | 6.8E−04 |
| SM(32:1)/LPC(15:0) [sn1] | 1.36 | 1.0E−06 | 1.33 | 5.3E−05 | 1.77 | 2.3E−06 | 1.78 | 2.2E−05 | 1.71 | 7.1E−03 |
| SM(32:2)/PC(O-38:2) | 1.36 | 1.2E−06 | 1.37 | 1.1E−05 | 1.96 | 1.2E−07 | 1.87 | 1.5E−05 | 2.45 | 2.7E−05 |
| PC(40:2)/PC(39:4) | 1.36 | 1.8E−06 | 1.29 | 4.8E−04 | 1.69 | 5.9E−05 | 1.81 | 5.9E−05 | 1.90 | 3.6E−03 |
| PC(40:2)/LPC(O-24:0) | 1.35 | 2.6E−06 | 1.32 | 1.4E−04 | 1.71 | 2.4E−05 | 1.82 | 2.9E−05 | 2.03 | 1.2E−03 |
| PC(38:1)/LPC(15:0) [sn1] | 1.33 | 2.8E−06 | 1.29 | 2.9E−04 | 1.79 | 5.7E−07 | 1.72 | 3.9E−05 | 1.86 | 1.3E−03 |
| SM(34:2)/LPC(O-24:0) | 1.32 | 6.5E−06 | 1.42 | 6.9E−07 | 1.97 | 1.3E−08 | 2.11 | 3.6E−08 | 1.75 | 3.2E−03 |
| PC(38:1)/LPC(20:2) [sn2] | 1.32 | 9.6E−06 | 1.41 | 9.5E−07 | 1.65 | 2.9E−05 | 1.69 | 1.1E−04 | 1.81 | 3.0E−03 |
| SM(44:2)/LPC(O-24:0) | 1.32 | 1.3E−05 | 1.29 | 4.0E−04 | 1.77 | 6.7E−06 | 1.90 | 6.9E−06 | 2.15 | 4.4E−04 |
| PE(P-38:6)/Glc/GalCer(d18:1/23:0) | 1.31 | 1.6E−05 | 1.30 | 2.8E−04 | 1.55 | 3.4E−04 | 1.59 | 7.5E−04 | 1.83 | 3.2E−03 |
| PE(P-38:6)/CE(17:0) | 1.31 | 1.9E−05 | 1.29 | 3.9E−04 | 1.72 | 1.7E−05 | 1.69 | 2.8E−04 | 1.77 | 8.0E−03 |
| PC(40:6)/LPC(18:1) [sn1] | 1.31 | 2.0E−05 | 1.36 | 2.4E−05 | 2.07 | 3.1E−08 | 2.10 | 5.7E−07 | 2.05 | 1.0E−03 |
| Cer(d18:2/24:1)/PE(P-36:2) | 1.30 | 2.7E−05 | 1.31 | 1.4E−04 | 1.76 | 2.6E−06 | 1.67 | 1.4E−04 | 1.70 | 7.4E−03 |
| PC(38:1)/PC(P-40:5) | 1.30 | 3.1E−05 | 1.29 | 2.6E−04 | 1.79 | 2.0E−06 | 1.69 | 1.4E−04 | 1.86 | 2.9E−03 |
| SM(44:2)/Glc/GalCer(d18:1/23:0) | 1.30 | 3.1E−05 | 1.28 | 5.6E−04 | 1.57 | 3.5E−04 | 1.69 | 2.3E−04 | 2.08 | 7.5E−04 |
| LPC(20:4) [sn2]/LPC(18:1) [sn2] | 1.30 | 3.5E−05 | 1.39 | 5.7E−06 | 1.75 | 7.6E−06 | 1.94 | 3.4E−06 | 1.79 | 5.3E−03 |
| Cer(d18:2/24:1)/LPC(18:1) [sn2] | 1.29 | 7.8E−05 | 1.39 | 5.6E−06 | 1.84 | 2.9E−06 | 1.89 | 1.4E−05 | 1.81 | 7.3E−03 |
| PE(P-38:6)/LPC(20:2) [sn2] | 1.28 | 9.3E−05 | 1.32 | 1.5E−04 | 1.69 | 3.6E−05 | 1.74 | 1.3E−04 | 1.89 | 3.9E−03 |
| SM(33:2)/LPC(15:0) [sn1] | 1.26 | 2.2E−04 | 1.31 | 1.1E−04 | 2.15 | 3.5E−10 | 2.29 | 1.7E−09 | 1.98 | 3.2E−04 |
| PC(40:2)/LPC(20:2) [sn2] | 1.25 | 3.3E−04 | 1.28 | 5.9E−04 | 1.54 | 6.0E−04 | 1.61 | 7.3E−04 | 1.75 | 8.4E−03 |
| PE(P-38:6)/LPE(16:0) [sn2] | 1.25 | 4.9E−04 | 1.28 | 5.4E−04 | 1.55 | 5.6E−04 | 1.68 | 3.4E−04 | 1.84 | 4.7E−03 |
| SM(38:1)/LPC(18:1) [sn1] | 1.24 | 5.7E−04 | 1.35 | 1.5E−05 | 1.67 | 8.1E−06 | 1.80 | 4.1E−06 | 1.90 | 8.3E−04 |
| PE(P-38:6)/LPE(16:0) [sn1] | 1.24 | 5.8E−04 | 1.27 | 7.8E−04 | 1.55 | 5.5E−04 | 1.71 | 2.4E−04 | 1.83 | 5.5E−03 |
| PC(38:1)/LPC(18:1) [sn1] | 1.23 | 7.7E−04 | 1.29 | 1.7E−04 | 1.70 | 1.6E−06 | 1.74 | 6.5E−06 | 1.92 | 2.8E−04 |

FL: subjects with fatty liver disease vs. healthy controls, NAFLD: subjects with non-alcoholic fatty liver disease vs. healthy controls, FL(severe): subjects with severe fatty liver disease vs. healthy controls, NAFLD(severe): subjects with severe non-alcoholic fatty liver disease vs. healthy controls, DM2: subjects who developed type 2 diabetes during the follow-up vs. healthy controls. Other abbreviations are described in the detailed description of the present disclosure.

Table 8 shows results of Odds Ratios based on individual fatty liver biomarker values from Group A, Group B, Group E and Group F, in subjects, whose liver fat content was determined four years after the lipid measurements, as compared to a control group. As can be seen, Odds Ratios based on combination biomarker values of the at least one fatty liver biomarker from Group A and the at least one fatty liver biomarker from Group B and Odds Ratios based on combination biomarker values of the at least one fatty liver biomarker from Group E and the at least one fatty liver biomarker from Group F, shown in Tables 6 and 7, provide stronger association with fatty liver disease than the individual markers in Table 8, improving thus the prognostic and diagnostic performance of the biomarkers.

TABLE 8

Odds Ratios (OR) based on individual fatty liver biomarker values from Group A, Group B, Group E and Group F in subjects, whose liver fat content was determined four years after the lipid measurements, as compared to a control group in Young Finns Study cohort.

| Lipid | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| AcylCarnitine(16:0) | 1.65 | 8.6E−14 | 1.62 | 3.2E−10 | 1.90 | 1.2E−06 | 1.95 | 9.3E−06 | 1.09 | 6.7E−01 |
| CE(16:1) | 1.92 | 8.6E−24 | 1.82 | 2.1E−16 | 2.37 | 6.8E−13 | 2.40 | 1.3E−10 | 1.53 | 2.9E−02 |
| CE(16:2) | 1.58 | 1.0E−12 | 1.53 | 5.5E−09 | 2.14 | 2.0E−09 | 2.03 | 6.5E−07 | 1.40 | 9.8E−02 |

TABLE 8-continued

Odds Ratios (OR) based on individual fatty liver biomarker values from Group A, Group B,
Group E and Group F in subjects, whose liver fat content was determined four years after
the lipid measurements, as compared to a control group in Young Finns Study cohort.

| Lipid | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| CE(17:0) | 0.83 | 3.2E−03 | 0.83 | 7.6E−03 | 0.76 | 2.5E−02 | 0.80 | 1.0E−01 | 0.75 | 1.7E−01 |
| CE(18:0) | 1.51 | 1.6E−10 | 1.62 | 7.4E−11 | 1.52 | 8.2E−04 | 1.62 | 7.7E−04 | 1.23 | 3.4E−01 |
| CE(18:1) | 0.95 | 3.7E−01 | 0.93 | 3.0E−01 | 0.92 | 5.2E−01 | 0.94 | 6.7E−01 | 0.81 | 3.2E−01 |
| CE(20:3) | 1.61 | 8.1E−14 | 1.62 | 1.8E−11 | 2.36 | 3.5E−12 | 2.63 | 5.6E−12 | 1.37 | 1.3E−01 |
| CE(22:4) | 0.87 | 2.4E−02 | 0.86 | 3.0E−02 | 0.91 | 4.2E−01 | 0.93 | 5.8E−01 | 0.82 | 3.4E−01 |
| Cer(d16:1/16:0) | 1.35 | 3.5E−06 | 1.41 | 3.1E−06 | 1.57 | 4.4E−04 | 1.71 | 2.7E−04 | 1.28 | 2.5E−01 |
| Cer(d16:1/18:0) | 2.14 | 1.3E−24 | 2.35 | 6.7E−23 | 3.08 | 4.7E−14 | 3.26 | 7.5E−12 | 2.10 | 1.5E−03 |
| Cer(d16:1/20:0) | 1.68 | 4.0E−14 | 1.88 | 3.8E−15 | 2.02 | 2.3E−07 | 2.07 | 2.8E−06 | 2.01 | 2.6E−03 |
| Cer(d16:1/22:0) | 1.64 | 9.1E−14 | 1.67 | 5.4E−12 | 1.81 | 3.0E−06 | 1.75 | 8.4E−05 | 1.29 | 2.3E−01 |
| Cer(d16:1/24:1) | 1.59 | 1.0E−12 | 1.63 | 3.6E−11 | 1.63 | 9.3E−05 | 1.62 | 5.8E−04 | 1.20 | 3.9E−01 |
| Cer(d18:1/16:0) | 1.37 | 7.2E−07 | 1.37 | 1.2E−05 | 1.56 | 3.0E−04 | 1.55 | 1.7E−03 | 1.25 | 2.9E−01 |
| Cer(d18:1/18:0) | 2.19 | 3.6E−29 | 2.34 | 6.3E−26 | 2.89 | 2.6E−16 | 3.03 | 5.5E−14 | 1.98 | 5.2E−04 |
| Cer(d18:1/20:0) | 1.64 | 4.7E−14 | 1.77 | 6.2E−14 | 2.18 | 1.4E−09 | 2.32 | 8.7E−09 | 1.86 | 3.4E−03 |
| Cer(d18:1/22:0) | 1.88 | 1.7E−21 | 1.90 | 1.5E−17 | 2.27 | 8.5E−11 | 2.35 | 2.5E−09 | 1.36 | 1.3E−01 |
| Cer(d18:1/23:0) | 1.48 | 7.1E−11 | 1.48 | 7.3E−09 | 1.78 | 2.1E−07 | 1.89 | 3.1E−07 | 1.15 | 4.9E−01 |
| Cer(d18:1/24:1) | 1.68 | 2.4E−16 | 1.68 | 2.9E−13 | 2.00 | 3.9E−09 | 2.12 | 1.6E−08 | 1.57 | 2.2E−02 |
| Cer(d18:1/26:1) | 1.27 | 1.0E−04 | 1.15 | 4.9E−02 | 1.52 | 2.6E−04 | 1.45 | 3.7E−03 | 1.39 | 9.2E−02 |
| Cer(d18:2/18:0) | 1.76 | 1.1E−15 | 2.01 | 4.8E−17 | 2.45 | 6.7E−10 | 2.61 | 6.3E−09 | 1.43 | 1.1E−01 |
| Cer(d18:2/22:0) | 1.35 | 1.8E−06 | 1.42 | 1.1E−06 | 1.48 | 1.5E−03 | 1.52 | 2.6E−03 | 1.27 | 2.5E−01 |
| Cer(d18:2/24:1) | 1.27 | 1.7E−04 | 1.29 | 3.6E−04 | 1.51 | 9.4E−04 | 1.49 | 4.6E−03 | 1.21 | 3.6E−01 |
| Cer(d20:1/22:0) | 1.55 | 7.9E−13 | 1.54 | 4.7E−10 | 1.93 | 1.0E−08 | 2.02 | 8.1E−08 | 1.29 | 2.0E−01 |
| Cer(d20:1/24:1) | 1.46 | 2.1E−10 | 1.45 | 2.6E−08 | 1.82 | 3.8E−08 | 1.87 | 2.2E−07 | 1.41 | 7.4E−02 |
| DAG(14:0/18:1) | 2.17 | 4.8E−29 | 2.27 | 4.5E−25 | 2.64 | 1.7E−13 | 2.73 | 1.7E−11 | 1.83 | 4.0E−03 |
| DAG(14:0/18:2) | 1.85 | 3.9E−20 | 1.95 | 2.6E−18 | 2.07 | 9.6E−09 | 2.14 | 1.4E−07 | 1.87 | 3.3E−03 |
| DAG(16:0/16:1) | 2.40 | 1.8E−35 | 2.41 | 1.2E−28 | 3.10 | 6.4E−18 | 3.33 | 9.5E−16 | 2.17 | 1.4E−04 |
| DAG(16:0/18:1) | 2.34 | 1.8E−35 | 2.45 | 5.9E−31 | 2.88 | 4.0E−18 | 3.04 | 4.6E−16 | 2.09 | 1.1E−04 |
| DAG(16:0/18:2) | 1.99 | 3.4E−25 | 2.13 | 1.1E−23 | 2.39 | 9.6E−13 | 2.63 | 5.7E−12 | 2.03 | 3.5E−04 |
| DAG(16:0/20:4) | 2.27 | 4.9E−33 | 2.33 | 3.7E−28 | 2.64 | 8.9E−16 | 2.73 | 9.5E−14 | 1.75 | 4.2E−03 |
| DAG(16:0/22:6) | 1.89 | 2.7E−21 | 1.88 | 1.6E−16 | 2.52 | 1.4E−12 | 2.58 | 2.8E−10 | 2.49 | 1.6E−05 |
| DAG(16:1/16:1) | 1.99 | 9.7E−26 | 1.89 | 3.2E−18 | 2.50 | 4.3E−14 | 2.51 | 1.7E−11 | 1.77 | 3.5E−03 |
| DAG(16:1/18:1) | 2.10 | 2.5E−27 | 2.14 | 9.7E−23 | 2.50 | 5.5E−13 | 2.66 | 1.9E−11 | 1.86 | 2.6E−03 |
| DAG(18:0/18:1) | 2.76 | 8.1E−46 | 2.84 | 1.1E−38 | 3.19 | 5.5E−21 | 3.28 | 3.0E−18 | 2.09 | 8.4E−05 |
| DAG(18:0/18:2) | 2.19 | 4.6E−31 | 2.34 | 3.4E−28 | 2.51 | 1.6E−14 | 2.64 | 9.1E−13 | 2.03 | 2.0E−04 |
| DAG(18:0/20:4) | 1.74 | 3.0E−17 | 1.81 | 1.5E−15 | 2.03 | 3.8E−09 | 2.22 | 7.5E−09 | 2.03 | 4.6E−04 |
| DAG(18:1/18:1) | 1.97 | 2.2E−25 | 2.13 | 4.7E−24 | 2.24 | 3.9E−12 | 2.46 | 1.4E−11 | 1.67 | 7.8E−03 |
| DAG(18:1/18:2) | 1.59 | 2.5E−13 | 1.75 | 2.2E−14 | 1.73 | 3.9E−06 | 1.89 | 3.0E−06 | 1.48 | 5.3E−02 |
| DAG(18:1/18:3) | 1.63 | 1.0E−13 | 1.78 | 2.8E−14 | 1.59 | 1.8E−04 | 1.80 | 4.7E−05 | 1.82 | 4.0E−03 |
| DAG(18:1/20:4) | 2.05 | 3.8E−27 | 2.21 | 1.8E−25 | 2.30 | 2.0E−12 | 2.46 | 1.8E−11 | 1.58 | 2.2E−02 |
| DAG(18:2/18:2) | 1.32 | 1.0E−05 | 1.43 | 6.8E−07 | 1.32 | 2.3E−02 | 1.45 | 8.0E−03 | 1.54 | 3.9E−02 |
| DAG(18:2/20:4) | 1.66 | 4.8E−15 | 1.84 | 6.1E−16 | 1.81 | 8.9E−07 | 2.03 | 3.5E−07 | 1.52 | 4.5E−02 |
| Gb3(d18:1/16:0) | 0.58 | 2.9E−17 | 0.56 | 2.0E−15 | 0.54 | 2.9E−07 | 0.55 | 1.1E−05 | 0.80 | 2.9E−01 |
| Gb3(d18:1/22:0) | 0.61 | 5.9E−16 | 0.58 | 1.7E−14 | 0.64 | 5.1E−05 | 0.67 | 1.3E−03 | 0.73 | 1.1E−01 |
| Gb3(d18:1/23:0) | 0.56 | 1.1E−20 | 0.58 | 9.2E−15 | 0.58 | 6.4E−07 | 0.62 | 1.3E−04 | 0.82 | 3.3E−01 |
| Gb3(d18:1/24:1) | 0.59 | 1.7E−16 | 0.57 | 3.8E−14 | 0.59 | 8.4E−06 | 0.58 | 3.1E−05 | 0.88 | 5.4E−01 |
| Glc/GalCer(d16:1/18:0) | 1.35 | 4.8E−06 | 1.36 | 4.4E−05 | 1.77 | 2.7E−05 | 1.85 | 7.7E−05 | 1.42 | 1.2E−01 |
| Glc/GalCer(d16:1/23:0) | 0.94 | 3.0E−01 | 0.95 | 4.3E−01 | 0.89 | 3.1E−01 | 0.85 | 2.4E−01 | 0.76 | 1.6E−01 |
| Glc/GalCer(d18:1/23:0) | 0.81 | 1.1E−03 | 0.81 | 2.6E−03 | 0.85 | 2.0E−01 | 0.84 | 2.2E−01 | 0.67 | 6.6E−02 |
| Glc/GalCer(d18:2/20:0) | 0.72 | 4.5E−08 | 0.74 | 8.5E−06 | 0.83 | 1.0E−01 | 0.80 | 8.3E−02 | 0.80 | 2.5E−01 |
| Glc/GalCer(d18:2/22:0) | 0.73 | 7.3E−07 | 0.76 | 8.6E−05 | 0.81 | 7.8E−02 | 0.83 | 1.8E−01 | 0.67 | 4.8E−02 |
| Glc/GalCer(d18:2/23:0) | 0.77 | 1.6E−05 | 0.81 | 2.1E−03 | 0.89 | 3.4E−01 | 0.90 | 4.5E−01 | 0.69 | 7.1E−02 |
| Glc/GalCer(d18:2/24:0) | 0.86 | 1.1E−02 | 0.88 | 6.7E−02 | 0.83 | 1.3E−01 | 0.89 | 4.1E−01 | 0.58 | 5.7E−03 |
| LPC(14:0) [sn1] | 1.42 | 6.3E−08 | 1.39 | 8.3E−06 | 1.34 | 2.2E−02 | 1.25 | 1.1E−01 | 1.10 | 6.6E−01 |
| LPC(14:0) [sn2] | 1.43 | 4.6E−08 | 1.39 | 7.2E−06 | 1.42 | 5.9E−03 | 1.35 | 3.7E−02 | 1.15 | 5.0E−01 |
| LPC(15:0) [sn1] | 0.80 | 2.3E−04 | 0.84 | 1.3E−02 | 0.64 | 1.5E−04 | 0.68 | 4.5E−03 | 0.61 | 1.2E−02 |
| LPC(15:0) [sn2] | 0.79 | 1.2E−04 | 0.83 | 6.5E−03 | 0.66 | 4.1E−04 | 0.71 | 1.1E−02 | 0.76 | 1.7E−01 |
| LPC(16:0) [sn1] | 1.28 | 9.5E−05 | 1.24 | 2.8E−03 | 1.11 | 3.8E−01 | 1.07 | 6.3E−01 | 0.80 | 2.9E−01 |
| LPC(16:0) [sn2] | 1.26 | 2.8E−04 | 1.21 | 8.4E−03 | 1.09 | 5.1E−01 | 1.05 | 7.5E−01 | 0.83 | 3.8E−01 |
| LPC(17:0) [sn1] | 0.69 | 9.1E−10 | 0.73 | 3.0E−06 | 0.54 | 1.7E−08 | 0.57 | 4.4E−06 | 0.57 | 2.6E−03 |
| LPC(17:0) [sn2] | 0.69 | 1.4E−09 | 0.72 | 6.9E−07 | 0.57 | 3.9E−08 | 0.60 | 5.8E−06 | 0.61 | 2.0E−03 |
| LPC(18:1) [sn1] | 0.88 | 3.9E−02 | 0.82 | 4.9E−03 | 0.66 | 2.7E−04 | 0.64 | 3.7E−04 | 0.56 | 2.0E−03 |
| LPC(18:1) [sn2] | 0.94 | 2.8E−01 | 0.86 | 3.2E−02 | 0.73 | 8.2E−03 | 0.70 | 6.2E−03 | 0.59 | 7.7E−03 |
| LPC(18:2) [sn1] | 0.73 | 1.8E−07 | 0.69 | 9.5E−08 | 0.55 | 3.1E−08 | 0.54 | 5.2E−07 | 0.54 | 8.2E−04 |
| LPC(18:2) [sn2] | 0.75 | 4.2E−06 | 0.71 | 1.2E−06 | 0.57 | 1.3E−06 | 0.56 | 1.3E−05 | 0.60 | 9.4E−03 |
| LPC(19:0) [sn1] | 0.58 | 5.5E−18 | 0.60 | 2.9E−13 | 0.45 | 1.2E−12 | 0.46 | 3.7E−10 | 0.47 | 3.7E−05 |
| LPC(19:0) [sn2] | 0.63 | 8.3E−15 | 0.62 | 1.5E−12 | 0.52 | 1.1E−11 | 0.51 | 3.3E−10 | 0.61 | 1.2E−03 |
| LPC(20:0) [sn1] | 0.62 | 7.0E−15 | 0.62 | 7.2E−12 | 0.47 | 7.1E−12 | 0.46 | 3.3E−10 | 0.49 | 7.3E−05 |
| LPC(20:0) [sn2] | 0.63 | 1.0E−13 | 0.63 | 4.6E−10 | 0.49 | 1.1E−10 | 0.48 | 3.0E−09 | 0.53 | 6.6E−04 |
| LPC(20:1) [sn1] | 0.58 | 1.3E−16 | 0.56 | 5.8E−15 | 0.44 | 1.1E−10 | 0.42 | 1.3E−09 | 0.59 | 1.1E−02 |
| LPC(20:1) [sn2] | 0.61 | 2.0E−14 | 0.58 | 5.7E−13 | 0.49 | 2.5E−08 | 0.47 | 1.5E−07 | 0.64 | 3.7E−02 |
| LPC(20:2) [sn1] | 0.76 | 1.1E−05 | 0.71 | 9.1E−07 | 0.63 | 1.6E−04 | 0.62 | 5.9E−04 | 0.60 | 1.1E−02 |
| LPC(20:2) [sn2] | 0.86 | 1.2E−02 | 0.79 | 9.7E−04 | 0.78 | 4.1E−02 | 0.76 | 5.2E−02 | 0.71 | 9.7E−02 |
| LPC(20:3) [sn2] | 1.54 | 5.6E−11 | 1.50 | 3.6E−08 | 1.73 | 1.7E−05 | 1.91 | 9.0E−06 | 1.13 | 5.8E−01 |

TABLE 8-continued

Odds Ratios (OR) based on individual fatty liver biomarker values from Group A, Group B, Group E and Group F in subjects, whose liver fat content was determined four years after the lipid measurements, as compared to a control group in Young Finns Study cohort.

| Lipid | FL OR | FL p-value | NAFLD OR | NAFLD p-value | FL (severe) OR | FL (severe) p-value | NAFLD (severe) OR | NAFLD (severe) p-value | DM2 OR | DM2 p-value |
|---|---|---|---|---|---|---|---|---|---|---|
| LPC(20:4) [sn2] | 1.16 | 1.8E−02 | 1.13 | 8.2E−02 | 1.15 | 2.7E−01 | 1.19 | 2.1E−01 | 0.92 | 7.1E−01 |
| LPC(20:5) [sn2] | 1.18 | 6.7E−03 | 1.11 | 1.4E−01 | 1.15 | 2.6E−01 | 1.08 | 5.7E−01 | 1.37 | 1.4E−01 |
| LPC(22:0) [sn1] | 0.62 | 1.7E−13 | 0.61 | 1.4E−11 | 0.47 | 1.3E−10 | 0.44 | 1.0E−09 | 0.45 | 4.0E−05 |
| LPC(22:0) [sn2] | 0.65 | 5.0E−12 | 0.63 | 1.2E−10 | 0.48 | 5.3E−10 | 0.47 | 6.6E−09 | 0.50 | 3.5E−04 |
| LPC(22:1) [sn1] | 0.70 | 2.8E−07 | 0.69 | 2.3E−06 | 0.60 | 3.4E−04 | 0.55 | 2.5E−04 | 0.75 | 2.1E−01 |
| LPC(22:6) [sn1] | 0.81 | 5.2E−04 | 0.75 | 5.2E−05 | 0.78 | 4.3E−02 | 0.75 | 4.1E−02 | 0.85 | 4.3E−01 |
| LPC(22:6) [sn2] | 0.82 | 1.8E−03 | 0.77 | 1.8E−04 | 0.88 | 3.1E−01 | 0.87 | 3.3E−01 | 0.99 | 9.7E−01 |
| LPC(24:0) [sn1] | 0.68 | 1.7E−09 | 0.63 | 2.5E−10 | 0.53 | 1.6E−07 | 0.48 | 1.2E−07 | 0.47 | 1.3E−04 |
| LPC(24:0) [sn2] | 0.69 | 3.3E−09 | 0.64 | 5.9E−10 | 0.54 | 2.3E−07 | 0.48 | 7.6E−08 | 0.54 | 7.5E−04 |
| LPC(O-16:0) | 0.82 | 8.2E−04 | 0.84 | 9.3E−03 | 0.68 | 4.7E−04 | 0.70 | 5.4E−03 | 0.74 | 1.1E−01 |
| LPC(O-18:0) | 0.69 | 1.1E−09 | 0.72 | 1.1E−06 | 0.56 | 1.3E−07 | 0.58 | 1.3E−05 | 0.53 | 3.1E−04 |
| LPC(O-18:1) | 0.70 | 3.8E−09 | 0.73 | 3.7E−06 | 0.60 | 2.3E−06 | 0.63 | 1.9E−04 | 0.68 | 4.2E−02 |
| LPC(O-20:0) | 0.61 | 7.8E−16 | 0.62 | 6.3E−12 | 0.49 | 1.6E−10 | 0.49 | 1.2E−08 | 0.48 | 3.6E−05 |
| LPC(O-20:1) | 0.57 | 5.6E−19 | 0.58 | 8.0E−15 | 0.47 | 1.0E−11 | 0.48 | 2.4E−09 | 0.54 | 9.5E−04 |
| LPC(O-22:0) | 0.65 | 5.3E−12 | 0.65 | 9.0E−10 | 0.54 | 3.0E−08 | 0.53 | 3.0E−07 | 0.51 | 2.6E−04 |
| LPC(O-22:1) | 0.50 | 1.8E−26 | 0.51 | 9.4E−21 | 0.42 | 7.5E−15 | 0.41 | 2.0E−12 | 0.49 | 1.4E−04 |
| LPC(O-24:0) | 0.79 | 9.8E−05 | 0.78 | 4.0E−04 | 0.71 | 3.6E−03 | 0.68 | 4.8E−03 | 0.63 | 1.9E−02 |
| LPC(O-24:1) | 0.63 | 1.5E−13 | 0.63 | 5.5E−11 | 0.53 | 3.6E−08 | 0.53 | 7.6E−07 | 0.60 | 7.8E−03 |
| LPC(O-24:2) | 0.47 | 7.1E−29 | 0.47 | 5.9E−23 | 0.40 | 3.1E−14 | 0.39 | 3.6E−12 | 0.49 | 3.1E−04 |
| LPC(P-16:0) | 0.73 | 8.5E−08 | 0.73 | 1.8E−06 | 0.61 | 1.1E−06 | 0.61 | 1.9E−05 | 0.67 | 2.4E−02 |
| LPC(P-18:0) | 0.63 | 3.7E−14 | 0.64 | 9.4E−11 | 0.50 | 8.2E−11 | 0.53 | 9.4E−08 | 0.54 | 5.8E−04 |
| LPC(P-18:1) | 0.60 | 8.1E−16 | 0.62 | 1.3E−11 | 0.54 | 1.2E−08 | 0.57 | 5.4E−06 | 0.71 | 7.3E−02 |
| LPE(16:0) [sn1] | 0.89 | 6.3E−02 | 0.83 | 9.9E−03 | 0.88 | 2.8E−01 | 0.79 | 9.3E−02 | 0.72 | 1.3E−01 |
| LPE(16:0) [sn2] | 0.89 | 5.0E−02 | 0.82 | 6.2E−03 | 0.87 | 2.5E−01 | 0.80 | 1.1E−01 | 0.71 | 1.0E−01 |
| LPE(20:1) [sn1] | 0.86 | 1.5E−02 | 0.80 | 1.8E−03 | 0.77 | 3.9E−02 | 0.66 | 4.0E−03 | 0.85 | 4.5E−01 |
| LPE(22:6) [sn1] | 0.96 | 5.0E−01 | 0.90 | 1.2E−01 | 1.11 | 3.8E−01 | 0.99 | 9.4E−01 | 1.04 | 8.5E−01 |
| LPE(P-16:0) | 1.07 | 2.6E−01 | 1.07 | 3.6E−01 | 1.08 | 5.4E−01 | 1.11 | 4.5E−01 | 1.04 | 8.6E−01 |
| LPE(P-18:0) | 0.89 | 5.2E−02 | 0.89 | 1.1E−01 | 0.78 | 4.2E−02 | 0.84 | 2.1E−01 | 0.72 | 1.0E−01 |
| LPE(P-20:0) | 0.74 | 8.7E−07 | 0.75 | 2.3E−05 | 0.59 | 1.4E−06 | 0.62 | 8.0E−05 | 0.63 | 8.4E−03 |
| LacCer(d18:1/16:0) | 0.62 | 2.3E−13 | 0.62 | 3.5E−11 | 0.62 | 9.7E−05 | 0.63 | 8.3E−04 | 0.63 | 2.5E−02 |
| LacCer(d18:1/22:0) | 0.87 | 2.8E−02 | 0.89 | 9.3E−02 | 0.89 | 3.4E−01 | 0.92 | 5.4E−01 | 0.86 | 4.7E−01 |
| LacCer(d18:1/24:0) | 0.95 | 3.7E−01 | 0.91 | 1.9E−01 | 0.96 | 7.2E−01 | 0.88 | 3.9E−01 | 0.69 | 9.2E−02 |
| LacCer(d18:1/24:1) | 0.67 | 2.7E−10 | 0.69 | 1.6E−07 | 0.64 | 1.7E−04 | 0.67 | 3.3E−03 | 0.76 | 1.9E−01 |
| LacCer(d18:2/24:1) | 0.67 | 5.5E−11 | 0.71 | 8.4E−08 | 0.73 | 6.3E−03 | 0.73 | 1.7E−02 | 0.84 | 3.8E−01 |
| PC(31:0) | 0.85 | 9.7E−03 | 0.85 | 2.2E−02 | 0.91 | 4.4E−01 | 0.94 | 6.6E−01 | 0.74 | 1.6E−01 |
| PC(31:1) | 1.41 | 5.3E−08 | 1.34 | 3.3E−05 | 1.69 | 2.3E−05 | 1.69 | 1.9E−04 | 1.25 | 3.0E−01 |
| PC(32:0) | 1.18 | 8.1E−03 | 1.09 | 2.2E−01 | 1.43 | 3.3E−03 | 1.35 | 3.0E−02 | 1.10 | 6.5E−01 |
| PC(32:1) | 1.88 | 8.1E−23 | 1.75 | 4.8E−12 | 2.34 | 1.1E−12 | 2.30 | 5.8E−10 | 1.58 | 1.9E−02 |
| PC(33:2) | 0.73 | 3.0E−07 | 0.74 | 2.0E−05 | 0.72 | 5.7E−03 | 0.75 | 4.3E−02 | 0.72 | 1.1E−01 |
| PC(33:3) | 0.87 | 2.9E−02 | 0.91 | 1.6E−01 | 0.81 | 9.1E−02 | 0.86 | 2.7E−01 | 0.85 | 4.5E−01 |
| PC(34:1) | 1.59 | 1.2E−12 | 1.56 | 1.8E−09 | 1.84 | 2.1E−06 | 1.89 | 1.2E−05 | 1.19 | 4.1E−01 |
| PC(34:2) | 1.10 | 1.1E−01 | 1.03 | 6.7E−01 | 1.15 | 2.7E−01 | 1.10 | 4.7E−01 | 0.99 | 9.6E−01 |
| PC(34:3) | 1.01 | 8.6E−01 | 0.90 | 1.5E−01 | 0.99 | 9.3E−01 | 0.93 | 6.2E−01 | 0.94 | 7.8E−01 |
| PC(34:5) | 1.44 | 2.2E−08 | 1.39 | 7.9E−06 | 1.51 | 1.2E−03 | 1.42 | 1.4E−02 | 1.51 | 6.2E−02 |
| PC(35:2) | 0.65 | 4.8E−11 | 0.64 | 1.1E−09 | 0.53 | 1.5E−06 | 0.55 | 6.3E−05 | 0.45 | 1.8E−04 |
| PC(35:3) | 0.72 | 1.2E−07 | 0.68 | 7.5E−08 | 0.63 | 1.9E−04 | 0.62 | 1.0E−03 | 0.65 | 3.8E−02 |
| PC(36:1) | 1.59 | 2.7E−13 | 1.61 | 4.3E−11 | 1.86 | 2.1E−07 | 1.89 | 3.7E−06 | 1.16 | 4.7E−01 |
| PC(36:2) | 1.14 | 3.1E−02 | 1.13 | 9.2E−02 | 1.16 | 2.3E−01 | 1.10 | 5.2E−01 | 0.96 | 8.6E−01 |
| PC(36:3) | 1.87 | 1.4E−21 | 1.84 | 1.2E−16 | 2.38 | 1.0E−12 | 2.47 | 3.3E−11 | 1.45 | 6.7E−02 |
| PC(36:4) | 1.74 | 1.4E−16 | 1.71 | 1.4E−12 | 2.32 | 5.9E−10 | 2.33 | 3.7E−08 | 1.85 | 5.6E−03 |
| PC(36:5) | 1.41 | 3.2E−08 | 1.32 | 7.5E−05 | 1.56 | 2.1E−04 | 1.46 | 5.2E−03 | 1.71 | 8.4E−03 |
| PC(36:6) | 1.09 | 1.5E−01 | 1.10 | 2.0E−01 | 1.36 | 1.3E−02 | 1.34 | 3.8E−02 | 1.17 | 4.7E−01 |
| PC(36:7) | 1.13 | 4.7E−02 | 1.03 | 7.0E−01 | 1.10 | 4.4E−01 | 0.96 | 7.5E−01 | 0.61 | 3.1E−02 |
| PC(37:1) | 0.90 | 7.7E−02 | 0.92 | 2.1E−01 | 0.94 | 5.9E−01 | 0.96 | 7.9E−01 | 0.76 | 1.6E−01 |
| PC(37:2) | 0.63 | 6.1E−13 | 0.63 | 1.4E−10 | 0.55 | 5.5E−07 | 0.53 | 3.3E−06 | 0.52 | 1.1E−03 |
| PC(37:6) | 0.70 | 9.3E−09 | 0.70 | 6.1E−07 | 0.74 | 1.3E−02 | 0.77 | 5.5E−02 | 0.85 | 4.2E−01 |
| PC(38:1) | 1.18 | 7.3E−03 | 1.18 | 1.5E−02 | 1.42 | 2.4E−03 | 1.44 | 5.7E−03 | 1.44 | 6.4E−02 |
| PC(38:2) | 1.51 | 6.7E−11 | 1.51 | 8.6E−09 | 1.96 | 2.9E−08 | 1.94 | 1.2E−06 | 1.51 | 4.3E−02 |
| PC(38:3) | 2.24 | 9.5E−31 | 2.40 | 2.1E−27 | 3.31 | 2.6E−18 | 3.71 | 2.1E−16 | 1.68 | 1.2E−02 |
| PE(38:4) | 2.08 | 8.1E−24 | 2.13 | 8.1E−20 | 2.69 | 7.2E−12 | 2.73 | 4.7E−10 | 1.36 | 1.6E−01 |
| PC(38:4) | 1.64 | 7.3E−14 | 1.70 | 2.2E−12 | 2.09 | 1.3E−08 | 2.17 | 1.1E−07 | 1.30 | 2.2E−01 |
| PC(38:5) | 1.45 | 3.0E−09 | 1.41 | 1.2E−06 | 1.63 | 3.2E−05 | 1.55 | 1.1E−03 | 1.57 | 2.5E−02 |
| PC(38:6) | 0.98 | 7.8E−01 | 0.93 | 2.8E−01 | 1.24 | 9.4E−02 | 1.18 | 2.5E−01 | 1.20 | 4.1E−01 |
| PC(38:7) | 0.92 | 1.9E−01 | 0.85 | 1.4E−02 | 0.91 | 4.5E−01 | 0.88 | 3.2E−01 | 1.07 | 7.6E−01 |
| PC(39:4) | 0.76 | 1.5E−05 | 0.79 | 7.9E−04 | 0.72 | 7.6E−03 | 0.71 | 1.2E−02 | 0.68 | 5.4E−02 |
| PC(17:0_22:6) | 0.70 | 6.8E−09 | 0.70 | 3.6E−07 | 0.75 | 1.5E−02 | 0.75 | 3.2E−02 | 0.81 | 2.9E−01 |
| PC(40:2) | 1.15 | 3.1E−02 | 1.10 | 1.6E−01 | 1.36 | 1.6E−02 | 1.43 | 1.7E−02 | 1.46 | 8.2E−02 |
| PC(40:4) | 2.09 | 1.1E−27 | 2.17 | 1.2E−23 | 2.35 | 1.5E−12 | 2.34 | 2.3E−10 | 1.16 | 4.7E−01 |
| PC(40:5) | 1.79 | 1.5E−18 | 1.81 | 2.7E−15 | 1.83 | 1.2E−06 | 1.74 | 8.7E−05 | 1.18 | 4.4E−01 |
| PC(40:6) | 1.30 | 3.9E−05 | 1.29 | 4.0E−04 | 1.86 | 2.5E−06 | 1.84 | 4.7E−05 | 1.56 | 4.4E−02 |
| PC(O-32:0) | 0.73 | 5.2E−07 | 0.73 | 6.7E−06 | 0.78 | 4.3E−02 | 0.78 | 6.8E−02 | 0.66 | 3.6E−02 |
| PC(O-32:1) | 0.77 | 1.2E−05 | 0.72 | 2.2E−06 | 0.81 | 5.7E−02 | 0.79 | 5.9E−02 | 0.88 | 5.3E−01 |

TABLE 8-continued

Odds Ratios (OR) based on individual fatty liver biomarker values from Group A, Group B, Group E and Group F in subjects, whose liver fat content was determined four years after the lipid measurements, as compared to a control group in Young Finns Study cohort.

|  | FL | | NAFLD | | FL (severe) | | NAFLD (severe) | | DM2 | |
|---|---|---|---|---|---|---|---|---|---|---|
| Lipid | OR | p-value | OR | p-value | OR | p-value | OR | p-value | OR | p-value |
| PC(O-34:0) | 0.69 | 7.3E−09 | 0.71 | 1.7E−06 | 0.71 | 5.1E−03 | 0.76 | 4.2E−02 | 0.58 | 8.2E−03 |
| PC(O-34:1) | 0.51 | 2.9E−23 | 0.50 | 2.5E−19 | 0.43 | 6.4E−11 | 0.44 | 1.0E−08 | 0.49 | 8.1E−04 |
| PC(O-34:2) | 0.72 | 2.1E−07 | 0.72 | 5.7E−06 | 0.58 | 1.2E−05 | 0.64 | 1.7E−03 | 0.61 | 1.7E−02 |
| PC(O-36:2) | 0.55 | 4.5E−20 | 0.55 | 4.3E−16 | 0.44 | 8.6E−12 | 0.48 | 2.5E−08 | 0.54 | 2.6E−04 |
| PC(O-36:3) | 0.59 | 5.6E−16 | 0.59 | 3.7E−13 | 0.48 | 6.2E−09 | 0.53 | 7.2E−06 | 0.55 | 4.4E−03 |
| PC(O-36:5) | 1.13 | 5.4E−02 | 1.07 | 3.6E−01 | 1.14 | 2.9E−01 | 1.06 | 6.7E−01 | 1.40 | 8.7E−02 |
| PC(O-38:0) | 0.73 | 2.1E−06 | 0.73 | 2.9E−05 | 0.70 | 5.7E−03 | 0.71 | 1.8E−02 | 0.52 | 4.3E−03 |
| PC(O-38:2) | 0.75 | 2.9E−06 | 0.80 | 1.7E−03 | 0.75 | 1.7E−02 | 0.84 | 2.0E−01 | 0.61 | 9.0E−03 |
| PC(O-38:4) | 0.89 | 4.7E−02 | 0.93 | 2.7E−01 | 0.87 | 2.4E−01 | 0.90 | 4.5E−01 | 0.56 | 2.9E−03 |
| PC(O-38:6) | 0.91 | 1.2E−01 | 0.89 | 1.1E−01 | 1.06 | 6.5E−01 | 1.05 | 7.2E−01 | 1.20 | 3.9E−01 |
| PC(O-40:3) | 0.74 | 4.9E−07 | 0.72 | 9.2E−07 | 0.75 | 6.7E−03 | 0.73 | 9.3E−03 | 0.76 | 1.4E−01 |
| PC(O-40:4) | 0.88 | 3.0E−02 | 0.91 | 1.8E−01 | 0.87 | 2.3E−01 | 0.91 | 4.8E−01 | 0.62 | 9.6E−03 |
| PC(O-40:6) | 0.64 | 2.1E−12 | 0.62 | 2.7E−11 | 0.63 | 8.5E−05 | 0.62 | 2.5E−04 | 0.63 | 1.4E−02 |
| PC(P-36:2) | 0.44 | 4.5E−30 | 0.43 | 7.7E−25 | 0.27 | 1.4E−17 | 0.30 | 4.1E−13 | 0.41 | 6.5E−05 |
| PC(P-32:0) | 0.70 | 7.5E−09 | 0.68 | 7.7E−08 | 0.66 | 5.8E−04 | 0.66 | 2.4E−03 | 0.62 | 1.9E−02 |
| PC(P-32:1) | 0.75 | 1.4E−06 | 0.68 | 1.4E−08 | 0.79 | 3.7E−02 | 0.74 | 1.5E−02 | 0.95 | 8.2E−01 |
| PC(P-34:1) | 0.47 | 6.1E−27 | 0.45 | 3.2E−23 | 0.40 | 2.4E−12 | 0.39 | 3.1E−10 | 0.48 | 5.0E−04 |
| PC(P-36:1) | 0.43 | 7.8E−32 | 0.41 | 2.6E−26 | 0.30 | 1.4E−16 | 0.30 | 4.2E−13 | 0.39 | 3.3E−05 |
| PC(P-38:4) | 0.97 | 6.3E−01 | 1.00 | 9.6E−01 | 0.90 | 3.7E−01 | 0.96 | 7.9E−01 | 0.70 | 8.4E−02 |
| PC(P-38:6) | 0.83 | 2.1E−03 | 0.80 | 1.0E−03 | 0.80 | 7.1E−02 | 0.79 | 8.3E−02 | 1.03 | 9.0E−01 |
| PC(P-40:2) | 0.69 | 3.9E−09 | 0.69 | 1.3E−07 | 0.70 | 2.3E−03 | 0.72 | 1.6E−02 | 0.63 | 1.3E−02 |
| PC(P-40:4) | 0.72 | 1.9E−07 | 0.73 | 9.6E−06 | 0.61 | 3.3E−05 | 0.60 | 1.8E−04 | 0.50 | 4.3E−04 |
| PC(P-40:5) | 0.91 | 1.2E−01 | 0.91 | 2.0E−01 | 0.79 | 5.7E−02 | 0.84 | 2.1E−01 | 0.78 | 2.3E−01 |
| PE(32:1) | 1.72 | 5.2E−18 | 1.63 | 2.7E−12 | 2.09 | 1.5E−10 | 1.99 | 5.3E−08 | 1.63 | 1.1E−02 |
| PE(34:1) | 1.60 | 1.4E−14 | 1.55 | 9.1E−11 | 1.81 | 4.7E−08 | 1.73 | 4.4E−06 | 1.46 | 4.4E−02 |
| PE(34:2) | 1.31 | 9.8E−06 | 1.28 | 3.5E−04 | 1.49 | 3.0E−04 | 1.46 | 2.4E−03 | 1.41 | 7.1E−02 |
| PE(36:1) | 1.80 | 2.1E−20 | 1.78 | 2.7E−16 | 2.05 | 5.6E−10 | 1.98 | 1.0E−07 | 1.55 | 2.3E−02 |
| PE(36:2) | 1.61 | 3.3E−14 | 1.61 | 1.4E−11 | 1.78 | 7.9E−07 | 1.75 | 1.5E−05 | 1.51 | 3.9E−02 |
| PE(36:5) | 1.33 | 5.7E−06 | 1.25 | 1.7E−03 | 1.51 | 5.9E−04 | 1.38 | 1.9E−02 | 1.63 | 1.6E−02 |
| PE(38:1) | 1.51 | 1.7E−11 | 1.49 | 6.9E−09 | 1.70 | 2.2E−06 | 1.61 | 1.5E−04 | 1.72 | 3.5E−03 |
| PE(38:3) | 1.72 | 3.0E−17 | 1.74 | 1.2E−14 | 2.08 | 1.5E−09 | 2.07 | 6.5E−08 | 1.57 | 2.8E−02 |
| PE(38:4) | 1.54 | 4.4E−12 | 1.54 | 7.0E−10 | 1.76 | 1.4E−06 | 1.72 | 3.7E−05 | 1.48 | 5.3E−02 |
| PE(38:5) | 1.50 | 1.0E−10 | 1.44 | 2.0E−07 | 1.75 | 2.7E−06 | 1.66 | 1.4E−04 | 1.59 | 2.0E−02 |
| PE(40:4) | 1.87 | 3.4E−22 | 1.87 | 7.1E−18 | 2.06 | 1.3E−09 | 1.97 | 2.3E−07 | 1.38 | 1.1E−01 |
| PE(40:5) | 1.75 | 1.3E−18 | 1.74 | 1.0E−14 | 1.82 | 4.2E−07 | 1.74 | 3.3E−05 | 1.47 | 5.4E−02 |
| PE(40:6) | 1.49 | 2.1E−10 | 1.46 | 6.0E−08 | 1.91 | 5.6E−08 | 1.84 | 5.0E−06 | 1.84 | 2.5E−03 |
| PE(O-34:2) | 0.81 | 6.0E−04 | 0.80 | 1.3E−03 | 0.67 | 8.6E−04 | 0.72 | 1.5E−02 | 0.87 | 5.0E−01 |
| PE(O-36:1) | 0.93 | 2.5E−01 | 0.92 | 2.6E−01 | 0.85 | 1.8E−01 | 0.86 | 2.7E−01 | 0.95 | 7.9E−01 |
| PE(P-36:2) | 0.90 | 7.8E−02 | 0.90 | 1.5E−01 | 0.72 | 4.9E−03 | 0.75 | 3.3E−02 | 0.62 | 1.4E−02 |
| PE(P-36:4) | 1.38 | 2.8E−07 | 1.37 | 8.9E−06 | 1.46 | 2.0E−03 | 1.63 | 4.4E−04 | 1.17 | 4.6E−01 |
| PE(P-38:6) | 1.18 | 9.9E−03 | 1.14 | 5.9E−02 | 1.51 | 1.0E−03 | 1.54 | 2.4E−03 | 1.55 | 4.2E−02 |
| PE(P-40:6) | 0.89 | 5.1E−02 | 0.87 | 4.2E−02 | 0.91 | 4.6E−01 | 0.98 | 8.6E−01 | 0.98 | 9.1E−01 |
| PG(34:1) | 1.48 | 4.7E−10 | 1.46 | 6.8E−08 | 1.70 | 7.1E−06 | 1.64 | 1.8E−04 | 1.56 | 2.6E−02 |
| PG(36:1) | 2.41 | 1.7E−35 | 2.55 | 1.5E−30 | 3.18 | 9.2E−19 | 3.28 | 2.3E−15 | 1.97 | 8.2E−04 |
| PI(32:0) | 1.36 | 2.3E−07 | 1.28 | 3.0E−04 | 1.70 | 4.1E−07 | 1.65 | 2.5E−05 | 1.33 | 1.3E−01 |
| PI(32:1) | 2.07 | 2.1E−28 | 1.92 | 1.6E−21 | 2.72 | 9.4E−16 | 2.60 | 2.1E−12 | 1.82 | 2.6E−03 |
| PI(34:2) | 1.52 | 1.0E−11 | 1.47 | 2.8E−08 | 1.96 | 3.4E−09 | 1.87 | 7.2E−07 | 1.43 | 6.8E−02 |
| PI(36:4) | 1.76 | 1.3E−18 | 1.73 | 2.1E−14 | 2.49 | 1.5E−13 | 2.36 | 3.1E−10 | 1.37 | 1.3E−01 |
| PI(38:1) | 0.92 | 1.7E−01 | 0.83 | 8.6E−03 | 0.95 | 6.8E−01 | 0.89 | 3.9E−01 | 0.86 | 4.7E−01 |
| PI(40:5) | 2.04 | 2.1E−24 | 1.86 | 9.9E−16 | 2.42 | 1.0E−11 | 2.22 | 3.0E−08 | 1.68 | 1.3E−02 |
| SM(31:0) | 0.91 | 1.1E−01 | 0.93 | 3.2E−01 | 0.89 | 3.5E−01 | 0.99 | 9.5E−01 | 1.01 | 9.8E−01 |
| SM(d17:1/14:0) | 0.73 | 3.7E−07 | 0.77 | 1.6E−04 | 0.72 | 5.2E−03 | 0.80 | 1.0E−01 | 0.77 | 2.0E−01 |
| SM(31:2) | 1.00 | 9.8E−01 | 1.09 | 2.4E−01 | 1.30 | 3.5E−02 | 1.50 | 5.4E−03 | 1.46 | 7.9E−02 |
| SM(32:0) | 1.04 | 5.3E−01 | 1.05 | 5.1E−01 | 1.13 | 3.3E−01 | 1.17 | 2.5E−01 | 1.12 | 5.9E−01 |
| SM(32:1) | 1.11 | 8.5E−02 | 1.16 | 3.5E−02 | 1.18 | 1.7E−01 | 1.32 | 5.2E−02 | 1.06 | 7.7E−01 |
| SM(32:2) | 1.00 | 9.6E−01 | 1.07 | 3.1E−01 | 1.34 | 1.8E−02 | 1.43 | 1.2E−02 | 1.30 | 2.2E−01 |
| SM(33:0) | 0.75 | 4.4E−06 | 0.78 | 4.0E−04 | 0.84 | 1.6E−01 | 0.89 | 4.1E−01 | 1.05 | 8.2E−01 |
| SM(33:2) | 1.04 | 5.4E−01 | 1.17 | 2.9E−02 | 1.60 | 1.1E−04 | 1.92 | 2.5E−06 | 1.41 | 1.0E−01 |
| SM(34:1) | 0.81 | 5.8E−04 | 0.83 | 2.2E−03 | 0.82 | 1.1E−01 | 0.90 | 4.5E−01 | 0.96 | 8.5E−01 |
| SM(34:2) | 1.11 | 1.0E−01 | 1.18 | 2.0E−02 | 1.53 | 4.7E−04 | 1.61 | 5.7E−04 | 1.27 | 2.6E−01 |
| SM(36:0) | 1.99 | 3.3E−26 | 2.06 | 9.5E−23 | 2.85 | 1.2E−17 | 3.10 | 4.0E−16 | 2.39 | 3.4E−06 |
| SM(36:1) | 1.38 | 4.1E−07 | 1.49 | 4.0E−08 | 1.87 | 6.8E−07 | 2.22 | 3.8E−08 | 1.75 | 8.3E−03 |
| SM(36:2) | 1.37 | 8.5E−07 | 1.52 | 1.7E−08 | 2.13 | 6.7E−09 | 2.45 | 3.3E−09 | 1.71 | 1.4E−02 |
| SM(37:1) | 0.57 | 2.7E−17 | 0.59 | 6.5E−13 | 0.57 | 8.1E−06 | 0.63 | 7.3E−04 | 0.78 | 2.4E−01 |
| SM(37:2) | 0.52 | 5.6E−22 | 0.48 | 1.1E−20 | 0.38 | 3.0E−13 | 0.39 | 2.7E−10 | 0.55 | 5.1E−03 |
| SM(38:0) | 1.79 | 3.3E−18 | 1.87 | 2.4E−16 | 2.53 | 3.4E−12 | 2.84 | 1.2E−11 | 2.13 | 4.7E−04 |
| SM(38:1) | 1.20 | 3.0E−03 | 1.28 | 6.5E−03 | 1.39 | 7.3E−03 | 1.53 | 2.4E−03 | 1.37 | 1.4E−01 |
| SM(39:1) | 1.00 | 9.4E−01 | 1.07 | 3.5E−01 | 1.06 | 6.3E−01 | 1.25 | 1.1E−01 | 1.00 | 9.9E−01 |
| SM(39:2) | 0.71 | 9.3E−10 | 0.71 | 1.8E−08 | 0.69 | 1.0E−05 | 0.68 | 6.2E−05 | 0.87 | 4.3E−01 |
| SM(d18:0/22:0) | 2.08 | 4.5E−26 | 2.17 | 1.1E−22 | 2.95 | 2.0E−15 | 3.41 | 1.3E−14 | 1.62 | 2.1E−02 |
| SM(40:1) | 1.41 | 7.1E−08 | 1.44 | 5.8E−07 | 1.61 | 1.7E−04 | 1.80 | 5.6E−05 | 1.24 | 3.1E−01 |
| SM(40:2) | 1.08 | 2.2E−01 | 1.09 | 2.0E−01 | 1.12 | 3.6E−01 | 1.25 | 1.0E−01 | 1.18 | 4.4E−01 |

TABLE 8-continued

Odds Ratios (OR) based on individual fatty liver biomarker values from Group A, Group B, Group E and Group F in subjects, whose liver fat content was determined four years after the lipid measurements, as compared to a control group in Young Finns Study cohort.

| Lipid | FL OR | p-value | NAFLD OR | p-value | FL (severe) OR | p-value | NAFLD (severe) OR | p-value | DM2 OR | p-value |
|---|---|---|---|---|---|---|---|---|---|---|
| SM(41:0) | 1.65 | 6.3E−15 | 1.71 | 1.6E−13 | 2.26 | 3.7E−11 | 2.57 | 4.2E−11 | 1.72 | 7.5E−03 |
| SM(41:1) | 1.20 | 4.4E−03 | 1.27 | 1.0E−03 | 1.46 | 4.1E−03 | 1.81 | 1.2E−04 | 0.94 | 7.6E−01 |
| SM(41:2) | 0.75 | 3.5E−06 | 0.80 | 1.2E−03 | 0.78 | 4.5E−02 | 0.88 | 3.5E−01 | 0.73 | 1.1E−01 |
| SM(42:1) | 1.35 | 8.4E−07 | 1.31 | 9.2E−05 | 1.42 | 2.9E−03 | 1.52 | 1.5E−03 | 1.03 | 9.0E−01 |
| SM(44:2) | 1.12 | 7.4E−02 | 1.08 | 2.7E−01 | 1.42 | 6.2E−03 | 1.51 | 4.4E−03 | 1.56 | 4.0E−02 |
| SM(44:3) | 0.67 | 1.2E−10 | 0.63 | 1.0E−10 | 0.71 | 3.1E−03 | 0.67 | 2.3E−03 | 0.94 | 7.7E−01 |
| LPC(MHDA) [sn1] | 0.63 | 5.1E−14 | 0.62 | 2.4E−11 | 0.46 | 3.0E−11 | 0.47 | 1.1E−08 | 0.43 | 9.1E−06 |
| LPC(MHDA) [sn2] | 0.65 | 7.3E−12 | 0.67 | 8.2E−09 | 0.53 | 3.0E−08 | 0.57 | 6.1E−06 | 0.55 | 1.9E−04 |

FL: subjects with fatty liver disease vs. healthy controls, NAFLD: subjects with non-alcoholic fatty liver disease vs. healthy controls, FL(severe): subjects with severe fatty liver disease vs. healthy controls, NAFLD(severe): subjects with severe non-alcoholic fatty liver disease vs. healthy controls, DM2: subjects who developed type 2 diabetes during the follow-up vs. healthy controls. Other abbreviations are de-described in the detailed description of the present disclosure.

The invention claimed is:

1. An in vitro method for assessing whether a subject is at risk to develop or is suffering from fatty liver disease and treating the subject indicated as being at risk to develop or suffering from fatty liver disease comprising:
   (a) assaying a sample from said subject to determine a concentration of at least one fatty liver biomarker from Group E;
   (b) assaying a sample from said subject to determine a concentration of at least one fatty liver biomarker from Group F;
   (c) determining that the subject is suffering from or is at an increased risk of developing fatty liver disease, if said sample contains an increased combination biomarker value of the at least one fatty liver biomarker from Group E and the at least one fatty liver biomarker from Group F, when compared to a control,
   wherein the at least one fatty liver biomarker from Group E is not DAG(18:1/18:2), Cer(d18:1/24:0), Cer(d18:1/24:1), LPC(16:0) [sn1], LPC(16:0) [sn2], PC(34:2), PC(38:4), PC(38:6), PC(40:6), PE(38:2), PE(36:2), SM(42:1), SM(36:0), TG(16:0/16:0/18:1), TG(16:0/18:0/18:1), TG(16:0/18:1/18:1), and/or TG(16:0/16:0/16:0),
   wherein the at least one fatty liver biomarker from Group F is LPC(MHDA) [sn1] and/or LPC(MHDA) [sn2], and
   (d) treating the subject indicated as suffering from or at an increased risk of developing fatty liver disease,
   wherein the treating comprises a lifestyle intervention to effect a change in diet, weight management and/or physical activity.

2. A method of detecting in a sample from a subject a concentration of at least one fatty liver biomarker from Group E and a concentration of at least one fatty liver biomarker from Group F by mass spectrometry comprising:
   (a) assaying the sample from said subject to determine the concentration of the at least one fatty liver biomarker from Group E; and
   (b) assaying the sample from said subject to determine the concentration of the at least one fatty liver biomarker from Group F, wherein the at least one fatty liver biomarker from Group F is LPC(MHDA) [sn1] and/or LPC(MHDA) [sn2].

3. An in vitro method for assessing a progression of fatty liver disease in a subject and treating the subject indicated as suffering from the progression of fatty liver disease comprising:
   (a) assaying a sample from said subject to determine a concentration of at least one fatty liver biomarker from Group E;
   (b) assaying a sample from said subject to determine a concentration of at least one fatty liver biomarker from Group F;
   (c) determining that fatty liver disease has progressed, if said sample contains an increased combination biomarker value of the at least one fatty liver biomarker from Group E and the at least one fatty liver biomarker from Group F, when compared to a control,
   wherein the at least one fatty liver biomarker from Group E is not DAG(18:1/18:2), Cer(d18:1/24:0), Cer(d18:1/24:1), LPC(16:0) [sn1], LPC(16:0) [sn2], PC(34:2), PC(38:4), PC(38:6), PC(40:6), PE(38:2), PE(36:2), SM(42:1), SM(36:0), TG(16:0/16:0/18:1), TG(16:0/18:0/18:1), TG(16:0/18:1/18:1), and/or TG(16:0/16:0/16:0),
   wherein the at least one fatty liver biomarker from Group F is LPC(MHDA) [sn1] and/or LPC(MHDA) [sn2], and
   (d) treating the subject indicated as suffering from progressed fatty liver disease,
   wherein the treating comprises a lifestyle intervention to effect a change in diet, weight management and/or physical activity.

4. The method of claim 1, wherein the method comprises determining the concentration of at least 2 fatty liver biomarkers from Group E and at least 2 fatty liver biomarkers from Group F.

5. The method of claim 1, wherein the fatty liver biomarker concentration from Group E and the fatty liver biomarker concentration from Group F are determined by using mass spectrometry, nuclear magnetic resonance spectroscopy, fluorescence spectroscopy or dual polarization interferometry, an immunoassay, enzymatic assay, colorimetric assay, fluorometric assay, a rapid test and/or with a binding moiety capable of specifically binding the biomarker, and optionally wherein the sample is a serum sample or a plasma sample.

6. The method of claim 1, wherein the method comprises a step of spiking the sample with at least one isotope-labelled biomarker, optionally wherein the at least one isotope-labelled biomarker is/are deuterium-labelled, $^{13}$C-labelled or $^{15}$N-labelled.

7. The method of claim 1, wherein the subject is identified as being at risk to develop fatty liver disease and wherein the treating prevents the development of fatty liver disease.

8. The method of claim 1, wherein the method further comprises requesting a test from a laboratory which provides the results of an assay useful for determining the concentration of the at least one fatty liver biomarker from Group E and the at least one fatty liver biomarker from Group F, wherein the treating further comprises escalating a prior treatment, wherein the prior treatment comprises a lifestyle intervention to effect a change in diet, weight management and/or physical activity.

9. The method of claim 1, wherein the combination biomarker value is a concentration ratio of the at least one fatty liver biomarker from Group E and the at least one fatty liver biomarker from Group F, optionally wherein the combination biomarker value of the at least one fatty liver biomarker from Group E and the at least one fatty liver biomarker from Group F is selected from Table 7, and further optionally wherein the method is a screening method.

10. The method of claim 3, wherein the progression of the subject's condition from a healthy condition to a fatty liver phase, to non-alcoholic steatohepatitis (NASH) and/or to fibrosis, cirrhosis, liver failure and/or liver cancer, the progression of the subject's condition from a healthy condition to non-alcoholic fatty liver disease (NAFLD) or the progression from a fatty liver stage or NASH to fibrosis, cirrhosis, liver failure and/or liver cancer is assessed.

11. The method of claim 3, wherein the severity of fatty liver disease is assessed, optionally wherein the progress of fatty liver disease is monitored to assess if an administered treatment has affected the progress of the disease.

12. The method of claim 3, wherein the progression from NAFLD to NASH, the progression from NAFLD to severe fatty liver stages or the progression from NAFLD to fibrosis, cirrhosis, liver failure and/or liver cancer is assessed.

13. The method of claim 1, wherein the combination of the concentrations of the at least one fatty liver biomarker from Group E and the at least one fatty liver biomarker from Group F is (are) selected from Table 7.

14. The method of claim 2, wherein the sample is a serum sample or a plasma sample and/or wherein the method comprises a step of spiking the sample with at least one isotope-labelled biomarker, optionally wherein the at least one isotope-labelled biomarker is/are deuterium-labelled, $^{13}$C-labelled or $^{15}$N-labelled.

15. The method of claim 2, wherein the method comprises determining the concentration of at least 2 fatty liver biomarkers from Group E and at least 2 fatty liver biomarkers from Group F, optionally wherein the combination of the concentrations of the at least one fatty liver biomarker from Group E and the at least one fatty liver biomarker from Group F is (are) selected from Table 7.

16. The method of claim 3, wherein the method comprises determining the concentration of at least 2 fatty liver biomarkers from Group E and at least 2 fatty liver biomarkers from Group F, optionally wherein the combination of the concentrations of the at least one fatty liver biomarker from Group E and the at least one fatty liver biomarker from Group F is (are) selected from Table 7.

17. The method of claim 2, wherein the at least one fatty liver biomarker from Group E is not DAG(18:1/18:2), Cer(d18:1/24:0), Cer(d18:1/24:1), LPC(16:0) [sn1], LPC (16:0) [sn2], PC(34:2), PC(38:4), PC(38:6), PC(40:6), PE(38:2), PE(36:2), SM(42:1), SM(36:0), TG(16:0/16:0/18:1), TG(16:0/18:0/18:1), TG(16:0/18:1/18:1), and/or TG(16:0/16:0/16:0).

* * * * *

UNITED STATES PATENT AND TRADEMARK OFFICE
CERTIFICATE OF CORRECTION

PATENT NO. : 12,313,634 B2
APPLICATION NO. : 16/762612
DATED : May 27, 2025
INVENTOR(S) : Kevin Huynh et al.

Page 1 of 1

It is certified that error appears in the above-identified patent and that said Letters Patent is hereby corrected as shown below:

On the Title Page

Item (57) Abstract, Line 12, after "...control." the following sentence was omitted: "Methods for assessing the progression of fatty liver disease are also provided."

Signed and Sealed this
Fifth Day of August, 2025

Coke Morgan Stewart
*Acting Director of the United States Patent and Trademark Office*